US008992932B2

(12) United States Patent
Lerchen et al.

(10) Patent No.: US 8,992,932 B2
(45) Date of Patent: Mar. 31, 2015

(54) BINDER-DRUG CONJUGATES (ADCS) AND USE THEREOF

(71) Applicant: Seattle Genetics, Inc., Bothell, WA (US)

(72) Inventors: Hans-Georg Lerchen, Leverkusen (DE); Lars Linden, Düsseldorf (DE); Sherif El Sheikh, Essen (DE); Jörg Willuda, Glienicke/Nordbahn (DE); Charlotte Christine Kopitz, Berlin (DE); Joachim Schuhmacher, Wuppertal (DE); Simone Greven, Dormagen (DE); Christoph Mahlert, Wuppertal (DE); Beatrix Stelte-Ludwig, Wülfrath (DE); Sven Golfier, Berlin (DE); Rudolf Beier, Berlin (DE); Iring Heisler, Wuppertal (DE); Axel Harrenga, Wuppertal (DE); Karl-Heinz Thierauch, Berlin (DE); Sandra Bruder, Leverkusen (DE); Heike Petrul, Berlin (DE); Hannah Jöriβen, Essen (DE); Sandra Borkowski, Hohen Neuendorf (DE)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 13/656,681

(22) Filed: Oct. 20, 2012

(65) Prior Publication Data

US 2013/0095123 A1    Apr. 18, 2013

Related U.S. Application Data

(63) Continuation-in-part of application No. PCT/EP2012/057247, filed on Apr. 20, 2012, and a continuation-in-part of application No. PCT/EP2012/057249, filed on Apr. 20, 2012, and a continuation-in-part of application No. PCT/EP2012/057245, filed on Apr. 20, 2012, and a continuation-in-part of application No. PCT/EP2012/057243, filed on Apr. 20, 2012.

(30) Foreign Application Priority Data

| Apr. 21, 2011 | (EP) | 11163467 |
|---|---|---|
| Apr. 21, 2011 | (EP) | 11163470 |
| Apr. 21, 2011 | (EP) | 11163472 |
| Apr. 21, 2011 | (EP) | 11163474 |
| Jun. 1, 2011 | (EP) | 11168556 |
| Jun. 1, 2011 | (EP) | 11168557 |
| Jun. 1, 2011 | (EP) | 11168558 |
| Jun. 1, 2011 | (EP) | 11168559 |
| Dec. 14, 2011 | (EP) | 11193609 |
| Dec. 14, 2011 | (EP) | 11193618 |
| Dec. 14, 2011 | (EP) | 11193621 |
| Dec. 14, 2011 | (EP) | 11193623 |

(51) Int. Cl.
| A61K 39/00 | (2006.01) |
|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 17/14 | (2006.01) |
| C12P 21/08 | (2006.01) |
| A61K 39/395 | (2006.01) |

(Continued)

(52) U.S. Cl.
CPC ............... *C07K 5/06* (2013.01); *A61K 39/3955* (2013.01); *A61K 47/48415* (2013.01); *C07K 16/18* (2013.01); *A61K 45/06* (2013.01); *A61K 47/48569* (2013.01); *A61K 47/48384* (2013.01); *A61K 47/48038* (2013.01); *C07K 7/06* (2013.01); *A61K 47/48638* (2013.01); *A61K 47/486* (2013.01); *C07K 16/30* (2013.01); *C07K 7/02* (2013.01)
USPC ...................... 424/179.1; 530/330; 530/391.9

(58) Field of Classification Search
None
See application file for complete search history.

(56) References Cited

U.S. PATENT DOCUMENTS

| 6,884,869 B2 | 4/2005 | Senter et al. |
| 7,498,298 B2 | 3/2009 | Doronina et al. |

(Continued)

FOREIGN PATENT DOCUMENTS

| WO | 01/18032 A2 | 3/2001 |
| WO | 01/23553 A2 | 4/2001 |

(Continued)

OTHER PUBLICATIONS

Vippagunta et al "Crystalline Solids" Advanced Drug Delivery Reviews 48:3-26. Published 2001.*

(Continued)

*Primary Examiner* — Maury Audet
*Assistant Examiner* — Zachary J Miknis
(74) *Attorney, Agent, or Firm* — Buchanan Ingersoll & Rooney PC

(57) ABSTRACT

The present application relates to new binder-drug conjugates (ADCs) of N,N-dialkylauristatins that are directed against the target C4.4a, to active metabolites of these ADCs, to processes for preparing these ADCs, to the use of these ADCs for treating and/or preventing illnesses, and also to the use of these ADCs for producing medicaments for treating and/or preventing illnesses, more particularly hyperproliferative and/or angiogenic diseases such as, for example, cancer diseases. Such treatments may be practiced as a monotherapy or else in combination with other medicaments or further therapeutic measures.

12 Claims, No Drawings

(51) Int. Cl.
| | |
|---|---|
| A61K 47/48 | (2006.01) |
| C07K 16/18 | (2006.01) |
| A61K 45/06 | (2006.01) |
| C07K 5/06 | (2006.01) |
| C07K 7/06 | (2006.01) |
| C07K 16/30 | (2006.01) |
| C07K 7/02 | (2006.01) |

(56) References Cited

U.S. PATENT DOCUMENTS

| | | |
|---|---|---|
| 7,553,816 B2 | 6/2009 | Senter et al. |
| 7,659,241 B2 | 2/2010 | Senter et al. |
| 8,288,352 B2 | 10/2012 | Doronina et al. |
| 8,343,928 B2 | 1/2013 | Doronina et al. |
| 8,609,105 B2 | 12/2013 | Senter et al. |
| 2002/0147138 A1 | 10/2002 | Firestone et al. |
| 2009/0111756 A1 | 4/2009 | Doronina et al. |
| 2011/0020343 A1 | 1/2011 | Senter et al. |
| 2013/0066055 A1 | 3/2013 | Lerchen et al. |
| 2013/0122024 A1 | 5/2013 | Lerchen et al. |
| 2013/0157960 A1 | 6/2013 | Lerchen et al. |
| 2013/0261064 A1 | 10/2013 | Lerchen et al. |
| 2014/0080763 A1 | 3/2014 | Lerchen et al. |
| 2014/0127240 A1 | 5/2014 | Lerchen et al. |

FOREIGN PATENT DOCUMENTS

| | | |
|---|---|---|
| WO | 02/088172 A2 | 11/2002 |
| WO | 03/026577 A2 | 4/2003 |
| WO | 2004/010957 A2 | 2/2004 |
| WO | 2005/081711 A2 | 9/2005 |
| WO | 2005/101017 A1 | 10/2005 |
| WO | 2006/041641 A2 | 4/2006 |
| WO | 2006/071441 A2 | 7/2006 |
| WO | 2006/132670 A2 | 12/2006 |
| WO | 2007/008603 A1 | 1/2007 |
| WO | 2007/008848 A2 | 1/2007 |
| WO | WO 2007008603 A1 * | 1/2007 |
| WO | 2007/059082 A1 | 5/2007 |
| WO | 2007/070538 A2 | 6/2007 |
| WO | 2008/133641 A2 | 11/2008 |
| WO | 2009/045957 A1 | 4/2009 |
| WO | 2009/068204 A1 | 6/2009 |
| WO | 2009/099728 A1 | 8/2009 |
| WO | 2009/114711 A2 | 9/2009 |
| WO | 2009/117531 A1 | 9/2009 |
| WO | 2009/140242 A1 | 11/2009 |
| WO | 2011/070088 A1 | 6/2011 |
| WO | WO 2011070088 A1 * | 6/2011 |
| WO | WO 2011154359 A1 * | 12/2011 |
| WO | 2012/041805 A1 | 4/2012 |
| WO | 2012/087962 A2 | 6/2012 |
| WO | 2012/123423 A1 | 9/2012 |
| WO | 2012/143495 A2 | 10/2012 |
| WO | 2012/143496 A2 | 10/2012 |
| WO | 2012/143497 A2 | 10/2012 |
| WO | 2012/143499 A2 | 10/2012 |
| WO | 2013/087716 A2 | 6/2013 |

OTHER PUBLICATIONS

Alley et al., "The Pharmacologic Basis for Antibody-Auristatin Conjugate Activity" Journal of Pharmacology and Experimental Therapeutics, Sep. 1, 2009, vol. 330, No. 3, pp. 932-938 (XP055037536).
Alley et al., "Contribution of Linker Stability to the Activities of Anticancer Immunoconjugates" Bioconjugate Chemistry, Mar. 1, 2008, vol. 19, No. 3, pp. 759-765 (XP055037546).
Junutula et al., "Site-specific Conjugation of a Cytotoxic Drug to an Antibody Improves the Therapeutic Index" Nature Biotechnology, Aug. 1, 2008, vol. 26, No. 8, pp. 925-932 (XP002499771).
Lee et al., "EphA2 Immunoconjugate as Molecularly Targeted Chemotherapy for Ovarian Carcinoma" Journal of the National Cancer Institute, Sep. 2, 2009, vol. 101, No. 17, pp. 1193-1205 (XP002563033).
Smith et al., "CD133/Prominin-1 is a Potential Therapeutic Target for Antibody-drug Conjugates in Hepatocellular and Gastric Cancers" British Journal of Cancer, Jul. 1, 2008, vol. 99, No. 1, pp. 100-109 (XP002619785).
Oflazoglu et al., "Potent Anticarcinoma Activity of the Humanized Anti-CD70 Antibody h1F6 Conjugated to the Tubulin Inhibitor Auristatin via an Uncleavable Linker" Clinical Cancer Research, Oct. 1, 2008, vol. 14, No. 19, pp. 6171-6180 (XP055037556).
Jeffrey et al. "Development and properties of beta-glucuronide linkers for monoclonal antibody-drug conjugates" Bioconjugate Chemistry, May 1, 2006, vol. 17, No. 3, pp. 831-840 (XP002423719).
Sanderson et al., "Enhanced in vivo drug-linker stability of an anti-CD70 Auristatin Immunoconjugate" Proceedings of the American Association for Cancer Research, Apr. 1, 2006, vol. 47, pp. 469 (XP009151906).
Kai et al. Improved Efficacy of [alpha] v [beta] 3-Targeted Albumin Conjugates by Conjugation of a Novel Auristatin Derivative, Molecular Pharmaceutics, Aug. 8, 2007, vol. 4, No. 5, pp. 686-694 (XP055037690).
Hassan et al., "Mesothelin: A new Target for Immunotherapy" Clinical Cancer Research, Jun. 15, 2004, vol. 10 No. 12, Part 1, pp. 3937-3942 (XP009076012).
Doronina et al., "Novel Peptide Linkers for Highly Potent Antibody-Auristatin Conjugate" Bioconjugate Chemistry, Oct. 1, 2008, vol. 19, No. 10, pp. 1960-1963, (XP008098503).
Hansen et al., "Structural Analysis and Tissue Localization of Human C4.4A: a protein Homologue of the Urokinase Receptor" Biochemical Journal, Jun. 15, 2004, vol. 380, No. part 3, pp. 845-857 (XP002626955).
Hansen et al., "Production, Characterization and use of Mono- and Polyclonal Antibodies against C4.4A, a Homologue of the Urokinase Receptor" Thrombosis and Haemostasis, Apr. 1, 2005, vol. 93, No. 4, pp. A33 (XP009145645).
Hansen et al., "Tumour cell Expression of C4.4A, a Structural Homologue of the Urokinase Receptor, Correlates with Poor Prognosis in Non-Small Cell Lung Cancer" Lung Cancer, Oct. 6, 2007, vol. 58, No. 2, pp. 260-266 (XP022288745).
Paret et al., "P1. Overexpression of the C4.4A Protein, a uPAP Homologue, in cancer" European Journal of Cancer, Supplement, Jun. 1, 2006, vol. 4, No. 6, pp. 27 (XP024988580).
Schatz et al., "Efficacy and candidate biomarker evaluation for the anti-MN immunoconjugate BAY 79-4620, MN-IC in MN (CAIX) positive preclinical xenograft models" Proceedings of the American Association for Cancer Research Annual Meeting &101st Annual meeting of the American-Association-for-Cancer-Research; Washington, DC, Apr. 17-21, 2010, Retrieved from the Internet: URL:http://www.abstractsonline.com/Plan/AbstractPrintView.aspx?mID=2521&sKey=65acb1f 8-b2ff-4de7-8263-3a6476c83579&cKey=fe0879a b-6c0b-4713-9b65-5cee80a3769f.
Petrul et al., "In vitro and in vivo efficacy of the anti-MN immunoconjugate BAY 79-4620, MN-IC, in MN (CAIX) expressing preclinical tumor models" Proceedings of the American Association for Cancer Research Annual Meeting & 101st Annual meeting of the American-Association-for-Cancer-Research; Washington, DC, Apr. 17-21, 2010, Retrieved from the Internet: URL:http://www.abstractsonline.com/Plan/AbstractPrintView.aspx?mID=2521&sKey=0152bd2 b-26f2-4944-bd70-fb360b0532bc&cKey=6ac152e3-23b2-4f61-9d59-7cd69df4ab9c.
International Search Report (Form PCT/ISA/210) dated Oct. 23, 2012, issued in International Application No. PCT/EP2012/057249. (14 pages).
International Search Report (Form PCT/ISA/210) dated Jan. 17, 2013, issued in International Application No. PCT/EP2012/057247. (14 pages).
International Search Report (Form PCT/ISA/210) dated Jan. 17, 2013, issued in International Application No. PCT/EP2012/057245. (12 pages).
International Search Report (Form PCT/ISA/210) dated Oct. 23, 2012, issued in International Application No. PCT/EP2012/057243. (16 pages).
Konishi et al., "Expression of C4.4A at the invasive front is a novel prognostic marker for disease recurrence of colorectal cancer" Cancer Science, (Oct. 210), vol. 101, No. 10, pp. 2269-2277.

(56) References Cited

OTHER PUBLICATIONS

Karkan et al., "A Unique Carrier for Delivery of Therapeutic Compounds beyond the Blood-Brain Barrier" PLoS ONE, (Jun. 25, 2008), vol. 3, Issue 6, e2469, 14 pages.

Rosel et al., "Cloning and Functional Characterization of a new Phosphatidyl-Inositol Anchored Molecule of a Metastasizing rat Pancreatic Tumor" Oncogene, (Oct. 15, 1998), vol. 17, No. 15, pp. 1989-2002.

Seiter et al., "Upregulation of C4.4A Expression During Progression of Melanoma" The Journal of Investigative Dermatology, (Feb. 2001), vol. 116, No. 2, pp. 344-347.

Fletcher et al., "hAG-2 and hAG-3, Human Homologues of Genes involved in Differentiation, are Associated with Oestrogen Receptor-Positive Breast Tumours and Interact with Metastasis gene C4.4a and Dystroglycan" British Journal of Cancer, (2008), vol. 88, pp. 579-585.

Paret et al., " C4.4A as a Candidate Marker in the Diagnosis of Colorectal Cancer" British Journal of Cancer, (Oct. 22, 2007), vol. 97, No. 8, pp. 1146-1156.

Paret et al., "Ly6 family member C4.4A binds Laminins 1 and 5, Associates with Galectin-3 and supports cell Migration" International Journal of Cancer, (Jul. 10, 2005), vol. 115, No. 5, pp. 724-733.

Adams et al., "Monoclonal Antibody Therapy of Cancer" Nature Biotechnology, (Sep. 7, 2005), vol. 23, No. 9, pp. 1147-1157.

Lambert, "Drug-Conjugated Monoclonal Antibodies for the Treatment of Cancer" Current Opinion in Pharmacology, (Oct. 2005), vol. 5, Issue 5, pp. 543-549.

Wu et al. "Arming Antibodies: Prospects and Challenges for Immunoconjugates" Nature Biotechnology, (Sep. 7, 2005), vol. 23, No. 9, pp. 1137-1146.

Senter, "Potent Antibody Drug Conjugates for Cancer Therapy" Current Opinion in Chemical Biology, (Jun. 2009), vol. 13, Issue 3, pp. 235-244.

Ducry et al., "Antibody-Drug Conjugates: Linking Cytotoxic Payloads to Monoclonal Antibodies" Bioconjugate Chem., (2010), vol. 21, No. 1, pp. 5-13.

Arap et al., "Cancer Treatment by Targeted Drug Delivery to Tumor Vasculature in a Mouse Model" Science, (Jan. 16, 1998), vol. 279, No. 5349, pp. 377-380.

Wurfel et al., "Cloning of the Human Homologue of the Metastasis-Associated Rat C4.4A" Gene, (Jan. 10, 2001), vol. 262, Issues 1-2, pp. 35-41.

Pettit et al., "The Dolastatins" Prog. Chem. Org. Nat. Prod., (1997), vol. 70, pp. 1-79.

Pettit et al., "Antineoplastic Agents 337. Synthesis of Dolastatin 10 Structural Modifications" Anti-Cancer Drug Design, (1995), vol. 10, No. 7, pp. 529-544.

Pettit et al., "Antineoplastic Agents 365. Dolastatin 10 SAR Probes" Anti-Cancer Drug Design, (1998), vol. 13, No. 4, pp. 243-277.

Doronina et al., "Enhanced Activity of Monomethylauristatin F through Monoclonal Antibody Delivery: Effects of Linker Technology on Efficacy and Toxicity" Bioconjugate Chemistry, (2006), vol. 17, No. 1, pp. 114-124.

Notification Concerning Transmittal of Copy of International Preliminary Report on Patentability (Forms PCT/IB/326 and PCT/IB/373) and the Written Opinion of the International Searching Authority (Form PCT/ISA/237) issued on Oct. 31, 2013, by the International Bureau of WIPO in International Application No. PCT/EP2012/057243. (26 pages).

Lerchen et al., U.S. Appl. No. 14/113,070, entitle "Novel Binder-Drug Conjugates (ADCs) and Use of Same" filed Jan. 17, 2014.

Kim et al., "Anti-CD30 Diabody-Drug Conjugates with Potent Antitumor Activity" Molecular Cancer Therapeutics, (Aug. 2008), vol. 7, No. 8, pp. 2486-2497.

Lerchen et al., U.S. Appl. No. 14/269,577, entitled "Novel Binder-Drug Conjugates (ADCS) and Use Thereof".

Lerchen et al., U.S. Appl. No. 14/364,203, entitled "New Antibody Drug Conjugates (ADCS) and the Use Thereof" National Stage Entry of PCT/EP2012/075277.

\* cited by examiner

BINDER-DRUG CONJUGATES (ADCS) AND USE THEREOF

This application is a continuation-in-part of International Application PCT/EP/2012/057245, filed Apr. 20, 2012, which claims priority to EP11163472.1, filed Apr. 21, 2012, EP11168559.0, filed Jun. 1, 2011, and EP11193609.2, filed Dec. 14, 2011. This application is also a continuation-in-part of International Application PCT/EP/2012/057243, filed Apr. 20, 2012, which claims priority to EP11163470.5, filed Jun. Apr. 21, 2011, EP11168558.2, filed Jun. 1, 2011, and EP11193618.3, filed Dec. 14, 2011. This application is also a continuation-in-part of International Application PCT/EP/2012/057247, filed Apr. 20, 2012, which claims priority to EP11163467.1, filed Jun. Apr. 21, 2011, EP11168557.4, filed Jun. 1, 2011, and EP11193621.7, filed Dec. 14, 2011. This application is also a continuation-in-part of International Application PCT/EP/2012/057249, filed Apr. 20, 2012, which claims priority to EP11163474.7, filed Jun. Apr. 21, 2011, EP11168556.6, filed Jun. 1, 2011, and EP11193623.3, filed Dec. 14, 2011. Each of the applications is incorporated by reference herein in its entirety for all purposes.

The present application relates to new binder-drug conjugates (ADCs) of N,N-dialkylauristatins that are directed against the target C4.4a, to active metabolites of these ADCs, to processes for preparing these ADCs, to the use of these ADCs for treating and/or preventing illnesses, and also to the use of these ADCs for producing medicaments for treating and/or preventing illnesses, more particularly hyperproliferative and/or angiogenic diseases such as, for example, cancer diseases. Such treatments may be practised as a monotherapy or else in combination with other medicaments or further therapeutic measures.

Cancer diseases are the consequence of uncontrolled cell growth in a wide variety of tissues. In many cases the new cells penetrate existing tissue (invasive growth), or they metastase into remote organs. Cancer diseases occur in a wide variety of organs, and the illnesses often progress in a tissue-specific manner. The designation "cancer disease" as a generic term therefore describes a large group of defined diseases of different organs, tissues and cell types.

Early-stage tumours may be able to be removed by surgical and radiotherapeutic measures. Metastasized tumours can generally only be given palliative therapy by means of chemotherapeutic agents. The objective in that case is to achieve the optimum combination of improving quality of life and prolonging remaining lifetime.

The majority of the chemotherapeutic agents which are presently administered parenterally are often not target-directed at the tumour tissue or the tumour cells, but instead, as a result of their systemic administration, are distributed non-specifically within the body, hence including at locations at which exposure to the drug is undesirable, such as in healthy cells, tissues and organs, for example. This may lead to unwanted side-effects and even to serious effects of general toxicity, which then often greatly limit the therapeutically useful dose range of the drug, or necessitate complete cessation of medication.

The improved and selective availability of these chemotherapeutic agents in the tumour cell or the immediately surrounding tissue, and the associated boost in effect, on the one hand, and minimization of toxic side-effects, on the other hand, have therefore been a focal point for a number of years in the development of new chemotherapeutic agents. Many attempts have been made to date to develop efficient methods of introducing the drug into the target cell. Optimizing the association between drug and intracellular target and minimizing the intercellular distribution of drug, to adjacent cells, for example, nevertheless continue to constitute a difficult problem.

Monoclonal antibodies, for example, are suitable for the target-directed addressing of tumour tissue and tumour cells. The significance of such antibodies for the clinical treatment of cancer diseases has seen a considerable general increase in recent years, based on the activity of such agents as trastuzumab (Herceptin), rituximab (Rituxan), cetuximab (Erbitux) and bevacizumab (Avastin), which have since been approved for the therapy of individual, specific tumour diseases [see e.g. G. P. Adams and L. M. Weiner, *Nat. Biotechnol.* 23, 1147-1157 (2005)]. Consequently there has also been a marked increase in interest in so-called immunoconjugates such as, for example, the aforementioned ADCs, in which an internalizing antibody directed against a tumour-associated antigen is joined covalently via a linking unit ("linker") to a cytotoxic agent. Following introduction of the ADC into the tumour cell and subsequent cleavage of the conjugate, either the cytotoxic agent itself or another metabolite with cytotoxic activity, formed from the cytotoxic agent, is released within the tumour cell, where it is able to develop its effect directly and selectively. In this way it would be possible to keep the damage to normal tissue within significantly closer limits in comparison to a conventional chemotherapy of the cancer disease [see e.g. J. M. Lambert, *Curr. Opin. Pharmacol.* 5, 543-549 (2005); A. M. Wu and P. D. Senter, *Nat. Biotechnol.* 23, 1137-1146 (2005); P. D. Senter, *Curr. Opin. Chem. Biol.* 13, 235-244 (2009); L. Ducry and B. Stump, *Bioconjugate Chem.* 21, 5-13 (2010)].

Instead of antibodies, it is also possible for binders from the small-molecule drug sphere to be used as binders which bind selectively to a specific target location ("target"), such as to a receptor, for example [see e.g. E. Ruoslahti et al., *Science* 279, 377-380 (1998); D. Karkan et al., *PLoS ONE* 3 (6), e2469 (Jun. 25, 2008)]. Also known are conjugates of cytotoxic drug and addressing ligand that exhibit a defined cleavage point between ligand and drug for the release of the drug. A "predetermined break point" of this kind may exist, for example, within a peptide chain which can be cleaved selectively at a particular site by a specific enzyme at the location of action [see e.g. R. A. Firestone and L. A. Telan, US Patent Application US 2002/0147138].

Especially suitable for the target-directed addressing of tumour tissue and tumour cells are monoclonal antibodies directed against the antigen C4.4a. C4.4a (gene: LYPD3) was first described as a metastasis-associated, cell surface protein in rat pancreas tumour cells (Rösel M. et al., Oncogene 1998, 17(15):1989-2002). Human C4.4a was isolated from its placental cDNA library (Würfel, J. et. al. Gene 2001, 262:35-41). C4.4a exhibits structural homology with the uPA receptor and contains two LY6 domains, which exhibit the typical three-finger folding pattern and are linked via 9 disulphide bridges (Jacobsen B. & Ploug M., Current Medicinal Chemistry 2008, 15:2559-2573). C4.4a is anchored in the cell via glycophosphatidylinositol (GPI). The protein is highly glycosylated and contains numerous N- and O-glycosylation sites. C4.4a exhibits strong expression in tumour cells of lung cancer, large bowel cancer, breast cancer, ovarian cancer, pancreatic cancer, kidney cancer, head-and-neck tumours and melanomas. RNA analyses have shown C4.4a expression in ~50% of primary pulmonary tumours and 75% of lung cancer metastases, although expression in healthy lung tissue was not detectable (Würfel J. et. al., Gene 2001, 262:35-41). C4.4a can be used as a prognostic marker in non-small-cell lung cancer—a high level of C4.4a expression correlates with a poor prognosis (Hansen L. et al., Lung Cancer 2007, 58:260-266). The same is true for large bowel cancer. C4.4a is cleaved off from the surface of the tumour cell and can be used as a prognostic serum marker (K. Konishi et al., Cancer Science 2010). A detailed expression analysis of melanomas has shown that C4.4a is expressed in ~60% of primary malignant melanomas and in 100% of lymph-node and skin metastases (Seiter S. et al., J Invest Dermatol. 2001, 116(2): 344-347). Upregulation of C4.4a gene expression is observed in breast cancer tissue as compared with adjacent normal tissues (Fletcher G. C., Br. J. Cancer 2003, 88(4):579-585). C4.4a is an ideal target protein for a tumour therapy, since C4.4a expression in healthy tissues is confined to skin keratinocytes and oesophageal endothelial cells, and also to placenta cells (Würfel J. et. al., Gene 2001, 262:35-41). WO01/23553 describes the use of a C4.4a inhibitor (e.g. an anti-C4.4a antibody) which in a cancer therapy is able to inhibit C4.4a expression or activity.

The precise function of C4.4a is unknown. In the course of wound healing, it is upregulated in migrating keratinocytes (Hansen L. et al., Biochem J. 2004, 380:845-857). It is thought that C4.4a plays a part in tumour cell invasion, presumably through interaction with the extracellular matrix (Rösel M. et al., Oncogene 1998, 17(15):1989-2002; Paret C. et al., British Journal of Cancer 2007, 97:1146-1156). Potential ligands are laminin 1 and 5, and also galectin 3 (Paret C., Int. J. Cancer 2005, 115:724-733).

Auristatin E (AE) and monomethylauristatin E (MMAE) are synthetic analogues of the dolastatins, a specific group of linear pseudopeptides which were originally isolated from marine sources and which have in some cases very potent cytotoxic activity with respect to tumour cells [for a review see e.g. G. R. Pettit, *Prog. Chem. Org. Nat. Prod.* 70, 1-79 (1997); G. R. Pettit et al., *Anti-Cancer Drug Design* 10, 529-544 (1995); G. R. Pettit et al., *Anti-Cancer Drug Design* 13, 243-277 (1998)].

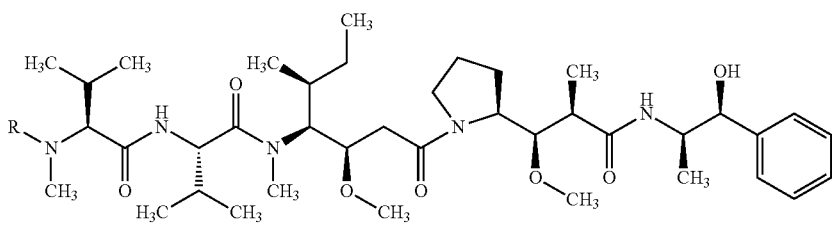

Auristatin E (AE): R = CH$_3$
Monomethylauristatin E (MMAE): R = H

MMAE, however, possesses the disadvantage of a comparatively high systemic toxicity. For improving tumour selectivity, MMAE is used more particularly in conjunction with enzymatically cleavable valine-citrulline linkers in the ADC setting for more targeted tumour therapy [WO 2005/081711-A2; S. O. Doronina et al., *Bioconjugate Chem.* 17, 114-124 (2006)]. Following proteolytic cleavage, MMAE is released preferably intracellularly from corresponding ADCs.

When employed in the form of antibody-drug conjugates (ADCs), however, MMAE is not compatible with linking units (linkers) between antibody and drug that do not have an enzymatically cleavable predetermined break point [S. O. Doronina et al., *Bioconjugate Chem.* 17, 114-124 (2006)].

Monomethylauristatin F (MMAF) is an auristatin derivative having a C-terminal phenylalanine unit which exhibits only moderate antiproliferative activity in comparison to MMAE. This fact is very probably attributable to the free carboxyl group, whose polarity and charge adversely affect the capacity of this compound to access cells. In this connection, the methyl ester of MMAF (MMAF-OMe) has been described, as a neutral-charged prodrug derivative with cell access capability, which, in comparison to MMAF, has an in vitro cytotoxicity for various carcinoma cell lines that is increased by a number of orders of magnitude [S. O. Doronina et al., *Bioconjugate Chem.* 17, 114-124 (2006)]. It can be assumed that this effect is brought about by MMAF itself, which, following uptake of the prodrug into the cells, is rapidly released by intracellular ester hydrolysis.

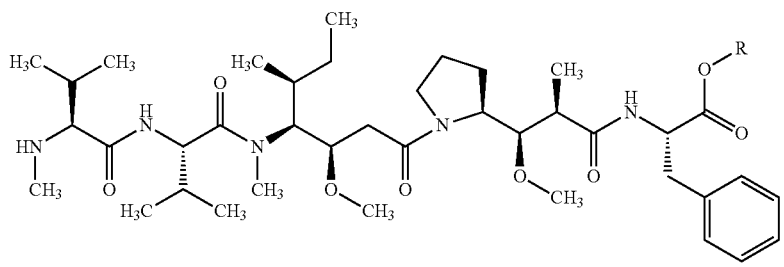

Monomethylauristatin F (MMAF): R = H
Monomethylauristatin F methyl ester (MMAF—OMe): R = CH₃

However, drug compounds based on simple ester derivatives are generally subject to the risk of chemical instability on account of non-specific ester hydrolysis, independent of the intended site of action, by means, for example, of esterases that are present in the blood plasma; this non-specific hydrolysis may significantly restrict the usefulness of such compounds in therapy.

Monomethylauristatin F (MMAF) and also various ester derivatives and amide derivatives thereof have been disclosed in WO 2005/081711-A2. Further auristatin analogues with a C-terminal, amidically substituted phenylalanine unit are described in WO 01/18032-A2. WO 02/088172-A2 and WO 2007/008603-A1 claim MMAF analogues which relate to side-chain modifications of the phenylalanine, while WO 2007/008848-A2 claims those in which the carboxyl group of the phenylalanine has been modified. Auristatin conjugates linked via the C-terminus have been recently described in WO 2009/117531-A1 [see also S. O. Doronina et al., *Bioconjugate Chem.* 19, 1960-1963 (2008)].

Furthermore, auristatin derivatives such as MMAE and MMAF are also substrates for transporter proteins which are expressed by many tumour cells, and this may lead to the development of resistance to these drugs.

The problem addressed with the present invention was that of providing new binder-drug conjugates (ADCs) which, through combination of new N,N-dialkylauristatin derivatives with innovative, suitable linkers and binder, exhibit a very attractive activity profile, such as, for example, in terms of their specific tumour effect and/or the reduced potential of the metabolites formed intracellularly to be a substrate with respect to transporter proteins, and which are therefore suitable for the treatment and/or prophylaxis of hyperproliferative and/or angiogenic diseases, such as cancer diseases, for example.

The present invention provides binder-drug conjugates of the general formula (Ia)

in which n is a number from 1 to 50,

AK is a binder, the group §-G-L$^1$-B-L$^2$-§§ is a linker, where

§ marks the linkage site with the group AK and

§§ marks the linkage site with the nitrogen atom,

D is a group of the formula

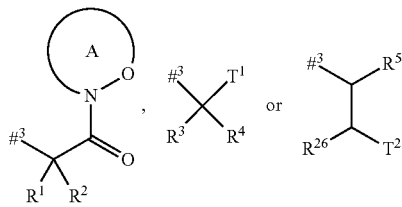

where

³ marks the linkage site with the nitrogen atom,

R$^1$ is hydrogen or methyl,

R$^2$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or R$^1$ and R$^2$ together with the carbon atom to which they are bonded form a (1S,2R)-2-phenylcyclopropane-1,1-diyl group of the formula

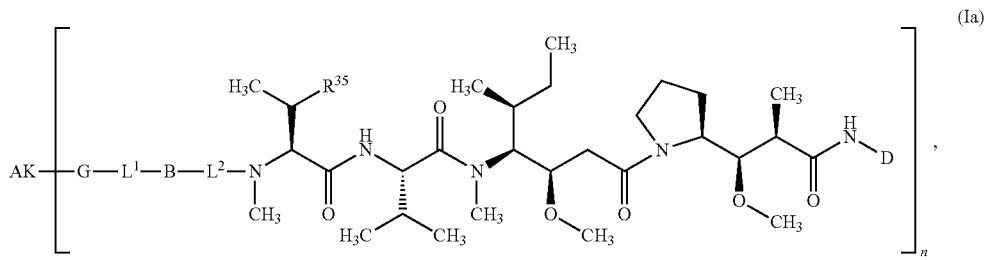

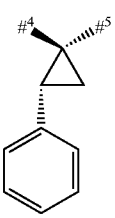

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

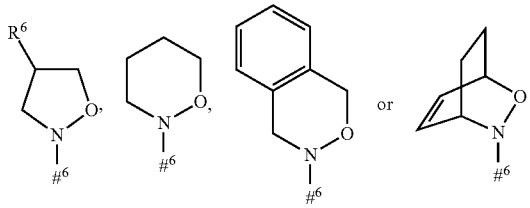

in which
⁶ marks the linkage site with the carbonyl group,
$R^6$ is hydrogen, hydroxy or benzyloxy,
$R^3$ is hydrogen or methyl,
$R^4$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or
$R^3$ and $R^4$ together with the carbon atom to which they are bonded form a (1S,2R)-2-phenylcyclopropane-1,1-diyl group of the formula

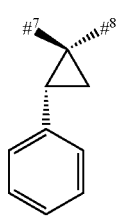

in which
⁷ marks the linkage site with the adjacent nitrogen atom,
⁸ marks the linkage site with the group $T^1$,
$T^1$ is a group of the formula —C(=O)—OR⁷, —C(=O)—NR⁸R⁹, —C(=O)—NH—NH—R¹⁰ or —CH₂—O—R¹¹,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl, or
$R^8$ and $R^9$ together with the nitrogen atom to which they are bonded form a 4- to 7-membered heterocycle,
$R^{10}$ is benzoyl,
$R^{11}$ is benzyl, which may be substituted in the phenyl group by methoxycarbonyl or carboxyl, $R^5$ is hydrogen, methyl or a group of the formula

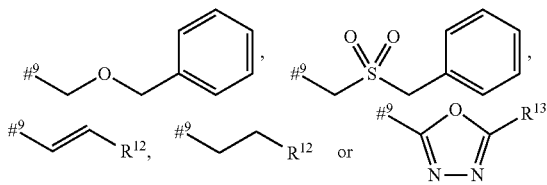

in which
⁹ marks the linkage site with —CHC(R²⁶)-T²,
$R^{12}$ is phenyl which may be substituted by methoxycarbonyl, carboxyl or a group of the formula —S(O)₂OH,
$R^{13}$ is phenyl which may be substituted by methoxycarbonyl or carboxyl,
$R^{26}$ is hydrogen or hydroxy,
$T^2$ is phenyl, benzyl, 1H-indol-3-yl or 1H-indol-3-ylmethyl,
$R^{35}$ is methyl or hydroxy,
and also their salts, solvates and solvates of the salts.

Compounds of the invention are the compounds of the formula (Ia) and (I) and their salts, solvates and solvates of the salts, the compounds of the formulae identified below and encompassed by formula (Ia) and (I), and their salts, solvates and solvates of the salts, and also the compounds identified below as working examples and encompassed by formula (Ia) and (I), and their salts, solvates and solvates of the salts, to the extent that the compounds identified below and encompassed by formula (Ia) and (I) are not already salts, solvates and solvates of the salts.

Depending on their structure, the compounds of the invention may exist in different stereoisomeric forms, i.e. in the form of configurational isomers or else where appropriate as conformational isomers (enantiomers and/or diastereoisomers, including those in the case of atropisomers). The present invention therefore encompasses the enantiomers and diastereomers and their respective mixtures. The stereoisomerically homogeneous constituents can be isolated from such mixtures of enantiomers and/or diastereomers in a known way; for this purpose it is preferred to use chromatographic processes, more particularly HPLC chromatography on an achiral or chiral phase.

Where the compounds of the invention can occur in tautomeric forms, the present invention encompasses all of the tautomeric forms.

The present invention also encompasses all suitable isotopic variants of the compounds of the invention. An isotopic variant of a compound of the invention is understood here to mean a compound in which at least one atom within the compound of the invention has been exchanged for another atom of the same atomic number but with a different atomic mass from the atomic mass which occurs commonly or predominantly in nature. Examples of isotopes which can be incorporated into an inventive compound are those of hydrogen, carbon, nitrogen, oxygen, phosphorus, sulphur, fluorine, chlorine, bromine and iodine such as ²H (deuterium), ³H (tritium), ¹³C, ¹⁴C, ¹⁵N, ¹⁷O, ¹⁸O, ³²P, ³³P, ³³S, ³⁴S, ³⁵S, ³⁶S, ¹⁸F, ³⁶Cl, ⁸²Br, ¹²³I, ¹²⁴I, ¹²⁹I and ¹³¹I. Particular isotope variants of a compound of the invention, such as more particularly those in which one or more radioactive isotopes are incorporated, may be of benefit, for example, for investigating the mechanism of action or the distribution of drug in the body; owing to the comparative ease of preparation and detectability, compounds labelled with ³H or ¹⁴C isotopes are especially suitable for these purposes. Furthermore, the incorporation of isotopes, such as of deuterium, for example, may lead to certain therapeutic advantages as a consequence of greater metabolic stability of the compound, such as an extension to the half-life in the body or a reduction in the active dose required, for example; such modifications of the compounds of the invention may therefore, where appropriate, also constitute a preferred embodiment of the present invention. Isotopic variants of the compounds of the invention can be prepared by the processes known to the skilled person, as for example in accordance with the methods described later on below and the procedures reproduced in the working examples, by using corresponding isotopic modifications of the respective reagents and/or starting compounds.

Preferred salts in the context of the present invention are physiologically acceptable salts of the compounds of the invention. Also encompassed are salts which although themselves not suitable for pharmaceutical applications may nevertheless be used, for example, for isolating or purifying the compounds of the invention.

Physiologically acceptable salts of the compounds of the invention encompass acid addition salts of mineral acids, carboxylic acids and sulphonic acids, examples being salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also encompass salts of customary bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Solvates in the context of the invention are those forms of the compounds of the invention that form a complex in the solid or liquid state through coordination with solvent molecules. Hydrates are one specific form of solvates, in which the coordination takes place with water. Preferred solvates in the context of the present invention are hydrates.

Furthermore, the present invention also encompasses prodrugs of the compounds of the invention. The term "prodrugs" here identifies compounds which may themselves be biologically active or inactive but are converted during their residence in the body into compounds of the invention (by metabolism or hydrolysis, for example).

In the context of the present invention the definitions of the substituents, unless otherwise specified, are as follows:

($C_1$-$C_4$)-Alkyl in the context of the invention is a linear or branched alkyl radical having 1 to 4 carbon atoms. By way of example and with preference, the following may be mentioned: methyl, ethyl, n-propyl, isopropyl, n-butyl, isobutyl, 1-methylpropyl and tert-butyl.

Alkanediyl in the context of the invention is a linear, amdivalent alkyl radical having the particular number of carbon atoms indicated. By way of example and of preference, the following may be mentioned: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene).

($C_3$-$C_7$)-Cycloalkyl and 3- to 7-membered carbocycle respectively in the context of the invention is a monocyclic, saturated cycloalkyl group having 3 to 7 carbon atoms. By way of example and of preference, the following may be mentioned: cyclopropyl, cyclobutyl, cyclopentyl, cyclohexyl and cycloheptyl.

The side group of an α-amino acid in the definition of $R^{19}$ encompasses not only the side groups of the naturally occurring α-amino acids but also the side groups of homologues and isomers of these α-amino acids. The α-amino acid here may be in the L or D configuration or else may be present as a mixture of the L and D forms. Examples that may be given of side groups are as follows: methyl (alanine), propan-2-yl (valine), propan-1-yl (norvaline), 2-methylpropan-1-yl (leucine), 1-methylpropan-1-yl (isoleucine), butan-1-yl (norleucine), tert-butyl (2-tert-butylglycine), phenyl (2-phenylglycine), benzyl(phenylalanine), p-hydroxybenzyl(tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 2-aminoethyl (2,4-diaminobutyric acid), aminomethyl (2,3-diaminopropionic acid), 3-guanidinopropan-1-yl (arginine), 3-ureidopropan-1-yl (citrulline). Preferred α-amino acid side groups in the definition of $R^{19}$ are methyl (alanine), propan-2-yl (valine), 2-methylpropan-1-yl (leucine), benzyl(phenylalanine), imidazol-4-ylmethyl (histidine), hydroxymethyl (serine), 1-hydroxyethyl (threonine), 4-aminobutan-1-yl (lysine), 3-aminopropan-1-yl (ornithine), 2-aminoethyl (2,4-diaminobutyric acid), aminomethyl (2,3-diaminopropionic acid), 3-guanidinopropan-1-yl (arginine). The L configuration is preferred in each case.

A 4- to 7-membered heterocycle in the context of the invention is a monocyclic, saturated heterocycle having a total of 4 to 7 ring atoms, which contains one or two ring heteroatoms from the series N, O, S, SO and/or $SO_2$ and is linked via a ring carbon atom or optionally a ring nitrogen atom. Preference is given to a 5- to 7-membered heterocycle having one or two ring heteroatoms from the series N, O and/or S, more preferably a 5- or 6-membered heterocycle having one or two ring heteroatoms from the series N and/or O. By way of example, the following may be mentioned: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to pyrrolidinyl, tetra-hydrofuranyl, piperidinyl, piperazinyl, tetrahydropyranyl and morpholinyl.

In the formula of the group which may be represented by A, B, D, G, $L^1$, $L^2$, $L^4$, $R^1$, $R^2$, $R^3$, $R^4$ and $R^5$, respectively, the end point of the line at which the symbol #$^6$, *, , #$^3$, #$^1$, #$^2$, ##$^1$, ##$^2$, ##$^3$, ##$^4$, *, ****, #$^4$, #$^5$, #$^6$, #$^7$, #$^8$ or #$^9$ is located is not a carbon atom or a $CH_2$ group, but instead is part of the bond to the atom designated in each case, to which the A, B, D, G, $L^1$, $L^2$, $L^4$, $R^1$, $R^2$, $R^3$, $R^4$ or $R^5$ is bonded.

In the context of the present invention, all radicals which occur multiply have their definition independently of one another. If radicals in the compounds of the invention are substituted, the radicals, unless otherwise specified, may be substituted one or more times. Substitution by one or by two identical or different substituent(s) is preferred. Particularly preferred is substitution by one substituent.

In the context of the present invention the terms used, unless otherwise specified, have the following definitions:

The term "linker" is understood in the broadest sense as a chemical unit which comprises a covalent bond or a series of atoms that links a binder covalently to a drug. The term "linker" is understood preferably as a series of atoms in the sense of the present invention that links a binder covalently to a drug. Furthermore, linkers may be represented, for example, by divalent chemical units, such as alkyldiyls, aryldiyls, heteroaryldiyls, heterocyclyldiyls, dicarbonyl acid esters, dicarbonyl acid amides.

The term "binder" is understood in the broadest sense as a molecule which binds to a target molecule which is present on a particular target cell population to be addressed with the binder-drug conjugate. The term "binder" should be understood in its broadest interpretation and encompasses, for example, lectins, proteins which are able to bind particular sugar chains, or phospholipid-binding proteins. Such binders comprise, for example, high molecular mass proteins (binding proteins), polypeptides or peptides (binding peptides), non-peptidic (e.g. aptamers (U.S. Pat. No. 5,270,163) (review article by Keefe A D., et al., Nat. Rev. Drug Discov. 2010; 9:537-550), or vitamins) and all other cell-binding molecules or substances. Binding proteins are, for example, antibodies and antibody fragments or antibody mimetics such as, for example, affibodies, adnectins, anticalins, DARPins, avimers, nanobodies (review articles by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand-receptor pair, such as VEGF in the ligand-receptor pair VEGF/KDR, such as transferrin of the ligand-receptor pair transferrin/transferrin receptor, or cytokines/cytokine receptor, such as TNFalpha in the ligand receptor pair TNFalpha/TNFalpha receptor.

Preferred binders in accordance with the invention are (more particularly human, monoclonal) antibodies or antigen-binding antibody fragments which bind to C4.4a. In the case of anti-C4.4a antibodies, n, in other words the number of toxophore molecules per antibody molecule, is preferably in the range from 1 to 10, more preferably 2 to 8.

A "target molecule" is understood in the broadest sense to be a molecule which is present in the target cell population, and may be a protein (e.g. a receptor of a growth factor) or a non-peptidic molecule (e.g. a sugar or phospholipid). Preferably it is a receptor or an antigen.

The term "extracellular" target molecule describes a target molecule which is attached to the cell and which is located on the outside of a cell or the part of a target molecule which is located on the outside of a cell, i.e. a binder may bind to an intact cell at its extracellular target molecule. An extracellular target molecule may be anchored in the cell membrane or may be part of the cell membrane. The skilled person knows of methods for identifying extracellular target molecules. For proteins this may be done via determination of the transmembrane domain(s) and the orientation of the protein in the membrane. This data is generally recorded in protein databases (e.g. SwissProt).

The term "cancer target molecule" describes a target molecule which is multiply present on one or more cancer cell types in comparison to non-cancer cells of the same tissue type. The cancer target molecule is preferably present selectively on one or more cancer cell types in comparison to non-cancer cells of the same tissue type, with "selectively" describing an at least twofold accumulation on cancer cells in comparison to non-cancer cells of the same tissue type (a "selective cancer target molecule"). The use of cancer target molecules allows selective therapy of cancer cells with the conjugates of the invention.

The binder may be linked via a bond to the linker. Known from the literature are various possibilities of covalent coupling (conjugation) of organic molecules to antibody. The linking of the binder may take place by means of a heteroatom of the binder. Inventive heteroatoms of the binder that may be used for linking are sulphur (in one embodiment via a sulphhydryl group of the binder), oxygen (in accordance with the invention by means of a carboxyl or hydroxy group of the binder) and nitrogen (in one embodiment via a primary or secondary amine group or amide group of the binder). Preferred in accordance with the invention is the conjugation of the toxophores to the antibody via one or more sulphur atoms of cysteine residues of the antibody and/or via one or more NH groups of lysine residues of the antibody. These heteroatoms may be present in the natural binder or may be introduced by means of methods of chemistry or molecular biology. In accordance with the invention, the linking of the binder to the toxophore has little influence over the binding activity of the binder to the target molecule. In a preferred embodiment the linking has no influence on the binding activity of the binder to the target molecule.

The term "antibody" is understood in accordance with the present invention in its broadest sense and encompasses immunoglobulin molecules, examples being intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains), which are linked typically by disulphide bridges. Each heavy chain comprises a variable domain of the heavy chain (abbreviated to VH) and a constant domain of the heavy chain. The constant domain of the heavy chain may encompass, for example, three domains CH1, CH2 and CH3. Each light chain comprises a variable domain (abbreviated to VL) and a constant domain. The constant domain of the light chain comprises one domain (abbreviated to CL). The VH and VL domains may be further subdivided into regions having hypervariability, also called complementarity-determining regions (abbreviated to CDR), and regions having a low sequence variability ("framework region", abbreviated to FR). Each VH and VL region is typically composed of three CDRs and up to four FRs. For example, in the following order from the amino terminus to the carboxy terminus: FR1, CDR1, FR2, CDR2, FR3, CDR3, FR4. An antibody may be obtained from any species suitable for the antibody, such as, for example, rabbit, lama, camel, mouse or rat. In one embodiment the antibody is of human or murine origin. An antibody may for example be human, humanized or chimeric.

The term "monoclonal" antibody identifies antibodies which have been obtained from a population of substantially homogeneous antibodies, i.e. individual antibodies of the population are identical except for naturally occurring mutations which may occur in small numbers. Monoclonal antibodies recognize a single antigenic binding site with a high specificity. The term "monoclonal antibody" does not refer to a particular production method.

The term "intact" antibody refers to antibodies which comprise not only an antigen-binding domain but also the constant domain of the light and heavy chain. The constant domain may be a naturally occurring domain, or a variant thereof in which one or more amino acid positions have been altered.

The term "modified intact" antibody refers to intact antibodies which have been fused with another polypeptide or protein, not originating from an antibody, via the amino terminus or carboxyl terminus thereof, by means of a covalent bond (e.g. a peptide linkage). Furthermore, antibodies may be modified by introducing reactive cysteines at defined locations, in order to facilitate coupling to a toxophore (see Junutula et al. Nat. Biotechnol. 2008 August; 26(8):925-32).

The term "human" antibody identifies antibodies which can be obtained from a human being or are synthetic human antibodies. A "synthetic" human antibody is an antibody which in parts or as a whole is obtainable from synthetic sequences in silico which are based on the analysis of human antibody sequences. A human antibody may be encoded, for example, by a nucleic acid which has been isolated from a library of antibody sequences which are of human origin. One example of such antibodies can be found in Söderlind et al., Nature Biotech. 2000, 18:853-856.

The term "humanized" or "chimeric" antibody describes antibodies which consist of a non-human and of a human sequence component. In these antibodies, part of the sequences of the human immunoglobulin (recipient) is replaced by sequence components of a non-human immunoglobulin (donor). In many cases the donor is a murine immunoglobulin. With humanized antibodies, amino acids of the CDR in the recipient are replaced by amino acids of the donor. In some cases, amino acids of the framework as well are replaced by corresponding amino acids of the donor. In some cases the humanized antibody contains amino acids which were present neither in the recipient nor in the donor and which were inserted during the optimization of the antibody. In the case of chimeric antibodies, for example, the variable domains of the donor immunoglobulin, or else the entire Fab fraction, in other words VL–CL and VH+CH1, are fused with the constant regions of a human antibody.

The term complementarity-determining region (CDR) as used here refers to those amino acids in a variable antibody domain that are necessary for binding to the antigen. Every variable region typically has three CDR regions, identified as CDR1, CDR2 and CDR3. Each CDR region may comprise amino acids according to the definition of Kabat and/or amino acids of a hypervariable loop, defined according to Chotia. The definition according to Kabat encompasses, for example, the region of approximately amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immulological Interest, 5th Ed. Public Health Service, National Institutes of Health, Bethesda, Md. (1991)). The definition according to Chotia encompasses, for example, the region of approximately amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain Chothia and Lesk; J Mol Biol 196: 901-917 (1987)). In some cases a CDR may comprise amino acids from one CDR region as defined by Kabat and Chotia.

Depending on the amino acid sequence of the constant domain of the heavy chain, antibodies may be divided into different classes. There are five main classes of intact antibodies: IgA, IgD, IgE, IgG and IgM, and a number of them may be broken down into further subclasses (isotypes), e.g. IgG1, IgG2, IgG3, IgG4, IgA1 and IgA2. The constant domains of the heavy chain that correspond to the different classes are identified as [alpha/α], [delta/δ], [epsilon/ε], [gamma/γ] and [mu/μ]. Both the three-dimensional structure and the subunit structure of antibodies are known.

The term "functional fragment" or "antigen-binding antibody fragments" of a antibody/immunoglobulin is defined as a fragment of an antibody/immunoglobulin (e.g. the variable domains of an IgG) which further encompasses the antigen binding domains of the antibody/immunoglobulin. The "antigen binding domain" of an antibody typically encompasses one or more hypervariable regions of an antibody, e.g. the CDR1, CDR2 and/or CDR3 region. However, the "framework" or "scaffold" region of an antibody may also play a part with regard to the binding of the antibody to the antigen. The framework region forms the scaffold for the CDRs. The antigen-binding domain preferably encompasses at least amino acids 4 to 103 of the variable light chain and amino acid 5 to 109 of the variable heavy chain, more preferably amino acid 3 to 107 of the variable light chain and 4 to 111 of the variable heavy chain, particular preference being given to the complete variable light and heavy chains, i e amino acid 1-109 of the VL and 1 to 113 of the VH (numbering according to WO97/08320).

"Functional fragments" or "antigen-binding antibody fragments" of the invention encompass, non-conclusively, Fab, Fab', F(ab')$_2$ and Fv fragments, diabodies, Single Domain Antibodies (DAbs), linear antibodies, individual chains of antibodies (single-chain Fv, abbreviated to ScFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). Antibodies other than "multispecific" or "multifunctional" antibodies are those having identical binding sites. Multispecific antibodies may be specific for different epitopes of an antigen or may be specific for epitopes of more than one antigen (see, for example WO93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; or Kostelny et al., 1992, J. Immunol. 148: 1547 1553). An F(ab')$_2$ or Fab molecule may be constructed such that the number of intermolecular disulphide interactions occurring between the Ch1 and the CL domains can be reduced or else completely prevented.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat. Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1):65-93) or Phage Display Technologies (Clackson et al., Nature. 1991 Aug. 15; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of the cell. A preferred antibody or binder is one which has been purified to an extent of more than 95%, relative to the antibody or binder (determined for example by Lowry method, UV-Vis spectroscopy or by SDS capillary gel electrophoresis), the purification thereof being such that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with smaller Kd values than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule.

Antibodies which are specific against a cancer cell antigen can be prepared by a person of ordinary skill in the art by means of methods with which he or she is familiar (such as recombinant expression, for example) or may be acquired commercially (as for example from Merck KGaA, Germany). Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells.

The compounds of the formula (I) represent a subgroup of the compounds of the formula (Ia).

A preferred subject of the invention are binder-drug conjugates of the general formula (Ia) in which D is

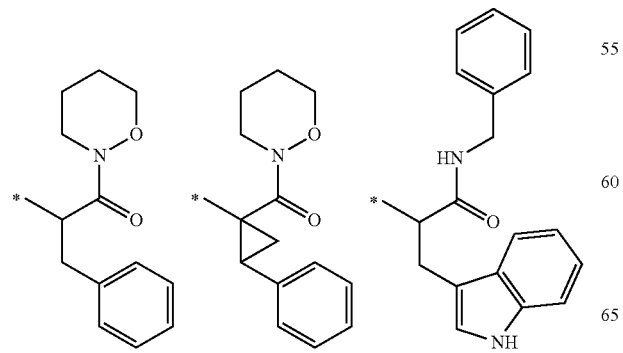

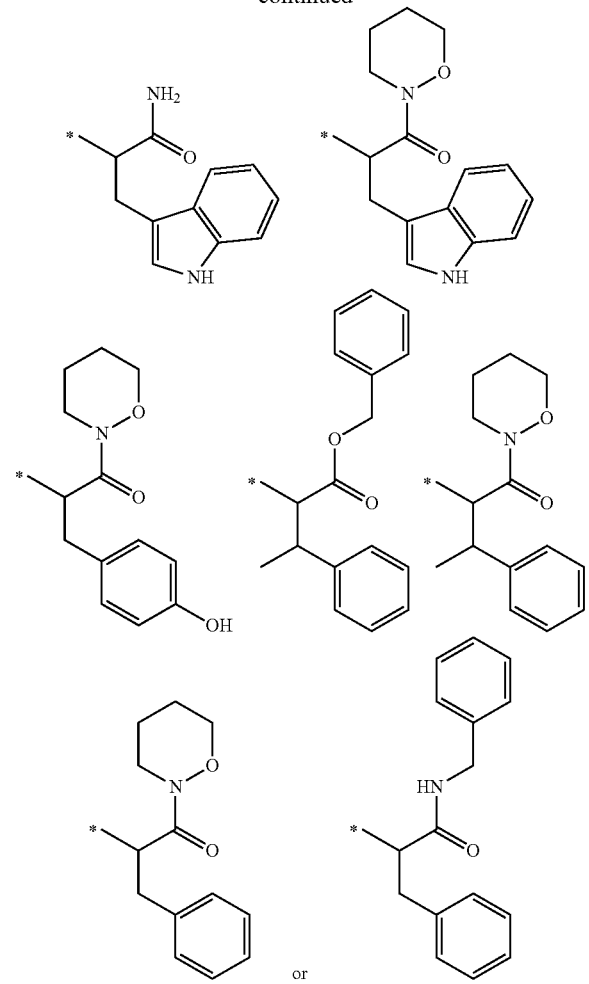

or wherein the asterisks marks the linkage site with the nitrogen atom; and the remainder of the variables are as defined.

A preferred subject of the invention are binder-drug conjugates of the general formula (Ia) in which
n is a number from 1 to 50,
AK is $AK_1$ or $AK_2$
  where
  $AK_1$ is a binder (preferably an antibody or antigen-binding antibody fragment (e.g., an anti-C4.4a antibody or anti-C4.4a antigen-binding antibody fragment)) which is bonded via a sulphur atom of the binder to the group G,
  $AK_2$ is a binder (preferably an antibody or antigen-binding antibody fragment (e.g., an anti-C4.4a antibody or anti-C4.4a antigen-binding antibody fragment)) which is bonded via a nitrogen atom of the binder to the group G,
G when AK=$AK_1$, is a group of the formula

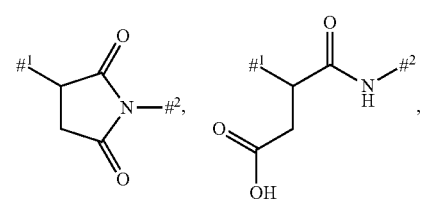

-continued

[structures shown]

where
¹ marks the linkage site with the sulphur atom of the binder,
² marks the linkage site with the group L¹,
or
when AK=AK₂, is carbonyl,
$L^1$ is a bond, linear $(C_1-C_{10})$-alkanediyl, a group of the formula

[structures: ##¹—CH₂CH₂—[O—]ₘ—##² or ##¹—L^{1A}—B¹—L^{1B}—##²]

where
m is a number from 2 to 6,
¹ marks the linkage site with the group G,
² marks the linkage site with the group B,
$L^{1A}$ is linear $(C_2-C_{10})$-alkanediyl,
$B^1$ is a group of the formula

[structures shown]

in which
⁵ marks the linkage site with the group $L^{1A}$,
⁶ marks the linkage site with the group $L^{1B}$,
$L^5$ is a bond or $(C_2-C_4)$-alkanediyl,
$L^6$ is a bond or a group of the formula

[structures shown]

in which
⁷ marks the linkage site with the carbonyl group,
⁸ marks the linkage site with $L^{1B}$,
$R^{33}$ is hydrogen, $(C_1-C_4)$-alkylcarbonyl, tert-butyloxycarbonyl or benzyloxycarbonyl,
$R^{34}$ is hydrogen or methyl,
$R^{29}$ is hydrogen or $(C_1-C_4)$-alkyl,
$R^{30}$ is hydrogen or $(C_1-C_4)$-alkyl,
or
$R^{29}$ and $R^{30}$ together with the atoms to which they are bonded form a 5- or 6-membered heterocycle,
$R^{31}$ is hydrogen or $(C_1-C_4)$-alkyl,
$R^{32}$ is hydrogen or $(C_1-C_4)$-alkyl,
or $R^{31}$ and $R^{32}$ together with the atoms to which they are bonded form a 5- or 6-membered heterocycle,
$L^{1B}$ is linear $(C_2-C_{10})$-alkanediyl,
and
where $(C_1-C_{10})$-alkanediyl may be substituted by 1 to 4 substituents selected independently of one another from the group consisting of methyl, hydroxy and benzyl,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
B is a bond or a group of the formula

[structures shown]

where
* marks the linkage site with $L^1$,
** marks the linkage site with $L^2$,
P is O or NH,
$L^3$ is a bond or $(C_2-C_4)$-alkanediyl,
$L^4$ is a bond or a group of the formula

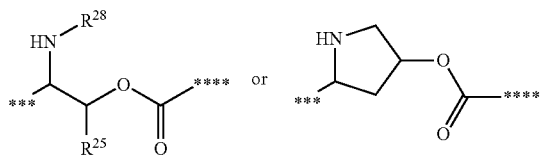

in which
*** marks the linkage site with the carbonyl group,
**** marks the linkage site with $L^2$,
$R^{25}$ is hydrogen or methyl,
$R^{28}$ is hydrogen, $(C_1-C_4)$-alkylcarbonyl, tert-butyloxycarbonyl or benzyloxycarbonyl,
$Q^1$ is a 4- to 7-membered heterocycle,
$Q^2$ is a 3- to 7-membered carbocycle or a 4- to 7-membered heterocycle,
$R^{14}$ is hydrogen or $(C_1-C_4)$-alkyl,
$R^{15}$ is hydrogen or $(C_1-C_4)$-alkyl,
or
$R^{14}$ and $R^{15}$ together with the atoms to which they are bonded form a 5- or 6-membered heterocycle,
$R^{16}$ is hydrogen or $(C_1-C_4)$-alkyl,
$R^{17}$ is hydrogen or $(C_1-C_4)$-alkyl,
or
$R^{16}$ and $R^{17}$ together with the atoms to which they are bonded form a 5- or 6-membered heterocycle,
$R^{18}$ is hydrogen or $(C_1-C_4)$-alkyl,
$R^{19}$ is hydrogen or the side group of a natural α-amino acid or of its homologues or isomers,
$R^{20}$ is hydrogen or $(C_1-C_4)$-alkyl,
or
$R^{19}$ and $R^{20}$ together with the atoms to which they are bonded form a pyrrolidinyl ring,
$R^{21}$ is hydrogen or $(C_1-C_4)$-alkyl,
$R^{22}$ is hydrogen or $(C_1-C_4)$-alkyl,
or
$R^{21}$ and $R^{22}$ together with the atoms to which they are bonded form a 3- to 7-membered carbocycle,
$R^{23}$ is $(C_1-C_4)$-alkyl,
$R^{24}$ is hydrogen or $(C_1-C_4)$-alkyl,
$R^{27}$ is hydrogen or $(C_1-C_4)$-alkyl,
$R^{36}$ is hydrogen, $(C_1-C_4)$-alkylcarbonyl, tert-butyloxycarbonyl or benzyloxycarbonyl,
$R^{37}$ is hydrogen or methyl,
or
$R^{36}$ and $R^{37}$ together with the atoms to which they are bonded form a pyrrolidine ring,
$L^2$ is linear $(C_2-C_{10})$-alkanediyl or is a group of the formula

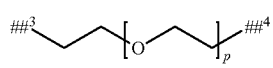

where
p is a number from 2 to 6,
³ marks the linkage site with the group B,
⁴ marks the linkage site with the nitrogen atom, where $(C_2-C_{10})$-alkanediyl may be substituted by 1 to 4 substituents selected independently of one another from the group consisting of methyl, hydroxy and benzyl,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
D is a group of the formula

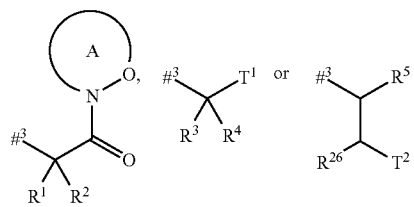

in which
³ marks the linkage site with the nitrogen atom,
$R^1$ is hydrogen or methyl,
$R^2$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl,
or
$R^1$ and $R^2$ together with the carbon atom to which they are bonded form a (1S,2R)-2-phenylcyclopropane-1,1-diyl group of the formula

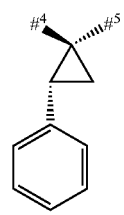

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

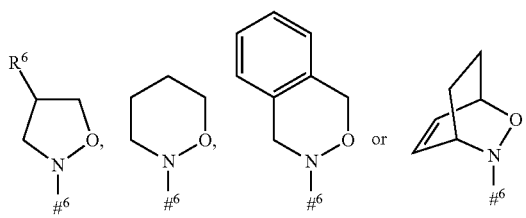

in which
⁶ marks the linkage site with the carbonyl group,
$R^6$ is hydrogen, hydroxy or benzyloxy,
$R^3$ is hydrogen or methyl,
$R^4$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or $R^3$ and $R^4$ together with the carbon atom to which they are bonded form a (1S,2R)-2-phenylcyclopropane-1,1-diyl group of the formula

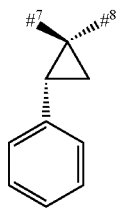

in which $\#^7$ marks the linkage site with the adjacent nitrogen atom, $\#^8$ marks the linkage site with the group $T^1$, $T^1$ is a group of the formula —C(=O)—OR$^7$, —C(=O)—NR$^8$R$^9$, —C(=O)—NH—NH—R$^{10}$ or —CH$_2$—O—R$^{11}$, in which $R^7$ is hydrogen, methyl, ethyl, n-propyl, tert-butyl, benzyl or adamantylmethyl, $R^8$ is hydrogen or methyl, $R^9$ is hydrogen, methyl, ethyl, n-propyl or benzyl, or $R^8$ and $R^9$ together with the nitrogen atom to which they are bonded form a 4- to 7-membered heterocycle, $R^{10}$ is benzoyl, $R^{11}$ is benzyl, which may be substituted in the phenyl group by methoxycarbonyl or carboxyl, $R^5$ is hydrogen, methyl or a group of the formula

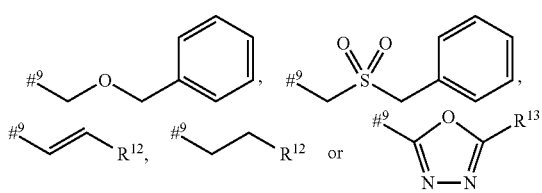

in which $\#^9$ marks the linkage site with —CHC(R$^{26}$)-T$^2$, $R^{12}$ is phenyl which may be substituted by methoxycarbonyl, carboxyl or a group of the formula —S(O)$_2$OH, $R^{13}$ is phenyl which may be substituted by methoxycarbonyl or carboxyl, $R^{26}$ is hydrogen or hydroxy, $T^2$ is phenyl, benzyl, 1H-indol-3-yl or 1H-indol-3-ylmethyl, $R^{35}$ is methyl or hydroxy, and also their salts, solvates and solvates of the salts.

A preferred subject of the present invention are binder-drug conjugates of the general formula (Ia) as indicated above, in which n is a number from 1 to 50, AK is AK$_1$ or AK$_2$ where AK$_1$ is a binder (preferably an antibody or antigen-binding antibody fragment (e.g., an anti-C4.4a antibody or anti-C4.4a antigen-binding antibody fragment)) which is bonded via a sulphur atom of the binder to the group G, AK$_2$ is a binder (preferably an antibody or antigen-binding antibody fragment (e.g., an anti-C4.4a antibody or anti-C4.4a antigen-binding antibody fragment)) which is bonded via a nitrogen atom of the binder to the group G, G when AK=AK$_1$, is a group of the formula

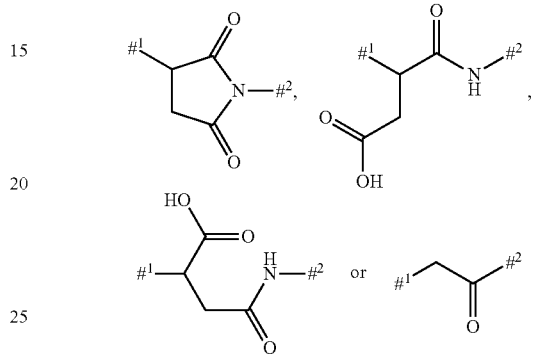

in which $\#^1$ marks the linkage site with the sulphur atom of the binder, $\#^2$ marks the linkage site with the group $L^1$, or when AK=AK$_2$, is carbonyl, $L^1$ is a bond, linear (C$_1$-C$_{10}$)-alkanediyl, a group of the formula

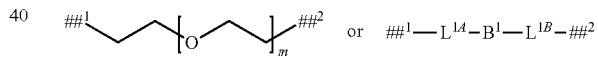

where m is a number from 2 to 6, $\#\#^1$ marks the linkage site with the group G, $\#\#^2$ marks the linkage site with the group B, $L^{1A}$ is linear (C$_2$-C$_{10}$)-alkanediyl, $B^1$ is a group of the formula

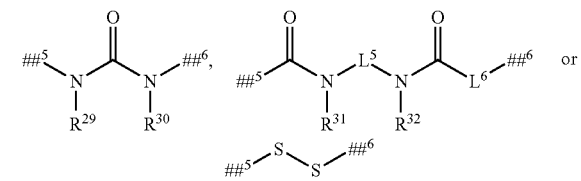

in which $\#\#^5$ marks the linkage site with the group $L^{1A}$, $\#\#^6$ marks the linkage site with the group $L^{1B}$, $L^5$ is a bond or (C$_2$-C$_4$)-alkanediyl, $L^6$ is a bond or a group of the formula

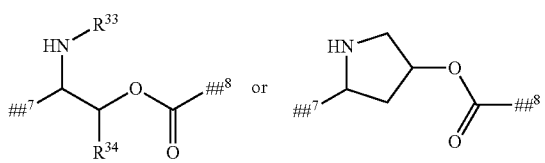

in which
⁷ marks the linkage site with the carbonyl group,
⁸ marks the linkage site with $L^{1B}$,
$R^{33}$ is hydrogen $(C_1-C_4)$-alkylcarbonyl, tert-butyloxycarbonyl or benzyloxycarbonyl,
$R^{34}$ is hydrogen or methyl,
$R^{29}$ is hydrogen or $(C_1-C_4)$-alkyl,
$R^{30}$ is hydrogen or $(C_1-C_4)$-alkyl,
or
$R^{29}$ and $R^{30}$ together with the atoms to which they are bonded form a 5- or 6-membered heterocycle,
$R^{31}$ is hydrogen or $(C_1-C_4)$-alkyl,
$R^{32}$ is hydrogen or $(C_1-C_4)$-alkyl,
or
$R^{31}$ and $R^{32}$ together with the atoms to which they are bonded form a 5- or 6-membered heterocycle,
$L^{1B}$ is linear $(C_2-C_{10})$-alkanediyl,
and
where $(C_1-C_{10})$-alkanediyl may be substituted by 1 to 4 substituents selected independently of one another from the group consisting of methyl, hydroxy and benzyl,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
B is a bond or a group of the formula

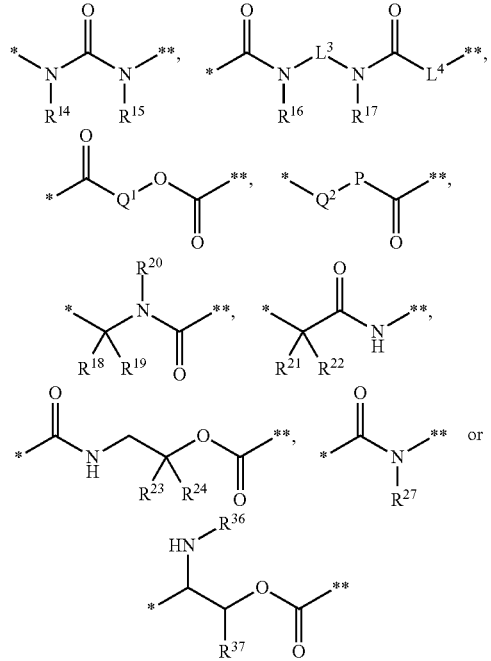

where
* marks the linkage site with $L^1$,
** marks the linkage site with $L^2$, P is O or NH,
$L^3$ is a bond or $(C_2-C_4)$-alkanediyl,
$L^4$ is a bond or a group of the formula

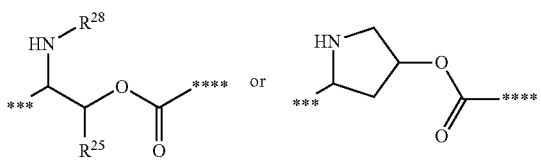

in which
*** marks the linkage site with the carbonyl group,
**** marks the linkage site with $L^2$,
$R^{25}$ is hydrogen or methyl,
$R^{28}$ is hydrogen, $(C_1-C_4)$-alkylcarbonyl, tert-butyloxycarbonyl or benzyloxycarbonyl,
$Q^1$ is a 4- to 7-membered heterocycle,
$Q^2$ is a 3- to 7-membered carbocycle or a 4- to 7-membered heterocycle,
$R^{14}$ is hydrogen or $(C_1-C_4)$-alkyl,
$R^{15}$ is hydrogen or $(C_1-C_4)$-alkyl,
or
$R^{14}$ and $R^{15}$ together with the atoms to which they are bonded form a 5- or 6-membered heterocycle,
$R^{16}$ is hydrogen or $(C_1-C_4)$-alkyl,
$R^{17}$ is hydrogen or $(C_1-C_4)$-alkyl,
or
$R^{16}$ and $R^{17}$ together with the atoms to which they are bonded form a 5- or 6-membered heterocycle,
$R^{18}$ is hydrogen or $(C_1-C_4)$-alkyl,
$R^{19}$ is hydrogen or the side group of a natural α-amino acid or of its homologues or isomers,
$R^{20}$ is hydrogen or $(C_1-C_4)$-alkyl,
or
$R^{19}$ and $R^{20}$ together with the atoms to which they are bonded form a pyrrolidinyl ring,
$R^{21}$ is hydrogen or $(C_1-C_4)$-alkyl,
$R^{22}$ is hydrogen or $(C_1-C_4)$-alkyl,
or
$R^{21}$ and $R^{22}$ together with the atoms to which they are bonded form a 3- to 7-membered carbocycle,
$R^{23}$ is $(C_1-C_4)$-alkyl,
$R^{24}$ is hydrogen or $(C_1-C_4)$-alkyl,
$R^{27}$ is hydrogen or $(C_1-C_4)$-alkyl,
$R^{36}$ is hydrogen, $(C_1-C_4)$-alkylcarbonyl, tert-butyloxycarbonyl or benzyloxycarbonyl,
$R^{37}$ is hydrogen or methyl,
or
$R^{36}$ and $R^{37}$ together with the atoms to which they are bonded form a pyrrolidine ring,
$L^2$ is linear $(C_2-C_{10})$-alkanediyl or is a group of the formula

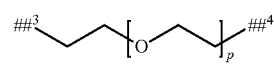

where
p is a number from 2 to 6,
³ marks the linkage site with the group B,
⁴ marks the linkage site with the nitrogen atom,
where $(C_2-C_{10})$-alkanediyl may be substituted by 1 to 4 substituents selected independently of one another from the group consisting of methyl, hydroxy and benzyl,
and where two carbon atoms of the alkanediyl chain in 1,2, 1,3 or 1,4 relation to one another, with inclusion of any carbon atoms situated between them, may be bridged to form a ($C_3$-$C_6$)-cycloalkyl ring or a phenyl ring, D is a group of the formula

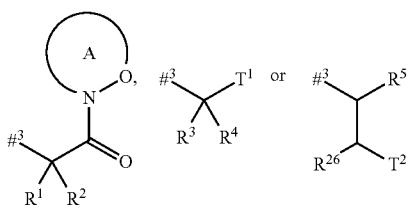

in which

³ marks the linkage site with the nitrogen atom, $R^1$ is hydrogen or methyl, $R^2$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or $R^1$ and $R^2$ together with the carbon atom to which they are bonded form a (1S,2R)-2-phenylcyclopropane-1,1-diyl group of the formula

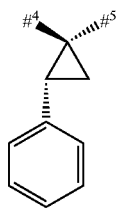

in which

⁴ marks the linkage site with the adjacent nitrogen atom,

⁵ marks the linkage site with the carbonyl group, the ring A with the N—O moiety present therein is a mono- or bicyclic, optionally substituted heterocycle of the formula

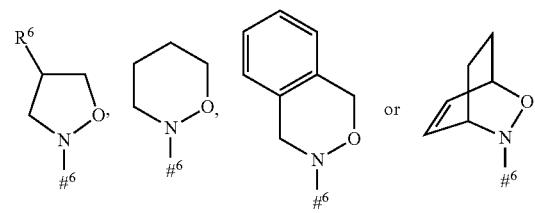

in which

⁶ marks the linkage site with the carbonyl group, $R^6$ is hydrogen, hydroxy or benzyloxy, $R^3$ is hydrogen or methyl, $R^4$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or $R^3$ and $R^4$ together with the carbon atom to which they are bonded form a (1S,2R)-2-phenylcyclopropane-1,1-diyl group of the formula

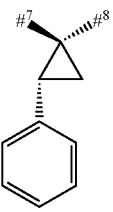

in which

⁷ marks the linkage site with the adjacent nitrogen atom,

⁸ marks the linkage site with the group $T^1$, $T^1$ is a group of the formula —C(=O)—$OR^7$, —C(=O)—$NR^8R^9$, —C(=O)—NH—NH—$R^{10}$ or —$CH_2$—O—$R^{11}$, in which $R^7$ is hydrogen, methyl, ethyl, n-propyl, tert-butyl, benzyl or adamantylmethyl, $R^8$ is hydrogen or methyl, $R^9$ is hydrogen, methyl, ethyl, n-propyl or benzyl, or $R^8$ and $R^9$ together with the nitrogen atom to which they are bonded form a 4- to 7-membered heterocycle, $R^{10}$ is benzoyl, $R^{11}$ is benzyl, which may be substituted in the phenyl group by methoxycarbonyl or carboxyl, $R^5$ is hydrogen, methyl or a group of the formula

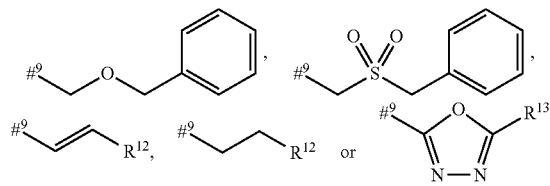

in which

⁹ marks the linkage site with —CHC($R^{26}$)-$T^2$, $R^{12}$ is phenyl which may be substituted by methoxycarbonyl, carboxyl or a group of the formula —S(O)$_2$OH, $R^{13}$ is phenyl which may be substituted by methoxycarbonyl or carboxyl, $R^{26}$ is hydrogen or hydroxy, $T^2$ is phenyl, benzyl, 1H-indol-3-yl or 1H-indol-3-ylmethyl, $R^{35}$ is methyl or hydroxy, and also their salts, solvates and solvates of the salts.

Preferred subject of the invention are binder-drug conjugates of the general formula (Ia), in which n is a number from 1 to 20, AK is $AK_1$ or $AK_2$ Where $AK_1$ is an antibody or an antigen-binding antibody fragment and is bonded via the sulphur atom of a cysteine residue of the binder to the group G (e.g., an antibody or an antigen-binding antibody fragment which binds to C4.4a and is bonded via the sulphur atom of a cysteine residue of the binder to the group G), $AK_2$ is an antibody or an antigen-binding antibody fragment and is bonded via the NH side group of a lysine residue of the binder to the group G (e.g., an antibody or an antigen-binding antibody fragment which binds to C4.4a and is bonded via the NH side group of a lysine residue of the binder to the group G), G when $AK=AK_1$, is a group of the formula in which
$\#^1$ marks the linkage site with the cysteine residue of the binder,
$\#^2$ marks the linkage site with the group $L^1$,
or
when $AK=AK_2$, is carbonyl,
$L^1$ is a bond, linear $(C_2-C_6)$-alkanediyl, a group of the formula where
m is a number from 2 to 6,
$\#\#^1$ marks the linkage site with the group G,
$\#\#^2$ marks the linkage site with the group B,
$L^{1A}$ is linear $(C_2-C_6)$-alkanediyl,
$B^1$ is a group of the formula in which
$\#\#^5$ marks the linkage site with the group $L^{1A}$,
$\#\#^6$ marks the linkage site with the group $L^{1B}$,
$L^5$ is a bond,
$L^6$ is a bond or a group of the formula in which
$\#\#^7$ marks the linkage site with the carbonyl group,
$\#\#^8$ marks the linkage site with $L^{1B}$,
$R^{33}$ is hydrogen, methylcarbonyl or tert-butyloxycarbonyl,
$R^{34}$ is hydrogen or methyl,
$R^{29}$ is hydrogen,
$R^{30}$ is hydrogen,
$R^{31}$ is hydrogen or methyl,
$R^{32}$ is hydrogen or methyl,
$L^{1B}$ is linear $(C_2-C_6)$-alkanediyl,
and
where $(C_2-C_6)$-alkanediyl may be substituted by 1 or 2 methyl substituents,
B is a bond or a group of the formula where
* marks the linkage site with $L^1$,
** marks the linkage site with $L^2$,
$L^3$ is a bond or ethane-1,2-diyl,
$L^4$ is a bond or a group of the formula in which
*** marks the linkage site with the carbonyl group,
**** marks the linkage site with $L^2$,
$R^{25}$ is hydrogen or methyl,
$R^{28}$ is hydrogen, methylcarbonyl or tert-butyloxycarbonyl,
$Q^1$ is a 4- to 7-membered heterocycle,
$R^{14}$ is hydrogen,
$R^{15}$ is hydrogen,
$R^{16}$ is hydrogen or methyl,
$R^{17}$ is hydrogen or methyl,
or
$R^{16}$ and $R^{17}$ together with the atoms to which they are bonded form a piperazinyl ring, $R^{18}$ is hydrogen,
$R^{19}$ is hydrogen, methyl, propan-2-yl, 2-methylpropan-1-yl or 1-methylpropan-1-yl,
$R^{20}$ is hydrogen or methyl,
or
$R^{19}$ and $R^{20}$ together with the atoms to which they are bonded form a pyrrolidinyl ring,
$R^{21}$ is hydrogen or methyl,
$R^{22}$ is hydrogen or methyl,
or
$R^{21}$ and $R^{22}$ together with the atoms to which they are bonded form a cyclopropyl ring,
$R^{23}$ is methyl,
$R^{24}$ is hydrogen or methyl,
$R^{27}$ is hydrogen,
$R^{36}$ is hydrogen, methylcarbonyl or tert-butyloxycarbonyl,
$R^{37}$ is hydrogen or methyl,
or
$R^{36}$ and $R^{37}$ together with the atoms to which they are bonded form a pyrrolidine ring,
$L^2$ is linear $(C_2\text{-}C_6)$-alkanediyl or is a group of the formula where
p is a number from 2 to 6,
$\#\#^3$ marks the linkage site with the group B,
$\#\#^4$ marks the linkage site with the nitrogen atom,
where $(C_2\text{-}C_{10})$-alkanediyl may be substituted by 1 or 2 methyl substituents,
D is a group of the formula where
$\#^3$ marks the linkage site with the nitrogen atom,
$R^1$ is hydrogen,
$R^2$ is 1-hydroxyethyl, benzyl, 4-hydroxybenzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula in which $\#^4$ marks the linkage site with the adjacent nitrogen atom,
$\#^5$ marks the linkage site with the carbonyl group,
the ring A with the N—O moiety present therein is a mono- or bicyclic, optionally substituted heterocycle of the formula in which
$\#^6$ marks the linkage site with the carbonyl group,
$R^6$ is hydrogen, hydroxy or benzyloxy,
$R^3$ is hydrogen,
$R^4$ is 1-hydroxyethyl, benzyl, 4-hydroxybenzyl, 1-phenylethyl or 1H-indol-3-ylmethyl, or
$R^3$ and $R^4$ together with the carbon atom to which they are bonded form a (1S,2R)-2-phenylcyclopropane-1,1-diyl group of the formula in which
$\#^7$ marks the linkage site with the adjacent nitrogen atom,
$\#^8$ marks the linkage site with the group $T^1$,
$T^1$ is a group of the formula —C(=O)—OR$^7$, —C(=O)—NR$^8$R$^9$, —C(=O)—NH—NH—R$^{10}$ or —CH$_2$—O—R$^{11}$,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
or
$R^8$ and $R^9$ together with the nitrogen atom to which they are bonded form a 4- to 7-membered heterocycle,
$R^{10}$ is benzoyl,
$R^{11}$ is benzyl, which may be substituted in the phenyl group by methoxycarbonyl or carboxyl,
$R^5$ is hydrogen, methyl or a group of the formula in which $\#^9$ marks the linkage site with —CHC($R^{26}$)-$T^2$, $R^{12}$ is phenyl which may be substituted by methoxycarbonyl, carboxyl or a group of the formula —S(O)$_2$OH, $R^{13}$ is phenyl which may be substituted by methoxycarbonyl or carboxyl, $R^{26}$ is hydrogen or hydroxy, $T^2$ is phenyl, benzyl, 1H-indol-3-yl or 1H-indol-3-ylmethyl, $R^{35}$ is methyl or hydroxy, and also their salts, solvates and solvates of the salts.

Preferred subject matter of the present invention are binder-drug conjugates of the general formula (Ia) as indicated above, in which n is a number from 1 to 20, AK is $AK_1$ or $AK_2$ where $AK_1$ is an antibody or an antigen-binding antibody fragment and is bonded via the sulphur atom of a cysteine residue of the binder to the group G (e.g., an antibody or an antigen-binding antibody fragment which binds to C4.4a and is bonded via the sulphur atom of a cysteine residue of the binder to the group G), $AK_2$ is an antibody or an antigen-binding antibody fragment and is bonded via the NH side group of a lysine residue of the binder to the group G (e.g., an antibody or an antigen-binding antibody fragment which binds to C4.4a and is bonded via the NH side group of a lysine residue of the binder to the group G)

G when AK=$AK_1$, is a group of the formula

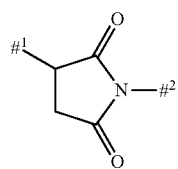

in which $\#^1$ marks the linkage site with the cysteine residue of the binder, $\#^2$ marks the linkage site with the group $L^1$, or when AK=$AK_2$, is carbonyl, $L^1$ is a bond, linear (C$_2$-C$_6$)-alkanediyl, a group of the formula

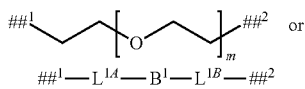

where m is a number from 2 to 6, $\#\#^1$ marks the linkage site with the group G, $\#\#^2$ marks the linkage site with the group B, $L^{1A}$ is linear (C$_2$-C$_6$)-alkanediyl, $B^1$ is a group of the formula

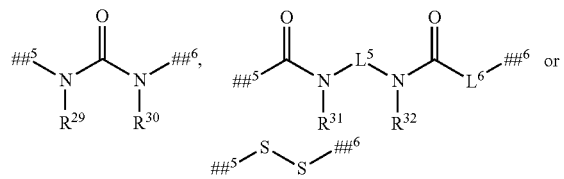

in which $\#\#^5$ marks the linkage site with the group $L^{1A}$, $\#\#^6$ marks the linkage site with the group $L^{1B}$, $L^5$ is a bond, $L^6$ is a bond or a group of the formula

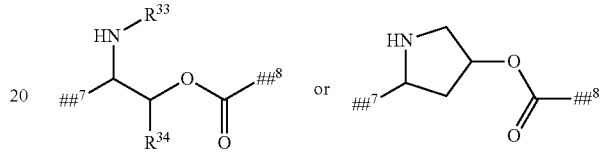

in which $\#\#^7$ marks the linkage site with the carbonyl group, $\#\#^8$ marks the linkage site with $L^{1B}$, $R^{33}$ is hydrogen, methylcarbonyl or tert-butyloxycarbonyl, $R^{34}$ is hydrogen or methyl, $R^{29}$ is hydrogen, $R^{30}$ is hydrogen, $R^{31}$ is hydrogen or methyl, $R^{32}$ is hydrogen or methyl, $L^{1B}$ is linear (C$_2$-C$_6$)-alkanediyl, and where (C$_2$-C$_6$)-alkanediyl may be substituted by 1 or 2 methyl substituents, B is a bond or a group of the formula

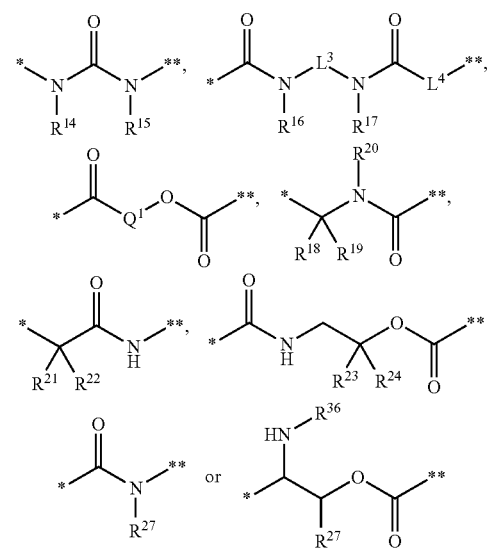

where

* marks the linkage site with $L^1$,

** marks the linkage site with $L^2$, $L^3$ is a bond or ethane-1,2-diyl, $L^4$ is a bond or a group of the formula in which
*** marks the linkage site with the carbonyl group,
**** marks the linkage site with $L^2$,
$R^{25}$ is hydrogen or methyl,
$R^{28}$ is hydrogen, methylcarbonyl or tert-butyloxycarbonyl,
$Q^1$ is a 4- to 7-membered heterocycle,
$R^{14}$ is hydrogen,
$R^{15}$ is hydrogen,
$R^{16}$ is hydrogen or methyl,
$R^{17}$ is hydrogen or methyl,
or
$R^{16}$ and $R^{17}$ together with the atoms to which they are bonded form a piperazinyl ring,
$R^{18}$ is hydrogen,
$R^{19}$ is hydrogen, methyl, propan-2-yl, 2-methylpropan-1-yl or 1-methylpropan-1-yl,
$R^{20}$ is hydrogen or methyl,
or
$R^{19}$ and $R^{20}$ together with the atoms to which they are bonded form a pyrrolidinyl ring,
$R^{21}$ is hydrogen or methyl,
$R^{22}$ is hydrogen or methyl,
or
$R^{21}$ and $R^{22}$ together with the atoms to which they are bonded form a cyclopropyl ring,
$R^{23}$ is methyl,
$R^{24}$ is hydrogen or methyl,
$R^{27}$ is hydrogen,
$R^{36}$ is hydrogen, $(C_1-C_4)$-alkylcarbonyl, tert-butyloxycarbonyl, or benzyloxycarbonyl,
$R^{37}$ is hydrogen or methyl,
$L^2$ is linear $(C_2-C_6)$-alkanediyl or is a group of the formula where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 or 2 methyl substituents,
D is a group of the formula where
$\#^3$ marks the linkage site with the nitrogen atom,
$R^1$ is hydrogen, $R^2$ is 1-hydroxyethyl, benzyl, 4-hydroxybenzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula in which
$\#^4$ marks the linkage site with the adjacent nitrogen atom,
$\#^5$ marks the linkage site with the carbonyl group,
the ring A with the N—O moiety present therein is a mono- or bicyclic, optionally substituted heterocycle of the formula in which
$\#^6$ marks the linkage site with the carbonyl group,
$R^6$ is hydrogen, hydroxy or benzyloxy,
$R^3$ is hydrogen,
$R^4$ is 1-hydroxyethyl, benzyl, 4-hydroxybenzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula in which
$\#^7$ marks the linkage site with the adjacent nitrogen atom,
$\#^8$ marks the linkage site with the group $T^1$,
$T^1$ is a group of the formula —C(=O)—OR$^7$, —C(=O)—NR$^8$R$^9$, —C(=O)—NH—NH—R$^{10}$ or —CH$_2$—O—R$^{11}$, in which $R^7$ is hydrogen, methyl, ethyl, n-propyl, tert-butyl, benzyl or adamantylmethyl, $R^8$ is hydrogen or methyl, $R^9$ is hydrogen, methyl, ethyl, n-propyl or benzyl, or $R^8$ and $R^9$ together with the nitrogen atom to which they are bonded form a 4- to 7-membered heterocycle, $R^{10}$ is benzoyl, $R^{11}$ is benzyl, which may be substituted in the phenyl group by methoxycarbonyl or carboxyl, $R^5$ is hydrogen, methyl or a group of the formula

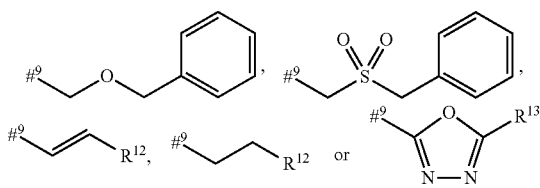

in which $\#^9$ marks the linkage site with —CHC($R^{26}$)-$T^2$, $R^{12}$ is phenyl which may be substituted by methoxycarbonyl, carboxyl or a group of the formula —S(O)$_2$OH, $R^{13}$ is phenyl which may be substituted by methoxycarbonyl or carboxyl, $R^{26}$ is hydrogen or hydroxy, $T^2$ is phenyl, benzyl, 1H-indol-3-yl or 1H-indol-3-ylmethyl, $R^{35}$ is methyl or hydroxy, and also their salts, solvates and solvates of the salts.

Preferred subject matter of the invention are binder-drug conjugates of the general formula (Ia), in which n is a number from 1 to 10, AK is $AK_1$ or $AK_2$ where $AK_1$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the sulphur atom of a cysteine residue of the binder to the group G, $AK_2$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the NH side group of a lysine residue of the binder to the group G, G when AK=$AK_1$, is a group of the formula

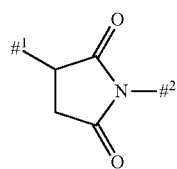

in which $\#^1$ marks the linkage site with the cysteine residue of the binder, $\#^2$ marks the linkage site with the group $L^1$, or when AK=$AK_2$, is carbonyl, $L^1$ is a bond, linear (C$_2$-C$_6$)-alkanediyl, a group of the formula

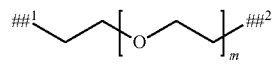

where m is a number 2 or 3, $\#\#^1$ marks the linkage site with the group G, $\#\#^2$ marks the linkage site with the group B, where (C$_2$-C$_6$)-alkanediyl may be substituted by 1 or 2 methyl substituents, B is a bond or a group of the formula

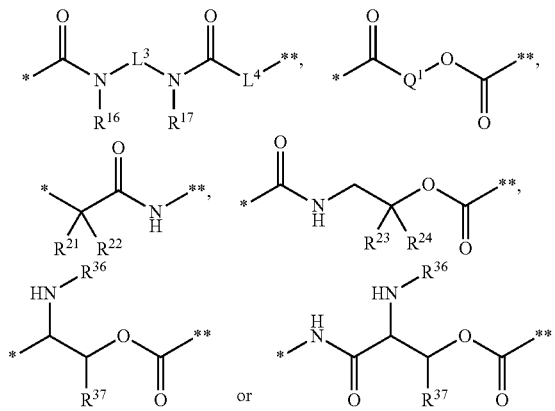

where

\* marks the linkage site with $L^1$,

\*\* marks the linkage site with $L^2$, $L^3$ is a bond or ethane-1,2-diyl, $L^4$ is a bond or a group of the formula

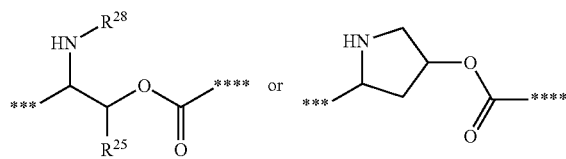

in which

\*\*\* marks the linkage site with the carbonyl group,

\*\*\*\* marks the linkage site with $L^2$, $R^{25}$ is methyl, $R^{28}$ is hydrogen, methylcarbonyl or tert-butyloxycarbonyl, $Q^1$ is piperidine-1,4-diyl, $R^{16}$ is hydrogen or methyl, $R^{17}$ is hydrogen or methyl, or $R^{16}$ and $R^{17}$ together with the atoms to which they are bonded form a piperazinyl ring, $R^{21}$ is hydrogen or methyl, $R^{22}$ is hydrogen or methyl, or $R^{21}$ and $R^{22}$ together with the atoms to which they are bonded form a cyclopropyl ring, $R^{23}$ is methyl,
$R^{24}$ is hydrogen,
$R^{36}$ is hydrogen, methylcarbonyl or tert-butyloxycarbonyl,
$R^{37}$ is hydrogen or methyl,
$L^2$ is linear $(C_2-C_6)$-alkanediyl or is a group of the formula

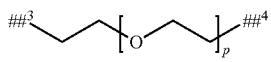

where
p is a number from 2 to 6,
$^3$ marks the linkage site with the group B,
$^4$ marks the linkage site with the nitrogen atom,
D is a group of the formula

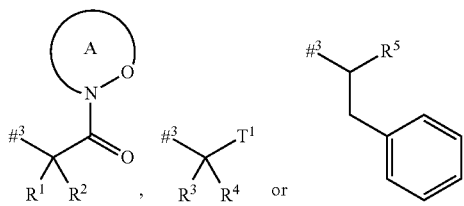

where
$^3$ marks the linkage site with the nitrogen atom,
$R^1$ is hydrogen,
$R^2$ is 1-hydroxyethyl, benzyl, 4-hydroxybenzyl, 1-phenylethyl or 1H-indol-3-ylmethyl, or
$R^1$ and $R^2$ together with the carbon atom to which they are bonded form a (1S,2R)-2-phenylcyclopropane-1,1-diyl group of the formula

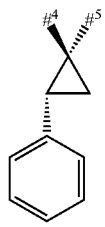

in which
$^4$ marks the linkage site with the adjacent nitrogen atom,
$^5$ marks the linkage site with the carbonyl group,
the ring A with the N—O moiety present therein is a mono- or bicyclic, optionally substituted heterocycle of the formula

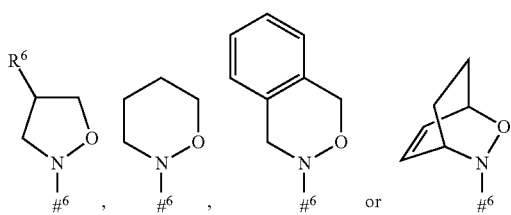

in which
$^6$ marks the linkage site with the carbonyl group,
$R^6$ is hydrogen, hydroxy or benzyloxy,
$R^3$ is hydrogen,
$R^4$ is benzyl, 4-hydroxybenzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula

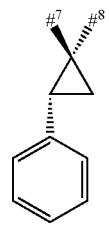

in which
$^7$ marks the linkage site with the adjacent nitrogen atom,
$^8$ marks the linkage site with the group $T^1$,
$T^1$ is a group of the formula —C(=O)—OR$^7$, —C(=O)—NR$^8$R$^9$ or —CH$_2$—O—R$^{11}$, in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
$R^{11}$ is benzyl, which may be substituted in the phenyl group by methoxycarbonyl or carboxyl,
$R^5$ is hydrogen, methyl or a group of the formula

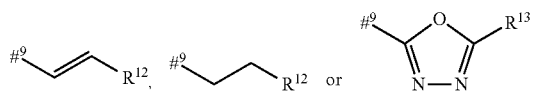

in which
$^9$ marks the linkage site with —CHCH$_2$-phenyl,
$R^{12}$ is phenyl which may be substituted by methoxycarbonyl, carboxyl or a group of the formula —S(O)$_2$OH,
$R^{13}$ is phenyl which may be substituted by methoxycarbonyl or carboxyl,
$R^{35}$ is methyl or hydroxy,
and also their salts, solvates and solvates of the salts.
Preferred subject matter of the present invention are binder-drug conjugates of the general formula (Ia), as indicated above, in which
n is a number from 1 to 10,
AK is AK$_1$ or AK$_2$
where
AK$_1$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the sulphur atom of a cysteine residue of the binder to the group G,
AK$_2$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the NH side group of a lysine residue of the binder to the group G, G when $AK=AK_1$, is a group of the formula

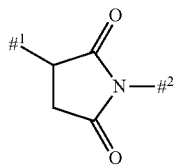

in which
$^1$ marks the linkage site with the cysteine residue of the binder,
$^2$ marks the linkage site with the group $L^1$,
or
when $AK=AK_2$, is carbonyl,
$L^1$ is a bond, linear $(C_2-C_6)$-alkanediyl, a group of the formula

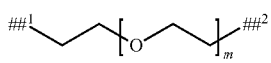

where
m is a number 2 or 3,
$^1$ marks the linkage site with the group G,
$^2$ marks the linkage site with the group B,
where $(C_2-C_6)$-alkanediyl may be substituted by 1 or 2 methyl substituents,
B is a bond or a group of the formula

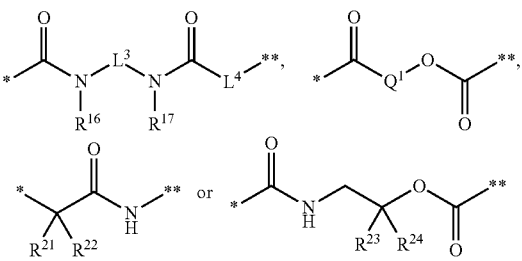

where
* marks the linkage site with $L^1$,
** marks the linkage site with $L^2$,
$L^3$ is a bond or ethane-1,2-diyl,
$L^4$ is a bond or a group of the formula

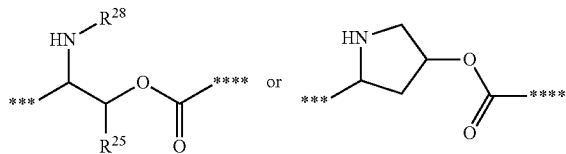

in which
*** marks the linkage site with the carbonyl group,
**** marks the linkage site with $L^2$,
$R^{25}$ is methyl,
$R^{28}$ is hydrogen, methylcarbonyl or tert-butyloxycarbonyl, $Q^1$ is piperidine-1,4-diyl,
$R^{16}$ is hydrogen or methyl,
$R^{17}$ is hydrogen or methyl,
or
$R^{16}$ and $R^{17}$ together with the atoms to which they are bonded form a piperazinyl ring,
$R^{21}$ is hydrogen or methyl,
$R^{22}$ is hydrogen or methyl,
or
$R^{21}$ and $R^{22}$ together with the atoms to which they are bonded form a cyclopropyl ring,
$R^{23}$ is methyl,
$R^{24}$ is hydrogen,
$L^2$ is linear $(C_2-C_6)$-alkanediyl or is a group of the formula

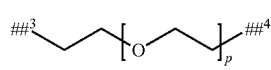

where
p is a number from 2 to 6,
$^3$ marks the linkage site with the group B,
$^4$ marks the linkage site with the nitrogen atom,
D is a group of the formula

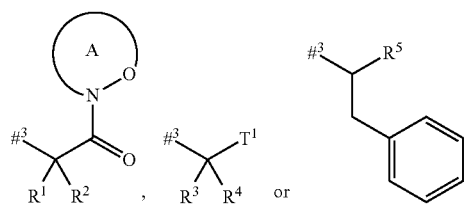

where
$^3$ marks the linkage site with the nitrogen atom,
$R^1$ is hydrogen,
$R^2$ is 1-hydroxyethyl, benzyl, 1-hydroxybenzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula

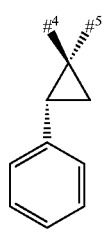

in which
$^4$ marks the linkage site with the adjacent nitrogen atom,
$^5$ marks the linkage site with the carbonyl group,
the ring A with the N—O moiety present therein is a mono- or bicyclic, optionally substituted heterocycle of the formula

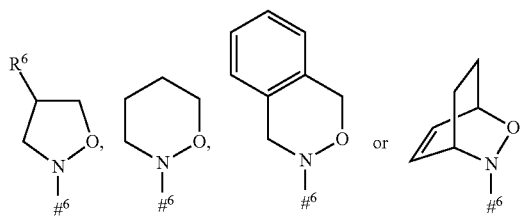

in which
⁶ marks the linkage site with the carbonyl group,
$R^6$ is hydrogen, hydroxy or benzyloxy,
$R^3$ is hydrogen,
$R^4$ is benzyl, 1-hydroxybenzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula

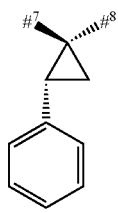

in which
⁷ marks the linkage site with the adjacent nitrogen atom,
⁸ marks the linkage site with the group $T^1$,
$T^1$ is a group of the formula —C(=O)—OR⁷, —C(=O)—NR⁸R⁹ or —CH₂—O—R¹¹,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
$R^{11}$ is benzyl, which may be substituted in the phenyl group by methoxycarbonyl or carboxyl,
$R^5$ is hydrogen, methyl or a group of the formula

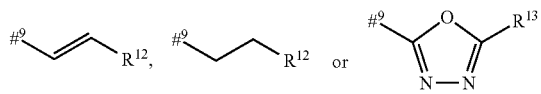

in which
⁹ marks the linkage site with —CHCH₂-phenyl,
$R^{12}$ is phenyl which may be substituted by methoxycarbonyl, carboxyl or a group of the formula —S(O)₂OH,
$R^{13}$ is phenyl which may be substituted by methoxycarbonyl or carboxyl,
$R^{35}$ is methyl or hydroxy,
and also their salts, solvates and solvates of the salts.
Preferred subject matter of the present invention are binder-drug conjugates of the general formula (Ia) as indicated above, in which
n is a number from 1 to 10,
AK is $AK_2$, where
$AK_2$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the NH side group of a lysine residue of the binder to the group G,
G is carbonyl,
$L^1$ is a bond,
B is a bond,
$L^2$ is linear $(C_3-C_6)$-alkanediyl or is a group of the formula

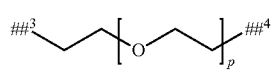

where
p is a number 2 or 3,
³ marks the linkage site with the group B,
⁴ marks the linkage site with the nitrogen atom,
D is a group of the formula

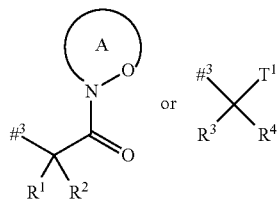

where
³ marks the linkage site with the nitrogen atom,
$R^1$ is hydrogen,
$R^2$ is benzyl or 1H-indol-3-ylmethyl,
or
$R^1$ and $R^2$ together with the carbon atom to which they are bonded form a (1S,2R)-2-phenylcyclopropane-1,1-diyl group of the formula

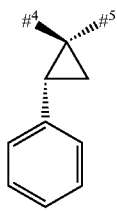

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

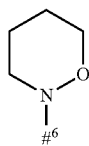

in which
6 marks the linkage site with the carbonyl group,
R3 is hydrogen,
R4 is benzyl or 1H-indol-3-ylmethyl,
or
R3 and R4 together with the carbon atom to which they are bonded form a (1S,2R)-2-phenylcyclopropane-1,1-diyl group of the formula

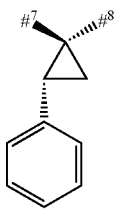

in which
7 marks the linkage site with the adjacent nitrogen atom,
8 marks the linkage site with the group T1,
T1 is a group of the formula —C(=O)—OR7 or —C(=O)—NR8R9
in which
R7 is hydrogen, methyl, ethyl, n-propyl, tert-butyl, benzyl or adamantylmethyl,
R8 is hydrogen,
R9 is hydrogen or benzyl,
R35 is methyl,
and also their salts, solvates and solvates of the salts.

Preferred subject matter of the present invention are binder-drug conjugates of the general formula (Ia) as indicated above, in which
n is a number from 1 to 10,
AK is AK2,
where
AK2 is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the NH side group of a lysine residue of the binder to the group G,
G is carbonyl,
L1 is a bond,
B is a bond,
L2 is linear (C3-C6)-alkanediyl or is a group of the formula

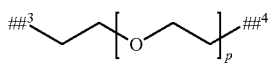

where
p is a number 2 or 3,
3 marks the linkage site with the group B,
4 marks the linkage site with the nitrogen atom,
D is a group of the formula

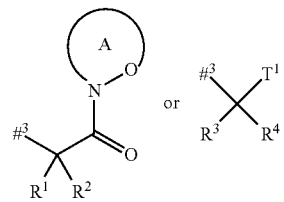

where
3 marks the linkage site with the nitrogen atom,
R1 is hydrogen,
R2 is 4-hydroxybenzyl or 1H-indol-3-ylmethyl,
or
R1 and R2 together with the carbon atom to which they are bonded form a (1S,2R)-2-phenylcyclopropane-1,1-diyl group of the formula

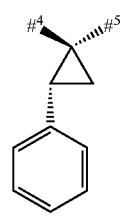

in which
4 marks the linkage site with the adjacent nitrogen atom,
5 marks the linkage site with the carbonyl group,
the ring A with the N—O moiety present therein is a mono- or bicyclic, optionally substituted heterocycle of the formula

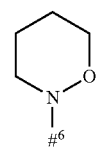

in which
6 marks the linkage site with the carbonyl group,
R3 is hydrogen,
R4 is 4-hydroxybenzyl or 1H-indol-3-ylmethyl,
or
R3 and R4 together with the carbon atom to which they are bonded form a (1S,2R)-2-phenylcyclopropane-1,1-diyl group of the formula

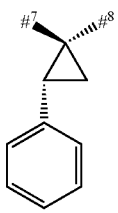

in which
7 marks the linkage site with the adjacent nitrogen atom,
8 marks the linkage site with the group $T^1$,
$T^1$ is a group of the formula —C(=O)—OR$^7$ or —C(=O)—NR$^8$R$^9$
in which
R$^7$ is hydrogen, methyl, ethyl, n-propyl, tert-butyl, benzyl or adamantylmethyl,
R$^8$ is hydrogen,
R$^9$ is hydrogen or benzyl,
R$^{35}$ is methyl,
and also their salts, solvates and solvates of the salts.

Preferred subject matter of the present invention are binder-drug conjugates of the general formula (Ia) as indicated above, in which
n is a number from 1 to 10,
AK is AK$_1$,
where
AK$_1$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the sulphur atom of a cysteine residue of the binder to the group G,
G is a group of the formula

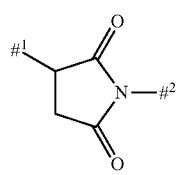

where
$^1$ marks the linkage site with the cysteine residue of the binder,
$^2$ marks the linkage site with the group $L^1$,
$L^1$ is a bond, linear $(C_3$-$C_5)$-alkanediyl or a group of the formula

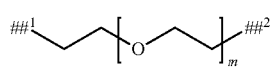

where
m is a number 2 or 3,
$^1$ marks the linkage site with the group G,
$^2$ marks the linkage site with the group B,
where $(C_3$-$C_5)$-alkanediyl may be substituted by 1 or 2 methyl substituents,
B is a bond or a group of the formula

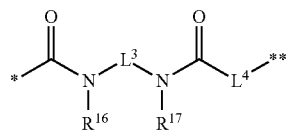

where
* marks the linkage site with $L^1$,
** marks the linkage site with $L^2$,
$L^3$ is a bond or ethane-1,2-diyl,
$L^4$ is a bond or a group of the formula

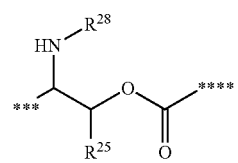

in which
*** marks the linkage site with the carbonyl group,
**** marks the linkage site with $L^2$,
R$^{25}$ is methyl,
R$^{28}$ is hydrogen, methylcarbonyl or tert-butyloxycarbonyl,
R$^{16}$ is hydrogen or methyl,
R$^{17}$ is hydrogen or methyl,
or
R$^{16}$ and R$^{17}$ together with the atoms to which they are bonded form a piperazinyl ring,
$L^2$ is linear $(C_3$-$C_5)$-alkanediyl or is a group of the formula

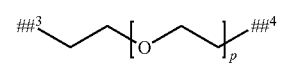

where
p is a number 2 or 3,
$^3$ marks the linkage site with the group B,
$^4$ marks the linkage site with the nitrogen atom,
D is a group of the formula

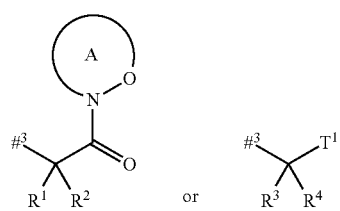

where
$^3$ marks the linkage site with the nitrogen atom,
R$^1$ is hydrogen,
R$^2$ is benzyl or 1H-indol-3-ylmethyl,
or
R$^1$ and R$^2$ together with the carbon atom to which they are bonded form a (1S,2R)-2-phenylcyclopropane-1,1-diyl group of the formula

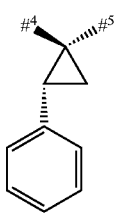

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

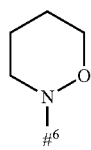

in which
⁶ marks the linkage site with the carbonyl group,
$R^3$ is hydrogen,
$R^4$ is benzyl or 1H-indol-3-ylmethyl,
or
$R^3$ and $R^4$ together with the carbon atom to which they are bonded form a (1S,2R)-2-phenylcyclopropane-1,1-diyl group of the formula

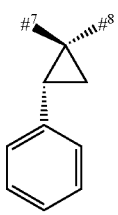

in which
⁷ marks the linkage site with the adjacent nitrogen atom,
⁸ marks the linkage site with the group $T^1$,
$T^1$ is a group of the formula —C(=O)—OR⁷ or —C(=O)—NR⁸R⁹,
in which
$R^7$ is hydrogen, methyl, ethyl, n-propyl, tert-butyl, benzyl or adamantylmethyl,
$R^8$ is hydrogen,
$R^9$ is hydrogen or benzyl,
$R^{35}$ is methyl,
and also their salts, solvates and solvates of the salts.

Preferred subject matter of the present invention are binder-drug conjugates of the general formula (Ia) as indicated above, in which
n is a number from 1 to 10,
AK is $AK_1$,
where
$AK_1$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the sulphur atom of a cysteine residue of the binder to the group G,
G is a group of the formula

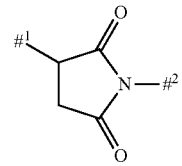

where
¹ marks the linkage site with the cysteine residue of the binder,
² marks the linkage site with the group $L^1$,
$L^1$ is a bond, linear $(C_3-C_5)$-alkanediyl or a group of the formula

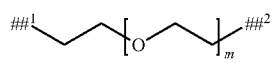

where
m is a number 2 or 3,
¹ marks the linkage site with the group G,
² marks the linkage site with the group B,
where $(C_3-C_5)$-alkanediyl may be substituted by 1 or 2 methyl substituents,
B is a bond or a group of the formula

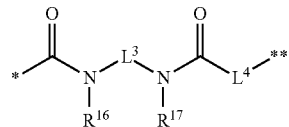

where
* marks the linkage site with $L^1$,
** marks the linkage site with $L^2$,
$L^3$ is a bond or ethane-1,2-diyl,
$L^4$ is a bond or a group of the formula

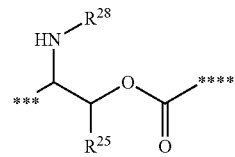

in which
*** marks the linkage site with the carbonyl group,
**** marks the linkage site with $L^2$,
$R^{25}$ is methyl,
$R^{28}$ is hydrogen, methylcarbonyl or tert-butyloxycarbonyl,
$R^{16}$ is hydrogen or methyl,
$R^{17}$ is hydrogen or methyl,
or R$^{16}$ and R$^{17}$ together with the atoms to which they are bonded form a piperazinyl ring, L$^2$ is linear (C$_3$-C$_5$)-alkanediyl or is a group of the formula

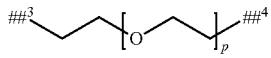

where p is a number 2 or 3,

$^3$ marks the linkage site with the group B,

$^4$ marks the linkage site with the nitrogen atom,

D is a group of the formula

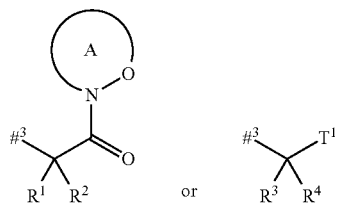

where

$^3$ marks the linkage site with the nitrogen atom,

R$^1$ is hydrogen,

R$^2$ is 4-hydroxybenzyl or 1H-indol-3-ylmethyl, or

R$^1$ and R$^2$ together with the carbon atom to which they are bonded form a (1S,2R)-2-phenylcyclopropane-1,1-diyl group of the formula

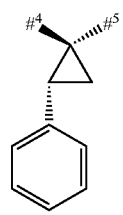

in which

$^4$ marks the linkage site with the adjacent nitrogen atom,

$^5$ marks the linkage site with the carbonyl group, the ring A with the N—O moiety present therein is a mono- or bicyclic, optionally substituted heterocycle of the formula

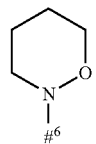

in which

$^6$ marks the linkage site with the carbonyl group,

R$^3$ is hydrogen,

R$^4$ is 4-hydroxybenzyl or 1H-indol-3-ylmethyl, or

R$^3$ and R$^4$ together with the carbon atom to which they are bonded form a (1S,2R)-2-phenylcyclopropane-1,1-diyl group of the formula

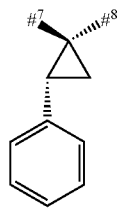

in which

$^7$ marks the linkage site with the adjacent nitrogen atom,

$^8$ marks the linkage site with the group T$^1$,

T$^1$ is a group of the formula —C(=O)—OR$^7$ or —C(=O)—NR$^8$R$^9$, in which

R$^7$ is hydrogen, methyl, ethyl, n-propyl, tert-butyl, benzyl or adamantylmethyl, R$^8$ is hydrogen, R$^9$ is hydrogen or benzyl, R$^{35}$ is methyl, and also their salts, solvates and solvates of the salts.

Additionally provided by the present invention are compounds of the formula (XXXa)

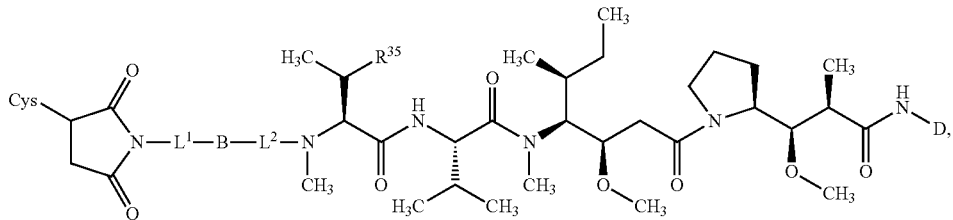

(XXXa)

in which

Cys is a cysteine residue which is bonded via the sulphur atom of the side chain to a carbon atom of the succinimide, L$^1$ is a bond, linear (C$_1$-C$_{10}$)-alkanediyl, a group of the formula

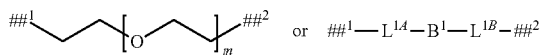

where
m is a number from 2 to 6,
$\#\#^1$ marks the linkage site with the group G,
$\#\#^2$ marks the linkage site with the group B,
$L^{1A}$ is linear $(C_2-C_{10})$-alkanediyl,
$B^1$ is a group of the formula

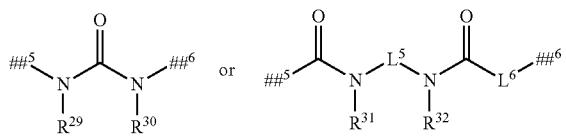

in which
$\#\#^5$ marks the linkage site with the group $L^{1A}$,
$\#\#^6$ marks the linkage site with the group $L^{1B}$,
$L^5$ is a bond or $(C_2-C_4)$-alkanediyl,
$L^6$ is a bond,
$R^{29}$ is hydrogen or $(C_1-C_4)$-alkyl,
$R^{30}$ is hydrogen or $(C_1-C_4)$-alkyl,
or
$R^{29}$ and $R^{30}$ together with the atoms to which they are bonded form a 5- or 6-membered heterocycle,
$R^{31}$ is hydrogen or $(C_1-C_4)$-alkyl,
$R^{32}$ is hydrogen or $(C_1-C_4)$-alkyl,
or
$R^{31}$ and $R^{32}$ together with the atoms to which they are bonded form a 5- or 6-membered heterocycle,
$L^{1B}$ is linear $(C_2-C_{10})$-alkanediyl,
and
where $(C_1-C_{10})$-alkanediyl may be substituted by 1 to 4 substituents selected independently of one another from the group consisting of methyl, hydroxy and benzyl,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
B is a bond or a group of the formula

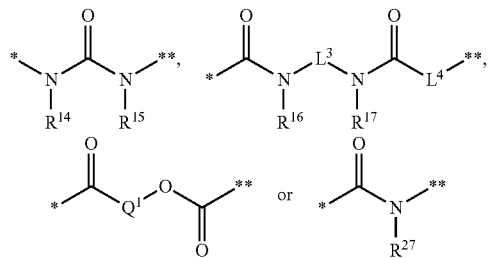

where
\* marks the linkage site with $L^1$,
\*\* marks the linkage site with $L^2$,
P is O or NH,
$L^3$ is a bond or $(C_2-C_4)$-alkanediyl,
$L^4$ is a bond,
$Q^1$ is a 4- to 7-membered heterocycle,
$Q^2$ is a 3- to 7-membered carbocycle or a 4- to 7-membered heterocycle,
$R^{14}$ is hydrogen or $(C_1-C_4)$-alkyl,
$R^{15}$ is hydrogen or $(C_1-C_4)$-alkyl,
or
$R^{14}$ and $R^{15}$ together with the atoms to which they are bonded form a 5- or 6-membered heterocycle,
$R^{16}$ is hydrogen or $(C_1-C_4)$-alkyl,
$R^{17}$ is hydrogen or $(C_1-C_4)$-alkyl,
or
$R^{16}$ and $R^{17}$ together with the atoms to which they are bonded form a 5- or 6-membered heterocycle,
$R^{18}$ is hydrogen or $(C_1-C_4)$-alkyl,
$R^{19}$ is hydrogen or the side group of a natural α-amino acid or of its homologues or isomers,
$R^{20}$ is hydrogen or $(C_1-C_4)$-alkyl,
or
$R^{19}$ and $R^{20}$ together with the atoms to which they are bonded form a pyrrolidinyl ring,
$R^{21}$ is hydrogen or $(C_1-C_4)$-alkyl,
$R^{22}$ is hydrogen or $(C_1-C_4)$-alkyl,
or
$R^{21}$ and $R^{22}$ together with the atoms to which they are bonded form a 3- to 7-membered carbocycle,
$R^{23}$ is $(C_1-C_4)$-alkyl,
$R^{24}$ is hydrogen or $(C_1-C_4)$-alkyl,
$R^{27}$ is hydrogen or $(C_1-C_4)$-alkyl,
$L^2$ is linear $(C_2-C_{10})$-alkanediyl or is a group of the formula

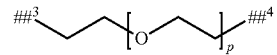

where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 to 4 substituents selected independently of one another from the group consisting of methyl, hydroxy and benzyl,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
D is a group of the formula

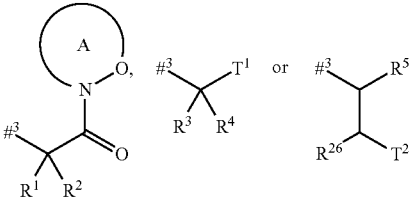

where
$\#^3$ marks the linkage site with the nitrogen atom,
$R^1$ is hydrogen or methyl,
$R^2$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl,
or
$R^1$ and $R^2$ together with the carbon atom to which they are bonded form a (1S,2R)-2-phenylcyclopropane-1,1-diyl group of the formula

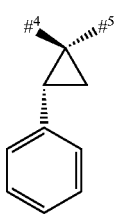

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

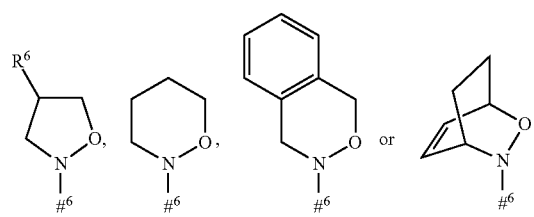

in which
⁶ marks the linkage site with the carbonyl group,
$R^6$ is hydrogen, hydroxy or benzyloxy,
$R^3$ is hydrogen or methyl,
$R^4$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl,
or
$R^3$ and $R^4$ together with the carbon atom to which they are bonded form a (1S,2R)-2-phenylcyclopropane-1,1-diyl group of the formula

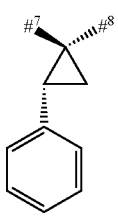

in which
⁷ marks the linkage site with the adjacent nitrogen atom,
⁸ marks the linkage site with the group $T^1$,
$T^1$ is a group of the formula —C(=O)—$OR^7$, —C(=O)—$NR^8R^9$, —C(=O)—NH—NH—$R^{10}$ or —$CH_2$—O—$R^{11}$,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
or $R^8$ and $R^9$ together with the nitrogen atom to which they are bonded form a 4- to 7-membered heterocycle,
$R^{10}$ is benzoyl,
$R^{11}$ is benzyl, which may be substituted in the phenyl group by methoxycarbonyl or carboxyl,
$R^5$ is hydrogen, methyl or a group of the formula

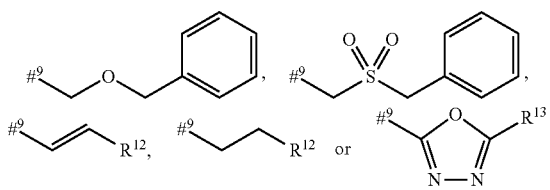

in which
⁹ marks the linkage site with —CHC($R^{26}$)-$T^2$,
$R^{12}$ is phenyl which may be substituted by methoxycarbonyl, carboxyl or a group of the formula —S(O)$_2$OH,
$R^{13}$ is phenyl which may be substituted by methoxycarbonyl or carboxyl,
$R^{26}$ is hydrogen or hydroxy,
$T^2$ is phenyl, benzyl, 1H-indol-3-yl or 1H-indol-3-ylmethyl,
$R^{35}$ is methyl or hydroxy,
and also their salts, solvates and solvates of the salts.
Preferred subject matter of the present invention are compounds of the formula (XXXa) as indicated above, in which
Cys is a cysteine residue which is bonded via the sulphur atom of the side chain via a carbon atom of the succinimide,
$L^1$ is a bond, linear ($C_2$-$C_6$)-alkanediyl, a group of the formula

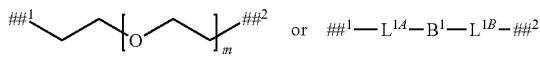

where
m is a number 2 or 3,
¹ marks the linkage site with the group G,
² marks the linkage site with the group B,
$L^{1A}$ is linear ($C_2$-$C_6$)-alkanediyl,
$B^1$ is a group of the formula

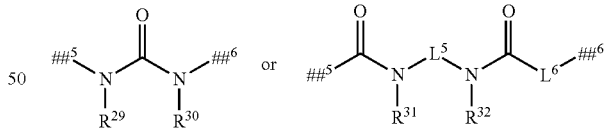

in which
⁵ marks the linkage site with the group $L^{1A}$,
⁶ marks the linkage site with the group $L^{1B}$,
$L^5$ is a bond,
$L^6$ is a bond,
$R^{29}$ is hydrogen,
$R^{30}$ is hydrogen,
$R^{31}$ is hydrogen or methyl,
$R^{32}$ is hydrogen or methyl,
$L^{1B}$ is linear ($C_2$-$C_6$)-alkanediyl,
and
where ($C_2$-$C_6$)-alkanediyl may be substituted by 1 or 2 methyl substituents,
B is a bond or a group of the formula

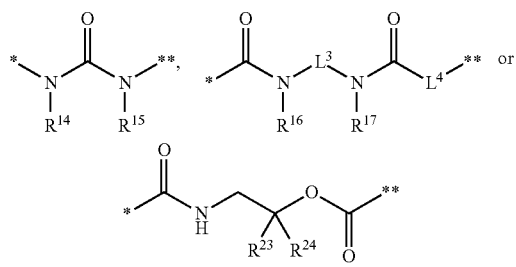

where
* marks the linkage site with $L^1$,
** marks the linkage site with $L^2$,
$L^3$ is a bond or ethane-1,2-diyl,
$L^4$ is a bond,
$R^{14}$ is hydrogen,
$R^{15}$ is hydrogen,
$R^{16}$ is hydrogen or methyl,
$R^{17}$ is hydrogen or methyl,
or
$R^{16}$ and $R^{17}$ together with the atoms to which they are bonded form piperazinyl ring,
$R^{23}$ is methyl,
$R^{24}$ is hydrogen or methyl,
$L^2$ is linear $(C_2\text{-}C_6)$-alkanediyl or is a group of the formula

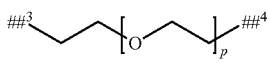

where
p is a number 2 or 3,
$\#\#^3$ marks the linkage site with the group B,
$\#\#^4$ marks the linkage site with the nitrogen atom,
D is a group of the formula

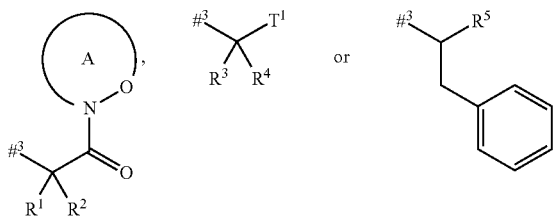

where
$\#^3$ marks the linkage site with the nitrogen atom,
$R^1$ is hydrogen,
$R^2$ is 1-hydroxyethyl, benzyl, 4-hydroxybenzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula

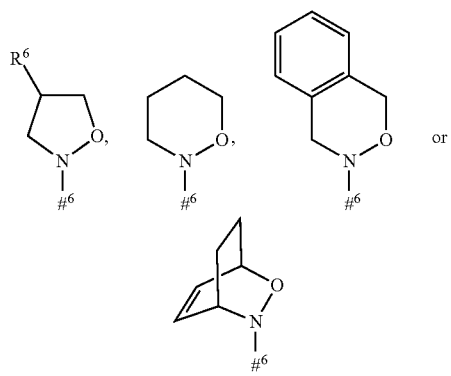

in which
$\#^4$ marks the linkage site with the adjacent nitrogen atom,
$\#^5$ marks the linkage site with the carbonyl group,
the ring A with the N—O moiety present therein is a mono- or bicyclic, optionally substituted heterocycle of the formula

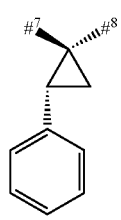

in which
$\#^6$ marks the linkage site with the carbonyl group,
$R^6$ is hydrogen, hydroxy or benzyloxy,
$R^3$ is hydrogen,
$R^4$ is 1-hydroxyethyl, benzyl, 4-hydroxybenzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula

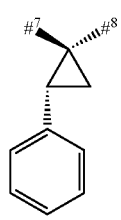

in which
$\#^7$ marks the linkage site with the adjacent nitrogen atom,
$\#^8$ marks the linkage site with the group $T^1$,
$T^1$ is a group of the formula —C(=O)—$OR^7$, —C(=O)—$NR^8R^9$, —C(=O)—NH—NH—$R^{10}$ or —CH$_2$—O—$R^{11}$,
in which
$R^7$ is hydrogen, methyl, ethyl, n-propyl, tert-butyl, benzyl or adamantylmethyl,
$R^8$ is hydrogen or methyl, $R^9$ is hydrogen, methyl, ethyl, n-propyl or benzyl, or $R^8$ and $R^9$ together with the nitrogen atom to which they are bonded form a 4- to 7-membered heterocycle, $R^{10}$ is benzoyl, $R^{11}$ is benzyl which may be substituted in the phenyl group by methoxycarbonyl or carboxyl, $R^5$ is hydrogen, methyl or a group of the formula

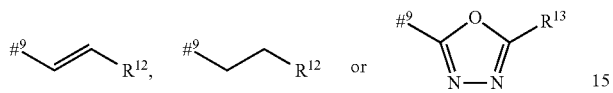

in which $\#^9$ marks the linkage site with —CHCH$_2$-phenyl, $R^{12}$ is phenyl which may be substituted by methoxycarbonyl, carboxyl or a group of the formula —S(O)$_2$OH, $R^{13}$ is phenyl which may be substituted by methoxycarbonyl or carboxyl, $R^{35}$ is methyl or hydroxy, and also their salts, solvates and solvates of the salts.

Preferred subject matter of the present invention are compounds of the formula (XXXa) as indicated above, in which Cys is a cysteine residue which is bonded via the sulphur atom of the side chain via a carbon atom of the succinimide, $L^1$ is a bond or linear ($C_2$-$C_6$)-alkanediyl, B is a bond or a group of the formula

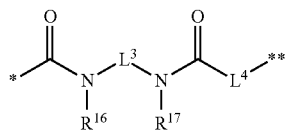

where

\* marks the linkage site with $L^1$,

\*\* marks the linkage site with $L^2$, $L^3$ is a bond, $L^4$ is a bond, $R^{16}$ is hydrogen or methyl, $R^{17}$ is hydrogen or methyl, $L^2$ is linear ($C_2$-$C_6$)-alkanediyl or is a group of the formula

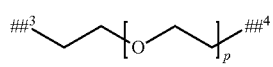

where p is a number 2 or 3, $\#\#^3$ marks the linkage site with the group B, $\#\#^4$ marks the linkage site with the nitrogen atom, D is a group of the formula

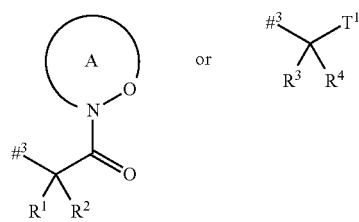

where $\#^3$ marks the linkage site with the nitrogen atom, $R^1$ is hydrogen, $R^2$ is benzyl or 1H-indol-3-ylmethyl, or $R^1$ and $R^2$ together with the carbon atom to which they are bonded form a (1S,2R)-2-phenylcyclopropane-1,1-diyl group of the formula

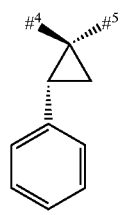

in which $\#^4$ marks the linkage site with the adjacent nitrogen atom, $\#^5$ marks the linkage site with the carbonyl group, the ring A with the N—O moiety present therein is a mono- or bicyclic, optionally substituted heterocycle of the formula

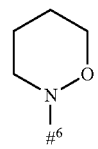

in which $\#^6$ marks the linkage site with the carbonyl group, $R^3$ is hydrogen, $R^4$ is benzyl or 1H-indol-3-ylmethyl, or $R^3$ and $R^4$ together with the carbon atom to which they are bonded form a (1S,2R)-2-phenylcyclopropane-1,1-diyl group of the formula

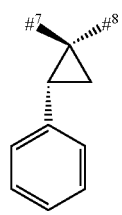

in which $\#^7$ marks the linkage site with the adjacent nitrogen atom,

8 marks the linkage site with the group T1,

T1 is a group of the formula —C(=O)—OR7 or —C(=O)—NR8R9, in which

R7 is hydrogen,

R8 is hydrogen,

R9 is hydrogen,

R35 is methyl, and also their salts, solvates and solvates of the salts.

Preferred subject matter of the present invention are compounds of the formula (XXXa) as indicated above, in which Cys is a cysteine residue which is bonded via the sulphur atom of the side chain via a carbon atom of the succinimide, L1 is a bond or linear (C2-C6)-alkanediyl, B is a bond or a group of the formula

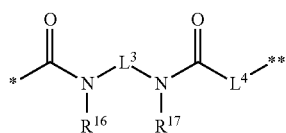

where

* marks the linkage site with L1,

** marks the linkage site with L2,

L3 is a bond,

L4 is a bond,

R16 is hydrogen or methyl,

R17 is hydrogen or methyl,

L2 is linear (C2-C6)-alkanediyl or is a group of the formula

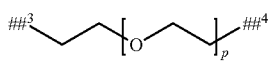

where p is a number 2 or 3,

3 marks the linkage site with the group B,

4 marks the linkage site with the nitrogen atom,

D is a group of the formula

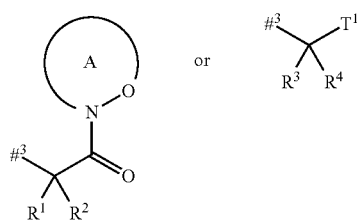

where

3 marks the linkage site with the nitrogen atom,

R1 is hydrogen,

R2 is 4-hydroxybenzyl or 1H-indol-3-ylmethyl, or

R1 and R2 together with the carbon atom to which they are bonded form a (1S,2R)-2-phenylcyclopropane-1,1-diyl group of the formula

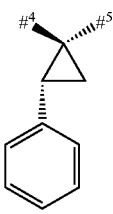

in which

4 marks the linkage site with the adjacent nitrogen atom,

5 marks the linkage site with the carbonyl group, the ring A with the N—O moiety present therein is a mono- or bicyclic, optionally substituted heterocycle of the formula

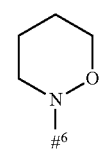

in which

6 marks the linkage site with the carbonyl group,

R3 is hydrogen,

R4 is 4-hydroxybenzyl or 1H-indol-3-ylmethyl, or

R3 and R4 together with the carbon atom to which they are bonded form a (1S,2R)-2-phenylcyclopropane-1,1-diyl group of the formula

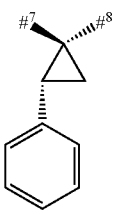

in which

7 marks the linkage site with the adjacent nitrogen atom,

8 marks the linkage site with the group T1,

T1 is a group of the formula —C(=O)—OR7 or —C(=O)—NR8R9, in which

R7 is hydrogen,

R8 is hydrogen,

R9 is hydrogen,

R35 is methyl, and also their salts, solvates and solvates of the salts.

The present invention additionally provides compounds of the formula (XXXI)

(XXXI)

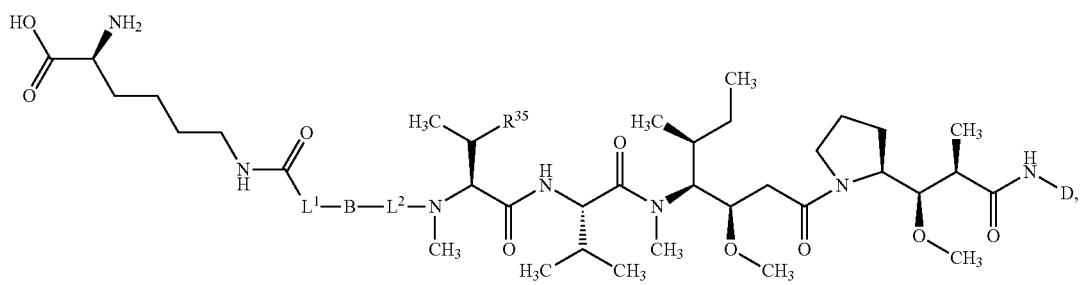

in which
L¹ is a bond, linear $(C_1-C_{10})$-alkanediyl, a group of the formula

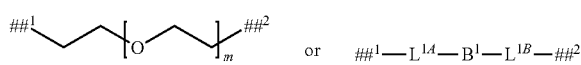

where
m is a number from 2 to 6,
$\#\#^1$ marks the linkage site with the group G,
$\#\#^2$ marks the linkage site with the group B,
$L^{1A}$ is linear $(C_2-C_{10})$-alkanediyl,
B¹ is a group of the formula

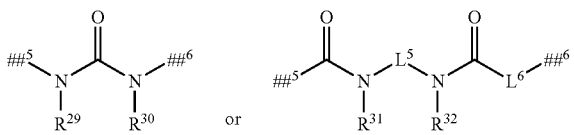

in which
$\#\#^5$ marks the linkage site with the group $L^{1A}$,
$\#\#^6$ marks the linkage site with the group $L^{1B}$,
$L^5$ is a bond or $(C_2-C_4)$-alkanediyl,
$L^6$ is a bond,
$R^{29}$ is hydrogen or $(C_1-C_4)$-alkyl,
$R^{30}$ is hydrogen or $(C_1-C_4)$-alkyl,
or
$R^{29}$ and $R^{30}$ together with the atoms to which they are bonded form a 5- or 6-membered heterocycle,
$R^{31}$ is hydrogen or $(C_1-C_4)$-alkyl,
$R^{32}$ is hydrogen or $(C_1-C_4)$-alkyl,
or
$R^{31}$ and $R^{32}$ together with the atoms to which they are bonded form a 5- or 6-membered heterocycle,
$L^{1B}$ is linear $(C_2-C_{10})$-alkanediyl,
and
where $(C_1-C_{10})$-alkanediyl may be substituted by 1 to 4 substituents selected independently of one another from the group consisting of methyl, hydroxy and benzyl,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
B is a bond or a group of the formula

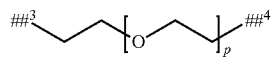

where
* marks the linkage site with $L^1$,
** marks the linkage site with $L^2$,
P is O or NH,
$Q^1$ is a 4- to 7-membered heterocycle,
$Q^2$ is a 3- to 7-membered carbocycle or a 4- to 7-membered heterocycle,
$R^{18}$ is hydrogen or $(C_1-C_4)$-alkyl,
$R^{19}$ is hydrogen or the side group of a natural α-amino acid or of its homologues or isomers,
$R^{20}$ is hydrogen or $(C_1-C_4)$-alkyl,
or
$R^{19}$ and $R^{20}$ together with the atoms to which they are bonded form a pyrrolidinyl ring,
$R^{21}$ is hydrogen or $(C_1-C_4)$-alkyl,
$R^{22}$ is hydrogen or $(C_1-C_4)$-alkyl,
or
$R^{21}$ and $R^{22}$ together with the atoms to which they are bonded form a 3- to 7-membered carbocycle,
$R^{27}$ is hydrogen or $(C_1-C_4)$-alkyl,
$L^2$ is linear $(C_2-C_{10})$-alkanediyl or is a group of the formula

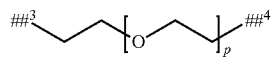

where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 to 4 substituents selected independently of one another from the group consisting of methyl, hydroxy and benzyl,
and where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring, D is a group of the formula in which $\#^3$ marks the linkage site with the nitrogen atom, $R^1$ is hydrogen or methyl, $R^2$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or $R^1$ and $R^2$ together with the carbon atom to which they are bonded form a (1S,2R)-2-phenylcyclopropane-1,1-diyl group of the formula in which $\#^4$ marks the linkage site with the adjacent nitrogen atom, $\#^5$ marks the linkage site with the carbonyl group, the ring A with the N—O moiety present therein is a mono- or bicyclic, optionally substituted heterocycle of the formula in which $\#^6$ marks the linkage site with the carbonyl group, $R^6$ is hydrogen, hydroxy or benzyloxy, $R^3$ is hydrogen or methyl, $R^4$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl, or $R^3$ and $R^4$ together with the carbon atom to which they are bonded form a (1S,2R)-2-phenylcyclopropane-1,1-diyl group of the formula in which $\#^7$ marks the linkage site with the adjacent nitrogen atom, $\#^8$ marks the linkage site with the group $T^1$, $T^1$ is a group of the formula —C(=O)—OR$^7$, —C(=O)—NR$^8$R$^9$, —C(=O)—NH—NH—R$^{10}$ or —CH$_2$—O—R$^{11}$, in which $R^7$ is hydrogen, methyl, ethyl, n-propyl, tert-butyl, benzyl or adamantylmethyl, $R^8$ is hydrogen or methyl, $R^9$ is hydrogen, methyl, ethyl, n-propyl or benzyl, or $R^8$ and $R^9$ together with the nitrogen atom to which they are bonded form a 4- to 7-membered heterocycle, $R^{10}$ is benzoyl, $R^{11}$ is benzyl, which may be substituted in the phenyl group by methoxycarbonyl or carboxyl, $R^5$ is hydrogen, methyl or a group of the formula in which $\#^9$ marks the linkage site with —CHC(R$^{26}$)-T$^2$, $R^{12}$ is phenyl which may be substituted by methoxycarbonyl, carboxyl or a group of the formula —S(O)$_2$OH, $R^{13}$ is phenyl which may be substituted by methoxycarbonyl or carboxyl, $R^{26}$ is hydrogen or hydroxy, $T^2$ is phenyl, benzyl, 1H-indol-3-yl or 1H-indol-3-ylmethyl, $R^{35}$ is methyl or hydroxy, and also their salts, solvates and solvates of the salts.

Preferred subject matter of the present invention are compounds of the formula (XXXI) as indicated above, in which L¹ is a bond, linear $(C_2-C_6)$-alkanediyl or a group of the formula

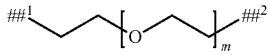

where
  m is a number 2 or 3,
  ##¹ marks the linkage site with the group G,
  ##² marks the linkage site with the group B,
  where $(C_2-C_6)$-alkanediyl may be substituted by 1 or 2 methyl substituents,
B is a bond or a group of the formula

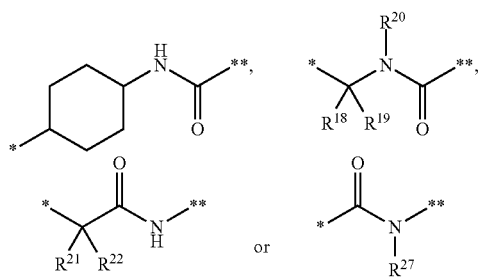

where
  * marks the linkage site with L¹,
  ** marks the linkage site with L²,
  $R^{18}$ is hydrogen,
  $R^{19}$ is methyl, propan-2-yl, 2-methylpropan-1-yl or 1-methylpropan-1-yl,
  $R^{20}$ is hydrogen or $(C_1-C_4)$-alkyl,
  or
  $R^{19}$ and $R^{20}$ together with the atoms to which they are bonded form a pyrrolidinyl ring,
  $R^{21}$ is hydrogen or methyl,
  $R^{22}$ is hydrogen or methyl,
  or
  $R^{21}$ and $R^{22}$ together with the atoms to which they are bonded form a cyclopropyl ring,
  $R^{27}$ is hydrogen or methyl,
L² is linear $(C_2-C_6)$-alkanediyl or is a group of the formula

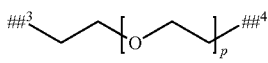

where
  p is a number 2 or 3,
  ##³ marks the linkage site with the group B,
  ##⁴ marks the linkage site with the nitrogen atom,
  where $(C_2-C_{10})$-alkanediyl may be substituted by 1 or 2 methyl substituents,
  and
  where two carbon atoms of the alkanediyl chain in 1,4 relation to one another, with inclusion of any carbon atoms situated between them, may be bridged to form a phenyl ring,
D is a group of the formula

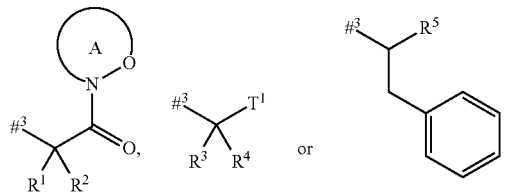

in which
  #³ marks the linkage site with the nitrogen atom,
  $R^1$ is hydrogen,
  $R^2$ is 1-hydroxyethyl, benzyl, 4-hydroxybenzyl, 1-phenylethyl or 1H-indol-3-ylmethyl,
or
  $R^1$ and $R^2$ together with the carbon atom to which they are bonded form a (1S,2R)-2-phenylcyclopropane-1,1-diyl group of the formula

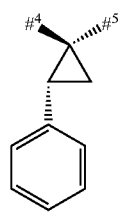

in which
  #⁴ marks the linkage site with the adjacent nitrogen atom,
  #⁵ marks the linkage site with the carbonyl group,
  the ring A with the N—O moiety present therein is a mono- or bicyclic, optionally substituted heterocycle of the formula

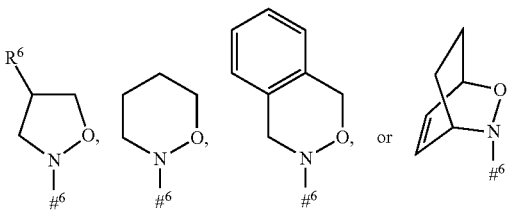

in which
  #⁶ marks the linkage site with the carbonyl group,
  $R^6$ is hydrogen, hydroxy or benzyloxy,
  $R^3$ is hydrogen,
  $R^4$ is 1-hydroxyethyl, benzyl, 4-hydroxybenzyl, 1-phenylethyl or 1H-indol-3-ylmethyl,
or
  $R^3$ and $R^4$ together with the carbon atom to which they are bonded form a (1S,2R)-2-phenylcyclopropan-1,1-diyl group of the formula

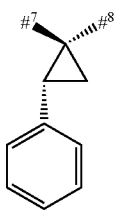

in which
[7] marks the linkage site with the adjacent nitrogen atom,
[8] marks the linkage site with the group $T^1$,
$T^1$ is a group of the formula —C(=O)—OR[7], —C(=O)—NR[8]R[9], —C(=O)—NH—NH—R[10] or —CH$_2$—O—R[11],
in which
R[7] is hydrogen, methyl, ethyl, n-propyl, tert-butyl, benzyl or adamantylmethyl,
R[8] is hydrogen or methyl,
R[9] is hydrogen, methyl, ethyl, n-propyl or benzyl,
or
R[8] and R[9] together with the nitrogen atom to which they are bonded form a 4- to 7-membered heterocycle,
R[10] is benzoyl,
R[11] is benzyl, which may be substituted in the phenyl group by methoxycarbonyl or carboxyl,
R[5] is hydrogen, methyl or a group of the formula

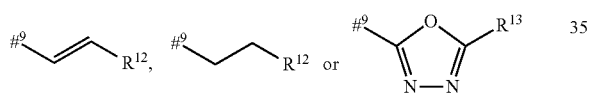

in which
[9] marks the linkage site with —CHCH$_2$-phenyl,
R[12] is phenyl which may be substituted by methoxycarbonyl, carboxyl or a group of the formula —S(O)$_2$OH,
R[13] is phenyl which may be substituted by methoxycarbonyl or carboxyl,
R[35] is methyl or hydroxy,
and also their salts, solvates and solvates of the salts.

Preferred subject matter of the present invention are compounds of the formula (XXXI) as indicated above, in which
$L^1$ is a bond,
B is a bond,
$L^2$ is linear (C$_2$-C$_6$)-alkanediyl or is a group of the formula

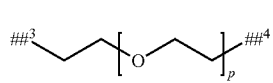

where
p is a number 2 or 3,
[3] marks the linkage site with the group B,
[4] marks the linkage site with the nitrogen atom,
D is the group of the formula

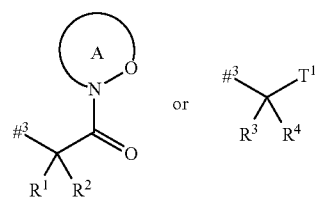

where
[3] marks the linkage site with the nitrogen atom,
R[1] is hydrogen,
R[2] is benzyl or 1H-indol-3-ylmethyl,
or
R[1] and R[2] together with the carbon atom to which they are bonded form a (1S,2R)-2-phenylcyclopropane-1,1-diyl group of the formula

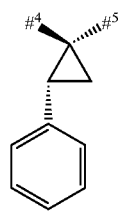

in which
[4] marks the linkage site with the adjacent nitrogen atom,
[5] marks the linkage site with the carbonyl group,
the ring A with the N—O moiety present therein is a mono- or bicyclic, optionally substituted heterocycle of the formula

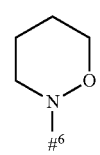

in which
[6] marks the linkage site with the carbonyl group,
R[6] is hydrogen, hydroxy or benzyloxy,
R[3] is hydrogen,
R[4] is benzyl or 1H-indol-3-ylmethyl,
or
R[3] and R[4] together with the carbon atom to which they are bonded form a (1S,2R)-2-phenylcyclopropane-1,1-diyl group of the formula

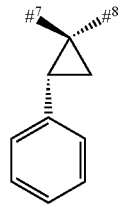

in which
[7] marks the linkage site with the adjacent nitrogen atom,
[8] marks the linkage site with the group $T^1$, $T^1$ is a group of the formula —C(=O)—OR$^7$ or —C(=O)—NR$^8$R$^9$, in which R$^7$ is hydrogen, R$^8$ is hydrogen, R$^9$ is hydrogen, R$^{35}$ is methyl, and also their salts, solvates and solvates of the salts.

Preferred subject matter of the present invention are compounds of the formula (XXXI) as indicated above, in which L$^1$ is a bond, B is a bond, L$^2$ is linear (C$_2$-C$_6$)-alkanediyl or is a group of the formula

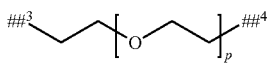

where p is a number 2 or 3,

$^3$ marks the linkage site with the group B,

$^4$ marks the linkage site with the nitrogen atom,

D is a group of the formula

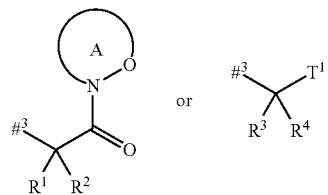

where

$^3$ marks the linkage site with the nitrogen atom,

R$^1$ is hydrogen,

R$^2$ 4-hydroxybenzyl or 1H-indol-3-ylmethyl, or

R$^1$ and R$^2$ together with the carbon atom to which they are bonded form a (1S,2R)-2-phenylcyclopropane-1,1-diyl group of the formula

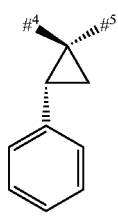

in which

$^4$ marks the linkage site with the adjacent nitrogen atom,

$^5$ marks the linkage site with the carbonyl group, the ring A with the N—O moiety present therein is a mono- or bicyclic, optionally substituted heterocycle of the formula

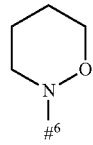

in which

$^6$ marks the linkage site with the carbonyl group,

R$^6$ is hydrogen, hydroxy or benzyloxy,

R$^3$ is hydrogen,

R$^4$ is 4-hydroxybenzyl or 1H-indol-3-ylmethyl, or

R$^3$ and R$^4$ together with the carbon atom to which they are bonded form a (1S,2R)-2-phenylcyclopropane-1,1-diyl group of the formula

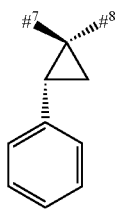

in which

$^7$ marks the linkage site with the adjacent nitrogen atom,

$^8$ marks the linkage site with the group T$^1$,

T$^1$ is a group of the formula —C(=O)—OR$^7$ or —C(=O)—NR$^8$R$^9$, in which

R$^7$ is hydrogen,

R$^8$ is hydrogen,

R$^9$ is hydrogen,

R$^{35}$ is methyl, and also their salts, solvates and solvates of the salts.

Preferred subject matter of the present invention are compounds of the formulae (XXXa) and (XXXI) selected from the following group:

N-[6-(3-{[(2R)-2-amino-2-carboxyethyl]sulphanyl}-2,5-dioxopyrrolidin-1-yl)hexyl]-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide, N-[6-(3-{[(2R)-2-amino-2-carboxyethyl]sulphanyl}-2,5-dioxopyrrolidin-1-yl)hexyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, N-(6-{[(5S)-5-amino-5-carboxypentyl]amino}-6-oxohexyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate, N-(6-{[(5S)-5-amino-5-carboxypentyl]amino}-6-oxohexyl)-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide, and also their salts, solvates and solvates of the salts.

The present invention additionally provides binder-drug conjugates of the general formula (I)

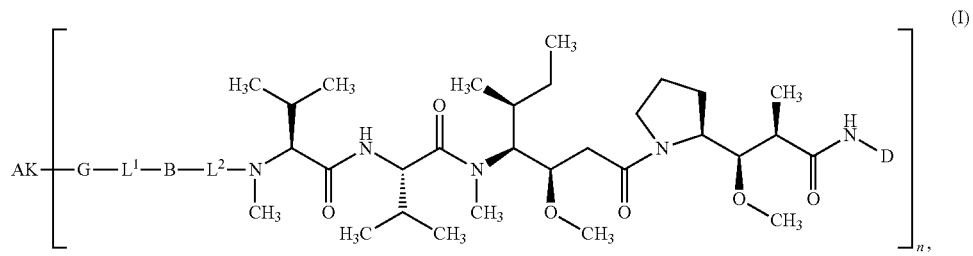

in which
n is a number from 1 to 50,
AK is a binder,
the group §-G-L$^1$-B-L$^2$-§§ is a linker,
where
§ marks the linkage site with the group AK and
§§ marks the linkage site with the nitrogen atom,
D is a group of the formula

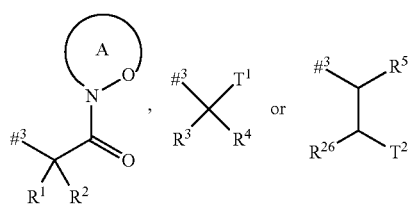

where
$^3$ marks the linkage site with the nitrogen atom,
R$^1$ is hydrogen,
R$^2$ is 1-hydroxyethyl, benzyl, 1-phenylethyl or 1H-indol-3-ylmethyl,
or
R$^1$ and R$^2$ together with the carbon atom to which they are bonded form a (1S,2R)-2-phenylcyclopropane-1,1-diyl group of the formula

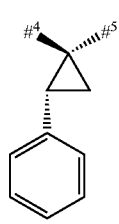

in which
$^4$ marks the linkage site with the adjacent nitrogen atom,
$^5$ marks the linkage site with the carbonyl group,
the ring A with the N—O moiety present therein is a mono- or bicyclic, optionally substituted heterocycle of the formula

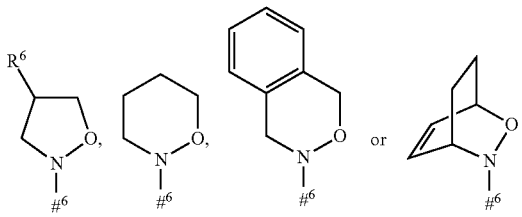

in which
$^6$ marks the linkage site with the carbonyl group,
R$^6$ is hydrogen, hydroxy or benzyloxy,
R$^3$ is hydrogen,
R$^4$ 1-hydroxyethyl, benzyl, 1-phenylethyl or 1H-indol-3-ylmethyl,
or
R$^3$ and R$^4$ together with the carbon atom to which they are bonded form a (1S,2R)-2-phenylcyclopropane-1,1-diyl group of the formula

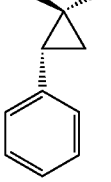

in which
$^7$ marks the linkage site with the adjacent nitrogen atom,
$^8$ marks the linkage site with the group T$^1$,
T$^1$ is a group of the formula —C(=O)—OR$^7$, —C(=O)—NR$^8$R$^9$, —C(=O)—NH—NH—R$^{10}$ or —CH$_2$—O—R$^{11}$,
in which
R$^7$ is hydrogen, methyl, ethyl, n-propyl, tert-butyl, benzyl or adamantylmethyl,
R$^8$ is hydrogen or methyl,
R$^9$ is hydrogen, methyl, ethyl, n-propyl or benzyl,
or
R$^8$ and R$^9$ together with the nitrogen atom to which they are bonded form a 4- to 7-membered heterocycle,
R$^{10}$ is benzoyl,
R$^{11}$ is benzyl, which may be substituted in the phenyl group by methoxycarbonyl or carboxyl,
R$^5$ is hydrogen, methyl or a group of the formula

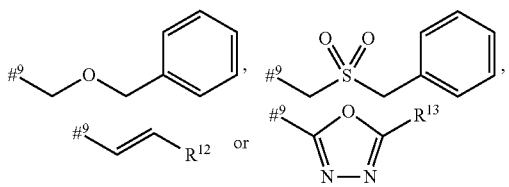

in which
⁹ marks the linkage site with —CHC($R^{26}$)-$T^2$,
$R^{12}$ is phenyl which may be substituted by methoxycarbonyl, carboxyl or a group of the formula —S(O)$_2$OH,
$R^{13}$ is phenyl which may be substituted by methoxycarbonyl or carboxyl,
$R^{26}$ is hydrogen or hydroxy,
$T^2$ is phenyl, benzyl, 1H-indol-3-yl or 1H-indol-3-ylmethyl,
and also their salts, solvates and solvates of the salts.

Preferred subject matter of the invention are binder-drug conjugates of the general formula (I), in which
n is a number from 1 to 50,
AK is $AK_1$ or $AK_2$
where
  $AK_1$ is a binder which is bonded via a sulphur atom of the binder to the group G,
  $AK_2$ is a binder which is bonded via a nitrogen atom of the binder to the group G,
G when AK=$AK_1$, is a group of the formula

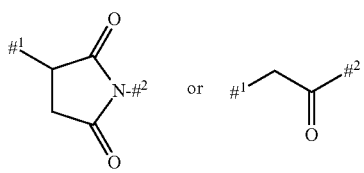

where
¹ marks the linkage site with the sulphur atom of the binder,
² marks the linkage site with the group $L^1$,
or
when AK=$AK_2$, is carbonyl,
$L^1$ is a bond, linear ($C_1$-$C_{10}$)-alkanediyl or is a group of the formula

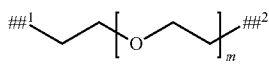

where
m is a number from 2 to 6,
¹ marks the linkage site with the group G,
² marks the linkage site with the group B,
where ($C_1$-$C_{10}$)-alkanediyl may be substituted by 1 to 4 methyl substituents,
and
where two carbon atoms of the alkanediyl chain in 1,2, 1,3 or 1,4 relation to one another, with inclusion of any carbon atoms situated between them, may be bridged to form a ($C_3$-$C_6$)-cycloalkyl ring or a phenyl ring,
B is a bond or a group of the formula

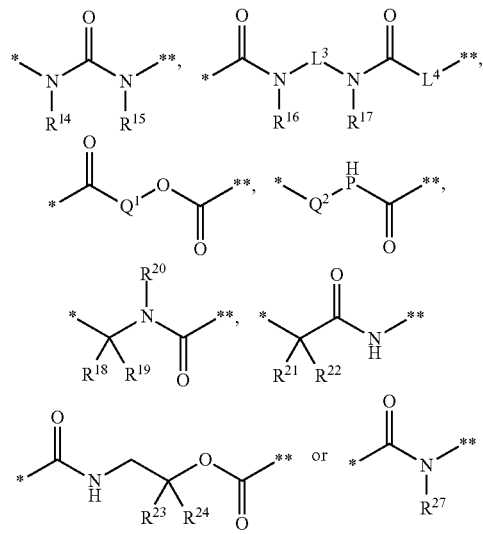

where
\* marks the linkage site with $L^1$,
\*\* marks the linkage site with $L^2$,
P is O or NH,
$L^3$ is a bond or ($C_2$-$C_4$)-alkanediyl,
$L^4$ is a bond or a group of the formula

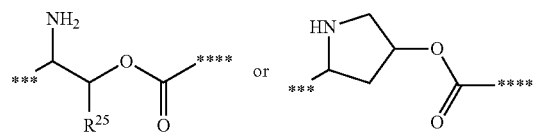

in which
\*\*\* marks the linkage site with the carbonyl group,
\*\*\*\* marks the linkage site with $L^2$,
$R^{25}$ is hydrogen or methyl,
$Q^1$ is a 4- to 7-membered heterocycle,
$Q^2$ is a 3- to 7-membered carbocycle or a 4- to 7-membered heterocycle,
$R^{14}$ is hydrogen or ($C_1$-$C_4$)-alkyl,
$R^{15}$ is hydrogen or ($C_1$-$C_4$)-alkyl,
or
$R^{14}$ and $R^{15}$ together with the atoms to which they are bonded form a 5- or 6-membered heterocycle,
$R^{16}$ is hydrogen or ($C_1$-$C_4$)-alkyl,
$R^{17}$ is hydrogen or ($C_1$-$C_4$)-alkyl,
or
$R^{16}$ and $R^{17}$ together with the atoms to which they are bonded form a 5- or 6-membered heterocycle,
$R^{18}$ is hydrogen or ($C_1$-$C_4$)-alkyl,
$R^{19}$ is hydrogen or the side group of a natural α-amino acid or of its homologues or isomers,
$R^{20}$ is hydrogen or ($C_1$-$C_4$)-alkyl,
or
$R^{19}$ and $R^{20}$ together with the atoms to which they are bonded form a pyrrolidinyl ring,
$R^{21}$ is hydrogen or ($C_1$-$C_4$)-alkyl,
$R^{22}$ is hydrogen or ($C_1$-$C_4$)-alkyl,
or
$R^{21}$ and $R^{22}$ together with the atoms to which they are bonded form a 3- to 7-membered carbocycle,
$R^{23}$ is ($C_1$-$C_4$)-alkyl, $R^{24}$ is hydrogen or $(C_1-C_4)$-alkyl,
$R^{27}$ is hydrogen or $(C_1-C_4)$-alkyl,
$L^2$ is linear $(C_2-C_{10})$-alkanediyl or is a group of the formula

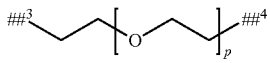

where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 to 4 methyl substituents,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
D has the definitions indicated above,
and also their salts, solvates and solvates of the salts.

Preferred subject matter of the invention are binder-drug conjugates of the general formula (I), in which
n is a number from 1 to 50,
AK is $AK_1$ or $AK_2$
where
  $AK_1$ is an antibody or an antigen-binding antibody fragment and are bonded via a sulphur atom to the group G,
  $AK_2$ is an antibody or an antigen-binding antibody fragment and are bonded via a nitrogen atom to the group G,
G, $L^1$, B, $L^2$ and D have the definitions indicated above,
and also their salts, solvates and solvates of the salts.

Preferred subject matter of the present invention are binder-drug conjugates of the general formula (I), in which
n is a number from 1 to 20,
AK is $AK_1$ or $AK_2$
where
  $AK_1$ is an antibody or antigen-binding antibody fragment (e.g., an antibody or an antigen-binding antibody fragment which binds to C4.4a) and is bonded via the sulphur atom of a cysteine residue of the binder to the group G,
  $AK_2$ is an antibody or antigen-binding antibody fragment (e.g., an antibody or an antigen-binding antibody fragment which binds to C4.4a) and is bonded via the NH side group of a lysine residue of the binder to the group G,
G when $AK=AK_1$, is a group of the formula

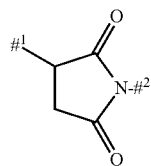

in which
$\#^1$ marks the linkage site with the cysteine residue of the binder,
$\#^2$ marks the linkage site with the group $L^1$,
or
when $AK=AK_2$, is carbonyl,
$L^1$ is a bond, linear $(C_2-C_6)$-alkanediyl or is a group of the formula

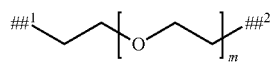

where
m is a number from 2 to 6,
$\#\#^1$ marks the linkage site with the group G,
$\#\#^2$ marks the linkage site with the group B,
where $(C_2-C_6)$-alkanediyl may be substituted by 1 or 2 methyl substituents,
B is a bond or a group of the formula

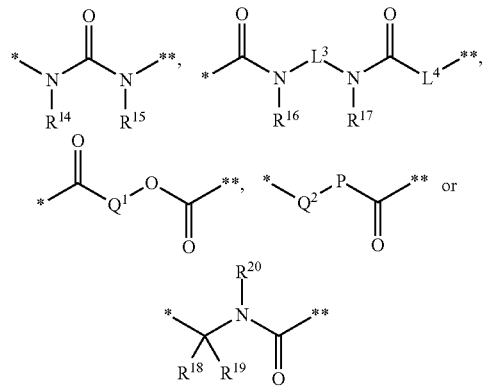

where
* marks the linkage site with $L^1$,
** marks the linkage site with $L^2$,
P is O or NH,
$L^3$ is a bond or ethane-1,2-diyl,
$L^4$ is a bond or a group of the formula

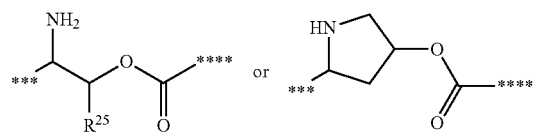

in which
*** marks the linkage site with the carbonyl group,
**** marks the linkage site with $L^2$,
$R^{25}$ is methyl,
$Q^1$ is a 4- to 6-membered carbocycle or piperidine-1,4-diyl,
$Q^2$ is cyclopentyl or cyclohexyl,
$R^{14}$ is hydrogen,
$R^{15}$ is hydrogen,
$R^{16}$ is hydrogen or methyl,
$R^{17}$ is hydrogen or methyl,
or
  $R^{16}$ and $R^{17}$ together with the atoms to which they are bonded form a piperazinyl ring,
$R^{18}$ is hydrogen,
$R^{19}$ is hydrogen, methyl, propan-2-yl, 2-methylpropan-1-yl or 1-methylpropan-1-yl,
$R^{20}$ is hydrogen or methyl,
or
  $R^{19}$ and $R^{20}$ together with the atoms to which they are bonded form a pyrrolidinyl ring,
$L^2$ is linear $(C_2-C_6)$-alkanediyl or is a group of the formula

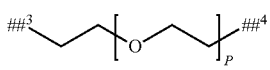

where
p is a number from 2 to 6,
³ marks the linkage site with the group B,
⁴ marks the linkage site with the nitrogen atom,
where $(C_2\text{-}C_6)$-alkanediyl may be substituted by 1 or 2 methyl substituents,
D is a group of the formula

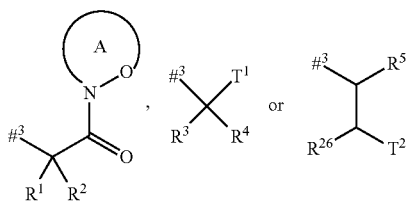

where
³ marks the linkage site with the nitrogen atom,
$R^1$ is hydrogen,
$R^2$ is 1-hydroxyethyl, benzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula

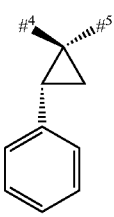

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

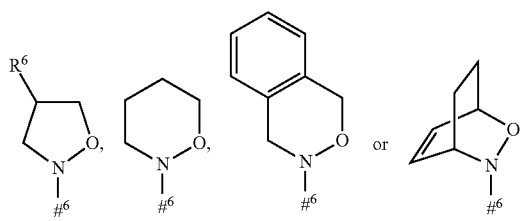

in which
⁶ marks the linkage site with the carbonyl group,
$R^6$ is hydrogen, hydroxy or benzyloxy,
$R^3$ is hydrogen,
$R^4$ is 1-hydroxyethyl, benzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula

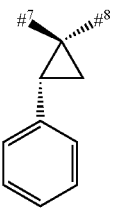

in which
⁷ marks the linkage site with the adjacent nitrogen atom,
⁸ marks the linkage site with the group $T^1$,
$T^1$ is a group of the formula —C(=O)—OR⁷, —C(=O)—NR⁸R⁹, —C(=O)—NH—NH—R¹⁰ or —CH₂—O—R¹¹,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
or
$R^8$ and $R^9$ together with the nitrogen atom to which they are bonded form a 4- to 7-membered heterocycle,
$R^{10}$ is benzoyl,
$R^{11}$ is benzyl, which may be substituted in the phenyl group by methoxycarbonyl or carboxyl,
$R^5$ is hydrogen, methyl or a group of the formula

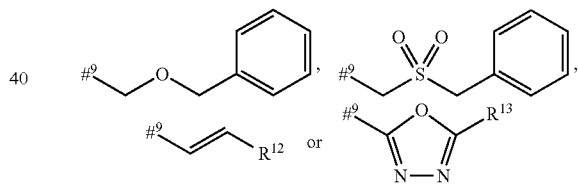

in which
⁹ marks the linkage site with —CHC(R²⁶)-T²,
$R^{12}$ is phenyl which may be substituted by methoxycarbonyl, carboxyl or a group of the formula —S(O)₂OH,
$R^{13}$ is phenyl which may be substituted by methoxycarbonyl or carboxyl,
$R^{26}$ is hydrogen or hydroxy,
$T^2$ is phenyl, benzyl, 1H-indol-3-yl or 1H-indol-3-ylmethyl,
and also their salts, solvates and solvates of the salts.
Particularly preferred subject matter of the present invention are binder-drug conjugates of the general formula (I), in which
n is a number from 1 to 10,
AK is $AK_1$ or $AK_2$
where
$AK_1$ is an antibody or antigen-binding antibody fragment (e.g., an antibody which comprises the six CDR sequences of an antibody listed in Table 2, the variable light and variable heavy chain of an antibody listed in Table 2 or the light and heavy chain of an antibody listed in Table 2), and is bonded via the sulphur atom of a cysteine residue of the binder to the group G, AK$_2$ is an antibody or antigen-binding antibody fragment (e.g., an antibody which comprises the six CDR sequences of an antibody listed in Table 2, the variable light and variable heavy chain of an antibody listed in Table 2 or the light and heavy chain of an antibody listed in Table 2), and is bonded via the NH side group of a lysine residue of the binder to the group G, G when AK=AK$_1$, is a group of the formula

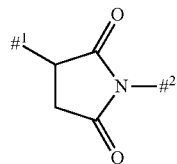

in which
$^1$ marks the linkage site with the cysteine residue of the binder,
$^2$ marks the linkage site with the group L$^1$,
or
when AK=AK$_2$, is carbonyl,
L$^1$ is a bond, linear (C$_2$-C$_6$)-alkanediyl or is a group of the formula

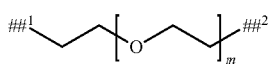

where
m is a number 2 or 3,
$^1$ marks the linkage site with the group G,
$^2$ marks the linkage site with the group B,
where (C$_2$-C$_6$)-alkanediyl may be substituted by 1 or 2 methyl substituents, B is a bond or a group of the formula

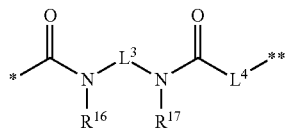

where
* marks the linkage site with L$^1$,
** marks the linkage site with L$^2$,
L$^3$ is a bond or ethane-1,2-diyl,
L$^4$ is a bond or a group of the formula

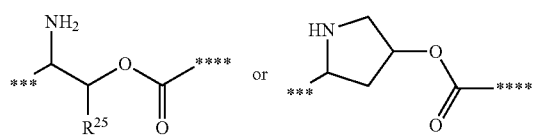

where
*** marks the linkage site with the carbonyl group,
**** marks the linkage site with L$^2$,
R$^{25}$ is methyl,
R$^{16}$ is hydrogen or methyl,
R$^{17}$ is hydrogen or methyl,
or
R$^{16}$ and R$^{17}$ together with the atoms to which they are bonded form a piperazinyl ring,
L$^2$ is linear (C$_2$-C$_6$)-alkanediyl,
D is a group of the formula

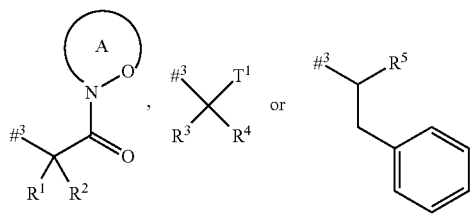

where
$^3$ marks the linkage site with the nitrogen atom,
R$^1$ is hydrogen,
R$^2$ is 1-hydroxyethyl, benzyl, 1-phenylethyl or 1H-indol-3-ylmethyl,
or
R$^1$ and R$^2$ together with the carbon atom to which they are bonded form a (1S,2R)-2-phenylcyclopropane-1,1-diyl group of the formula

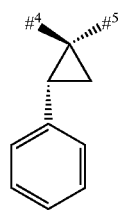

in which
$^4$ marks the linkage site with the adjacent nitrogen atom,
$^5$ marks the linkage site with the carbonyl group,
the ring A with the N—O moiety present therein is a mono- or bicyclic, optionally substituted heterocycle of the formula

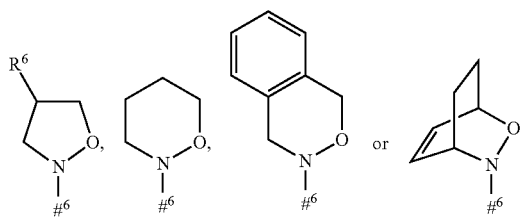

in which
$^6$ marks the linkage site with the carbonyl group,
R$^6$ is hydrogen, hydroxy or benzyloxy,
R$^3$ is hydrogen,
R$^4$ is benzyl, 1-phenylethyl or 1H-indol-3-ylmethyl,
or
R$^3$ and R$^4$ together with the carbon atom to which they are bonded form a (1S,2R)-2-phenylcyclopropane-1,1-diyl group of the formula

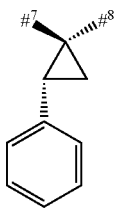

in which
⁷ marks the linkage site with the adjacent nitrogen atom,
⁸ marks the linkage site with the group $T^1$,
$T^1$ is a group of the formula —C(=O)—OR⁷, —C(=O)—NR⁸R⁹ or —CH₂—O—R¹¹,
in which
$R^7$ is hydrogen, methyl, ethyl, n-propyl, benzyl or adamantylmethyl,
$R^8$ is hydrogen or methyl,
$R^9$ is hydrogen, methyl, ethyl, n-propyl or benzyl,
$R^{11}$ is benzyl, which may be substituted in the phenyl group by methoxycarbonyl or carboxyl,
$R^5$ is hydrogen or a group of the formula

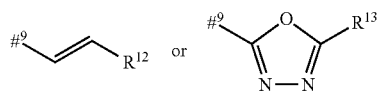

in which
⁹ marks the linkage site with —CHC(R²⁶)phenyl,
$R^{12}$ is phenyl which may be substituted by methoxycarbonyl, carboxyl or a group of the formula —S(O)₂OH,
$R^{13}$ is phenyl which may be substituted by methoxycarbonyl or carboxyl,
and also their salts, solvates and solvates of the salts.

Particularly preferred subject matter of the present invention are binder-drug conjugates of the general formula (I), in which
n is a number from 1 to 10,
AK is $AK_1$ or $AK_2$
  where
  $AK_1$ is an antibody or antigen-binding antibody fragment (e.g., an antibody which comprises the six CDR sequences of the antibody B01-3, B01-10 or D02-6, the variable light and variable heavy chain of the antibody B01-3, B01-10 or D02-6 or the light and heavy chain of the antibody B01-3, B01-10 or D02-6), and is bonded via the sulphur atom of a cysteine residue of the binder to the group G,
  $AK_2$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and is bonded via the NH side group of a lysine residue of the binder to the group G,
G when AK=$AK_1$, is a group of the formula

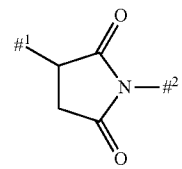

in which
¹ marks the linkage site with the cysteine residue of the binder,
² marks the linkage site with the group $L^1$,
or
when AK=$AK_2$, is carbonyl,
$L^1$ is a bond, linear $(C_2\text{-}C_6)$-alkanediyl or is a group of the formula

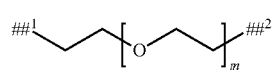

where
m is a number 2 or 3,
¹ marks the linkage site with the group G,
² marks the linkage site with the group B,
where $(C_2\text{-}C_6)$-alkanediyl may be substituted by 1 or 2 methyl substituents,
B is a bond or a group of the formula

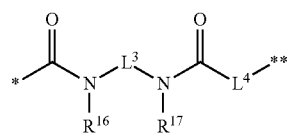

where
* marks the linkage site with $L^1$,
** marks the linkage site with $L^2$,
$L^3$ is a bond or ethane-1,2-diyl,
$L^4$ is a bond or a group of the formula

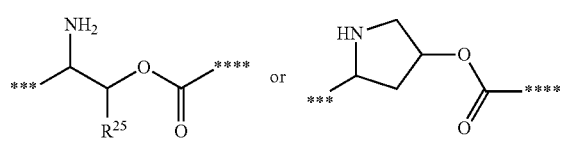

in which
*** marks the linkage site with the carbonyl group,
**** marks the linkage site with $L^2$,
$R^{25}$ is methyl,
$R^{16}$ is hydrogen or methyl,
$R^{17}$ is hydrogen or methyl,
or
$R^{16}$ and $R^{17}$ together with the atoms to which they are bonded form a piperazinyl ring,
$L^2$ is linear $(C_2\text{-}C_6)$-alkanediyl,
D is a group of the formula

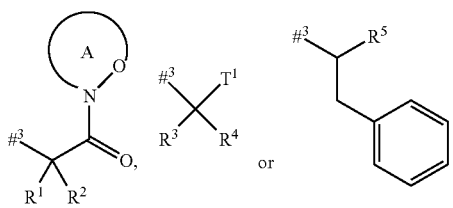

where
³ marks the linkage site with the nitrogen atom,
R¹ is hydrogen,
R² is 1-hydroxyethyl, benzyl, 1-phenylethyl or 1H-indol-3-ylmethyl,
or
R¹ and R² together with the carbon atom to which they are bonded form a (1S,2R)-2-phenylcyclopropane-1,1-diyl group of the formula

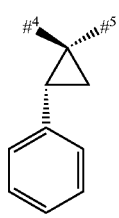

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

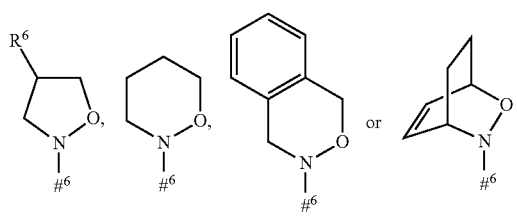

in which
⁶ marks the linkage site with the carbonyl group,
R⁶ is hydrogen, hydroxy or benzyloxy,
R³ is hydrogen,
R⁴ is benzyl, 1-phenylethyl or 1H-indol-3-ylmethyl,
or
R³ and R⁴ together with the carbon atom to which they are bonded form a (1S,2R)-2-phenylcyclopropane-1,1-diyl group of the formula

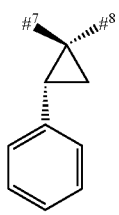

in which
⁷ marks the linkage site with the adjacent nitrogen atom,
⁸ marks the linkage site with the group T,
T¹ is a group of the formula —C(=O)—OR⁷, —C(=O)—NR⁸R⁹ or —CH₂—O—R¹¹,
in which
R⁷ is hydrogen, methyl, ethyl, n-propyl, benzyl or adamantylmethyl,
R⁸ is hydrogen or methyl,
R⁹ is hydrogen, methyl, ethyl, n-propyl or benzyl,
R¹¹ is benzyl, which may be substituted in the phenyl group by methoxycarbonyl or carboxyl,
R⁵ is hydrogen or a group of the formula

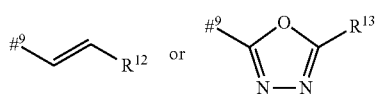

in which
⁹ marks the linkage site with —CHC(R²⁶)phenyl,
R¹² is phenyl which may be substituted by methoxycarbonyl, carboxyl or a group of the formula —S(O)₂OH,
R¹³ is phenyl which may be substituted by methoxycarbonyl or carboxyl,
and also their salts, solvates and solvates of the salts.

The present invention additionally provides compounds of the formula (XXX)

(XXX)

[Structure of compound XXX shown]

in which

Cys is a cysteine residue which is bonded via the sulphur atom of the side chain to a carbon atom of the succinimide.

$L^1$ is a bond, linear $(C_1-C_{10})$-alkanediyl or is a group of the formula

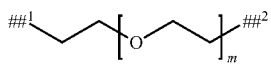

in which m is a number from 2 to 6, $\#\#^1$ marks the linkage site with the group G, $\#\#^2$ marks the linkage site with the group B, where $(C_1-C_{10})$-alkandiyl may be substituted by 1 to 4 methyl substituents, and where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring, B is a bond or a group of the formula

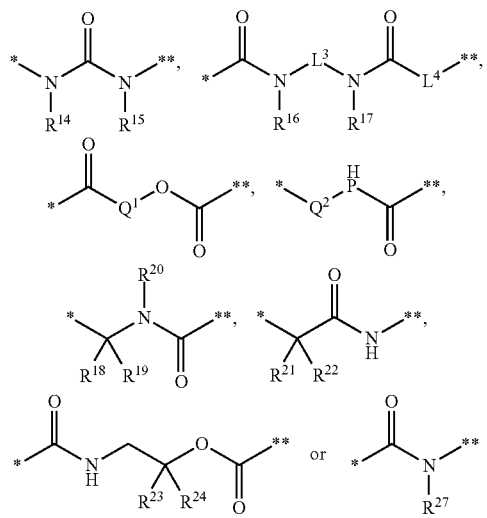

where

\* marks the linkage site with $L^1$,

\*\* marks the linkage site with $L^2$,

P is O or NH, $L^3$ is a bond or $(C_2-C_4)$-alkanediyl, $L^4$ is a bond or a group of the formula

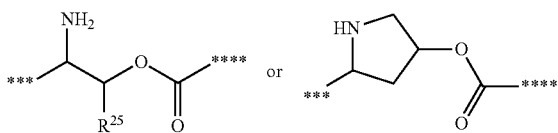

in which

\*\*\* marks the linkage site with the carbonyl group,

\*\*\*\* marks the linkage site with $L^2$, $R^{25}$ is hydrogen or methyl $Q^1$ is a 3- to 7-membered carbocycle or a 4- to 7-membered aza heterocycle, $Q^2$ is a 3- to 7-membered carbocycle or a 4- to 7-membered aza heterocycle, $R^{14}$ is hydrogen or $(C_1-C_4)$-alkyl, $R^{15}$ is hydrogen or $(C_1-C_4)$-alkyl, or $R^{14}$ and $R^{15}$ together with the atoms to which they are bonded form a 5- or 6-membered heterocycle, $R^{16}$ is hydrogen or $(C_1-C_4)$-alkyl, $R^{17}$ is hydrogen or $(C_1-C_4)$-alkyl, or $R^{16}$ and $R^{17}$ together with the atoms to which they are bonded form a 5- or 6-membered heterocycle, $R^{18}$ is hydrogen or $(C_1-C_4)$-alkyl, $R^{19}$ is hydrogen or the side group of a natural α-amino acid or of its homologues or isomers, $R^{20}$ is hydrogen or $(C_1-C_4)$-alkyl, or $R^{19}$ and $R^{20}$ together with the atoms to which they are bonded form a pyrrolidinyl ring, $R^{21}$ is hydrogen or $(C_1-C_4)$-alkyl, $R^{22}$ is hydrogen or $(C_1-C_4)$-alkyl, or $R^{21}$ and $R^{22}$ together with the atoms to which they are bonded form a 3- to 7-membered carbocycle, $R^{23}$ is $(C_1-C_4)$-alkyl, $R^{24}$ is hydrogen or $(C_1-C_4)$-alkyl, $R^{27}$ is hydrogen or $(C_1-C_4)$-alkyl, $L^2$ is linear $(C_2-C_{10})$-alkanediyl or is a group of the formula

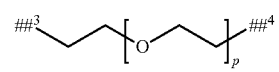

where p is a number from 2 to 6, $\#\#^3$ marks the linkage site with the group B, $\#\#^4$ marks the linkage site with the nitrogen atom, where $(C_2-C_{10})$-alkanediyl may be substituted by 1 to 4 substituents, and where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring, D is a group of the formula

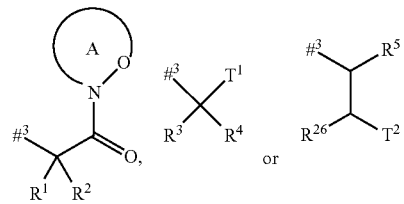

in which $\#^3$ marks the linkage site with the nitrogen atom, $R^1$ is hydrogen, $R^2$ is 1-hydroxyethyl, benzyl, 1-phenylethyl or 1H-indol-3-ylmethyl, or $R^1$ and $R^2$ together with the carbon atom to which they are bonded form a (1S,2R)-2-phenylcyclopropane-1,1-diyl group of the formula

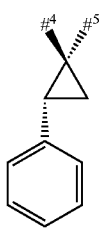

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

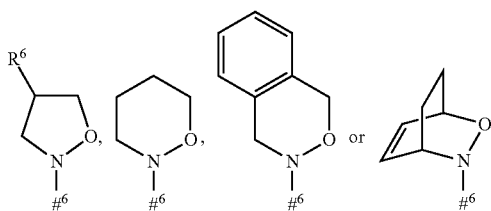

in which
⁶ marks the linkage site with the carbonyl group,
$R^6$ is hydrogen, hydroxy or benzyloxy,
$R^3$ is hydrogen,
$R^4$ is 1-hydroxyethyl, benzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula

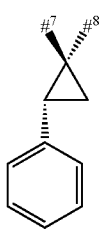

in which
⁷ marks the linkage site with the adjacent nitrogen atom,
⁸ marks the linkage site with the group $T^1$,
$T^1$ is a group of the formula —C(=O)—$OR^7$, —C(=O)—$NR^8R^9$, —C(=O)—NH—NH—$R^{10}$ or —$CH_2$—O—$R^{11}$,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
or
$R^8$ and $R^9$ together with the nitrogen atom to which they are bonded form a 4- to 7-membered heterocycle,
$R^{10}$ is benzoyl,
$R^{11}$ is benzyl, which may be substituted in the phenyl group by methoxycarbonyl or carboxyl,
$R^5$ is hydrogen, methyl or a group of the formula

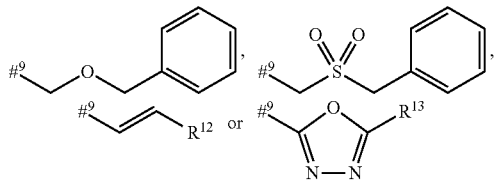

in which
⁹ marks the linkage site with —CHC($R^{26}$)-$T^2$,
$R^{12}$ is phenyl which may be substituted by methoxycarbonyl, carboxyl or a group of the formula —S(O)$_2$OH,
$R^{13}$ is phenyl which may be substituted by methoxycarbonyl or carboxyl,
$R^{26}$ is hydrogen or hydroxy,
$T^2$ is phenyl, benzyl, 1H-indol-3-yl or 1H-indol-3-ylmethyl,
and also their salts, solvates and solvates of the salts.
Particularly preferred in the context of the present invention in addition are also compounds of the formula (XXX), in which
Cys is a cysteine residue which is bonded via the sulphur atom of the side chain via a carbon atom of the succinimide,
$L^1$ is a bond, linear ($C_2$-$C_6$)-alkanediyl or is a group of the formula

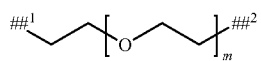

in which
m is a number from 2 to 6,
¹ marks the linkage site with the group G,
² marks the linkage site with the group B,
where ($C_2$-$C_6$)-alkandiyl may be substituted by 1 or 2 methyl substituents,
B is a bond or a group of the formula

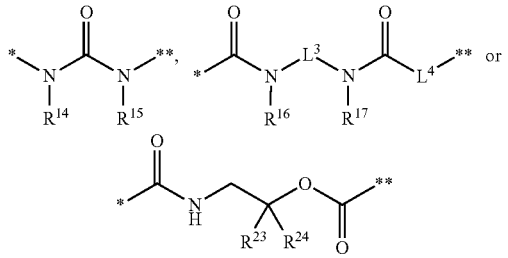

where
* marks the linkage site with $L^1$,
** marks the linkage site with $L^2$,
$L^3$ is a bond or ethane-1,2-diyl,
$L^4$ is a bond,
$R^{14}$ is hydrogen,
$R^{15}$ is hydrogen,
$R^{16}$ is hydrogen or methyl,
$R^{17}$ is hydrogen or methyl,
or $R^{16}$ and $R^{17}$ together with the atoms to which they are bonded form a piperazinyl ring,
$R^{23}$ is methyl,
$R^{24}$ is hydrogen or methyl,
$L^2$ is linear $(C_2-C_6)$-alkanediyl or is a group of the formula

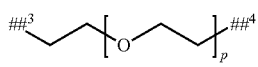

where
p is a number 2 or 3,
$\#\#^3$ marks the linkage site with the group B,
$\#\#^4$ marks the linkage site with the nitrogen atom,
D is a group of the formula

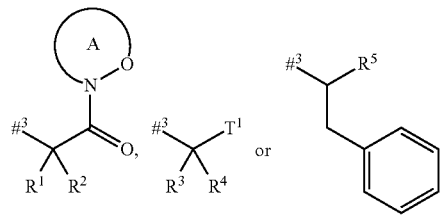

in which
$\#^3$ marks the linkage site with the nitrogen atom,
$R^1$ is hydrogen,
$R^2$ is 1-hydroxyethyl, benzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula

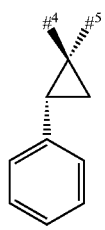

in which
$\#^4$ marks the linkage site with the adjacent nitrogen atom,
$\#^5$ marks the linkage site with the carbonyl group,
the ring A with the N—O moiety present therein is a mono- or bicyclic, optionally substituted heterocycle of the formula

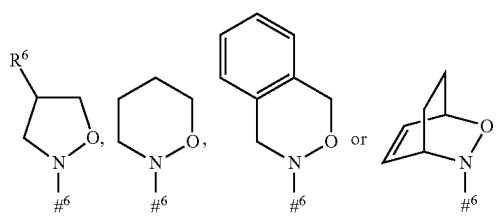

in which
$\#^6$ marks the linkage site with the carbonyl group,
$R^6$ is hydrogen, hydroxy or benzyloxy,
$R^3$ is hydrogen,
$R^4$ is benzyl, 1-phenylethyl or 1H-indol-3-ylmethyl,
or
$R^3$ and $R^4$ together with the carbon atom to which they are bonded form a (1S,2R)-2-phenylcyclopropane-1,1-diyl group of the formula

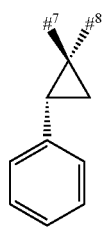

in which
$\#^7$ marks the linkage site with the adjacent nitrogen atom,
$\#^8$ marks the linkage site with the group T,
$T^1$ is a group of the formula —C(=O)—OR$^7$, —C(=O)—NR$^8$R$^9$, —C(=O)—NH—NH—R$^{10}$ or —CH$_2$—O—R$^{11}$,
in which
$R^7$ is hydrogen, methyl, ethyl, n-propyl, benzyl or adamantylmethyl,
$R^8$ is hydrogen or methyl,
$R^9$ is hydrogen, methyl, ethyl, n-propyl or benzyl,
$R^{10}$ is benzoyl,
$R^{11}$ is benzyl, which may be substituted in the phenyl group by methoxycarbonyl or carboxyl,
$R^5$ is hydrogen or a group of the formula

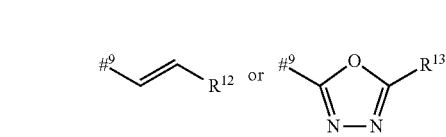

in which
$\#^9$ marks the linkage site with —CHC(R$^{26}$)phenyl,
$R^{12}$ is phenyl which may be substituted by methoxycarbonyl, carboxyl or a group of the formula —S(O)$_2$OH,
$R^{13}$ is phenyl which may be substituted by methoxycarbonyl or carboxyl,
and also their salts, solvates and solvates of the salts.

Preferred in the context of the present invention are also compounds of the formula (Ia), in which n=1-20, more preferably n=1-10 and very preferably n=2-8.

Preferred in the context of the present invention are also compounds of the formula (Ia), in which
AK is AK$_1$
where
AK$_1$ is an antibody or antigen-binding antibody fragment (e.g., an antibody or an antigen-binding antibody fragment which binds to C4.4a) and is bonded via the sulphur atom of a cysteine residue of the binder to the group G,
G is a group of the formula

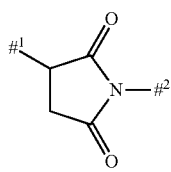

where
¹ marks the linkage site with the cysteine residue of the binder,
² marks the linkage site with the group $L^1$,
and
n, $L^1$, B, $L^2$, D and $R^{35}$ have the definitions indicated above, and also their salts, solvates and solvates of the salts.

Preferred in the context of the present invention are also compounds of the formula (Ia), in which AK is $AK_2$
where
$AK_2$ is an antibody or antigen-binding antibody fragment (e.g., an antibody or an antigen-binding antibody fragment which binds to C4.4a) and is bonded via the NH side group of a lysine residue of the binder to the group G,
G is carbonyl,
and
n, $L^1$, B, $L^2$, D and $R^{35}$ have the definitions indicated above, and also their salts, solvates and solvates of the salts.

Preference in the context of the present invention is also given to compounds of the formula (Ia), in which AK is $AK_1$
where
$AK_1$ is an antibody or antigen-binding antibody fragment (e.g., an antibody which comprises the six CDR sequences of the antibody B01-3, B01-10 or D02-6, the variable light and variable heavy chain of the antibody B01-3, B01-10 or D02-6 or the light and heavy chain of the antibody B01-3, B01-10 or D02-6), and which is attached via the sulphur atom of a cysteine residue of the binder to the group G,
G is a group of the formula

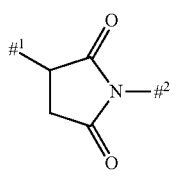

where
¹ marks the linkage site with the cysteine residue of the binder,
² marks the linkage site with the group $L^1$,
and
n, $L^1$, B, $L^2$, D and $R^{35}$ have the definitions indicated above, and also their salts, solvates and solvates of the salts.

Preference in the context of the present invention is also given to compounds of the formula (Ia), in which AK is $AK_2$
where
$AK_2$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and which is bonded via the NH side group of a lysine residue of the binder to the group G,
G is carbonyl,
and
n, $L^1$, B, $L^2$, D and $R^{35}$ have the definitions indicated above, and also their salts, solvates and solvates of the salts.

Preference in the context of the present invention is also given to compounds of the general formula (Ia), in which AK is $AK_2$
where
$AK_2$ is an antibody or antigen-binding antibody fragment (e.g., an antibody which comprises the six CDR sequences of the antibody B01-3, B01-10, M31-B01 or D02-6, the variable light and variable heavy chain of the antibody B01-3, B01-10, M31-B01 or D02-6 or the light and heavy chain of the antibody B01-3, B01-10, M31-B01 or D02-6), and which is bonded via the NH side group of a lysine residue of the binder to the group G,
G is carbonyl,
$L^1$ is a bond,
B is a bond,
$L^2$ is linear $(C_3-C_6)$-alkanediyl or is a group of the formula

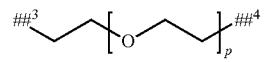

where
p is a number 2 or 3,
³ marks the linkage site with the group B,
⁴ marks the linkage site with the nitrogen atom,
n, D and $R^{35}$ have the definitions indicated above,
and also their salts, solvates and solvates of the salts.

Preference in the context of the present invention is also given to compounds of the general formula (Ia), in which AK is $AK_1$
where
$AK_1$ is an antibody or antigen-binding antibody fragment (e.g., an antibody which comprises the six CDR sequences of the antibody B01-3, B01-10 or D02-6, the variable light and variable heavy chain of the antibody B01-3, B01-10 or D02-6 or the light and heavy chain of the antibody B01-3, B01-10 or D02-6), and which is attached via the sulphur atom of a cysteine residue of the binder to the group G,
G is a group of the formula

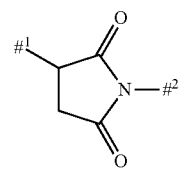

where
¹ marks the linkage site with the cysteine residue of the binder,
² marks the linkage site with the group $L^1$,
$L^1$ is a bond, linear $(C_3-C_5)$-alkanediyl or a group of the formula

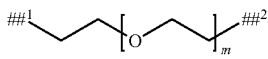

where
m is a number 2 or 3,
¹ marks the linkage site with the group G,
² marks the linkage site with the group B,
where $(C_3-C_5)$-alkanediyl may be substituted by 1 or 2 methyl substituents,
B is a bond or a group of the formula

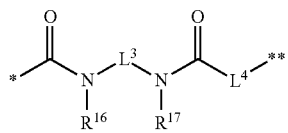

where
* marks the linkage site with $L^1$,
** marks the linkage site with $L^2$,
$L^3$ is a bond or ethane-1,2-diyl,
$L^4$ is a bond or a group of the formula

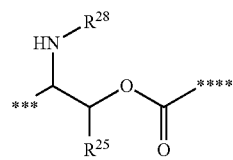

in which
*** marks the linkage site with the carbonyl group,
**** marks the linkage site with $L^2$,
$R^{25}$ is methyl,
$R^{28}$ is hydrogen, methylcarbonyl or tert-butyloxycarbonyl,
$R^{16}$ is hydrogen or methyl,
$R^{17}$ is hydrogen or methyl,
or
$R^{16}$ and $R^{17}$ together with the atoms to which they are bonded form a piperazinyl ring,
$L^2$ is linear $(C_3-C_5)$-alkanediyl or is a group of the formula

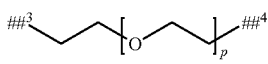

where
p is a number 2 or 3,
³ marks the linkage site with the group B,
⁴ marks the linkage site with the nitrogen atom,
and
n, D and $R^{35}$ have the definitions indicated above,
and also their salts, solvates and solvates of the salts.

Preferred in the context of the present invention are also compounds of the formula (Ia), (XXXa) and (XXXI), in which
$L^1$ is a bond,
B is a bond,
$L^2$ is linear $(C_3-C_6)$-alkanediyl or is a group of the formula

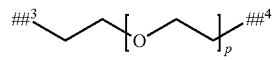

where
p is a number 2 or 3,
³ marks the linkage site with the group B,
⁴ marks the linkage site with the nitrogen atom,
and
n, AK, Cys, G, D and $R^{35}$ have the definitions indicated above,
and also their salts, solvates and solvates of the salts.

Preferred in the context of the present invention are also compounds of the formula (Ia), in which $L^1$ is linear $(C_1-C_{10})$-alkanediyl or a group of the formula

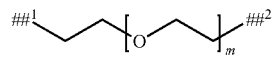

where
m is a number from 2 to 6,
¹ marks the linkage site with the group G,
² marks the linkage site with the group B,
where $(C_1-C_{10})$-alkanediyl may be substituted by 1 to 4 substituents selected independently of one another from the group consisting of methyl, hydroxyl and benzyl,
B is a bond or a group of the formula

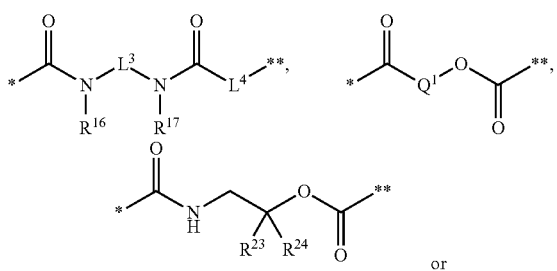

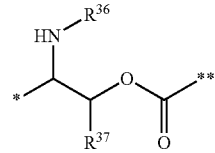

where
* marks the linkage site with $L^1$,
** marks the linkage site with $L^2$,
$L^3$ is a bond or $(C_2-C_4)$-alkanediyl,
$L^4$ is a group of the formula

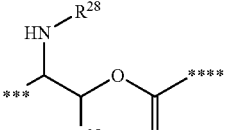 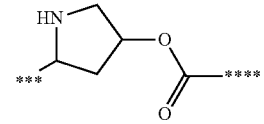

in which
*** marks the linkage site with the carbonyl group,
**** marks the linkage site with $L^2$,
$R^{25}$ is hydrogen or methyl,
$R^{28}$ is hydrogen, $(C_1-C_4)$-alkylcarbonyl, tert-butyloxycarbonyl or benzyloxycarbonyl, $Q^1$ is a 4- to 7-membered heterocycle,
$R^{16}$ is hydrogen or $(C_1-C_4)$-alkyl,
$R^{17}$ is hydrogen or $(C_1-C_4)$-alkyl,
or
$R^{16}$ and $R^{17}$ together with the atoms to which they are bonded form a 5- or 6-membered heterocycle,
$R^{23}$ is $(C_1-C_4)$-alkyl,
$R^{24}$ is hydrogen or $(C_1-C_4)$-alkyl,
$R^{36}$ is hydrogen, $(C_1-C_4)$-alkylcarbonyl, tert-butyloxycarbonyl or benzyloxycarbonyl,
$R^{37}$ is hydrogen or methyl,
or
$R^{36}$ and $R^{37}$ together with the atoms to which they are bonded form a pyrrolidine ring,
$L^2$ is linear $(C_2-C_{10})$-alkanediyl or is a group of the formula

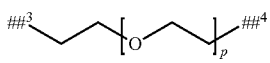

where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 to 4 substituents selected independently of one another from the group consisting of methyl, hydroxyl and benzyl,
and
n, AK, G, D and $R^{35}$ have the definitions indicated above,
and also their salts, solvates and solvates of the salts.

Preferred in the context of the present invention are also compounds of the formula (Ia), in which
$L^1$ is linear $(C_2-C_6)$-alkanediyl or a group of the formula

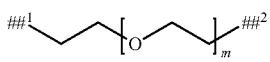

where
m is a number 2 or 3,
$\#\#^1$ marks the linkage site with the group G,
$\#\#^2$ marks the linkage site with the group B,
B is a bond or a group of the formula

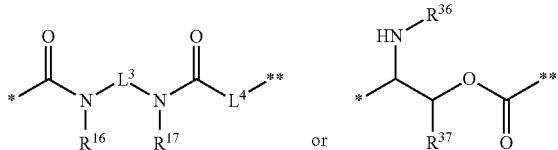

where
* marks the linkage site with $L^1$,
** marks the linkage site with $L^2$,
$L^3$ is a bond or ethane-1,2-diyl,
$L^4$ is a group of the formula

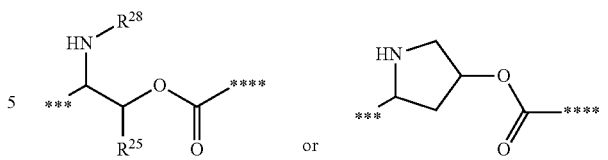

where
*** marks the linkage site with the carbonyl group,
**** marks the linkage site with $L^2$,
$R^{25}$ is hydrogen or methyl,
$R^{28}$ is hydrogen, methylcarbonyl or tert-butyloxycarbonyl,
$R^{16}$ is hydrogen or methyl,
$R^{17}$ is hydrogen or methyl,
or
$R^{16}$ and $R^{17}$ together with the atoms to which they are bonded form a piperazinyl ring,
$R^{36}$ is hydrogen, methylcarbonyl or tert-butyloxycarbonyl,
$R^{37}$ is hydrogen or methyl,
or
$R^{36}$ and $R^{37}$ together with the atoms to which they are bonded form a pyrrolidine ring,
$L^2$ is linear $(C_2-C_6)$-alkanediyl or is a group of the formula

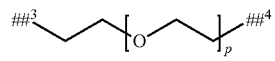

where
p is a number 2 or 3,
$\#\#^3$ marks the linkage site with the group B,
$\#\#^4$ marks the linkage site with the nitrogen atom,
and
n, AK, G, D and $R^{35}$ have the definitions indicated above,
and also their salts, solvates and solvates of the salts.

Preferred in the context of the present invention are also compounds of the formula (Ia) and (XXXa), in which
G is a group of the formula

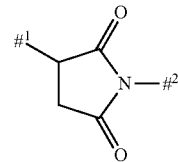

in which
$\#^1$ marks the linkage site with the cysteine residue of the binder,
$\#^2$ marks the linkage site with the group $L^1$,
$L^1$ is linear $(C_3-C_5)$-alkanediyl or a group of the formula

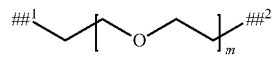

in which
m is a number 2 or 3,
$\#\#^1$ marks the linkage site with the group G,
$\#\#^2$ marks the linkage site with the group B,
where $(C_3-C_5)$-alkanediyl may be substituted by 1 or 2 methyl substituents, B is a bond or a group of the formula

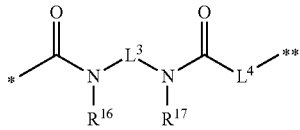

where
* marks the linkage site with $L^1$,
** marks the linkage site with $L^2$,
$L^3$ is a bond or ethane-1,2-diyl,
$L^4$ is a bond,
$L^2$ is linear $(C_3-C_5)$-alkanediyl or is a group of the formula

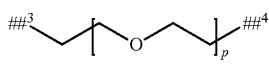

where
p is a number 2 or 3,
$\#\#^3$ marks the linkage site with the group B,
$\#\#^4$ marks the linkage site with the nitrogen atom,
and
n, $AK_1$, Cys, D, $R^{16}$ and $R^{17}$ have the definitions indicated above,
and also their salts, solvates and solvates of the salts.

Preferred in the context of the present invention are also compounds of the formula (Ia) and (XXXa), in which
B is a bond or a group of the formula

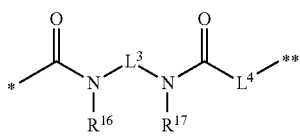

where
* marks the linkage site with $L^1$,
** marks the linkage site with $L^2$,
$L^3$ is a bond or ethane-1,2-diyl,
$L^4$ is a bond,
n, AK, Cys, G, $L^1$, $L^2$, D, $R^{16}$, $R^{17}$ and $R^{35}$ have the definitions indicated above,
and also their salts, solvates and solvates of the salts.

Preferred in the context of the present invention are also compounds of the formula (Ia), (XXXa) and (XXXI), in which
$L^1$ is a bond, linear $(C_3-C_5)$-alkanediyl or a group of the formula

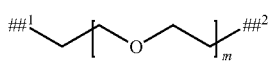

where
m is a number 2 or 3,
$\#\#^1$ marks the linkage site with the group G,
$\#\#^2$ marks the linkage site with the group B,
where $(C_3-C_5)$-alkanediyl may be substituted by 1 or 2 methyl substituents,
B is a bond or a group of the formula

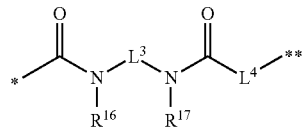

where
* marks the linkage site with $L^1$,
** marks the linkage site with $L^2$,
$L^3$ is a bond,
$L^4$ is a bond
$R^{16}$ is hydrogen,
$R^{17}$ is hydrogen,
$L^2$ is linear $(C_3-C_6)$-alkanediyl or is a group of the formula

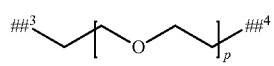

where
p is a number 2 or 3,
$\#\#^3$ marks the linkage site with the group B,
$\#\#^4$ marks the linkage site with the nitrogen atom,
n, AK, Cys, G, D and $R^{35}$ have the definitions indicated above,
and also their salts, solvates and solvates of the salts.

Preferred in the context of the present invention are also compounds of the formula (Ia), (XXXa) and (XXXI), in which
$L^1$ is a bond,
B is a bond,
$L^2$ is linear $(C_3-C_6)$-alkanediyl or is a group of the formula

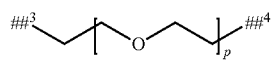

where
p is a number 2 or 3,
$\#\#^3$ marks the linkage site with the group B,
$\#\#^4$ marks the linkage site with the nitrogen atom,
n, AK, Cys, G, D and $R^{35}$ have the definitions indicated above,
and also their salts, solvates and solvates of the salts.

Preferred in the context of the present invention are also compounds of the formula (Ia), (XXXa) and (XXXI), in which
$L^1$ is linear $(C_3-C_5)$-alkanediyl or a group of the formula

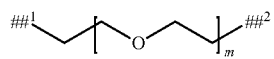

where
m is a number 2 or 3,
$\#\#^1$ marks the linkage site with the group G,
$\#\#^2$ marks the linkage site with the group B,
where $(C_3-C_5)$-alkanediyl may be substituted by 1 or 2 methyl substituents,
B is a group of the formula

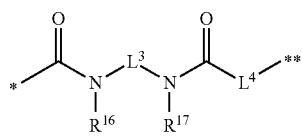

where
* marks the linkage site with $L^1$,
** marks the linkage site with $L^2$,
$L^3$ is a bond,
$L^4$ is a bond,
$R^{16}$ is hydrogen,
$R^{17}$ is hydrogen,
$L^2$ is linear $(C_3-C_6)$-alkanediyl or is a group of the formula

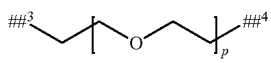

where
p is a number 2 or 3,
$\#\#^3$ marks the linkage site with the group B,
$\#\#^4$ marks the linkage site with the nitrogen atom,
n, AK, Cys, G, D and $R^{35}$ have the definitions indicated above,
and also their salts, solvates and solvates of the salts.

Preferred in the context of the present invention are also compounds of the formula (Ia), in which
n is a number from 2 to 8, preferably 2 to 5,
AK is $AK_1$ or $AK_2$,
  where
  $AK_1$ is an antibody or antigen-binding antibody fragment (e.g., an antibody or an antigen-binding antibody fragment which binds to C4.4a) and is bonded via the sulphur atom of a cysteine residue of the binder to the group G,
  $AK_2$ is an antibody or antigen-binding antibody fragment (e.g., is an antibody or an antigen-binding antibody fragment which binds to C4.4a) and is bonded via the NH side group of a lysine residue of the binder to the group G,
G when AK=$AK_1$, is a group of the formula

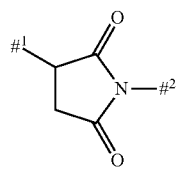

in which
$\#^1$ marks the linkage site with the cysteine residue of the binder,
$\#^2$ marks the linkage site with the group $L^1$,
or
when AK=$AK_2$, is carbonyl,
$L^1$ is a bond, linear $(C_3-C_5)$-alkanediyl or a group of the formula

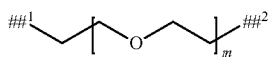

where
m is a number 2 or 3,
$\#\#^1$ marks the linkage site with the group G,
$\#\#^2$ marks the linkage site with the group B,
where $(C_3-C_5)$-alkanediyl may be substituted by 1 or 2 methyl substituents,
B is a bond or a group of the formula

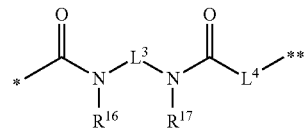

where
* marks the linkage site with $L^1$,
** marks the linkage site with $L^2$,
$L^3$ is a bond,
$L^4$ is a bond,
$R^{16}$ is hydrogen,
$R^{17}$ is hydrogen,
$L^2$ is linear $(C_3-C_6)$-alkanediyl or is a group of the formula

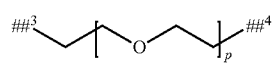

where
p is a number 2 or 3,
$\#\#^3$ marks the linkage site with the group B,
$\#\#^4$ marks the linkage site with the nitrogen atom,
and
D and $R^{35}$ have the definitions indicated above,
and also their salts, solvates and solvates of the salts.

Preferred in the context of the present invention are also compounds of the formula (Ia), in which
n is a number from 2 to 8, preferably 2 to 5,
AK is $AK_1$ or $AK_2$,
  where
  $AK_1$ is an antibody or antigen-binding antibody fragment (e.g., an antibody or an antigen-binding antibody fragment which binds to C4.4a) and is bonded via the sulphur atom of a cysteine residue of the binder to the group G,
  $AK_2$ is an antibody or antigen-binding antibody fragment (e.g., an antibody or an antigen-binding antibody fragment which binds to C4.4a) and is bonded via the NH side group of a lysine residue of the binder to the group G,
G when AK=$AK_1$, is a group of the formula

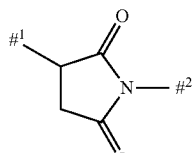

in which
$\#^1$ marks the linkage site with the cysteine residue of the binder,
$\#^2$ marks the linkage site with the group $L^1$,
or
when AK=$AK_2$, is carbonyl, $L^1$ is a bond,
B is a bond,
$L^2$ is linear $(C_3\text{-}C_6)$-alkanediyl or is a group of the formula

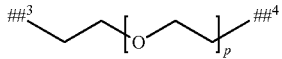

where
p is a number 2 or 3,
$\#\#^3$ marks the linkage site with the group B,
$\#\#^4$ marks the linkage site with the nitrogen atom,
D and $R^{35}$ have the definitions indicated above,
and also their salts, solvates and solvates of the salts.
Preferred in the context of the present invention are also compounds of the formula (Ia), in which
n is a number from 2 to 8, preferably 2 to 5,
AK is $AK_1$,
where
$AK_1$ is an antibody or antigen-binding antibody fragment (e.g., an antibody or an antigen-binding antibody fragment which binds to C4.4a) and is bonded via the sulphur atom of a cysteine residue of the binder to the group G,
G is a group of the formula

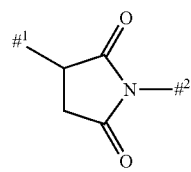

where
$\#^1$ marks the linkage site with the cysteine residue of the binder,
$\#^2$ marks the linkage site with the group $L^1$,
$L^1$ is linear $(C_3\text{-}C_5)$-alkanediyl or a group of the formula

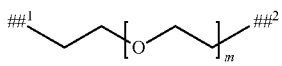

where
m is a number 2 or 3,
$\#\#^1$ marks the linkage site with the group G,
$\#\#^2$ marks the linkage site with the group B,
where $(C_3\text{-}C_5)$-alkanediyl may be substituted by 1 or 2 methyl substituents,
B is a group of the formula

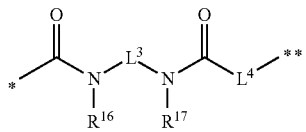

where
\* marks the linkage site with $L^1$,
\*\* marks the linkage site with $L^2$,
$L^3$ is a bond,
$L^4$ is a bond,
$R^{16}$ is hydrogen,
$R^{17}$ is hydrogen,
$L^2$ is linear $(C_3\text{-}C_6)$-alkanediyl or is a group of the formula

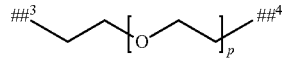

where
p is a number 2 or 3,
$\#\#^3$ marks the linkage site with the group B,
$\#\#^4$ marks the linkage site with the nitrogen atom,
D and $R^{35}$ have the definitions indicated above,
and also their salts, solvates and solvates of the salts.
Preferred in the context of the present invention are also compounds of the formula (Ia), in which
$L^1$ is a bond, linear $(C_3\text{-}C_5)$-alkanediyl, a group of the formula

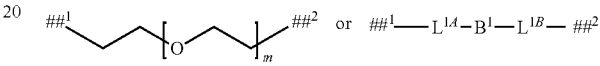

where
m is a number 2 or 3,
$\#\#^1$ marks the linkage site with the group G,
$\#\#^2$ marks the linkage site with the group B,
$L^{1A}$ is linear $(C_3\text{-}C_6)$-alkanediyl,
$B^1$ is a group of the formula

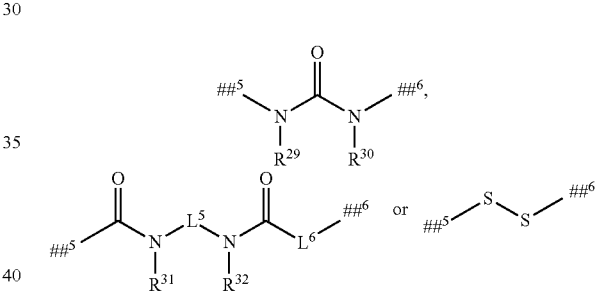

in which
$\#\#^5$ marks the linkage site with the group $L^{1A}$,
$\#\#^6$ marks the linkage site with the group $L^{1B}$,
$L^5$ is a bond or ethane-1,2-diyl,
$L^6$ is a bond or a group of the formula

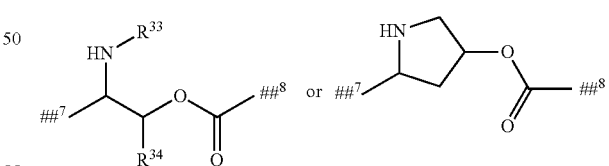

in which
$\#\#^7$ marks the linkage site with the carbonyl group,
$\#\#^8$ marks the linkage site with $L^{1B}$,
$R^{33}$ is hydrogen, $(C_1\text{-}C_4)$-alkylcarbonyl or tert-butyloxycarbonyl,
$R^{34}$ is hydrogen or methyl,
$R^{29}$ is hydrogen or methyl,
$R^{30}$ is hydrogen or methyl,
$R^{31}$ is hydrogen or methyl,
$R^{32}$ is hydrogen or methyl,
$L^{1B}$ is linear $(C_3\text{-}C_6)$-alkanediyl, B is a bond or a group of the formula

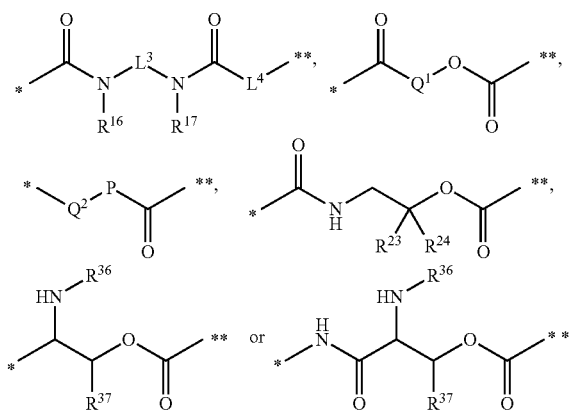

where
* marks the linkage site with $L^1$,
** marks the linkage site with $L^2$,
P is O,
$L^3$ is a bond or ethane-1,2-diyl,
$L^4$ is a group of the formula

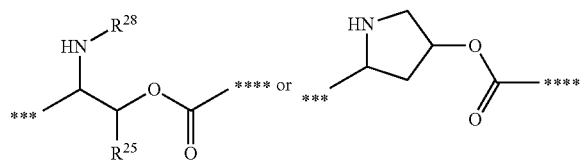

in which
*** marks the linkage site with the carbonyl group,
**** marks the linkage site with $L^2$,
$R^{25}$ is hydrogen or methyl,
$R^{28}$ is hydrogen, $(C_1-C_4)$-alkylcarbonyl or tert-butyloxycarbonyl,
$Q^1$ is a 4- to 7-membered heterocycle,
$Q^2$ is a 3- to 7-membered carbocycle or a 4- to 7-membered heterocycle,
$R^{16}$ is hydrogen or methyl,
$R^{17}$ is hydrogen or methyl,
$R^{23}$ is $(C_1-C_4)$-alkyl,
$R^{24}$ is hydrogen or $(C_1-C_4)$-alkyl,
$R^{36}$ is hydrogen, $(C_1-C_4)$-alkylcarbonyl or tert-butyloxycarbonyl,
$R^{37}$ is hydrogen or methyl,
or
$R^{36}$ and $R^{37}$ together with the atoms to which they are bonded form a pyrrolidine ring,
$L^2$ is linear $(C_2-C_6)$-alkanediyl or is a group of the formula

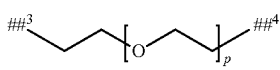

where
p is a number 2 or 3,
$\#\#^3$ marks the linkage site with the group B,
$\#\#^4$ marks the linkage site with the nitrogen atom,
and also their salts, solvates and solvates of the salts.

Preferred in the context of the present invention are also compounds of the formula (Ia), in which
$L^1$ is linear $(C_3-C_5)$-alkanediyl or a group of the formula

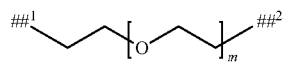

where
m is a number 2 or 3,
$\#\#^1$ marks the linkage site with the group G,
$\#\#^2$ marks the linkage site with the group B,
B is a group of the formula

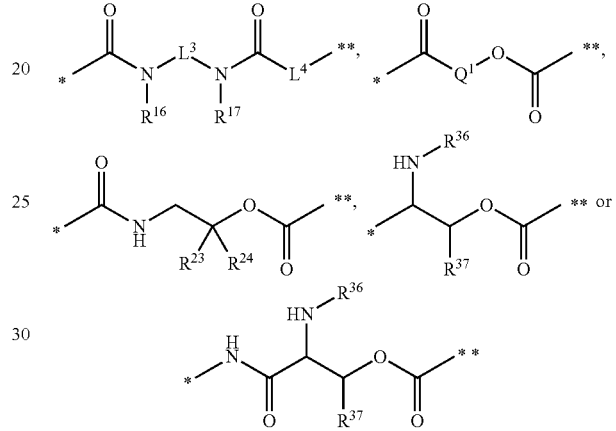

where
* marks the linkage site with $L^1$,
** marks the linkage site with $L^2$,
$L^3$ is a bond or ethane-1,2-diyl,
$L^4$ is a group of the formula

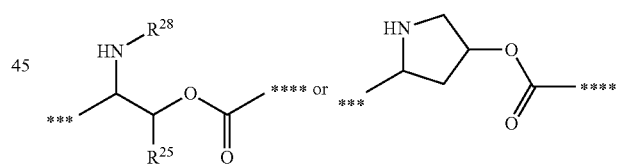

in which
*** marks the linkage site with the carbonyl group,
**** marks the linkage site with $L^2$,
$R^{25}$ is methyl,
$R^{28}$ is hydrogen, methylcarbonyl or tert-butyloxycarbonyl,
$Q^1$ is piperidine-1,4-diyl,
$R^{16}$ is hydrogen or methyl,
$R^{17}$ is hydrogen or methyl,
$R^{23}$ is methyl,
$R^{24}$ is hydrogen,
$R^{36}$ is hydrogen, methylcarbonyl or tert-butyloxycarbonyl,
$R^{37}$ is hydrogen or methyl,
$L^2$ is linear $(C_2-C_6)$-alkanediyl or is a group of the formula

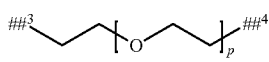

where
p is a number 2 or 3,
³ marks the linkage site with the group B,
⁴ marks the linkage site with the nitrogen atom,
and also their salts, solvates and solvates of the salts.

Preferred in the context of the present invention are also compounds of the formula (Ia), (XXXa) and (XXXI), in which
D is a group of the formula

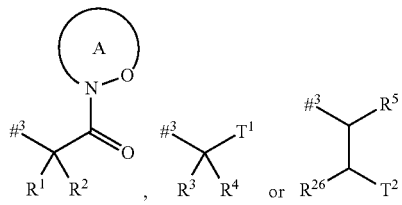

where
³ marks the linkage site with the nitrogen atom,
$R^1$ is hydrogen or methyl,
$R^2$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl,
or
$R^1$ and $R^2$ together with the carbon atom to which they are bonded form a (1S,2R)-2-phenylcyclopropane-1,1-diyl group of the formula

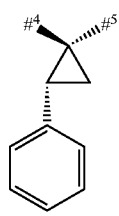

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

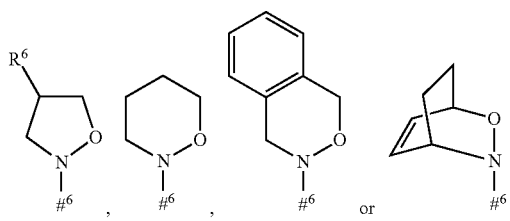

in which
⁶ marks the linkage site with the carbonyl group,
$R^6$ is hydrogen, hydroxy or benzyloxy,
$R^3$ is hydrogen or methyl,
$R^4$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl,
or
$R^3$ and $R^4$ together with the carbon atom to which they are bonded form a (1S,2R)-2-phenylcyclopropane-1,1-diyl group of the formula

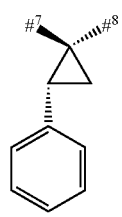

in which
⁷ marks the linkage site with the adjacent nitrogen atom,
⁸ marks the linkage site with the group $T^1$,
$T^1$ is a group of the formula —C(=O)—O$R^7$, —C(=O)—N$R^8R^9$, —C(=O)—NH—NH—$R^{10}$ or —CH$_2$—O—$R^{11}$,
in which
$R^7$ is hydrogen, methyl, ethyl, n-propyl, tert-butyl, benzyl or adamantylmethyl,
$R^8$ is hydrogen or methyl,
$R^9$ is hydrogen, methyl, ethyl, n-propyl or benzyl,
or
$R^8$ and $R^9$ together with the nitrogen atom to which they are bonded form a 4- to 7-membered heterocycle,
$R^{10}$ is benzoyl,
$R^{11}$ is benzyl, which may be substituted in the phenyl group by methoxycarbonyl or carboxyl
$R^5$ is hydrogen, methyl or a group of the formula

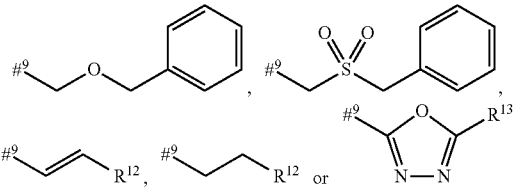

in which
⁹ marks the linkage site with —CHC($R^{26}$)-$T^2$,
$R^{12}$ is phenyl which may be substituted by methoxycarbonyl, carboxyl or a group of the formula —S(O)$_2$OH,
$R^{13}$ is phenyl which may be substituted by methoxycarbonyl or carboxyl,
$R^{26}$ is hydrogen,
$T^2$ is phenyl, benzyl, 1H-indol-3-yl or 1H-indol-3-ylmethyl,
and
n, AK, Cys, G, $L^1$, B, $L^2$, D and $R^{35}$ have the definitions indicated above,
and also their salts, solvates and solvates of the salts.

Preferred in the context of the present invention are also compounds of the formula (Ia), (XXXa) and (XXXI), in which
D is a group of the formula

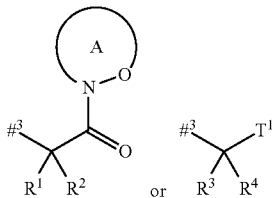

where
³ marks the linkage site with the nitrogen atom,
R¹ is hydrogen,
R² is benzyl, 4-hydroxybenzyl, 1-phenylethyl or 1H-indol-3-ylmethyl,
the ring A with the N—O moiety present therein is a heterocycle of formula

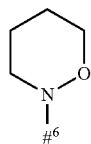

in which
⁶ marks the linkage site with the carbonyl group,
R³ is hydrogen,
R⁴ is benzyl, 4-hydroxybenzyl, 1-phenylethyl or 1H-indol-3-ylmethyl,
T¹ is a group of the formula —C(═O)—OR⁷ or —C(═O)—NR⁸R⁹,
in which
R⁷ is hydrogen,
R⁸ is hydrogen,
R⁹ is hydrogen,
n, AK, Cys, G, L¹, B, L², D and R³⁵ have the definitions indicated above,
and also their salts, solvates and solvates of the salts.

Preferred in the context of the present invention are also compounds of the formula (Ia), (XXXa) and (XXXI), in which
D is a group of the formula

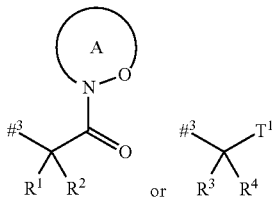

where
³ marks the linkage site with the nitrogen atom,
R¹ is hydrogen,
R² is benzyl, 4-hydroxybenzyl, 1-phenylethyl or 1H-indol-3-ylmethyl,
the ring A with the N—O moiety present therein is a heterocycle of formula

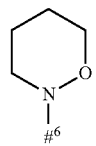

in which
⁶ marks the linkage site with the carbonyl group,
R³ is hydrogen,
R⁴ is benzyl, 4-hydroxybenzyl, 1-phenylethyl or 1H-indol-3-ylmethyl,
T¹ is a group of the formula —C(═O)—NR⁸R⁹,
in which
R⁸ is hydrogen,
R⁹ is hydrogen,
n, AK, Cys, G, L¹, B, L², D and R³⁵ have the definitions indicated above,
and also their salts, solvates and solvates of the salts.

Preferred in the context of the present invention are also compounds of the formula (Ia), (XXXa) and (XXXI), in which
D is a group of the formula

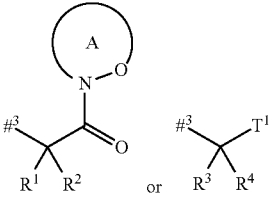

where
³ marks the linkage site with the nitrogen atom,
R¹ is hydrogen,
R² is 4-hydroxybenzyl or 1H-indol-3-ylmethyl,
the ring A with the N—O moiety present therein is a heterocycle of the formula

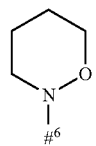

in which
⁶ marks the linkage site with the carbonyl group,
R³ is hydrogen,
R⁴ is 4-hydroxybenzyl or 1H-indol-3-ylmethyl,
T¹ is a group of the formula —C(═O)—NR⁸R⁹,
in which
R⁸ is hydrogen,
R⁹ is hydrogen,
n, AK, Cys, G, L¹, B, L², D and R³⁵ have the definitions indicated above,
and also their salts, solvates and solvates of the salts.

Preferred in the context of the present invention are also compounds of the formula (Ia), (XXXa) and (XXXI), in which D is a group of the formula

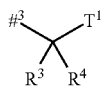

where
³ marks the linkage site with the nitrogen atom,
R³ is hydrogen,
R⁴ is 4-hydroxybenzyl or 1H-indol-3-ylmethyl,
T¹ is a group of the formula —C(=O)—OR⁷ or —C(=O)—NR⁸R⁹,
in which
R⁷ is hydrogen,
R⁸ is hydrogen,
R⁹ is hydrogen,
n, AK, Cys, G, L¹, B, L², D and R³⁵ have the definitions indicated above,
and also their salts, solvates and solvates of the salts.

Preferred in the context of the present invention are also compounds of the formula (Ia), (XXXa) and (XXXI), in which
D is a group of the formula

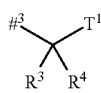

where
³ marks the linkage site with the nitrogen atom,
R³ is hydrogen,
R⁴ is 4-hydroxybenzyl or 1H-indol-3-ylmethyl,
T¹ is a group of the formula —C(=O)—NR⁸R⁹,
in which
R⁸ is hydrogen,
R⁹ is hydrogen,
n, AK, Cys, G, L¹, B, L², D and R³⁵ have the definitions indicated above,
and also their salts, solvates and solvates of the salts.

Preferred in the context of the present invention are also compounds of the formula (Ia), (XXXa) and (XXXI), in which
D is a group of the formula

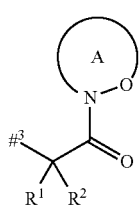

where
³ marks the linkage site with the nitrogen atom,
R¹ is hydrogen or methyl,
R² is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-ylmethyl or 1H-indol-3-ylmethyl,
or R¹ and R² together with the carbon atom to which they are bonded form a (1S,2R)-2-phenylcyclopropane-1,1-diyl group of the formula

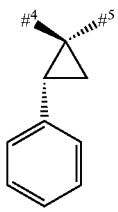

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

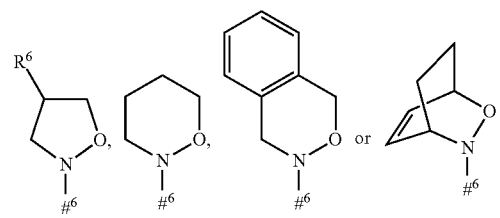

in which
⁶ marks the linkage site with the carbonyl group,
R⁶ is hydrogen, hydroxy or benzyloxy,
and
n, AK, Cys, G, L¹, B, L² and R³⁵ have the definitions indicated above,
and also their salts, solvates and solvates of the salts.

Preferred in the context of the present invention are also compounds of the formula (Ia), (XXXa) and (XXXI), in which
D is a group of the formula

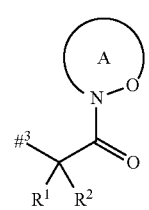

where
³ marks the linkage site with the nitrogen atom,
R¹ is hydrogen,
R² is benzyl, 4-hydroxybenzyl, 1-phenylethyl or 1H-indol-3-ylmethyl,
or
R¹ and R² together with the carbon atom to which they are bonded form a (1S,2R)-2-phenylcyclopropane-1,1-diyl group of the formula

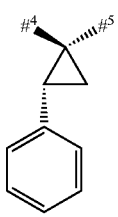

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

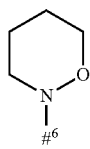

in which
⁶ marks the linkage site with the carbonyl group,
and
n, AK, Cys, G, $L^1$, B, $L^2$ and $R^{35}$ have the definitions indicated above,
and also their salts, solvates and solvates of the salts.

Preferred in the context of the present invention are also compounds of the formula (Ia), (XXXa) and (XXXI), in which
$R^{35}$ is hydroxyl,
and
n, AK, Cys, G, $L^1$, B, $L^2$, D and $R^{35}$ have the definitions indicated above,
and also their salts, solvates and solvates of the salts.

Preferred in the context of the present invention are also compounds of the formula (Ia), (XXXa) and (XXXI), in which
$R^{35}$ is methyl,
and
n, AK, Cys, G, $L^1$, B, $L^2$, D and $R^{35}$ have the definitions indicated above,
and also their salts, solvates and solvates of the salts.

Particularly preferred in the context of the present invention are, furthermore, also compounds of the formula (XXXa), in which
Cys is an L-cysteine residue which is bonded via the sulphur atom of the side chain via a carbon atom of the succinimide,
and also their salts, solvates and solvates of the salts.

Preferred in the context of the present invention are also compounds of the formula (I) and (XXX), in which
D is a group of the formula

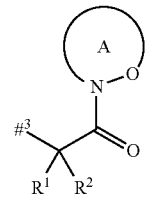

where
³ marks the linkage site with the nitrogen atom,
$R^1$ is hydrogen,
$R^2$ is benzyl, 1-phenylethyl or 1H-indol-3-ylmethyl,
or
$R^1$ and $R^2$ together with the carbon atom to which they are bonded form a (1S,2R)-2-phenylcyclopropane-1,1-diyl group of the formula

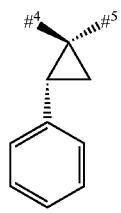

in which
⁴ marks the linkage site with the adjacent nitrogen atom,
⁵ marks the linkage site with the carbonyl group,
the ring A with the N—O moiety present therein is a mono- or bicyclic, optionally substituted heterocycle of the formula

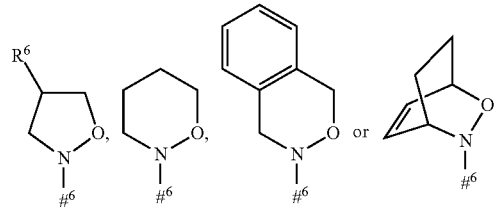

in which
⁶ marks the linkage site with the carbonyl group,
$R^6$ is hydrogen, hydroxy or benzyloxy,
n, AK, Cys, G, $L^1$, $L^2$ and B have the definitions indicated above,
and also their salts, solvates and solvates of the salts.

Particularly preferred in the context of the present invention are also compounds of the formula (I) and (XXX), in which
D is a group of the formula

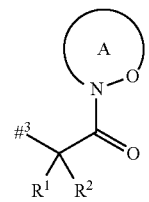

where
³ marks the linkage site with the nitrogen atom,
R¹ is hydrogen,
R² is benzyl or 1H-indol-3-ylmethyl,
or
R¹ and R² together with the carbon atom to which they are bonded form a (1S,2R)-2-phenylcyclopropane-1,1-diyl group of the formula in which
⁴ marks the linkage site with the adjacent nitrogen atom,
⁵ marks the linkage site with the carbonyl group,
the ring A with the N—O moiety present therein is a heterocycle of the formula in which
⁶ marks the linkage site with the carbonyl group,
n, AK, Cys, G, L¹, L² and B have the definitions indicated above,
and also their salts, solvates and solvates of the salts.

A further particularly preferred subject of the present invention are compounds of the formula (I), in which
D is a group of the formula where
T¹ is —C(═O)—OH or —C(═O)—NH₂ and
n, AK, G, L¹, B, L², #³, R³ and R⁴ have the definitions indicated above.

Preferred in the context of the present invention are also compounds of the formula (I), in which
n=1-20, more preferably n=1-10 and very preferably n=2-8.

Preferred in the context of the present invention are also compounds of the formula (I) and (XXX), in which
B is a bond or a group of the formula where
* marks the linkage site with L¹,
** marks the linkage site with L²,
L³ is a bond or ethane-1,2-diyl,
L⁴ is a bond,
n, AK, Cys, G, L¹, L², D, R¹⁶ and R¹⁷ have the definitions indicated above,
and also their salts, solvates and solvates of the salts.

Particularly preferred in the context of the present invention are also compounds of the formula (I) and (XXX), in which
B is a bond or a group of the formula where
* marks the linkage site with L¹,
** marks the linkage site with L²,
L³ and L⁴ is a bond,
n, AK, Cys, G, L¹, L², D, R¹⁶ and R¹⁷ have the definitions indicated above,
and also their salts, solvates and solvates of the salts.

Preferred in the context of the present invention are also binder-drug conjugates of the general formula (I), in which
AK is AK₁,
where
AK₁ is a binder which is bonded via the sulphur atom of a cysteine residue of the binder to the group G,
G is a group of the formula where
¹ marks the linkage site with the cysteine residue of the binder,
² marks the linkage site with the group L¹,
L¹ is a bond, linear (C₁-C₁₀)-alkanediyl or is a group of the formula where
m is a number from 2 to 6,
¹ marks the linkage site with the group G,
² marks the linkage site with the group B,
where (C₁-C₁₀)-alkanediyl may be substituted by 1 to 4 methyl substituents,
and
where two carbon atoms of the alkanediyl chain in 1,2, 1,3 or 1,4 relation to one another, with inclusion of any carbon atoms situated between them, may be bridged to form a (C₃-C₆)-cycloalkyl ring or a phenyl ring, B is a bond or a group of the formula

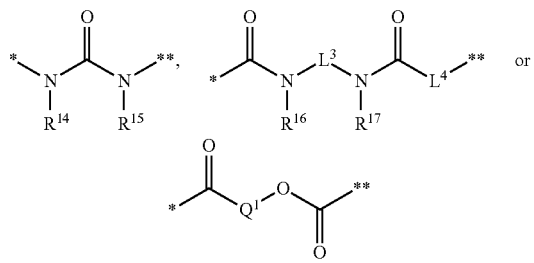

where
* marks the linkage site with $L^1$,
** marks the linkage site with $L^2$,
$L^3$ is a bond or $(C_2-C_4)$-alkanediyl,
$L^4$ is a bond or a group of the formula

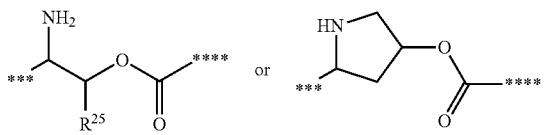

in which
*** marks the linkage site with the carbonyl group,
**** marks the linkage site with $L^2$,
$R^{25}$ is hydrogen or methyl,
$Q^1$ is a 4- to 7-membered heterocycle,
$R^{14}$ is hydrogen or $(C_1-C_4)$-alkyl,
$R^{15}$ is hydrogen or $(C_1-C_4)$-alkyl,
or
$R^{14}$ and $R^{15}$ together with the atoms to which they are bonded form a 5- or 6-membered heterocycle,
$R^{16}$ is hydrogen or $(C_1-C_4)$-alkyl,
$R^{17}$ is hydrogen or $(C_1-C_4)$-alkyl,
or
$R^{16}$ and $R^{17}$ together with the atoms to which they are bonded form a 5- or 6-membered heterocycle,
$L^2$ is linear $(C_2-C_{10})$-alkanediyl or is a group of the formula

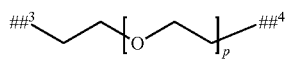

where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 to 4 methyl substituents,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
and also their salts, solvates and solvates of the salts.

Preferred in the context of the present invention are also binder-drug conjugates of the general formula (I), in which AK is $AK_2$,
where
$AK_2$ is a binder which is bonded via the NH side group of a lysine residue of the binder to the group G, G is carbonyl,
$L^1$ is a bond, linear $(C_1-C_{10})$-alkanediyl or is a group of the formula

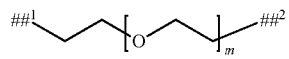

where
m is a number from 2 to 6,
$\#\#^1$ marks the linkage site with the group G,
$\#\#^2$ marks the linkage site with the group B,
where $(C_1-C_{10})$-alkanediyl may be substituted by 1 to 4 methyl substituents,
and
where two carbon atoms of the alkanediyl chain in 1,2, 1,3 or 1,4 relation to one another, with inclusion of any carbon atoms situated between them, may be bridged to form a $(C_3-C_6)$-cycloalkyl ring or a phenyl ring,
B is a bond or a group of the formula

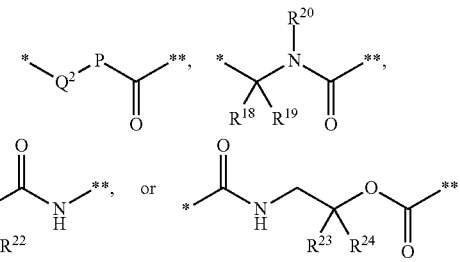

where
* marks the linkage site with $L^1$,
** marks the linkage site with $L^2$,
P is O or NH,
$Q^2$ is a 3- to 7-membered carbocycle or a 4- to 7-membered heterocycle,
$R^{18}$ is hydrogen or $(C_1-C_4)$-alkyl,
$R^{19}$ is hydrogen or the side group of a natural α-amino acid or of its homologues or isomers,
$R^{20}$ is hydrogen or $(C_1-C_4)$-alkyl,
or
$R^{19}$ and $R^{20}$ together with the atoms to which they are bonded form a pyrrolidinyl ring,
$R^{21}$ is hydrogen or $(C_1-C_4)$-alkyl,
$R^{22}$ is hydrogen or $(C_1-C_4)$-alkyl,
or
$R^{21}$ and $R^{22}$ together with the atoms to which they are bonded form a 3- to 7-membered carbocycle,
$R^{23}$ is $(C_1-C_4)$-alkyl,
$R^{24}$ is hydrogen or $(C_1-C_4)$-alkyl,
$L^2$ is linear $(C_2-C_{10})$-alkanediyl or is a group of the formula

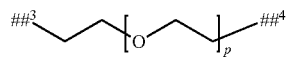

where
p is a number from 2 to 6,
$\#\#^3$ marks the linkage site with the group B,
$\#\#^4$ marks the linkage site with the nitrogen atom,
where $(C_2-C_{10})$-alkanediyl may be substituted by 1 to 4 methyl substituents, and
where two carbon atoms of the alkanediyl chain in 1,2, 1,3 or 1,4 relation to one another, with inclusion of any carbon atoms situated between them, may be bridged to form a ($C_3$-$C_6$)-cycloalkyl ring or a phenyl ring,
and also their salts, solvates and solvates of the salts.

Particularly preferred in the context of the present invention are binder-drug conjugates of the formula (Ia), in which
n is a number from 2 to 8,
AK is $AK_1$ or $AK_2$,
where
$AK_1$ is an antibody or antigen-binding antibody fragment (e.g., a human or humanized antibody or an antigen-binding antibody fragment which binds to C4.4a) and is bonded via the sulphur atom of a cysteine residue of the binder to the group G,
$AK_2$ is an antibody or antigen-binding antibody fragment (e.g., a human or humanized antibody or an antigen-binding antibody fragment which binds to C4.4a) and is bonded via the NH side group of a lysine residue of the binder to the group G,
G when AK=$AK_1$, is a group of the formula

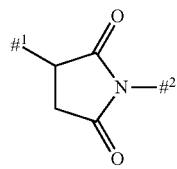

in which
$\#^1$ marks the linkage site with the cysteine residue of the binder,
$\#^2$ marks the linkage site with the group $L^1$,
or
when AK=$AK_2$, is carbonyl,
$L^1$ is a bond, linear ($C_2$-$C_6$)-alkanediyl or is a group of the formula

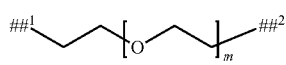

where
m is a number 2 or 3,
$\#\#^1$ marks the linkage site with the group G,
$\#\#^2$ marks the linkage site with the group B,
where ($C_2$-$C_6$)-alkanediyl may be substituted by 1 or 2 methyl substituents,
B is a bond or a group of the formula

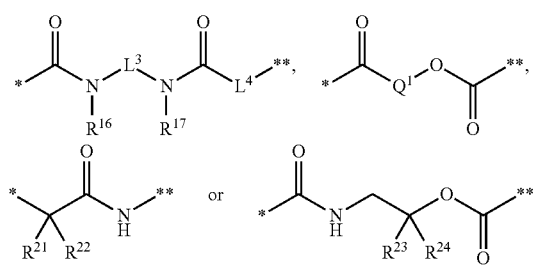

where
\* marks the linkage site with $L^1$,
\*\* marks the linkage site with $L^2$,
$L^3$ is a bond or ethane-1,2-diyl,
$L^4$ is a bond or a group of the formula

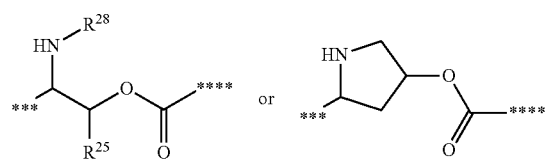

in which
\*\*\* marks the linkage site with the carbonyl group,
\*\*\*\* marks the linkage site with $L^2$,
$R^{25}$ is methyl,
$R^{28}$ is hydrogen, methylcarbonyl or tert-butyloxycarbonyl,
$Q^1$ is piperidine-1,4-diyl,
$R^{16}$ is hydrogen or methyl,
$R^{17}$ is hydrogen or methyl,
or
$R^{16}$ and $R^{17}$ together with the atoms to which they are bonded form a piperazinyl ring,
$R^{21}$ is hydrogen or methyl,
$R^{22}$ is hydrogen or methyl,
or
$R^{21}$ and $R^{22}$ together with the atoms to which they are bonded form a cyclopropyl ring,
$R^{23}$ is methyl,
$R^{24}$ is hydrogen,
$L^2$ is linear ($C_2$-$C_6$)-alkanediyl or is a group of the formula

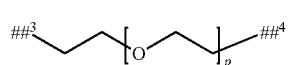

where
p is a number from 2 to 6,
$\#\#^3$ marks the linkage site with the group B,
$\#\#^4$ marks the linkage site with the nitrogen atom,
D is a group of the formula

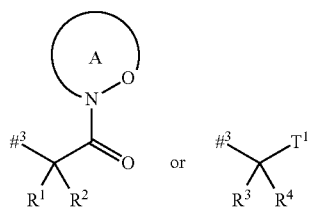

where
$\#^3$ marks the linkage site with the nitrogen atom,
$R^1$ is hydrogen,
$R^2$ is 4-hydroxybenzyl or 1H-indol-3-ylmethyl,
the ring A with the N—O moiety present therein is

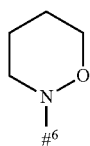

in which
⁶ marks the linkage site with the carbonyl group,
$R^3$ is hydrogen,
$R^4$ is 4-hydroxybenzyl or 1H-indol-3-ylmethyl,
$T^1$ is a group of the formula —C(=O)—NR⁸R⁹,
$R^8$ is hydrogen or methyl,
$R^9$ is hydrogen, methyl, or ethyl,
$R^{35}$ is methyl,
and also their salts, solvates and solvates of the salts.

Particularly preferred in the context of the present invention are binder-drug conjugates of the formula (Ia), in which
n is a number from 2 to 8, preferably 2 to 5,
AK is $AK_1$,
where
$AK_1$ is an antibody or antigen-binding antibody fragment (e.g., a human or humanized antibody or an antigen-binding antibody fragment which binds to C4.4a) and is bonded via the sulphur atom of a cysteine residue of the binder to the group G,
G is a group of the formula

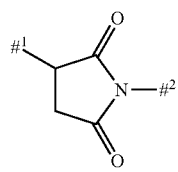

where
¹ marks the linkage site with the cysteine residue of the binder,
² marks the linkage site with the group $L^1$,
$L^1$ is pentane-1,5-diyl,
B is a group of the formula

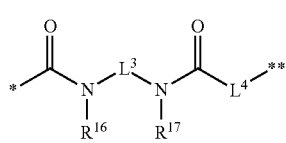

where
* marks the linkage site with $L^1$,
** marks the linkage site with $L^2$,
$L^3$ is a bond,
$L^4$ is a bond,
$R^{16}$ is hydrogen,
$R^{17}$ is hydrogen,
$L^2$ is propane-1,3-diyl,
D is a group of the formula

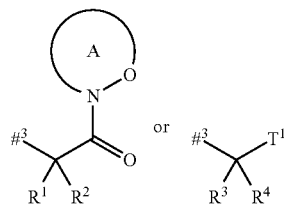

where
³ marks the linkage site with the nitrogen atom,
$R^1$ is hydrogen,
$R^2$ is 4-hydroxybenzyl or 1H-indol-3-ylmethyl,
the ring A with the N—O moiety present therein is

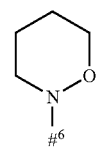

in which
⁶ marks the linkage site with the carbonyl group,
$R^3$ is hydrogen,
$R^4$ is 4-hydroxybenzyl or 1H-indol-3-ylmethyl,
$T^1$ is a group of the formula —C(=O)—NR⁸R⁹,
$R^8$ is hydrogen,
$R^9$ is hydrogen,
$R^{35}$ is methyl,
and also their salts, solvates and solvates of the salts.

Particularly preferred in the context of the present invention are binder-drug conjugates of the formula (Ia), in which
n is a number from 2 to 8, preferably 2 to 5,
AK is $AK_1$,
where
$AK_1$ is an antibody or antigen-binding antibody fragment (e.g., a human or humanized antibody or an antigen-binding antibody fragment which binds to C4.4a) and is bonded via the sulphur atom of a cysteine residue of the binder to the group G,
G is a group of the formula

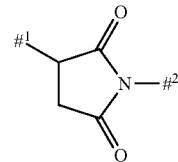

where
¹ marks the linkage site with the cysteine residue of the binder,
² marks the linkage site with the group $L^1$,
$L^1$ is a bond,
B is a bond,
$L^2$ is hexane-1,6-diyl,
and D has the definition indicated above,
and also their salts, solvates and solvates of the salts.

Particularly preferred in the context of the present invention are binder-drug conjugates of the formula (Ia), in which
n is a number from 2 to 8, preferably 2 to 5,
AK is $AK_2$, where
AK₂ is an antibody or antigen-binding antibody fragment (e.g., a human or humanized antibody or an antigen-binding antibody fragment which binds to C4.4a) and is bonded via the NH side group of a lysine residue of the binder to the group G,
G is carbonyl,
$L^1$ is a bond,
B is a bond,
$L^2$ is pentane-1,5-diyl,
D is a group of the formula

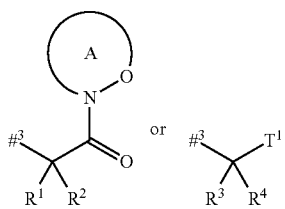

where
$\#^3$ marks the linkage site with the nitrogen atom,
$R^1$ is hydrogen,
$R^2$ is 4-hydroxybenzyl or 1H-indol-3-ylmethyl,
the ring A with the N—O moiety present therein is

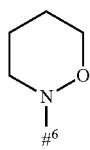

in which
$\#^6$ marks the linkage site with the carbonyl group,
$R^3$ is hydrogen,
$R^4$ is 4-hydroxybenzyl or 1H-indol-3-ylmethyl,
$T^1$ is a group of the formula —C(=O)—NR⁸R⁹,
$R^8$ is hydrogen,
$R^9$ is hydrogen,
$R^{35}$ is methyl,
and also their salts, solvates and solvates of the salts.

Particularly preferred in the context of the present invention are binder-drug conjugates of the formula (Ia), in which
n is a number from 2 to 8, preferably 2 to 5,
AK is AK₂,
where
AK₂ is an antibody or antigen-binding antibody fragment (e.g., a human or humanized antibody or an antigen-binding antibody fragment which binds to C4.4a) and is bonded via the NH side group of a lysine residue of the binder to the group G,
G is carbonyl,
$L^1$ is a bond,
B is a bond,
$L^2$ is a group of the formula

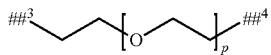

where
p is the number 3, $\#\#^3$ marks the linkage site with the group B,
$\#\#^4$ marks the linkage site with the nitrogen atom,
and D has the meaning indicated above,
and also their salts, solvates and solvates of the salts.

Particularly preferred in the context of the present invention are binder-drug conjugates of the formula (Ia), in which A preferred subject of the invention are binder-drug conjugates of the general formula (Ia) in which D is

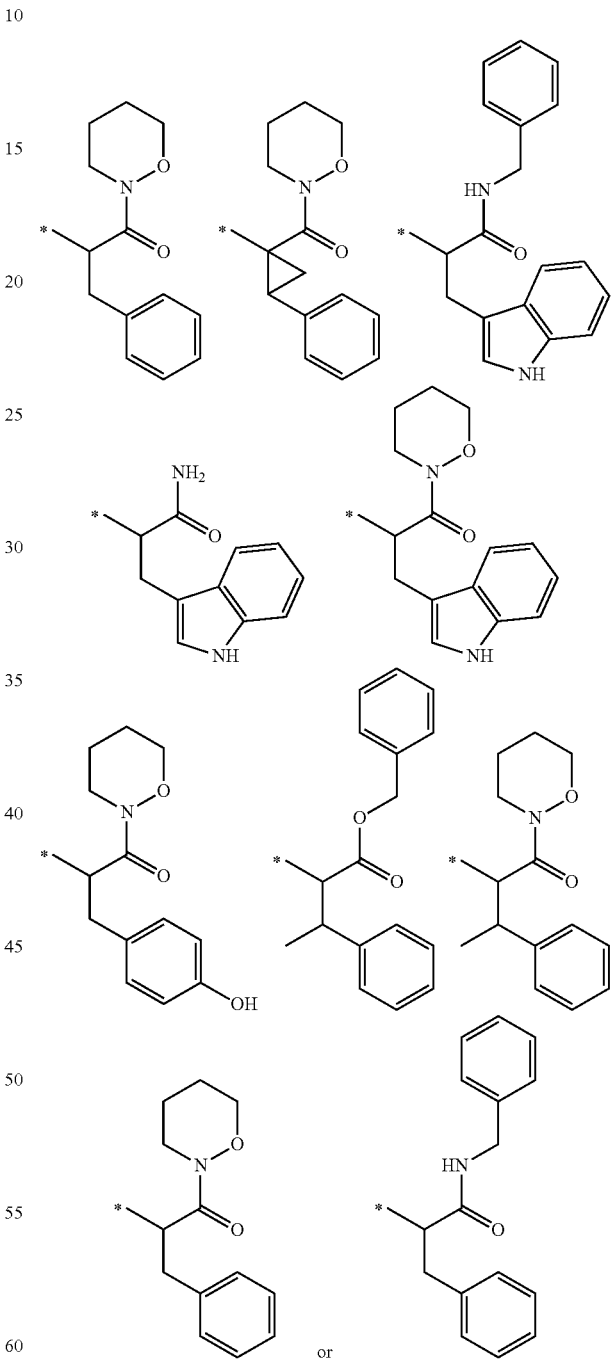

wherein the asterisks marks the linkage site with the nitrogen atom; and the linker §-G-$L^1$-B-$L^2$-§§ and the remainder of the variables are as defined in any of the embodiments provided herein; and also their salts, solvates and solvates of the salts.

A preferred subject of the invention are binder-drug conjugates of the general formula (Ia) in which D is as shown in any of the exemplary drug-binder conjugates provided herein; and the linker §-G-L¹-B-L²-§§ and the remainder of the variables are as defined in any of the embodiments provided herein; and also their salts, solvates and solvates of the salts.

Exemplary drug-binder conjugates are as follows:

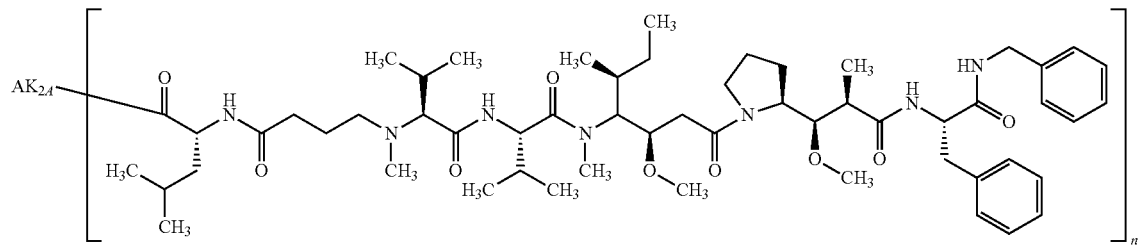

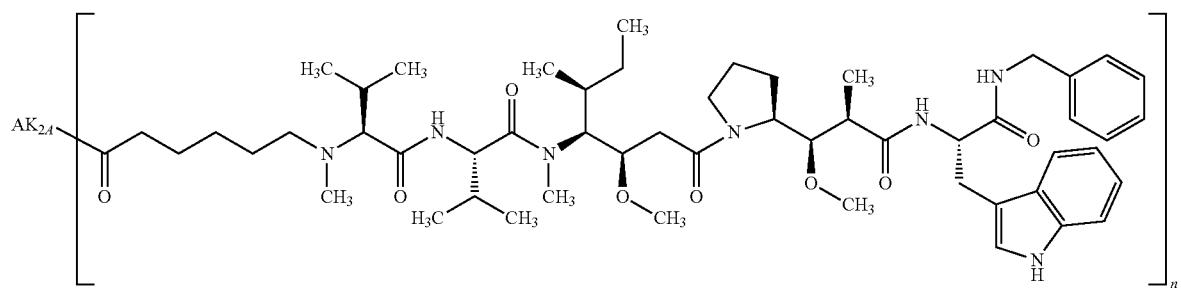

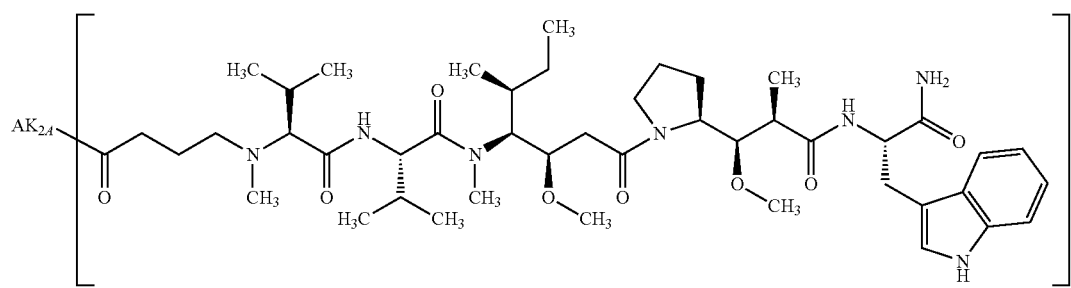

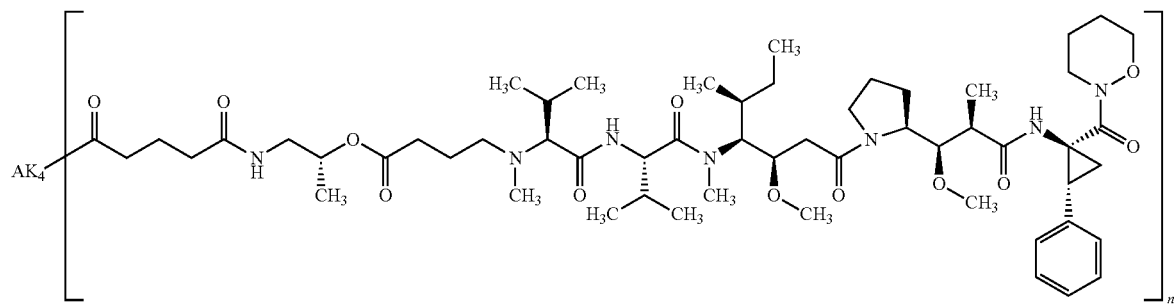

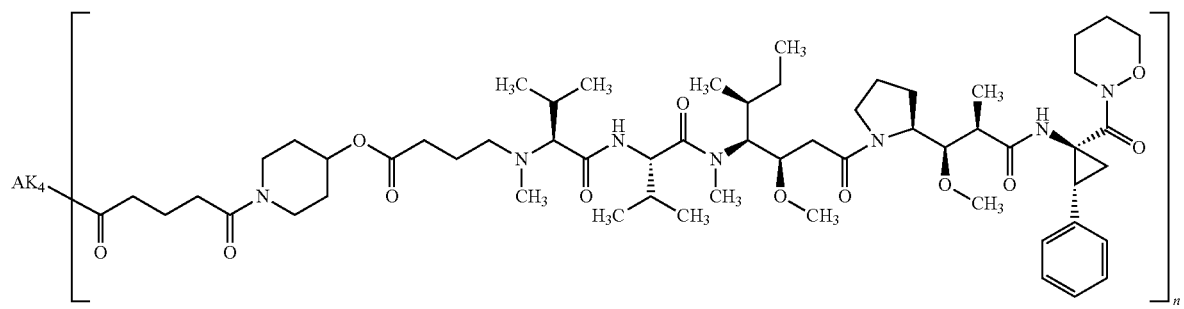

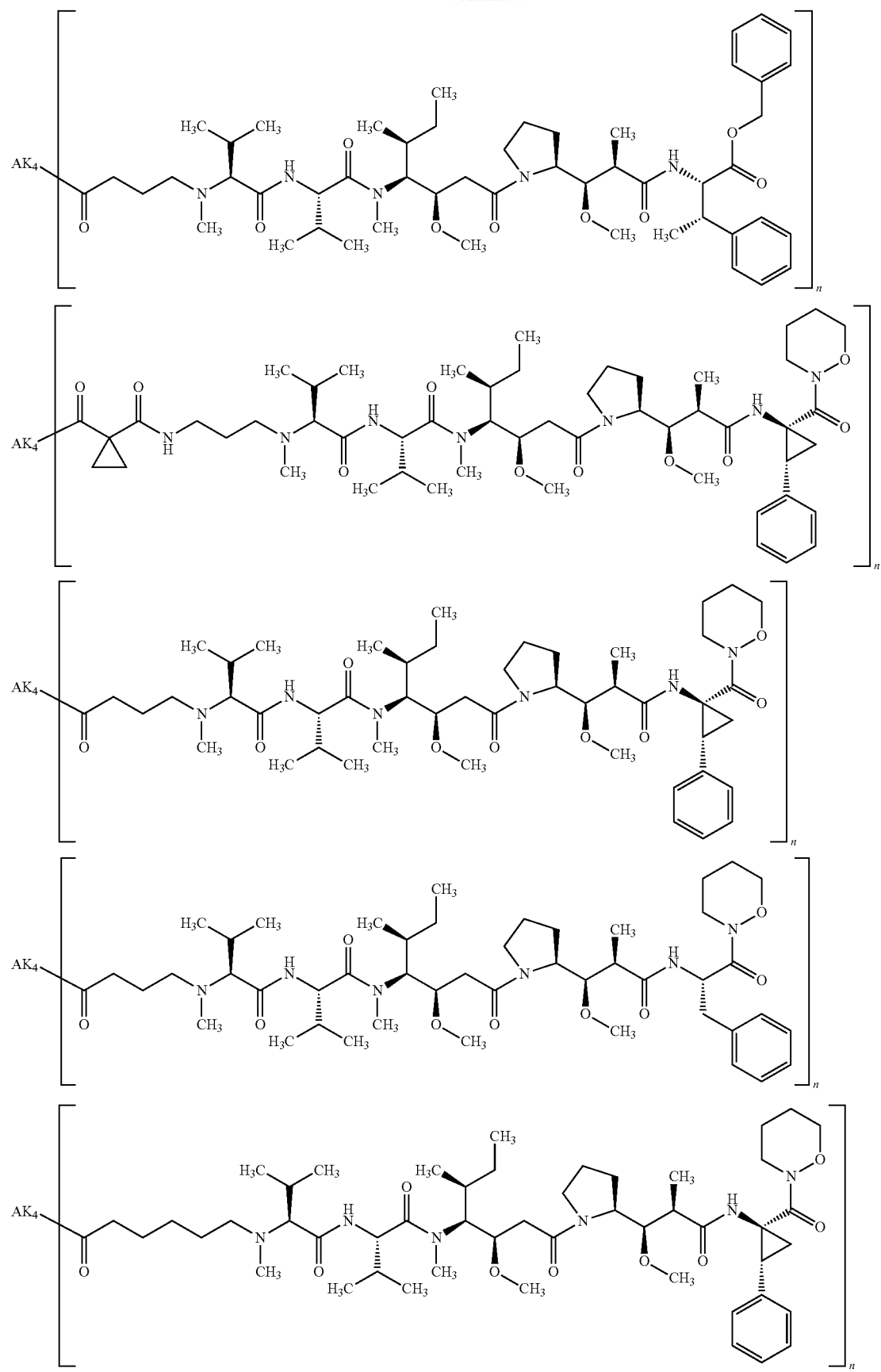

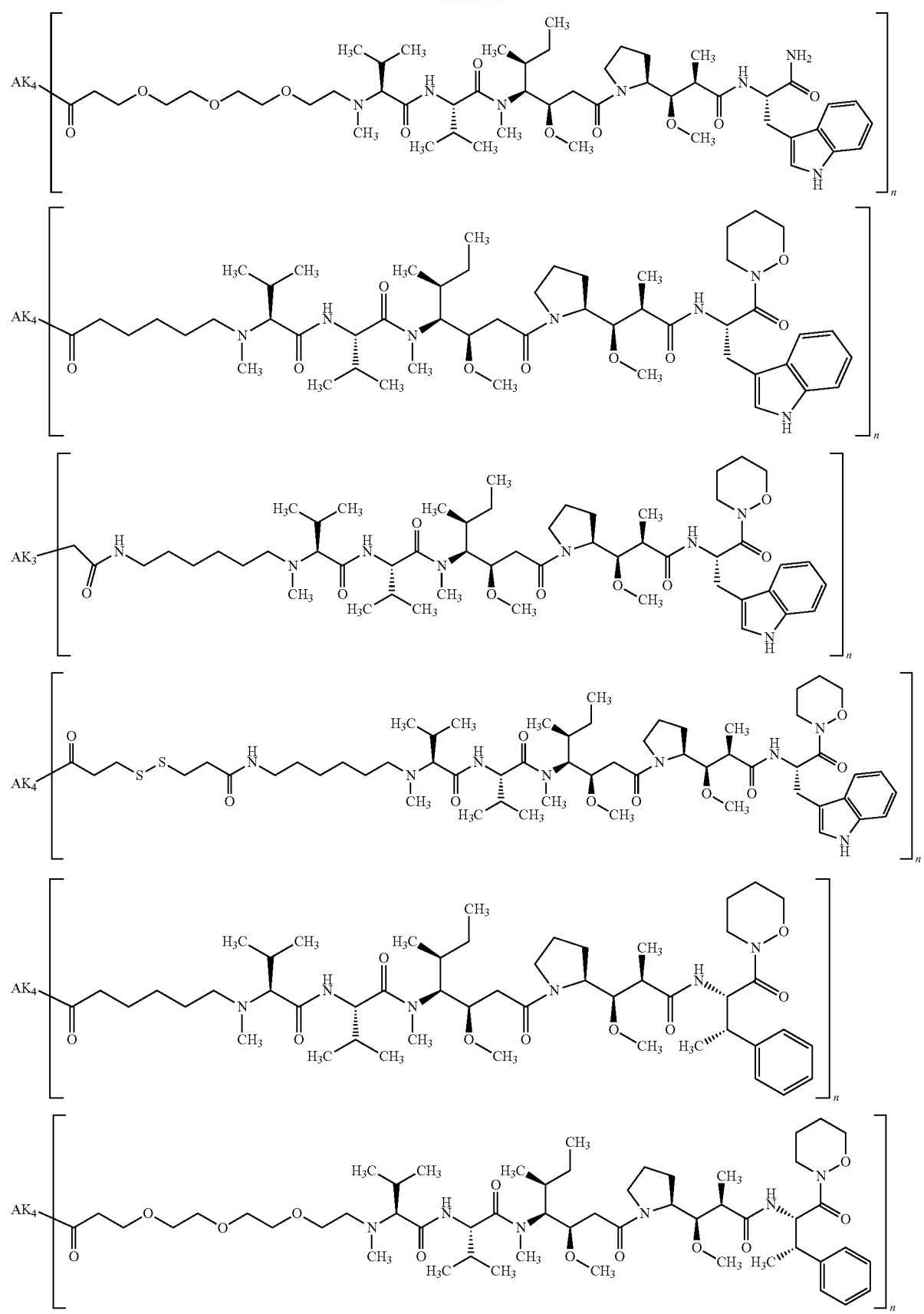

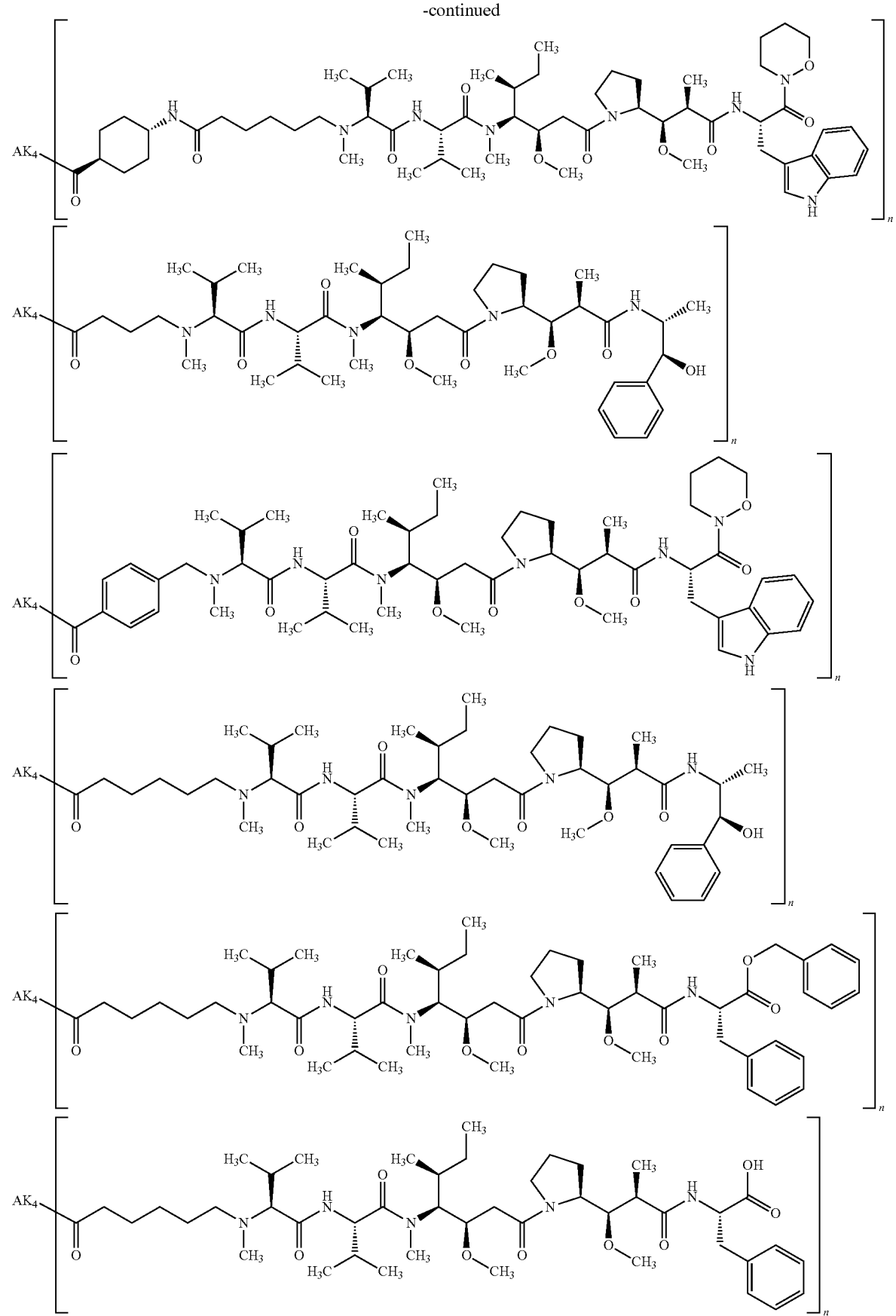

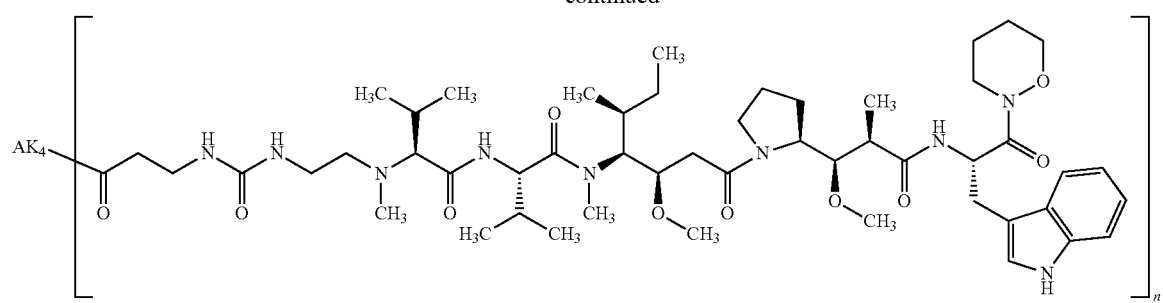
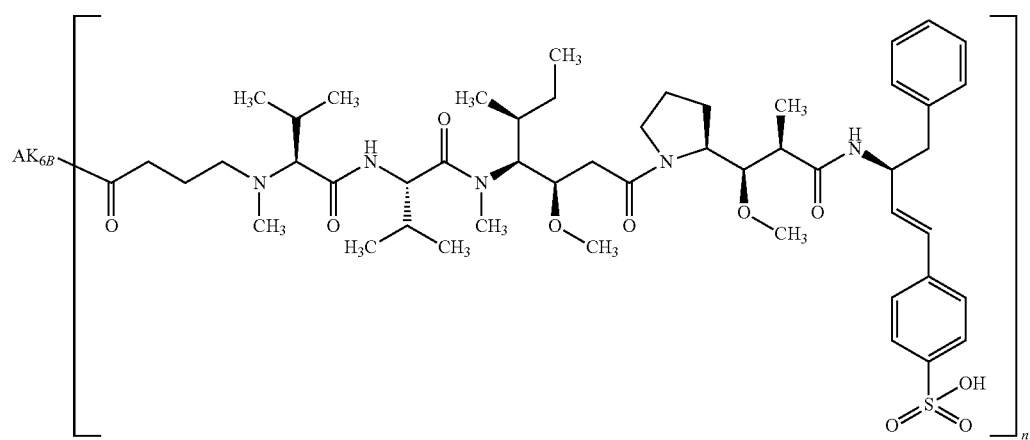
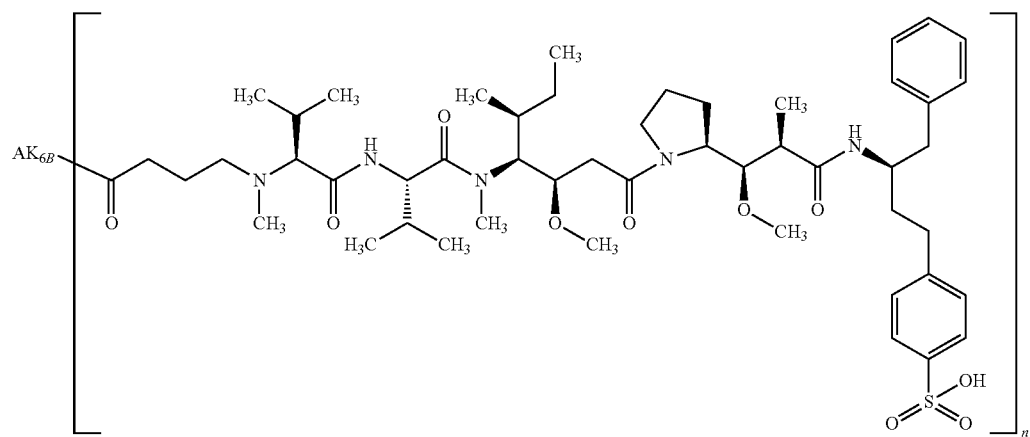
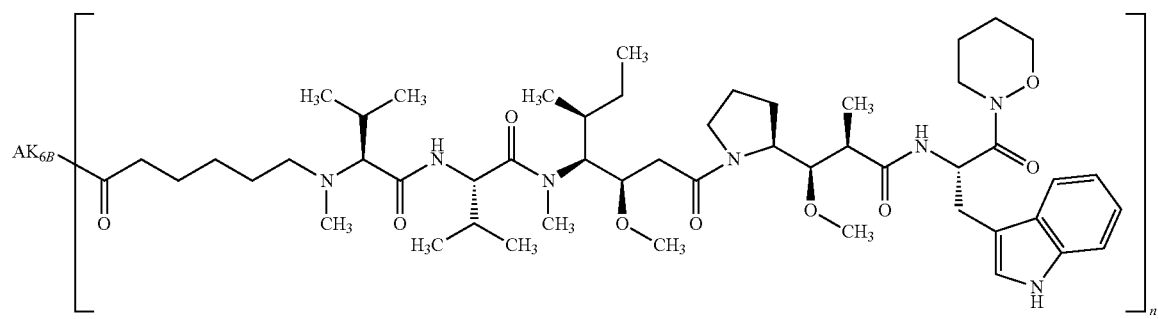

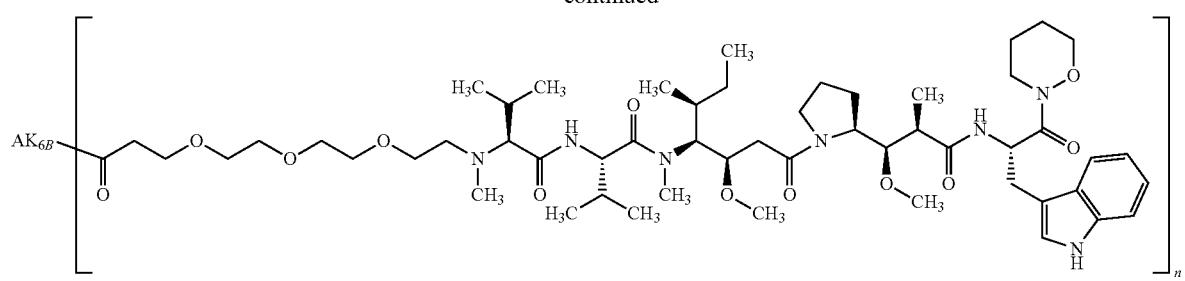
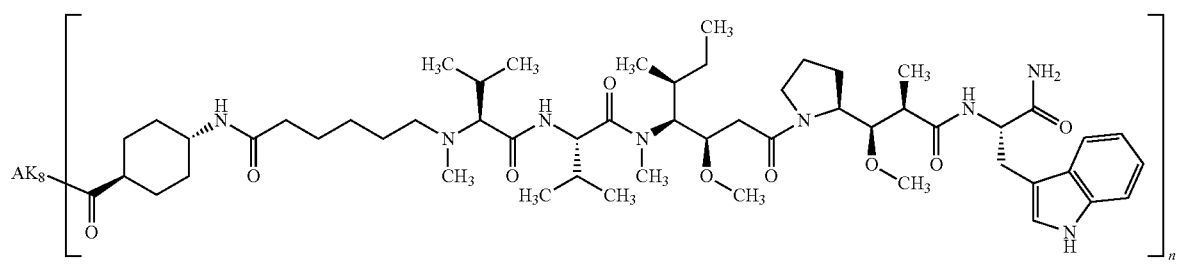
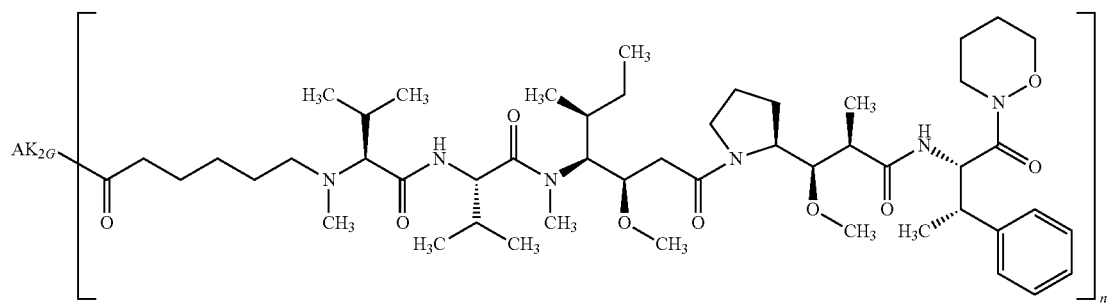
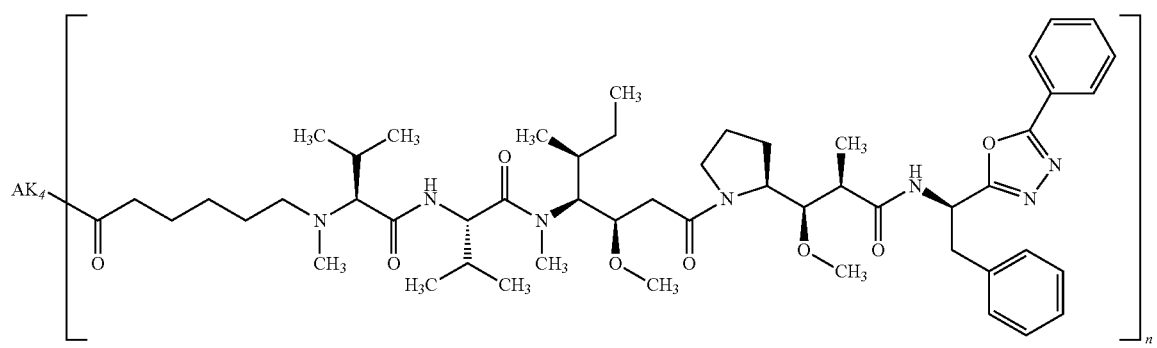
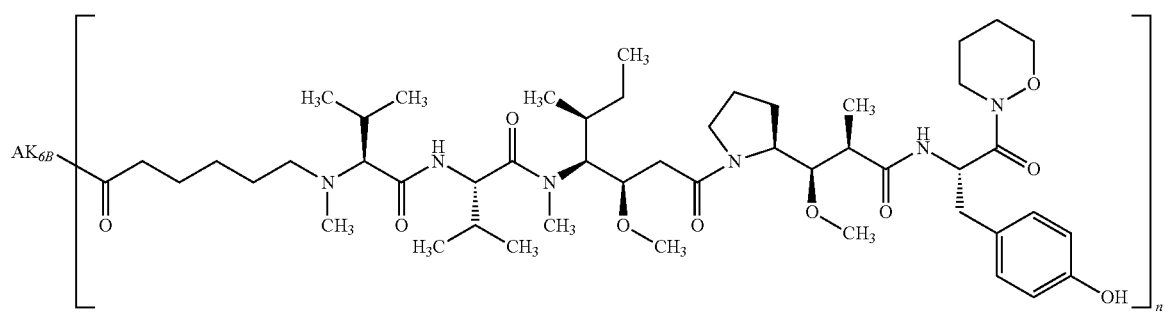

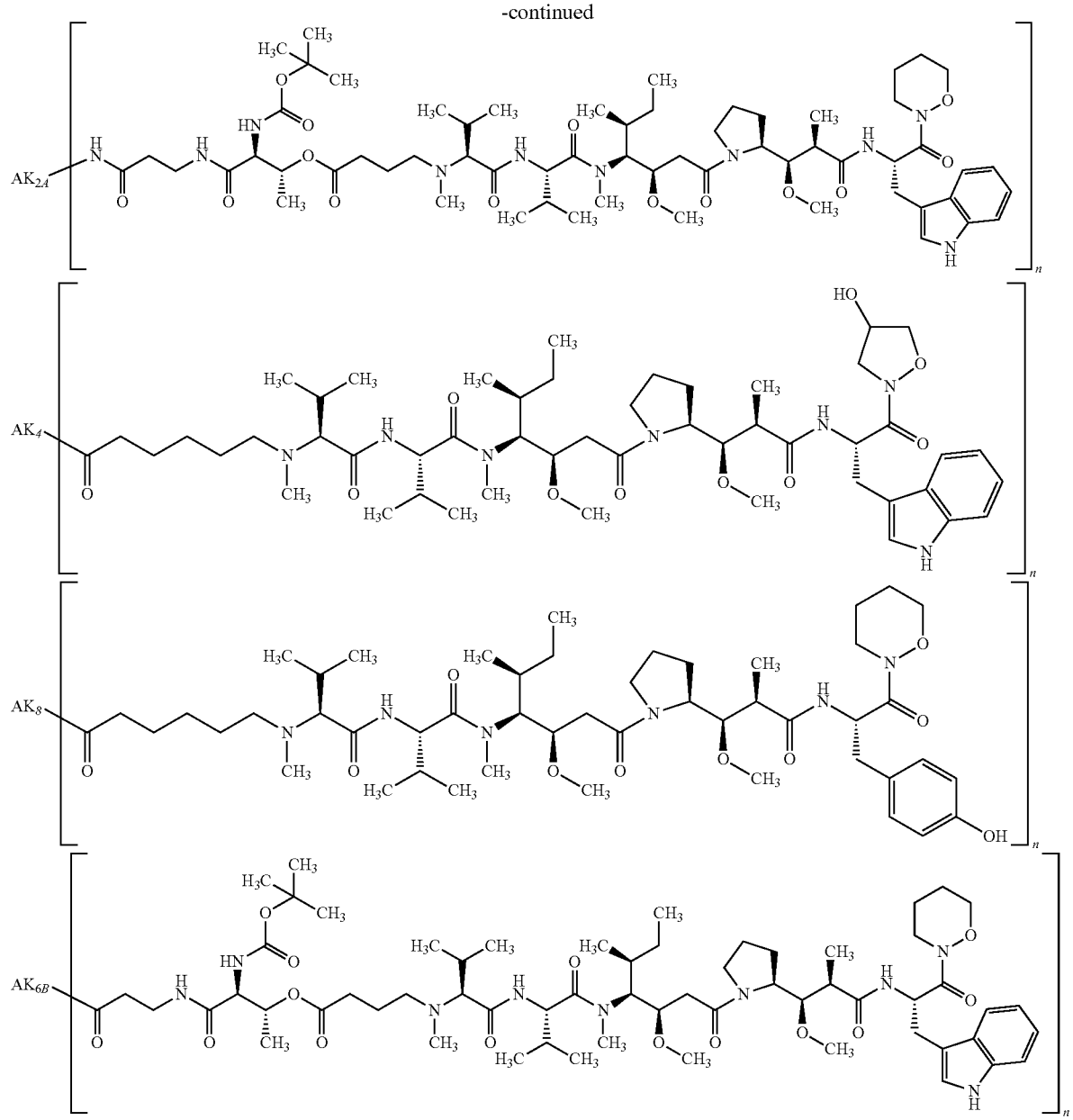

and also their salts, solvates and solvates of the salts, wherein AK (e.g., $AK_{2A}$, $AK_4$, $AK_3$, $AK_{6B}$, $AK_8$, or $AK_{2G}$) is an antibody or antigen-binding antibody fragment (preferably a human or humanized monoclonal antibody or antigen-binding fragment thereof) and is, in some embodiments, bonded via a nitrogen atom of the antibody or antigen binding fragment thereof to the drug-linker and n is from 1 to 20, preferably 1 to 10.

Exemplary drug conjugate are also as follows:

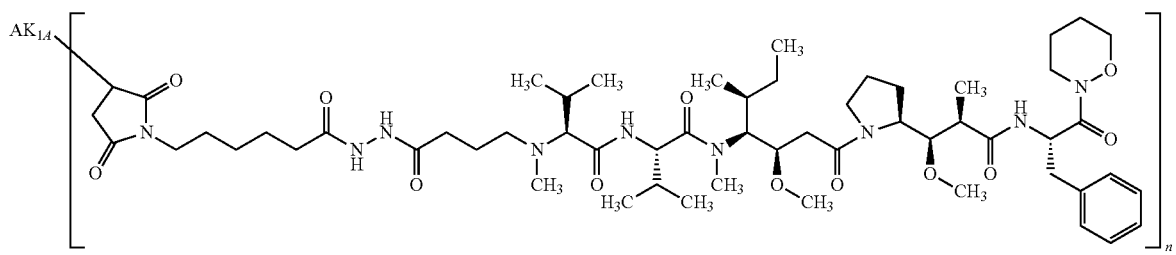

-continued
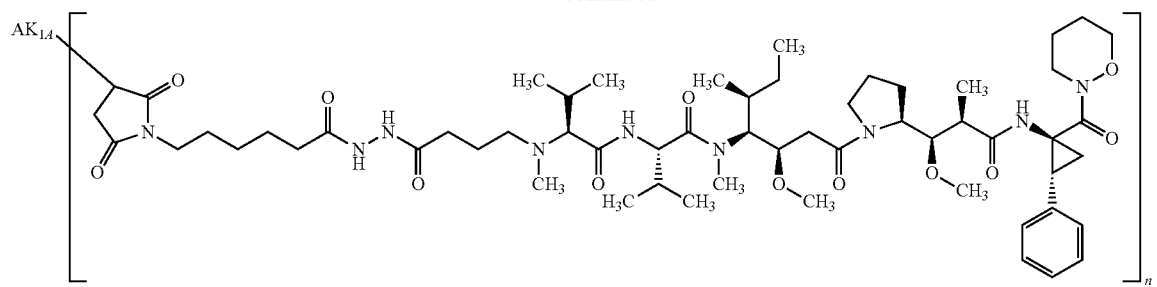
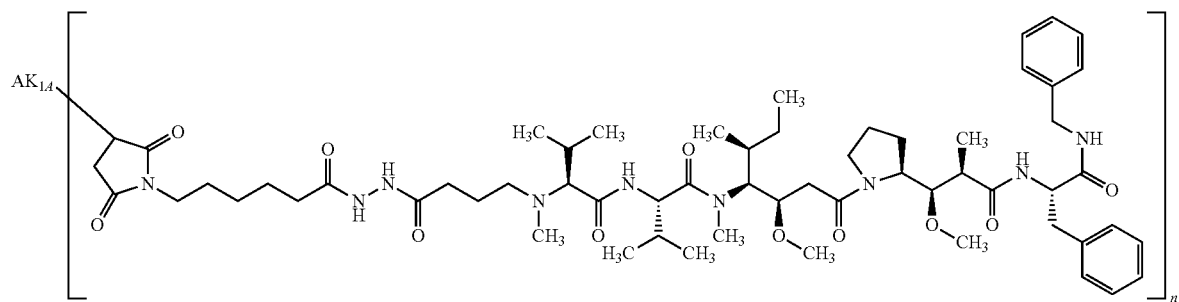
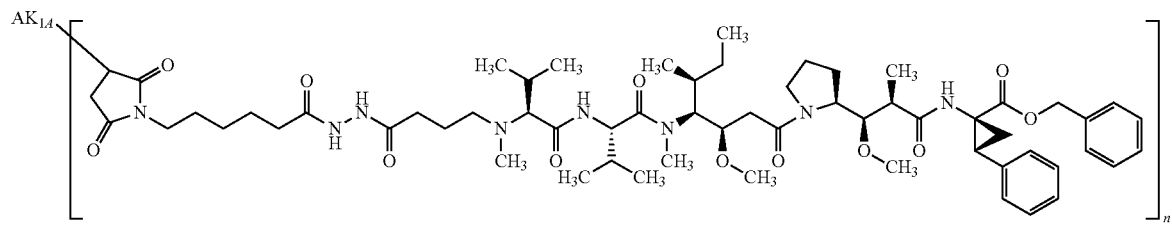
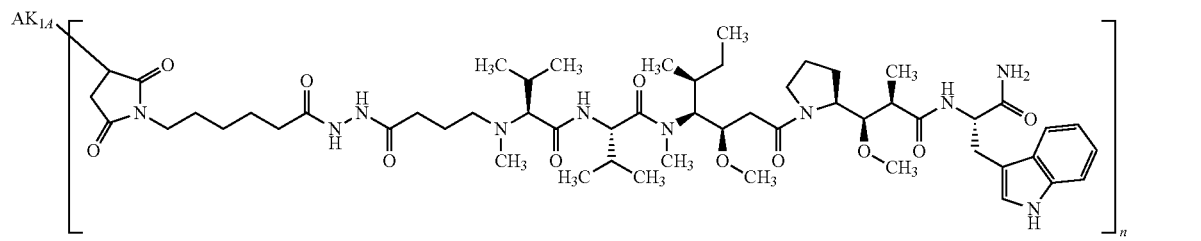
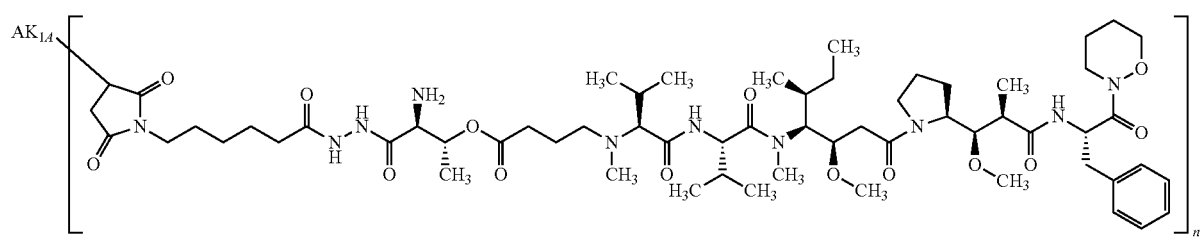
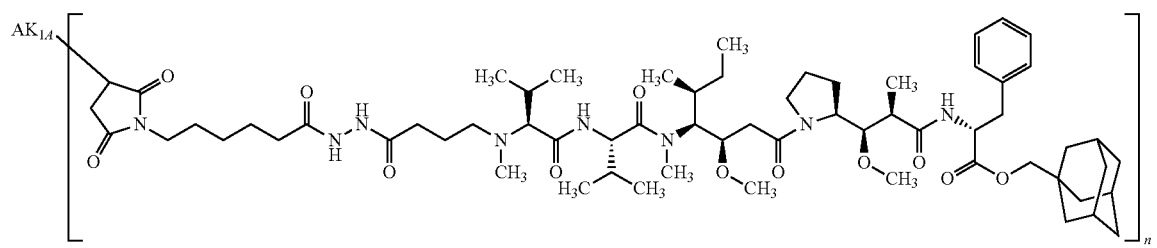

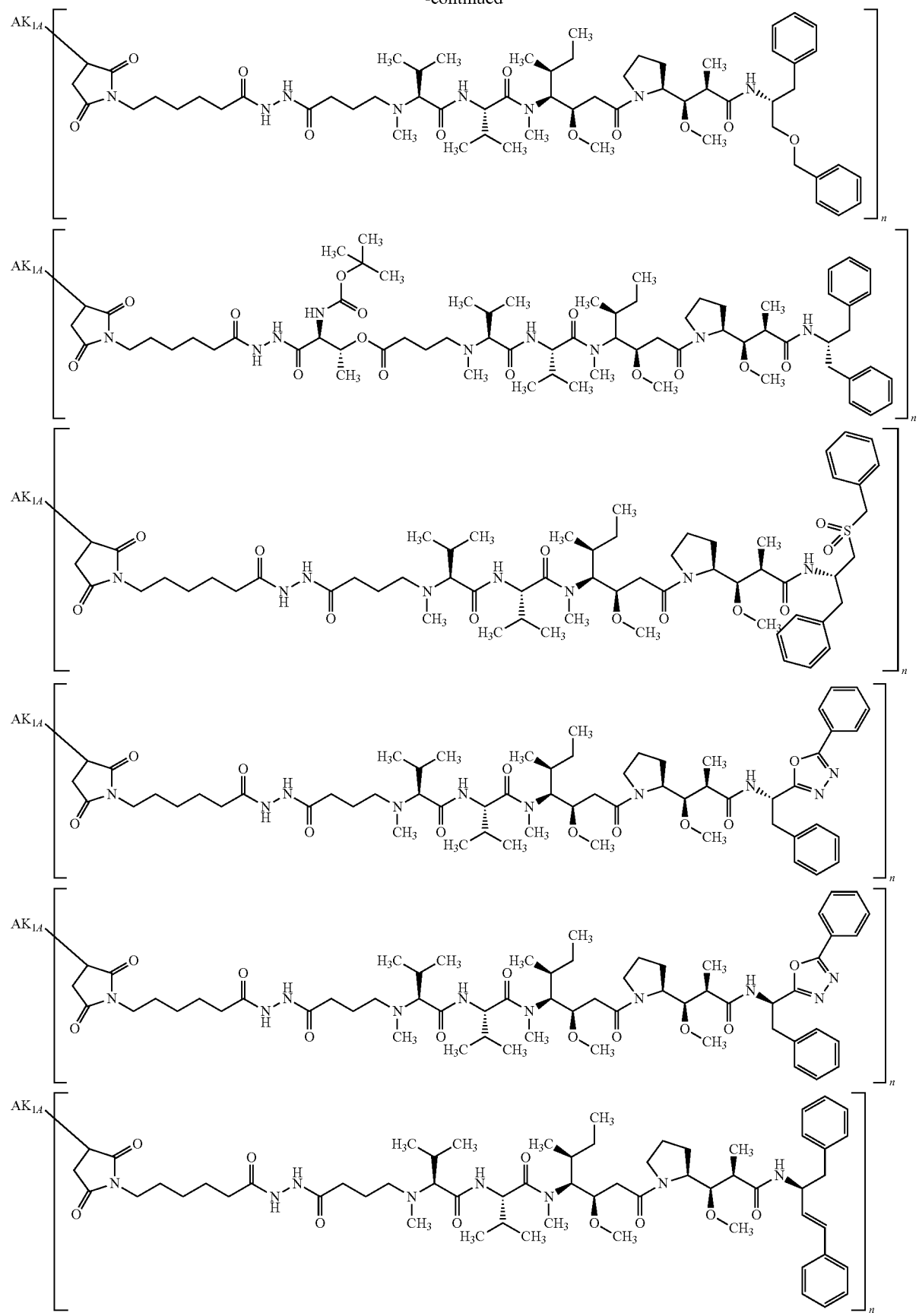

-continued
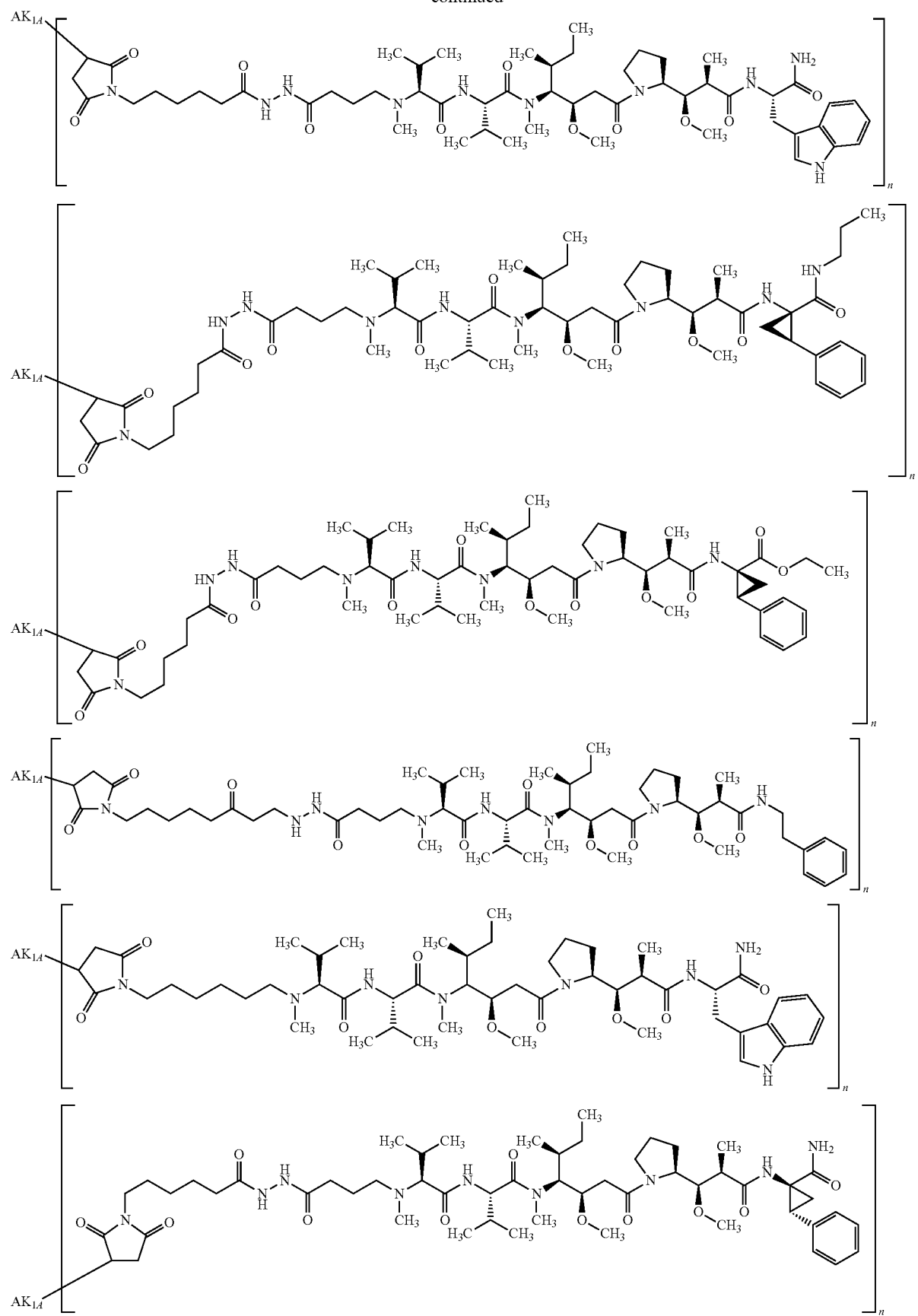

-continued
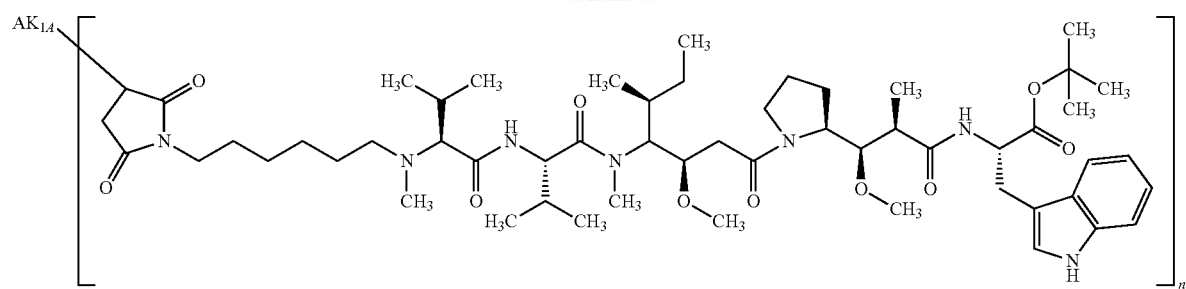
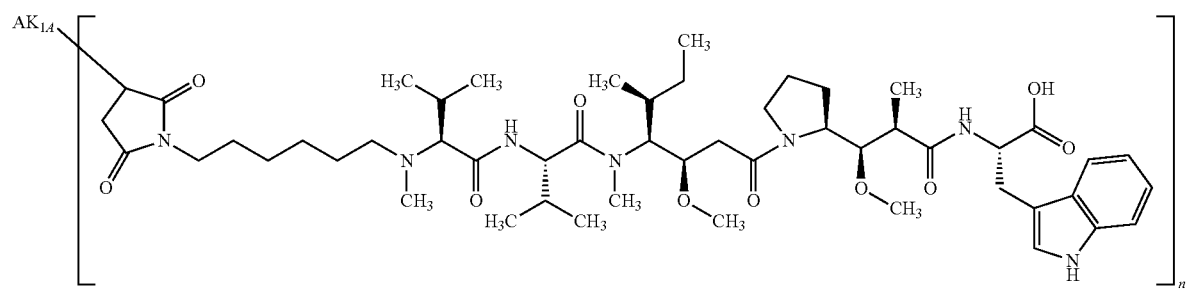
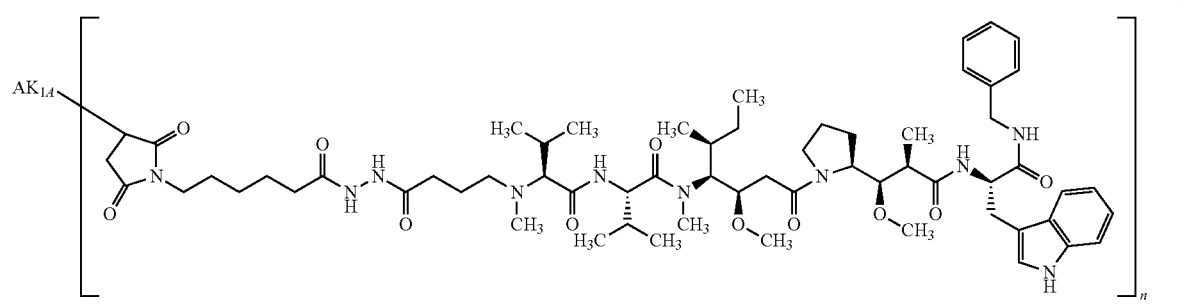
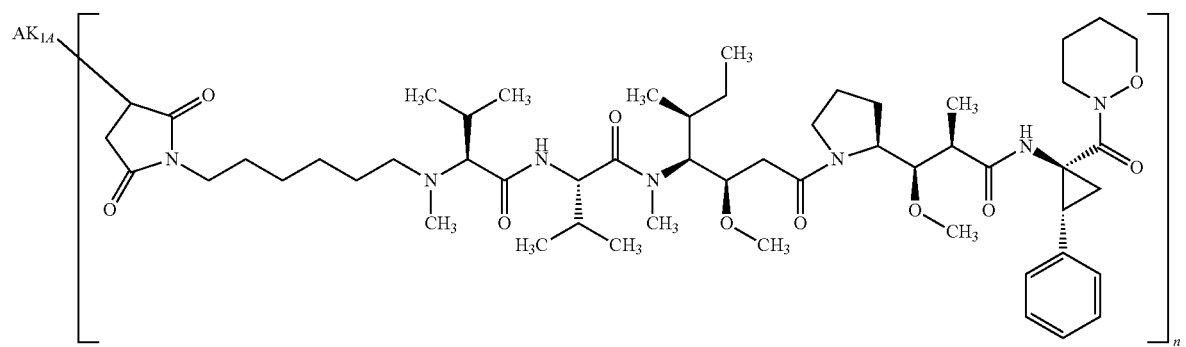
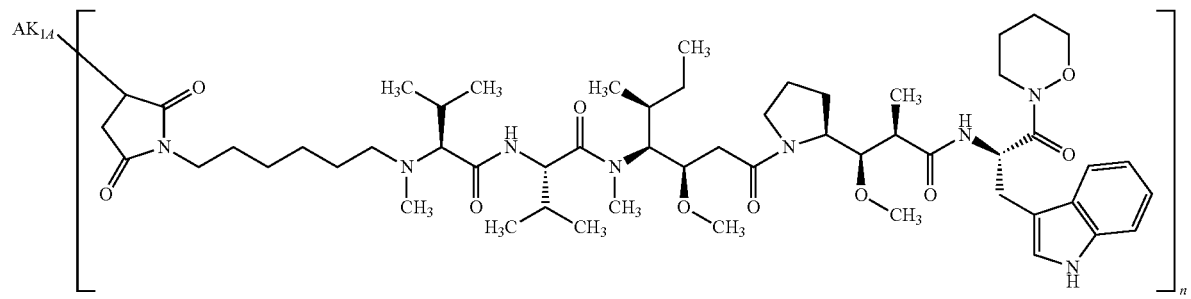

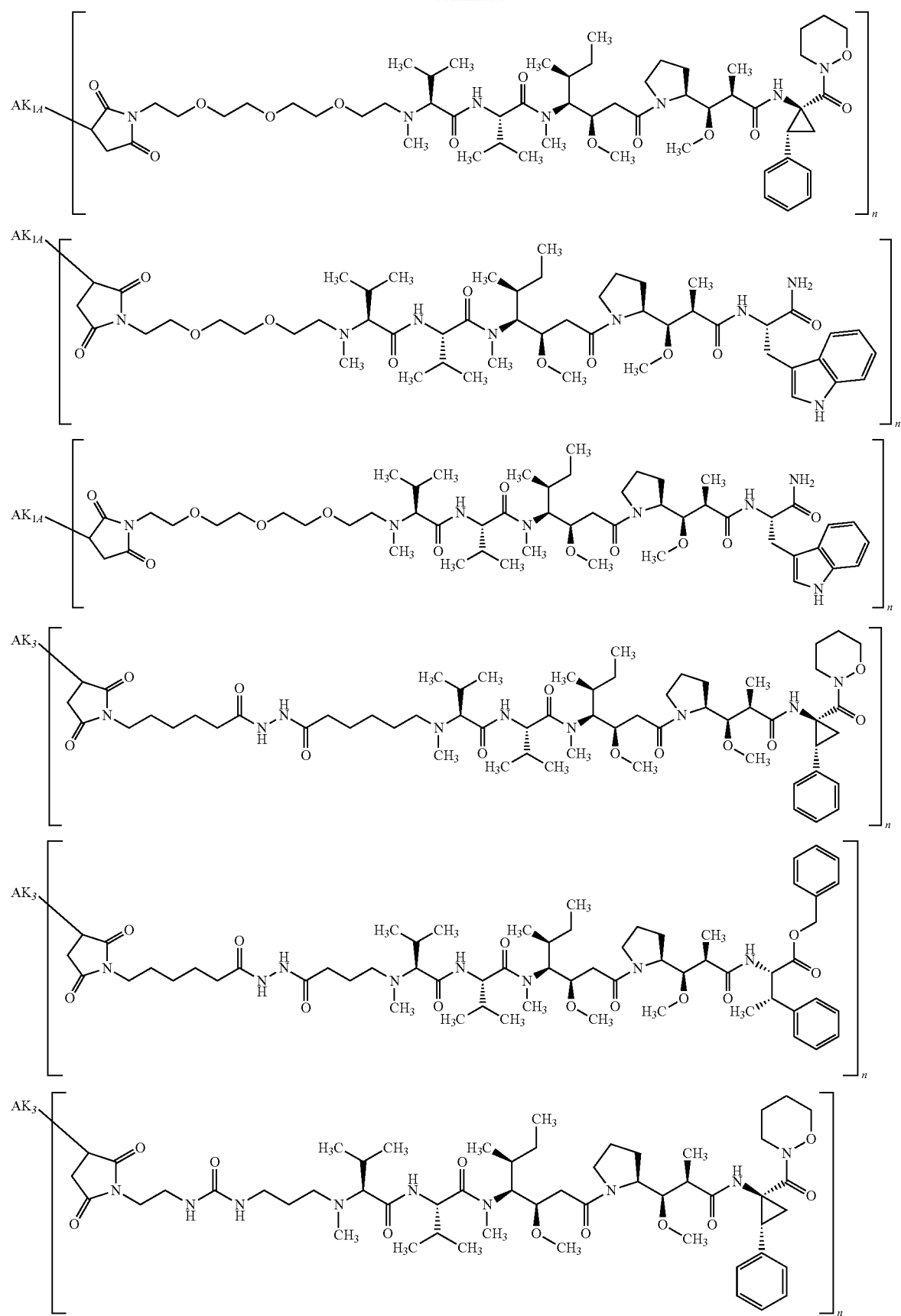

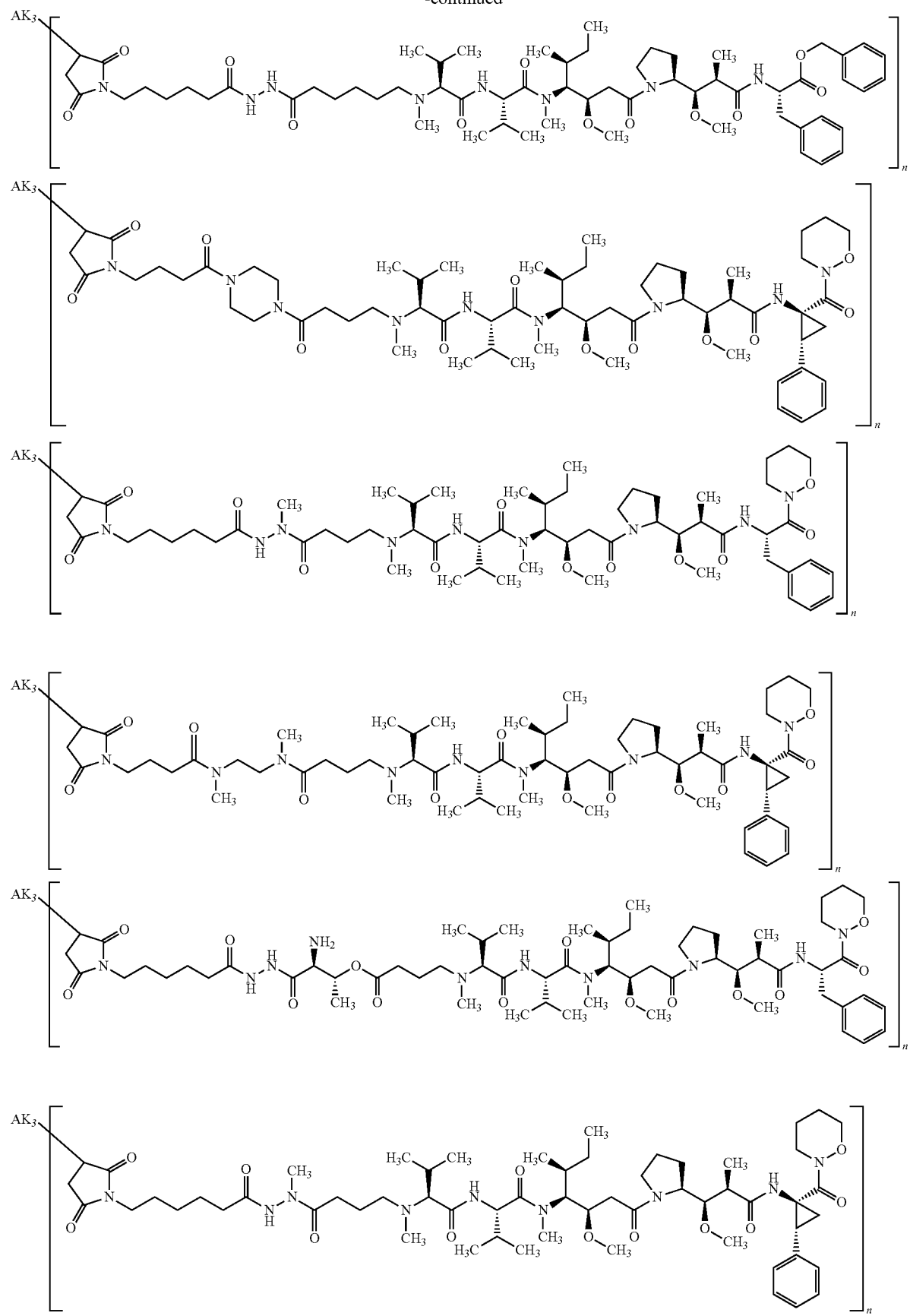

-continued
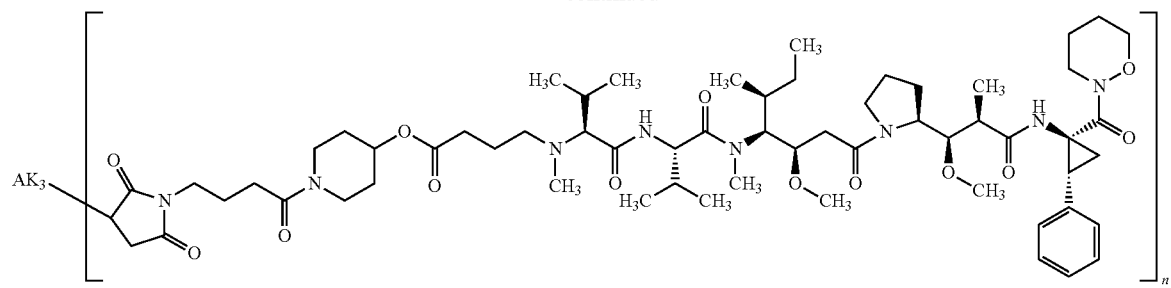
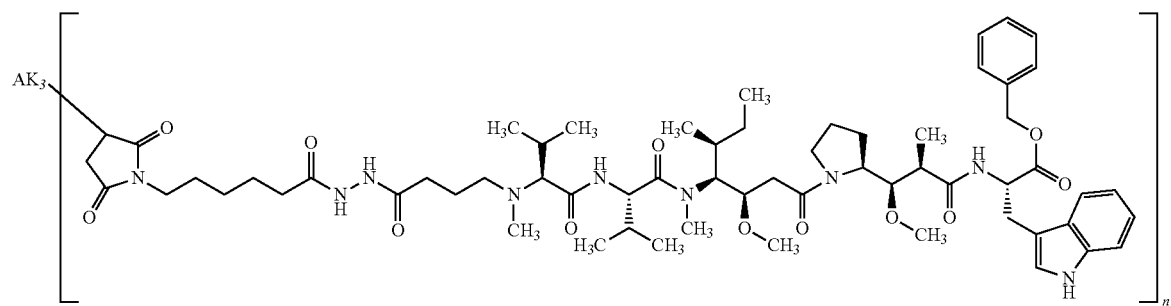
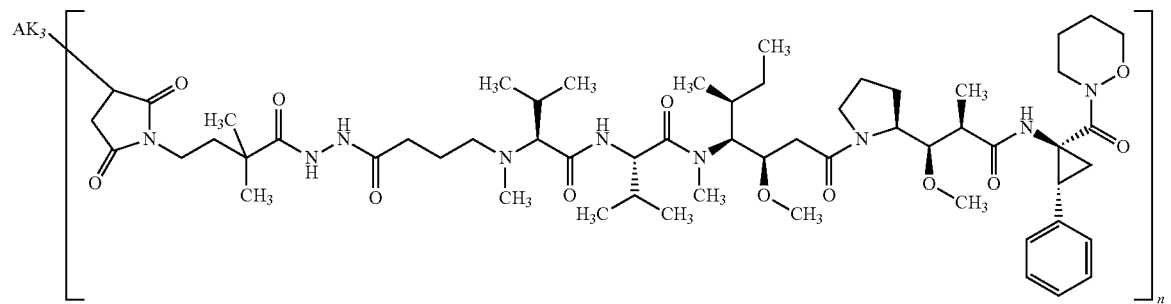
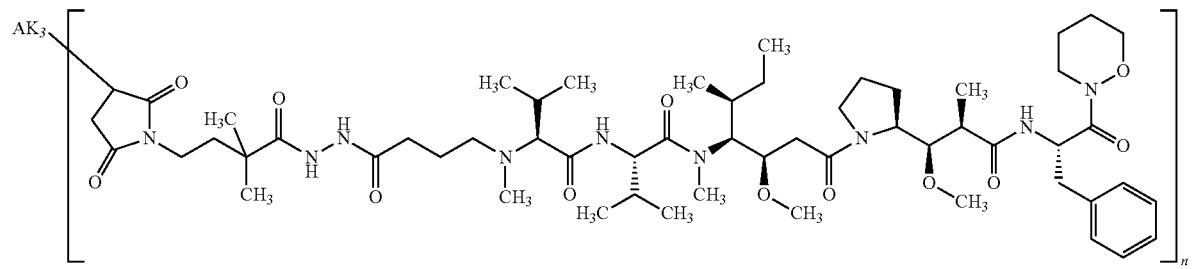
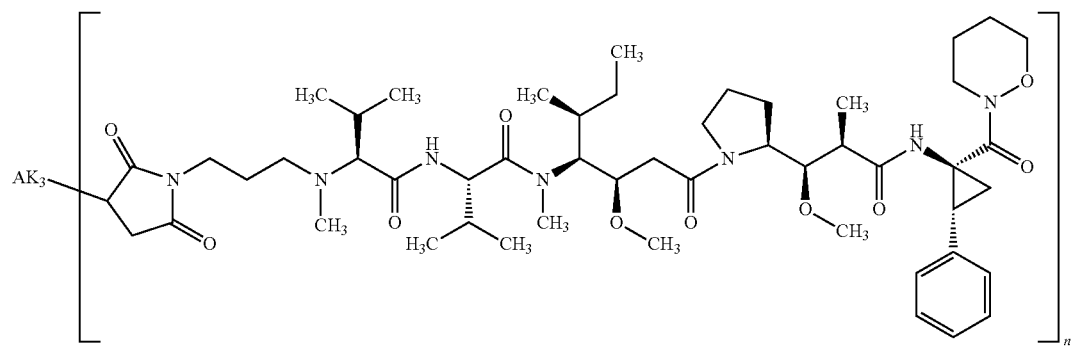

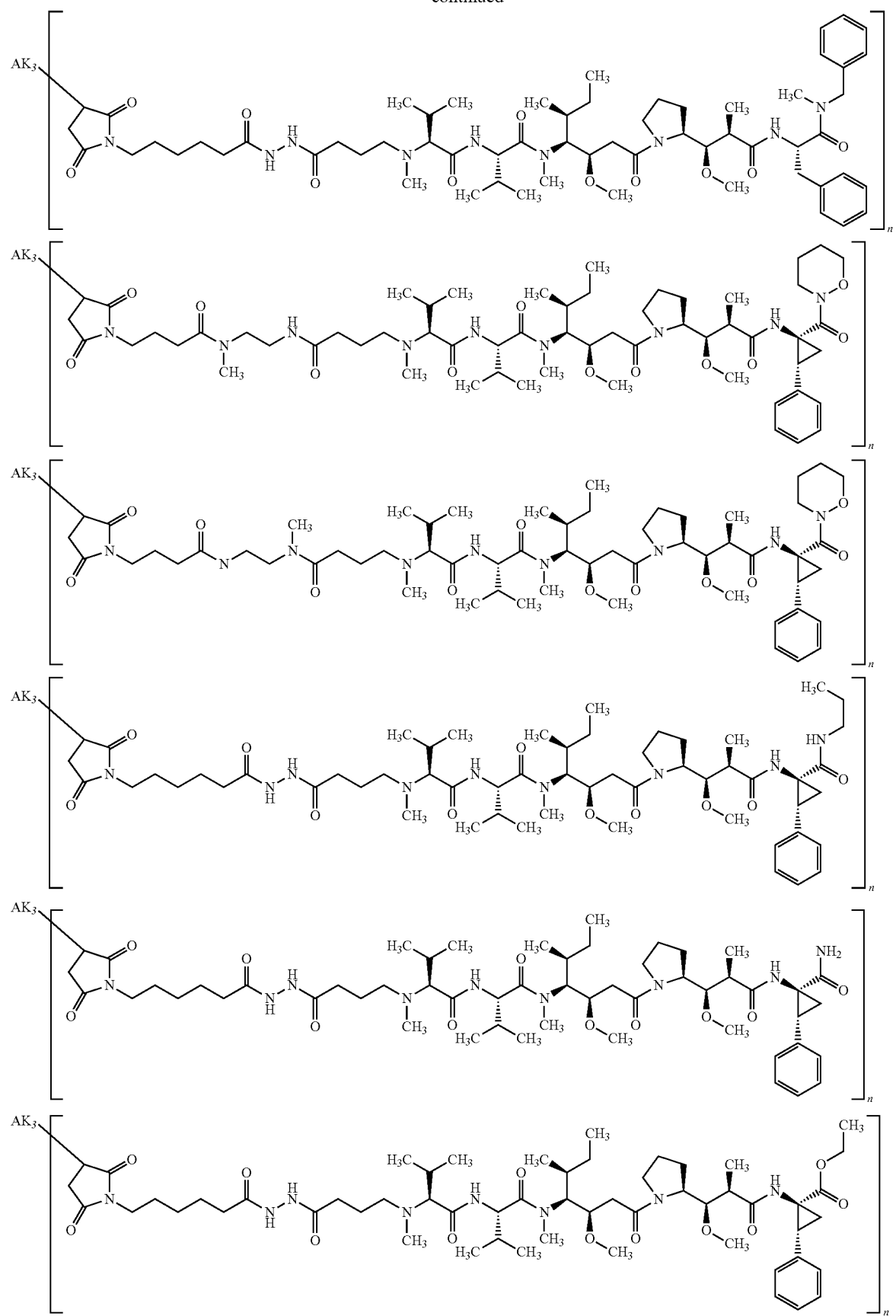

-continued
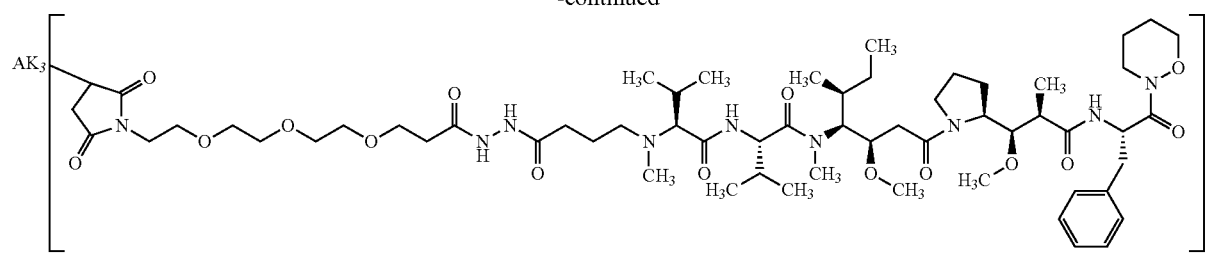
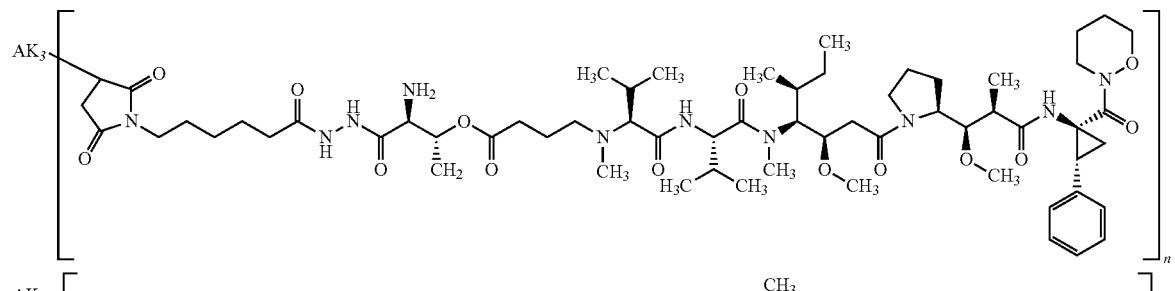
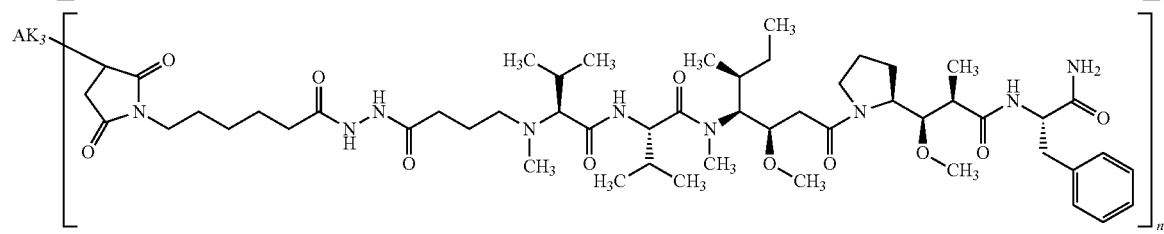
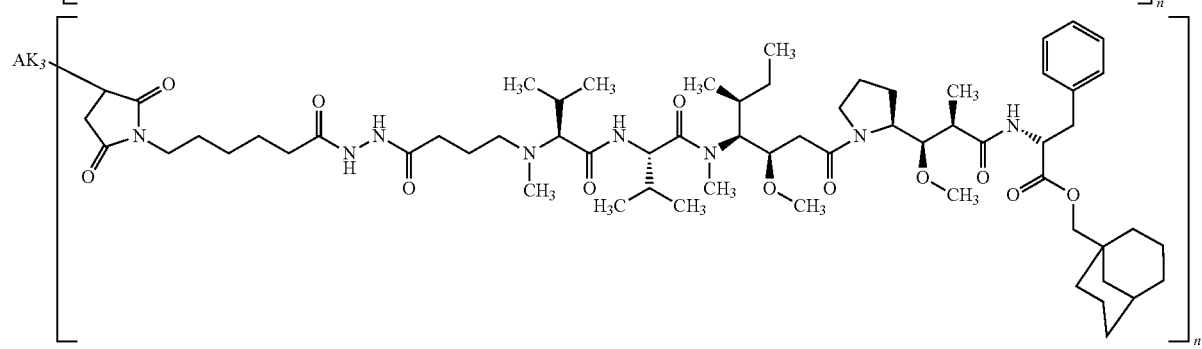
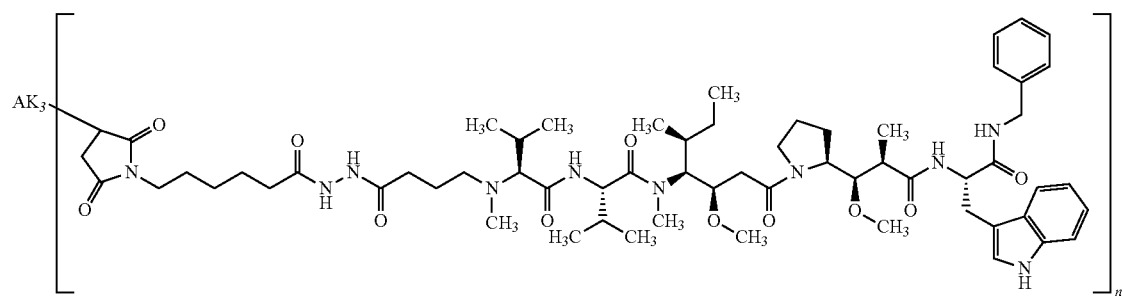
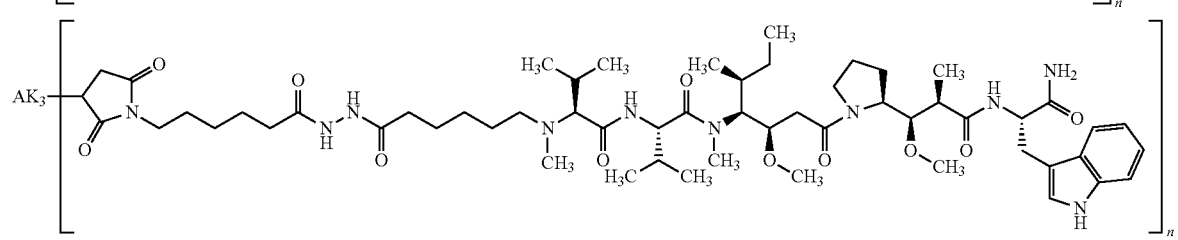

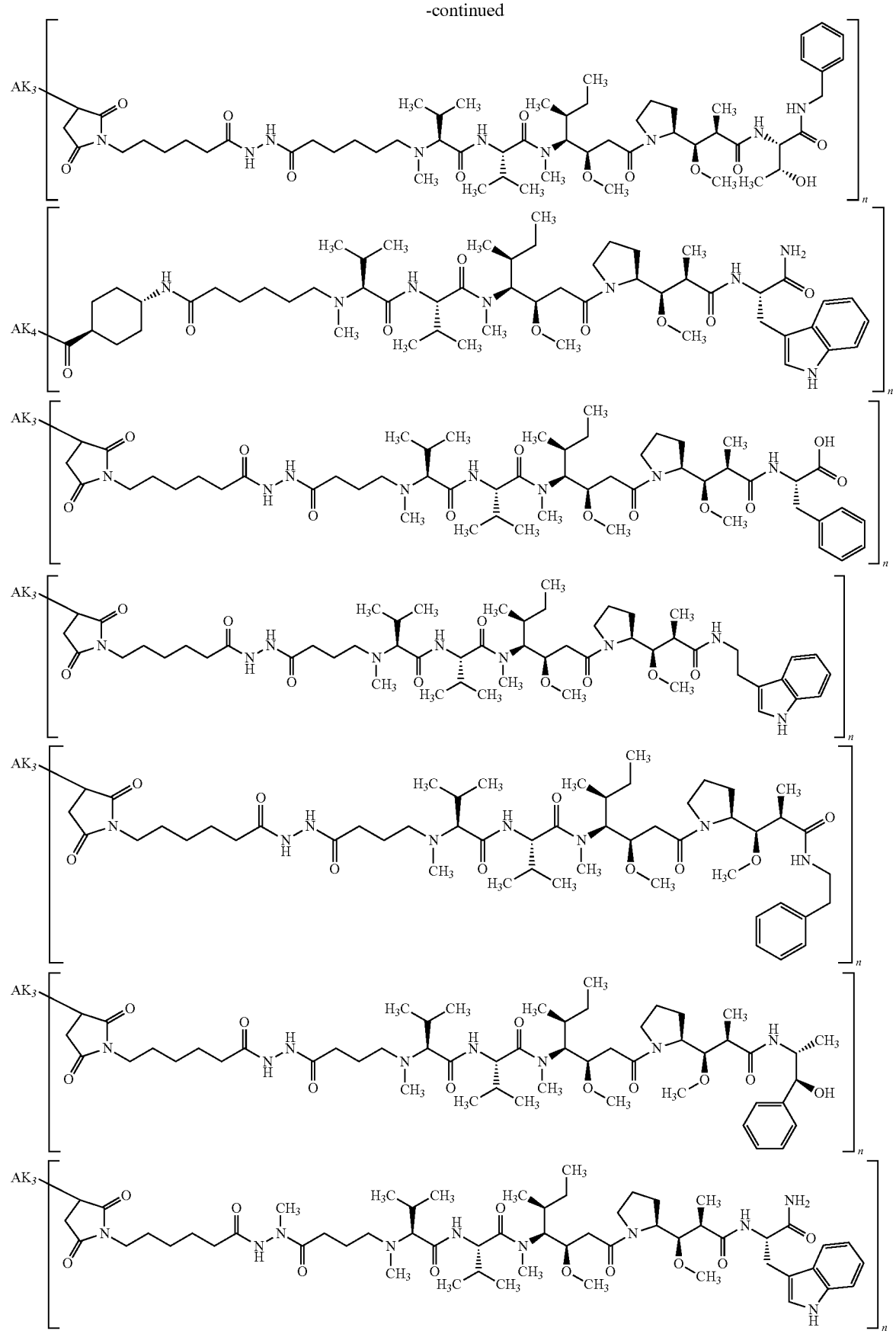

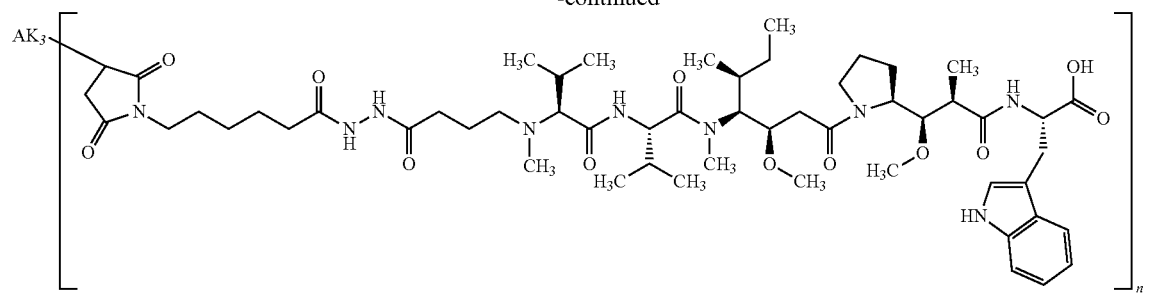
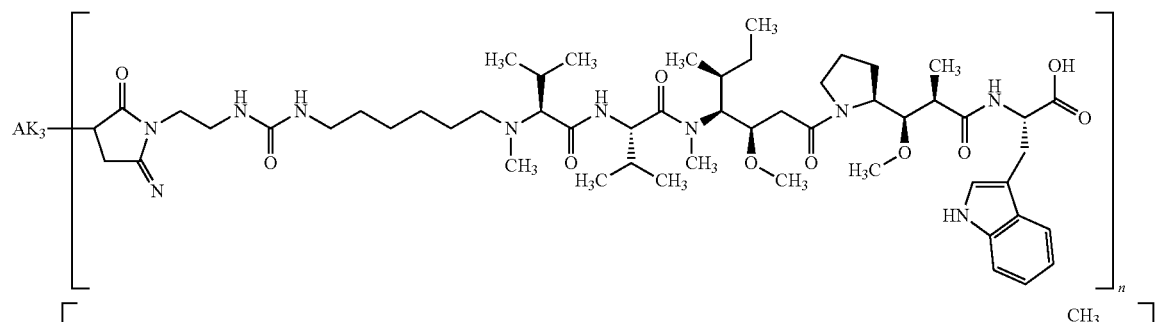
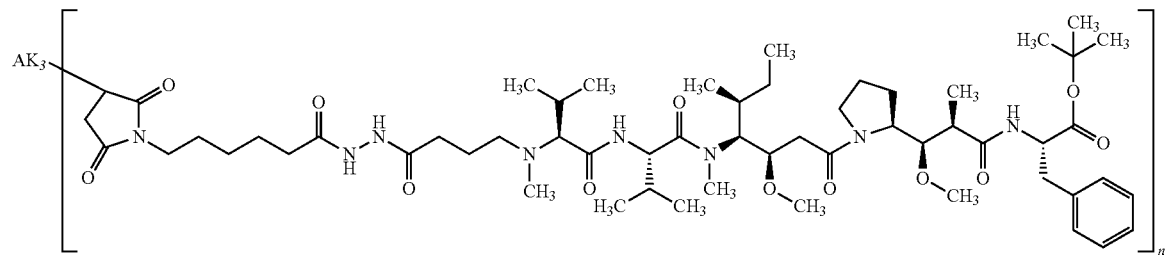
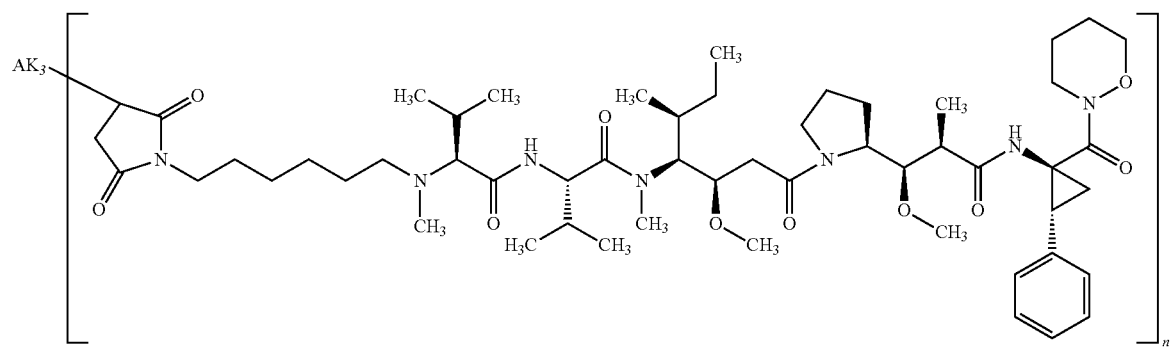
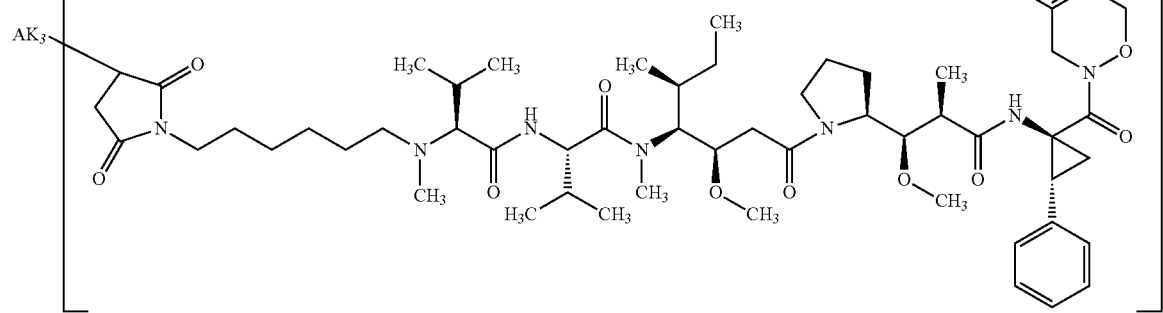

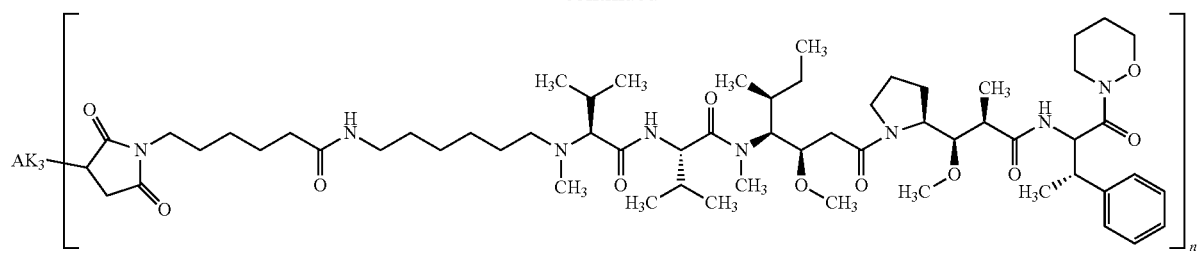
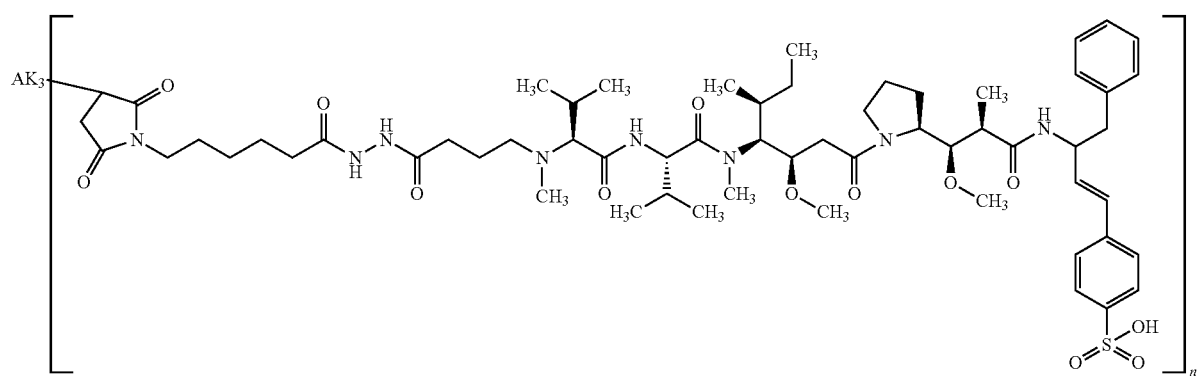
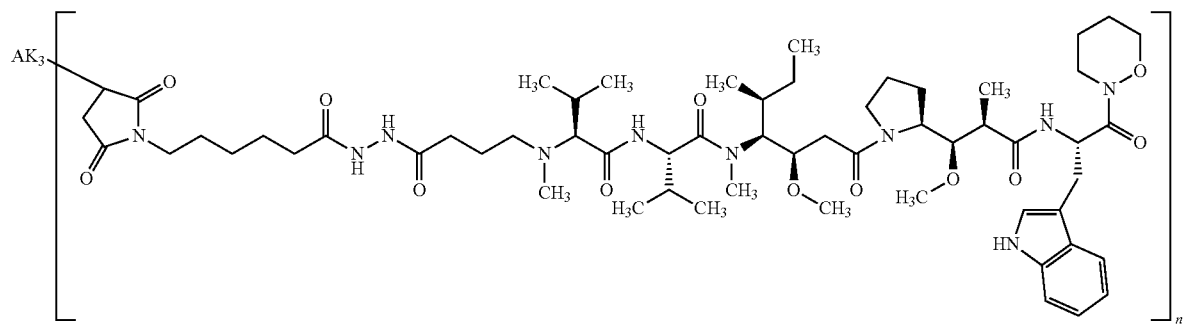
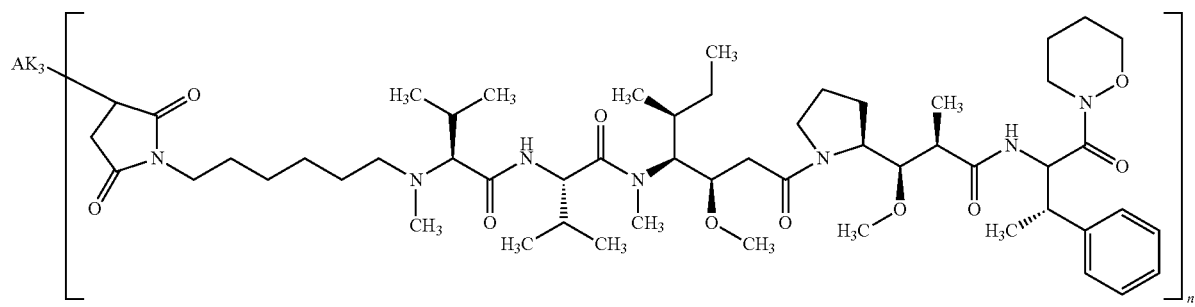
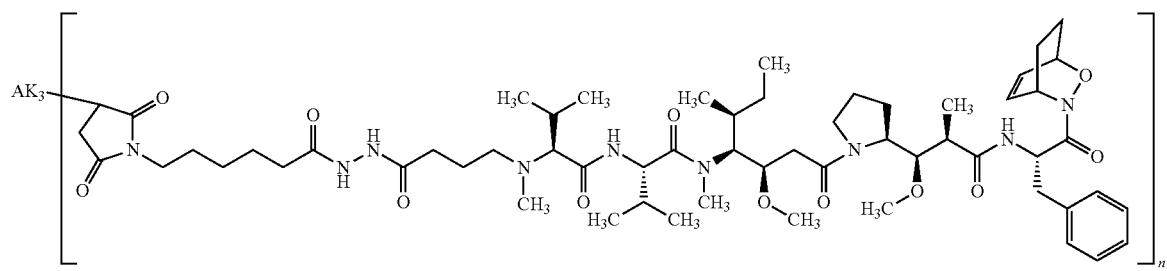

161
-continued
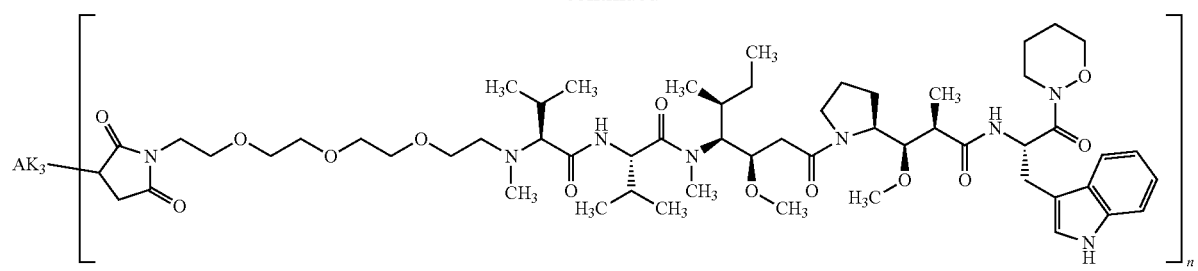
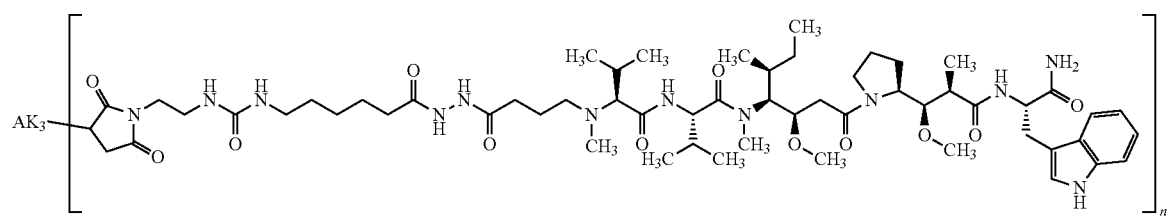
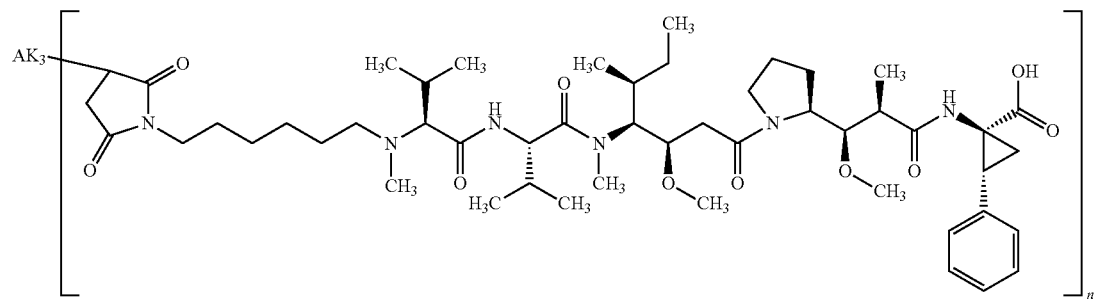
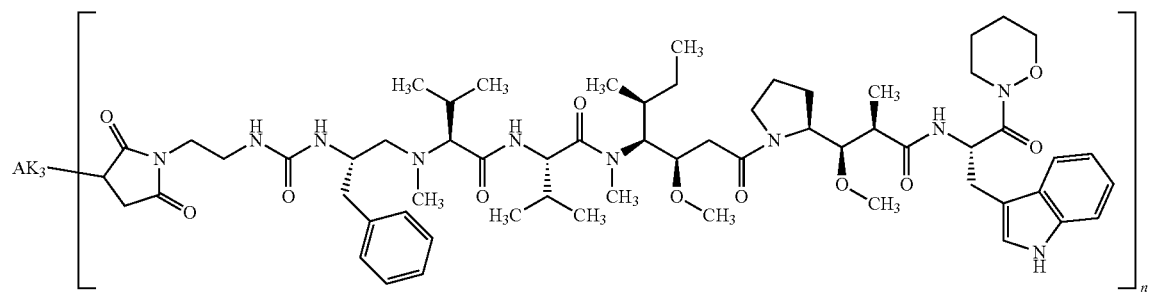
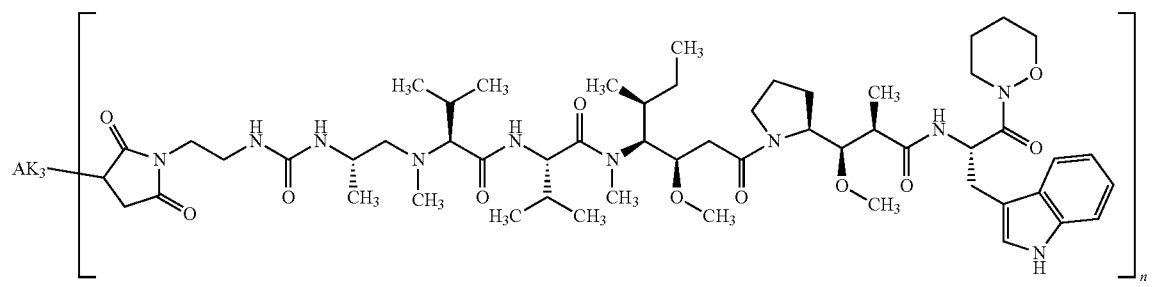

-continued
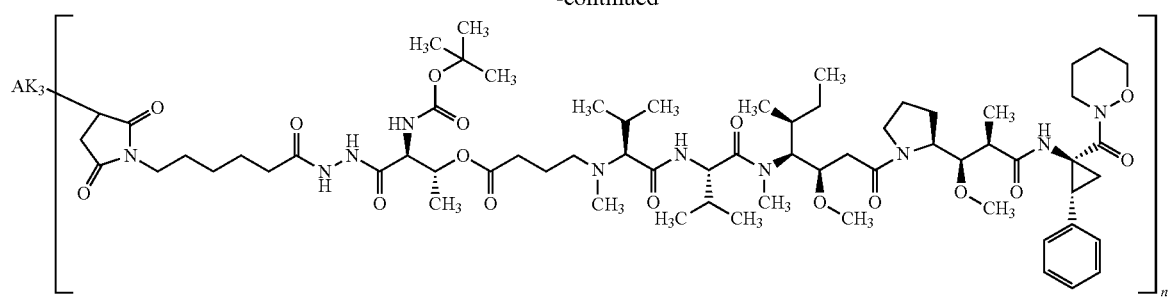
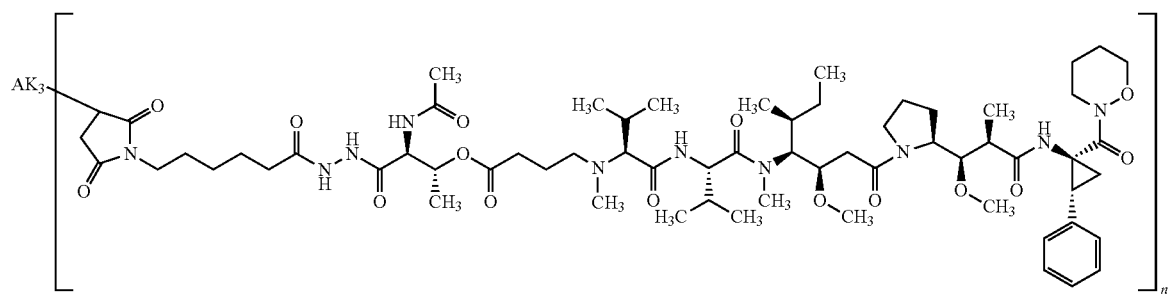
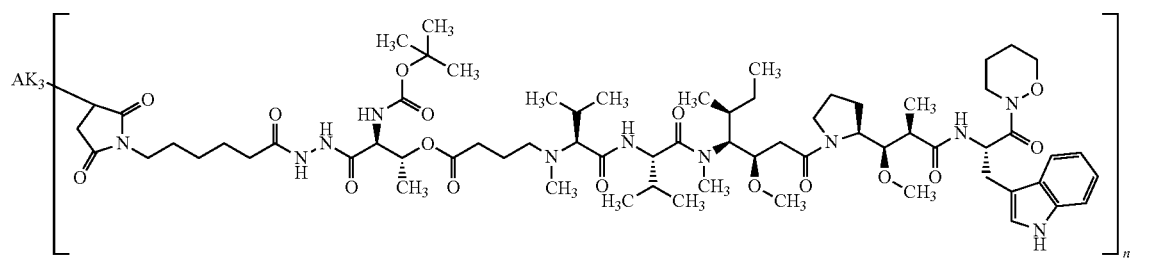
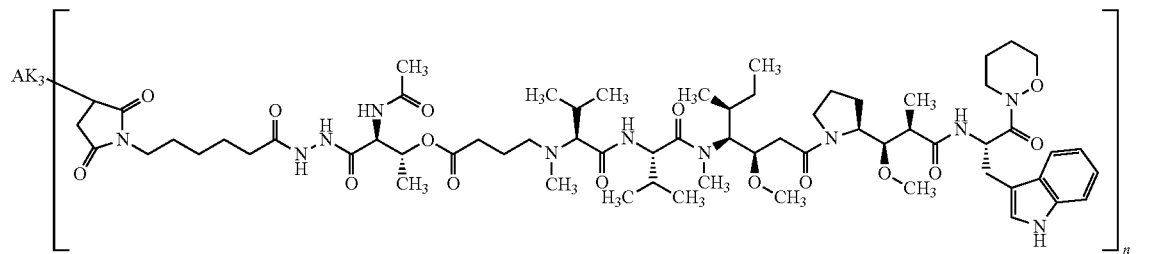
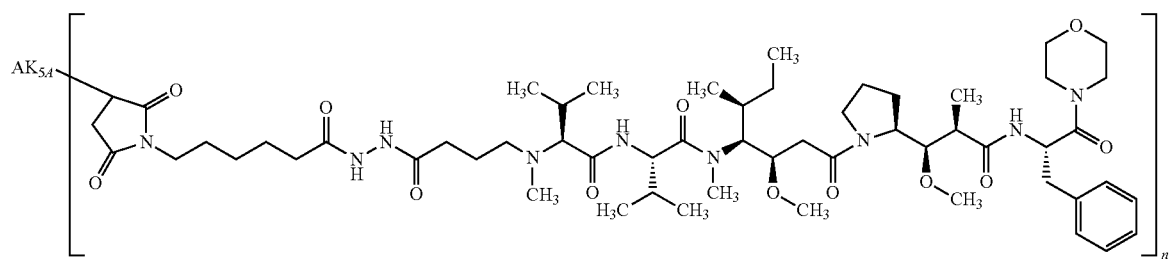
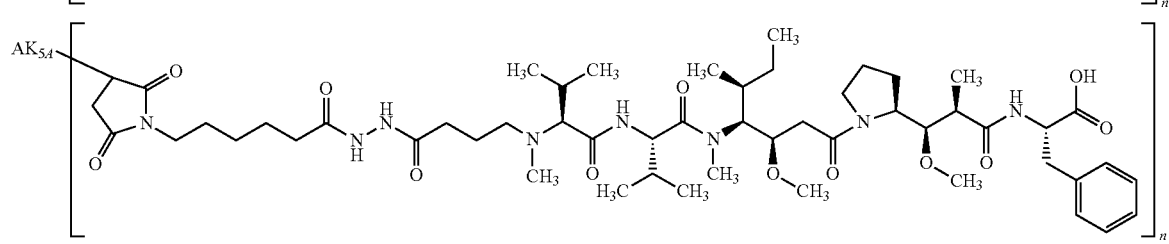

-continued
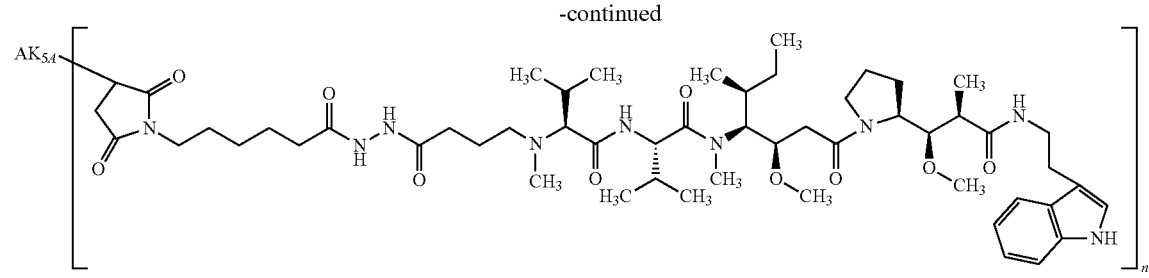
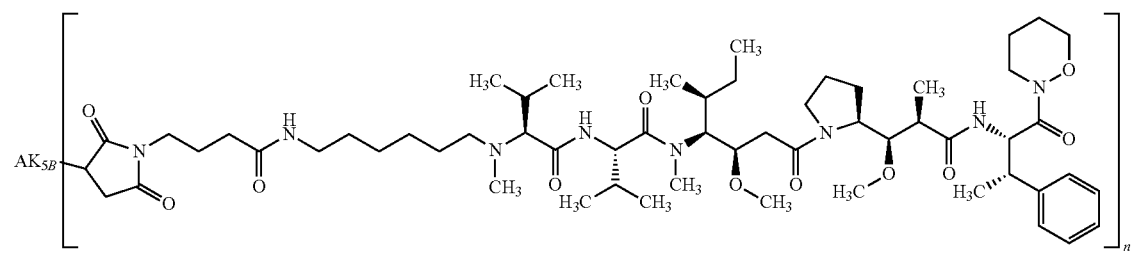
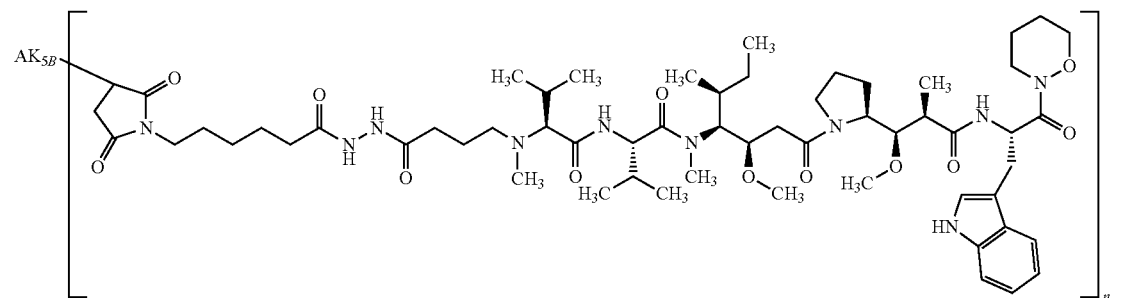
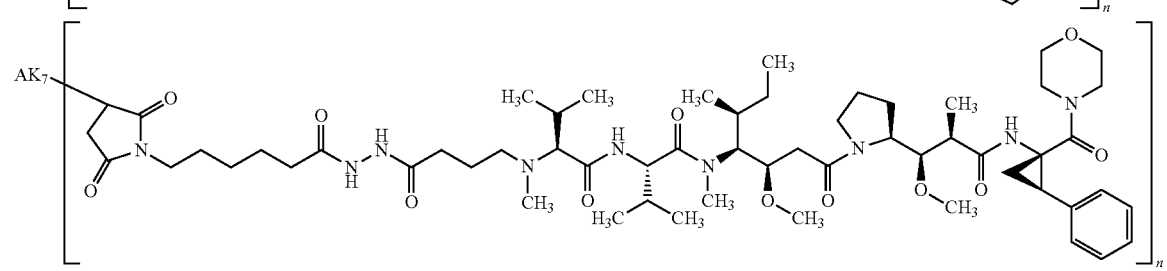
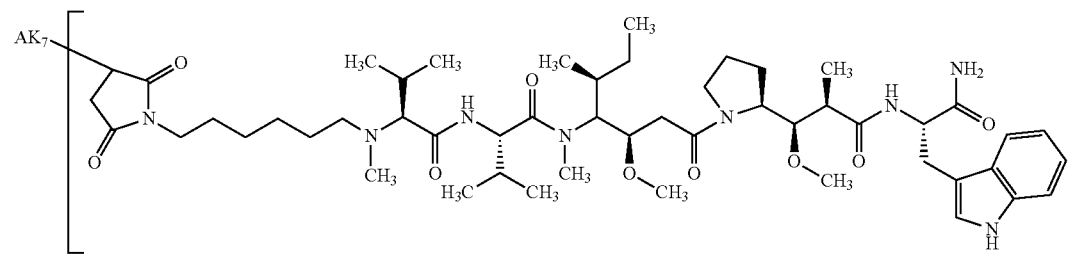
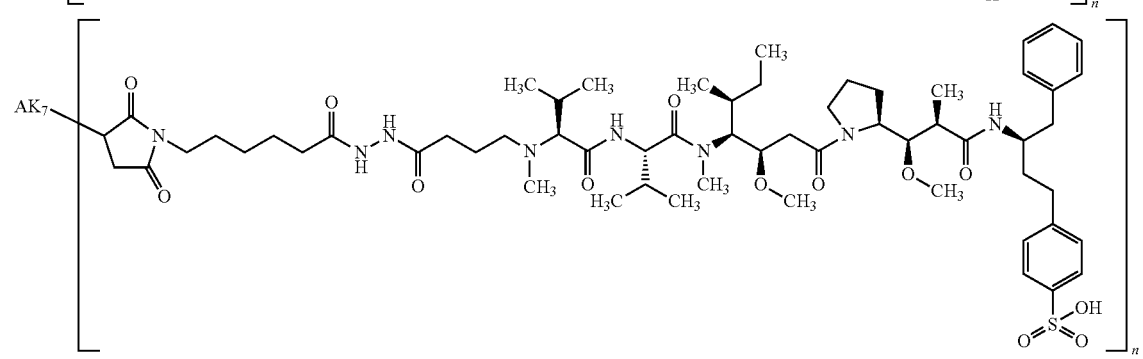

-continued
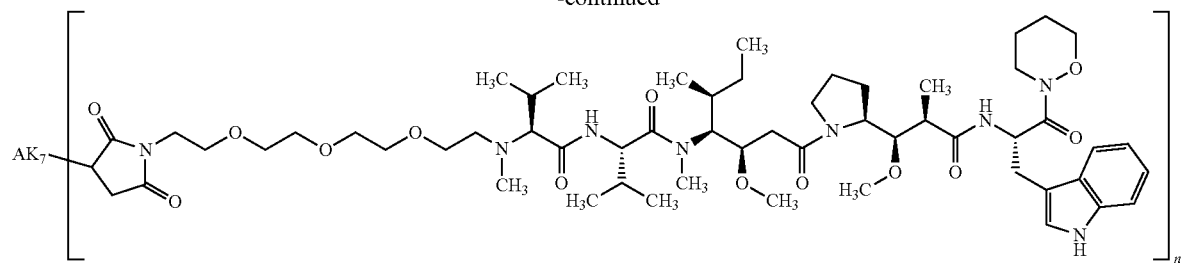
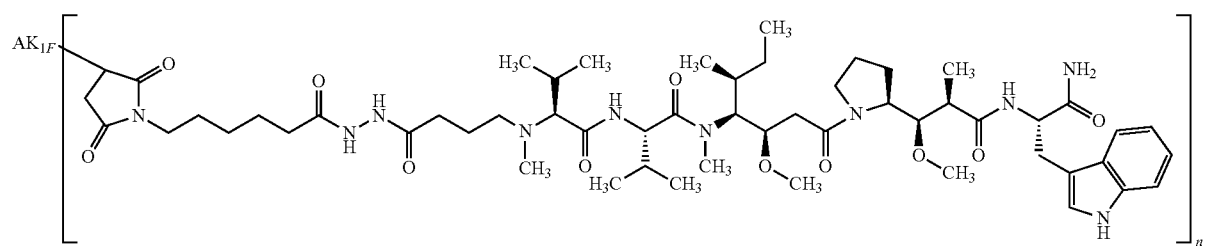
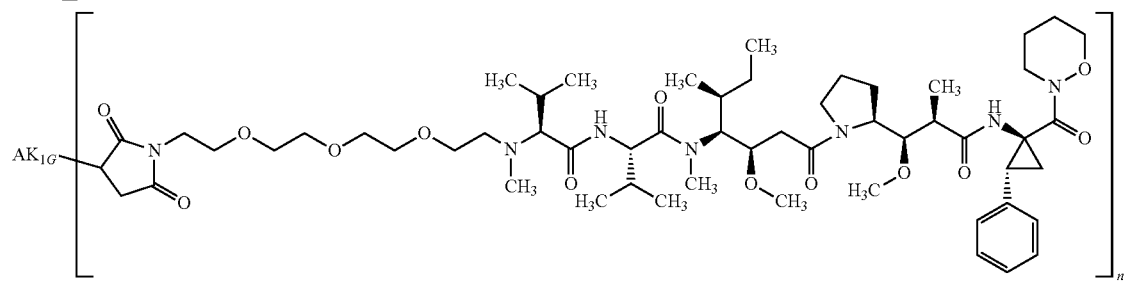
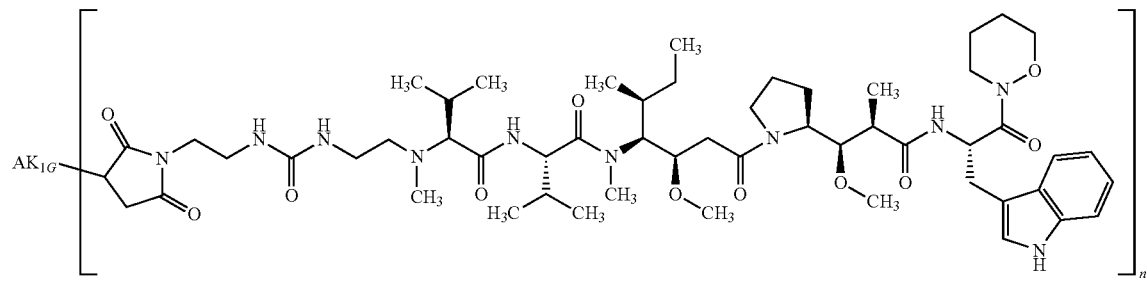
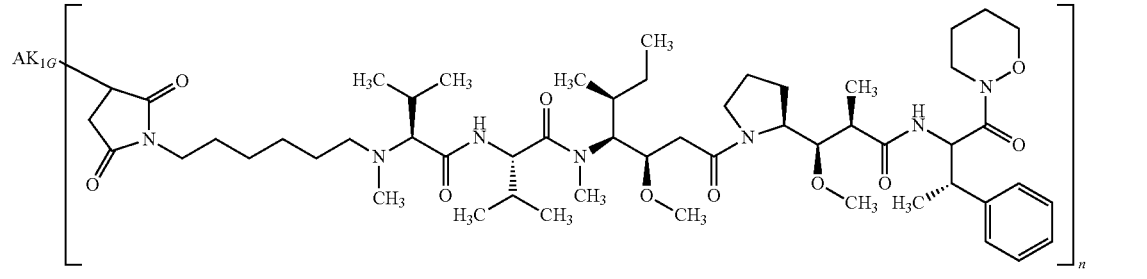
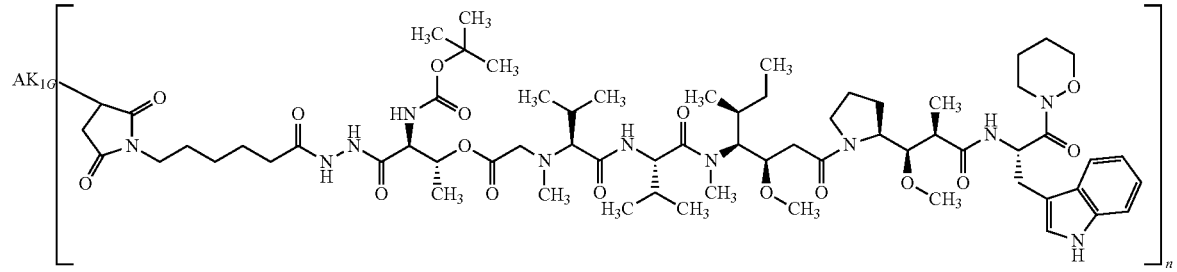

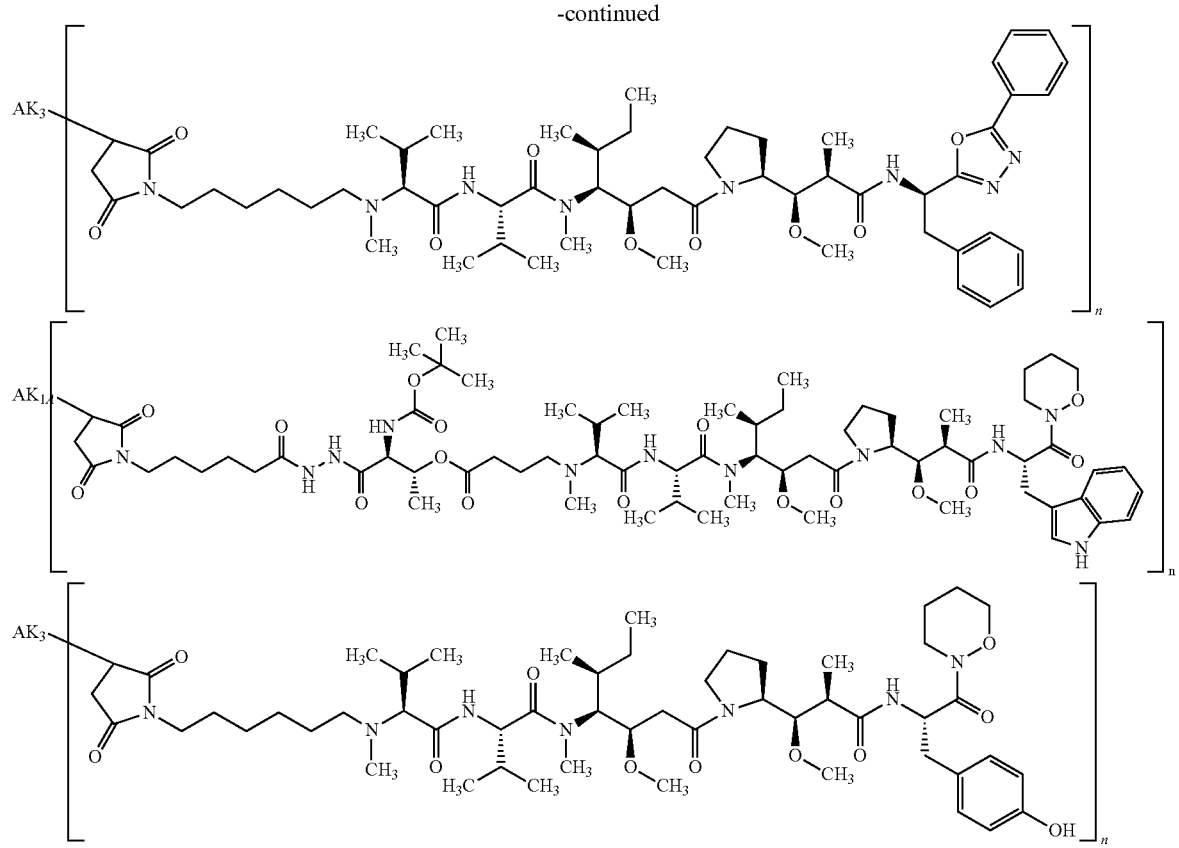

and also their salts, solvates and solvates of the salts, wherein AK (e.g., $AK_{1A}$, $AK_3$, $AK_4$, $AK_{5A}$, $AK_{5B}$, $AK_7$, $AK_{1F}$, or $AK_{1G}$) is an antibody or antigen-binding antibody fragment (preferably a human or humanized monoclonal antibody or antigen-binding fragment thereof) and is, in some embodiments, bonded via the sulphur atom of a cysteine residue of to the antibody or antigen binding fragment thereof to the drug-linker, and n is from 1 to 20, preferably 1 to 10.

Particularly preferred in the context of the present invention are also drug-binder conjugates selected from the following compounds:

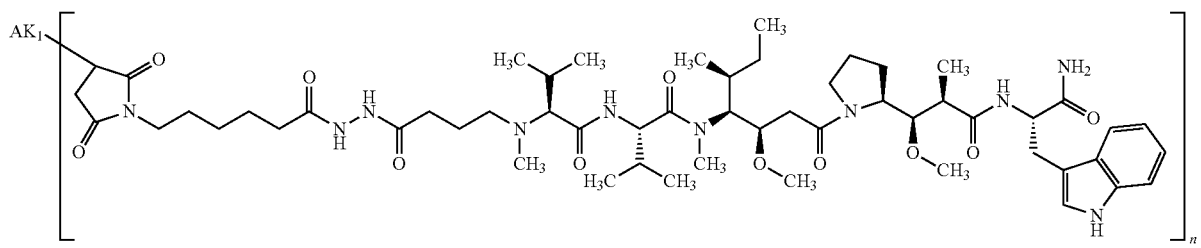

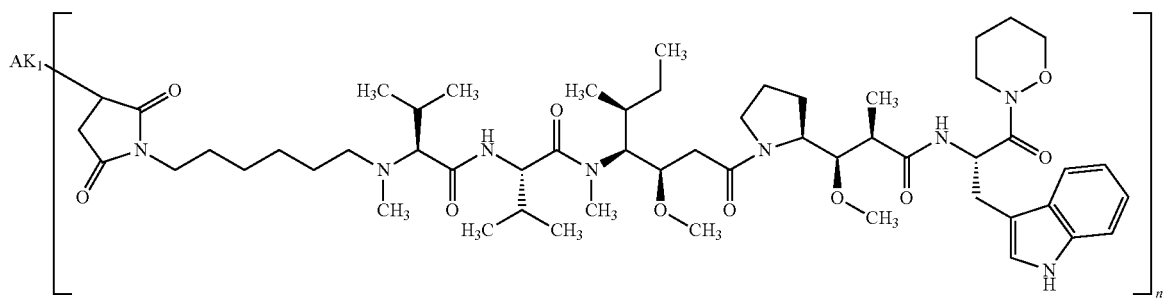

-continued

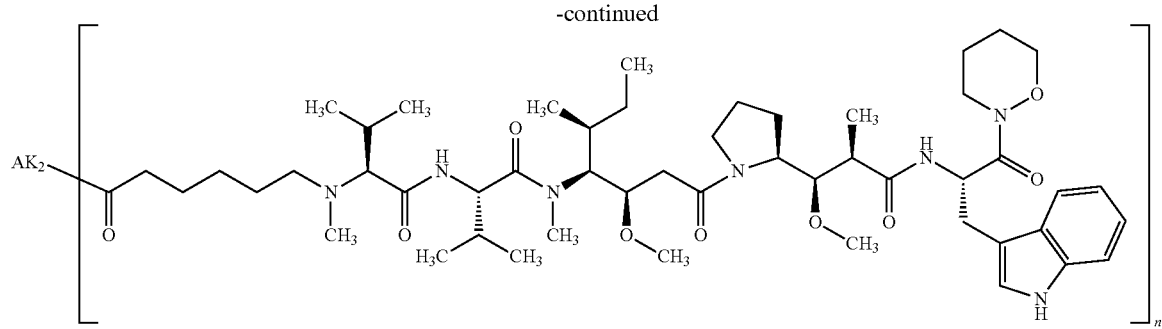

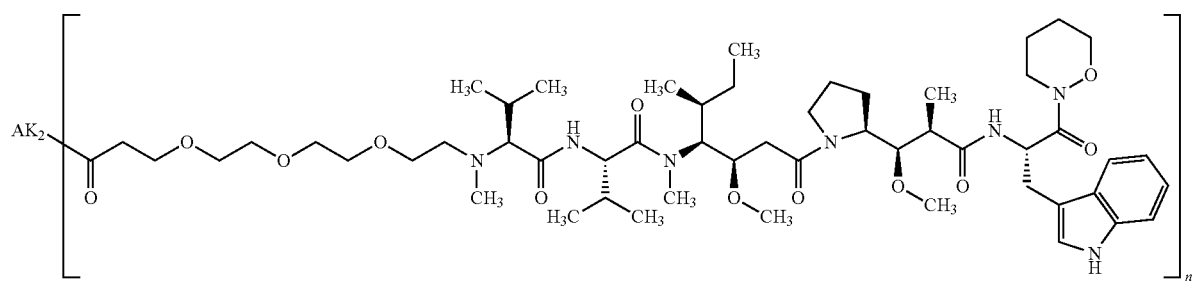

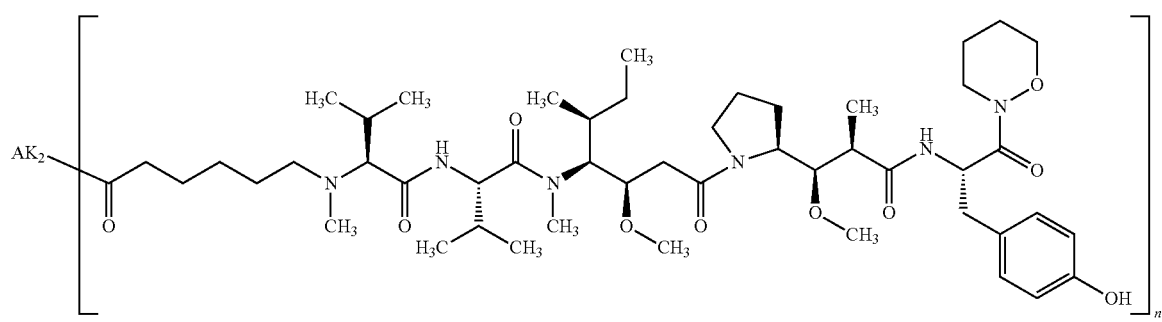

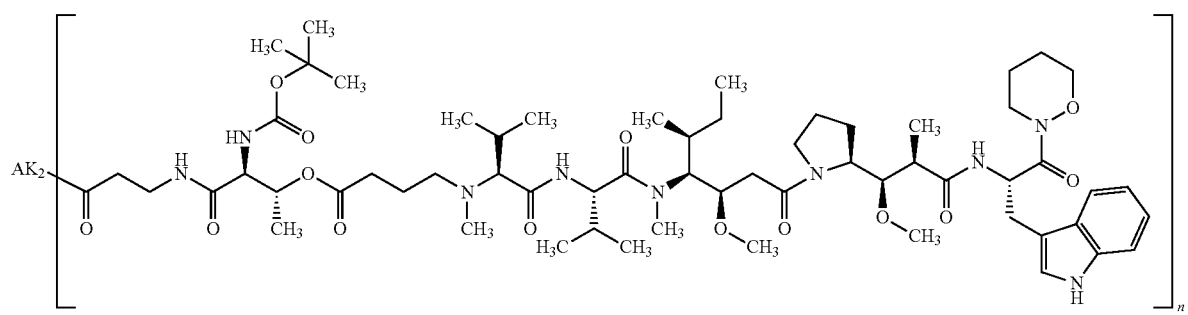

where in each case n is a number from 2 to 8, preferably 2 to 5, $AK_1$ is a human or humanized antibody or an antigen-binding antibody fragment (e.g., a human or humanized antibody or an antigen-binding antibody fragment which binds to C4.4a) and is bonded via the sulphur atom of a cysteine residue of the binder to the group G, and $AK_2$ is a human or humanized antibody or an antigen-binding antibody fragment (e.g., a human or humanized antibody or an antigen-binding antibody fragment which binds to C4.4a) and is bonded via the NH side group of a lysine residue of the binder to the group G.

More particularly preferred in the context of the present invention are binder-drug conjugates selected from the following compounds:

173                                   174
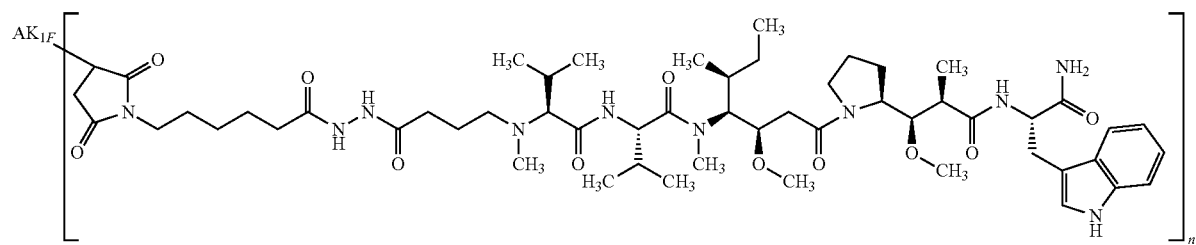
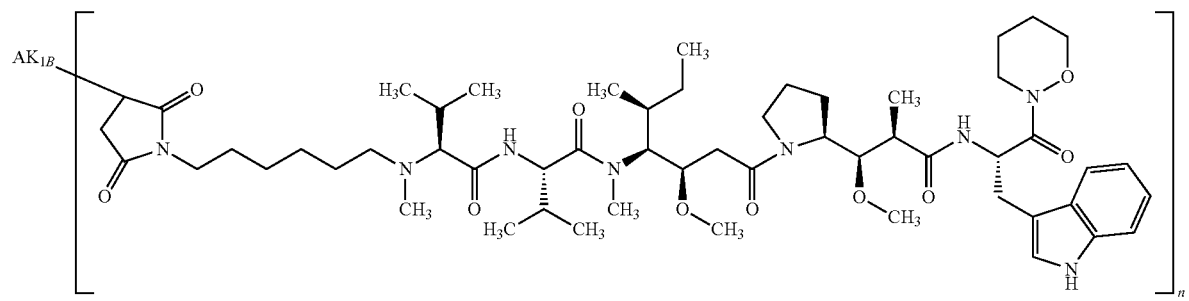
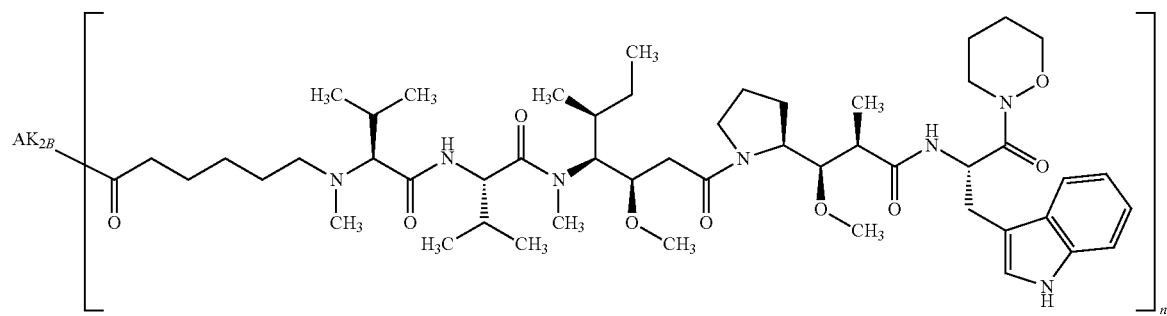
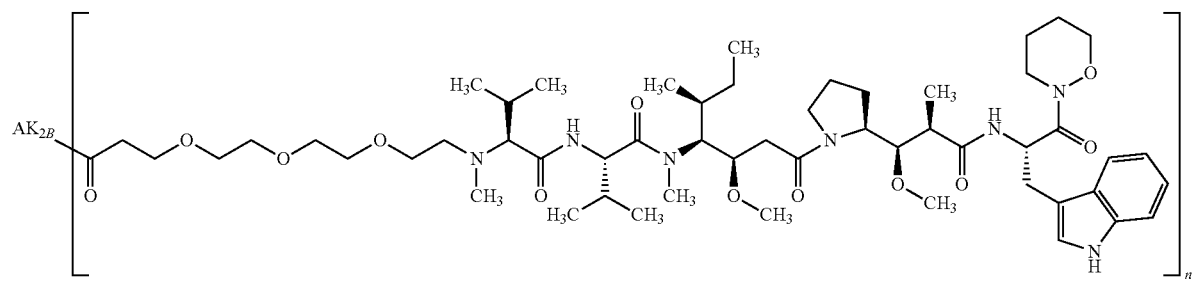
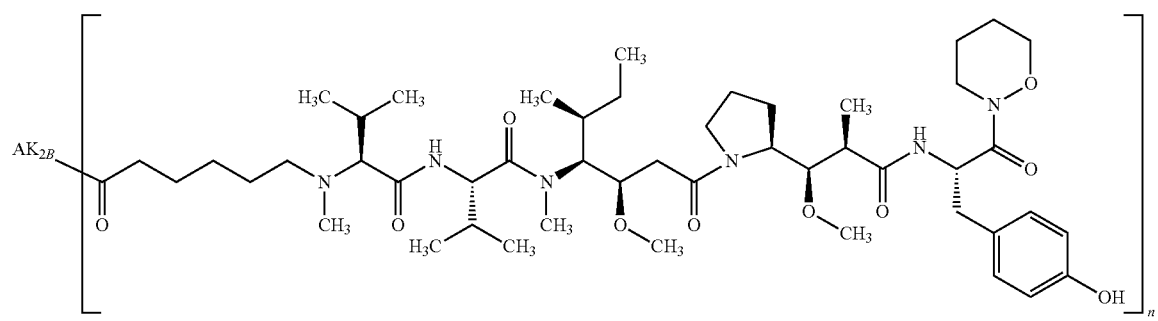

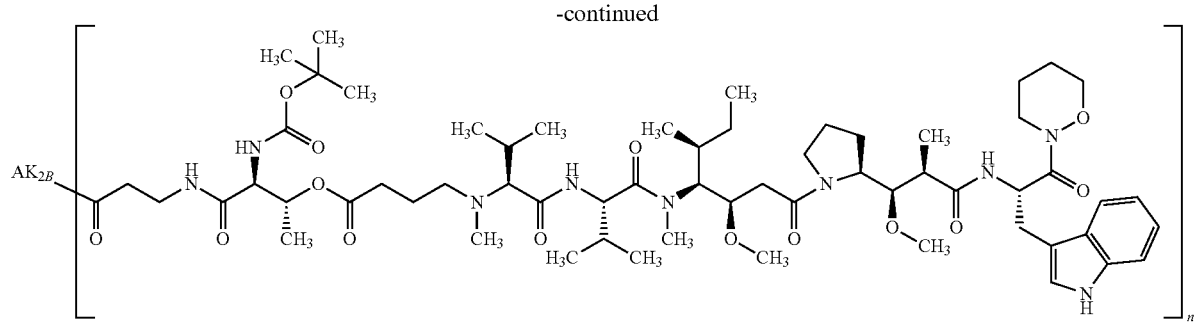

where in each case
n is a number from 2 to 8, preferably 2 to 5,
and
AK is a human or humanized antibody or an antigen-binding antibody fragment (e.g., a human or humanized antibody or an antigen-binding antibody fragment which binds to C4.4a).

In all of these formulae, the antibody may be any one of the antibodies described herein.

More particularly preferred in the context of the present invention are binder-drug conjugates selected from the following compounds:

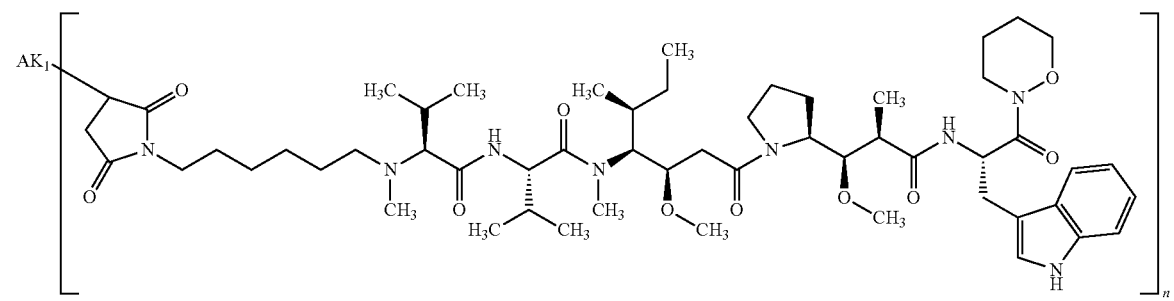

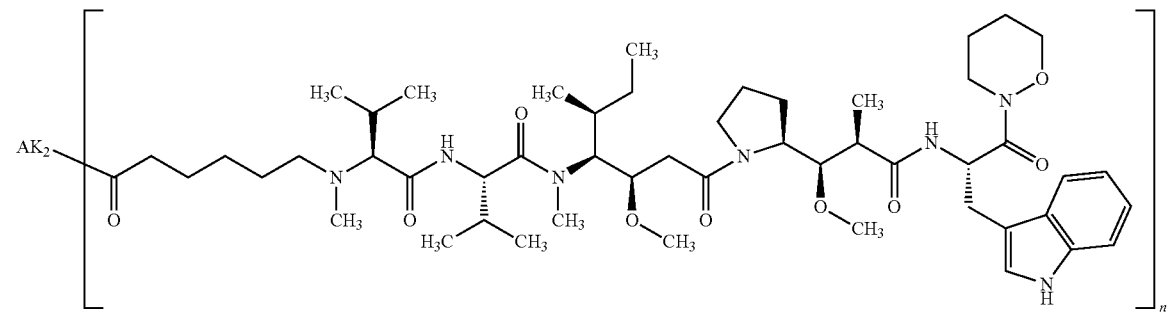

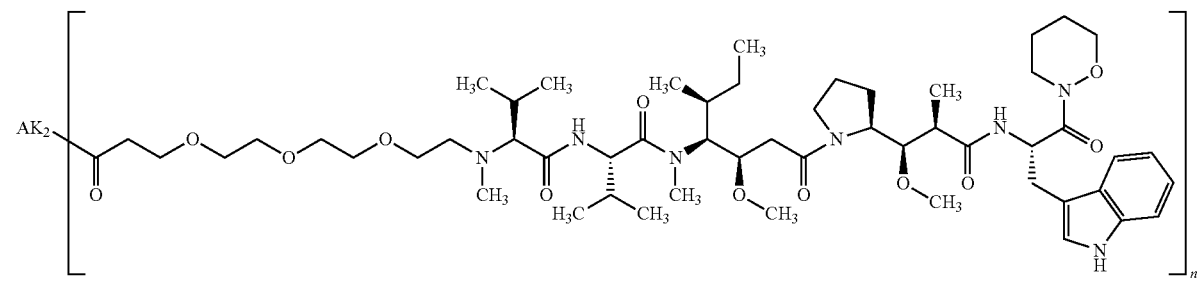

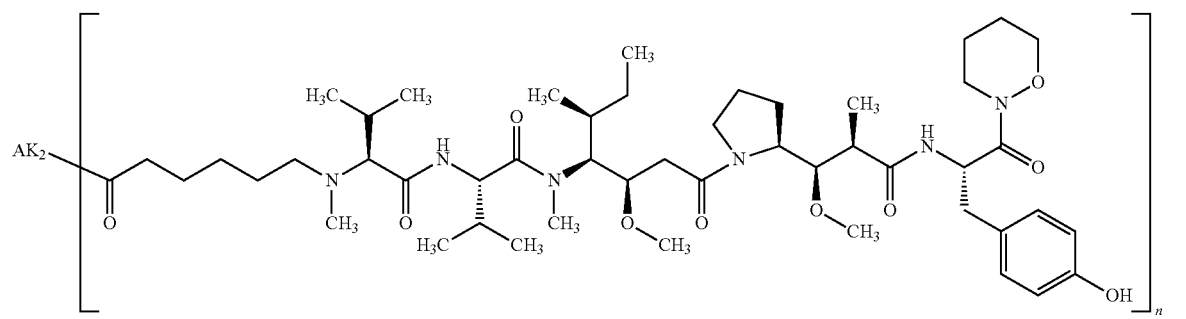

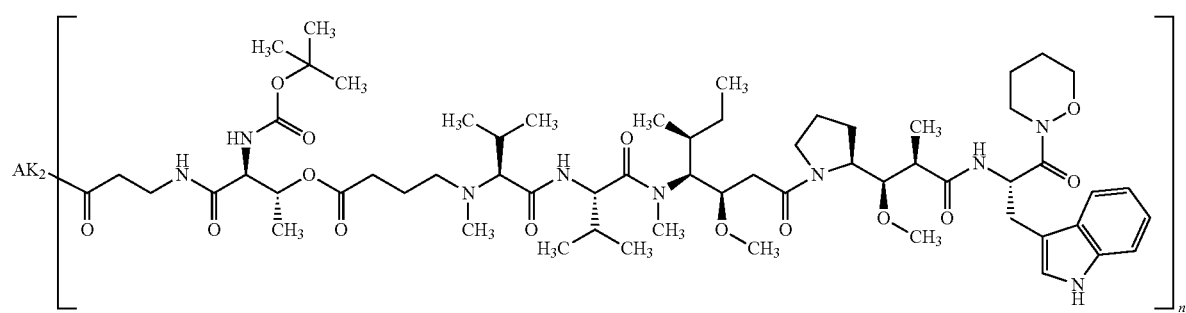

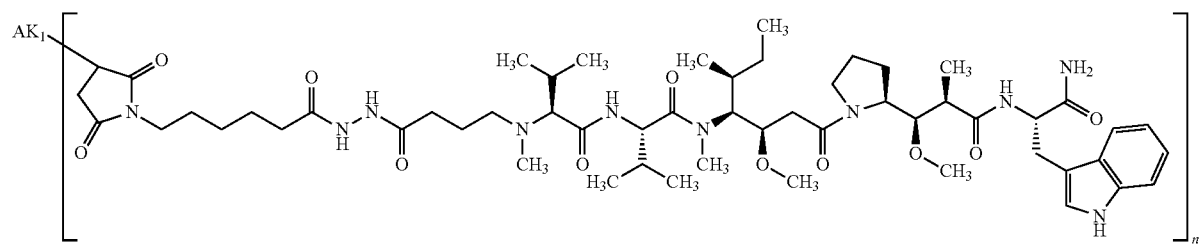

in which n is a number 2 to 8, preferably 2 to 5, and

AK$_1$ is a human or humanized antibody or an antigen-binding antibody fragment (e.g., a human or humanized antibody or an antigen-binding antibody fragment which binds to C4.4a) and is bonded via a cysteine residue to the toxophor-linker unit, AK$_2$ is a human or humanized antibody or an antigen-binding antibody fragment (e.g., a human or humanized antibody or an antigen-binding antibody fragment which binds to C4.4a) and is bonded via a lysine residue to the toxophor-linker unit).

More particularly preferred in the context of the present invention are binder-drug conjugates selected from the following compounds:

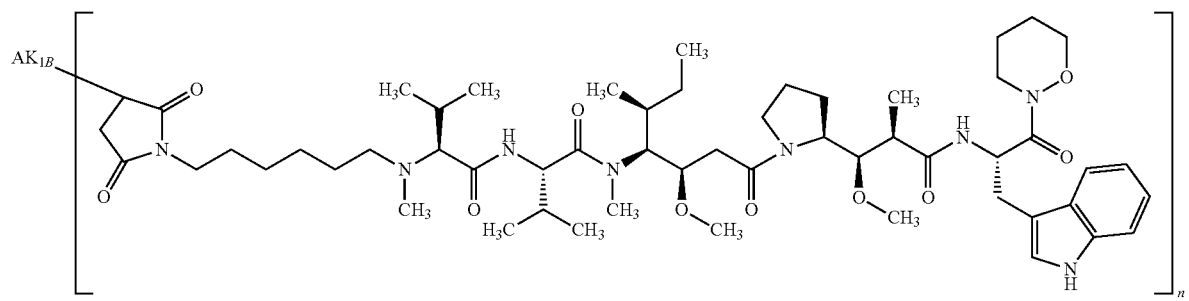

-continued
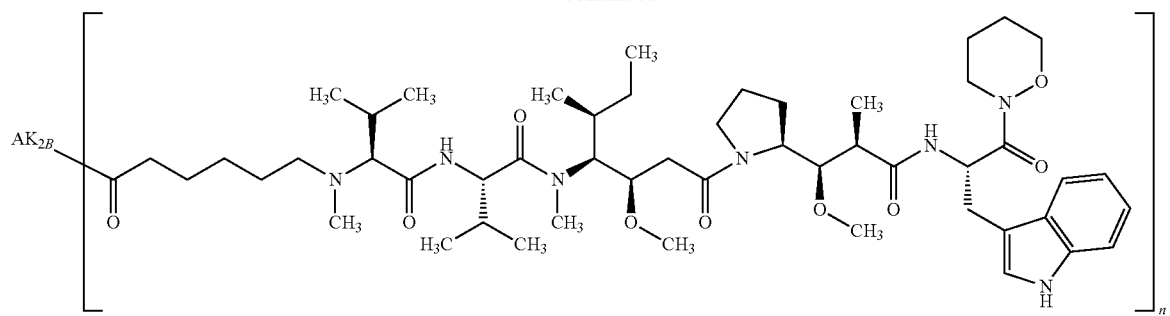
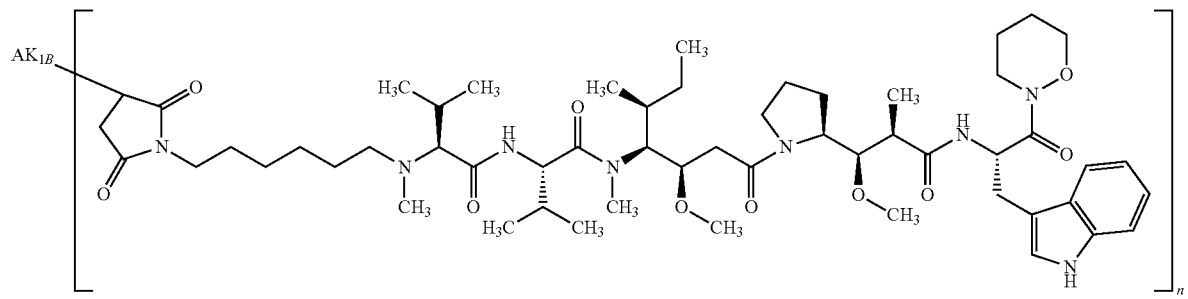
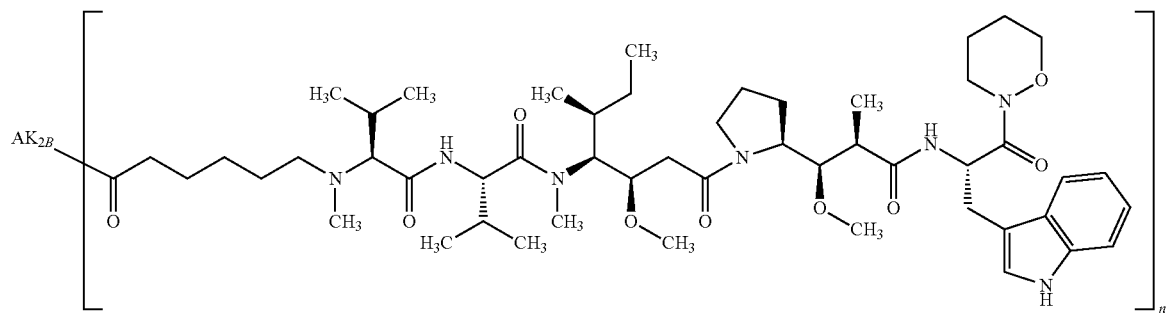
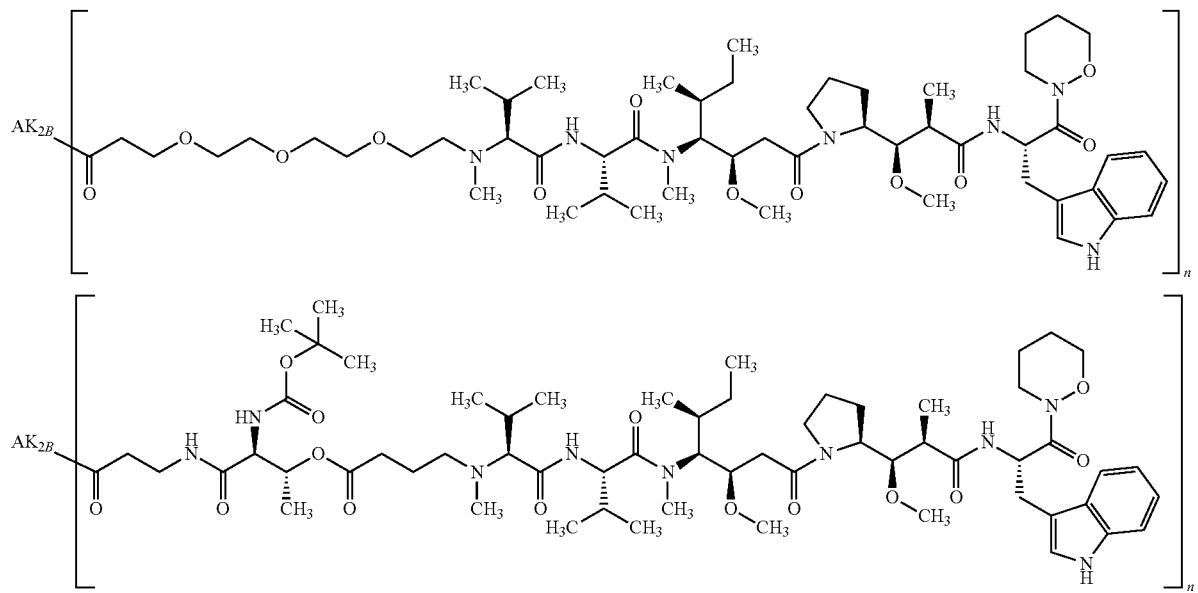

-continued
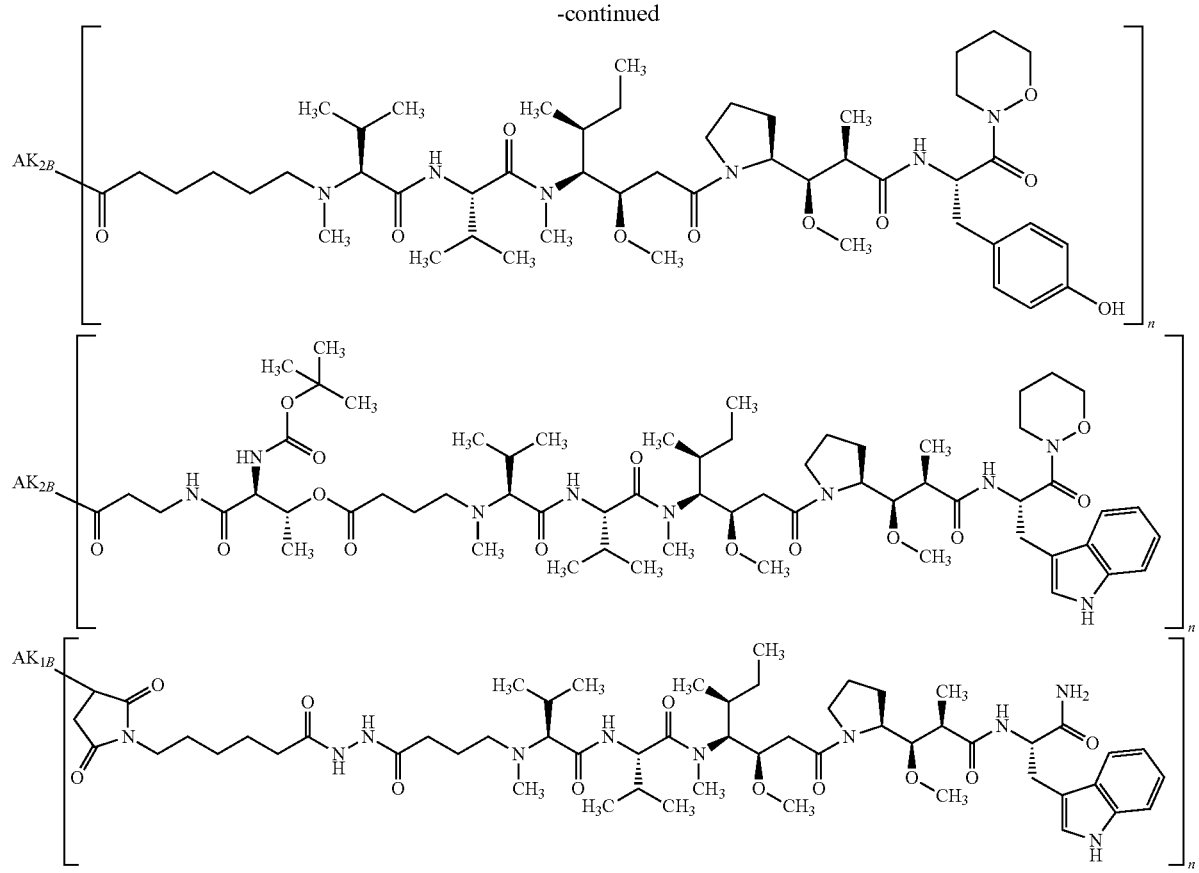
in which
n is a number 2 to 8, preferably 2 to 5,
and
$AK_{1B}$ and $AK_{2B}$ is B01-3.
Exemplary cysteine adducts are as follows:
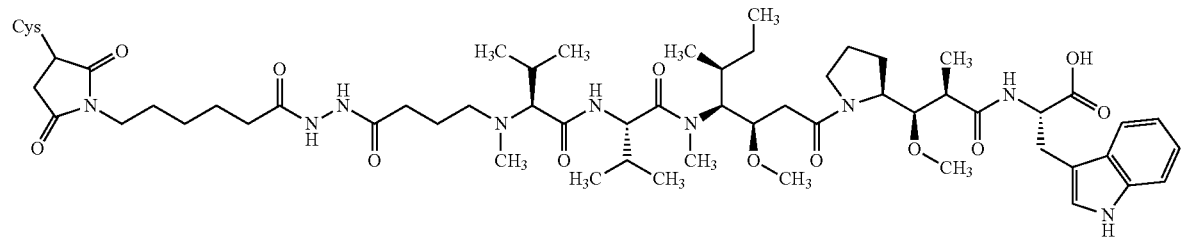
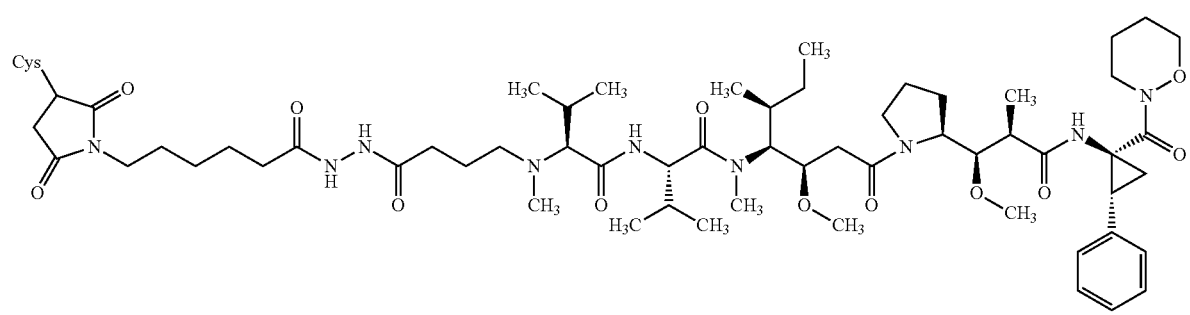

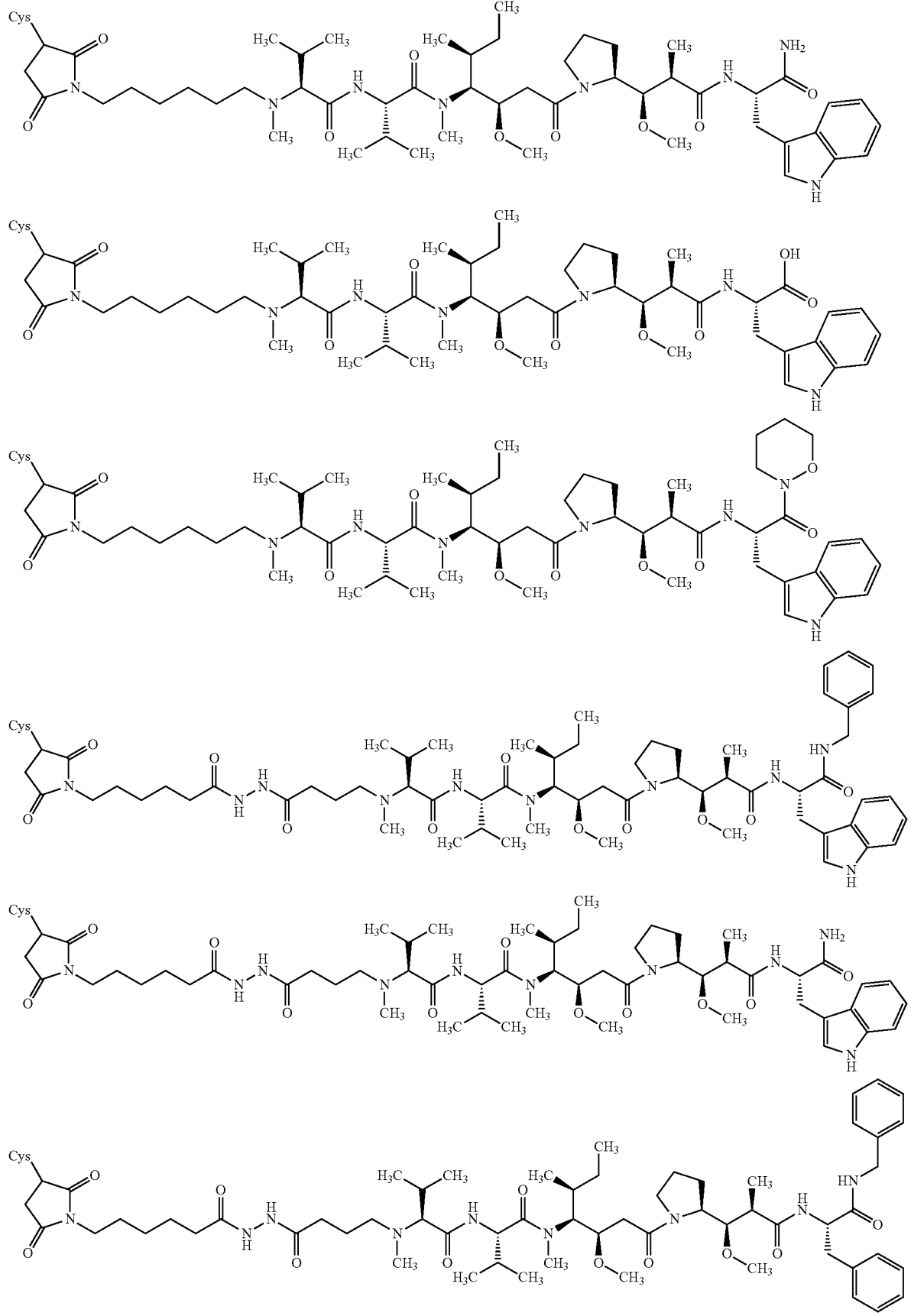

-continued

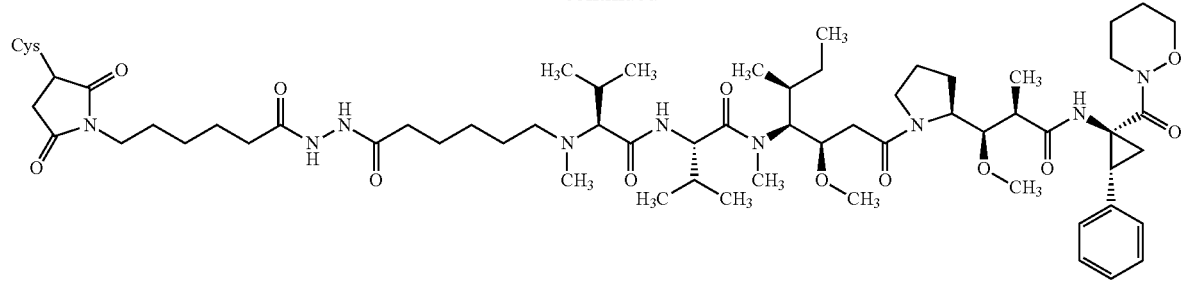

The definitions of radicals that are indicated individually in the respective combinations and preferred combinations of radicals are also replaced arbitrarily by radical definitions of other combinations, independently of the respective combinations of radicals that are indicated.

Especially preferred are combinations of two or more of the abovementioned preference ranges.

Further provided by the invention is a process for preparing the compounds of the invention of the formula (Ia), characterized in that a solution of the binder (preferably in buffer such as, for example, PBS buffer)
[A] is admixed with a suitable reducing agent, such as, for example, dithiothreitol or tris(2-carboxyethyl)phosphine hydrochloride, and is subsequently reacted with a compound of the formula (IIa)

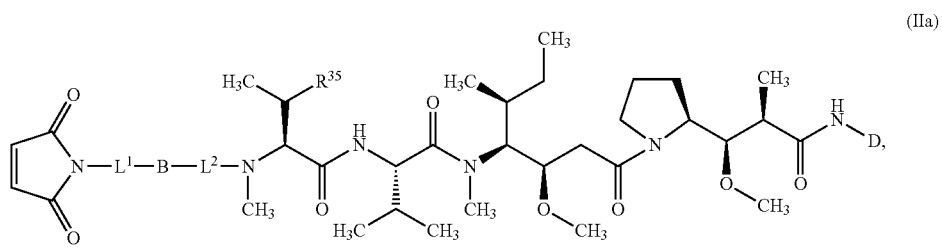
(IIa)

in which D, $L^1$, B, $L^2$ and $R^{35}$ each have the definitions indicated above,
to give a compound of the formula (I-A)

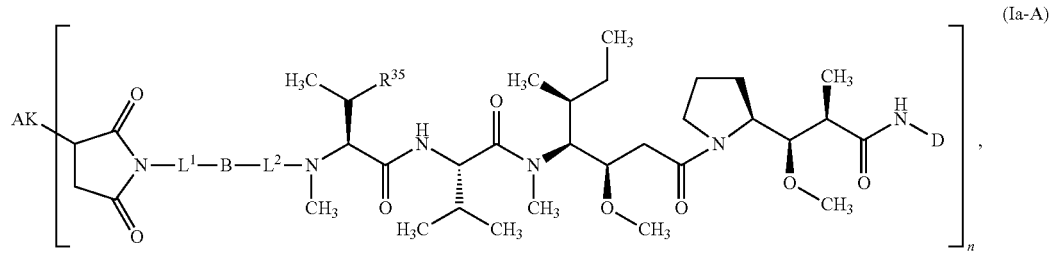
(Ia-A)

in which n, $AK_2$, D, $L^1$, B, $L^2$ and $R^{35}$ each have the definitions indicated above,
or
[B] is reacted with a compound of formula (IIIa

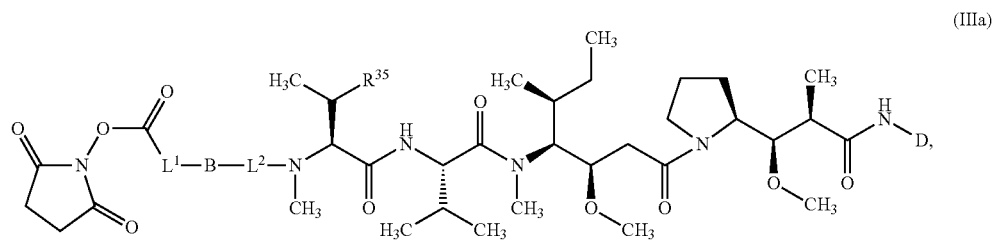

(IIIa)

in which D, $L^1$, B, $L^2$ and $R^{35}$ each have the definitions indicated above,
to give a compound of the formula (Ia-B)

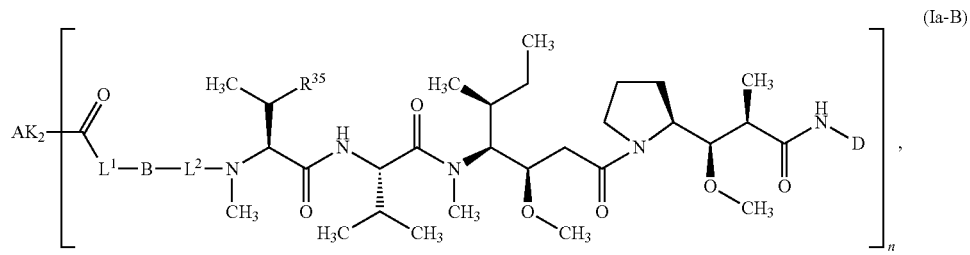

(Ia-B)

in which n, $AK_2$, D, $L^1$, B, $L^2$ and $R^{35}$ each have the definitions indicated above.

Further provided by the invention is a process for preparing the compounds of the invention of the formula (I), characterized in that a solution of the binder in PBS buffer
[A] is admixed with a suitable reducing agent, such as, for example, dithiothreitol or tris(2-carboxyethyl)phosphine hydrochloride, and is subsequently reacted with a compound of the formula (II)

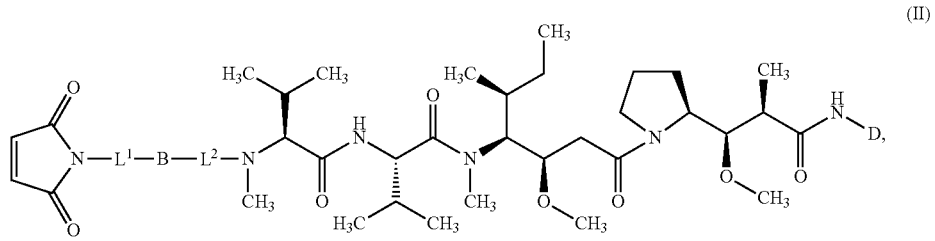

(II)

in which D, $L^1$, B and $L^2$ each have the definitions indicated above,
to give a compound of the formula (I-A)

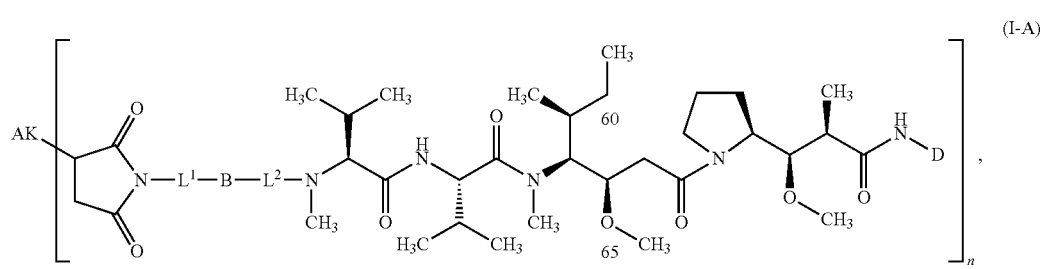

(I-A)

in which n, $AK_1$, D, $L^1$, B and $L^2$ each have the definitions indicated above,
or
[B] is reacted with a compound of the formula (III)

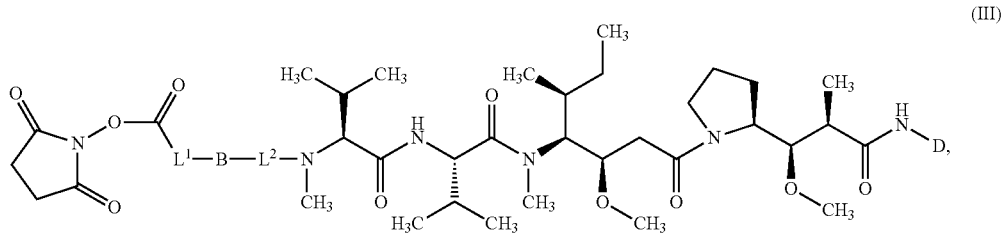

in which D, $L^1$, B and $L^2$ each have the definitions indicated above,
to give a compound of the formula (I-B)

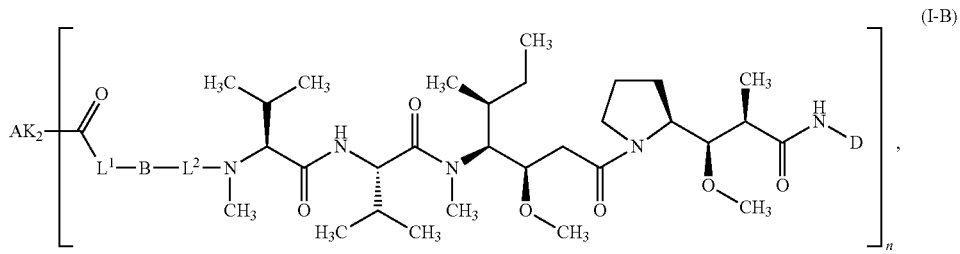

in which n, $AK_2$, D, $L^1$, B and $L^2$ each have the definitions indicated above.

Cysteine Coupling:

The partial reduction of the antibody and also the subsequent conjugation of the (partially) reduced antibody with a compound of the formula (II) or (IIIa) takes place in accordance with the methods known to the skilled person, see e.g. Ducry et. al., Bioconj. Chem. 2010, 21, 5 and references herein, Klussman et. al., Bioconj. Chem. 2004, 15(4), 765-773. The mild reduction of the antibody is accomplished preferably by addition of 2-6 equivalents of TCEP to the antibody, which is present in a suitable buffer solution, preferably phosphate buffer, and by stirring for 30-180 minutes at temperatures between 15 and 40° C., preferably at RT. This is followed by the conjugation, by addition of a solution of a compound of the formula (II) or (IIIa) in DMSO, acetonitrile or DMF to the solution of the (partially) reduced antibody in PBS buffer, and subsequent reaction at a temperature of 0° C. to +40° C., more particularly of +10° C. to +30° C., for a period of 30 minutes to 6 hours, more particularly 1 to 2 hours.

Lysine Coupling:

First of all the compounds of the formula (III) or (IIa) or comparable activated carboxyl components are prepared by conventional methods of peptide chemistry. They are then taken up in inert solvents such as DMSO or DMF, for example, and added to the antibody, which is preferably present in phosphate buffer at a neutral pH. The solution is stirred for 1-16 h at a temperature between 15 and 40° C., preferably RT.

The preparation processes described above are elucidated by way of example using the schemes below (Scheme 1 and 2):

Scheme 1

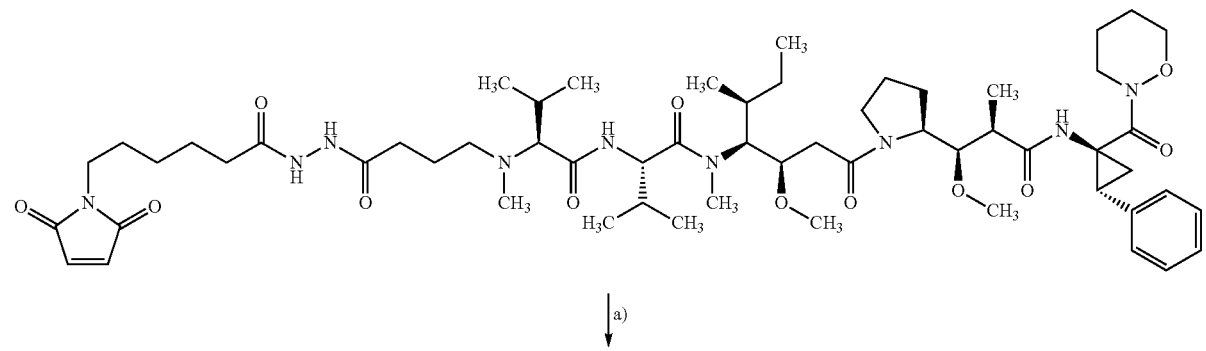

a)

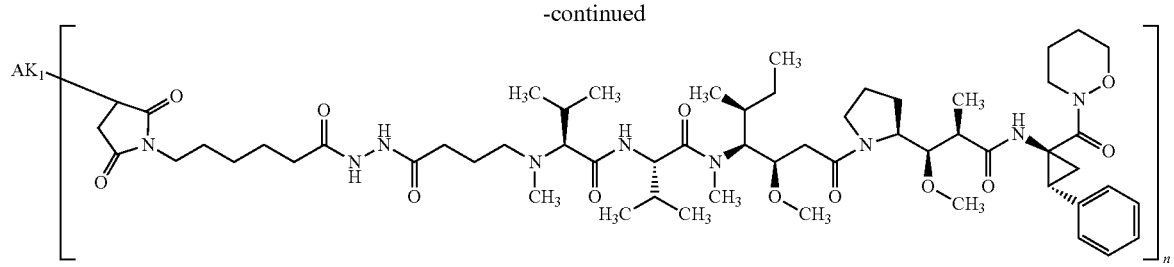

[a]: 1. AK (antibody), TCEP, PBS buffer, RT; 2. Addition of the maleimide derivative in DMSO, RT].

Scheme 2

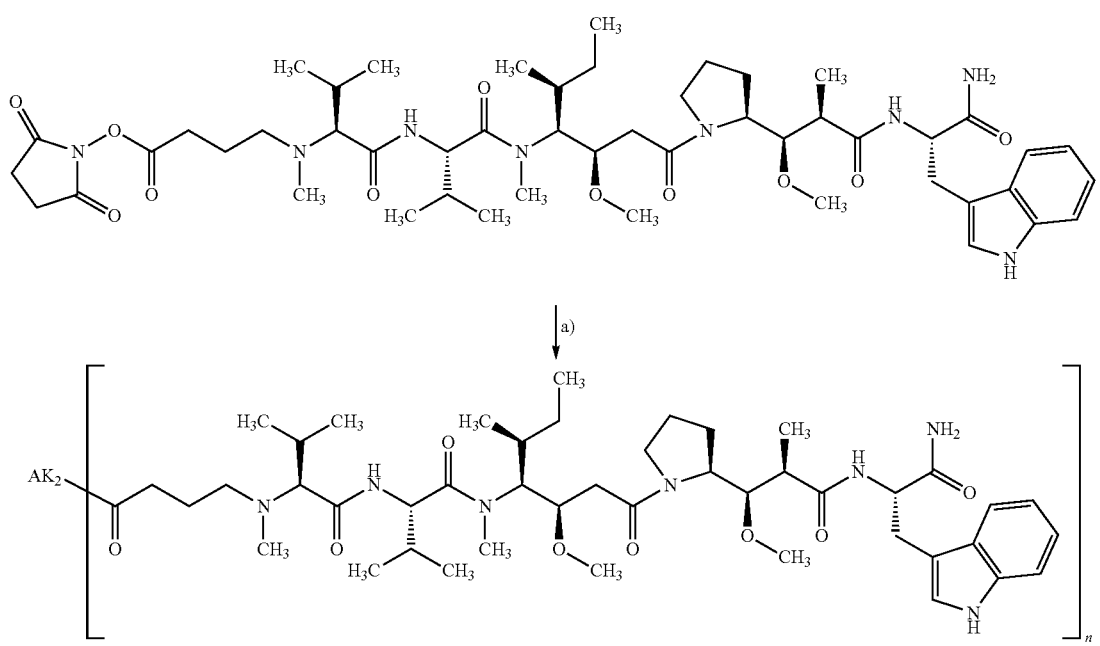

[a]: AK (antibody), PBS buffer, RT admix with activatied carboxyl derivative of the linker-drug components].

The compounds of the formula (II) in which $L^1$ and B are a bond can be prepared by subjecting a compound of the formula (IV)

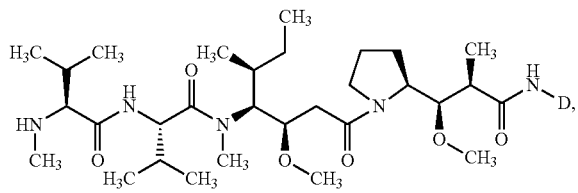

in which D has the definition indicated above, to reductive amination in an inert solvent with a compound of the formula (V)

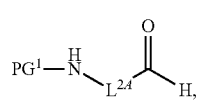

in which $L^{2A}$ has the above-defined definition of $L^2$, but is shortened by one carbon atom in the alkyl chain length, $PG^1$ is an amino-protective group such as, for example, (9H-fluoren-9-ylmethoxy)carbonyl, tert-butoxycarbonyl or benzyloxycarbonyl, to give a compound of the formula (VI)

(VI)

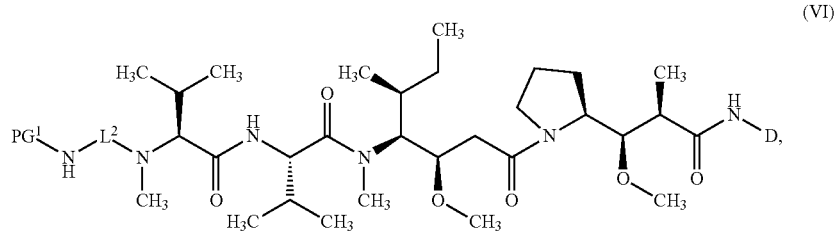

in which D, $L^2$ and $PG^1$ have the definition indicated above, eliminating the protective group $PG^1$ from this compound by methods known to the skilled person, and reacting the deprotected compound in an inert solvent in the presence of a suitable base with methyl 2,5-dioxo-2,5-dihydro-1H-pyrrole-1-carboxylate to give a compound of the formula (II-A)

(II-A)

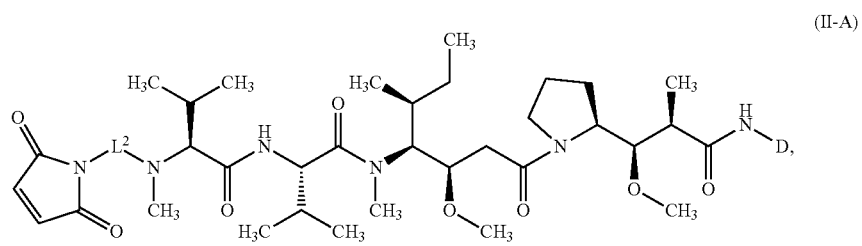

in which D and $L^2$ each have the definitions indicated above.

The compounds of the formula (II) in which B is a group of the formula ($B^1$)

($B^1$)

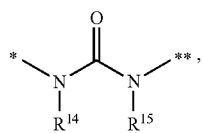

in which *, **, $R^{14}$ and $R^{15}$ each have the conditions indicated above,
can be prepared by eliminating the protective group $PG^1$ from a compound of the formula (VI) by methods known to the skilled person, and reacting the deprotected compound in an inert solvent in the presence of a suitable base with a compound of the formula (VII)

(VII)

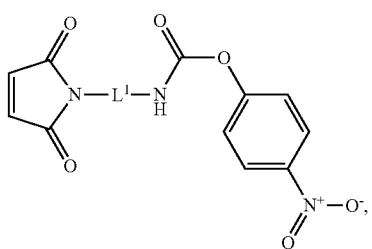

in which $L^1$ has the definition indicated above,
to give a compound of the formula (II-B)

(II-B)

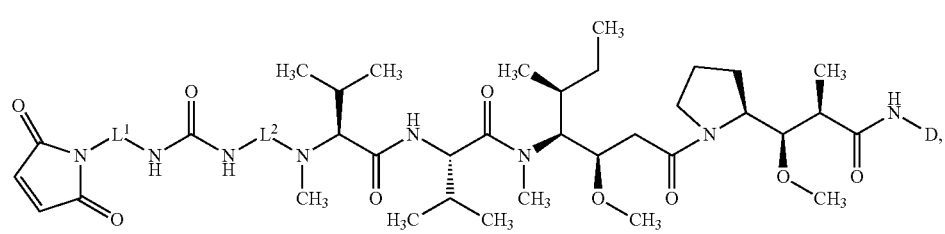

in which D, $L^1$ and $L^2$ each have the definitions indicated above.

The compounds of the formula (II) in which B is a group of the formula ($B^2$)

(B²)

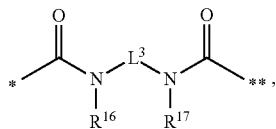

in which *, **, L³, R¹⁶ and R¹⁷ each have the conditions indicated above can be prepared by subjecting a compound of the formula (IV)
to reductive amination in an inert solvent with a compound of the formula (VIII)

(VIII)

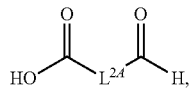

in which
$L^{2A}$ has the above-defined definition of $L^2$, but is shortened by one carbon atom in the alkyl chain length,
to give a compound of the formula (IX)

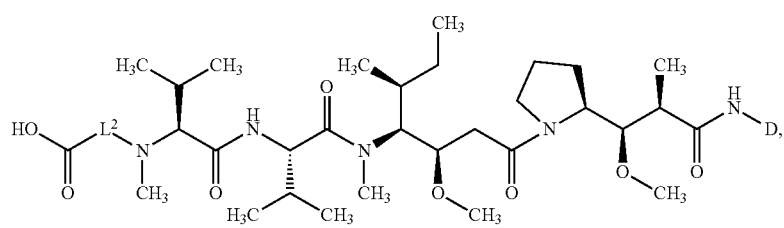

in which D and $L^2$ have the definitions indicated above,
and reacting this compound in an inert solvent in the presence of a suitable coupling reagent and a suitable base with a compound of the formula (X)

(X)

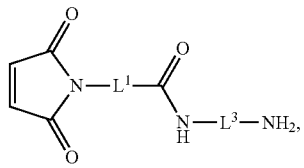

in which $L^1$ and $L^3$ each have the definitions indicated above,
to give a compound of the formula (II-C)

in which D, $L^1$, $L^2$ and $L^3$ each have the definitions indicated above.

Compound of the formula (II), in which B is a group of the formula (B³)

(B³)

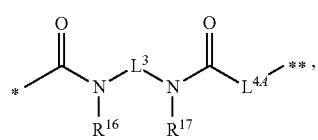

in which *, **, L³, R¹⁶ and R¹⁷ each have the conditions indicated above and
$L^{4A}$ is a group of the formula

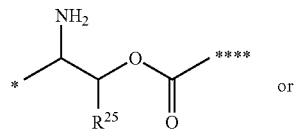 or

-continued

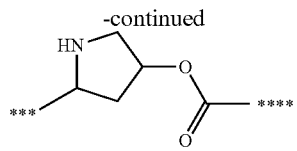

in which
*** marks the linkage site with the carbonyl group,
**** marks the linkage site with $L^2$,
$R^{25}$ is hydrogen or methyl,
can be prepared by reacting a compound of the formula (IX) in an inert solvent in the presence of a suitable base and a suitable coupling reagent with a compound of the formula (XI-A) or (XI-B)

(II-C)

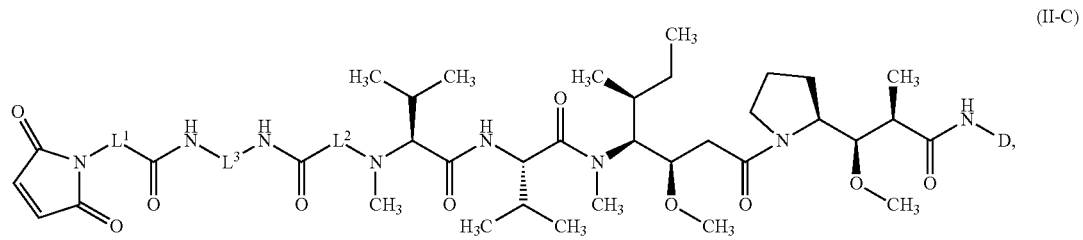

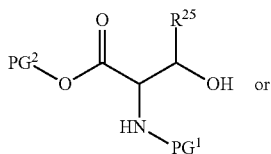 (XI-A)

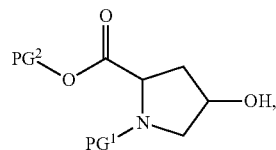 (XI-B)

in which $R^{25}$ and $PG^1$ each have the definitions indicated above and
$PG^2$ is a suitable carboxyl-protective group, more particularly benzyl, to give a compound (XII-A) or (XII-B)

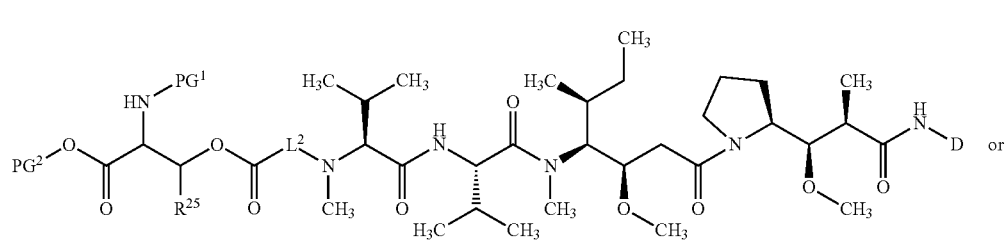
(XII-A)

(XII-B)

in which D, $PG^1$, $PG^2$ and $L^2$ have the definitions indicated above,
eliminating the protective group $PG^2$ from this compound subsequently, by methods known to the skilled person, and reacting the deprotected compound in an inert solvent in the presence of a suitable coupling reagent and a suitable base with a compound of the formula (X), and finally, eliminating the protective group PG1 from this compound, by methods known to the skilled person, to give a compound of the formula (II-D-A) or (II-D-B)

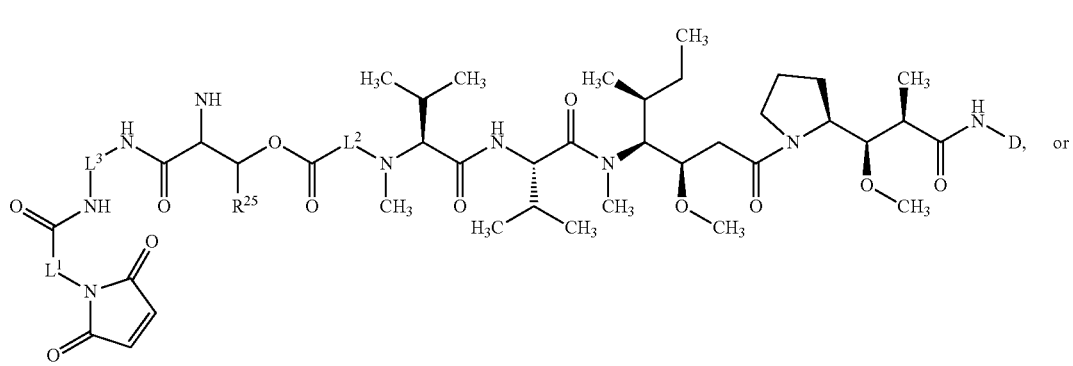
(II-D-A)

-continued (II-D-B)

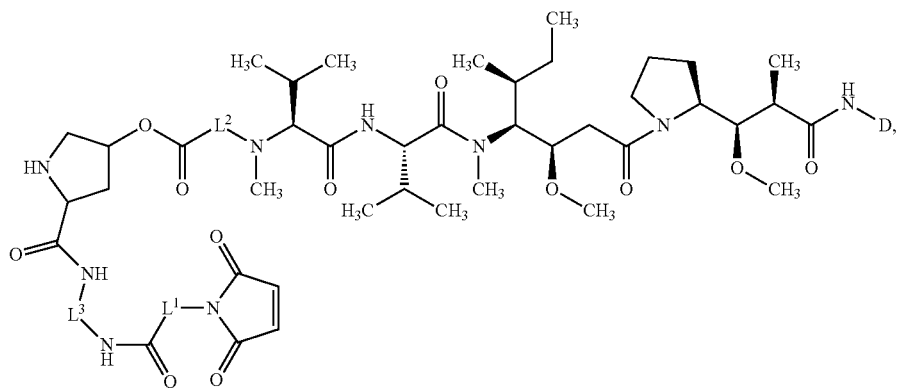

in which D, $L^1$, $L^2$ and $L^3$ have the definitions indicated above.

Compound of the formula (II), in which B is a group of the formula ($B^4$)

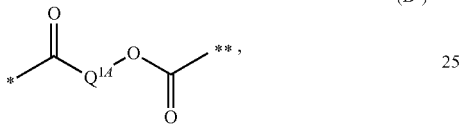

($B^4$)

in which *, ** each have the conditions indicated above and $Q^{1A}$ is an N-linked 4- to 7-membered heterocycle, can be prepared by reacting a compound of the formula (IX) in an inert solvent in the presence of a suitable base and a suitable coupling reagent with a compound of the formula (XXI)

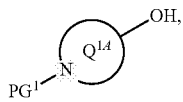

(XXI)

in which $PG^1$ and $Q^{1A}$ each have the definitions indicated above, to give a compound of the formula (XXII)

(XXII)

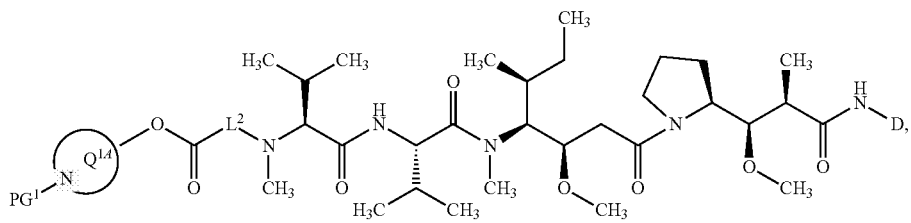

in which $PG^1$, $Q^{1A}$, D and $L^2$ have the definitions indicated above, eliminating the protective group $PG^1$ from this compound, by methods known to the skilled person, and subsequently reacting the deprotected compound in an inert solvent in the presence of a suitable coupling reagent and a suitable base with a compound of the formula (XXIII)

(XXIII)

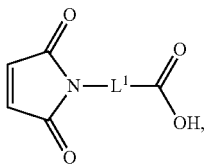

in which $L^1$ has the definition indicated above, to give a compound of the formula (II-D)

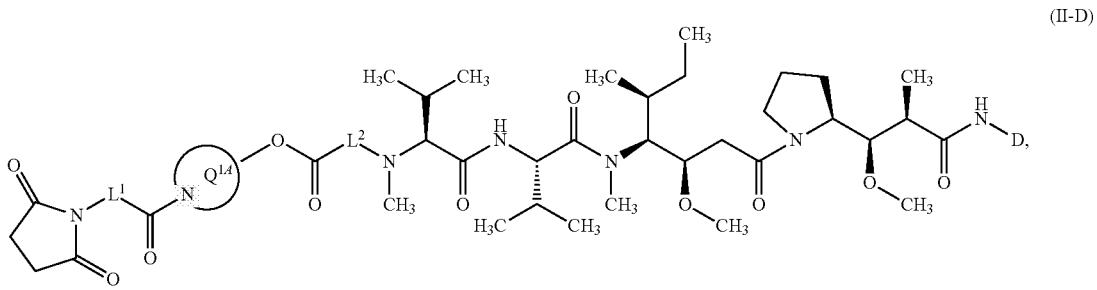
(II-D)

in which $Q^{1A}$, D, $L^1$ and $L^2$ have the definitions indicated above.

The compounds of the formula (III), in which $L^1$ and B are a bond can be prepared by reacting a compound of the formula (IX) in an inert solvent in the presence of a suitable coupling reagent and a suitable base with N-hydroxysuccinimide to give a compound of the formula (III-A)

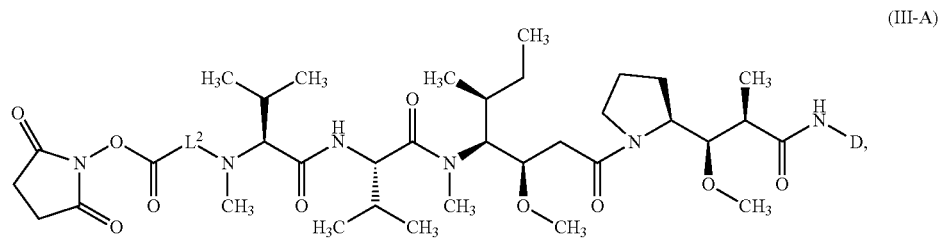
(III-A)

in which D and $L^2$ each have the definitions indicated above.

The compounds of the formula (III), in which $L^1$ is a bond and B is a group of the formula ($B^{5A}$)

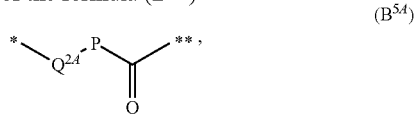
($B^{5A}$)

in which *, ** and P each have the definitions indicated above and $Q^{2A}$ is a 3- to 7-membered carbocycle, can be prepared by reacting a compound of the formula (IX) in an inert solvent in the presence of a suitable coupling reagent and a suitable base with a compound of the formula (XIII)

(XIII)

in which P, $Q^{2A}$ and $PG^2$ each have the definitions indicated above, to give a compound of the formula (XIV)

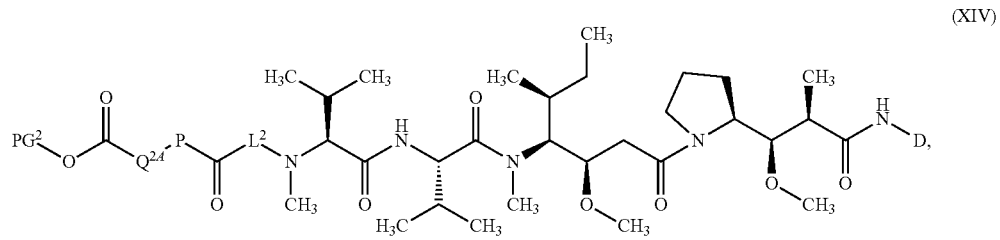
(XIV)

in which D, P, $Q^{2A}$, $L^2$ and $PG^2$ each have the definitions indicated above, eliminating the protective group $PG^2$ from this compound by methods known to the skilled person, and subsequently reacting the deprotected compound in an inert solvent in the presence of a suitable base with N-hydroxysuccinimide to give a compound of the formula (III-B)

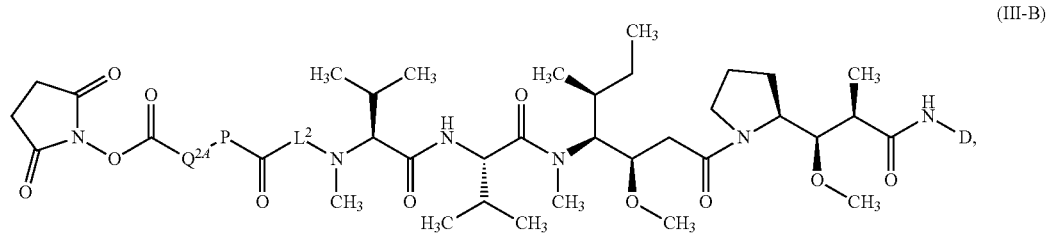

(III-B)

in which D, P, $Q^{2A}$ and $L^2$ each have the definitions indicated above.

The compounds of the formula (III), in which $L^1$ is a bond and B is a group of the formula ($B^6$)

($B^6$)

in which *, **, $R^{18}$, $R^{19}$ and $R^{20}$ each have the definitions indicated above, can be prepared by reacting a compound of the formula (IX) in an inert solvent in the presence of a suitable coupling reagent and a suitable base with a compound of the formula (XV)

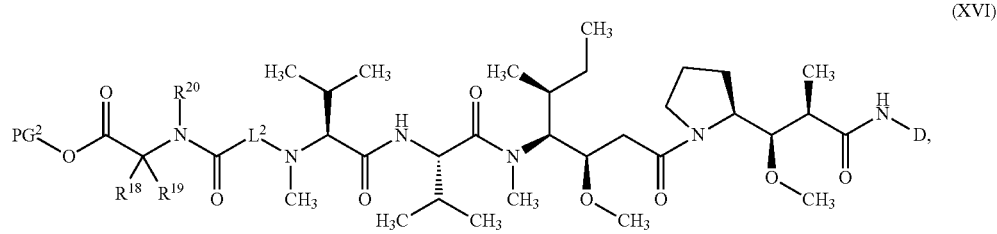

(XV)

in which $R^{18}$, $R^{19}$, $R^{20}$ and $PG^2$ each have the definitions indicated above,
to give a compound of the formula (XVI)

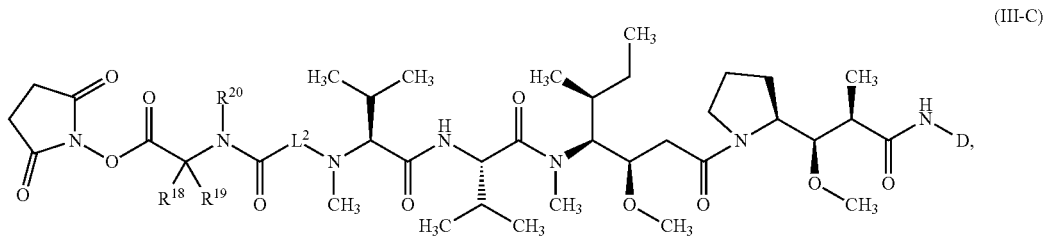

(XVI)

in which D, $R^{18}$, $R^{19}$, $R^{20}$, $L^2$ and $PG^2$ each have the definitions indicated above,
eliminating the protective group $PG^2$ from this compound by methods known to the skilled person, and subsequently reacting the deprotected compound in an inert solvent in the presence of a suitable coupling reagent and a suitable base with N-hydroxysuccinimide to give a compound of the formula (III-C)d

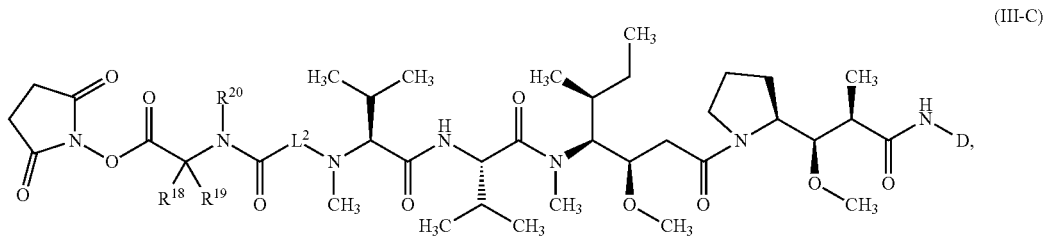

(III-C)

in which D, $R^{18}$, $R^{19}$, $R^{20}$ and $L^2$ each have the definitions indicated above.

The compounds of the formula (III), in which $L^1$ is a bond and B is a group of the formula ($B^7$)

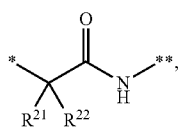 (B⁷)

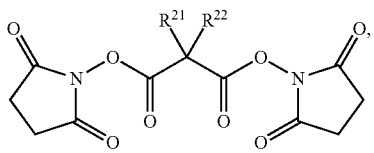 (XVII)

in which *, **, $R^{21}$ and $R^{22}$ each have the definitions indicated above, can be prepared by eliminating the protective group $PG^1$ from a compound of the formula (VI) by methods known to the skilled person, and reacting the resultant deprotected compound in an inert solvent in the presence of a suitable base with a compound of the formula (XVII)

in which $R^{21}$ and $R^{22}$ each have the definitions indicated above, to give a compound of the formula (III-D)

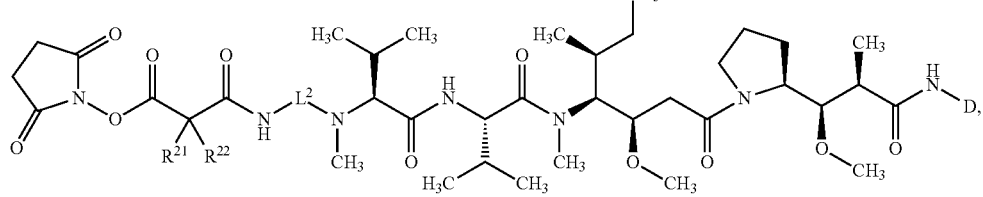 (III-D)

in which D, $R^{21}$, $R^{22}$ and $L^2$ each have the definitions indicated above.

The compounds of the formula (III), in which B is a group of the formula (B⁸)

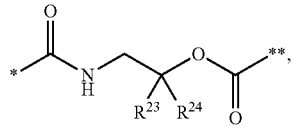 (B⁸)

in which *, **, $R^{23}$ and $R^{24}$ each have the definitions indicated above, can be prepared by reacting a compound of the formula (IX) in an inert solvent in the presence of a suitable coupling reagent and a suitable base with a compound of the formula (XVIII)

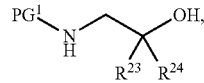 (XVIII)

in which $R^{23}$, $R^{24}$ and $PG^1$ each have the definitions indicated above, to give a compound of the formula (XIX)

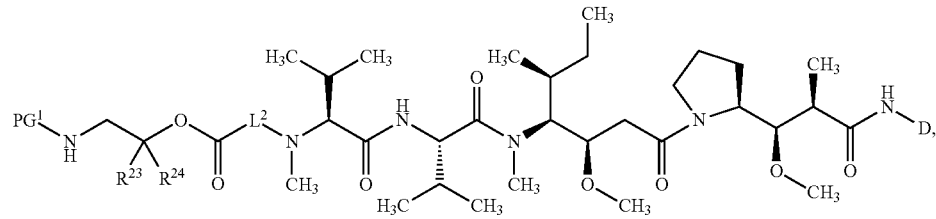 (XIX)

in which D, $R^{23}$, $R^{24}$, $L^2$ and $PG^1$ each have the definitions indicated above, eliminating the protective group $PG^1$ from this compound by methods known to the skilled person, and subsequently reacting the deprotected compound in an inert solvent in the presence of a suitable coupling reagent and a suitable base with a compound of the formula (XX)

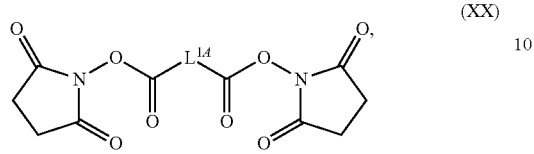

(XX)

in which
$L^{1A}$ is linear $(C_1\text{-}C_{10})$-alkanediyl or is a group of the formula

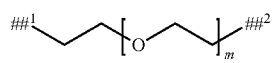

where
m is a number from 2 to 6,
$\#\#^1$ marks the linkage site with the group G,
$\#\#^2$ marks the linkage site with the group B,
where $(C_1\text{-}C_{10})$-alkanediyl may be substituted by 1 to 4 methyl substituents,
and
where two carbon atoms of the alkanediyl chain in 1,2, 1,3 or 1,4 relation to one another, with inclusion of any carbon atoms situated between them, may be bridged to form a $(C_3\text{-}C_6)$-cycloalkyl ring or a phenyl ring, to give a compound of the formula (III-E)

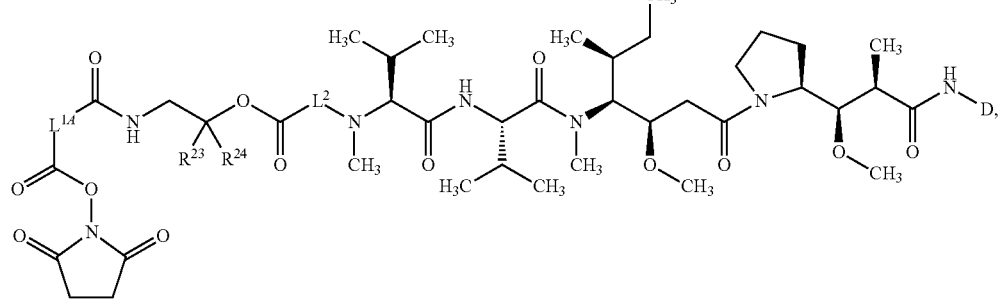

(III-E)

in which D, $R^{23}$, $R^{24}$, $L^{1A}$ and $L^2$ each have the definitions indicated above.

The compounds of the formula (III), in which B is a group of the formula ($B^{5B}$)

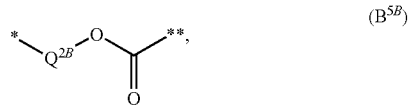

($B^{5B}$)

in which * and ** each have the definitions indicated above and
$Q^{2B}$ is an N-linked 4- to 7-membered heterocycle, can be prepared by reacting a compound of the formula (IX) in an inert solvent in the presence of a suitable base and a suitable coupling reagent with a compound of the formula (XXIV)

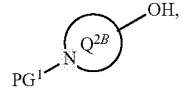

(XXIV)

in which $PG^1$ and $Q^{2B}$ each have the definitions indicated above, to give a compound of the formula (XXV)

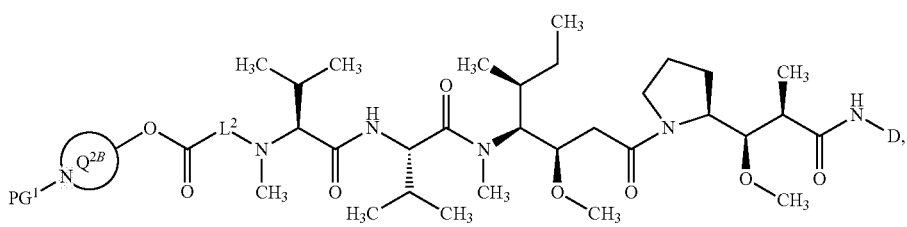

(XXV)

in which PG$^1$, Q$^{2B}$, D and L$^2$ have the definitions indicated above,
eliminating the protective group PG$^1$ from this compound by methods known to the skilled person,
and subsequently converting the deprotected compound in an inert solvent in the presence of a suitable base with a compound of the formula (XX) into a compound of the formula (III-F)

Examples of inert solvents for these coupling reactions are ethers such as diethyl ether, diisopropyl ether, tert-butyl methyl ether, tetrahydrofuran, 1,4-dioxane, 1,2-dimethoxyethane or bis(2-methoxyethyl)ether, hydrocarbons such as benzene, toluene, xylene, pentane, hexane, heptane, cyclohexane or petroleum fractions, halogenated hydrocarbons such as dichloromethane, trichloromethane, tetrachloromethane, 1,2-dichloroethane, trichloroethylene or chlo-

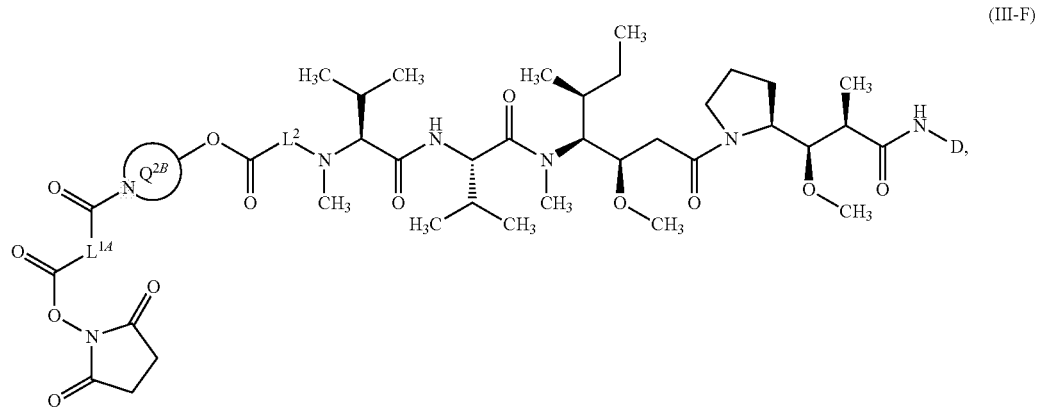

(III-F)

in which Q$^{2B}$, D, L$^{1A}$ and L$^2$ have the definitions indicated above.

The reactions (IV)+(V)→(VI) and (IV)+(VIII)→(IX) take place in the solvents which are customary for a reductive amination and are inert under the reaction conditions, optionally in the presence of an acid and/or of a water-removing agent as catalyst. Such solvents include, for example, alcohols such as methanol, ethanol, n-propanol, isopropanol, n-butanol or tert-butanol, ethers such as tetrahydrofuran, 1,4-dioxane, 1,2-dimethoxyethane or bis(2-methoxyethyl)ether, or other solvents such as dichloromethane, 1,2-dichloroethane, N,N-dimethylformamide or else water. It is also possible to use mixtures of these solvents. As solvent it is preferred to use a 1,4-dioxane/water mixture, with addition of acetic acid or dilute hydrochloric acid as catalyst.

Reducing agents suitable for this reaction are, in particular, complex borohydrides, such as, for example, sodium borohydride, sodium cyanoborohydride, sodium triacetoxyborohydride, tetra-n-butylammonium borohydride or borane-pyridine complex. It is preferred to use sodium cyanoborohydride or borane-pyridine complex.

The reactions (IV)+(V)→(VI) and (IV)+(VIII)→(IX) take place in general in a temperature range from 0° C. to +120° C., preferably at +50° C. to +100° C. The reactions may be carried out under atmospheric, increased or reduced pressure (e.g. from 0.5 to 5 bar); it is usual to operate at atmospheric pressure.

The above-described coupling reactions (IX)+(X)→(II-C), (XII-A) or (XII-B)+(X)→(II-D-A) or (II-D-B), (IX)+(XIII)→(XIV), (IX)+(XV)→(XVI) and (XXII)+(XXIII)→(II-D) (amide formation from amine component and carboxylic acid component respectively) are carried out by standard methods of peptide chemistry [see e.g. M. Bodanszky, *Principles of Peptide Synthesis*, Springer-Verlag, Berlin, 1993; M. Bodanszky and A. Bodanszky, *The Practice of Peptide Synthesis*, Springer-Verlag, Berlin, 1984; H.-D. Jakubke and H. Jeschkeit, *Aminosäuren, Peptide, Proteine*, Verlag Chemie, Weinheim, 1982].

robenzene, or dipolar-aprotic solvents such as acetone, methyl ethyl ketone, acetonitrile, ethyl acetate, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP). It is also possible to use mixtures of such solvents. Preference is given to using N,N-dimethylformamide.

Examples of suitable activating/condensing agents for these couplings include carbodiimides such as N,N'-diethyl-, N,N'-dipropyl-N,N'-diisopropyl-N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, phosphorus compounds such as propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium-tetrafluoroborate (TCTU), optionally in combination with further auxiliaries such as 1-hydroxybenzotriazole (HOBt) or N-hydroxysuccinimide (HOSu), and also, as bases, alkali metal carbonates, e.g. sodium or potassium carbonate, or tertiary amine bases such as triethylamine, N-methylmorpholine, N-methylpiperidine, N,N-diisopropylethylamine, pyridine or 4-N,N-dimethylaminopyridine.

In the context of the present invention, as activating/condensing agents for such coupling reactions, it is preferred to use N-(3-dimethylaminoisopropyl)-N'-ethylcarbodiimide hydrochloride (EDC) in combination with 1-hydroxybenzotriazole (HOBt) and N,N-diisopropylethylamine, or O-(7-azabenzotriazol-1-yl)-N,N,N',N'-tetramethyluronium hexafluorophosphate (HATU) likewise in conjunction with N,N-diisopropylethylamine.

The coupling reactions (IX)+(X)→(II-C), (XII-A) or (XII-B)+(X)→(II-D-A) or (II-D-B), (IX)+(XIII)→(XIV), (IX)+(XV)→(XVI) and (XXII)+(XXIII)→(II-D) are carried out in general in a temperature range from −20° C. to +60° C., preferably at 0° C. to +40° C. The reactions may take place under atmospheric, at increased or at reduced pressure (e.g. from 0.5 to 5 bar); it is usual to operate under atmospheric pressure.

The esterifications (IX)+(XVIII)→(XII) and (IX)+(XI-A) or (XI-B)→(XII-A) or (XII-B), (IX)+(XXIV)→(XXV) and also (IX)+(XXI)→(XXII) take place in analogy to the above-described amide coupling reactions. These reactions take place preferably in dichloromethane, using N-(3-dimethylaminoisopropyl)-N'-ethylcarbodiimide hydrochloride (EDC) and 4-dimethylamino-pyridine at a temperature of +50° C. to 100° C. under atmospheric pressure.

The functional groups optionally present in the compounds—such as amino, hydroxyl and carboxyl groups in particular—may also be present in a temporarily protected form during the above-described process steps, if useful or necessary. In these cases, such protective groups are introduced and removed in accordance with customary methods known from peptide chemistry [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. Where two or more protected groups are present, they can be liberated again optionally simultaneously in a one-pot reaction, or else liberated again in separate reaction steps.

As an amino-protective group $PG^1$ it is preferred to use tert-butoxycarbonyl (Boc), benzyloxycarbonyl (Z) or (9H-fluoren-9-ylmethoxy)carbonyl (Fmoc); for a hydroxyl or carboxyl function it is preferred to use tert-butyl or benzyl as protective group $PG^2$. The elimination of a tert-butyl or tert-butoxycarbonyl group is typically accomplished by treatment with a strong acid, such as hydrogen chloride, hydrogen bromide or trifluoroacetic acid, in an inert solvent such as diethyl ether, 1,4-dioxane, dichloromethane or acetic acid; this reaction may optionally also be carried out without addition of an inert solvent. In the case of benzyl or benzyloxycarbonyl as protective group, this group is removed preferably by hydrogenolysis in the presence of a suitable palladium catalyst, such as palladium on activated carbon, for example. The (9H-fluoren-9-ylmethoxy)carbonyl group is generally eliminated using a secondary amine base such as diethylamine or piperidine.

The reaction (VI)→(II-A) takes place in a solvent which is inert under the reaction conditions, such as, for example, ethers such as tetrahydrofuran, 1,4-dioxane, 1,2-dimethoxyethane or bis(2-methoxyethyl)ether, alcohols such as methanol, ethanol, isopropanol, n-butanol or tert-butanol, or dipolar-aprotic solvents such as acetone, methyl ethyl ketone, acetonitrile, ethyl acetate, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP) or water. It is also possible to use mixtures of such solvents. Preference is given to using a mixture of 1,4-dioxane and water.

Suitable bases for the reaction (VI)→(II-A) are, for example, alkali metal carbonates such as potassium carbonate, sodium carbonate or lithium carbonate, alkali metal hydrogencarbonates such as sodium or potassium hydrogencarbonate or alkali metal alkoxides such as sodium methoxide, sodium ethoxide or potassium tert-butoxide. It is preferred to use sodium hydrogencarbonate.

The reaction (VI)→(II-A) takes place in a temperature range from 0° C. to +50° C., preferably at +10° C. to +30° C. The reaction may take place under atmospheric, under elevated or under reduced pressure (e.g. from 0.5 to 5 bar); it is usual to operate under atmospheric pressure.

The reaction (VI)+(VII)→(II-B) takes place in a solvent which is inert under the reaction conditions, such as, for example, ethers such as tetrahydrofuran, 1,4-dioxane, 1,2-dimethoxyethane or bis(2-methoxyethyl)ether, alcohols such as methanol, ethanol, isopropanol, n-butanol or tert-butanol, or dipolar-aprotic solvents such as acetone, methyl ethyl ketone, acetonitrile, ethyl acetate, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP) or water. It is also possible to use mixtures of such solvents. Preference is given to using DMF.

Suitable bases for the reaction (VI)+(VII)→(II-B) are, for example, tertiary amine bases such as triethylamine, N-methylmorpholine, N-methylpiperidine, N,N-diisopropylethylamine, pyridine or 4-N,N-dimethylaminopyridine. Preference is given to using N,N-diisopropylethylamine.

The reaction (VI)+(VII)→(II-B) takes place in a temperature range from 0° C. to +50° C., preferably at +10° C. to +30° C. The reaction may take place under atmospheric, under elevated or under reduced pressure (e.g. from 0.5 to 5 bar); it is usual to operate under atmospheric pressure.

The reactions (IX)→(III-A), (XIV)→(III-B) and (XVI)→(III-C) and also (VI)+(XVII)→(III-D), (XIX)+(XX)→(III-E) and (XXV)+(XX)→(III-F) take place in a solvent which is inert under the reaction conditions. Examples of suitable solvents are ethers such as diethyl ether, diisopropyl ether, tert-butyl methyl ether, tetrahydrofuran, 1,4-dioxane, 1,2-dimethoxyethane or bis(2-methoxyethyl)ether, hydrocarbons such as benzene, toluene, xylene, pentane, hexane, heptane, cyclohexane or petroleum fractions, halogenated hydrocarbons such as dichloromethane, trichloromethane, tetrachloromethane, 1,2-dichloroethane, trichloroethylene or chlorobenzene, or dipolar-aprotic solvents such as acetone, methyl ethyl ketone, acetonitrile, ethyl acetate, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP). It is also possible to use mixtures of such solvents. Preference is given to using N,N-dimethylformamide.

Suitable bases for these reactions are, for example, tertiary amines such as triethylamine, N-methylmorpholine, N-methylpiperidine, N,N-diisopropylethylamine, pyridine or 4-N,N-dimethylaminopyridine. Preference is given to using N,N-diisopropylethylamine, optionally with addition of 4-N,N-dimethylaminopyridine.

The reactions (IX)→(III-A), (XIV)→(III-B) and (XVI)→(III-C) and also (VI)+(XVII)→(III-D) and (XIX)+(XX)→(III-E) take place in a temperature range from 0° C. to +50° C., preferably at +10° C. to +30° C. The reaction may take place under atmospheric, under elevated or under reduced pressure (e.g. from 0.5 to 5 bar); it is usual to operate under atmospheric pressure.

The compounds of the formulae (II), (III), (1-A) and (1-B) are sub-quantities of the compounds of the formulae (IIa), (IIIa), (Ia-A) and (Ia-B), respectively, where $R^{35}$ is methyl. The preparation of the compounds (IIa) and (IIIa) takes place in analogy to the preparation of the compound of the formulae (II) and (III) as described above.

The above-described processes are illustrated by way of example by the following synthesis schemes (Scheme 3 to 13, 18):

Scheme 3
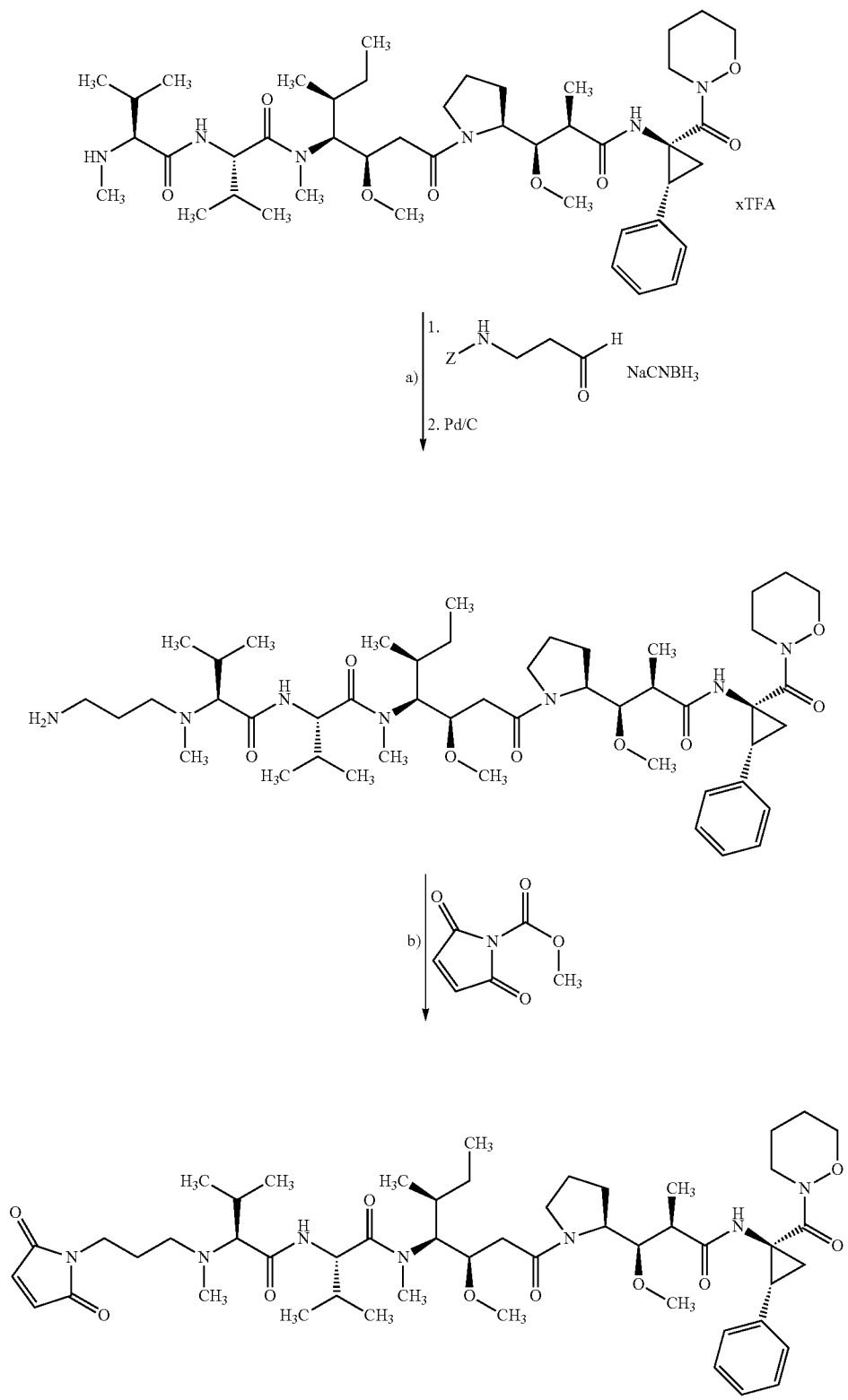
[a]: 1. Water/dioxane, 1N HCl, 100° C.; 2. H₂, Pd/C, methanol, RT; b): NaHCO₃, H₂O, dioxane, RT].

Scheme 4
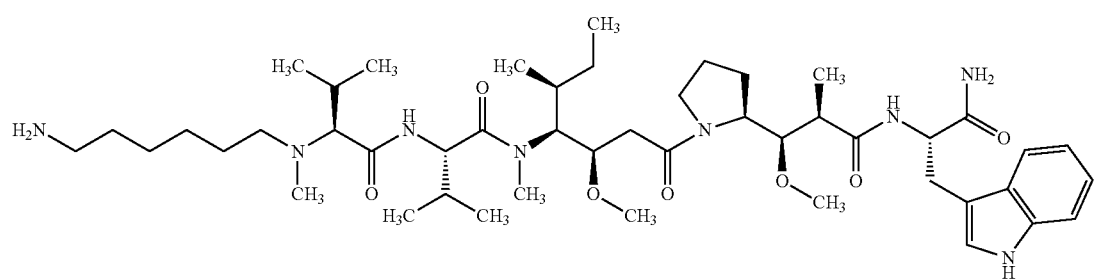
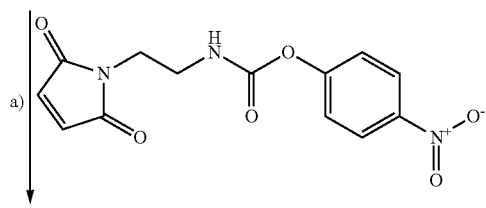
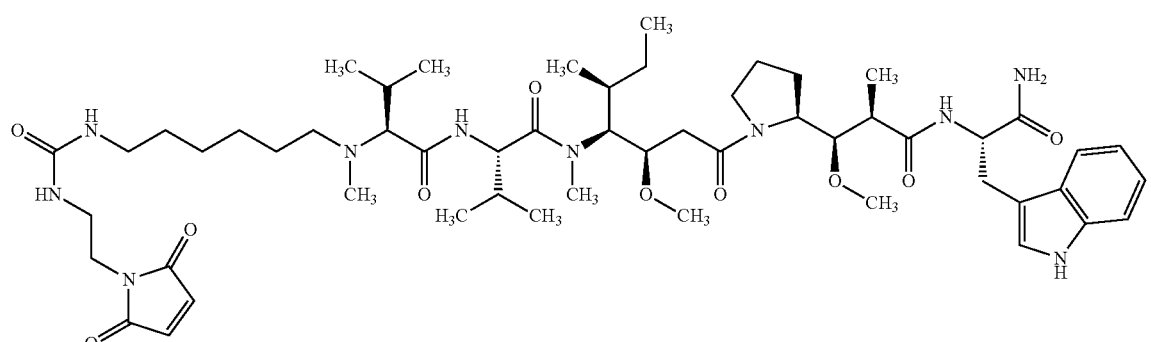
[a]: Diisopropylethylamine, DMF, RT].
Scheme 5
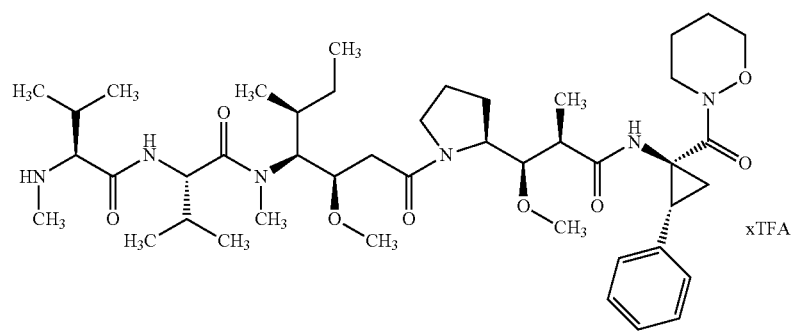
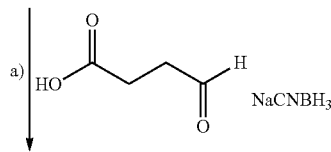

217 218
-continued
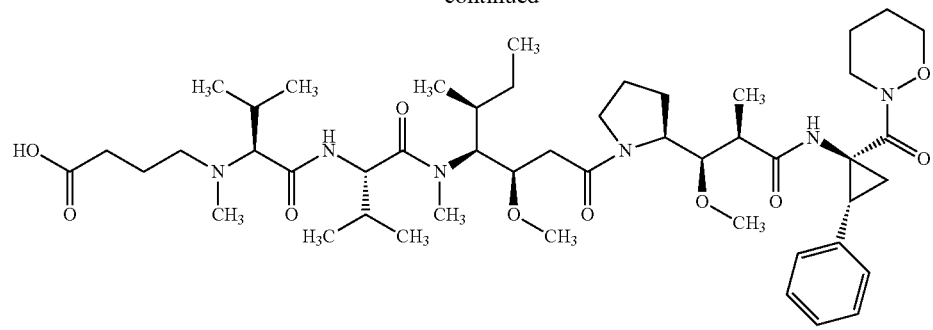
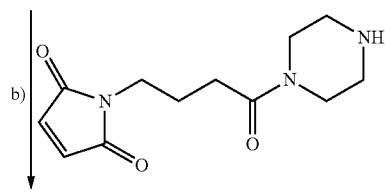
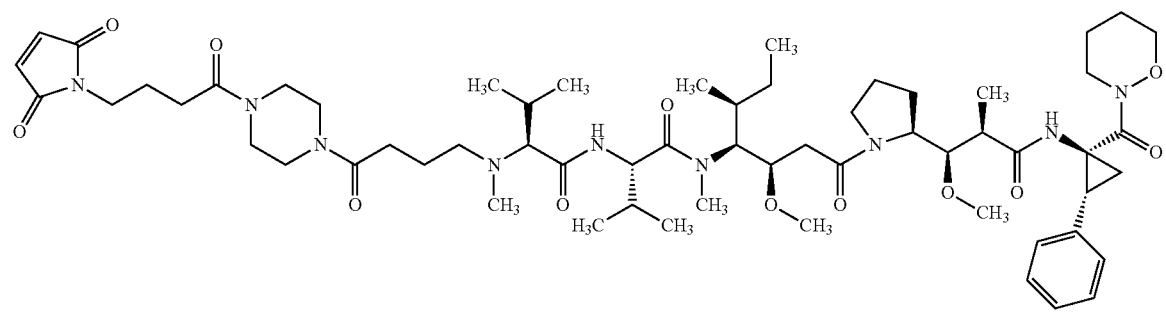
[a]: 1. Water/dioxane, 1N HCl, 100° C.; b): HATU, diisopropylamine, DMF, RT].
Scheme 6
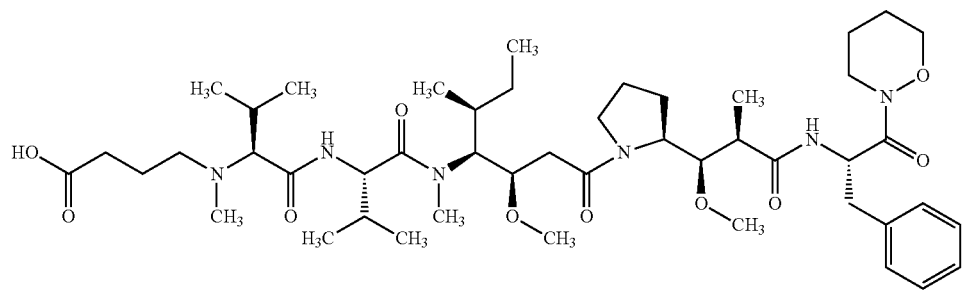
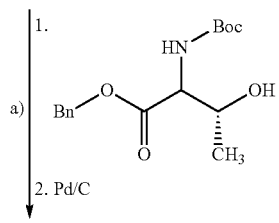

-continued
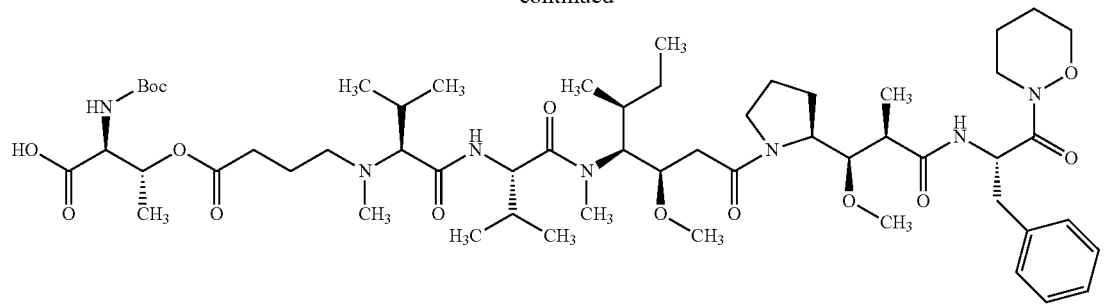
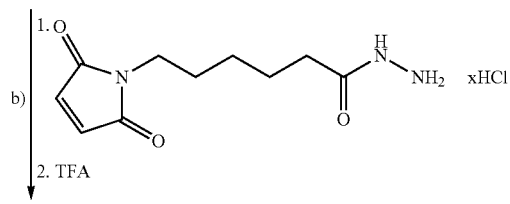
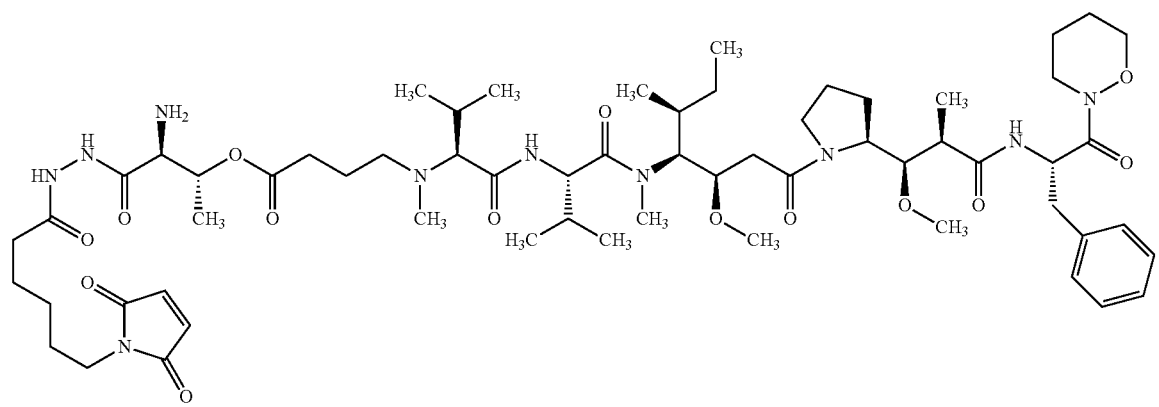
[a]: 1. EDCI, DMAP, dichloromethane, RT; 2. H₂, methanol, RT; b): 1. EDCI, HOBt, diisopropylamine, DMF, RT; 2. dichoromethane, RT].
Scheme 7
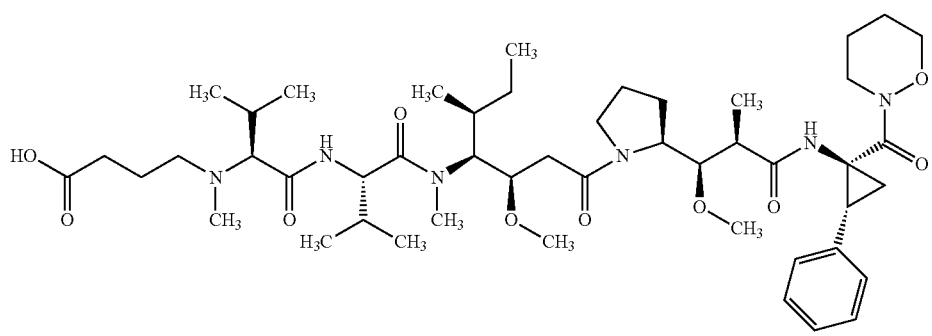
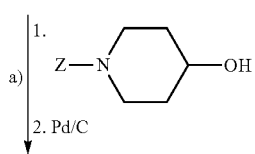

221 222
-continued
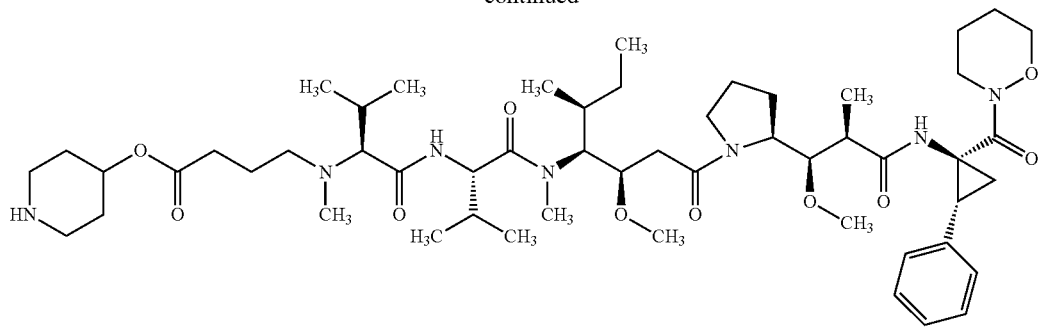
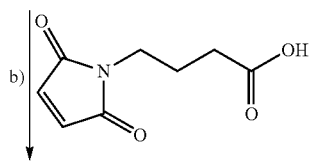
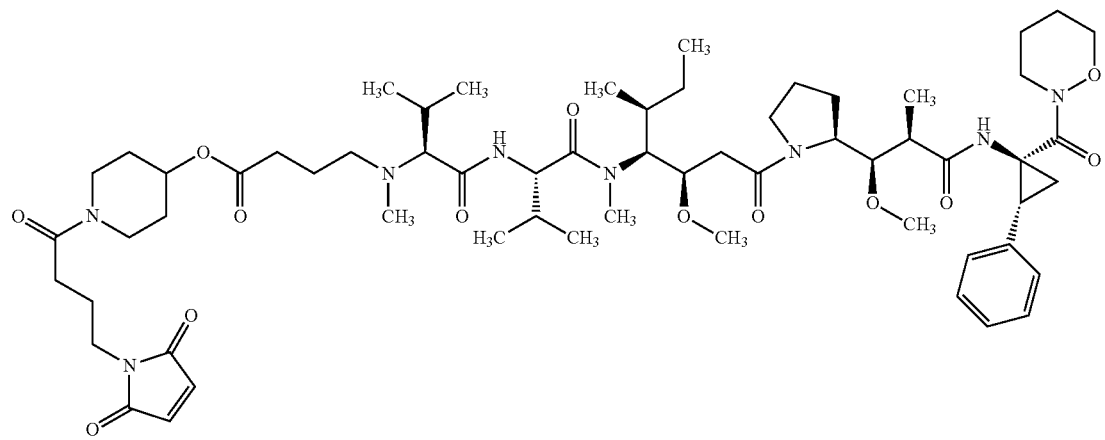
[a]: 1. EDCI, DMAP, dichloromethane, RT; 2. H₂, methanol, RT; b): HATU, diisopropylamine, DMF, RT].
Scheme 8
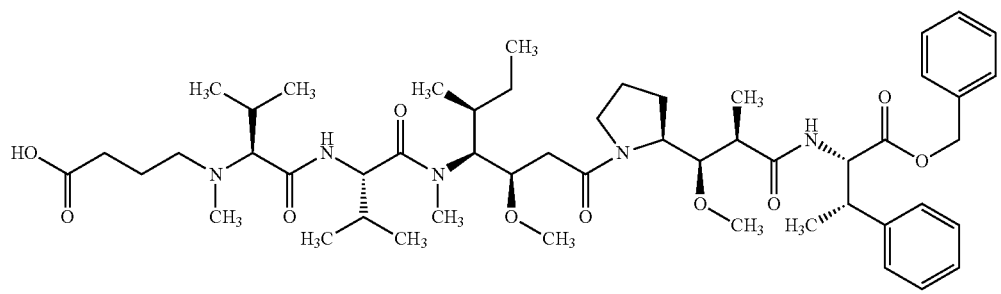
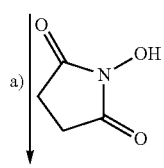

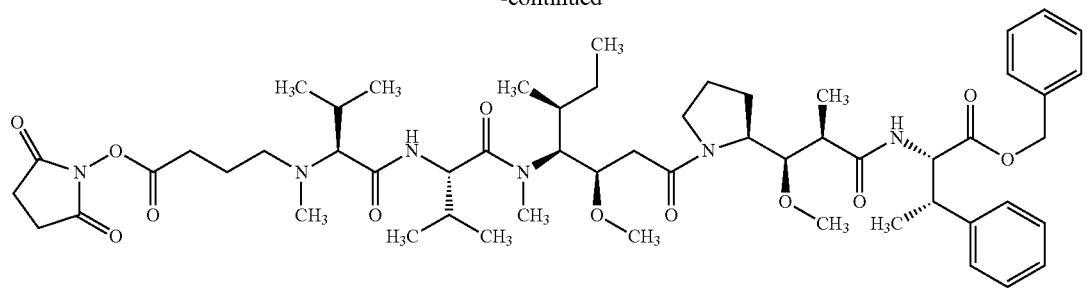
[a]: EDCI, dichloromethane, RT].
Scheme 9
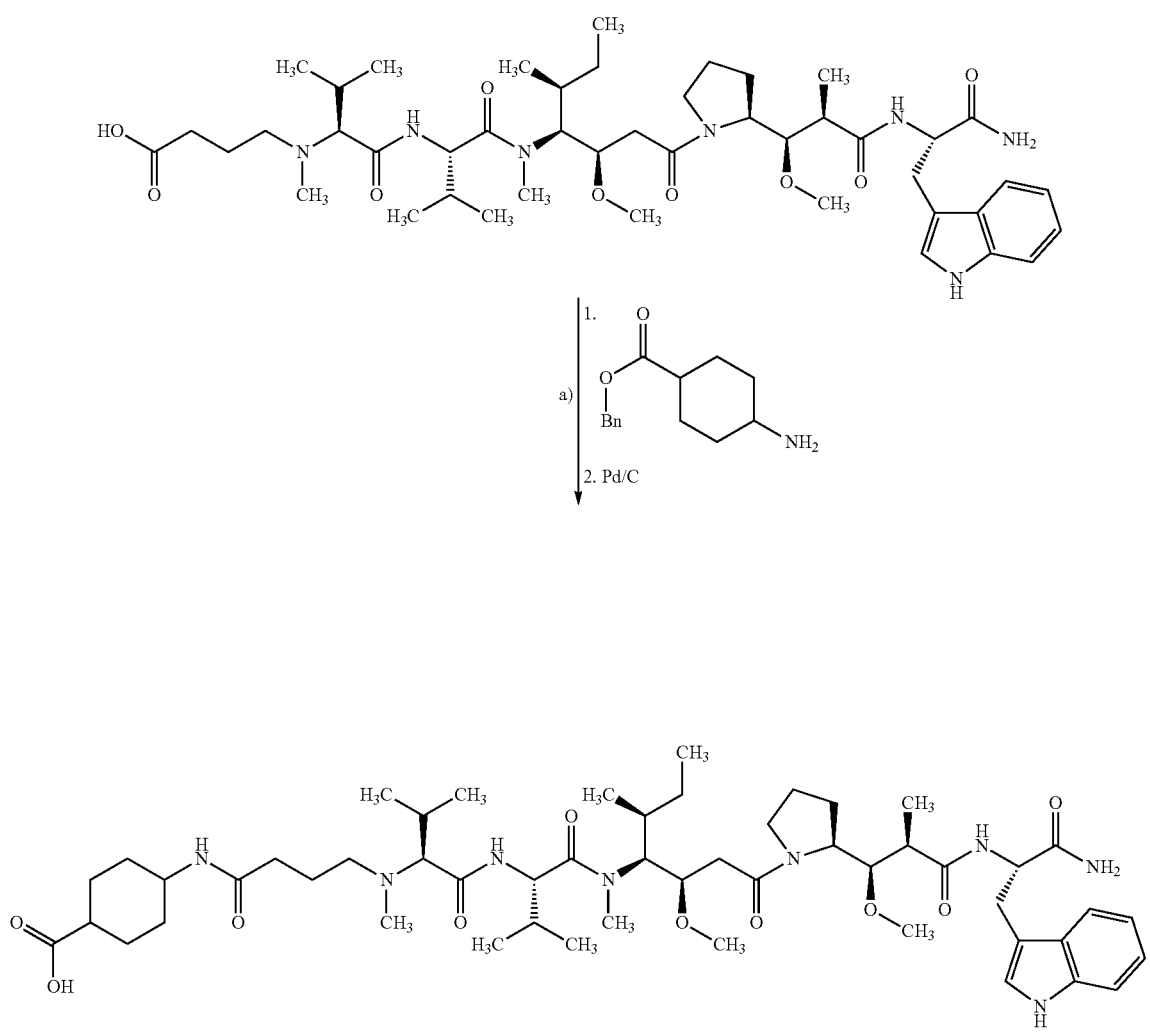

225 226
-continued
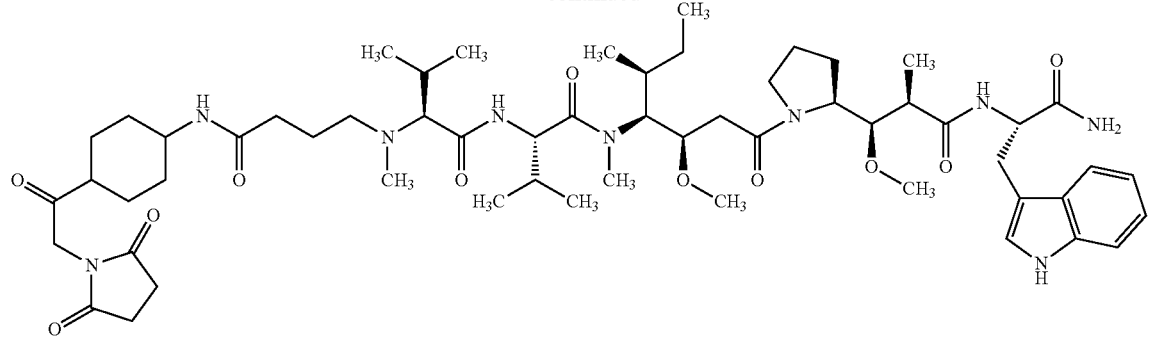
[a): 1. HATU, diisopropylethylamine, DMF, RT; 2. H₂, methanol, RT; b): EDCI, DMAP, dichloromethane, RT].
Scheme 10
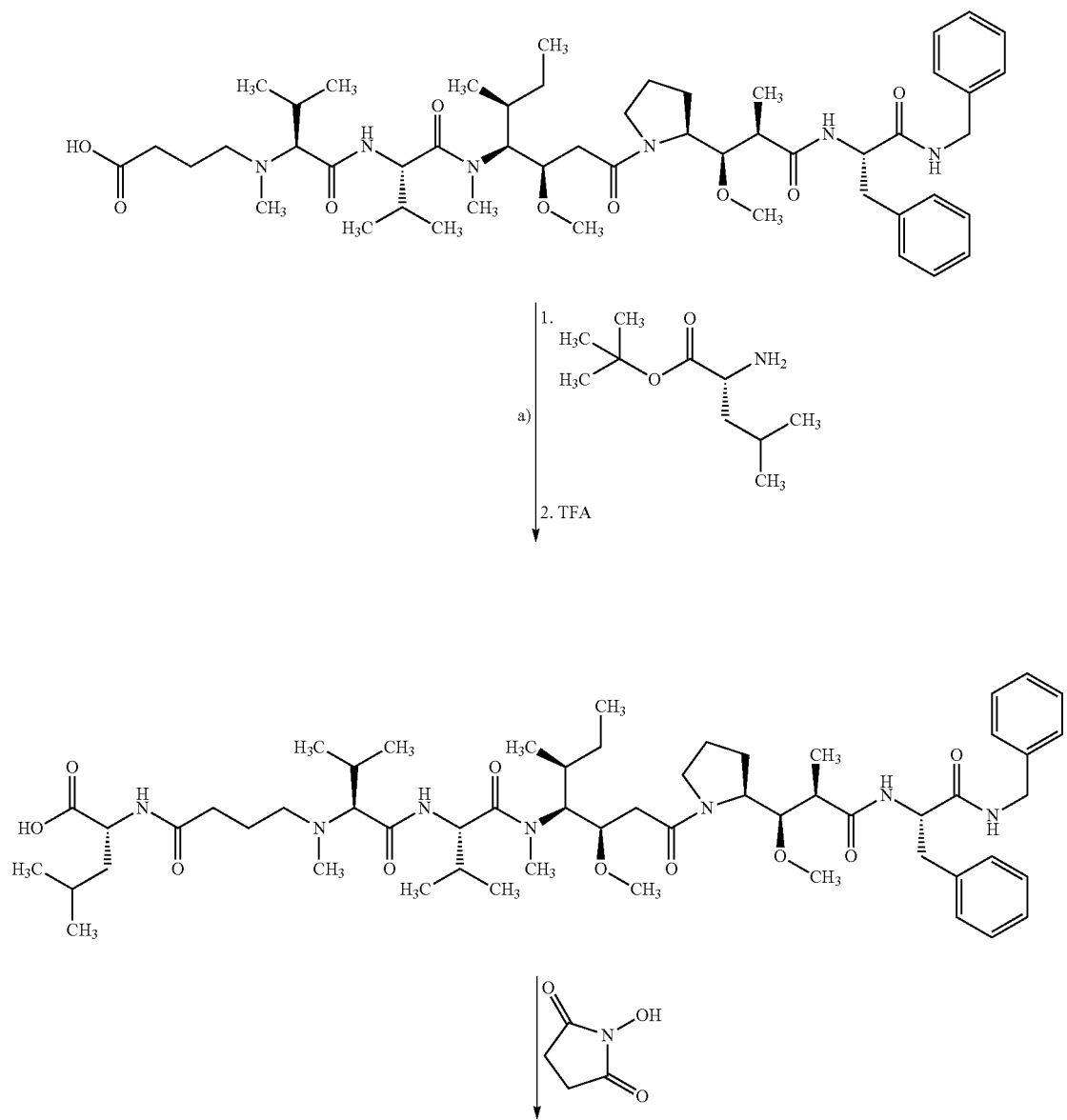

-continued
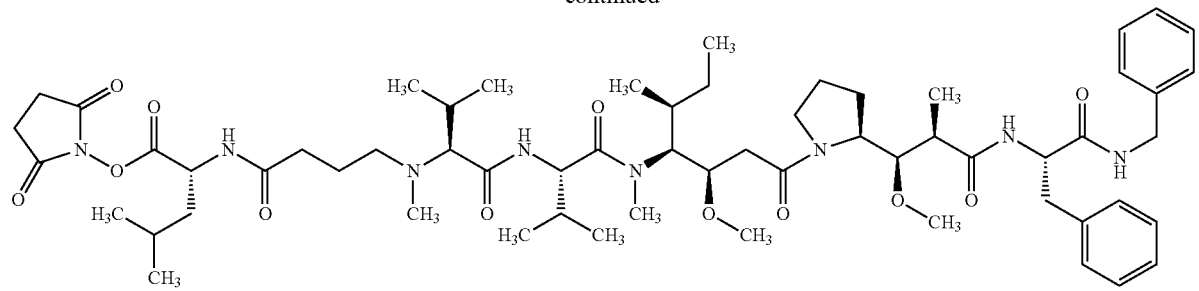
[a]: 1. HATU, diisopropylethylamine, DMF, RT; 2. dichloromethane, RT; b): EDCI, DMAP, dichloromethane, RT].
Scheme 11
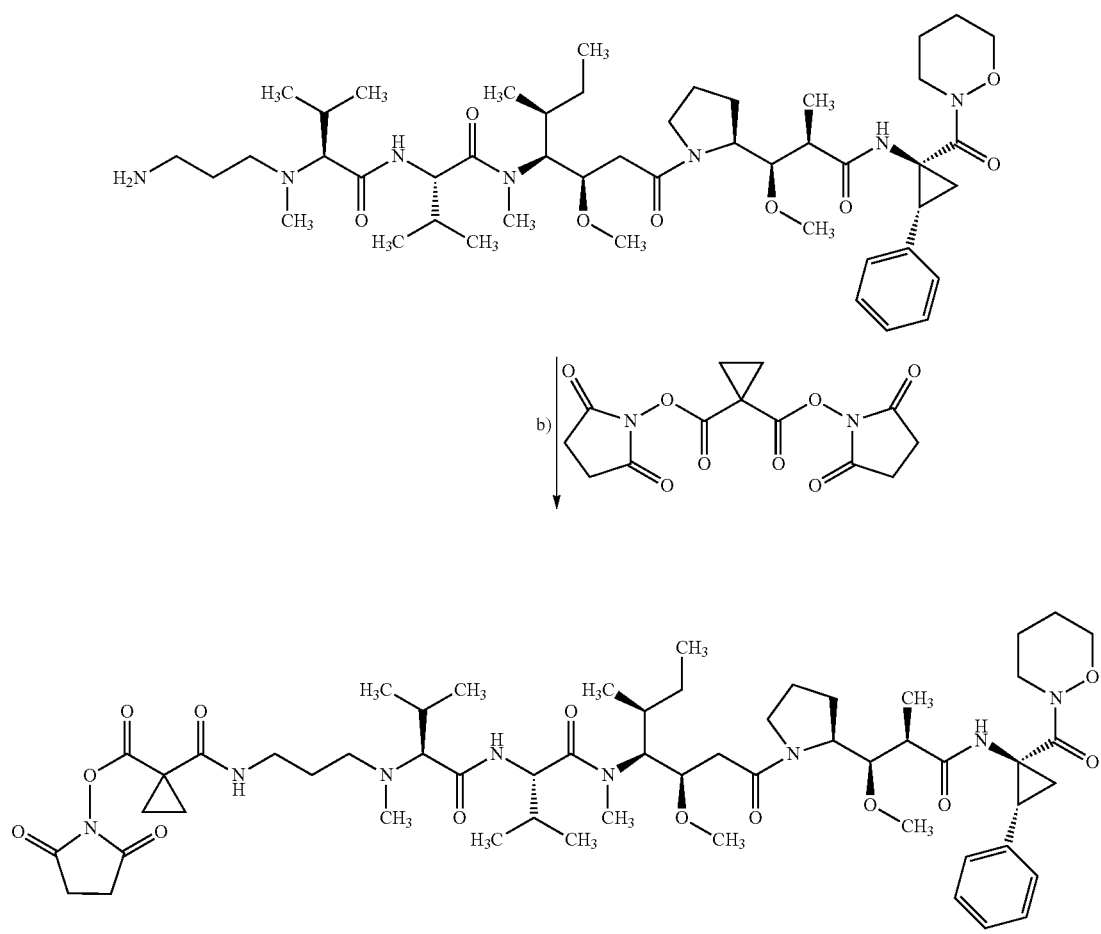
[a]: 1. Diisopropylethylamine, DMF, RT].

Scheme 12
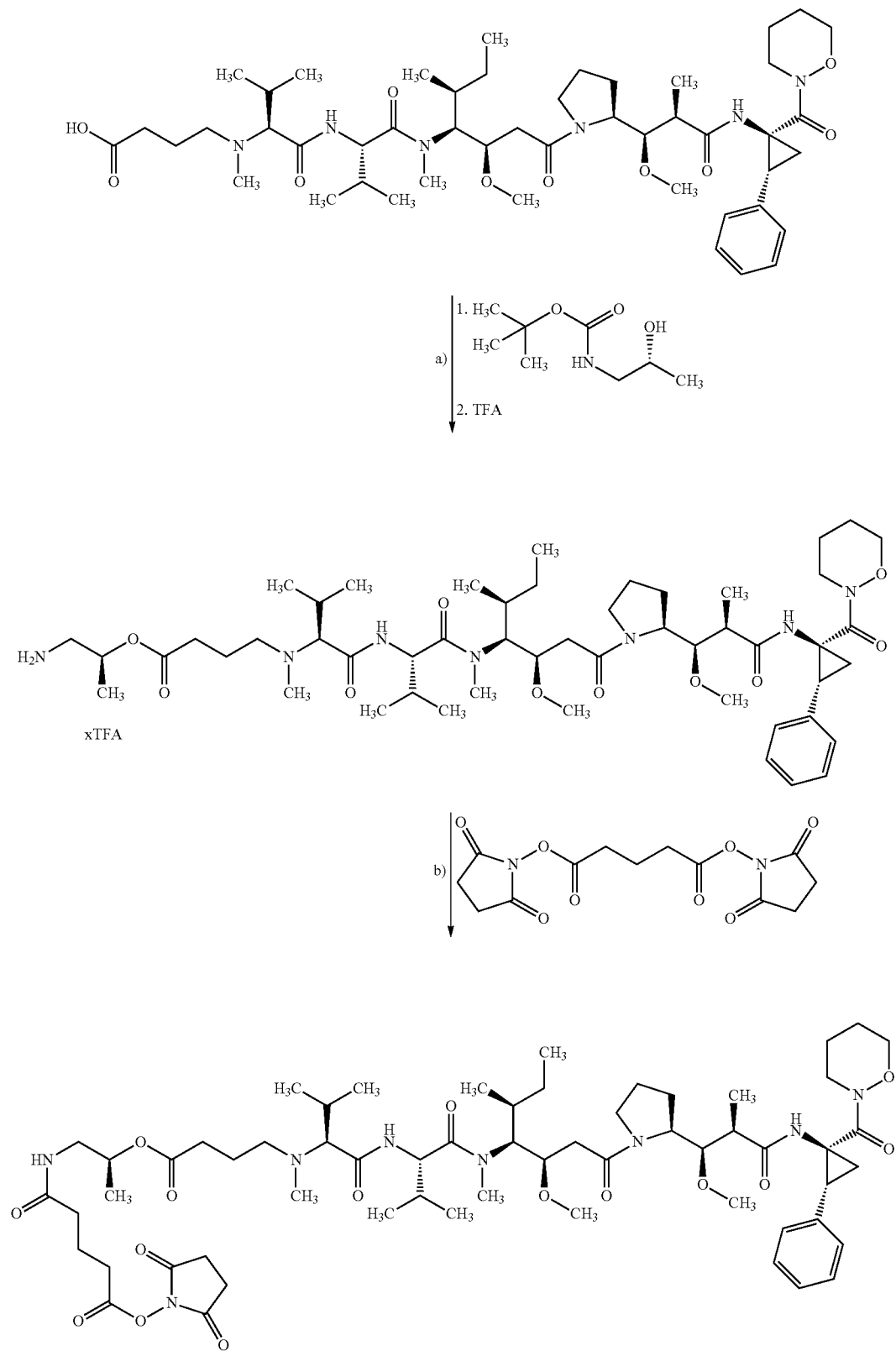
[a]: 1. EDCI, DMAP, dichloromethane, RT; 2. dichloromethane, RT; b): diisopropylamine, DMAP, dichloromethane, RT].

Scheme 13
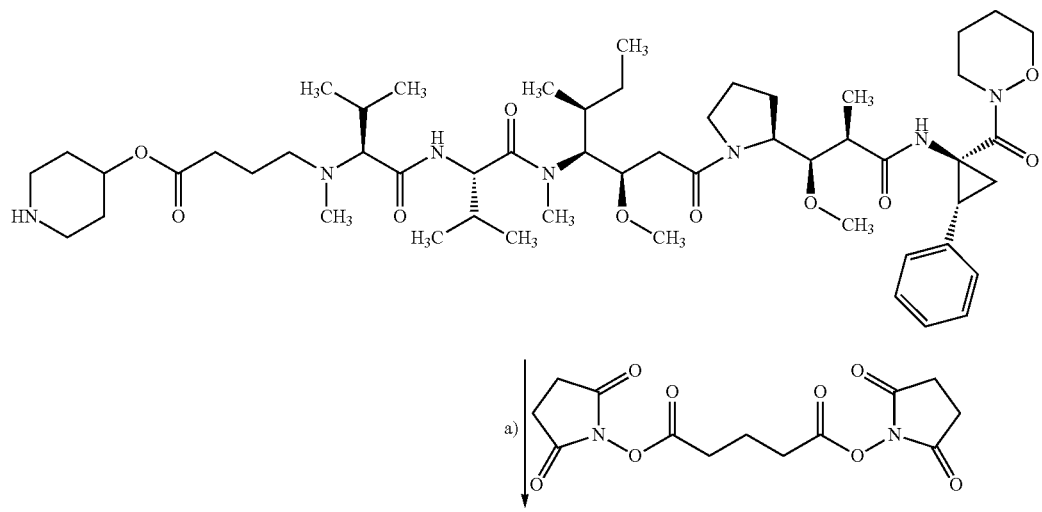
[a]: 1. DMAP, diisopropylamine, dichloromethane, RT].
45
Scheme 18
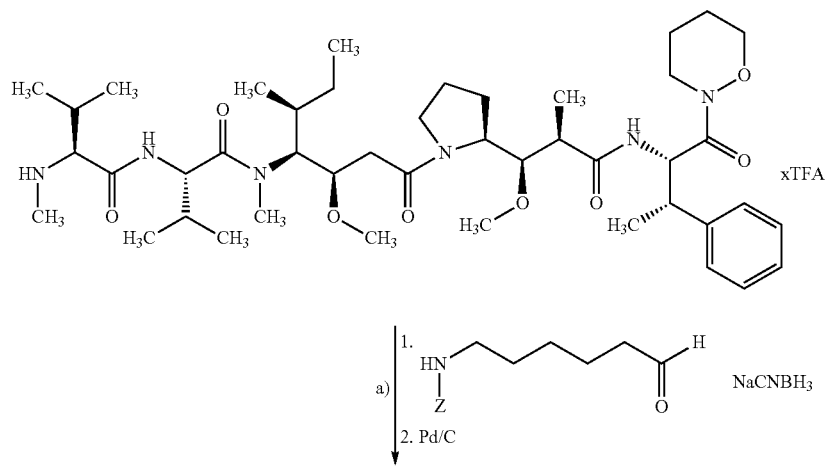

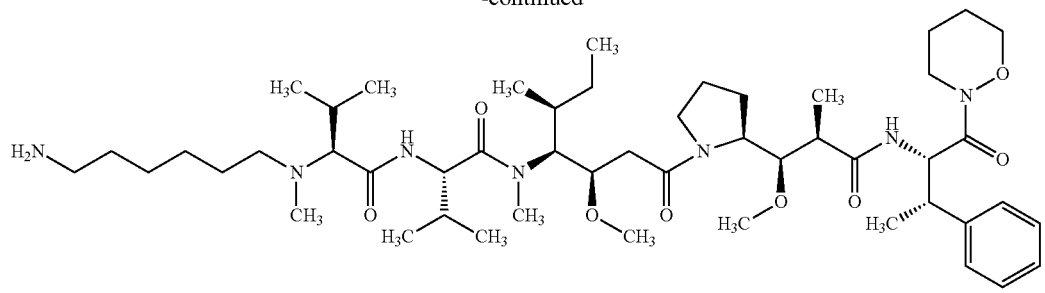

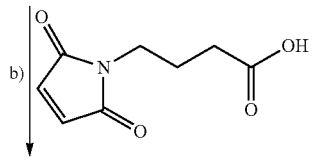

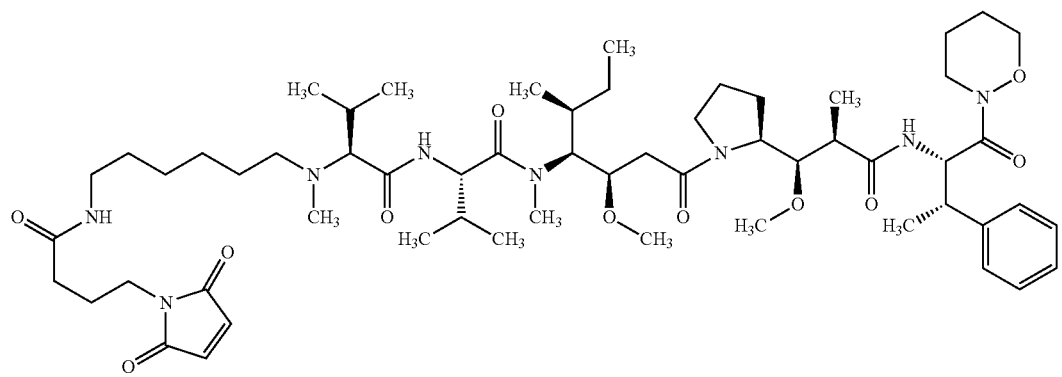

[a]: 1. Water/dioxane, 1N HCl, 100° C.; 2. H₂, Pd/C, methanol, RT; b): HATU, diisopropylethylamine, RT].

The compounds of the formula (IV) can be prepared from commercially available amino acid building blocks or those known from the literature (see, for example, Pettit et al., *Synthesis* 1996, 719; Shioiri et al., *Tetrahedron Lett.* 1991, 32, 931; Shioiri et al., *Tetrahedron* 1993, 49, 1913; Koga et al., *Tetrahedron Lett.* 1991, 32, 2395; Vidal et al., *Tetrahedron* 2004, 60, 9715; Poncet et al., *Tetrahedron* 1994, 50, 5345. Pettit et al., *J. Org. Chem.* 1994, 59, 1796) in analogy to processes known from the literature, in accordance with customary methods of peptide chemistry, and as described in the present experimental section. The synthesis schemes below (Scheme 14 to 16) illustrate the preparation by way of example.

Scheme 14

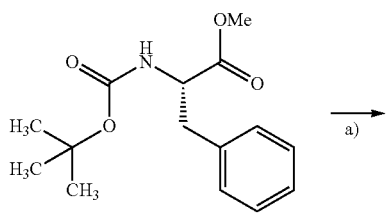

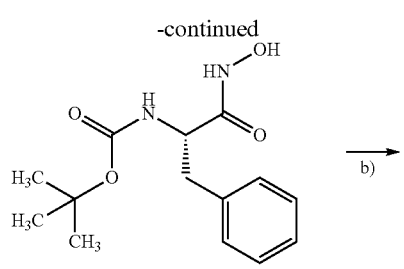

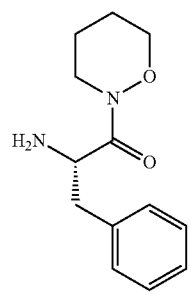

[a]: 1. Hydroxylamine hydrochloride, KOH, MeOH, 0° C. → RT;
b): BrCH₂(CH₂)₂CH₂Br, K₂CO₃, acetone, reflux].

Scheme 15
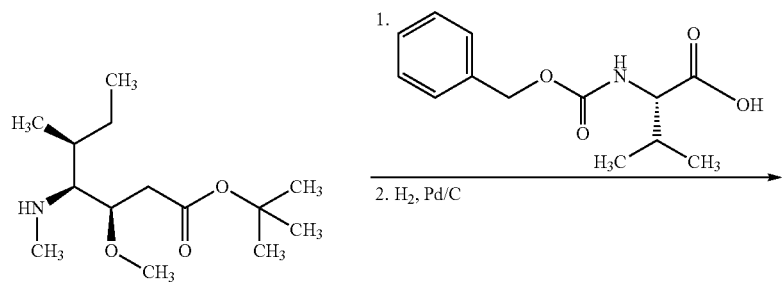
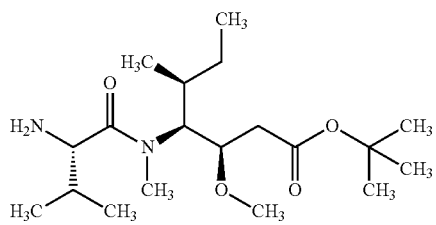
[a]: 1. Diisopropylethylamine, BEP, dichloromethane, -10° C. → Rt; 2. MeOH].
Scheme 16
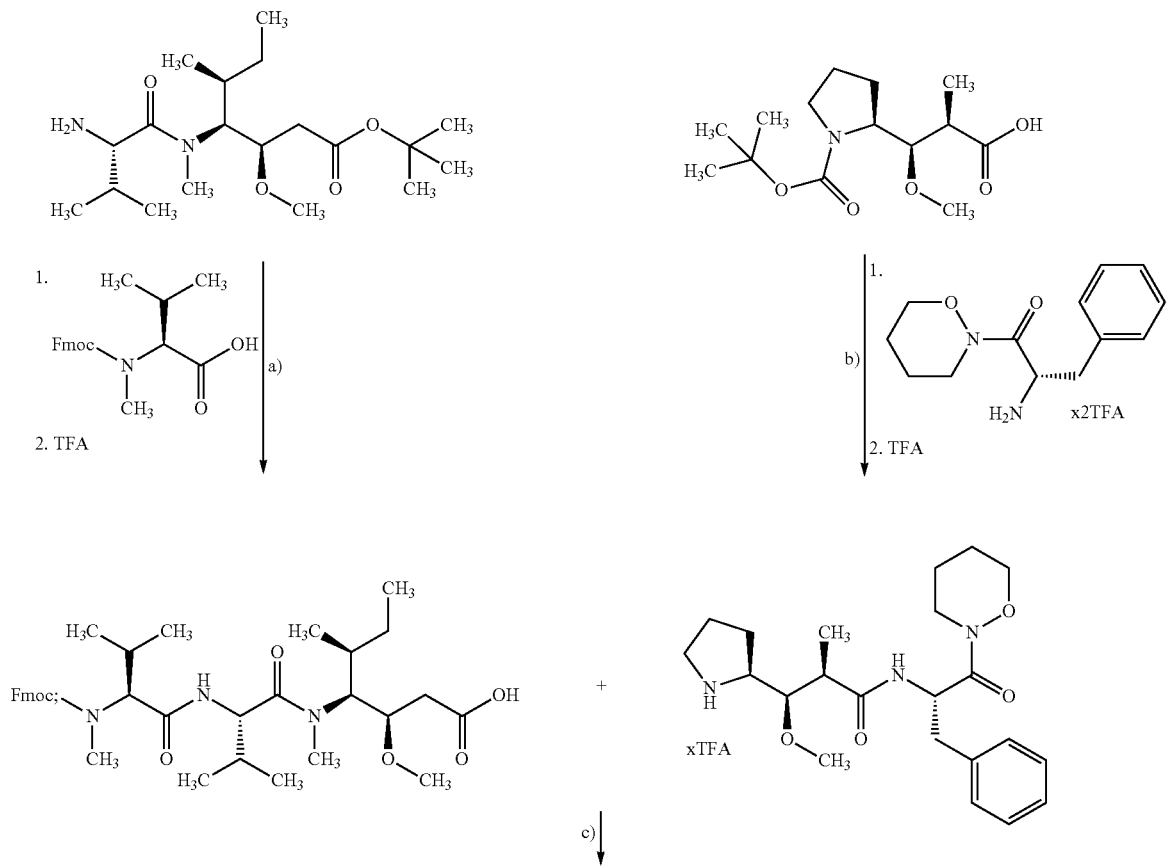

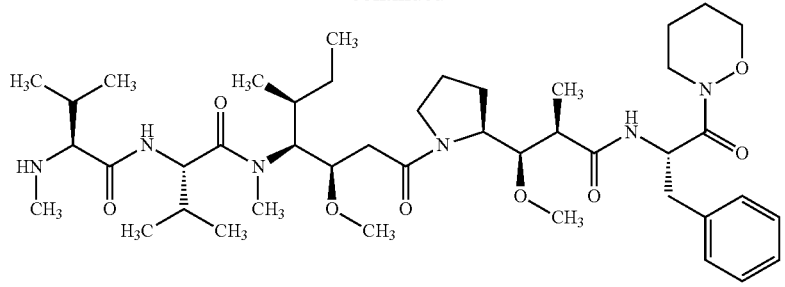

[a]: 1.Diisopropylethylamine, BEP, DMF, RT; 2. dichloromethane; b); 1. HATU, diisopropylethylamine, DMF, RT; 2. dichloromethane, RT; c): 1. HATU, diisopropylethylamine, DMF, RT; 2. piperidine, DMF, RT].

The compounds of the formulae (XI), (XIII), (XV), (XVII) and (XXI), including, where appropriate, chiral or diastereomeric forms thereof, are available commercially or are described as such in the literature, or they can be prepared by routes that are obvious to the skilled person, in analogy to methods published in the literature. Numerous comprehensive instructions and also literature information on the preparation of the starting materials are also given in the experimental section, in the section relating to the preparation of the starting compounds and intermediates.

The compounds of the formulae (V), (VII), (VIII), (X), (XVIII), (XX) and (XXIII), including, where appropriate, chiral or diastereomeric forms thereof, are known from the literature, or can be prepared by routes which are obvious to the skilled person, in analogy to methods published in the literature. Numerous comprehensive instructions and also literature information on the preparation of the starting materials are also given in the experimental section, in the section relating to the preparation of the starting compounds and intermediates.

Alternatively, individual steps of the preparation sequence may be carried out in a different order. This approach is illustrated by way of example in the synthesis schemes below (Scheme 17, 19 and 20).

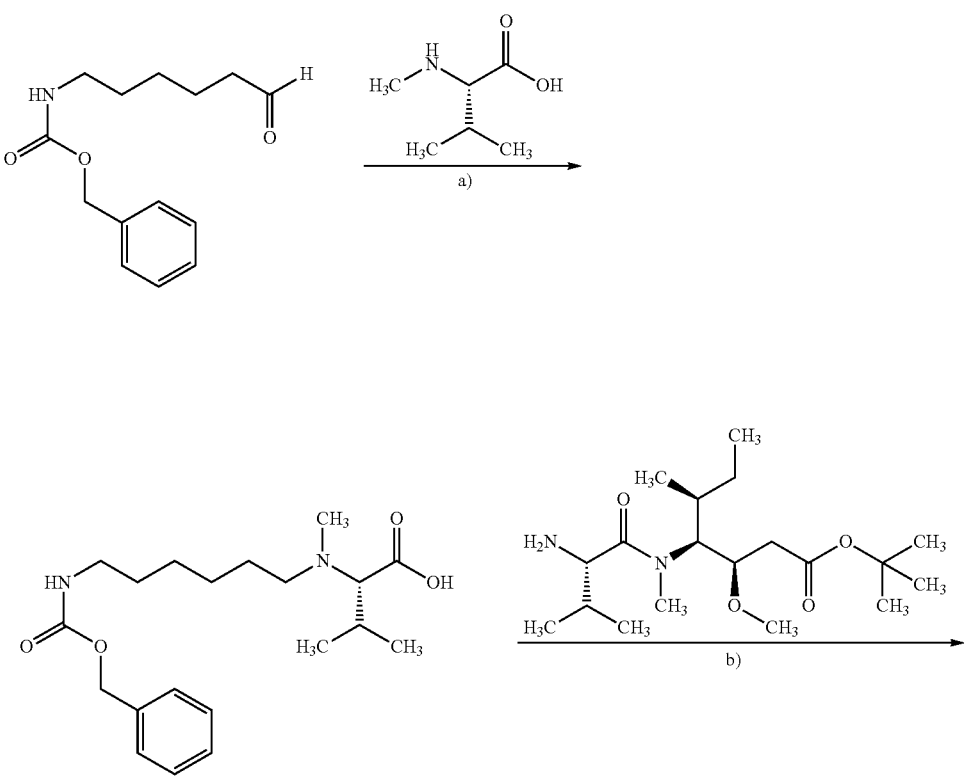

Scheme 17

-continued
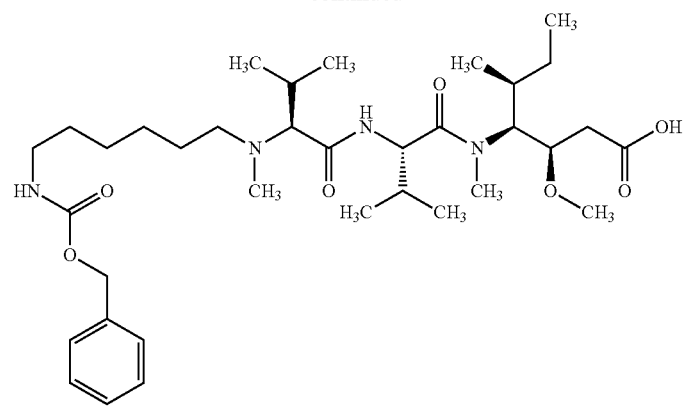
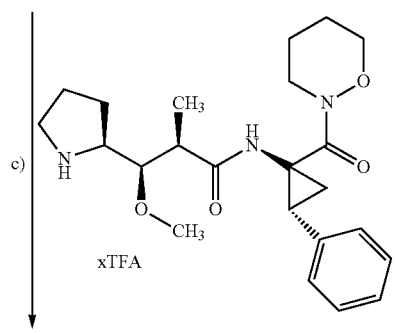
xTFA
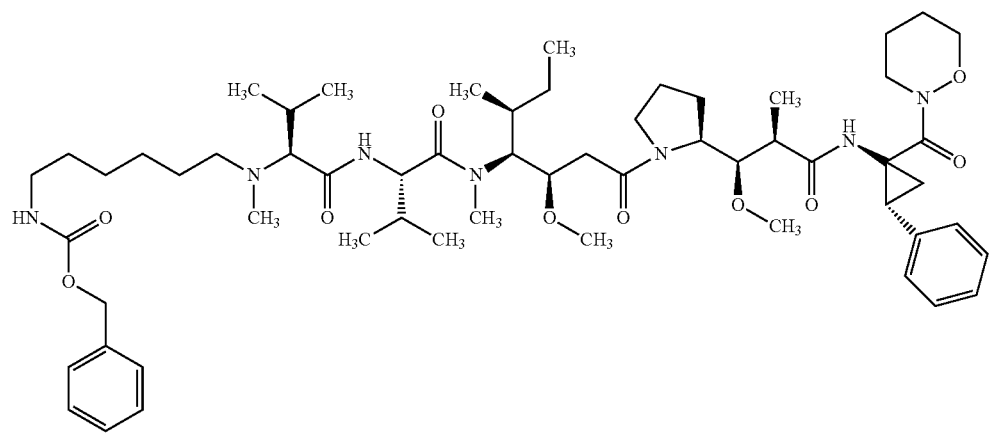

-continued
1. H₂
2. 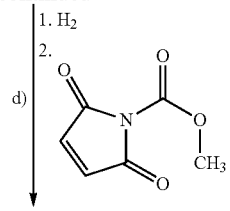
d)
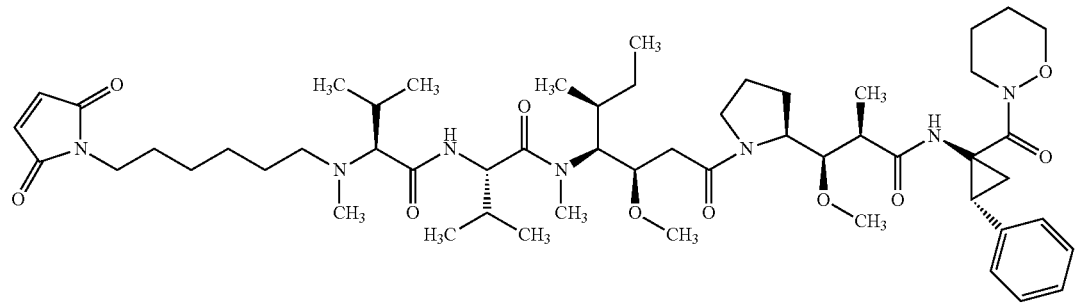
[a): Borane-pyridine complex, acetic acid, MeOH; b): 1. HOBt, EDCI, diisopropylethylamine, DMF, RT; 2. TFA, dichloromethane, RT; c): HATU, diisopropylethylamine, DMF, RT; d): 1. Pd/C, MeOH, RT; 2. NaHCO₃, dioxane, water].
Scheme 19
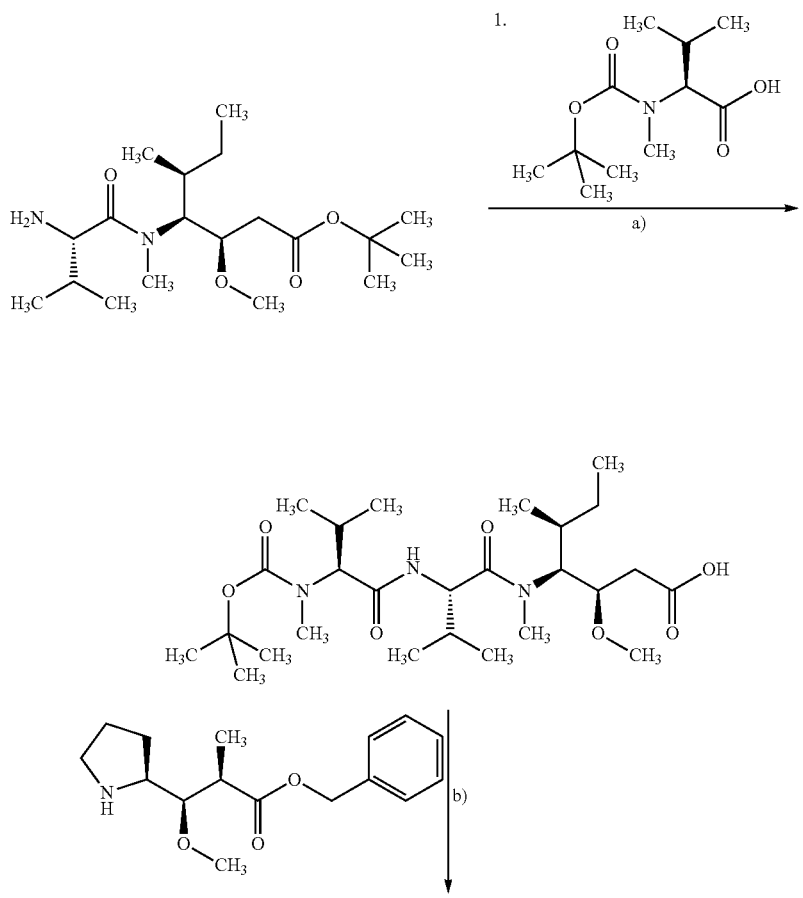

-continued
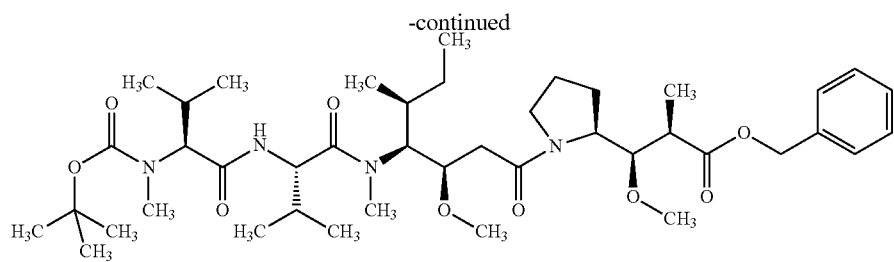
2.
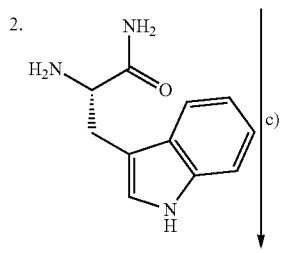
c)
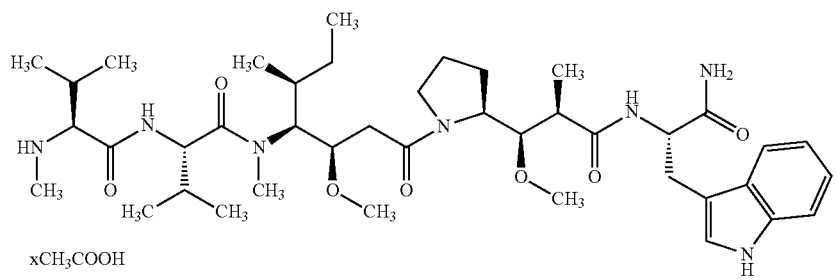
xCH₃COOH
[a): 1. HATU, diisopropylethylamine, DMF, RT; 2. TFA, dichloromethane, RT; 3.((H₃C)₃C(C=O))₂O, DMF, diisopropylethylamine; b): diisopropylethylamine, BEP, DMF, RT; c): 1. H₂, Pd/C (10%), methanol, RT; 2. HATU, diisopropylethylamine, DMF, RT; 3. TFA, dichloromethane, RT].
Scheme 20
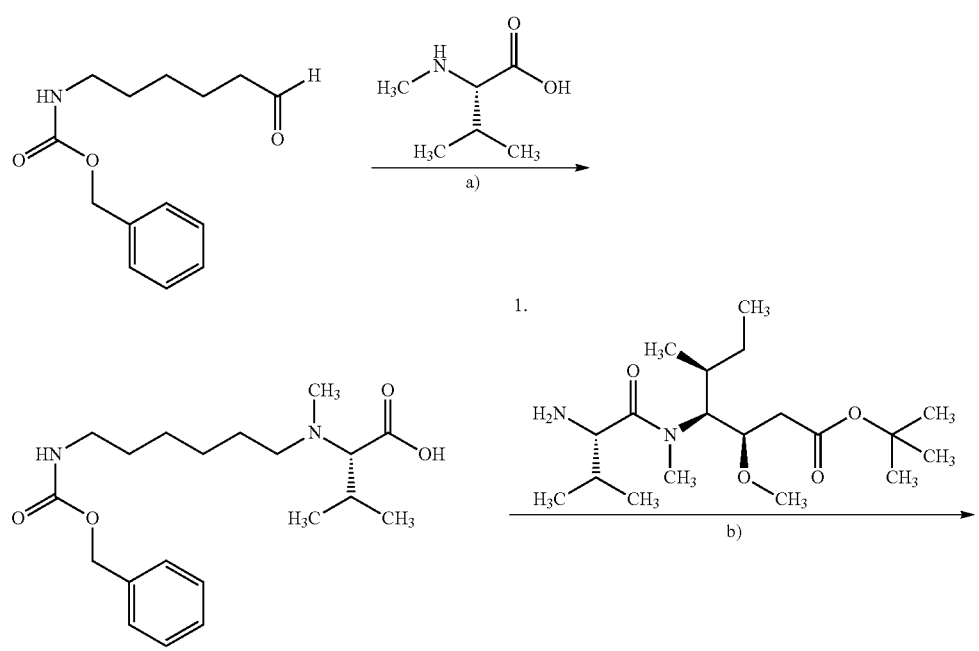

-continued

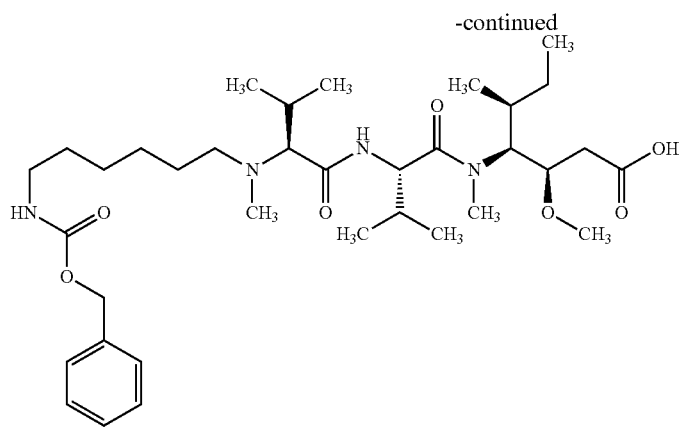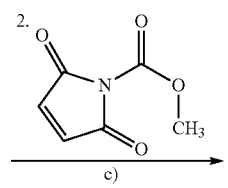

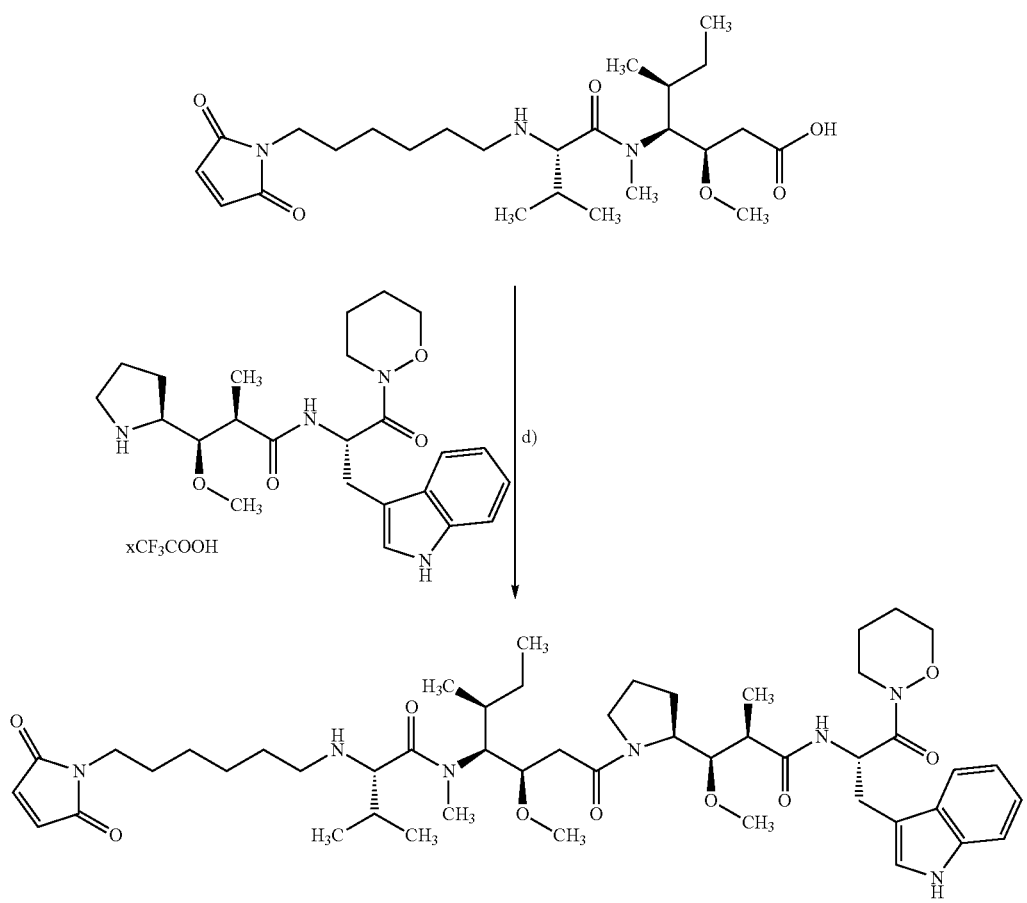

[a): Borane-pyridine complex, acetic acid, MeOH; b): 1. HOBt, EDCI, diisopropylethylamine, DMF, RT; 2. TFA, dichloromethane, RT; c): 1. H₂, Pd/C, MeOH, RT; 2. NaHCO₃, dioxane, water; d): HATU, diisopropylethylamine, DMF, RT;].

In one embodiment the binder binds to a target molecule which is present on a cancer cell. In one preferred embodiment the binder binds to a cancer target molecule.

In another preferred embodiment the target molecule is a selective cancer target molecule.

In one particularly preferred embodiment the target molecule is a protein.

In one embodiment the target molecule is an extracellular target molecule. In one preferred embodiment the extracellular target molecule is a protein.

Cancer target molecules are known to the skilled person. Examples thereof are listed below.

Examples of cancer target molecules are as follows:
(1) EGF receptor (NCBI reference sequence NP_005219.2) (SEQ ID NO: 412)
Sequence (1210 amino acids):

```
>gi|29725609|ref|NP_005219.2| epidermal growth factor receptor
isoform a precursor [Homo sapiens]
MRPSGTAGAALLALLAALCPASRALEEKKVCQGTSNKLTQLGTFEDHFLSLQRMFNNCEVVLGNLE

ITYVQRNYDLSFLKTIQEVAGYVLIALNTVERIPLENLQIIRGNMYYENSYALAVLSNYDANKTGL

KELPMRNLQEILHGAVRFSNNPALCNVESIQWRDIVSSDFLSNMSMDFQNHLGSCQKCDPSCPNGS

CWGAGEENCQKLTKIICAQQCSGRCRGKSPSDCCHNQCAAGCTGPRESDCLVCRKFRDEATCKDTC

PPLMLYNPTTYQMDVNPEGKYSFGATCVKKCPRNYVVTDHGSCVRACGADSYEMEEDGVRKCKKCE

GPCRKVCNGIGIGEFKDSLSINATNIKHFKNCTSISGDLHILPVAFRGDSFTHTPPLDPQELDILK

TVKEITGFLLIQAWPENRTDLHAFENLEIIRGRTKQHGQFSLAVVSLNITSLGLRSLKEISDGDVI

ISGNKNLCYANTINWKKLFGTSGQKTKIISNRGENSCKATGQVCHALCSPEGCWGPEPRDCVSCRN

VSRGRECVDKCNLLEGEPREFVENSECIQCHPECLPQAMNITCTGRGPDNCIQCAHYIDGPHCVKT

CPAGVMGENNTLVWKYADAGHVCHLCHPNCTYGCTGPGLEGCPTNGPKIPSIATGMVGALLLLLVV

ALGIGLFMRRRHIVRKRTLRRLLQERELVEPLTPSGEAPNQALLRILKETEFKKIKVLGSGAFGTV

YKGLWIPEGEKVKIPVAIKELREATSPKANKEILDEAYVMASVDNPHVCRLLGICLTSTVQLITQL

MPFGCLLDYVREHKDNIGSQYLLNWCVQIAKGMNYLEDRRLVHRDLAARNVLVKTPQHVKITDFGL

AKLLGAEEKEYHAEGGKVPIKWMALESILHRIYTHQSDVWSYGVTVWELMTFGSKPYDGIPASEIS

SILEKGERLPQPPICTIDVYMIMVKCWMIDADSRPKFRELIIEFSKMARDPQRYLVIQGDERMHLP

SPTDSNFYRALMDEEDMDDVVDADEYLIPQQGFFSSPSTSRTPLLSSLSATSNNSTVACIDRNGLQ

SCPIKEDSFLQRYSSDPTGALTEDSIDDTFLPVPEYINQSVPKRPAGSVQNPVYHNQPLNPAPSRD

PHYQDPHSTAVGNPEYLNTVQPTCVNSTFDSPAHWAQKGSHQISLDNPDYQQDFFPKEAKPNGIFK

GSTAENAEYLRVAPQSSEFIGA
```

The extracellular domain is marked by underlining.
(2) Mesothelin (SwissProt reference Q13421-3) (SEQ ID NO: 413)
Sequence (622 amino acids):

```
>sp|Q13421-3|MSLN_HUMAN Isoform 2 of Mesothelin OS = Homo sapiens
GN = MSLN
MALPTARPLLGSCGTPALGSLLFLLFSLGWVQPSRTLAGETGQEAAPLDGVLANPPNISS

LSPRQLLGFPCAEVSGLSTERVRELAVALAQKNVKLSTEQLRCLAHRLSEPPEDLDALPL

DLLLFLNPDAFSGPQACTRFFSRITKANVDLLPRGAPERQRLLPAALACWGVRGSLLSEA

DVRALGGLACDLPGRFVAESAEVLLPRLVSCPGPLDQDQQEAARAALQGGGPPYGPPSTW

SVSTMDALRGLLPVLGQPIIRSIPQGIVAAWRQRSSRDPSWRQPERTILRPRFRREVEKT

ACPSGKKAREIDESLIFYKKWELEACVDAALLATQMDRVNAIPFTYEQLDVLKHKLDELY

PQGYPESVIQHLGYLFLKMSPEDIRKWNVTSLETLKALLEVNKGHEMSPQVATLIDRFVK

GRGQLDKDTLDTLTAFYPGYLCSLSPEELSSVPPSSIWAVRPQDLDTCDPRQLDVLYPKA

RLAFQNMNGSEYFVKIQSFLGGAPTEDLKALSQQNVSMDLATFMKLRTDAVLPLTVAEVQ

KLLGPHVEGLKAEERHRPVRDWILRQRQDDLDTLGLGLQGGIPNGYLVLDLSMQEALSGT

PCLLGPGPVLTVLALLLASTLA
```

(3) Carboanhydrase IX (SwissProt reference Q16790)
Mesothelin is encoded by amino acids 296-598 Amino acids 37-286 code for "megakaryocyte-potentiating factor". Mesothelin is anchored in the cell membrane by a GPI anchor and is localized extracellularly.(SEQ ID NO: 414)
Sequence (459 amino acids):

```
>sp|Q16790|CAH9_HUMAN Carbonic anhydrase 9 OS = Homo sapiens
GN = CA9 PE = 1 SV = 2
MAPLCPSPWLPLLIPAPAPGLTVQLLLSLLLLVPVHPQRLPRMQEDSPLGGGSSGEDDPL

GEEDLPSEEDSPREEDPPGEEDLPGEEDLPGEEDLPEVKPKSEEEGSLKLEDLPTVEAPG

DPQEPQNNAHRDKEGDDQSHWRYGGDPPWPRVSPACAGRFQSPVDIRPQLAAFCPALRPL

ELLGFQLPPLPELRLRNNGHSVQLTLPPGLEMALGPGREYRALQLHLHWGAAGRPGSEHT

VEGHRFPAEIHVVHLSTAFARVDEALGRPGGLAVLAAFLEEGPEENSAYEQLLSRLEEIA

EEGSETQVPGLDISALLPSDFSRYFQYEGSLTTPPCAQGVIWTVFNQTVMLSAKQLHTLS

DTLWGPGDSRLQLNFRATQPLNGRVIEASFPAGVDSSPRAAEPVQLNSCLAAGDILALVF

GLLFAVTSVAFLVQMRRQHRRGTKGGVSYRPAEVAETGA
```

The extracellular domain is marked by underlining.

(4) C4.4a (NCBI reference sequence NP_055215.2; Synonym LYPD3) (SEQ ID NO: 3)
Sequence (346 amino acids):

```
>gi|93004088|ref|NP_055215.2| ly6/PLAUR domain-containing protein
3 precursor [Homo sapiens]
MDPARKAGAQAMIWTAGWLLLLLLRGGAQALECYSCVQKADDGCSPNKMKTVKCAPGVDVCTEAVG

AVETIHGQFSLAVRGCGSGLPGKNDRGLDLHGLLAFIQLQQCAQDRCNAKLULTSRALDPAGNESA

YPPNGVECYSCVGLSREACQGTSPPVVSCYNASDHVYKGCFDGNVTLTAANVTVSLPVRGCVQDEF

CTRDGVTGPGFTLSGSCCQGSRCNSDLRNKTYFSPRIPPLVRLPPPEPTTVASTTSVTTSTSAPVR

PTSTTKPMPAPTSQTPRQGVEHEASRDEEPRLTGGAAGHQDRSNSGQYPAKGGPQQPHNKGCVAPT

AGLAALLLAVAAGVLL
```

The matured, extracellular domain is marked by underlining (SEQ ID NO:1).

(5) CD52 (NCBI reference sequence NP_001794.2) (SEQ ID NO: 415)

```
>gi|68342030|ref|NP_001794.2| CAMPATH-1 antigen precursor
[Homo sapiens]
MKRFLFLLLTISLLVMVQIQTGLSGQNDTSQTSSPSASSNISGGIFLFFVANAIIHLFCFS
```

(6) Her2 (NCBI reference sequence NP_004439.2) (SEQ ID NO: 416)

```
>gi|54792096|ref|NP_004439.2| receptor tyrosine-protein kinase
erbB-2 isoform a [Homo sapiens]
MELAALCRWGLLLALLPPGAASTQVCTGTDMKLRLPASPETHLDMLRHLYQGCQVVQGNLELTYLP

TNASLSFLQDIQEVQGYVLIAHNQVRQVPLQRLRIVRGTQLFEDNYALAVLDNGDPLNNTTPVTGA

SPGGLRELQLRSLTEILKGGVLIQRNPQLCYQDTILWKDIFHKNNQLALTLIDTNRSRACHPCSPM

CKGSRCWGESSEDCQSLTRTVCAGGCARCKGPLPTDCCHEQCAAGCTGPKHSDCLACLHFNHSGIC

ELHCPALVTYNTDTFESMPNPEGRYTFGASCVTACPYNYLSTDVGSCTLVCPLHNQEVTAEDGTQR

CEKCSKPCARVCYGLGMEHLREVRAVTSANIQEFAGCKKIFGSLAFLPESFDGDPASNTAPLQPEQ

LQVFETLEEITGYLYISAWPDSLPDLSVFQNLQVIRGRILHNGAYSLTLQGLGISWLGLRSLRELG
```

-continued

```
SGLALIHHNTHLCFVHTVPWDQLFRNPHQALLHTANRPEDECVGEGLACHQLCARGHCWGPGPTQC

VNCSQFLRGQECVEECRVLQGLPREYVNARHCLPCHPECQPQNGSVTCFGPEADQCVACAHYKDPP

FCVARCPSGVKPDLSYMPIWKFPDEEGACQPCPINCTHSCVDLDDKGCPAEQRASPLTSIISAVVG

ILLVVVLGVVFGILIKRRQQKIRKYTMRRLLQETELVEPLTPSGAMPNQAQMRILKETELRKVKVL

GSGAFGTVYKGIWIPDGENVKIPVAIKVLRENTSPKANKEILDEAYVMAGVGSPYVSRLLGICLTS

TVQLVTQLMPYGCLLDHVRENRGRLGSQDLLNWCMQIAKGMSYLEDVRLVHRDLAARNVLVKSPNH

VKITDFGLARLLDIDETEYHADGGKVPIKWMALESILRRRFTHQSDVWSYGVTVWELMTFGAKPYD

GIPAREIPDLLEKGERLPQPPICTIDVYMIMVKCWMIDSECRPRFRELVSEFSRMARDPQRFVVIQ

NEDLGPASPLDSTFYRSLLEDDDMGDLVDAEEYLVPQQGFFCPDPAPGAGGMVHHRHRSSSTRSGG

GDLTLGLEPSEEEAPRSPLAPSEGAGSDVFDGDLGMGAAKGLQSLPTHDPSPLQRYSEDPTVPLPS

ETDGYVAPLTCSPQPEYVNQPDVRPQPPSPREGPLPAARPAGATLERPKTLSPGKNGVVKDVFAFG

GAVENPEYLTPQGGAAPQPHPPPAFSPAFDNLYYWDQDPPERGAPPSTFKGTPTAENPEYLGLDVPV
```

(7) CD20 (NCBI reference sequence NP_068769.2) (SEQ ID NO: 417)

```
>gi|23110987|ref|NP_068769.2| B-lymphocyte antigen CD20 [Homo sapiens]
MTTPRNSVNGTFPAEPMKGPIAMQSGPKPLFRRMSSLVGPTQSFFMRESKTLGAVQIMNGLFHIAL

GGLLMIPAGIYAPICVTVWYPLWGGIMYIISGSLLAATEKNSRKCLVKGKMIMNSLSLFAAISGMI

LSIMDILNIKISHFLKMESLNFIRAHTPYINIYNCEPANPSEKNSPSTQYCYSIQSLFLGILSVML

IFAFFQELVIAGIVENEWKRTCSRPKSNIVLLSAEEKKEQTIEIKEEVVGLTETSSQPKNEEDIEI

IPIQEEEEETETNFPEPPQDQESSPIENDSSP
```

(8) The lymphocyte-activating antigen CD30 (SwissProt ID P28908) (SEQ ID NO: 418)
>gi|68348711|ref|NP_001234.2| tumor necrosis factor receptor superfamily member 8 isoform 1 precursor [*Homo sapiens*]

```
MRVLLAALGLLFLGALRAFPQDRPFEDTCHGNPSHYYDKAVRRCCYRCPMGLFPTQQCPQRPTDCR

KQCEPDYYLDEADRCTACVTCSRDDLVEKTPCAWNSSRVCECRPGMFCSTSAVNSCARCFFHSVCP

AGMIVKFPGTAQKNTVCEPASPGVSPACASPENCKEPSSGTIPQAKPTPVSPATSSASTMPVRGGT

RLAQEAASKLTRAPDSPSSVGRPSSDPGLSPTQPCPEGSGDCRKQCEPDYYLDEAGRCTACVSCSR

DDLVEKTPCAWNSSRTCECRPGMICATSATNSRARCVPYPICAAETVTKPQDMAEKDTTFEAPPLG

TQPDCNPTPENGEAPASTSPTQSLLVDSQASKTLPIPTSAPVALSSTGKPVLDAGPVLFWVILVLV

VVVGSSAFLLCHRRACRKRIRQKLHLCYPVQTSQPKLELVDSRPRRSSTQLRSGASVTEPVAEERG

LMSQPLMETCHSVGAAYLESLPLQDASPAGGPSSPRDLPEPRVSTEHTNNKIEKIYIMKADTVIVG

TVKAELPEGRGLAGPAEPELEEELEADHTPHYPEQETEPPLGSCSDVMLSVEEEGKEDPLPTAASGK
```

(9) The lymphocyte adhesion molecule CD22 (SwissProt ID P20273) (SEQ ID NO: 419)
>gi|157168355|ref|NP_001762.2| B-cell receptor CD22 isoform 1 precursor [*Homo sapiens*]

```
MHLLGPWLLLLVLEYLAFSDSSKWVFEHPETLYAWEGACVWIPCTYRALDGDLESFILFHNPEYNK

NTSKFDGTRLYESTKDGKVPSEQKRVQFLGDKNKNCTLSIHPVHLNDSGQLGLRMESKTEKWMERI

HLNVSERPFPPHIQLPPEIQESQEVTLTCLLNFSCYGYPIQLQWLLEGVPMRQAAVTSTSLTIKSV
```

-continued

```
FTRSELKFSPQWSHHGKIVTCQLQDADGKFLSNDTVQLNVKHTPKLEIKVTPSDAIVREGDSVTMT

CEVSSSNPEYTTVSWLKDGTSLKKQNTFTLNLREVTKDQSGKYCCQVSNDVGPGRSEEVFLQVQYA

PEPSTVQILHSPAVEGSQVEFLCMSLANPLPTNYTWYHNGKEMQGRTEEKVHIPKILPWHAGTYSC

VAENILGTGQRGPGAELDVQYPPKKVTTVIQNPMPIREGDTVTLSCNYNSSNPSVTRYEWKPHGAW

EEPSLGVLKIQNVGWDNTTIACAACNSWCSWASPVALNVQYAPRDVRVRKIKPLSEIHSGNSVSLQ

CDFSSSHPKEVQFFWEKNGRLLGKESQLNFDSISPEDAGSYSCWVNNSIGQTASKAWTLEVLYAPR

RLRVSMSPGDQVMEGKSATLTCESDANPPVSHYTWFDWNNQSLPYHSQKLRLEPVKVQHSGAYWCQ

GTNSVGKGRSPLSTLTVYYSPETIGRRVAVGLGSCLAILILAICGLKLQRRWKRTQSQQGLQENSS

GQSFFVRNKKVRRAPLSEGPHSLGCYNPMMEDGISYTTLRFPEMNIPRTGDAESSEMQRPPPDCDD

TVTYSALHKRQVGDYENVIPDFPEDEGIHYSELIQFGVGERPQAQENVDYVILKH
```

(10) The myloid cell surface antigen CD33 (SwissProt ID P20138) (SEQ ID NO: 420)
>gi|130979981|ref|NP_001763.3| myeloid cell surface antigen CD33 isoform 1 precursor [Homo sapiens]

```
MPLLLLLPLLWAGALAMDPNFWLQVQESVTVQEGLCVLVPCTFFHPIPYYDKNSPVHGYWFREGAI

ISRDSPVATNKLDQEVQEETQGRFRLLGDPSRNNCSLSIVDARRRDNGSYFFRMERGSTKYSYKSP

QLSVHVTDLTHRPKILIPGTLEPGHSKNLTCSVSWACEQGTPPIFSWLSAAPTSLGPRTTHSSVLI

ITPRPQDHGTNLTCQVKFAGAGVTTERTIQLNVTYVPQNPTTGIFPGDGSGKQETRAGVVHGAIGG

AGVTALLALCLCLIFFIVKTHRRKAARTAVGRNDTHPTTGSASPKHQKKSKLHGPTETSSCSGAAP

TVEMDEELHYASLNFHGMNPSKDTSTEYSEVRTQ
```

(11) The transmembrane glycoprotein NMB (SwissProt ID Q14956) SEQ ID NO: 421)
gi|52694752|ref|NP_001005340.1| transmembrane glycoprotein NMB isoform a precursor [Homo sapiens]

```
MECLYYFLGFLLLAARLPLDAAKRFHDVLGNERPSAYMREHNQLNGWSSDENDWNEKLYPVWKRGD

MRWKNSWKGGRVQAVLTSDSPALVGSNITFAVNLIFPRCQKEDANGNIVYEKNCRNEAGLSADPYV

YNWTAWSEDSDGENGTGQSHHNVFPDGKPFPHHPGWRRWNFIYVFHTLGQYFQKLGRCSVRVSVNT

ANVTLGPQLMEVTVYRRHGRAYVPIAQVKDVYVVTDQIPVFVTMFQKNDRNSSDETFLKDLPIMFD

VLIHDPSHFLNYSTINYKWSFGDNTGLFVSTNHTVNHTYVLNGTFSLNLTVKAAAPGPCPPPPPPP

RPSKPTPSLATTLKSYDSNTPGPAGDNPLELSRIPDENCQINRYGHFQATITIVEGILEVNIIQMT

DVLMPVPWPESSLIDFVVTCQGSIPTEVCTIISDPTCEITQNTVCSPVDVDEMCLLTVRRTFNGSG

TYCVNLTLGDDTSLALTSTLISVPDRDPASPLRMANSALISVGCLAIFVTVISLLVYKKHKEYNPI

ENSPGNVVRSKGLSVFLNRAKAVFFPGNQEKDPLLKNQEFKGVS
```

(12) The adhesion molecule CD56 (SwissProt ID P13591) (SEQ ID NO: 422)
>gi|94420689|ref|NP_000606.3| neural cell adhesion molecule 1 isoform 1 [Homo sapiens]

```
MLQTKDLIWTLFFLGTAVSLQVDIVPSQGEISVGESKFFLCQVAGDAKDKDISWFSPNGEKLTPNQ

QRISVVWNDDSSSTLTIYNANIDDAGIYKCVVTGEDGSESEATVNVKIFQKLMFKNAPTPQEFREG

EDAVIVCDVVSSLPPTIIWKHKGRDVILKKDVRFIVLSNNYLQIRGIKKTDEGTYRCEGRILARGE

INFKDIQVIVNVPPTIQARQNIVNATANLGQSVTLVCDAEGFPEPTMSWTKDGEQIEQEEDDEKYI
```

-continued

```
FSDDSSQLTIKKVDKNDEAEYICIAENKAGEQDATIHLKVFAKPKITYVENQTAMELEEQVTLTCE

ASGDPIPSITWRTSTRNISSEEKTLDGHMVVRSHARVSSLTLKSIQYTDAGEYICTASNTIGQDSQ

SMYLEVQYAPKLQGPVAVYTWEGN

QVNITCEVFAYPSATISWFRDGQLLPSSNYSNIKIYNTPSASYLEVTPDSENDFGNYNCTAVNRIG

QESLEFILVQADTPSSPSIDQVEPYSSTAQVQFDEPEATGGVPILKYKAEWRAVGEEVWHSKWYDA

KEASMEGIVTIVGLKPETTYAVRLAALNGKGLGEISAASEFKTQPVQGEPSAPKLEGQMGEDGNSI

KVNLIKQDDGGSPIRHYLVRYRALSSEWKPEIRLPSGSDHVMLKSLDWNAEYEVYVVAENQQGKSK

AAHFVFRTSAQPTAIPANGSPTSGLSTGAIVGILIVIFVLLLVVVDITCYFLNKCGLFMCIAVNLC

GKAGPGAKGKDMEEGKAAFSKDESKEPIVEVRTEEERTPNHDGGKHTEPNETTPLTEPEKGPVEAK

PECQETETKPAPAEVKTVPNDATQTKENESKA
```

(13) The surface molecule CD70 (SwissProt ID P32970) (SEQ ID NO: 423)
>gi|4507605|ref|NP_001243.1| CD70 antigen [*Homo sapiens*]

```
MPEEGSGCSVRRRPYGCVLRAALVPLVAGLVICLVVCIQRFAQAQQQLPLESLGWDVAELQLNHTG

PQQDPRLYWQGGPALGRSFLHGPELDKGQLRIHRDGIYMVHIQVTLAICSSTTASRHHPTTLAVGI

CSPASRSISLLRLSFHQGCTIASQRLTPLARGDTLCTNLTGTLLPSRNTDETFFGVQWVRP
```

(14) The surface molecule CD74 (SwissProt ID PO4233) (SEQ ID NO: 424)
>gi|10835071|ref|NP_004346.1| HLA class II histocompatibility antigen gamma chain isoform b [*Homo sapiens*]

```
MHRRRSRSCREDQKPVMDDQRDLISNNEQLPMLGRRPGAPESKCSRGALY

TGFSILVTLLLAGQATTAYFLYQQQGRLDKLTVTSQNLQLENLRMKLPKP

PKPVSKMRMATPLLMQALPMGALPQGPMQNATKYGNMTEDHVMHLLQNAD

PLKVYPPLKGSFPENLRHLKNTMETIDWKVFESWMHHWLLFEMSRHSLEQ

KPTDAPPKESLELEDPSSGLGVTKQDLGPVPM
```

(15) The B-lymphocyte antigen CD19 (SwissProt ID P15391) (SEQ ID NO: 425)
>gi|296010921|ref|NP_001171569.1| B-lymphocyte antigen CD19 isoform 1 precursor [*Homo sapiens*]

```
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLAGSQS

YEDMRGILYAAPQLRSIRGQPGPNHEEDADSYENMDNPDGPDPAWGGGGR

MGTWSTR
```

(16) The surface protein mucin-1 (SwissProt ID P15941) (SEQ ID NO: 426)
>gi|65301117|ref|NP_002447.4| mucin-1 isoform 1 precursor [*Homo sapiens*]

```
MTPGTQSPFFLLLLLTVLTVVTGSGHASSTPGGEKETSATQRSSVPSSTE

KNALSTGVSFFFLSFHISNLQFNSSLEDPSTDYYQELQRDISEMFLQIYK

QGGFLGLSNIKFRPGSVVVQLTLAFREGTINVHDVETQFNQYKTEAASRY

NLTISDVSVSDVPFPFSAQSGAGVPGWGIALLVLVCVLVALAIVYLIALA

VCQCRRKNYGQLDIFPARDTYHPMSEYPTYHTHGRYVPPSSTDRSPYEKV

SAGNGGSSLSYTNPAVAATSANL
```

(17) The surface protein CD138 (SwissProt ID P18827) (SEQ ID NO: 427)
>gi|29568086|ref|NP_002988.3| syndecan-1 precursor [*Homo sapiens*]

```
MRRAALWLWLCALALSLQPALPQIVATNLPPEDQDGSGDDSDNFSGSGAG

ALQDITLSQQTPSTWKDTQLLTAIPTSPEPTGLEATAASTSTLPAGEGPK

EGEAVVLPEVEPGLTAREQEATPRPRETTQLPTTHQASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA
```

(18) The integrin alphaV (Genbank Accession No.: NP_002201.1) (SEQ ID NO: 428)
>gi|4504763|ref|NP_002201.1| integrin alpha-V isoform 1 precursor [*Homo sapiens*]

MAFPPRRRLRLGPRGLPLLLSGLLLPLCRAFNLDVDSPAEYSGPEGSYFG

FAVDFFVPSASSRMFLLVGAPKANTTQPGIVEGGQVLKCDWSSTRRCQPI

EFDATGNRDYAKDDPLEFKSHQWFGASVRSKQDKILACAPLYHWRTEMKQ

EREPVGTCFLQDGTKTVEYAPCRSQDIDADGQGFCQGGFSIDFTKADRVL

LGGPGSFYWQGQLISDQVAEIVSKYDPNVYSIKYNNQLATRTAQAIFDDS

YLGYSVAVGDFNGDGIDDFVSGVPRAARTLGMVYIYDGKNMSSLYNFTGE

QMAAYFGFSVAATDINGDDYADVFIGAPLFMDRGSDGKLQEVGQVSVSLQ

RASGDFQTTKLNGFEVFARFGSAIAPLGDLDQDGFNDIAIAAPYGGEDKK

GIVYIFNGRSTGLNAVPSQILEGQWAARSMPPSFGYSMKGATDIDKNGYP

DLIVGAFGVDRAILYRARPVITVNAGLEVYPSILNQDNKTCSLPGTALKV

SCFNVRFCLKADGKGVLPRKLNFQVELLLDKLKQKGAIRRALFLYSRSPS

HSKNMTISRGGLMQCEELIAYLRDESEFRDKLTPITIFMEYRLDYRTAAD

TTGLQPILNQFTPANISRQAHILLDCGEDNVCKPKLEVSVDSDQKKIYIG

DDNPLTLIVKAQNQGEGAYEAELIVSIPLQADFIGVVRNNEALARLSCAF

KTENQTRQVVCDLGNPMKAGTQLLAGLRFSVHQQSEMDTSVKFDLQIQSS

NLFDKVSPVVSHKVDLAVLAAVEIRGVSSPDHIFLPIPNWEHKENPETEE

DVGPVVQHIYELRNNGPSSFSKAMLHLQWPYKYNNNTLLYILHYDIDGPM

NCTSDMEINPLRIKISSLQTTEKNDTVAGQGERDHLITKRDLALSEGDIH

TLGCGVAQCLKIVCQVGRLDRGKSAILYVKSLLWTETFMNKENQNHSYSL

KSSASFNVIEFPYKNLPIEDITNSTLVTTNVTWGIQPAPMPVPVWVIILA

VLAGLLLLAVLVFVMYRMGFFKRVRPPQEEQEREQLQPHENGEGNSET

(19) The teratocarcinoma-derived growth factor 1 protein TDGF1 (Genbank Accession No.: NP_003203.1) (SEQ ID NO: 429)
>gi|4507425|ref|NP_003203.1| teratocarcinoma-derived growth factor 1 isoform 1 precursor [*Homo sapiens*]

MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGICLSIQSYY

(20) The prostate-specific membrane antigen PSMA (Swiss Prot ID: Q04609) (SEP ID NO: 430)
>gi|4758398|ref|NP_004467.1| glutamate carboxypeptidase 2 isoform 1 [*Homo sapiens*]

MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVSDIVPPFSAFSPQGMPEGDLVYVNYARTEDFFKLERDMKINCSGKI

VIARYGKVFRGNKVKNAQLAGAKGVILYSDPADYFAPGVKSYPDGWNLPG

GGVQRGNILNLNGAGDPLTPGYPANEYAYRRGIAEAVGLPSIPVHPIGYY

DAQKLLEKMGGSAPPDSSWRGSLKVPYNVGPGFTGNFSTQKVKMHIHSTN

EVTRIYNVIGTLRGAVEPDRYVILGGHRDSWVFGGIDPQSGAAVVHEIVR

SFGTLKKEGWRPRRTILFASWDAEEFGLLGSTEWAEENSRLLQERGVAYI

NADSSIEGNYTLRVDCTPLMYSLVHNLTKELKSPDEGFEGKSLYESWTKK

SPSPEFSGMPRISKLGSGNDFEVFFQRLGIASGRARYTKNWETNKFSGYP

LYHSVYETYELVEKFYDPMFKYHLTVAQVRGGMVFELANSIVLPFDCRDY

AVVLRKYADKIYSISMKHPQEMKTYSVSFDSLFSAVKNFTEIASKFSERL

QDFDKSNPIVLRMMNDQLMFLERAFIDPLGLPDRPFYRHVIYAPSSHNKY

AGESFPGIYDALFDIESKVDPSKAWGEVKRQIYVAAFTVQAAAETLSEVA

(21) The tyrosine protein kinase EPHA2 (Swiss Prot ID: P29317) (SEQ ID NO: 431)
>gi|32967311|ref|NP_004422.2| ephrin type-A receptor 2 precursor [*Homo sapiens*]

MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKGDSNSYNVRRTEGFSVTLDDLAPD

TTYLVQVQALTQEGQGAGSKVHEFQTLSPEGSGNLAVIGGVAVGVVLLLV

LAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKA

GYTEKQRVDFLGEAGIMGQFSHHNIIRLEGVISKYKPMMIITEYMENGAL

DKFLREKDGEFSVLQLVGMLRGIAAGMKYLANMNYVHRDLAARNILVNSN

LVCKVSDFGLSRVLEDDPEATYTTSGGKIPIRWTAPEAISYRKFTSASDV

WSFGIVMWEVMTYGERPYWELSNHEVMKAINDGFRLPTPMDCPSAIYQLM

MQCWQQERARRPKFADIVSILDKLIRAPDSLKTLADFDPRVSIRLPSTSG

SEGVPFRTVSEWLESIKMQQYTEHFMAAGYTAIEKVVQMTNDDIKRIGVR

LPGHQKRIAYSLLGLKDQVNTVGIPI

(22) The surface protein SLC44A4 (Genbank Accession No: NP_001171515) (SEQ ID NO: 432)
>gi|295849282|ref|NP_001171515.1| choline transporter-like protein 4 isoform 2 [*Homo sapiens*]

MGGKQRDEDDEAYGKPVKYDPSFRGPIKNRSCTDVICCVLFLLFILGYIV

VGIVAWLYGDPRQVLYPRNSTGAYCGMGENKDKPYLLYFNIFSCILSSNI

ISVAENGLQCPTPQTVITSLQQELCPSFLLPSAPALGRCFPWTNVTPPAL

-continued

```
PGITNDTTIQQGISGLIDSLNARDISVKIFEDFAQSWYWILVALGVALVL
SLLFILLLRLVAGPLVLVLILGVLGVLAYGIYYCWEEYRVLRDKGASISQ
LGFTTNLSAYQSVQETWLAALIVLAVLEAILLLMLIFLRQRIRIAIALLK
EASKAVGQMMSTMFYPLVTFVLLLICIAYWAMTALYLATSGQPQYVLWAS
NISSPGCEKVPINTSCNPTAHLVNSSCPGLMCVFQGYSSKGLIQRSVFNL
QIYGVLGLFWTLNWVLALGQCVLAGAFASFYWAFHKPQDIPTFPLISAFI
RTLRYHTGSLAFGALILTLVQIARVILEYIDHKLRGVQNPVARCIMCCFK
CCLWCLEKFIKFLNRNAYIMIAIYGKNFCVSAKNAFMLLMRNIVRVVVLD
KVTDLLLFFGKLLVVGGVGVLSFFFFSGRIPGLGKDFKSPHLNYYWLPIM
TSILGAYVIASGFFSVFGMCVDTLFLCFLEDLERNNGSLDRPYYMSKSLL
KILGKKNEAPPDNKKRKK
```

(23) The surface protein BMPR1B (SwissProt: O00238)
(24) The transport protein SLC7A5 (SwissProt: Q01650)
(25) The epithelial prostate antigen STEAP1 (SwissProt: Q9UHE8)
(26) The ovarian carcinoma antigen MUC16 (SwissProt: Q8WXI7)
(27) The transport protein SLC34A2 (SwissProt: O95436)
(28) The surface protein SEMA5b (SwissProt: Q9P283)
(29) The surface protein LYPD1 (SwissProt: Q8N2G4)
(30) The endothelin receptor type B EDNRB (SwissProt: P24530)
(31) The ring finger protein RNF43 (SwissProt: Q68DV7)
(32) The prostate carcinoma-associated protein STEAP2 (SwissProt: Q8NFT2)
(33) The cation channel TRPM4 (SwissProt: Q8TD43)
(34) The complement receptor CD21 (SwissProt: P20023)
(35) The B-cell antigen receptor complex-associated protein CD79b (SwissProt: P40259)
(36) The cell adhesion antigen CEACAM6 (SwissProt: P40199)
(37) The dipeptidase DPEP1 (SwissProt: P16444)
(38) The interleukin receptor IL20Ralpha (SwissProt: Q9UHF4)
(39) The proteoglycan BCAN (SwissProt: Q96GW7)
(40) The ephrin receptor EPHB2 (SwissProt: P29323)
(41) The prostate stem cell-associated protein PSCA (Genbank Accession No: NP_005663.2)
(42) The surface protein LHFPL3 (SwissProt: Q86UP9)
(43) The receptor protein TNFRSF13C (SwissProt: Q96RJ3)
(44) The B-cell antigen receptor complex-associated protein CD79a (SwissProt: P11912)
(45) The receptor protein CXCR5 (SwissProt: P32302)
(46) The ion channel P2X5 (SwissProt: Q93086)
(47) The lymphocyte antigen CD180 (SwissProt: Q99467)
(48) The receptor protein FCRL1 (SwissProt: Q96LA6)
(49) The receptor protein FCRL5 (SwissProt: Q96RD9)
(50) The MHC class II molecule Ia antigen HLA-DOB (Genbank Accession No: NP_002111.1)
(51) The T-cell protein VTCN1 (SwissProt: Q7Z7D3).
(52) The Lewis Y antigen
(53) The Lewix X antigen In one preferred subject of the invention the cancer target molecule is selected from the group consisting of the cancer target molecules (1)-(51). In one preferred subject of the invention the cancer target molecule is selected from the group consisting of the cancer target molecules (1)-(53).

In another particularly preferred subject of the invention the binder binds to an extracellular cancer target molecule which is selected from the group consisting of the cancer target molecules (1)-(51).

In another particularly preferred subject of the invention the binder binds specifically to an extracellular cancer target molecule which is selected from the group consisting of the cancer target molecules (1)-(51).

In one particularly preferred subject of the invention the cancer target molecule is selected from the group consisting of EGF receptor (NP_005219.2), mesothelin (Q13421-3), C4.4a (NP_055215.2) and carboanhydrase IX (CA IX; NP_001207.2), more particularly C4.4a (NP_055215.2).

In another particularly preferred subject of the invention the binder binds to an extracellular cancer target molecule which is selected from the group consisting of EGF receptor (NP_005219.2), mesothelin (Q13421-3), C4.4a (NP_055215.2) and carboanhydrase IX (CA IX; Q16790)), more particularly C4.4a (NP_055215.2).

In another particularly preferred subject of the invention the binder binds specifically to an extracellular cancer target molecule which is selected from the group consisting of EGF receptor (NP_005219.2), mesothelin (Q13421-3), C4.4a (NP_055215.2) and carboanhydrase IX (CA IX; Q16790)), more particularly C4.4a (NP_055215.2).

In one preferred embodiment the binder, after binding to its extracellular target molecule on the target cell, is internalized by the target cell as a result of the binding. The effect of this is that the binder-drug conjugate, which may be an immunoconjugate or an ADC, is taken up by the target cell.

In one embodiment the binder is a binding protein. In one preferred embodiment the binder is an antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In one preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')$_2$ and Fv fragments, diabodies, DAbs, linear antibodies and scFv. Particularly preferred are Fab, diabodies and scFv.

In one particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The skilled person knows how processes such as phage display libraries (e.g. Morphosys HuCAL Gold) can be compiled and used for discovering antibodies or antigen-binding antibody fragments (see WO 2007/070538, page 24 ff and Example 1 on page 70, Example 2 on page 72). Further processes for preparing antibodies that use DNA libraries from B-cells are described for example on page 26 (WO 2007/070538). Processes for humanizing antibodies are described on page 30-32 of WO2007070538 and in detail in Queen, et al., Pros. Natl. Acad. Sci. USA 86:10029-10033, 1989 or in WO 90/0786. Furthermore, processes for the recombinant expression of proteins in general and of antibodies in particular are known to the skilled person (see, for example, in Berger and Kimmel (Guide to Molecular Cloning Techniques, Methods in Enzymology, Vol. 152, Academic Press, Inc.); Sambrook, et al., (Molecular Cloning: A Laboratory Manual, (Second Edition, Cold Spring Harbor Laboratory Press; Cold Spring Harbor, N.Y.; 1989) Vol. 1-3); Current Protocols in Molecular Biolony, (F. M. Ausabel et al. [Eds.], Current Protocols, Green Publishing Associates, Inc./John Wiley & Sons, Inc.); Harlow et al., (Monoclonal Antibodies: A Laboratory Manual, Cold Spring Harbor Laboratory Press (19881, Paul [Ed.]); Fundamental Immunology, (Lippincott Williams & Wilkins (1998)); and Harlow, et al., (Using Antibodies: A Laboratory Manual, Cold Spring Harbor Laboratory Press (1998)). The skilled person knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The skilled person is able to use the processes described in WO 2007/070538 that have been used for preparing carboanhydrase IX (Mn) antibodies in analogy for the preparation of antibodies with different target molecule specificity.

EGFR Antibodies

Examples of antibodies which bind the cancer target molecules EGFR are cetuximab (INN number 7906), panitumumab (INN number 8499) and nimotuzumab (INN number 8545). Cetuximab (Drug Bank Accession Number DB00002) is a chimeric anti-EGFR1 antibody which is produced in SP2/0 mouse myeloma cells and is sold by ImClone Systems Inc/Merck KgaA/Bristol-Myers Squibb Co. Cetuximab is indicated for the treatment of metastasizing, EGFR expressing, colorectal carcinoma with wild type K-Ras gene. It has an affinity of 101° M.
Sequence:
Cetuximab light chain (kappa) (SEQ ID NO: 433):

DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Cetuximab heavy chain (SEP ID NO: 434):

QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

-continued

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Panitumumab (INN number 8499) (Drug Bank Accession Number DB01269) is a recombinant monoclonal human IgG2 antibody which binds specifically to the human EGF receptor 1 and is sold by Abgenix/Amgen. Panitumumab originates from the immunization of transgenic mice (XenoMouse). These mice are capable of producing human immunoglobulin (light and heavy chains). A specific B-cell clone was selected which produces antibodies against EGFR, and this clone was immortalized with CHO cells (Chinese hamster ovary cells). These cells are now used for the production of a 100% human antibody. Panitumumab is indicated for the treatment of EGFR-expressing, metastasizing colorectal carcinoma, which is resistant to chemotherapeutic treatment with fluoropyrimidine, oxaliplatin and irinotecan. It has an affinity of 10-11M.
Sequence:
Panitumumab light chain (kappa) (SEQ ID NO: 435):

DIQMTQSPSSLSASVGDRVTITCQASQDISNYLNWYQQKPGKAPKLLIYD

ASNLETGVPSRFSGSGSGTDFTFTISSLQPEDIATYFCQHFDHLPLAFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Panitumumab heavy chain (SEQ ID NO: 436):

QVQLQESGPGLVKPSETLSLTCTVSGGSVSSGDYYWTWIRQSPGKGLEWI

GHIYYSGNTNYNPSLKSRLTISIDTSKTQFSLKLSSVTAADTAIYYCVRD

RVTGAFDIWGQGTMVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPG

Nimotuzumab (INN number 8545) (EP 00586002, EP 00712863) is a humanized monoclonal IgG1 antibody which binds specifically to the human EGF receptor 1 and is sold by YM BioScienecs Inc. (Mississauga Canada). It is produced in non-secreting NSO cells (mammalian cell line). Nimotuzumab is approved for the treatment of head-and-neck tumours, highly malignant astrocytoma and glioblastoma multiforms (not in EU and US) and pancreatic carcinoma (Orphan drug, EMA). It has an affinity of $10^{-8}$M.

Further embodiments of EGFR antibodies are as follows:
Zalutumumab/2F8/HuMax-EGFr, from Genmab A/S (WO 02/100348, WO 2004/056847, INN number 8605)
Necitumumab/11F8, ImClone/IMC-11F8, from ImClone Systems Inc. [Eli Lilly & Co] (WO 2005/090407 (EP 01735348-A1, US 2007/0264253-A1, U.S. Pat. No. 7,598,350, WO 2005/090407-A1), INN number 9083)

Matuzumab/anti-EGFR MAb, Merck KGaA/anti-EGFR MAb, Takeda/EMD 72000/EMD-6200/EMD-72000 and EMD-55900/MAb 425/monoclonal antibody 425, from Merck KGaA/Takeda (WO 92/15683, INN number 8103 (Matuzumab))

RG-7160/GA-201/GA201/R-7160/R7160/RG7160/RO-4858696/RO-5083945/R04858696/R05083945, from Glycart Biotechnology AG (Roche Holding AG) (WO 2010/112413-A1, WO 2010/115554)

GT-MAB 5.2-GEX/CetuGEX, from Glycotope GmbH (WO 2008/028686-A2 (EP 01900750-A1, EP 01911766-A1, EP 02073842-A2, US 2010/0028947-A1)

ISU-101, from Isu Abxis Inc (ISU Chemical Co Ltd)/Scancell (WO 2008/004834-A1)

ABT-806/mAb-806/ch-806/anti-EGFR monoc. antibody 806, from Ludwig Institute for Cancer Research/Abbott/Life Science Pharmaceuticals (WO 02/092771, WO 2005/081854 and WO 2009/023265)

SYM-004 (consists of two chimeric IgG1 antibodies (992 and 1024)), from Symphogen A/S (WO 2010/022736-A2)

MR1-1/MR1-1 KDEL, from WAX Corp (Teva Pharmaceutical Industries Ltd) (Duke University), (Patent: WO2001/062931-A2)

Antibody against the deletion mutant, EGFRvIII, from Amgen/Abgenix (WO 2005/010151, U.S. Pat. No. 7,628,986)

SC-100, from Scancell Ltd (WO 01/088138-A1)

MDX-447/EMD 82633/BAB-447/H 447/MAb, EGFR, Medarex/Merck KgaA, from Bristol-Myers Squibb (US)/Merck KGaA (DE)/Takeda (JP), (WO 91/05871, WO 92/15683)

Anti-EGFR-Mab, from Xencor (WO 2005/056606)

DXL-1218/anti-EGFR monoclonal antibody (cancer), InNexus, from InNexus Biotechnology Inc., Pharmaprojects PH048638

In one preferred embodiment the anti-EGFR antibodies are selected from the group consisting of cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447, and DXL-1218.

In one particularly preferred embodiment the anti-EGFR antibodies are selected from the group consisting of cetuximab, panitumumab, nimotuzumab, zalutumumab, necitumumab and matuzumab.

The skilled person knows of processes which can be used to prepare further antibodies, from the CDR regions of the abovementioned antibodies by means of sequence variations, these further antibodies having a similar or better affinity and/or specificity for the target molecule.

In a further embodiment, the anti-EGFR antibodies or antigen-binding antibody fragments are selected from the group consisting of
antibodies or antigen-binding antibody fragments comprising the three CDR regions of the light chain and the three CDR regions of the heavy chain of one of the following antibodies: cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447, and DXL-1218.

In another embodiment the anti-EGFR antibodies or antigen-binding antibody fragments are selected from the group consisting of
antibodies or antigen-binding antibody fragments comprising the three CDR regions of the light chain and the three CDR regions of the heavy chain of one of the following antibodies: cetuximab, panitumumab, nimotuzumab, zalutumumab, necitumumab, matuzumab.

Carboanhydrase IX Antibodies

Examples of antibodies which bind the cancer target molecule carbonahydrase IX are described in WO 2007/070538-A2 (e.g. Claims 1-16).

In one preferred embodiment the anti-carboanhydrase IX antibodies or antigen-binding antibody fragments are selected from the group consisting of anti-carboanhydrase IX antibodies or antigen-binding antibody fragments 3ee9 (Claim 4 (a) in WO 2007/070538-A2), 3ef2 (Claim 4 (b) in WO2007/070538-A2), 1e4 (Claim 4 (c) in WO 2007/070538-A2), 3a4 (Claim 4 (d) in WO 2007/070538-A2), 3ab4 (Claim 4 (e) in WO 2007/070538-A2), 3ah10 (Claim 4 (f) in WO 2007/070538-A2), 3bb2 (Claim 4 (g) in WO 2007/070538-A2), 1aa1 (Claim 4 (h) in WO 2007/070538-A2), 5a6 (Claim 4 (i) in WO 2007/070538-A2) and 5aa3 (Claim 4 (j) in WO 2007/070538-A2).

In one preferred embodiment the anti-carboanhydrase IX antibodies or antigen-binding antibody fragments are selected from the group consisting of:
anti-carboanhydrase IX antibodies or antigen-binding antibody fragments thereof which comprise the sequences of the three CDR regions of the light chain and the sequences of the three CDR regions of the heavy chain of the antibody 3ee9 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 3ef2 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 1e4 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 3a4 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 3ab4 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 3ah10 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 3bb2 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 1aa1 (from WO 2007/070538-A2),
anti-carboanhydrase IX antibodies or antigen-binding antibody fragments thereof which comprise the sequences of the three CDR regions of the light chain and the sequences of the three CDR regions of the heavy chain of the antibody 5a6 (from WO 2007/070538-A2), and anti-carboanhydrase IX antibodies or antigen-binding antibody fragments thereof which comprise the sequences of the three CDR regions of the light chain and the sequences of the three CDR regions of the heavy chain of the antibody 5aa3 (from WO 2007/070538-A2).

The here-indicated sequences of the CDR regions are disclosed in Figures 2a-2c, page 128-130 in WO 2007/070538-A2.

In one preferred embodiment the anti-carboanhydrase IX antibodies or antigen-binding antibody fragments are selected from the group consisting of:
an antibody or antigen-binding fragment which comprises the amino acid sequence of the variable light and variable heavy chains of the antibody 3ee9, as indicated in WO 2007/070538-A2 in Figure 4b on page 137,
an antibody or antigen-binding fragment which comprises the amino acid sequence of the variable light and variable heavy chains of the antibody 3ef2, as indicated in WO 2007/070538-A2 in Figure 4c on page 138 and in Figure 4b on page 137,
an antibody or antigen-binding fragment which comprises the amino acid sequence of the variable light and variable heavy chains of the antibody 1e4, as indicated in WO 2007/070538-A2 in Figure 4a on page 136,
an antibody or antigen-binding fragment which comprises the amino acid sequence of the variable light and variable heavy chains of the antibody 3a4, as indicated in WO 2007/070538-A2 in Figure 4a on page 136,
an antibody or antigen-binding fragment which comprises the amino acid sequence of the variable light and variable heavy chains of the antibody 3ab4, as indicated in WO 2007/070538-A2 in Figure 4a on page 136,
an antibody or antigen-binding fragment which comprises the amino acid sequence of the variable light and variable heavy chains of the antibody 3ah10, as indicated in WO 2007/070538-A2 in Figure 4a on page 136,
an antibody or antigen-binding fragment which comprises the amino acid sequence of the variable light and variable heavy chains of the antibody 3bb2, as indicated in WO 2007/070538-A2 in Figure 4b on page 137,
an antibody or antigen-binding fragment which comprises the amino acid sequence of the variable light and variable heavy chains of the antibody 1aa1, as indicated in WO 2007/070538-A2 in Figure 4a on page 136,
an antibody or antigen-binding fragment which comprises the amino acid sequence of the variable light and variable heavy chains of the antibody 5a6, as indicated in WO 2007/070538-A2 in Figure 4b on page 137, and
an antibody or antigen-binding fragment which comprises the amino acid sequence of the variable light and variable heavy chains of the antibody 5aa3, as indicated in WO 2007/070538-A2 in Figure 4b on page 137.

In one particularly preferred embodiment the anti-carboanhydrase IX antibody is antibody 3ee9 from WO 2007/070538-A2.

In one particularly preferred embodiment the anti-carboanhydrase IX antibody or the antigen-binding antibody fragment comprises the amino acid sequences of the CDR regions of the variable heavy chain of the antibody 3ee9 (VH3-CDR1: GFTFSSYGMS (SEQ ID NO: 437); VH3-CDR2: GISSLGSTTYYADSVKG (SEQ ID NO: 438); VH3-CDR3: TGSPGTFMHGDH (SEQ ID NO: 439), see Figure 2a, page 128 in WO2007070538-A2) and the amino acid sequences of the CDR regions of the variable light chain of the antibody 3ee9 (VLk1-CDR1: RASQDINNYLS (SEQ ID NO: 440); VLk1-CDR2: YGASNLQS (SEQ ID NO: 441); VLk1-CDR3: QQYYGRPT (SEQ ID NO: 442), see Figure 2b, page 129 in WO 2007/070538-A2).

In one particularly preferred embodiment the anti-carboanhydrase IX antibody or the antigen-binding antibody fragment comprises the amino acid sequences of a variable heavy chain of the antibody 3ee9
(VH3:ELVESGGGLVQPGGSLRLSCAASGFTF-SSYGMSWVRQAPGKGLEWVSGISSLGST TYYADS-VKGRFTISRDNSKNTLYLQMNSLRAED-TAVYYCARTGSPGTFMHGDHWGQG TLVTVSS (SEQ ID NO: 443), see Figure 4b, page 137 in WO 2007070538-A2) and the amino acid sequences of the variable light chain of the antibody 3ee9
(VLk1:DIQMTQSPSSLSASVGDRVTIT-CRaSQDINNYLSWYQQKPGKAPKWYGASNLQS GVPSRFSGSGSGTDFTLTISSLQPED-FAVYYCQQYYGRPTTFGQGTKVEIKRT (SEQ ID NO: 444), see Figure 4b, page 137 in WO 2007070538-A2).

In one preferred embodiment the anti-carboanhydrase IX antibody 3ee9 is an IgG antibody.

In one particularly preferred embodiment the anti-carboanhydrase IX antibody 3ee9 is an IgG1 antibody (3ee9-IgG1), where the amino acid sequence of the heavy chain comprises the following sequence (SEQ ID NO: 445):

QVELVESGGGLVQPGGSLRLSCAASGFTFSSYGMSWVRQAPGKGLEWVSG

ISSLGSTTYYADSVKGRFTISRDNSKNTLYLQMNSLRAEDTAVYYCARTG

SPGTFMHGDHWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K and the amino acid sequences of the light chain comprises the following sequence (SEQ ID NO: 446):

DIQMTQSPSSLSASVGDRVTITCRASQDINNYLSWYQQKPGKAPKLLIYG

ASNLQSGVPSRFSGSGSGTDFTLTISSLQPEDFAVYYCQQYYGRPTTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC anti-carboanhydrase IX antibody 3ee9-IgG1:
A further aspect of the present invention is the provision of the anti-carboanhydrase IX antibody 3ee9-IgG1.
C4.4a Antibodies:
Binders particularly preferred in accordance with the invention are anti-C4.4a antibodies, more particularly human or humanized anti-C4.4a antibodies. The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Anti-C4.4a antibodies are described for example in WO 01/23553 or WO 2011070088. These antibodies can be used in accordance with the invention.

Examples of C4.4a antibodies and antigen-binding fragments are described below. The sequences of the antibodies are indicated in Table 1, with each line reproducing the respective CDR amino acid sequences of the variable light chain and of the variable heavy chain, respectively of the antibody listed in column 1. The amino acid sequences of the variable light chain and of the variable heavy chain, and the nucleic acid sequence of the antibody indicated in column 1 in each case, are also indicated.

In one embodiment the anti-C4.4a antibodies or antigen-binding antibody fragments bind to the S1 domain S1 (amino acid position 1-85 of SEQ ID NO: 1) of C4.4a.

In one embodiment the anti-C4.4a antibodies or antigen-binding antibody fragments are cross-reactive with human C4.4a (SEQ ID NO:1) and with murine C4.4a (SEQ ID NO:2).

In one embodiment the anti-C4.4a antibodies or antigen-binding antibody fragments thereof, after binding to a cell which expresses C4.4a, are internalized by the cell.

In another embodiment the anti-C4.4a antibodies or antigen-binding antibody fragments compete with the antibody M31-B01 and/or with the antibody M20-D02-S-A for binding to C4.4a. Antibodies M31-B01 and M20-D02-S-A compete for binding to C4.4a. The antibodies B01-1 to B01-12 were prepared from M31-B01 by means of affinity maturation and compete with M31-B01 for binding to C4.4a. The antibodies D02-1 to D02-13 were prepared from M20-D02-S-A by means of affinity maturation and compete with M20-D02-S-A for binding to C4.4a.

In a further embodiment the anti-C4.4a antibodies or antigen-binding antibody fragments comprise at least one, two or three of the CDR amino acid sequences given in Table 1 or Table 2.

In another embodiment the anti-C4.4a antibodies or antigen-binding antibody fragments comprise at least one, two or three CDR amino acid sequences of an antibody given in Table 1 or Table 2.

In a further embodiment the anti-C4.4a antibodies or antigen-binding antibody fragments comprise at least one, two or three CDR amino acid sequences of the variable light chain and at least one, two or three CDR amino acid sequences of the variable heavy chain of an antibody given in Table 1 or Table 2.

In another embodiment the anti-C4.4a antibodies or antigen-binding antibody fragments comprise which are at least 50%, 60%, 70%, 80%, 90% or 95% identical with the CDR amino acid sequences of the variable light chain and with the CDR amino acid sequences of the variable heavy chain, of an antibody given in Table 1 or Table 2.

In another embodiment the CDR sequences of the anti-C4.4a antibodies or antigen-binding antibody fragments comprise CDR sequences of the heavy chain which conform to the CDR sequences SEQ ID NO: 297 (CDR H1), SEQ ID NO: 298 (CDR H2) and SEQ ID NO: 299 (CDR H3) and CDR sequences of the light chain which conform to the CDR sequences SEQ ID NO: 300 (CDR L1), SEQ ID NO: 22 (CDR L2) and SEQ ID NO: 301 (CDR L3), or CDR sequences of the heavy chain which conform to the CDR sequences SEQ ID NO: 302 (CDR H1), SEQ ID NO: 303 (CDR H2) and SEQ ID NO: 304 (CDR H3) and CDR sequences of the light chain which conform to the CDR sequences SEQ ID NO: 305 (CDR L1), SEQ ID NO: 306 (CDR L2) and SEQ ID NO: 307 (CDR L3).

In another embodiment the anti-C4.4a antibodies or antigen-binding antibody fragments comprise which are at least 50%, 60%, 70%, 80%, 90% or 95% identical with the variable light chain and with the variable heavy chain, of an antibody given in Table 1 or Table 2.

In another embodiment the anti-C4.4a antibodies or antigen-binding antibody fragments comprise the three CDR amino acid sequences of the variable light chain and the three CDR amino acid sequences of the variable heavy chain of an antibody given in Table 1 or Table 2.

In another embodiment the anti-C4.4a antibodies or antigen-binding antibody fragments comprise a variable light chain and/or a variable heavy chain of an antibody given in Table 1 or Table 2.

In another embodiment the anti-C4.4a antibodies or antigen-binding antibody fragments comprise the variable light chain and the variable heavy chain of an antibody given in Table 1 or Table 2.

In one preferred embodiment the C4.4a antibodies and the antigen-binding antibody fragments are selected from the group consisting of antibody which comprises the CDR sequences of the variable heavy chain represented by the sequences SEQ ID NO: 75-77 and which comprises the CDR sequences of the variable light chain represented by the sequences SEQ ID NO: 78-80 (B01-10), antibody which comprises the CDR sequences of the variable heavy chain represented by the sequences SEQ ID NO: 5, 9 and 13 and which comprises the CDR sequences of the variable light chain represented by the sequences SEQ ID NO: 17, 21 and 25 (M31-B01), antibody which comprises the CDR sequences of the variable heavy chain represented by the sequences SEQ ID NO: 6, 10 and 14 an which comprises the CDR sequences of the variable light chain represented by the sequences SEQ ID NO: 18, 22 and 26 (M20-D02-S-A), antibody which comprises the CDR sequences of the variable heavy chain represented by the sequences SEQ ID NO: 7, 11 and 15 and which comprises the CDR sequences of the variable light chain represented by the sequences SEQ ID NO: 19, 23 and 27 (M60-G03), antibody which comprises the CDR sequences of the variable heavy chain represented by the sequences SEQ ID NO: 8, 12 and 16 and which comprise the CDR sequences of the variable light chain represented by the sequences SEQ ID NO: 20, 24 and 28 (36-H02), antibody which comprises the CDR sequences of the variable heavy chain represented by the sequences SEQ ID NO: 45-47 and which comprises the CDR sequences of the variable light chain represented by the sequences SEQ ID NO: 48-50 (B01-3), antibody which comprises the CDR sequences of the variable heavy chain represented by the sequences SEQ ID NO: 55-57 and which comprises the CDR sequences of the variable light chain represented by the sequences SEQ ID NO: 58-60 (B01-5), antibody which comprises the CDR sequences of the variable heavy chain represented by the sequences SEQ ID NO: 65-67 and which comprises the CDR sequences of variable light chain represented by the sequences SEQ ID NO: 68-70 (B01-7), antibody which comprises the CDR sequences of the variable heavy chain represented by the sequences SEQ ID NO: 85-87 and which comprises the CDR sequences of the variable light chain represented by the sequences SEQ ID NO: 88-90 (B01-12), antibody which comprises the CDR sequences of the variable heavy chain represented by the sequences SEQ ID NO: 95-97 and which comprises the CDR sequences of the variable light chain represented by the sequences SEQ ID NO: 98-100 (D02-4), antibody which comprises the CDR sequences of the variable heavy chain represented by the sequences SEQ ID NO: 105-107 and which comprises CDR sequences of the variable light chain represented by the sequences SEQ ID NO: 108-110 (D02-6), antibody which comprises the CDR sequences of the variable heavy chain represented by the sequences SEQ ID NO: 115-117 and which comprises the CDR sequences of the variable light chain represented by the sequences SEQ ID NO: 118-120 (D02-7), antibody which comprises the CDR sequences of the variable heavy chain represented by the sequences SEQ ID NO: 125-127 and which comprises the CDR sequences of the variable light chain represented by the sequences SEQ ID NO: 128-130 (D02-11), and antibody which comprises the CDR sequences of the variable heavy chain represented by the sequences SEQ ID NO: 135-137 which comprises the CDR sequences of the variable light chain represented by the sequences SEQ ID NO: 138-140 (D02-13).

In one preferred embodiment the C4.4a antibodies and the antigen-binding antibody fragments are selected from the group consisting of antibodies which comprise the amino acid sequence of the variable heavy chain represented by the sequence SEQ ID NO: 81 and which comprise the amino acid sequence of the variable light chain represented by the sequence SEQ ID NO: 82 (B01-7), antibodies which comprise the amino acid sequence of the variable heavy chain represented by the sequence SEQ ID NO: 33 and which comprise the amino acid sequence of the variable light chain represented by the sequence SEQ ID NO: 29 (M31-B01), antibodies which comprise the amino acid sequence of the variable heavy chain represented by the sequence SEQ ID NO: 34 and which comprise the amino acid sequence of the variable light chain represented by the sequence SEQ ID NO: 30 (M20-D02S-A), antibodies which comprise the amino acid sequence of the variable heavy chain represented by the sequence SEQ ID NO: 35 and which comprise the amino acid sequence of the variable light chain represented by the sequence SEQ ID NO: 31 (M60-G03), antibodies which comprise the amino acid sequence of the variable heavy chain represented by the sequence SEQ ID NO: 36 and which comprise the amino acid sequence of the variable light chain represented by the sequence SEQ ID NO: 32 (M36-H02), antibodies which comprise the amino acid sequence of the variable heavy chain represented by the sequence SEQ ID NO: 51 and which comprise the amino acid sequence of the variable light chain represented by the sequence SEQ ID NO: 52 (B01-3), antibodies which comprise the amino acid sequence of the variable heavy chain represented by the sequence SEQ ID NO: 61 and which comprise the amino acid sequence of the variable light chain represented by the sequence SEQ ID NO: 62 (B01-5), antibodies which comprise the amino acid sequence of the variable heavy chain represented by the sequence SEQ ID NO: 71 and which comprise the amino acid sequence of the variable light chain represented by the sequence SEQ ID NO: 72 (B01-7)

antibodies which comprise the amino acid sequence of the variable heavy chain represented by the sequence SEQ ID NO: 91 and which comprise the amino acid sequence of the variable light chain represented by the sequence SEQ ID NO: 92 (B01-12), antibodies which comprise the amino acid sequence of the variable heavy chain represented by the sequence SEQ ID NO: 101 and which comprise the amino acid sequence of the variable light chain represented by the sequence SEQ ID NO: 102 (D02-4), antibodies which comprise the amino acid sequence of the variable heavy chain represented by the sequence SEQ ID NO: 111 and which comprise the amino acid sequence of the variable light chain represented by the sequence SEQ ID NO: 112 (D02-6), antibodies which comprise the amino acid sequence of the variable heavy chain represented by the sequence SEQ ID NO: 121 and which comprise the amino acid sequence of the variable light chain represented by the sequence SEQ ID NO: 122 (D02-7), antibodies which comprise the amino acid sequence of the variable heavy chain represented by the sequence SEQ ID NO: 131 and which comprise the amino acid sequence of the variable light chain represented by the sequence SEQ ID NO: 132 (D02-11),
and antibodies which comprise the amino acid sequence of the variable heavy chain represented by the sequence SEQ ID NO: 141 and which comprise the amino acid sequence of the variable light chain represented by the sequence SEQ ID NO: 142 (D02-13).

In another embodiment the anti-C4.4a antibodies comprise the light chain and the heavy chain of an antibody given in Table 2.

In one preferred embodiment the anti-C4.4a antibodies comprise the light chain and the heavy chain of an antibody given in Table 2.

In one particularly preferred embodiment the C4.4a antibody is selected from the group consisting of
antibody which comprises the amino acid sequence of the light chain represented by SEQ ID NO: 346 and which comprises the amino acid sequence of the heavy chain represented by SEQ ID NO: 347 (M31-B01),
antibody which comprises the amino acid sequence of the light chain represented by SEQ ID NO: 352 and which comprises the amino acid sequence of the heavy chain represented by SEQ ID NO: 353 (B01-3),
antibody which comprises the amino acid sequence of the light chain represented by SEQ ID NO: 364 and which comprises the amino acid sequence of the heavy chain represented by SEQ ID NO: 365 (B01-10), and
antibody which comprises the amino acid sequence of the light chain represented by SEQ ID NO: 382 and which comprises the amino acid sequence of the heavy chain represented by SEQ ID NO: 383 (D02-6).

TABLE 1

Sequences of the C4.4a antibodies

| Antibody | SEQ ID NO: HCDR1 | SEQ ID NO: HCDR2 | SEQ ID NO: HCDR3 | SEQ ID NO: LCDR1 | SEQ ID NO: LCDR2 | SEQ ID NO: LCDR3 | SEQ ID NO: VH Protein | SEQ ID NO: VL Protein | SEQ ID NO: VH Nucleotide | SEQ ID NO: VL Nucleotide |
|---|---|---|---|---|---|---|---|---|---|---|
| M31-B01 | 5 | 9 | 13 | 17 | 21 | 25 | 33 | 29 | 41 | 37 |
| M20-D02 S-A | 6 | 10 | 14 | 18 | 22 | 26 | 34 | 30 | 42 | 38 |
| M60-G03 | 7 | 11 | 15 | 19 | 23 | 27 | 35 | 31 | 43 | 39 |
| M36-H02 | 8 | 12 | 16 | 20 | 24 | 28 | 36 | 32 | 44 | 40 |
| B01-3 | 45 | 46 | 47 | 48 | 49 | 50 | 51 | 52 | 53 | 54 |
| B01-5 | 55 | 56 | 57 | 58 | 59 | 60 | 61 | 62 | 63 | 64 |
| B01-7 | 65 | 66 | 67 | 68 | 69 | 70 | 71 | 72 | 73 | 74 |
| B01-10 | 75 | 76 | 77 | 78 | 79 | 80 | 81 | 82 | 83 | 84 |
| B01-12 | 85 | 86 | 87 | 88 | 89 | 90 | 91 | 92 | 93 | 94 |
| D02-4 | 95 | 96 | 97 | 98 | 99 | 100 | 101 | 102 | 103 | 104 |
| D02-6 | 105 | 106 | 107 | 108 | 109 | 110 | 111 | 112 | 113 | 114 |
| D02-7 | 115 | 116 | 117 | 118 | 119 | 120 | 121 | 122 | 123 | 124 |
| D02-11 | 125 | 126 | 127 | 128 | 129 | 130 | 131 | 132 | 133 | 134 |
| D02-13 | 135 | 136 | 137 | 138 | 139 | 140 | 141 | 142 | 143 | 144 |
| B01-nnl | 145 | 146 | 147 | 148 | 149 | 150 | 151 | 152 | 308 | 309 |
| B01-nn2 | 153 | 154 | 155 | 156 | 157 | 158 | 159 | 160 | 310 | 311 |
| B01-nn3 | 161 | 162 | 163 | 164 | 165 | 166 | 167 | 168 | 312 | 313 |
| B01-nn4 | 169 | 170 | 171 | 172 | 173 | 174 | 175 | 176 | 314 | 315 |
| B01-nn5 | 177 | 178 | 179 | 180 | 181 | 182 | 183 | 184 | 316 | 317 |
| B01-2 | 185 | 186 | 187 | 188 | 189 | 190 | 191 | 192 | 318 | 319 |
| B01-4 | 193 | 194 | 195 | 196 | 197 | 198 | 199 | 200 | 320 | 321 |
| B01-6 | 201 | 202 | 203 | 204 | 205 | 206 | 207 | 208 | 322 | 323 |
| B01-8 | 209 | 210 | 211 | 212 | 213 | 214 | 215 | 216 | 324 | 325 |
| B01-9 | 217 | 218 | 219 | 220 | 221 | 222 | 223 | 224 | 326 | 327 |
| B01-11 | 225 | 226 | 227 | 228 | 229 | 230 | 231 | 232 | 328 | 329 |
| B01-12 | 233 | 234 | 235 | 236 | 237 | 238 | 239 | 240 | 330 | 331 |
| D02-ogl | 241 | 242 | 243 | 244 | 245 | 246 | 247 | 248 | 332 | 333 |
| D02-5 | 249 | 250 | 251 | 252 | 253 | 254 | 255 | 256 | 334 | 335 |
| D02-8 | 257 | 258 | 259 | 260 | 261 | 262 | 263 | 264 | 336 | 337 |
| D02-9 | 265 | 266 | 267 | 268 | 269 | 270 | 271 | 272 | 338 | 339 |
| D02-10 | 273 | 274 | 275 | 276 | 277 | 278 | 279 | 280 | 340 | 341 |
| D02-11 | 281 | 282 | 283 | 284 | 285 | 286 | 287 | 288 | 342 | 343 |
| D02-12 | 289 | 290 | 291 | 292 | 293 | 294 | 295 | 296 | 344 | 345 |

TABLE 2

Sequences of the light and heavy chain of the C4.4a antibodies

| Antibody | Light chain SEQ ID NO: | Heavy chain SEQ ID NO: |
|---|---|---|
| M31-B01 | 346 | 347 |
| B01-1 | 348 | 349 |
| B01-2 | 350 | 351 |
| B01-3 | 352 | 353 |
| B01-4 | 354 | 355 |
| B01-5 | 356 | 357 |
| B01-6 | 358 | 359 |
| B01-7 | 360 | 361 |
| B01-8 | 362 | 363 |
| B01-10 | 364 | 365 |
| B01-11 | 366 | 367 |
| B01-12 | 368 | 369 |
| M20-D02 S-A | 370 | 371 |
| D02-1 | 372 | 373 |
| D02-2 | 374 | 375 |
| D02-3 | 376 | 377 |
| D02-4 | 378 | 379 |
| D02-5 | 380 | 381 |
| D02-6 | 382 | 383 |

TABLE 2-continued

Sequences of the light and heavy chain of the C4.4a antibodies

| Antibody | Light chain SEQ ID NO: | Heavy chain SEQ ID NO: |
|---|---|---|
| D02-7 | 384 | 385 |
| D02-8 | 386 | 387 |
| D02-9 | 388 | 389 |
| D02-10 | 390 | 391 |
| D02-11 | 392 | 393 |
| D02-12 | 394 | 395 |
| D02-13 | 396 | 397 |

Anti-C4.4a Antibody IgG:

A further aspect of the present invention is the provision of an anti-C4.4a IgG1 antibody which comprises the amino acid sequence of the light chain and of the heavy chain of an antibody given in Table 2.

Mesothelin Antibody

A further aspect of the present invention is the provision of a new anti-mesothelin antibody (MF-Ta) whose amino acid sequence comprises the CDR sequences of the variable heavy chain represented by the sequences SEQ ID NO:398 (HCDR1), SEQ ID NO:399 (HCDR2) and SEQ ID NO:400 (HCDR3) and the CDR sequences of the variable light chain represented by the sequences SEQ ID NO:401 (LCDR1), SEQ ID NO:402 (LCDR2) and SEQ ID NO:403 (LCDR3).

In one preferred embodiment the amino acid sequence of the anti-mesothelin antibody MF-Ta or antigen-binding antibody fragments comprises the sequence of the variable heavy chain represented by the sequences SEQ ID NO:404 and the sequence of the variable light chain represented by the sequence SEQ ID NO:405. In one preferred embodiment the amino acid sequence of the anti-mesothelin antibody MF-Ta or antigen-binding antibody fragments comprises the sequence of the variable heavy chain which is encoded by the nucleic acid sequence SEQ ID NO:406, and the sequence of the variable light chain which is encoded by the nucleic acid sequence SEQ ID NO:407.

In one particularly preferred embodiment the amino acid sequence of the anti-mesothelin antibody MF-Ta comprises the sequence of the heavy chain represented by the sequences SEQ ID NO:408 and the sequence of the light chain represented by the sequence SEQ ID NO:409.

In one particularly preferred embodiment the amino acid sequence of the anti-mesothelin antibody MF-Ta comprises the sequence of the heavy chain which is encoded with a nucleic acid sequence SEQ ID NO:410, and the sequence of the light chain with is encoded with a nucleic acid sequence SEQ ID NO: 411.

Further examples of antibodies which bind the cancer target molecule mesothelin are known to the skilled person and are described for example in WO 2009/068204 and can be used for the binder-drug conjugates of the invention.

In one embodiment of the binder-drug conjugates, the binder is an anti-mesothelin antibody or antigen-binding antibody fragment, where the antibody binds to mesothelin and exhibits invariant binding.

In one embodiment of the binder-drug conjugates, an anti-mesothelin antibody or antigen-binding antibody fragment comprises the amino acid sequences of the three CDR regions of the light chain and the amino acid sequences of the three CDR regions of the heavy chain of an antibody described in WOv2009/068204-A1 (Table 7; page 61-63).

In one preferred embodiment the mesothelin antibodies or antigen-binding antibody fragments are selected from the group consisting of anti-mesothelin antibodies or antigen-binding antibody fragments thereof which comprise the sequences of the three CDR regions of the light chain and the sequences of the three CDR regions of the heavy chain of the antibody MF-Ta, anti-mesothelin antibodies or antigen-binding antibody fragments thereof which comprise the sequences of the three CDR regions of the light chain and the sequences of the three CDR regions of the heavy chain of the antibody MF-J (WO2009068204-A1; Table 7; page 61), anti-mesothelin antibodies or antigen-binding antibody fragments thereof which comprise the sequences of the three CDR regions of the light chain and the sequences of the three CDR regions of the heavy chain of the antibody MOR06640 (WO 2009/068204-A1; Table 7; page 61), anti-mesothelin antibodies or antigen-binding antibody fragments thereof which comprise the sequences of the three CDR regions of the light chain and the sequences of the three CDR regions of the heavy chain of the antibody MF-226 (WO 2009/068204-A1; Table 7; page 61) and anti-mesothelin antibodies or antigen-binding antibody fragments thereof which comprise the sequences of the three CDR regions of the light chain and the sequences of the three CDR regions of the heavy chain of the antibody MOR06626 (WO 2009/068204-A1; Table 7; page 61).

In one particularly preferred embodiment the mesothelin antibodies or antigen-binding antibody fragments are selected from the group consisting of anti-mesothelin antibodies or antigen-binding antibody fragments thereof which comprise the sequence of the variable light chain and the sequence of the variable heavy chain of the antibody MF-Ta, anti-mesothelin antibodies or antigen-binding antibody fragments thereof which comprise the sequence of the variable light chain and the sequence of the variable heavy chain of the antibody MF-J (WO 2009/068204-A1; Table 7; page 61), anti-mesothelin antibodies or antigen-binding antibody fragments thereof which comprise the sequence of the variable light chain and the sequence of the variable heavy chain of the antibody MOR06640 (WO 2009/068204-A1; Table 7; page 61), anti-mesothelin antibodies or antigen-binding antibody fragments thereof which comprise the sequence of the variable light chain and the sequence of the variable heavy chain of the antibody MF-226 (WO 2009/068204-A1; Table 7; page 61), anti-mesothelin antibodies or antigen-binding antibody fragments thereof which comprise the sequence of the variable light chain and the sequence of the variable heavy chain of the antibody MOR06626 (WO 2009/068204-A1; Table 7; page 61).

Further Antibodies:

An example of an antibody which binds the cancer target molecule Her2 is trastuzumab (Genentech). Trastuzumab is a humanized antibody which is used for the treatment inter alia of breast cancer. One example of an antibody which binds the cancer target molecule CD20 is rituximab (Genentech). Rituximab (CAS number: 174722-31-7) is a chimeric antibody which is used for the treatment of non-Hodgkin's lymphoma. One example of an antibody which binds the cancer target molecule CD52 is alemtuzumab (Genzyme). Alemtuzumab (CAS number: 216503-57-0) is a humanized antibody which is used for the treatment of chronic lymphatic leukaemia.

Other examples of antibodies which bind to HER2, besides trastuzumab (INN 7637, CAS No: RN: 180288-69-1) and pertuzumab (Cas No: 380610-27-5), are antibodies as disclosed in WO 2009/123894-A2, WO 200/8140603-A2, or in WO 2011/044368-A2. An example of an anti-HER2 conjugate is trastuzumab-emtansine (INN No. 9295).

Examples of antibodies which bind the cancer target molecule CD30 and can be used for the treatment of cancer, e.g. Hodgkin's lymphoma, are brentuximab, iratumumab and antibodies as disclosed in WO 2008/092117, WO 2008/036688 or WO 2006/089232. An example of an anti-CD30 conjugate is brentuximab vedotine (INN No. 9144).

Examples of antibodies which bind the cancer target molecule CD22 and can be used for the treatment of cancer, e.g. lymphoma, are inotuzumab or epratuzumab. Examples of anti-CD22 conjugates are inotuzumab ozagamycin (INN No. 8574), or anti-CD22-MMAE and anti-CD22-MC-MMAE (CAS RN: 139504-50-0 and 474645-27-7).

Examples of antibodies which bind the cancer target molecule CD33 and can be used for the treatment of cancer, e.g. leukaemia, are gemtuzumab or lintuzumab (INN 7580). An example of an anti-CD33 conjugate is gemtuzumab-ozagamycin.

An example of an antibody which binds the cancer target molecule NMB and can be used for the treatment of cancer, e.g. melanoma or breast cancer, is glembatumumab (INN 9199). An example of an anti-NMB conjugate is glembatumumab vedotine (CAS RN: 474645-27-7).

An example of an antibody which binds the cancer target molecule CD56 and can be used for the treatment of cancer, e.g. multiple myeloma, small-cell carcinoma of the lung, MCC or ovarian carcinoma, is lorvotuzumab. An example of an anti-CD56 conjugate is lorvotuzumab mertansine (CAS RN: 139504-50-0).

Examples of antibodies which bind the cancer target molecule CD70 and can be used for the treatment of cancer, e.g. non-Hodgkin's lymphoma or kidney cell cancer, are disclosed in WO 2007/038637-A2 or WO 2008/070593-A2. An example of an anti-CD70 conjugate is SGN-75 (CD70 MMAF).

An example of an antibody which binds the cancer target molecule CD74 and can be used for the treatment of cancer, e.g. multiple myeloma, is milatuzumab. An example of an anti-CD74 conjugate is milatuzumab-doxorubicin (CAS RN: 23214-92-8).

An example of an antibody which binds the cancer target molecule CD19 and can be used for the treatment of cancer, e.g. non-Hodgkin's lymphoma, is disclosed in WO 2008/031056-A2. Further antibodies and examples of an anti-CD19 conjugate (SAR3419) are disclosed in WO 2008/047242-A2.

Examples of antibodies which bind the cancer target molecule mucin-1 and can be used for the treatment of cancer, e.g. non-Hodgkin's lymphoma, are clivatuzumab or the antibodies disclosed in WO 2003/106495-A2, WO 2008/028686-A2. Examples of anti-mucin conjugates are disclosed in WO 2005/009369-A2.

Examples of antibodies which bind the cancer target molecule CD138 and conjugates thereof which can be used for the treatment of cancer, e.g. multiple myeloma, are disclosed in WO 2009/080829-A1, WO 2009/080830-A1.

Examples of antibodies which bind the cancer target molecule integrin alphaV and can be used for the treatment of cancer, e.g. melanoma, sarcoma or carcinoma, are intetumumab (Cas RN: 725735-28-4), abciximab (Cas-RN: 143653-53-6), etaracizumab (Cas-RN: 892553-42-3) or the antibodies disclosed in U.S. Pat. No. 7,465,449, EP 19859-A1, WO 2002/012501-A1 or WO 2006/062779-A2. Examples of anti-integrin alphaV conjugates are intetumumab-DM4 and other ADCs disclosed in WO 2007/024536-A2.

Examples of antibodies which bind the cancer target molecule TDGF1 and can be used for the treatment of cancer are the antibodies disclosed in WO 02/077033-A1, U.S. Pat. No. 7,318,924, WO 2003/083041-A2 and WO 2002/088170-A2. Examples of anti-TDGF1 conjugates are disclosed in WO 2002/088170-A2.

Examples of antibodies which bind the cancer target molecule PSMA and can be used for the treatment of cancer, e.g. prostate carcinoma, are the antibodies disclosed in WO 97/35616-A1, WO 99/47554-A1, and WO 01/009192-A1. Examples of anti-PSMA conjugates are disclosed in WO 2009/026274-A1.

Examples of antibodies which bind the cancer target molecule EPHA2, can be used for preparing a conjugate and can be used for the treatment of cancer are disclosed in WO 2004/091375-A2.

Examples of antibodies which bind the cancer target molecule SLC44A4, can be used for preparing a conjugate and can be used for the treatment of cancer, e.g. pancreatic or prostate carcinoma, are disclosed in WO 2009/033094-A2 and US 2009/0175796-A1.

An example of an antibody which binds the cancer target molecule HLA-DOB is the antibody lym-1 (Cas-RN: 301344-99-0), which can be used for the treatment of cancer, e.g. non-Hodgkin's lymphoma. Examples of anti-HLA-DOB conjugates are disclosed for example in WO 2005/081711-A2.

Examples of antibodies which bind the cancer target molecule VTCN1, can be used for preparing a conjugate and can be used for the treatment of cancer, e.g. ovarian carcinoma, pancreatic, lung or breast cancer, are disclosed in WO 2006/074418-A2.

The compounds of the invention possess valuable pharmacological properties and can be used for the prevention and treatment of diseases in humans and animals.

The binder-drug conjugates (ADCs) of the invention, of the formula (Ia), exhibit a high and specific cytotoxic activity with regard to tumour cells, as may be shown on the basis of the assays set out in the present experimental section (C-1. to C-6.). This high and specific cytotoxic activity on the part of the binder-drug conjugates (ADCs) of the invention, of the formula (Ia), is achieved through the appropriate combination of the new N,N-dialkylauristatin derivative and binder with linkers which exhibit not only an enzymatically, hydrolytically or reductively cleavable predetermined break point, for the release of the toxophores, but also no such predetermined break point. More particularly, through the use of stable linkers which have no enzymatically, hydrolytically or reductively cleavable predetermined break point for the release of the toxophores, and which, following uptake of the ADCs into the tumour cell and following complete intracellular, enzymatic breakdown of the antibody, still remain wholly or partly intact, the activity is confined very specifically to the tumour cell. Compatibility between ADCs and stable linkers presupposes, among other things, that the metabolites formed intracellularly can be formed with sufficient efficacy, are able to reach their target and are able there to develop their antiproliferative activity on the target with sufficient potency, without being carried out of the tumour cell again beforehand by transporter proteins. The metabolites formed intracellularly after the compounds of the formula (Ia) of the invention have been taken up exhibit a reduced potential as a substrate with respect to transporter proteins, thereby suppressing their redistribution into the systemic circulation and hence the triggering of potential side effects by the toxophore itself.

The compatibility of the ADCs with a stabile linker chemistry and with the target in question, in conjunction with metabolites which represent a substrate for transporter proteins to a relatively low degree, offers an enlarged therapeutic window.

More particularly, the binder-drug conjugates of the invention, of the formula (Ia), exhibit a high and specific cytotoxic activity with respect to tumour cells which express C4.4a. The activity with respect to tumour cells which do not express C4.4a is significantly weaker at the same time.

On the basis of this profile of properties, the compounds of the invention are therefore suitable to a particular degree for the treatment of hyperproliferative diseases in humans and in mammals generally. The compounds are able on the one hand to inhibit, block, reduce or lower cell proliferation and cell division, and on the other hand to increase apoptosis.

The hyperproliferative diseases for the treatment of which the compounds of the invention can be employed include in particular the group of cancer and tumour diseases. In the context of the present invention, these are understood as meaning, in particular, the following diseases, but without being limited to them: mammary carcinomas and mammary tumours (ductal and lobular forms, also in situ), tumours of the respiratory tract (parvicellular and non-parvicellular carcinoma, bronchial carcinoma), cerebral tumours (e.g. of the brain stem and of the hypothalamus, astrocytoma, medulloblastoma, ependymoma and neuro-ectodermal and pineal tumours), tumours of the digestive organs (oesophagus, stomach, gall bladder, small intestine, large intestine, rectum), liver tumours (including hepatocellular carcinoma, cholangiocellular carcinoma and mixed hepatocellular and cholangiocellular carcinoma), tumours of the head and neck region (larynx, hypopharynx, nasopharynx, oropharynx, lips and oral cavity), skin tumours (squamous epithelial carcinoma, Kaposi sarcoma, malignant melanoma, Merkel cell skin cancer and non-melanomatous skin cancer), tumours of soft tissue (including soft tissue sarcomas, osteosarcomas, malignant fibrous histiocytomas, lymphosarcomas and rhabdomyosarcomas), tumours of the eyes (including intraocular melanoma and retinoblastoma), tumours of the endocrine and exocrine glands (e.g. thyroid and parathyroid glands, pancreas and salivary gland), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testicles in men). These also include proliferative blood diseases in solid form and as circulating blood cells, such as lymphomas, leukaemias and myeloproliferative diseases, e.g. acute myeloid, acute lymphoblastic, chronic lymphocytic, chronic myelogenic and hair cell leukaemia, and also AIDS-correlated lymphomas, Hodgkin's lymphomas, non-Hodgkin's lymphomas, cutaneous T-cell lymphomas, Burkitt's lymphomas and lymphomas in the central nervous system.

Preferred Hyperproliferative Diseases for Anti-CA9 Binder-Drug Conjugates

Hyperproliferative diseases for the treatment of which the compounds of the invention can be preferably employed are CA9-overexpressing tumours, mammary carcinomas and mammary tumours (e.g. ductal and lobular forms, also in situ); tumours of the respiratory tract (e.g. parvicellular and non-parvicellular carcinoma, bronchial carcinoma), including preferably non-parvicellular carcinoma of the lung; cerebral tumours (e.g. of the brain stem and of the hypothalamus, astrocytoma, medulloblastoma, ependymoma and/or neuroectodermal and pineal tumours); tumours of the digestive organs (oesophagus, stomach, gall bladder, small intestine, large intestine, rectum), including more preferably stomach tumours and intestinal tumours; liver tumours (including hepatocellular carcinoma, cholangiocellular carcinoma and mixed hepatocellular and cholangiocellular carcinoma); tumours of the head and neck region (e.g. larynx, hypopharynx, nasopharynx, oropharynx, lips, oral cavity, tongue and oesophagus); tumours of the urinary tract (tumours of the bladder, penis, kidney, renal pelvis and ureter), including more preferably tumours of the kidneys and of the bladder; and/or tumours of the reproductive organs (carcinomas of the endometrium, cervix, ovary, vagina, vulva and uterus in women and/or carcinomas of the prostate and testicles in men), including more preferably carcinomas of the cervix and uterus.

Preferred Hyperproliferative Diseases for Anti-EGFR Binder-Drug Conjugates

Hyperproliferative diseases for the treatment of which the compounds of the invention can be preferably employed are EGFR-overexpressing tumours, respiratory tract tumours (e.g. parvicellular and non-pavicellular carcinomas, bronchial carcinoma), including preferably non-parvicellular carcinoma of the lung; tumours of the digestive organs (e.g. oesophagus, stomach, gall bladder, small intestine, large intestine, rectum), including especially intestinal tumours; tumours of the endocrine and exocrine glands (e.g. thyroid and parathyroid glands, pancreas and salivary gland), including preferably pancreas; tumours of the head and neck region (e.g. larynx, hypopharynx, nasopharynx, oropharynx, lips, oral cavity, tongue and oesophagus); and/or gliomas.

Preferred Hyperproliferative Diseases for Anti-Mesothelin Binder-Drug Conjugates Hyperproliferative diseases for the treatment of which the compounds of the invention can be preferably employed are mesothelin-overexpressing tumours, tumours of the reproductive organs (carcinomas of the endometrium, cervix, ovary, vagina, vulva and uterus in women and/or carcinomas of the prostate and testicles in men), including preferably ovarian carcinomas; tumours of the endocrine and exocrine glands (e.g. thyroid and parathyroid glands, pancreas and salivary gland), including preferably pancreas; respiratory tract tumours (e.g. parvicellular and non-parvicellular carcinoma, bronchial carcinoma), including preferably non-parvicellular carcinoma of the lung; and/or mesotheliomas.

Preferred Hyperproliferative Diseases for Anti-C4.4a Binder-Drug Conjugates

Hyperproliferative diseases for the treatment of which the compounds of the invention can be preferably employed are C4.4a-overexpressing tumours, squamous epithelial carcinomas (e.g. of the cervix, vulva, vagina, of the anal duct, endometrium, fallopian tube, penis, scrotum, of the oesophagus, breast, of the bladder, of the bile duct, endometrium, uterus and ovary); mammary carcinomas and mammary tumours (e.g. ductal and lobular forms, also in situ); tumours of the respiratory tract (e.g. parvicellular and non-parvicellular carcinoma, bronchial carcinoma), including preferably non-parvicellular carcinoma of the lung, squamous epithelial carcinoma and adenocarcinoma of the lung; tumours of the head and neck region (e.g. larynx, hypopharynx, nasopharynx, oropharynx, lips, oral cavity, tongue and oesophagus, squamous epithelial carcinomas of the head and neck region); tumours of the urinary tract (tumours of the bladder, penis, kidney, renal pelvis and ureter, squamous epithelial carcinomas of the bladder), including more preferably tumours of the kidneys and of the bladder; skin tumours (squamous epithelial carcinoma, Kaposi sarcoma, malignant melanoma, Merkel cell skin cancer and non-melanomatous skin cancer), including more preferably melanomas; tumours of the endocrine and exocrine glands (e.g. thyroid and parathyroid glands, pancreas and salivary gland), including preferably pancreas; tumours of the digestive organs (e.g. oesophagus, stomach, gall bladder, small intestine, large intestine, rectum), including especially colorectal carcinomas; and/or tumours of the reproductive organs (carcinomas of the endometrium, cervix, ovary, vagina, vulva and uterus in women and/or carcinomas of the prostate and testicles in men), including more preferably uterine carcinomas.

These well-described diseases in humans can also occur with a comparable aetiology in other mammals and can be treated there with the compounds of the present invention.

In the context of this invention the term "treatment" or "treat" is used in the conventional sense and means attending to, caring for and nursing a patient with the aim of combating, reducing, attenuating or alleviating an illness or health abnormality and improving the living conditions impaired by this illness, such as, for example, with a cancer disease.

The present invention furthermore provides the use of the compounds of the invention for the treatment and/or prevention of diseases, in particular the abovementioned diseases.

The present invention furthermore provides the use of the compounds of the invention for the preparation of a medicament for the treatment and/or prevention of diseases, in particular the abovementioned diseases.

The present invention furthermore provides the use of the compounds of the invention in a method for the treatment and/or prevention of diseases, in particular the abovementioned diseases.

The present invention furthermore provides a method for the treatment and/or prevention of diseases, in particular the abovementioned diseases, using an effective amount of at least one of the compounds of the invention.

The anti-C4.4a binder-drug conjugate of the invention is used preferably for treating cancer in a patient, where the cancer cells of the patient that are to be treated have C4.4a expression. Treatment is administered more preferably to patients whose C4.4a expression in cancer cells is higher than in healthy cells.

One method of identifying patients who respond advantageously to an anti-C4.4a binder-drug conjugate for the treatment of cancer involves determining the C4.4a expression in cancer cells of the patient. In one embodiment the C4.4a expression is determined by C4.4a gene expression analysis. The skilled person knows of methods for gene expression analysis such as, for example, RNA detection, quantitative or qualitative polymerase chain reaction or fluorescence in situ hybridization (FISH). In another preferred embodiment the C4.4a expression is determined by means of immunohistochemistry with an anti-C4.4a antibody. The immunohistochemistry is carried out preferably on formaldehyde-fixed tissue. The antibody for use in the immunohistochemistry is the same antibody which is also used in the conjugate. The antibody for use in the immunohistochemistry is a second antibody which—preferably specifically—recognizes the C4.4a target protein.

The compounds according to the invention can be employed by themselves or, if required, in combination with one or more other pharmacologically active substances, as long as this combination does not lead to undesirable and unacceptable side effects. The present invention furthermore therefore provides medicaments comprising at least one of the compounds of the invention and one or more further drugs, in particular for the treatment and/or prevention of the abovementioned diseases.

For example, the compounds of the present invention can be combined with known antihyperproliferative, cytostatic or cytotoxic substances for the treatment of cancer diseases.

Suitable drugs in the combination which may be mentioned by way of example are as follows:

aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-n1, interferon-alpha-n3, interferon-beta, interferon-gamma-1α, interleukin-2, intron A, iressa, irinotecan, kytril, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, oraperd, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solumedrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, avastin, BAY 43-9006 (sorafenib), CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retic acid, satraplatin, seocalcitol, T-138067, tarceva, taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, zoledronic acid and combinations of these.

In a preferred embodiment, the compounds of the present invention can be combined with antihyperproliferative agents, which can be, by way of example—without this list being conclusive as follows:
aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythrohydroxynonyladenin, ethinyl-estradiol, etoposide, fludarabin phosphate, 5-fluorodeoxyuridine, 5-fluorodeoxyuridine mono-phosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

The compounds of the invention can also be combined in a very promising manner with biological therapeutics such as antibodies (e.g. avastin, rituxan, erbitux, herceptin). The compounds of the invention can also achieve positive effects in combination with therapies directed against angiogenesis, such as, for example, with avastin, axitinib, recentin, regorafenib, sorafenib or sunitinib. Combinations with inhibitors of the proteasome and of mTOR and also with antihormones and steroidal metabolic enzyme inhibitors are likewise particularly suitable because of their favourable profile of side effects.

Generally, the following aims can be pursued with the combination of compounds of the present invention with other agents having a cytostatic or cytotoxic action:
an improved activity in slowing down the growth of a tumour, in reducing its size or even in its complete elimination compared with treatment with an individual drug;
the possibility of employing the chemotherapeutics used in a lower dosage than in monotherapy;
the possibility of a more tolerable therapy with few side effects compared with individual administration;
the possibility of treatment of a broader spectrum of tumour diseases;
the achievement of a higher rate of response to the therapy;
a longer survival time of the patient compared with present-day standard therapy.

The compounds according to the invention can moreover also be employed in combination with radiotherapy and/or surgical intervention.

The present invention furthermore provides medicaments which comprise at least one compound of the invention, conventionally together with one or more inert, non-toxic, pharmaceutically suitable excipients, and the use thereof for the abovementioned purposes.

The compounds of the invention can act systemically and/or locally. They can be administered in a suitable manner for this purpose, such as for example orally, parenterally, pulmonally, nasally, sublingually, lingually, buccally, rectally, dermally, transdermally, conjunctivally, otically or as an implant or stent.

The compounds of the invention can be administered in suitable administration forms for these administration routes.

Administration forms which function according to the prior art, release the compounds of the invention rapidly and/or in a modified manner and contain the compounds of the invention in crystalline and/or amorphized and/or dissolved form are suitable for oral administration, such as e.g. tablets (non-coated or coated tablets, for example with coatings which are resistant to gastric juice or dissolve in a delayed manner or are insoluble and control the release of the compound of the invention), films/oblates or tablets, which disintegrate rapidly in the oral cavity, films/lyophilizates, capsules (for example hard or soft gelatine capsules), film-coated tablets, granules, pellets, powders, emulsions, suspensions, aerosols or solutions.

Parenteral administration can be effected with bypassing of an absorption step (e.g. intravenously, intraarterially, intracardially, intraspinally or intralumbally) or with inclusion of an absorption (e.g. intramuscularly, subcutaneously, intracutaneously, percutaneously or intraperitoneally). Administration forms which are suitable for parenteral administration include injection and infusion formulations in the form of solutions, suspensions, emulsions, lyophilizates or sterile powders.

For the other administration routes e.g. inhalation medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral and parenteral administration are preferred, in particular oral and intravenous administration.

The compounds of the invention can be converted into the administration forms mentioned. This can be effected in a manner known per se by mixing with inert, non-toxic, pharmaceutically suitable excipients. These excipients include inter alia carrier substances (for example microcrystalline cellulose, lactose, mannitol), solvents (e.g. liquid polyethylene glycols), emulsifiers and dispersing or wetting agents (for example sodium dodecyl sulphate, polyoxysorbitan oleate), binders (for example polyvinylpyrrolidone), synthetic and natural polymers (for example albumin), stabilizers (e.g. antioxidants, such as, for example, ascorbic acid), colorants (e.g. inorganic pigments, such as, for example, iron oxides) and taste and/or odour correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behaviour towards the active compound, nature of the formulation and point of time or interval at which administration takes place. Thus in some cases it may be sufficient to manage with less than the abovementioned minimum amount, while in other cases the upper limit mentioned must be exceeded. In the case where relatively large amounts are administered, it may be advisable to distribute these into several individual doses over the day.

The following working examples illustrate the invention. The invention is not limited to the examples.

The percentage figures in the following tests and examples are percentages by weight, unless stated otherwise; parts are parts by weight. Solvent ratios, dilution ratios and concentration data of liquid/liquid solutions in each case relate to the volume.

A. EXAMPLES

Abbreviations and Acronyms

A431NS human tumour cell line
A549 human tumour cell line
ABCB1 ATP-binding cassette sub-family B member 1 (synonym for P-gp and MDR1)
abs. absolute
ADC antibody-drug-conjugate
Ac acetyl
aq. aqueous, aqueous solution
ATP adenosine triphosphate
BCRP breast cancer resistance protein, an efflux transporter
Boc tert-butoxycarbonyl
br. broad (in NMR)
Ex. example
ca. circa, approximately
CAIX carboanhydrase IX
CI chemical ionization (in MS)
d doublet (in NMR)
d day(s)
TLC thin-layer chromatography
DCI direct chemical ionization (in MS)
dd doublet of a doublet (in NMR)
DMAP 4-N,N-dimethylaminopyridine
DME 1,2-dimethoxyethane
DMEM Dulbecco's modified eagle medium (standardized nutrient medium for cell culture)
DMF N,N-dimethylformamide
DMSO dimethyl sulphoxide
DPBS, D-PBS, PBS Dulbecco's phosphate-buffered saline solution PBS=DPBS=D-PBS, pH 7.4, from Sigma, No. D8537
  Composition:
  0.2 g KCl
  0.2 g $KH_2PO_4$ (anhydrous)
  8.0 g NaCl
  1.15 g $Na_2HPO_4$ (anhydrous)
  make up to 1 with $H_2O$
dt doublet of a triplet (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI-MicroTofq (name of the mass spectrometer, with Tof=time of flight and q=quadrupole)
FCS foetal calf serum
Fmoc (9H-fluoren-9-ylmethoxy)carbonyl
sat. Saturated
GTP guanosine 5'-triphosphate
h hour(s)
HATU O-(7-azabenzotriazol-1-yl)-N,N,N',N'-tetramethyluronium hexafluorophosphate
HCT-116 human tumour cell line
HEPES 4-(2-hydroxyethyl)piperazine-1-ethanesulphonic acid
HOAc acetic acid
HOBt 1-hydroxy-1H-benzotriazole hydrate
HOSu N-hydroxysuccinimide
HPLC high-pressure, high-performance liquid chromatography
HT29 human tumour cell line
$IC_{50}$ half-maximum inhibitory concentration
i.m. intramuscular, administration into the muscle
i.v. intravenous, administration into the vein
conc. Concentrated
LC-MS liquid chromatography-coupled mass spectrometry
LLC-PK1 cells Lewis lung carcinoma pork kidney cell line
L-MDR human MDR1 transfected LLC-PK1 cells
m multiplet (in NMR)
MDR1 multidrug resistance protein 1
min minute(s)
MS mass spectrometry
MTT 3-(4,5-dimethylthiazol-2-yl)-2,5-diphenyl-2H-tetrazolium bromide
NCI-H292 human tumour cell line
NCI-H520 human tumour cell line
NMM N-methylmorpholine
NMP N-methyl-2-pyrrolidinone
NMR nuclear magnetic resonance spectrometry
NMRI mouse strain, originating from Naval Medical Research Institute (NMRI)
Nude mice experimental animals
NSCLC non-small cell lung cancer (non-parvicellular bronchial carcinoma)
PBS phosphate-buffered saline solution
Pd/C palladium on activated carbon
P-gp P-glycoprotein, a transporter protein
PNGaseF enzyme for sugar elimination
quant. quantitative (for yield)
quart quartet (in NMR)
quint quintet (in NMR)
$R_f$ retention index (for TLC)
RT room temperature
$R_t$ retention time (for HPLC)
s singlet (in NMR)
s.c. subcutaneous, administration beneath the skin
SCC-4 human tumour cell line
SCC-9 human tumour cell line
SCID mice experimental mice with a severe combined immunodeficiency
t triplet (in NMR)
tert tertiary
TFA trifluoroacetic acid
THF tetrahydrofuran
UV ultraviolet spectrometry
v/v volume to volume ratio (of a solution)
Z benzyloxycarbonyl

HPLC and LC-MS Methods

Method 1 (LC-MS):
  Instrument: WATERS ACQUITY® SQD UPLC® liquid chromatography System; column: WATERS ACQUITY® UPLC® HSS T3 1.8µ 50 mm×1 mm liquid chromatography column; eluent A: 1 l water+0.25 ml 99% strength formic acid, eluent B: 1 l acetonitrile+0.25 ml 99% strength formic acid; gradient: 0.0 min 90% A→1.2 min 5% A→2.0 min 5% A; flow rate: 0.40 ml/min; oven: 50° C.; UV detection: 210-400 nm.

Method 2 (LC-MS):

Instrument: WATERS MICROMASS QUATTRO PREMIER™ mass spectrometer with WATERS UPLC® ACQUITY®; column: THERMO HYPERSIL GOLD 1.9μ 50 mm×1 mm liquid chromatography column; eluent A: 1 l water+0.5 ml 50% strength formic acid, eluent B: 1 l acetonitrile+0.5 ml 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):

Instrument: WATERS MICROMASS QUATTRO MICRO™ mass spectrometer with HPLC AGILENT Series 1100 liquid chromatography instrument; column: THERMO HYPERSIL GOLD™ 3μ 20 mm×4 mm liquid chromatography column; eluent A: 1 l water+0.5 ml 50% strength formic acid, eluent B: 1 l acetonitrile+0.5 ml 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):

MS instrument: WATERS MICROMASS ZQ™ mass spectrometer; HPLC instrument: HP 1100 Series liquid chromatography instrument; UV DAD; column: PHENOMENEX® GEMINI® 3μ 30 mm×3.00 mm liquid chromatography column; eluent A: 1 l water+0.5 ml 50% strength formic acid, eluent B: 1 l acetonitrile +0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (HPLC):

Instrument: HP 1090 Series II liquid chromatography instrument; column: MERCK CHROMOLITH® SPEEDROD RP-18e, 50 mm×4.6 mm liquid chromatography column; preliminary column: MERCK CHROMOLITH® Guard Cartridge Kit RP-18e, 5 mm×4.6 mm; injection volume: 5 μl; eluent A: 70% HClO$_4$ in water (4 ml/liter), eluent B: acetonitrile; gradient: 0.00 min 20% B→0.50 min 20% B→3.00 min 90% B→3.50 min 90% B→3.51 min 20% B→4.00 min 20% B; flow rate: 5 ml/min; column temperature: 40° C.

Method 6 (HPLC):

Instrument: WATERS ALLIANCE® 2695 with DAD 996 liquid chromatography instrument; column: MERCK CHROMOLITH® SPEEDROD RP-18e, 50 mm×4.6 mm liquid chromatography column; Ord. No.: 1.51450.0001, preliminary column: MERCK CHROMOLITH® Guard Cartridge Kit RP-18e, 5 mm×4.6 mm; Ord. No.: 1.51470.0001, eluent A: 70% HClO$_4$ in water (4 ml/liter), eluent B: acetonitrile; gradient: 0.00 min 5% B→0.50 min 5% B→3.00 min 95% B→4.00 min 95% B; flow rate: 5 ml/min.

Method 7 (LC-MS):

MS instrument: WATERS MICROMASS ZQ™ mass spectrometer; HPLC instrument: AGILENT 1100 Series liquid chromatography instrument; UV DAD; column: THERMO HYPERSIL GOLD™ 3μ20 mm×4 mm liquid chromatography column; eluent A: 1 l water+0.5 ml 50% strength formic acid, eluent B: 1 l acetonitrile+0.5 ml 50% strength formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 8 (LC-MS):

MS instrument: WATERS MICROMASS ZQ™ mass spectrometer; HPLC instrument: AGILENT 1100 Series liquid chromatography instrument; UV DAD; column: THERMO HYPERSIL GOLD™ 3μ 20 mm×4 mm liquid chromatography column; eluent A: 1 l water+0.5 ml 50% strength formic acid, eluent B: 1 l acetonitrile+0.5 ml 50% strength formic acid; gradient: 0.0 min 100% A→2.0 min 60% A→2.3 min 40% A→3.0 min 20% A→4.0 min 10% A→4.2 min 100% A (flow rate 2.5 ml/min); oven: 55° C.; flow rate: 2 ml/min; UV detection: 210 nm.

Method 9 (LC-MS):

Instrument: WATERS ACQUITY® SQD UPLC® liquid chromatography System; column: WATERS ACQUITY® UPLC® HSS T3 1.8μ 50 mm×1 mm liquid chromatography column; eluent A: 1 l water+0.25 ml 99% strength formic acid, eluent B: 1 l acetonitrile+0.25 ml 99% strength formic acid; gradient: 0.0 min 95% A→6.0 min 5% A→7.5 min 5% A; oven: 50° C.; flow rate: 0.35 ml/min; UV detection: 210-400 nm.

Method 10 (HPLC):

Instrument: AGILENT 1200 Series liquid chromatography instrument; column: AGILENT ECLIPSE XDB-C18 5μ 4.6 mm×150 mm liquid chromatography column; preliminary column: PHEMOMENEX® KRUDKATCHER™ Disposable Pre-Column; injection volume: 5 μl; eluent A: 1 l water+0.01% trifluoroacetic acid; eluent B: 1 l acetonitrile+0.01% trifluoroacetic acid; gradient: 0.00 min 10% B→1.00 min 10% B→1.50 min 90% B→5.5 min 10% B; flow rate: 2 ml/min; column temperature: 30° C.

For all reactants or reagents whose preparation is not explicitly described below, they were obtained commercially from generally available sources. For all other reactants or reacents whose preparation is likewise not described below, and which were not available commercially or were obtained from sources which are not generally available, a reference is given to the published literature in which their preparation is described.

Method 11 (LC-MS):

Instrument: WATERS ACQUITY® SQD UPLC® liquid chromatography; column: WATERS ACQUITY® UPLC® HSS T3 1.8μ 30×2 mm liquid chromatography column; eluent A: 1 l water+0.25 ml 99% strength formic acid, eluent B: 1 l acetonitrile+0.25 ml 99% strength formic acid; gradient: 0.0 min 90% A→1.2 min 5% A→2.0 min 5% A oven: 50° C.; flow rate: 0.60 ml/min; UV detection: 208-400 nm.

Method 12 (HPLC):

Instrument: AGILENT 1200 Series liquid chromatography instrument with column oven and DAD; column: MERCK CHROMOLITH® SPEEDROD RP-18e, 50 mm×4.6 mm liquid chromatography column; Ord. No.: 1.51450.0001; preliminary column: MERCK CHROMOLITH® Guard Cartridge Kit RP-18e, 5 mm×4.6 mm; Ord. No.: 1.51470.0001; eluent A: 70% HClO$_4$ in water (4 ml/liter), eluent B: acetonitrile; gradient: 0.00 min 5% B→0.50 min 5% B→3.00 min 95% B 4.00 min 95% B; flow rate: 5 ml/min; column temperature: 30° C.

Method 13 (LC-MS):

MS instrument: WATERS MICROMASS QUATTRO MICRO™ mass spectrometer; Instrument HPLC: AGILENT 1100 Series liquid chromatography instrument; column: YMC TRIART C18 3μ50×3 mm liquid chromatography column; eluent A: 1 l water+0.01 mol ammonium carbonate, eluent B: 1 l acetonitrile; gradient: 0.0 min 100% A→2.75 min 5% A→4.5 min 5% A; oven: 40° C.; flow rate: 1.25 ml/min; UV detection: 210 nm.

STARTING COMPOUNDS AND INTERMEDIATES

Starting Compound 1

2R,3R)-3-[(2S)-1-(tert-butoxycarbonyl)pyrrolidin-2-yl]-3-methoxy-2-methylpropanoic acid (Boc-dola-proine

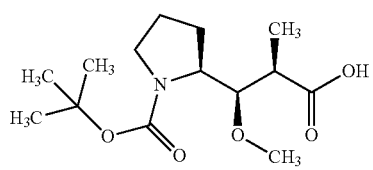 [SMILES: CO[C@H]([C@@H](C)C(=O)O)[C@@H]1CCCN1C(=O)OC(C)(C)C]

The title compound can be prepared in various ways according to literature methods; see, for example, Pettit et al., *Synthesis* 1996, 719; Shioiri et al., *Tetrahedron Lett.* 1991, 32, 931; Shioiri et al., *Tetrahedron* 1993, 49, 1913; Koga et al., *Tetrahedron Lett.* 1991, 32, 2395; Vidal et al., *Tetrahedron* 2004, 60, 9715; Poncet et al., *Tetrahedron* 1994, 50, 5345. It was prepared either as the free acid or as a 1:1 salt with dicyclohexylamine.

Starting Compound 2a tert-butyl (3R,4S,5S)-3-methoxy-5-methyl-4-(methylamino)heptanoate hydrochloride (dolaisoleucine-OtBu×HCl)

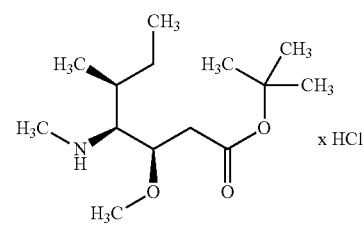 [SMILES: CC[C@H](C)[C@H](NC)[C@@H](CC(=O)OC(C)(C)C)OC]

The title compound can be prepared in various ways according to literature methods; see, for example, Pettit et al., *J. Org. Chem.* 1994, 59, 1796; Koga et al., *Tetrahedron Lett.* 1991, 32, 2395; Shioiri et al., *Tetrahedron Lett.* 1991, 32, 931; Shioiri et al., *Tetrahedron* 1993, 49, 1913.

Starting Compound 2b tert-butyl (3R,4S,5S)-3-methoxy-5-methyl-4-(methylamino)heptanoate (dolaisoleucine-O$^t$Bu)

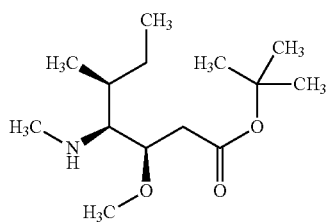 [SMILES: CC[C@H](C)[C@H](NC)[C@@H](CC(=O)OC(C)(C)C)OC]

The compound was prepared in analogy to starting compound 2a, except that the hydrogenation was performed without addition of 1N hydrochloric acid.

Starting Compound 3

Nα-(tert-butoxycarbonyl)-N-hydroxy-L-phenylalaninamide

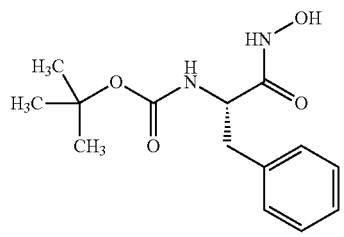 [SMILES: CC(C)(C)OC(=O)N[C@@H](Cc1ccccc1)C(=O)NO]

The title compound was prepared by the literature method (A. Ritter et al., *J. Org. Chem.* 1994, 59, 4602).

Yield: 750 mg (75% of theory)

LC-MS (Method 3): $R_t$=1.67 min; MS (ESIpos): m/z=281 (M+H)$^+$.

Starting Compound 4

1,2-oxazolidine hydrochloride

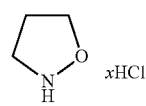

The title compound can be prepared by literature methods (see, for example, H. King, *J. Chem. Soc.* 1942, 432); it is also commercially available.

Starting Compound 5

1,2-oxazinane hydrochloride

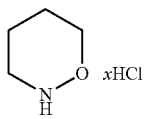

The title compound can be prepared by literature methods (see, for example, H. King, *J. Chem. Soc.* 1942, 432).

Starting Compound 6

2-oxa-3-azabicyclo[2.2.2]oct-5-ene

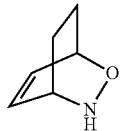

The title compound can be prepared in Boc-protected form by the literature method (see, for example, C. Johnson et al., *Tetrahedron Lett.* 1998, 39, 2059); the deprotection was effected in a customary manner by treatment with trifluoroacetic acid and subsequent neutralization.

Yield: 149 mg (89% of theory)

Starting Compound 7 tert-butyl (1S,2R)-1-(hydroxycarbamoyl)-2-phenylcyclopropyl carbamate

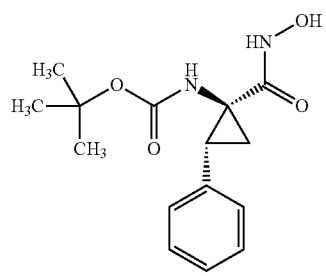 [SMILES: CC(C)(C)OC(=O)N[C@@]1(C(=O)NO)C[C@@H]1c1ccccc1]

The title compound was prepared by a literature method (A. Ritter et al., *J. Org. Chem.* 1994, 59, 4602) proceeding from commercially available (1S,2R)-1-[(tert-butoxycarbonyl) amino]-2-phenylcyclopropanecarboxylic acid (C. Cativiela et al., *Chirality* 1999, 11, 583).

Yield: 339 mg (59% of theory)

LC-MS (Method 1): R$_t$=0.82 min; MS (ESIpos): m/z=293 (M+H)$^+$.

Intermediate 1 tert-butyl (3R,4S,5S)-4-[{N-[(benzyloxy)carbonyl]-L-valyl}(methyl)amino]-3-methoxy-5-methylheptanoate

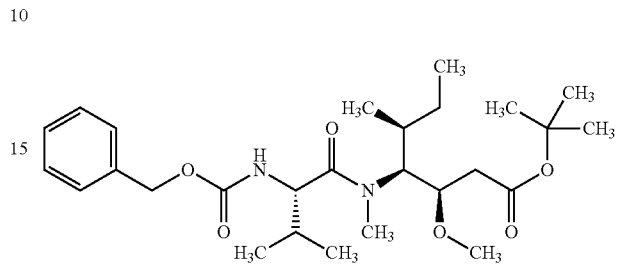

10.65 g (41.058 mmol) of tert-butyl (3R,4S,5S)-3-methoxy-5-methyl-4-(methylamino)heptanoate (starting compound 2b) were taken up in 250 ml of dichloromethane and the solution was cooled to −10° C. Then, while stirring, 10.317 g (41.058 mmol) of N-[(benzyloxy)carbonyl]-L-valine, 16.866 g (61.586 mmol) of 2-bromo-1-ethylpyridinium tetrafluoroborate (BEP) and 28.6 ml of N,N-diisopropylethylamine were added, and the mixture was subsequently stirred at RT for 20 h. The reaction mixture was then diluted with dichloromethane and shaken twice with saturated sodium chloride solution, dried over sodium sulphate, filtered and concentrated. The residue was purified by flash chromatography on silica gel with 4:1 petroleum ether/ethyl acetate as the eluent. The corresponding fractions were concentrated and the residue was dried under high vacuum overnight. 10.22 g (51% of theory) of the title compound were obtained as a yellowish oil.

HPLC (Method 5): Rt=2.3 min;

LC-MS (Method 2): Rt=1.59 min; MS (ESIpos): m/z=493 (M+H)$^+$.

Intermediate 2 tert-butyl (3R,4S,5S)-3-methoxy-5-methyl-4-[methyl (L-valyl)amino]heptanoate

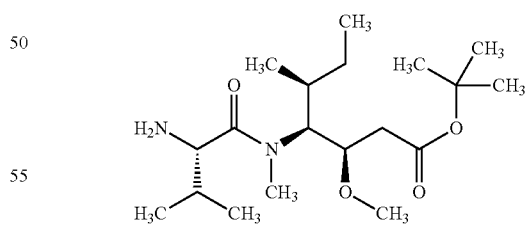

500 mg (1 mmol) of tert-butyl (3R,4S,5S)-4-[{N-[(benzyloxy)carbonyl]-L-valyl}(methyl)amino]-3-methoxy-5-methylheptanoate (intermediate 1) were dissolved in 50 ml of methanol and, after addition of 100 mg of 10% palladium on activated carbon, hydrogenated under standard hydrogen pressure at RT for 1 h. The catalyst was then filtered off and the solvent was removed under reduced pressure. This gave 370 mg (quant.) of the title compound as a virtually colourless oil.

HPLC (Method 5): $R_t$=1.59 min;
LC-MS (Method 1): $R_t$=0.74 min; MS (ESIpos): m/z=359 (M+H)$^+$.

Intermediate 3

N-[(9H-fluoren-9-ylmethoxy)carbonyl]-N-methyl-L-valyl-N-[(3R,4S,5S)-1-tert-butoxy-3-methoxy-5-methyl-1-oxoheptan-4-yl]-N-methyl-L-valinamide

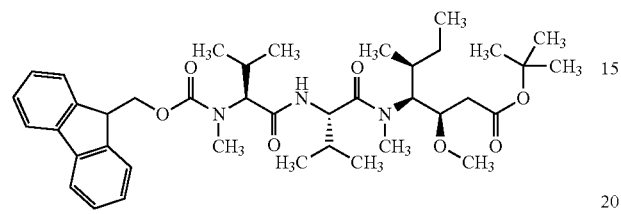

4.64 g (13.13 mmol) of N-[(9H-fluoren-9-ylmethoxy)carbonyl]-N-methyl-L-valine were dissolved in 20 ml of DMF and admixed successively with 4.28 g (11.94 mmol) of tert-butyl (3R,4S,5S)-3-methoxy-5-methyl-4-[methyl(L-valyl)amino]heptanoate (Intermediate 2), 2.75 g (14.33 mmol) of 1-(3-dimethylaminopropyl)-3-ethylcarbodiimide hydrochloride and 2.2 g (14.33 mmol) of 1-hydroxy-1H-benzotriazole hydrate. The mixture was stirred at RT overnight. The reaction mixture was then poured into a mixture of semisaturated aqueous ammonium chloride solution and ethyl acetate. The organic phase was removed, washed successively with saturated sodium hydrogencarbonate solution and saturated sodium chloride solution, dried over magnesium sulphate, filtered and concentrated. The residue was used directly in the next stage, without further purification.

Yield: 9.1 g (quant., 60% purity)
HPLC (Method 5): $R_t$=2.7 min;
LC-MS (Method 2): $R_t$=1.99 min; MS (ESIpos): m/z=694 (M+H)$^+$.

Intermediate 4

N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide

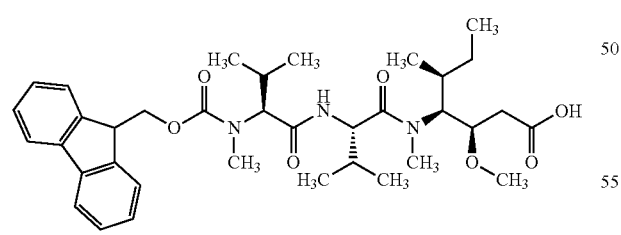

9.1 g of the crude product N-[(9H-fluoren-9-ylmethoxy)carbonyl]-N-methyl-L-valyl-N-[(3R,4S,5S)-1-tert-butoxy-3-methoxy-5-methyl-1-oxoheptan-4-yl]-N-methyl-L-valinamide (Intermediate 3) were taken up in 56.6 ml of dichloromethane, 56.6 ml of trifluoroacetic acid were added, and the mixture was stirred at RT for 2 h. Subsequently, the reaction mixture was concentrated under reduced pressure and the remaining residue was purified by flash chromatography, using dichloromethane, 3:1 dichloromethane/ethyl acetate and 15:5:0.5 dichloromethane/ethyl acetate/methanol as eluent. After purification of the corresponding fractions and concentration, 5.8 g (86% of theory) of the title compound were obtained as a colourless foam.

HPLC (Method 5): $R_t$=2.2 min;
LC-MS (Method 1): $R_t$=1.3 min; MS (ESIpos): m/z=638 (M+H)$^+$.

Intermediate 5 tert-butyl (2S)-1-(1,2-oxazinan-2-yl)-1-oxo-3-phenylpropan-2-yl carbamate

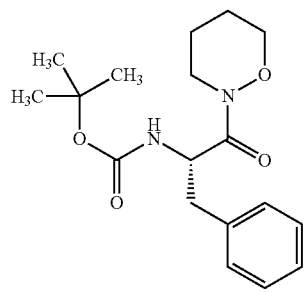 [SMILES: CC(C)(C)OC(=O)N[C@@H](Cc1ccccc1)C(=O)N1CCCCO1]

500 mg (1.9 mmol) of N-(tert-butoxycarbonyl)-L-phenylalanine were dissolved in 10 ml of DMF and admixed successively with 466 mg (3.8 mmol) of 1,2-oxazinane hydrochloride (Starting Compound 5), 433 mg (2.3 mmol) of 1-(3-dimethylaminopropyl)-3-ethylcarbodiimide hydrochloride, 382 mg (2.8 mmol) of 1-hydroxy-1H-benzotriazole hydrate and 731 mg (5.7 mmol) of N,N-diisopropylethylamine. The mixture was stirred at RT overnight. The reaction mixture was then poured into a mixture of semisaturated aqueous ammonium chloride solution and ethyl acetate. The organic phase was removed, washed successively with saturated sodium hydrogencarbonate solution and saturated sodium chloride solution, dried over magnesium sulphate, filtered and concentrated. 620 mg (98% of theory) of the title compound were obtained.

HPLC (Method 5): $R_t$=1.8 min;
LC-MS (Method 2): $R_t$=1.62 min; MS (ESIpos): m/z=235 (M-C$_4$H$_8$—CO$_2$+H)$^+$.

Intermediate 6

(2S)-2-amino-1-(1,2-oxazinan-2-yl)-3-phenylpropan-1-one trifluoroacetate

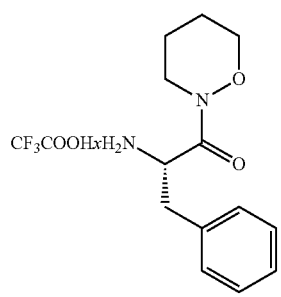

620 mg (1.85 mmol) of tert-butyl (2S)-1-(1,2-oxazinan-2-yl)-1-oxo-3-phenylpropan-2-yl carbamate (Intermediate 5) were taken up in 5 ml of dichloromethane, 10 ml of trifluoroacetic acid were added and the mixture was stirred at RT for 30 min. Subsequently, the reaction mixture was concentrated under reduced pressure and the remaining residue was lyophilized from water/acetonitrile. In this way, 779 mg (91% of theory) of the title compound were obtained as a colourless foam.

HPLC (Method 5): $R_t$=0.45 min;
LC-MS (Method 3): $R_t$=1.09 min; MS (ESIpos): m/z=235 (M+H)$^+$.

Intermediate 7

(2R,3R)-3-methoxy-2-methyl-N-[(2S)-1-(1,2-oxazinan-2-yl)-1-oxo-3-phenylpropan-2-yl]-3-[(2S)-pyrrolidin-2-yl]propanamide trifluoroacetate

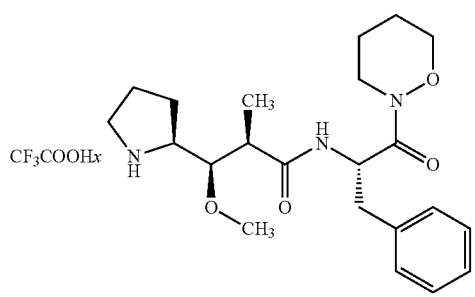 [SMILES: CO[C@@H]([C@@H]1CCCN1)[C@@H](C)C(=O)N[C@@H](Cc1ccccc1)C(=O)N1CCCCO1]

360 mg (1.25 mmol) of (2R,3R)-3-[(2S)-1-(tert-butoxycarbonyl)pyrrolidin-2-yl]-3-methoxy-2-methylpropanoic acid (Starting Compound 1) were taken up in 10 ml of DMF and admixed successively with 579.2 mg (1.25 mmol) of (2S)-2-amino-1-(1,2-oxazinan-2-yl)-3-phenylpropan-1-one trifluoroacetate (Intermediate 6), 714.5 mg (1.88 mmol) of O-(7-azabenzotriazol-1-yl)-N,N,N',N'-tetramethyluronium hexafluorophosphate (HATU) and 655 µl of N,N-diisopropylethylamine. The mixture was stirred at RT for 16 h. The reaction mixture was then concentrated, and the residue was taken up in ethyl acetate and extracted by shaking first with 5% aqueous citric acid solution, then with 5% aqueous sodium hydrogencarbonate solution and subsequently with saturated sodium chloride solution. The organic phase was concentrated and the residue was purified by flash chromatography on silica gel with 16:4 dichloromethane/methanol as the eluent. The corresponding fractions were combined and the solvent was removed under reduced pressure. After the residue had been dried under high vacuum, 503.5 mg (74% of theory) of the Boc-protected intermediate tert-butyl (2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidine-1-carboxylate were obtained.

HPLC (Method 12): $R_t$=2.0 min;
LC-MS (Method 1): $R_t$=1.12 min; MS (ESIpos): m/z=504 (M+H)$^+$.

503 mg (1 mmol) of this intermediate were taken up in 20 ml of dichloromethane, 10 ml of trifluoroacetic acid were added, and the mixture was stirred at RT for 30 min. Subsequently, the reaction mixture was concentrated under reduced pressure and redistilled with dichloromethane. The remaining residue was precipitated from ethyl acetate with n-pentane, and the solvent was decanted off. The residue thus obtained was dissolved in water and extracted by shaking with ethyl acetate, and the aqueous phase was subsequently lyophilized. In this way, 462 mg (89% of theory) of the title compound were obtained as a colourless foam.

HPLC (Method 12): $R_t$=1.53 min;
LC-MS (Method 11): $R_t$=0.57 min; MS (ESIpos): m/z=404 (M+H)$^+$.

Intermediate 8

N-(tert-butoxycarbonyl)-N-methyl-L-valyl-N-[(2R,3S,4S)-1-carboxy-2-methoxy-4-methylhexan-3-yl]-N-methyl-L-valinamide

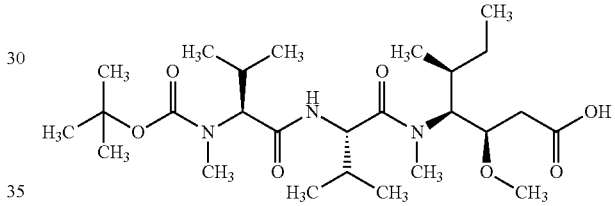

51 mg (0.08 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were dissolved in 10 ml of DMF, and 0.5 ml of piperidine was added. After stirring at RT for 10 min, the reaction mixture was concentrated under reduced pressure and the residue was stirred with diethyl ether. The insoluble constituents were filtered off and washed repeatedly with diethyl ether. Then the filter residue was taken up in 5 ml of dioxane/water and the solution was adjusted to pH 11 with 1 N sodium hydroxide solution. Under ultrasound treatment, a total of 349 mg (1.6 mmol) of di-tert-butyl dicarbonate were added in several portions, in the course of which the pH of the solution was kept at 11. After the reaction had ended, the dioxane was evaporated off and the aqueous solution was adjusted to a pH of 2-3 with citric acid. The mixture was extracted twice with 50 ml each time of ethyl acetate. The organic phases were combined, dried over magnesium sulphate and concentrated under reduced pressure. The residue was taken up in diethyl ether and the of the title compound was precipitated with pentane. The solvent was removed by decantation. The residue was digested several times more with pentane and finally dried under high vacuum. 40 mg (97% of theory) of the title compound were thus obtained.

HPLC (Method 6): $R_t$=2.2 min;

LC-MS (Method 2): $R_t$=1.32 min; MS (ESIpos): m/z=516 (M+H)$^+$.

Intermediate 9 tert-butyl (2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidine-1-carboxylate

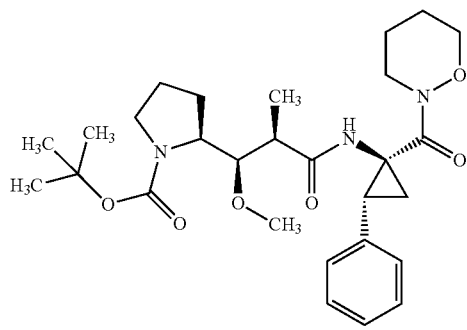 [SMILES: CO[C@H]([C@@H](C)C(=O)N[C@@]1(C(=O)N2CCCCO2)C[C@@H]1c1ccccc1)[C@@H]1CCCN1C(=O)OC(C)(C)C]

The title compound was prepared in analogy to the synthesis of Intermediates 5, 6 and 7 over three stages, by coupling of commercially available (1S,2R)-1-[(tert-butoxycarbonyl)amino]-2-phenylcyclopropanecarboxylic acid with 1,2-oxazinane hydrochloride (Starting Compound 5), subsequent deprotection with trifluoroacetic acid and coupling with Starting Compound 1. The end product was purified by preparative HPLC.

HPLC (Method 5): $R_t$=2.12 min;

LC-MS (Method 2): $R_t$=1.25 min; MS (ESIpos): m/z=516 (M+H)$^+$.

Intermediate 10

N-[(9H-fluoren-9-ylmethoxy)carbonyl]-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide

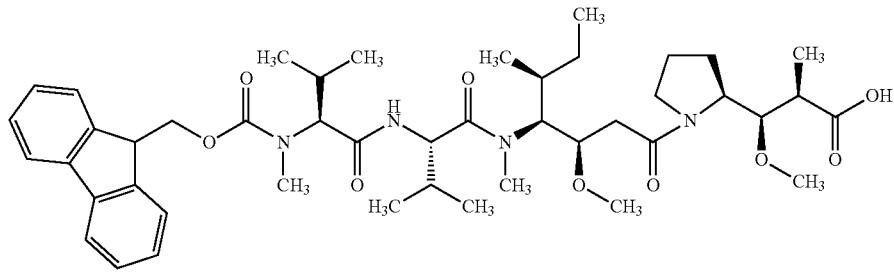 [SMILES: CC[C@H](C)[C@@H]([C@@H](CC(=O)N1CCC[C@H]1[C@H](OC)[C@@H](C)C(=O)O)OC)N(C)C(=O)[C@@H](NC(=O)[C@H](C(C)C)N(C)C(=O)OCC1c2ccccc2-c2ccccc21)C(C)C]

315 mg (0.494 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were dissolved in 12 ml of DMF, and admixed with 104 mg (0.543 mmol) of 1-(3-dimethylaminopropyl)-3-ethylcarbodiimide hydrochloride and 83 mg (0.543 mmol) of 1-hydroxy-1H-benzotriazole hydrate, and the mixture was stirred at RT for 90 min. Subsequently, 112 µl of N,N-diisopropylethylamine and 149 mg (0.494 mmol) of (2R,3R)-3-methoxy-2-methyl-3-[(2S)-pyrrolidin-2-yl]propanoic acid trifluoroacetate, which had been prepared beforehand from Starting Compound 1 by elimination of the Boc protecting group by means of trifluoroacetic acid, were added. The mixture was stirred at RT for 2 h and then concentrated under high vacuum. The remaining residue was purified twice by preparative HPLC. 140 mg (35% of theory) of the title compound were obtained in the form of a colourless foam.

HPLC (Method 5): $R_t$=2.40 min;

LC-MS (Method 1): $R_t$=1.38 min; MS (ESIpos): m/z=807 (M+H)$^+$.

Intermediate 11

N-[(benzyloxy)carbonyl]-N-methyl-L-threonyl-N-[(2R,3S,4S)-1-carboxy-2-methoxy-4-methylhexan-3-yl]-N-methyl-L-valinamide

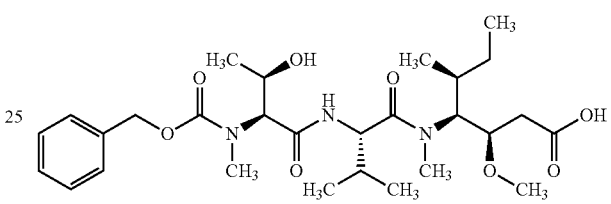

First, N-[(benzyloxy)carbonyl]-N-methyl-L-threonine was released from 237 mg (0.887 mmol) of its dicyclohexylamine salt thereof by taking it up in ethyl acetate and extractive shaking with 5% aqueous sulphuric acid. The organic phase was dried over magnesium sulphate, filtered and concentrated. The residue was taken up in 16 ml of DMF and admixed successively with 365 mg (1 mmol) of tert-butyl (3R,4S,5S)-3-methoxy-5-methyl-4-[methyl(L-valyl)amino]heptanoate (Intermediate 2), 185 mg (0.967 mmol) of 1-(3-dimethylaminopropyl)-3-ethylcarbodiimide hydrochloride and 148 mg (0.967 mmol) of 1-hydroxy-1H-benzotriazole hydrate. The mixture was stirred at RT for 2 h. The reaction mixture was then poured into a mixture of semisaturated aqueous ammonium chloride solution and ethyl acetate. The organic phase was removed, washed successively with saturated sodium hydrogencarbonate solution and saturated sodium chloride solution, dried over magnesium sulphate, filtered and concentrated. The residue was purified by preparative HPLC. 283 mg (53% of theory) of the tert-butyl ester intermediate N-[(benzyloxy)carbonyl]-N-methyl-L-threonyl-N-[(3R,4S,5S)-1-tert-butoxy-3-methoxy-5-methyl-1-oxoheptan-4-yl]-N-methyl-L-valinamide were thus obtained.

HPLC (Method 5): $R_t$=2.17 min.

283 mg (0.466 mmol) of this intermediate were taken up in 5 ml of dichloromethane, 5 ml of anhydrous trifluoroacetic acid were added, and the mixture was stirred at RT for 2 h. Subsequently, the reaction mixture was concentrated under high vacuum and the remaining residue was purified by means of preparative HPLC. This gave 156 mg (61% of theory) of the title compound as a colourless foam.

HPLC (Method 5): $R_t$=1.50 min;
LC-MS (Method 2): $R_t$=1.09 min; MS (ESIpos): m/z=552 (M+H)⁺.

Intermediate 12 benzyl N-{(2R,3R)-3-methoxy-2-methyl-3-[(2S)-pyrrolidin-2-yl]propanoyl}-L-phenylalaninate trifluoroacetate

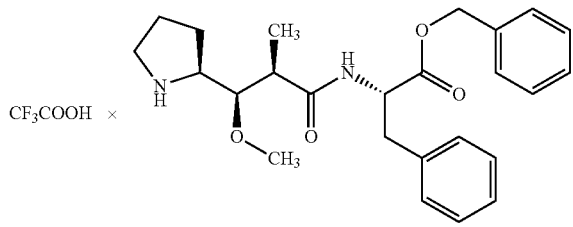 [SMILES: "CF3COOH" ; CO[C@@H]([C@@H]1CCCN1)[C@@H](C)C(=O)N[C@@H](Cc1ccccc1)C(=O)OCc1ccccc1]

In the first step, Starting Compound 1 was released from 600 mg (1.28 mmol) of the corresponding dicyclohexylammonium salt by dissolving the salt in 100 ml of ethyl acetate and extractive shaking, first with 50 ml of 0.5% sulphuric acid and then with saturated sodium chloride solution. Then the organic phase was dried over magnesium sulphate, filtered, concentrated and reacted immediately with benzyl L-phenylalaninate in analogy to the synthesis of Intermediate 7, and then deprotected.

Yield: 650 mg (94% over 2 stages)
HPLC (Method 6): $R_t$=1.76 min;
LC-MS (Method 2): $R_t$=1.68 min; MS (ESIpos): m/z=425 (M+H)⁺.

Intermediate 13 benzyl(βS)—N-{(2R,3R)-3-methoxy-2-methyl-3-[(2S)-pyrrolidin-2-yl]propanoyl}-β-methyl-L-phenylalaninate trifluoroacetate

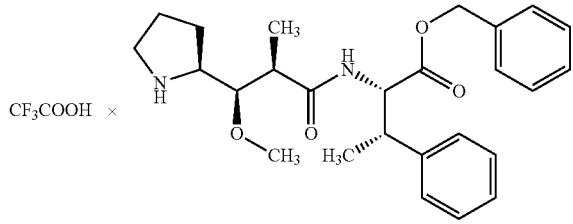 [SMILES: "CF3COOH" ; CO[C@@H]([C@@H]1CCCN1)[C@@H](C)C(=O)N[C@H](C(=O)OCc1ccccc1)[C@@H](C)c1ccccc1]

First, (2R,3R)-3-[(2S)-1-(tert-butoxycarbonyl)pyrrolidin-2-yl]-3-methoxy-2-methylpropanoic acid was released from 351 mg (0.75 mmol) of the dicyclohexylamine salt (Starting Compound 1) by taking it up in ethyl acetate and extractive shaking with aqueous 5% potassium hydrogensulphate solution. The organic phase was dried over magnesium sulphate, filtered and concentrated. The residue was taken up in 10 ml of DMF and admixed successively with 373 mg (0.75 mmol) of benzyl(βS)-β-methyl-L-phenylalaninate trifluoroacetate [prepared from commercially available (βS)—N-(tert-butoxycarbonyl)-β-methyl-L-phenylalanine by EDC/DMAP-mediated esterification with benzyl alcohol and subsequent detachment of the Boc protecting group with trifluoroacetic acid], 428 mg (1.125 mmol) of O-(7-azabenzotriazol-1-yl)-N,N,N',N'-tetramethyluronium hexafluorophosphate (HATU) and 392 µl of N,N-diisopropylethylamine. The mixture was stirred at RT for 20 h. The reaction mixture was then poured onto a mixture of semisaturated aqueous ammonium chloride solution and ethyl acetate. The organic phase was removed, washed successively with saturated sodium hydrogencarbonate solution and saturated sodium chloride solution, and subsequently concentrated. The residue was purified by means of preparative HPLC. This gave 230 mg (57% of theory) of the Boc-protected intermediate benzyl(βS)—N-{(2R,3R)-3-[(2S)-1-(tert-butoxycarbonyl)pyrrolidin-2-yl]-3-methoxy-2-methylpropanoyl}-β-methyl-L-phenylalaninate.

HPLC (Method 6): $R_t$=2.3 min;
LC-MS (Method 1): $R_t$=1.36 min; MS (ESIpos): m/z=539 (M+H)⁺.

230 mg (0.42 mmol) of this intermediate were taken up in 5 ml of dichloromethane, 5 ml of trifluoroacetic acid were added, and the mixture was stirred at RT for 30 min. Subsequently, the reaction mixture was concentrated under reduced pressure. The remaining residue was the reaction mixture dried further under reduced pressure and then lyophilized from acetonitrile/water. In this way, 230 mg (quant.) of the title compound were obtained.

HPLC (Method 6): $R_t$=1.6 min

Intermediate 14

N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide trifluoroacetate

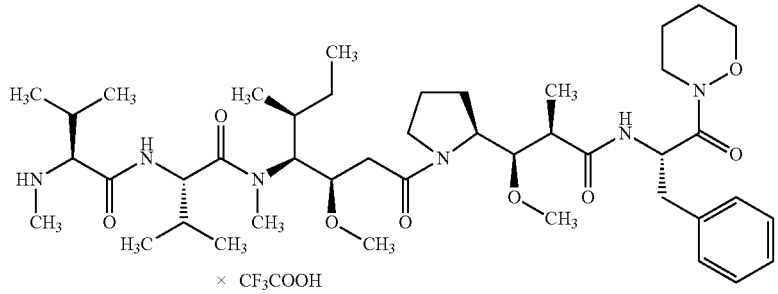 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@@H](NC)C(C)C)C(C)C ; "CF3COOH"]

143 mg (0.223 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 15 ml of DMF and admixed successively with 141 mg (0.22 mmol) of (2R,3R)-3-methoxy-2-methyl-N-[(2S)-1-(1,2-oxazinan-2-yl)-1-oxo-3-phenylpropan-2-yl]-3-[(2S)-pyrrolidin-2-yl]propanamide trifluoroacetate (Intermediate 7), 102 mg (0.27 mmol) of O-(7-azabenzotriazol-1-yl)-N,N,N',N'-tetramethyluronium hexafluorophosphate (HATU) and 128 µl (0.74 mmol) of

Intermediate 15

N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide trifluoroacetate

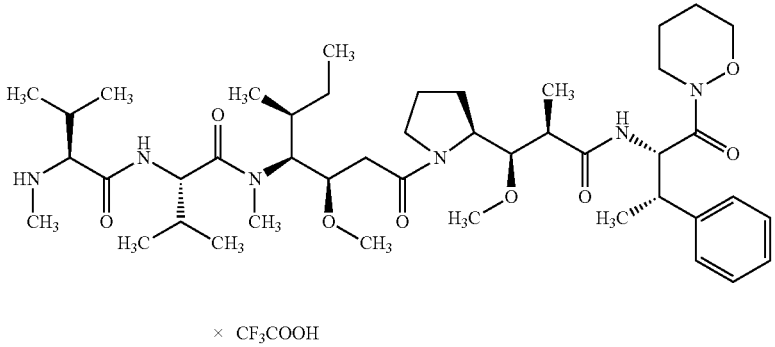 [SMILES: CC[C@H](C)[C@@H]([C@@H](CC(=O)N1CCC[C@H]1[C@H](OC)[C@@H](C)C(=O)N[C@H](C(=O)N1CCCCO1)[C@@H](C)c1ccccc1)OC)N(C)C(=O)[C@@H](NC(=O)[C@@H](NC)C(C)C)C(C)C ; "CF3COOH"]

× CF₃COOH

N,N-diisopropylethylamine. The mixture was stirred at RT for 3 h. The reaction mixture was then poured into a mixture of semisaturated aqueous ammonium chloride solution and ethyl acetate. The organic phase was removed, washed successively with saturated sodium hydrogencarbonate solution and saturated sodium chloride solution, dried over magnesium sulphate, filtered and concentrated. This gave 275 mg (quant.) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide.

HPLC (Method 5): $R_t$=2.73 min;
LC-MS (Method 4): $R_t$=3.19 min; MS (ESIpos): m/z=1023 (M+H)⁺.

46 mg (0.045 mmol) of this intermediate were dissolved in 4 ml of DMF. After 1 ml of piperidine had been added, the reaction mixture was stirred at RT for 1 h. Subsequently, the reaction mixture was concentrated under reduced pressure and the residue was purified by means of preparative HPLC (eluent: acetonitrile+0.01% TFA/water+0.01% TFA). 22 mg (54% of theory) of the title compound were obtained as a colourless foam.

HPLC (Method 5): $R_t$=1.68 min;
LC-MS (Method 2): $R_t$=1.03 min; MS (ESIpos): m/z=801 (M+H)⁺

¹H NMR (600 MHz, DMSO-d₆): δ=8.8 (m, 2H), 8.7 (m, 1H), 8.42 and 8.15 (2d, 1H), 7.3-7.1 (m, 5H), 5.12 and 4.95 (2m, 1H), 4.70 and 4.62 (2m, 1H), 4.62 and 4.50 (2t, 1H), 4.1-3.9 (m, 3H), 3.85 (m, 1H), 3.75-3.6 (m, 2H), 3.23, 3.18, 3.17, 3.14, 3.02 and 2.96 (6s, 9H), 3.1-2.9 and 2.75 (2m, 2H), 2.46 (m, 3H), 2.4-2.1 (m, 2H), 2.05 (br. m, 2H), 1.85-1.55 (br. m, 6H), 1.5-1.2 (br. m, 3H), 1.1-0.8 (m, 18H), 0.75 (t, 3H) [further signals hidden under H₂O peak].

126 mg (0.198 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 10 ml of DMF and admixed successively with 105 mg (0.198 mmol) of (2R,3R)-3-methoxy-2-methyl-N-[(2S,3S)-1-(1,2-oxazinan-2-yl)-1-oxo-3-phenylbutan-2-yl]-3-[(2S)-pyrrolidin-2-yl]propanamide trifluoroacetate (Intermediate 17), 41.6 mg (0.217 mmol) of 1-(3-dimethylaminopropyl)-3-ethylcarbodiimide hydrochloride, 33 mg (0.217 mmol) of 1-hydroxy-1H-benzotriazole hydrate and 79 µl (0.454 mmol) of N,N-diisopropylethylamine. The mixture was stirred at RT overnight. The reaction mixture was then poured into a mixture of semisaturated aqueous ammonium chloride solution and ethyl acetate. The organic phase was removed, washed successively with saturated sodium hydrogencarbonate solution and saturated sodium chloride solution, dried over magnesium sulphate, filtered and concentrated. This gave 220 mg (quant.) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide.

HPLC (Method 5): $R_t$=2.77 min;
LC-MS (Method 1): $R_t$=1.5 min; MS (ESIpos): m/z=1037 (M+H)⁺.

220 mg (0.212 mmol) of this intermediate were dissolved in 5 ml of DMF. After 1 ml of piperidine had been added, the reaction mixture was stirred at RT for 1 h. Subsequently, the reaction mixture was concentrated under reduced pressure and the residue was purified by means of preparative HPLC (eluent: acetonitrile+0.01% TFA/water+0.01% TFA). 91 mg (46% of theory) of the title compound were obtained as a colourless foam.

HPLC (Method 5): $R_t$=1.71 min;
LC-MS (Method 1): $R_t$=0.9 min; MS (ESIpos): m/z=815 (M+H)$^+$ $^1$H NMR (600 MHz, DMSO-d$_6$): δ=8.87 and 8.80 (2d, 2H), 8.75 (m, 1H), 8.40 and 7.98 (2d, 1H), 7.3-7.1 (m, 5H), 5.45 and 5.2 (2t, 1H), 4.78 and 4.62 (2m, 1H), 4.73 and 4.58 (2t, 1H), 4.2-4.0 (m, 3H), 3.7-3.6 (m, 1H), 3.35, 3.20, 3.18, 3.14, 3.12 and 3.00 (6s, 9H), 3.1 and 2.95 (2m, 2H), 2.46 (m, 3H), 2.4-2.0 (m, 4H), 1.9-1.6 (m, 4H), 1.6-1.2 (m, 5H), 1.1-0.75 (m, 21H), 0.80 (t, 3H) [further signals hidden under H$_2$O peak].

Intermediate 16

N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide trifluoroacetate

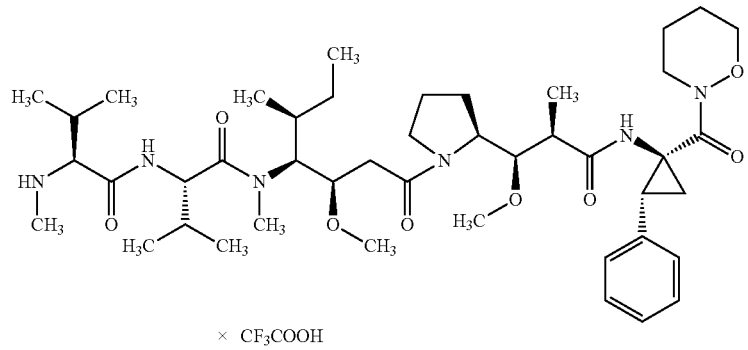 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@@H](NC)C(C)C)C(C)C ; "CF3COOH"]

× CF$_3$COOH 617 mg (1.2 mmol) of tert-butyl (2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidine-1-carboxylate (Intermediate 24) were taken up in 44 ml of dichloromethane, 4.4 ml of trifluoroacetic acid were added and the mixture was stirred at RT for 30 min. Subsequently, the reaction mixture was concentrated under reduced pressure and the remaining residue was lyophilized from dioxane/water. 702 mg (quant.) of the deprotected compound (2R,3R)-3-methoxy-2-methyl-N-[(1S,2R)-1-(1,2-oxazinan-2-ylcarbonyl)-2-phenylcyclopropyl]-3-[(2S)-pyrrolidin-2-yl]propanamide trifluoroacetate were obtained as a crude product, which was used in the following stage without further purification.

470 mg (0.74 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 57 ml of DMF and admixed successively with 390 mg (approx. 0.74 mmol) of the above-obtained (2R,3R)-3-methoxy-2-methyl-N-[(1S,2R)-1-(1,2-oxazinan-2-ylcarbonyl)-2-phenylcyclopropyl]-3-[(2S)-pyrrolidin-2-yl]propanamide trifluoroacetate, 336 mg (0.88 mmol) of O-(7-azabenzotriazol-1-yl)-N,N,N',N'-tetramethyluronium hexafluorophosphate (HATU) and 423 µl (2.4 mmol) of N,N-diisopropylethylamine. The mixture was stirred at RT for 2 h. The reaction mixture was then poured into a mixture of semisaturated aqueous ammonium chloride solution and ethyl acetate. The organic phase was removed, washed successively with saturated sodium hydrogencarbonate solution and saturated sodium chloride solution, dried over sodium sulphate, filtered and concentrated. The residue was purified by preparative HPLC. This gave 453 mg (59% of theory) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide.

HPLC (Method 5): $R_t$=2.58 min;
LC-MS (Method 1): $R_t$=3.10 min; MS (ESIpos): m/z=1035 (M+H)$^+$.

453 mg (0.438 mmol) of this intermediate were dissolved in 24 ml of DMF. After 2.4 ml of piperidine had been added, the reaction mixture was stirred at RT for 30 min. Subsequently, the reaction mixture was concentrated under reduced pressure and the residue was purified by preparative HPLC (eluent: acetonitrile/0.1% TFA in water). 260 mg (64% of theory) of the title compound were obtained as a colourless foam.

HPLC (Method 5): $R_t$=1.64 min;
LC-MS (Method 1): $R_t$=0.86 min; MS (ESIpos): m/z=813 (M+H)$^+$ $^1$H NMR (400 MHz, DMSO-d$_6$): δ=8.8 (m, 2H), 8.65 (m, 2H), 7.3-7.1 (m, 5H), 4.8-4.05 (m, 2H), 4.0 and 3.82 (2m, 2H), 3.8-3.5 (m, 8H), 3.32, 3.29, 3.20, 3.19, 3.12 and 3.00 (6s, 9H), 2.65 (t, 1H), 2.5-2.45 (m, 3H), 2.4-1.3 (m, 15H), 1.15-0.85 (m, 18H), 0.8 and 0.75 (2d, 3H) [further signals hidden under H$_2$O peak].

Intermediate 17

N-benzyl-N-methyl-L-phenylalaninamide trifluoroacetate

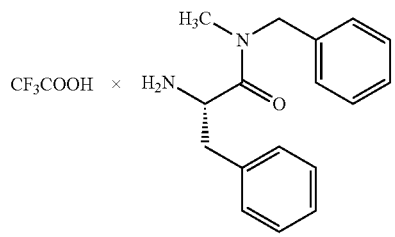 [SMILES: "CF3COOH" ; CN(Cc1ccccc1)C(=O)[C@@H](N)Cc1ccccc1]

1000 mg (3.77 mmol) of N-(tert-butoxycarbonyl)-L-phenylalanine were dissolved in 10 ml of DMF and admixed with 457 mg (3.77 mmol) of N-methylbenzylamine, 2150 mg (5.65 mmol) of O-(7-azabenzotriazol-1-yl)-N,N,N',N'-tetramethyluronium hexafluorophosphate and 657 µl of N,N-diisopropylethylamine. The reaction mixture was stirred at RT for 30 min and then concentrated under reduced pressure. The residue was taken up in dichloromethane and extracted by shaking three times with water. The organic phase was dried over magnesium sulphate and concentrated. The residue was purified by flash chromatography on silica gel with 3:1 petroleum ether/ethyl acetate as the eluent. The product fractions were concentrated and the residue was dried under high vacuum. This gave 1110 mg (75% of theory) of the Boc-protected intermediate N-benzyl-N$^\alpha$-(tert-butoxycarbonyl)-N-methyl-L-phenylalaninamide.

HPLC (Method 6): $R_t$=2.1 min;

LC-MS (Method 1): $R_t$=1.14 min; MS (ESIpos): m/z=369 (M+H)$^+$.

1108 mg (3.007 mmol) of this intermediate were taken up in 30 ml of dichloromethane, 10 ml of trifluoroacetic acid were added, and the mixture was stirred at RT for 30 min. Subsequently, the reaction mixture was concentrated under reduced pressure, the remaining residue was stirred with dichloromethane and the solvent was distilled off. The residue was stirred twice more with pentane, the solvent was decanted off again each time and the of the title compound was finally dried under high vacuum. 1075 mg (93% of theory) of the title compound were thus obtained as a resin.

HPLC (Method 6): $R_t$=1.6 min;

LC-MS (Method 1): $R_t$=0.6 min; MS (ESIpos): m/z=269 (M+H)$^+$.

Intermediate 18

N-benzyl-N$^\alpha$-{(2R,3R)-3-methoxy-2-methyl-3-[(2S)-pyrrolidin-2-yl]propanoyl}-N-methyl-L-phenylalaninamide trifluoroacetate

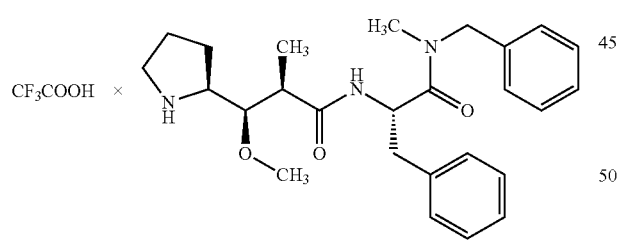

First, (2R,3R)-3-[(2S)-1-(tert-butoxycarbonyl)pyrrolidin-2-yl]-3-methoxy-2-methylpropanoic acid (Starting Compound 1) was released from 141 mg (0.491 mmol) of its dicyclohexylamine salt by taking it up in ethyl acetate and extractive shaking with 5% aqueous sulphuric acid. The organic phase was dried over magnesium sulphate, filtered and concentrated. The residue was taken up in 10 ml of DMF and 187.6 mg (0.49 mmol) of N-benzyl-N-methyl-L-phenylalaninamide trifluoroacetate (Intermediate 9), 190.3 mg (1.47 mmol) of O-(7-azabenzotriazol-1-yl)-N,N,N',N'-tetramethyluronium hexafluorophosphate (HATU) and 256 µl of N,N-diisopropylethylamine were added. The mixture was stirred at RT for 1 h. The reaction mixture was then concentrated, the residue was taken up in ethyl acetate and the solution was subsequently extracted by shaking successively with saturated ammonium chloride solution, saturated sodium hydrogencarbonate solution and water. The organic phase was dried over magnesium sulphate and concentrated. The residue was purified by flash chromatography on silica gel with 30:1 acetonitrile/water as the eluent. The product fractions were concentrated and the residue was dried under high vacuum. This gave 168 mg (64% of theory) of the Boc-protected intermediate tert-butyl (2S)-2-[(1R,2R)-3-({(2S)-1-[benzyl(methyl)amino]-1-oxo-3-phenylpropan-2-yl}amino)-1-methoxy-2-methyl-3-oxopropyl]pyrrolidine-1-carboxylate.

HPLC (Method 6): $R_t$=2.2 min;

LC-MS (Method 2): $R_t$=1.22 min; MS (ESIpos): m/z=538 (M+H)$^+$.

168 mg (0.312 mmol) of this intermediate were taken up in 15 ml of dichloromethane, 3 ml of trifluoroacetic acid were added, and the mixture was stirred at RT for 30 min. Subsequently, the reaction mixture was concentrated under reduced pressure. The remaining residue was stirred first with dichloromethane, then with diethyl ether, and the solvent was distilled off again each time. After drying under high vacuum, 170 mg (99% of theory) of the title compound were obtained as a resin.

HPLC (Method 6): $R_t$=1.7 min;

LC-MS (Method 1): $R_t$=0.73 min; MS (ESIpos): m/z=438 (M+H)$^+$.

Intermediate 19 methyl N-{(2R,3R)-3-methoxy-2-methyl-3-[(2S)-pyrrolidin-2-yl]propanoyl}-L-phenylalaninate trifluoroacetate

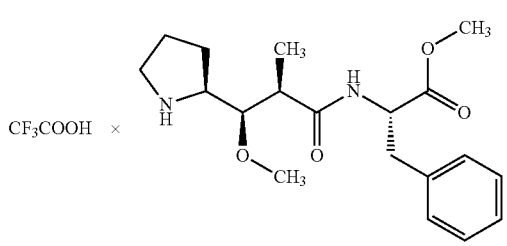 [SMILES: "CF3COOH" ; COC(=O)[C@H](Cc1ccccc1)NC(=O)[C@H](C)[C@@H](OC)[C@@H]1CCCN1]

The title compound was prepared in analogy to the synthesis of Intermediate 18, proceeding from (2R,3R)-3-[(2S)-1-(tert-butoxycarbonyl)pyrrolidin-2-yl]-3-methoxy-2-methylpropanoic acid (Starting Compound 1), which was released from the dicyclohexylamine salt, and methyl L-phenylalaninate hydrochloride.

HPLC (Method 5): $R_t$=0.6 min;

LC-MS (Method 3): $R_t$=1.17 min; MS (ESIpos): m/z=349 (M+H)$^+$.

Intermediate 20 benzyl N-{(2R,3R)-3-methoxy-2-methyl-3-[(2S)-pyrrolidin-2-yl]propanoyl}-L-tryptophanate trifluoroacetate

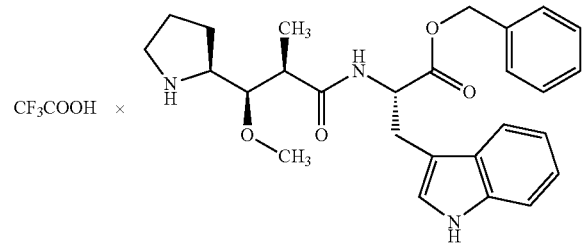 [SMILES: "CF3COOH" ; CO[C@@H]([C@@H]1CCCN1)[C@@H](C)C(=O)N[C@@H](Cc1c[nH]c2ccccc12)C(=O)OCc1ccccc1]

The title compound was prepared in analogy to the synthesis of Intermediate 18, proceeding from (2R,3R)-3-[(2S)-1-(tert-butoxycarbonyl)pyrrolidin-2-yl]-3-methoxy-2-methylpropanoic acid (Starting Compound 1), which was released from the dicyclohexylamine salt, and benzyl L-tryptophanate.

HPLC (Method 6): $R_t$=2.0 min;

LC-MS (Method 1): $R_t$=0.8 min; MS (ESIpos): m/z=464 (M+H)$^+$.

Intermediate 21 benzyl(1S,2R)-1-({(2R,3R)-3-methoxy-2-methyl-3-[(2S)-pyrrolidin-2-yl]propanoyl}amino)-2-phenylcyclopropanecarboxylate trifluoroacetate

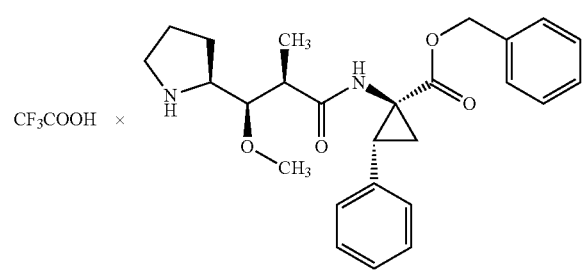 [SMILES: "CF3COOH" ; CO[C@@H]([C@@H]1CCCN1)[C@@H](C)C(=O)N[C@@]1(C(=O)OCc2ccccc2)C[C@@H]1c1ccccc1]

The title compound was prepared in analogy to the synthesis of Intermediate 18, proceeding from (2R,3R)-3-[(2S)-1-(tert-butoxycarbonyl)pyrrolidin-2-yl]-3-methoxy-2-methylpropanoic acid (Starting Compound 1), which was released from the dicyclohexylamine salt, and benzyl(1S,2R)-1-amino-2-phenylcyclopropanecarboxylate. Benzyl (1S,2R)-1-amino-2-phenylcyclopropanecarboxylate had been prepared beforehand by standard methods, by esterifying commercially available (1S,2R)-1-[(tert-butoxycarbonyl)amino]-2-phenylcyclopropanecarboxylic acid with benzyl alcohol and subsequent Boc detachment with trifluoroacetic acid.

HPLC (Method 5): $R_t$=1.5 min;

LC-MS (Method 2): $R_t$=0.93 min; MS (ESIpos): m/z=437 (M+H)$^+$.

Intermediate 22

6-(2,5-dioxo-2,5-dihydro-1H-pyrrol-1-yl)-N'-methyl-hexanehydrazide trifluoroacetate

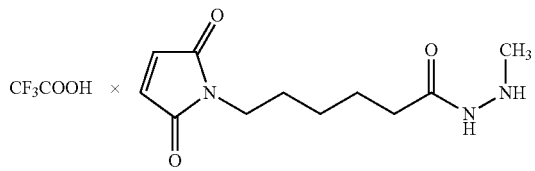 [SMILES: "CF3COOH" ; CNNC(=O)CCCCCN1C(=O)C=CC1=O]

100 mg (473 μmol) of 6-(2,5-dioxo-2,5-dihydro-1H-pyrrol-1-yl)hexanoic acid were dissolved in 71 μl of DMF and then admixed with 139 mg (947 μmol) of tert-butyl 1-methylhydrazinecarboxylate, 182 mg (947 μmol) of 1-(3-dimethylaminopropyl)-3-ethylcarbodiimide hydrochloride and 145 mg (947 μmol) of 1-hydroxy-1H-benzotriazole hydrate. The mixture was stirred at RT overnight and then concentrated under reduced pressure. The remaining residue was purified by means of preparative HPLC. After lyophilization from dioxane/water, 129 mg (80% of theory) of the protected intermediate were obtained as a colourless foam.

Subsequently, the 129 mg (380 μmol) were deblocked with 2 ml of trifluoroacetic acid in 8 ml of dichloromethane. After stirring at RT for 1 h, the reaction mixture was concentrated under reduced pressure. The residue was lyophilized from acetonitrile/water, which left 125 mg (83% of theory) of the title compound as a colourless foam.

LC-MS (Method 1): $R_t$=0.38 min; MS (ESIpos): m/z=240 (M+H)$^+$

Intermediate 23

N-(2-aminoethyl)-4-(2,5-dioxo-2,5-dihydro-1H-pyrrol-1-yl)-N-methylbutanamide trifluoroacetate

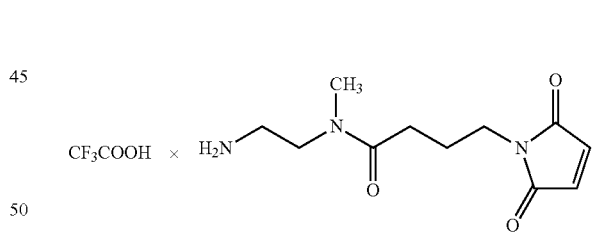

First, 35 mg (164 μmol) of tert-butyl 2-(methylamino)ethyl carbamate hydrochloride trifluoroacetate, 30 mg (164 μmol) of 4-(2,5-dioxo-2,5-dihydro-1H-pyrrol-1-yl)butanoic acid, 75 mg (197 μmol) of O-(7-azabenzotriazol-1-yl)-N,N,N',N'-tetramethyluronium hexafluorophosphate and 57 μl of N,N-diisopropylethylamine were combined in 5 ml of DMF and stirred at RT overnight. Subsequently, the solvent was removed under reduced pressure and the remaining residue was purified by means of preparative HPLC. The corresponding fractions were concentrated and, by lyophilization from dioxane/water, 35 mg (63% of theory) of the protected intermediate were obtained.

HPLC (Method 12): $R_t$=1.6 min;

LC-MS (Method 1): $R_t$=0.71 min; MS (ESIpos): m/z=340 (M+H)$^+$.

Subsequently, the entire amount of the protected intermediate was deblocked with 1 ml of trifluoroacetic acid in 5 ml of dichloromethane to obtain 28 mg (77% of theory) of the title compound.

LC-MS (Method 3): $R_t$=0.75 min; MS (ESIpos): m/z=240 (M+H)$^+$.

Intermediate 24

4-(2,5-dioxo-2,5-dihydro-1H-pyrrol-1-yl)-N-[2-(methylamino)ethyl]butanamide trifluoroacetate

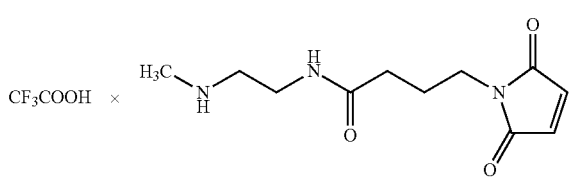 [SMILES: "CF3COOH" ; CNCCNC(=O)CCCN1C(=O)C=CC1=O]

First, 35 mg (164 μmol) of tert-butyl (2-aminoethyl)methyl carbamate hydrochloride trifluoroacetate, 30 mg (164 μmol) of 4-(2,5-dioxo-2,5-dihydro-1H-pyrrol-1-yl)butanoic acid, 75 mg (197 μmol) of O-(7-azabenzotriazol-1-yl)-N,N,N',N'-tetramethyluronium hexafluorophosphate and 57 μl of N,N-diisopropylethylamine were combined in 5 ml of DMF and stirred at RT for 30 min. Subsequently, the solvent was removed under reduced pressure and the remaining residue was purified by means of preparative HPLC. The corresponding fractions were concentrated and, by lyophilization from dioxane/water, 51 mg (91% of theory) of the protected intermediate were obtained.

HPLC (Method 12): $R_t$=1.6 min;

LC-MS (Method 1): $R_t$=0.77 min; MS (ESIpos): m/z=340 (M+H)$^+$.

Subsequently, the entire amount was deprotected with 1 ml of trifluoroacetic acid in 5 ml of dichloromethane to obtain 45 mg (69% of theory) of the title compound.

LC-MS (Method 1): $R_t$=0.19 min; MS (ESIpos): m/z=240 (M+H)$^+$.

Intermediate 25 benzyl(2R,3R)-3-methoxy-2-methyl-3-[(2S)-pyrrolidin-2-yl]propanoate trifluoroacetate First, (2R,3R)-3-[(2S)-1-(tert-butoxycarbonyl)pyrrolidin-2-yl]-3-methoxy-2-methylpropanoic acid was released from 1.82 g (388 mmol) of its dicyclohexylamine salt by taking it up in ethyl acetate and extractive shaking with 100 ml of 0.5% sulphuric acid. The organic phase was dried over magnesium sulphate, filtered and concentrated. The residue was taken up in 10 ml of dioxane and 10 ml of water, 1517 mg (4.66 mmol) of caesium carbonate were added, and the mixture was treated in an ultrasound bath for 5 min and concentrated under reduced pressure and redistilled once with DMF. The residue was then taken up in 15 ml of dichloromethane, and 1990 mg (11.64 mmol) of benzyl bromide were added. The mixture was treated in an ultrasound bath for 15 min and then concentrated under reduced pressure. The residue was partitioned between ethyl acetate and water, and the organic phase was removed and extracted by shaking with saturated sodium chloride solution and then concentrated. The residue was then purified by preparative HPLC. This gave 1170 mg (80% of theory) of the Boc-protected intermediate.

Subsequently, these 1170 mg were deprotected immediately with 5 ml of trifluoroacetic acid in 15 ml of dichloromethane. After stirring at RT for 15 min, the reaction mixture was concentrated under reduced pressure. The residue was lyophilized from dioxane. After drying under high vacuum, there remained 1333 mg (84% of theory) of the title compound as a yellow oil.

HPLC (Method 6): $R_t$=1.5 min;

LC-MS (Method 1): $R_t$=0.59 min; MS (ESIpos): m/z=278 (M+H)$^+$.

Intermediate 26

N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide

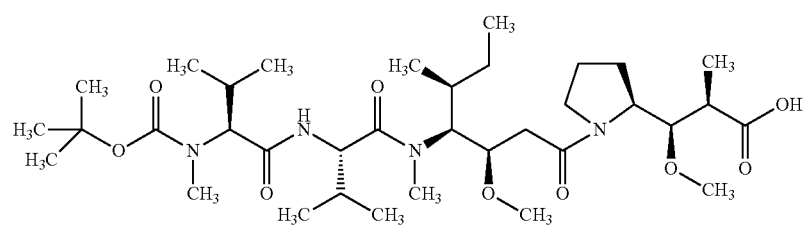 [SMILES: CC[C@H](C)[C@@H]([C@@H](CC(=O)N1CCC[C@H]1[C@H](OC)[C@@H](C)C(=O)O)OC)N(C)C(=O)[C@@H](NC(=O)[C@H](C(C)C)N(C)C(=O)OC(C)(C)C)C(C)C]

1200 mg (2.33 mmol) of N-(tert-butoxycarbonyl)-N-methyl-L-valyl-N-[(2R,3S,4S)-1-carboxy-2-methoxy-4-methylhexan-3-yl]-N-methyl-L-valinamide (Intermediate 5) were combined with 910.8 mg (2.33 mmol) of benzyl(2R,3R)-3-methoxy-2-methyl-3-[(2S)-pyrrolidin-2-yl]propanoate trifluoroacetate (Intermediate 14), 1327 mg (3.49 mmol) of O-(7-azabenzotriazol-1-yl)-N,N,N',N'-tetramethyluronium hexafluorophosphate and 2027 µl of N,N-diisopropylethylamine in 50 ml of DMF, and the mixture was stirred at RT for 5 min. Thereafter, the solvent was removed under reduced pressure. The remaining residue was taken up in ethyl acetate and extracted by shaking successively with 5% aqueous citric acid solution and saturated sodium hydrogencarbonate solution. The organic phase was removed and concentrated. The residue was purified by means of preparative HPLC. The product fractions were combined and concentrated, and the residue was dried under high vacuum. This gave 1000 mg (55% of theory) of the benzyl ester intermediate N-(tert-butoxycarbonyl)-N-methyl-L-valyl-N-[(3R,4S,5S)-1-{(2S)-2-[(1R,2R)-3-(benzyloxy)-1-methoxy-2-methyl-3-oxopropyl]pyrrolidin-1-yl}-3-methoxy-5-methyl-1-oxoheptan-4-yl]-N-methyl-L-valinamide as a resin.

LC-MS (Method 1): $R_t$=1.56 min; MS (ESIpos): m/z=775 (M+H)$^+$.

The entire amount of this intermediate obtained was taken up in 25 ml of a mixture of methanol and dichloromethane (20:1), and the benzyl ester group was removed by hydrogenation under standard hydrogen pressure with 10% palladium on activated carbon as a catalyst. After stirring at RT for 30 min, the catalyst was filtered off and the filtrate was concentrated under reduced pressure. This gave 803 mg (91% of theory) of the title compound as a white solid.

HPLC (Method 6): $R_t$=2.1 min;

LC-MS (Method 1): $R_t$=1.24 min; MS (ESIpos): m/z=685 (M+H)$^+$.

Intermediate 27

(1S,2R)-1-amino-2-phenyl-N-propylcyclopropanecarboxamide trifluoroacetate

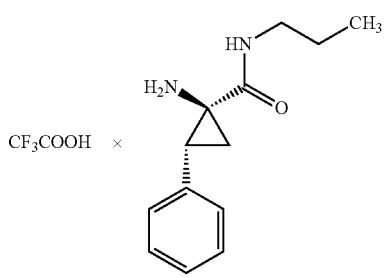 [SMILES: "CF3COOH" ; CCCNC(=O)[C@]1(N)C[C@@H]1c1ccccc1]

The title compound was prepared by coupling commercially available (1S,2R)-1-[(tert-butoxycarbonyl)amino]-2-phenylcyclopropanecarboxylic acid with n-propylamine in the presence of O-(7-azabenzotriazol-1-yl)-N,N,N',N'-tetramethyluronium hexafluorophosphate (HATU) and subsequent Boc detachment with trifluoroacetic acid (yield: 85% of theory over both stages).

HPLC (Method 6): $R_t$=1.2 min;

LC-MS (Method 1): $R_t$=0.52 min; MS (ESIpos): m/z=219 (M+H)$^+$.

Intermediate 28 ethyl (1S,2R)-1-amino-2-phenylcyclopropanecarboxylate trifluoroacetate

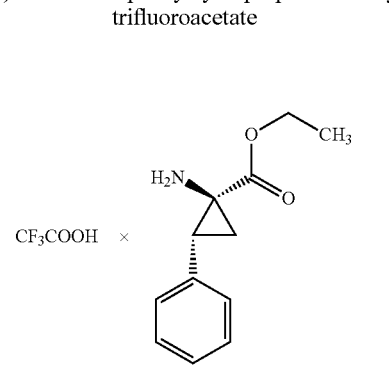

The title compound was prepared by standard methods, by esterifying commercially available (1S,2R)-1-[(tert-butoxycarbonyl)amino]-2-phenylcyclopropanecarboxylic acid with ethanol and subsequent Boc detachment with trifluoroacetic acid.

LC-MS (Method 1): $R_t$=0.50 min; MS (ESIpos): m/z=206 (M+H)$^+$.

Intermediate 29

4-(2,5-dioxo-2,5-dihydro-1H-pyrrol-1-yl)-2,2-dimethylbutanoic acid

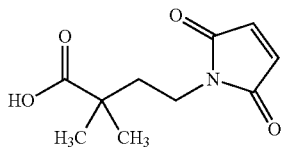

To a solution of 1.39 g (8.95 mmol) of N-methoxycarbonylmaleimide in 44 ml of saturated sodium hydrogencarbonate solution were added, at 0° C., 1.5 g (8.95 mmol) of 4-amino-2,2-dimethylbutyric acid, and the mixture was stirred for 40 min. Subsequently, the cooling bath was removed and the reaction mixture was stirred for a further 1 h. While cooling with ice, the reaction mixture was then adjusted to pH 3 by adding sulphuric acid, and extracted with ethyl acetate. The combined organic phases were dried over magnesium sulphate and concentrated. 1.17 g (79% purity, 49% of theory) of the title compound were obtained.

LC-MS (Method 1): $R_t$=0.64 min; m/z=212 (M+H)$^+$.

Intermediate 30 tert-butyl 2-[4-(2,5-dioxo-2,5-dihydro-1H-pyrrol-1-yl)-2,2-dimethylbutanoyl]hydrazinecarboxylate

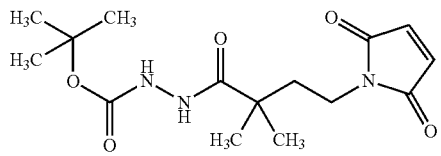 [SMILES: CC(C)(C)OC(=O)NNC(=O)C(C)(C)CCN1C(=O)C=CC1=O]

To a solution of 50 mg (237 µmol) of 4-(2,5-dioxo-2,5-dihydro-1H-pyrrol-1-yl)-2,2-dimethylbutanoic acid in 2 ml of THF were added, at 0° C., first 26 µl (237 µmol) of 4-methylmorpholine and then 31 µl (237 µmol) of isobutyl chloroformate. After removing the cooling bath and stirring at RT for a further 15 min, 31.3 mg (237 µmol) of tert-butyloxycarbonyl hydrazide were added. The reaction mixture was stirred overnight and then concentrated. The residue was purified by preparative HPLC. 50.8 mg (66% of theory) of the title compound were obtained.

LC-MS (Method 1): $R_t$=0.71 min; m/z=324 (M+H)$^+$.

Intermediate 31

4-(2,5-dioxo-2,5-dihydro-1H-pyrrol-1-yl)-2,2-dimethylbutanehydrazide trifluoroacetate

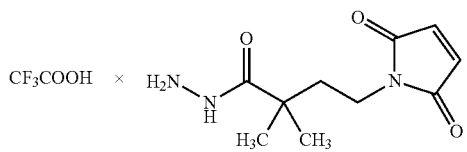 [SMILES: "CF3COOH" ; CC(C)(CCN1C(=O)C=CC1=O)C(=O)NN]

50 mg (154 mmol) of tert-butyl 2-[4-(2,5-dioxo-2,5-dihydro-1H-pyrrol-1-yl)-2,2-dimethylbutanoyl]hydrazinecarboxylate were dissolved in 2 ml of dichloromethane, and 0.4 ml of trifluoroacetic acid was added. The reaction mixture was stirred at RT for 30 min and then concentrated. 55.2 mg (93% purity, 99% of theory) of the title compound were obtained.

LC-MS (Method 1): $R_t$=0.36 min; m/z=226 (M+H)$^+$.

Intermediate 32 adamantan-1-ylmethyl N-(tert-butoxycarbonyl)-L-phenylalaninate

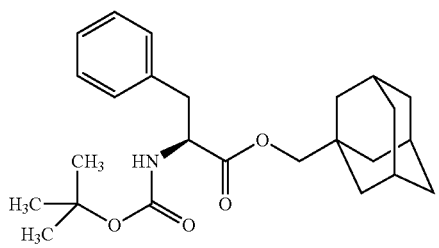 [SMILES: CC(C)(C)OC(=O)N[C@@H](Cc1ccccc1)C(=O)OCC12CC3CC(CC(C3)C1)C2]

To a solution of 500 mg (1.89 mmol) of N-Boc-L-phenylalanine in 25 ml of dichloromethane were added, at RT, 1192 mg (6.2 mmol) of EDC, 578 µl (4.1 mmol) of triethylamine, 345 mg (2.8 mmol) of DMAP and 345 mg (2.1 mmol) of 1-adamantylmethanol. The reaction mixture was stirred overnight, then diluted with 50 ml of dichloromethane, and was successively washed with 10% aqueous citric acid solution, water and saturated sodium chloride solution. The organic phase was dried over magnesium sulphate, then concentrated, and the residue was purified by preparative HPLC. 769 mg (90% of theory) of the title compound were obtained.

LC-MS (Method 2): $R_t$=1.84 min; m/z=414 (M+H)$^+$.

Intermediate 33 adamantan-1-ylmethyl L-phenylalaninate hydrochloride

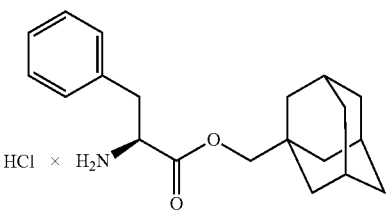 [SMILES: N[C@@H](Cc1ccccc1)C(=O)OCC12CC3CC(CC(C3)C1)C2 ; Cl]

769 mg (1.86 mmol) of adamantan-1-ylmethyl N-(tert-butoxycarbonyl)-L-phenylalaninate (Intermediate 13) were dissolved in 25 ml of a 4 N solution of hydrogen chloride in dioxane and stirred at RT for 1 h. Subsequently, the reaction mixture was concentrated and the residue was dried under reduced pressure. 619 mg (95% of theory) of the title compound were obtained.

LC-MS (Method 1): $R_t$=0.82 min; m/z=314 (M+H)$^+$.

Intermediate 34

N-(tert-butoxycarbonyl)-N-methyl-L-valyl-N-[(3R,4S,5S)-1-{(2S)-2-[(1R,2R)-3-{[(2S)-1-(adamantan-1-ylmethoxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

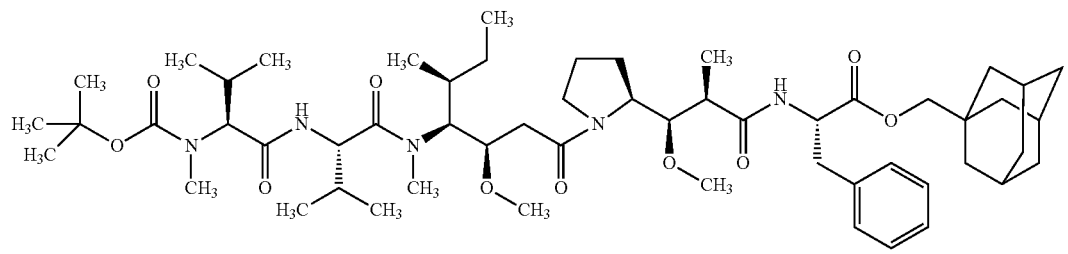 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCC12CC3CC(CC(C3)C1)C2)OC)N(C)C(=O)[C@@H](NC(=O)[C@H](C(C)C)N(C)C(=O)OC(C)(C)C)C(C)C]

To a solution of 20 mg (29 µmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide in 1 ml of DMF were added, at RT, 15.3 µl (88 µmol) of N,N-diisopropylethylamine, 6.7 mg (44 µmol) of HOBt and 6.7 mg (35 µmol) of EDC, and the mixture was stirred for 30 min. Subsequently, 10.1 mg (32 µmol) of adamantan-1-yl L-phenylalaninate hydrochloride were added. After stirring overnight, the reaction mixture was separated directly into its components via preparative HPLC. 27.5 mg (93% of theory) of the title compound were obtained.

LC-MS (Method 1): $R_t$=1.70 min; m/z=980 (M+H)$^+$.

Intermediate 35

N-methyl-L-valyl-N-[(3R,4S,5S)-1-{(2S)-2-[(1R,2R)-3-{[(2S)-1-(adamantan-1-ylmethoxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

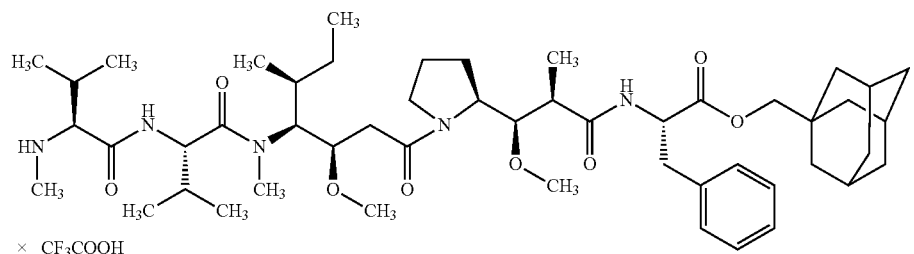

27.5 mg (28 µmol) of N-(tert-butoxycarbonyl)-N-methyl-L-valyl-N-[(3R,4S,5S)-1-{(2S)-2-[(1R,2R)-3-{[(2S)-1-(adamantan-1-ylmethoxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 1.8 ml of dichloromethane, and 361 µl of TFA were added. The reaction mixture was stirred for 30 min and then concentrated. The residue was taken up in water and lyophilized. 22.7 mg (81% of theory) of the title compound were obtained.

LC-MS (Method 1): $R_t$=1.14 min; m/z=880 (M+H)$^+$.

Intermediate 36 tert-butyl (2S)-1-(benzyloxy)-3-phenylpropan-2-yl carbamate

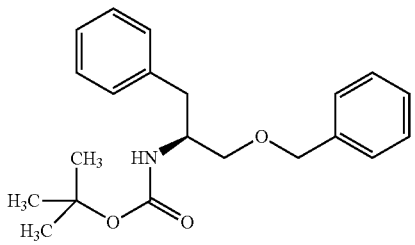 [SMILES: CC(C)(C)OC(=O)N[C@H](COCc1ccccc1)Cc1ccccc1]

Under an argon atmosphere, 500 mg (1.99 mmol) of N-Boc-L-phenylalaminol were dissolved in 5 ml of DMF and cooled to 0° C. Subsequently, 159 mg (3.98 mmol) of a 60% suspension of sodium hydride in paraffin oil were added. The reaction mixture was stirred until the evolution of gas had ended and then 260 µl (2.19 mmol) of benzyl bromide were added. The cooling bath was removed and the reaction mixture was stirred at RT for 2 h. Thereafter, the reaction mixture was concentrated, the residue was taken up in ice-water and the mixture was extracted with dichloromethane. The organic phase was washed with saturated sodium chloride solution, dried over magnesium sulphate and concentrated. The residue was purified by means of preparative HPLC. 226 mg (33% of theory) of the title compound were obtained.

LC-MS (Method 1): $R_t$=1.28 min; m/z=342 (M+H)$^+$.

Intermediate 37

(2S)-1-(benzyloxy)-3-phenylpropan-2-amine hydrochloride

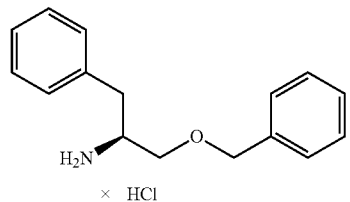 [SMILES: N[C@H](COCc1ccccc1)Cc1ccccc1 ; Cl]

220 mg (644 μmol) of tert-butyl (2S)-1-(benzyloxy)-3-phenylpropan-2-yl carbamate were dissolved in 11 ml of a 4 N solution of hydrogen chloride in dioxane and stirred at RT for 1 h. Then the reaction mixture was concentrated and the residue was dried under reduced pressure. 138 mg (77% of theory) of the title compound were obtained.

LC-MS (Method 1): $R_t$=0.65 min; m/z=242 (M+H)$^+$.

Intermediate 38

N-(tert-butoxycarbonyl)-N-methyl-L-valyl-N-[(3R,4S,5S)-1-{(2S)-2-[(1R,2R)-3-{[(2S)-1-(benzyloxy)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide To a solution of 20 mg (29 μmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide in 1 ml of DMF were added, at RT, 15.3 μl (88 μmol) of N,N-diisopropylethylamine, 6.7 mg (44 μmol) of HOBt and 6.7 mg (35 mmol) of EDC, and the mixture was stirred for 30 min. Subsequently, 7.8 mg (32 μmol) of (2S)-1-(benzyloxy)-3-phenylpropan-2-amine hydrochloride were added. After stirring overnight, the reaction mixture was separated directly into its components via preparative HPLC. 26 mg (98% of theory) of the title compound were obtained.

LC-MS (Method 1): $R_t$=1.51 min; m/z=909 (M+H)$^+$.

Intermediate 39

N-methyl-L-valyl-N-[(3R,4S,5S)-1-{(2S)-2-[(1R,2R)-3-{[(2S)-1-(benzyloxy)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

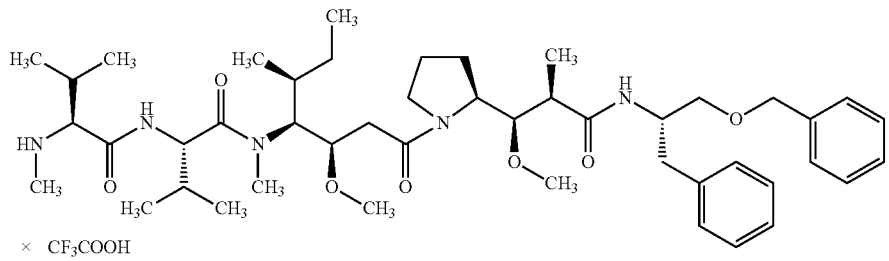

26 mg (29 μmol) of N-(tert-butoxycarbonyl)-N-methyl-L-valyl-N-[(3R,4S,5S)-1-{(2S)-2-[(1R,2R)-3-{[(2S)-1-(benzyloxy)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 1.8 ml of dichloromethane, and 370 μl of TFA were added. The reaction mixture was stirred at RT for 30 min and then concentrated. The residue was taken up in water and lyophilized. 26.4 mg (quant.) of the title compound were obtained.

LC-MS (Method 1): $R_t$=0.97 min; m/z=809 (M+H)$^+$.

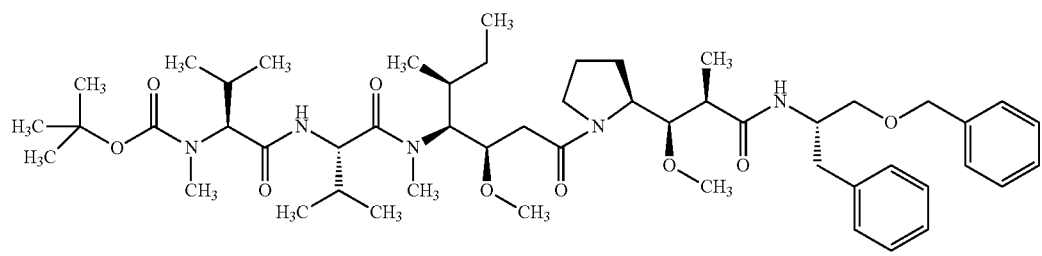 [SMILES: CC[C@H](C)[C@@H]([C@@H](CC(=O)N1CCC[C@H]1[C@H](OC)[C@@H](C)C(=O)N[C@H](COCc1ccccc1)Cc1ccccc1)OC)N(C)C(=O)[C@@H](NC(=O)[C@H](C(C)C)N(C)C(=O)OC(C)(C)C)C(C)C]

Intermediate 40

N-methyl-L-valyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide 1

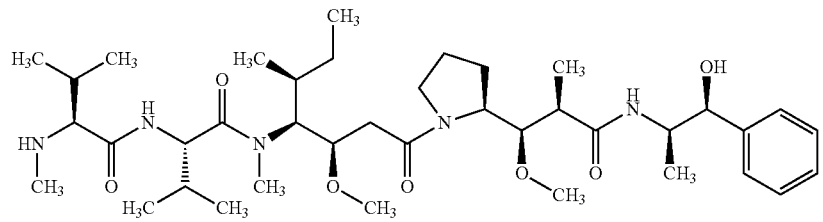 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

50 mg (70 μmol) of Intermediate 26 and 11 mg (70 μmol) of (1S,2R)-2-amino-1-phenylpropan-1-ol in 10 ml of DMF were admixed with 42 mg (0.11 μmol) of O-(7-azabenzotriazol-1-yl)-N,N,N',N'-tetramethyluronium hexafluorophosphate and 25 μl of N,N-diisopropylethylamine, and the reaction mixture was stirred at RT for 5 min. This was followed by concentration and purification of the residue by means of preparative HPLC. After combining the corresponding fractions, concentrating and drying under high vacuum, 49 mg (81%) of the protected intermediate were obtained. Subsequently, the Boc group was detached by known conditions with trifluoroacetic acid in dichloromethane. Concentration was followed by the purification of the title compound by preparative HPLC, and 26 mg (52%) of the title compound were obtained.

HPLC (Method 12): $R_t$=1.65 min;

LC-MS (Method 1): $R_t$=0.77 min; MS (ESIpos): m/z=718 (M+H)$^+$.

Intermediate 41

3-{2-[2-(2-aminoethoxy)ethoxy]ethoxy}propanoic acid trifluoroacetate

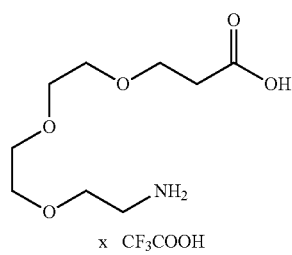 [SMILES: NCCOCCOCCOCCC(=O)O ; "CF3COOH"]

150 mg (541 μmol) of tert-butyl 3-{2-[2-(2-aminoethoxy)ethoxy]ethoxy}propanoate were dissolved in 3 ml of dichloromethane, 1.5 ml of trifluoroacetic acid were added, and the reaction mixture was stirred at RT for 1 h, then concentrated.

181 mg (100% of theory) of the title compound were obtained.

MS (EI): m/z 222 (M+H)$^+$

Intermediate 42

3-(2-{2-[2-(2,5-dioxo-2,5-dihydro-1H-pyrrol-1-yl)ethoxy]ethoxy}ethoxy)propanoic acid

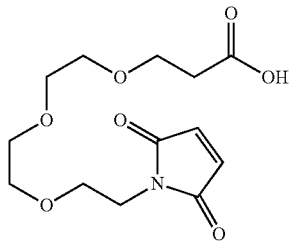 [SMILES: O=C(O)CCOCCOCCOCCN1C(=O)C=CC1=O]

186 mg (555 μmol) of 3-{2-[2-(2-aminoethoxy)ethoxy]ethoxy}propanoic acid trifluoroacetate were dissolved in 2.6 ml of saturated sodium hydrogencarbonate solution and admixed at 0° C. with 86 mg (555 μmol) of N-methoxycarbonylmaleimide. The reaction mixture was stirred at 0° C. for 40 min and at RT for 1 h, then cooled again to 0° C., adjusted to pH 3 with sulphuric acid and extracted 3× with 25 ml of ethyl acetate. The combined organic phases were dried over magnesium sulphate and concentrated.

126 mg (75% of theory) of the title compound were obtained.

LC-MS (Method 1): $R_t$=0.53 min; m/z=302 (M+H)$^+$.

Intermediate 43 tert-butyl 15-(2,5-dioxo-2,5-dihydro-1H-pyrrol-1-yl)-4-oxo-7,10,13-trioxa-2,3-diazapentadecan-1-oate

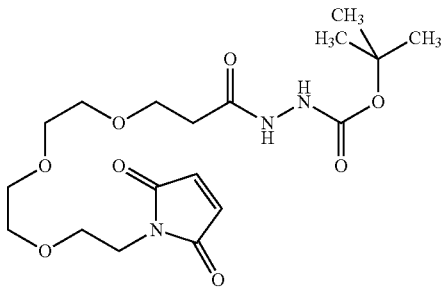 [SMILES: CC(C)(C)OC(=O)NNC(=O)CCOCCOCCOCCN1C(=O)C=CC1=O]

125 mg (417 μmol) of 3-(2-{2-[2-(2,5-dioxo-2,5-dihydro-1H-pyrrol-1-yl)ethoxy]ethoxy}ethoxy) propanoic acid were dissolved at 0° C. in 2.1 ml of THF and admixed with 46 μl (417 mmol) of 4-methylmorpholine and 54.5 μl (417 μmol) of isobutyl chloroformate. The ice bath was removed and the reaction mixture was stirred at RT for 30 min. Subsequently, at 0° C., 55 mg (417 μmol) of tert-butyloxycarbonyl hydrazide were added. The reaction mixture was warmed to RT overnight, concentrated and purified by preparative HPLC.

60 mg (33% of theory) of the title compound were obtained.

LC-MS (Method 1): $R_t$=0.66 min; m/z=416 (M+H)$^+$.

Intermediate 44

3-(2-{2-[2-(2,5-dioxo-2,5-dihydro-1H-pyrrol-1-yl)ethoxy]ethoxy}ethoxy)propanehydrazide trifluoroacetate

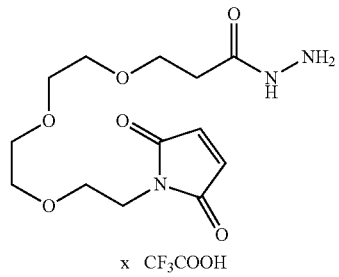 [SMILES: NNC(=O)CCOCCOCCOCCN1C(=O)C=CC1=O ; "CF3COOH"]

x CF$_3$COOH 60 mg (145 μmol) of tert-butyl 15-(2,5-dioxo-2,5-dihydro-1H-pyrrol-1-yl)-4-oxo-7,10,13-trioxa-2,3-diazapentadecan-1-oate were dissolved in 1 ml of dichloromethane, and 0.2 ml of trifluoroacetic acid was added. The reaction mixture was stirred at RT for 30 min and then concentrated.

62 mg (100% of theory) of the title compound were obtained.

LC-MS (Method 1): $R_t$=0.35 min; m/z=316 (M+H)$^+$.

Intermediate 45 benzyl(1S,2R)-1-amino-2-phenylcyclopropanecarboxylate trifluoroacetate

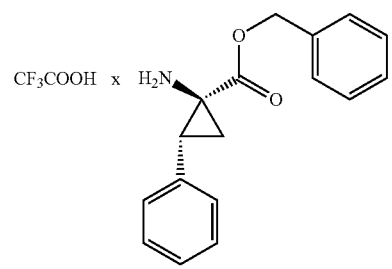 [SMILES: "CF3COOH" ; N[C@@]1(C(=O)OCc2ccccc2)C[C@@H]1c1ccccc1]

The title compound was prepared by standard methods, by esterifying commercially available (1S,2R)-1-[(tert-butoxycarbonyl)amino]-2-phenylcyclopropanecarboxylic acid with benzyl alcohol and subsequent Boc detachment with trifluoroacetic acid.

LC-MS (Method 1): $R_t$=0.72 min; MS (ESIpos): m/z=268 (M+H)$^+$.

Intermediate 46

N-(tert-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide

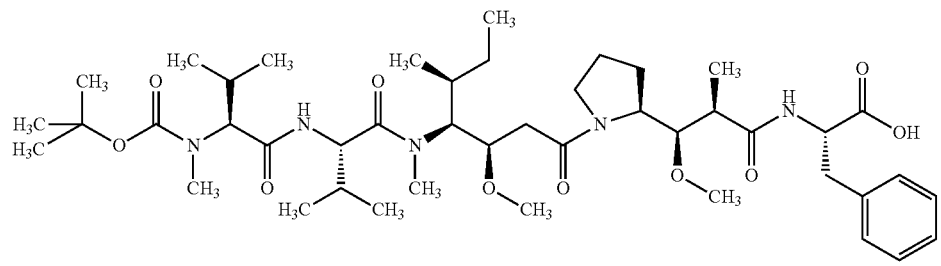 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OC(C)(C)C)C(C)C]

383 mg (0.743 mmol) of N-(tert-butoxycarbonyl)-N-methyl-L-valyl-N-[(2R,3S,4S)-1-carboxy-2-methoxy-4-methylhexan-3-yl]-N-methyl-L-valinamide (Intermediate 8) were combined with 485 mg (0.743 mmol) of benzyl N-{(2R,3R)-3-methoxy-2-methyl-3-[(2S)-pyrrolidin-2-yl]propanoyl}-L-phenylalaninate trifluoroacetate (Intermediate 12), 424 mg (1.114 mmol) of O-(7-azabenzotriazol-1-yl)-N,N,N',N'-tetramethyluronium hexafluorophosphate and 388 μl of N,N-diisopropylethylamine in 15 ml of DMF, and the mixture was stirred at RT for 10 min. Subsequently, the solvent was removed under reduced pressure. The remaining residue was taken up in ethyl acetate and extracted by shaking successively with 5% aqueous citric acid solution and saturated sodium hydrogencarbonate solution. The organic phase was removed and concentrated, and the residue was purified by means of preparative HPLC. The product fractions were combined and concentrated, and the residue was dried under high vacuum. 335 mg (48% of theory) of the benzyl ester intermediate were obtained as a foam.

LC-MS (Method 1): $R_t$=1.49 min; MS (ESIpos): m/z=922 (M+H)⁺.

100 mg (0.11 mmol) of this intermediate were taken up in 15 ml of methanol and the benzyl ester group was removed by hydrogenation under standard hydrogen pressure with 10% palladium on activated carbon as a catalyst. After stirring at RT for 1 h, the catalyst was filtered off and the filtrate was concentrated under reduced pressure. After lyophilization from dioxane, 85 mg (94% of theory) of the title compound were obtained as a solid.

HPLC (Method 12): $R_t$=2.4 min;

LC-MS (Method 1): $R_t$=1.24 min; MS (ESIpos): m/z=832 (M+H)⁺.

Intermediate 47

N-benzyl-L-tryptophanamide trifluoroacetate

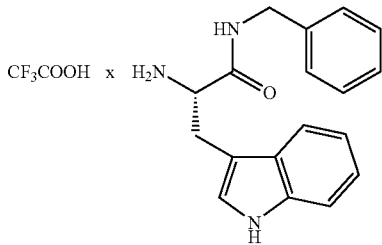 [SMILES: "CF3COOH" ; N[C@@H](Cc1c[nH]c2ccccc12)C(=O)NCc1ccccc1]

202 mg (0.5 mmol) of 2,5-dioxopyrrolidin-1-yl N-(tert-butoxycarbonyl)-L-tryptophanate and 45 mg (0.42 mmol) of benzylamine were dissolved in 10 ml of DMF, and 110 µl (630 µmol) of N,N-diisopropylethylamine were added. The reaction mixture was stirred at RT for 3 h. Subsequently, the reaction mixture was concentrated under reduced pressure and the residue was purified by flash chromatography on silica gel (eluent: 20:0.5:0.05 dichloromethane/methanol/ 17% aq. ammonia). The corresponding fractions were combined and concentrated. The resulting residue was digested with diethyl ether and then dried under high vacuum. Subsequently, this residue was taken up in 10 ml of dichloromethane, and 3 ml of anhydrous trifluoroacetic acid were added. After stirring at RT for 45 minutes, the mixture was concentrated and the residue was purified by preparative HPLC. After drying under high vacuum, 117 mg (57% of theory over both stages) of the title compound were obtained.

HPLC (Method 12): $R_t$=1.6 min;

LC-MS (Method 1): $R_t$=0.66 min; MS (ESIpos): m/z=294 (M+H)⁺.

Intermediate 48

(1S,2R)-1-amino-2-phenylcyclopropanecarboxamide trifluoroacetate

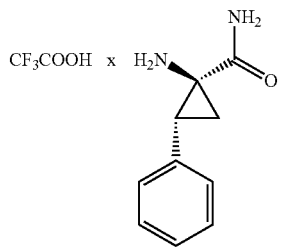 [SMILES: "CF3COOH" ; NC(=O)[C@]1(N)C[C@@H]1c1ccccc1]

50 mg (180 µmol) of commercially available (1S,2R)-1-[(tert-butoxycarbonyl)amino]-2-phenylcyclopropanecarboxylic acid were dissolved in 5 ml of DMF, 94 µl (541 µmol) of N,N-diisopropylethylamine, 31 mg (270 µmol) of N-hydroxysuccinimide and 41.5 mg (216 µmol) of EDC were added, and then the mixture was stirred at RT overnight. The reaction mixture was then concentrated, the residue was taken up in dioxane, 71 mg (901 µmol) of ammonium hydrogencarbonate were added, and the reaction mixture was then left to stand at RT for 3 days. The reaction mixture was then diluted with a 1:1 mixture of ethyl acetate and water. The organic phase was removed, dried over magnesium sulphate and concentrated. The resulting residue was subsequently taken up in 3 ml of dichloromethane, and 3 ml of anhydrous trifluoroacetic acid were added. Stirring at RT for 1 h was followed by concentration. The residue was stirred with pentane, filtered off with suction and lyophilized from dioxane. In this way, 32 mg (62% of theory over both stages) of the title compound were obtained.

HPLC (Method 6): $R_t$=0.38 min;

LC-MS (Method 1): $R_t$=0.20 min; MS (ESIpos): m/z=177 (M+H)⁺.

Intermediate 49

N^α-{(2R,3R)-3-methoxy-2-methyl-3-[(2S)-pyrrolidin-2-yl]propanoyl}-L-tryptophanamide trifluoroacetate

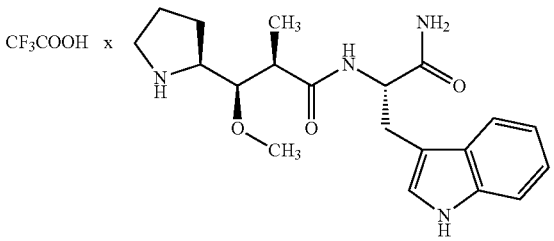 [SMILES: "CF3COOH" ; CO[C@@H]([C@@H]1CCCN1)[C@@H](C)C(=O)N[C@@H](Cc1c[nH]c2ccccc12)C(N)=O]

The title compound was prepared in analogy to the synthesis of Intermediate 13 from Starting Compound 1 and L-tryptophanamide hydrochloride.

HPLC (Method 5): $R_t$=1.4 min;

Intermediate 50

4-nitrophenyl 2-(2,5-dioxo-2,5-dihydro-1H-pyrrol-1-yl)ethyl carbamate

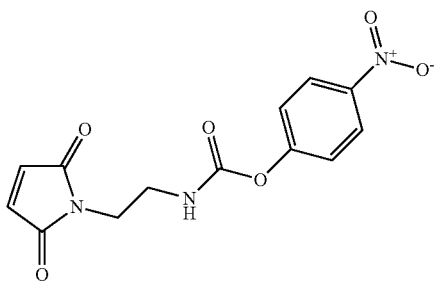 [SMILES: O=C(NCCN1C(=O)C=CC1=O)Oc1ccc([N+](=O)[O-])cc1]

813 mg (3.1 mmol) of triphenylphosphine were dissolved in 25 ml of THF and cooled to −70° C. under argon. After dropwise addition of 627 mg (3.1 mmol) of diisopropyl azodicarboxylate, the mixture was stirred for 5 min. Subsequently, 500 mg (3.1 mmol) of tert-butyl 2-aminoethyl carbamate dissolved in 5 ml of THF were added dropwise, and the reaction mixture was stirred at −70° C. for a further 5 min. Then 136.6 mg (1.55 mmol) of 2,2-dimethyl-1-propanol dissolved in 1 ml of THF and 301 mg (3.1 mmol) of maleimide were added, the reaction mixture was stirred at −70° C. for a further 10 min and then the mixture was warmed to RT. After stirring at RT for a further 16 h, the solvent was removed under reduced pressure and the residue was purified by means of preparative HPLC. This gave 463 mg (62%) of the protected intermediate.

After removing the Boc protecting group under standard conditions, 652 mg of 1-(2-aminoethyl)-1H-pyrrole-2,5-dione were obtained as the trifluoroacetate.

112.9 mg (543 µmol) of nitrophenyl chloroformate were dissolved in 30 ml of THF and, after addition of 100 mg (271.6 µmol) of 1-(2-aminoethyl)-1H-pyrrole-2,5-dione trifluoroacetate, the mixture was stirred at RT for 30 min. The mixture was filtered and the filtrate was concentrated to dryness and then slurried with diethyl ether. After filtration with suction and drying, 60 mg (95% of theory) of the title compound were obtained.

HPLC (Method 5): $R_t$=0.65 min;
LC-MS (Method 1): $R_t$=0.74 min; MS (ESIpos): m/z=306 (M+H)+.

Intermediate 51

(1S)-2-phenyl-1-(5-phenyl-1,3,4-oxadiazol-2-yl)ethanamine trifluoroacetate

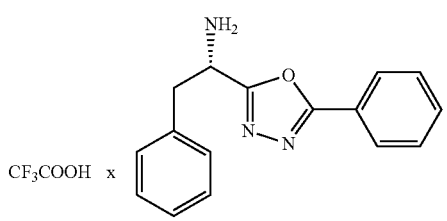 [SMILES: "CF3COOH" ; N[C@@H](Cc1ccccc1)c1nnc(-c2ccccc2)o1]

200 mg (0.75 mmol) of N-(tert-butoxycarbonyl)-L-phenylalanine were initially charged at 0° C. in 5.5 ml of dichloromethane, and 128 mg (0.79 mmol) of 1,1'-carbonyldiimidazole were added. After 30 min, 103 mg (0.75 mmol) of benzoyl hydrazide were added. After a further 45 min at 0° C., 500 mg (1.5 mmol) of carbon tetrabromide and 395 mg (1.5 mmol) of triphenylphosphine were finally added. The reaction mixture was stirred first at 0° C. for 2 h and then at RT overnight. The mixture was subsequently concentrated on a rotary evaporator, and the residue was dried under high vacuum. The crude product thus obtained was purified by means of preparative HPLC. 217 mg (78% of theory) of the Boc-protected intermediate tert-butyl (1S)-2-phenyl-1-(5-phenyl-1,3,4-oxadiazol-2-yl)ethyl carbamate were obtained.

LC-MS (Method 12): $R_t$=1.15 min; MS (ESIpos): m/z=366 (M+H)+

217 mg (0.59 mmol) of this intermediate were taken up in 3 ml of dichloromethane, 0.6 ml of trifluoroacetic acid were added, and the mixture was stirred at RT for 30 min. Subsequently, the reaction mixture was concentrated under reduced pressure. The remaining residue was the reaction mixture dried further under reduced pressure and then lyophilized from dioxane. In this way, 214 mg (90% of theory) of the title compound were obtained.

LC-MS (Method 11): $R_t$=0.62 min; MS (ESIpos): m/z=266 (M+H)+

Intermediate 52

(1R)-2-phenyl-1-(5-phenyl-1,3,4-oxadiazol-2-yl)ethanamine trifluoroacetate

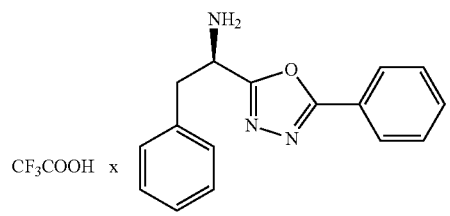 [SMILES: "CF3COOH" ; N[C@H](Cc1ccccc1)c1nnc(-c2ccccc2)o1]

200 mg (0.75 mmol) of N-(tert-butoxycarbonyl)-D-phenylalanine were initially charged at 0° C. in 5.5 ml of dichloromethane, and 128.3 mg (0.79 mmol) of 1,1'-carbonyldiimidazole were added. After 30 min, 103 mg (0.75 mmol) of benzoyl hydrazide were added. After a further 45 min at 0° C., 500 mg (1.5 mmol) of carbon tetrabromide and 395 mg (1.5 mmol) of triphenylphosphine were finally added. The reaction mixture was stirred first at 0° C. for 2 h and then at RT overnight. The mixture was subsequently concentrated on a rotary evaporator, and the residue was dried under high vacuum. The crude product thus obtained was purified by means of preparative HPLC. 219 mg (80% of theory) of the Boc-protected intermediate tert-butyl (1R)-2-phenyl-1-(5-phenyl-1,3,4-oxadiazol-2-yl)ethyl carbamate were obtained.

LC-MS (Method 2): $R_t$=1.36 min; MS (ESIpos): m/z=366 (M+H)+

219 mg (0.6 mmol) of this intermediate were taken up in 3 ml of dichloromethane, 0.6 ml of trifluoroacetic acid were added, and the mixture was stirred at RT for 30 min. Subsequently, the reaction mixture was concentrated under reduced pressure. The remaining residue was the reaction mixture dried further under reduced pressure and then lyophilized from dioxane. In this way, 196 mg (86% of theory) of the title compound were obtained as a solid.

HPLC (Method 10): $R_t$=2.41 min

Intermediate 53

(2S)-1-(benzylsulphonyl)-3-phenylpropan-2-amine

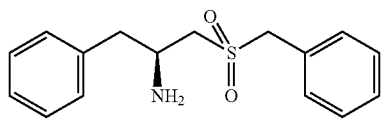 [SMILES: N[C@@H](Cc1ccccc1)CS(=O)(=O)Cc1ccccc1]

200 mg (1.13 mmol) of (4S)-4-benzyl-1,3-oxazolidin-2-one were initially charged in 3 ml of tert-butanol, and 280 mg (2.26 mmol) of benzyl mercaptan were added. The mixture was subsequently heated under reflux for 2 days. Thereafter, the reaction mixture was concentrated on a rotary evaporator and the resulting (2S)-1-(benzylsulphanyl)-3-phenylpropan-2-amine intermediate was converted further directly, without workup.

HPLC (Method 10): $R_t$=2.63 min

LC-MS (Method 1): $R_t$=0.67 min; MS (ESIpos): m/z=258 (M+H)$^+$

The crude intermediate obtained above was dissolved in a solution of 2 ml of 30% hydrogen peroxide and 5 ml of formic acid, and the mixture was stirred at RT for 12 h. Then the reaction mixture was added to saturated sodium sulphate solution and extracted three times with ethyl acetate. The organic phase was dried over magnesium sulphate and concentrated under reduced pressure. The crude product obtained was purified by means of preparative HPLC. 343 mg (61% of theory) of the title compound were thus obtained.

HPLC (Method 10): $R_t$=2.40 min;

LC-MS (Method 12): $R_t$=0.65 min; MS (ESIpos): m/z=290 (M+H)$^+$

Intermediate 54

(2S,3E)-1,4-diphenylbut-3-en-2-amine

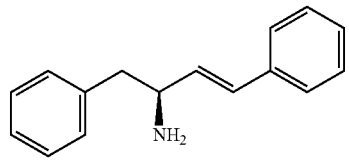 [SMILES: N[C@H](/C=C/c1ccccc1)Cc1ccccc1]

552.7 mg (9.85 mmol) of potassium hydroxide were dissolved in methanol, adsorbed onto 1.1 g of neutral aluminium oxide and then dried under high vacuum. To a solution of 240 mg (0.82 mmol) of (2S)-1-(benzylsulphonyl)-3-phenylpropan-2-amine and 1.56 g of the potassium hydroxide on aluminium oxide thus prepared in 6.2 ml of n-butanol were added dropwise, at 5-10° C., 307 µl (3.3 mmol) of dibromodifluoromethane. The reaction mixture was stirred at RT for 2 h, then filtered through Celite, and the residue was washed thoroughly with dichloromethane. The filtrate was concentrated and the resulting residue was dried under reduced pressure. The crude product thus obtained was purified by means of preparative HPLC. 98 mg (35% of theory) of the title compound were obtained with an E/Z diastereomer ratio of 4:1.

HPLC (Method 10): $R_t$=2.46 min;

LC-MS (Method 12): $R_t$=0.75 min; MS (ESIpos): m/z=224 (M+H)$^+$

The E/Z diastereomer mixture obtained above was dissolved in 2 ml of ethanol and 0.2 ml of N,N-diisopropylethylamine, and separated by means of HPLC on chiral phase [column: Daicel Chiralpak AD-H, 5 µm 250 mm×20 mm, eluent: hexane/(ethanol+0.2% diethylamine) 50:50 v/v; UV detection: 220 nm; temperature: 30° C.]. The appropriate fractions were concentrated on a rotary evaporator, and the residue was dried under reduced pressure. 45 mg of the title compound were obtained.

$^1$H NMR (400 MHz, DMSO-d$_6$) δ [ppm]=2.62-2.83 (m, 2H) 3.52-3.71 (m, 1H) 6.18-6.30 (m, 1H) 6.34-6.46 (m, 1H) 6.98-7.57 (m, 10H) [further signals hidden under solvent peaks].

Intermediate 55

N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetate

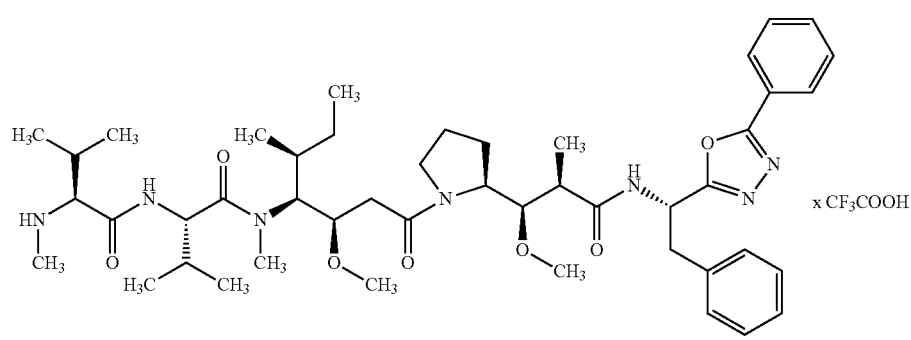 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@@H](NC)C(C)C)C(C)C]

20 mg (29 µmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide were dissolved in 1 ml of DMF, 13.3 mg (35 µmol) of HATU and 15.3 µl (88 µmol) of N,N-diisopropylethylamine were added, and the mixture was stirred at RT for 30 min. Subsequently, 12.2 mg (32 µmol) of (1S)-2-phenyl-1-(5-phenyl-1,3,4-oxadiazol-2-yl)ethanamine trifluoroacetate were added. The reaction mixture was stirred at RT overnight and then separated by preparative HPLC. This gave 22 mg (81% of theory) of N-(tert-butoxycarbonyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide.

LC-MS (Method 12): $R_t$=1.45 min; MS (ESIpos): m/z=933 $(M+H)^+$

By subsequently detaching the BOC protecting group with trifluoroacetic acid, 22.4 mg (98% of theory) of the title compound were then obtained.

LC-MS (Method 11): $R_t$=0.85 min; MS (ESIpos): m/z=833 $(M+H)^+$

Intermediate 56

N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetate

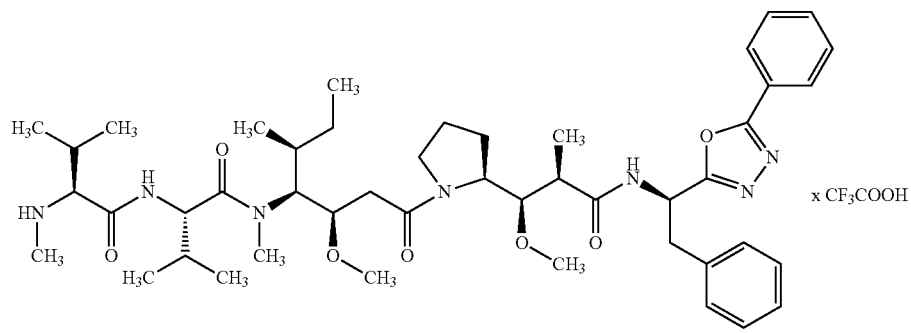 [SMILES: CC[C@H](C)[C@@H]([C@@H](CC(=O)N1CCC[C@H]1[C@H](OC)[C@@H](C)C(=O)N[C@H](Cc1ccccc1)c1nnc(-c2ccccc2)o1)OC)N(C)C(=O)[C@@H](NC(=O)[C@@H](NC)C(C)C)C(C)C]

N-(tert-Butoxycarbonyl)-N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide was prepared in analogy to the synthesis of Intermediate 55, by reaction of 20 mg (29 µmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide with 12.2 mg (32 µmol) of (1R)-2-phenyl-1-(5-phenyl-1,3,4-oxadiazol-2-yl)ethanamine trifluoroacetate.

Yield: 17 mg (64% of theory)

HPLC (Method 10): $R_t$=3.74 min;

LC-MS (Method 1): $R_t$=1.45 min; MS (ESIpos): m/z=933 $(M+H)^+$

By subsequently detaching the BOC protecting group with trifluoroacetic acid, 17.1 mg (99% of theory) of the title compound were then obtained.

HPLC (Method 10): $R_t$=2.55 min;

LC-MS (Method 11): $R_t$=0.85 min; MS (ESIpos): m/z=833 $(M+H)^+$

Intermediate 57

N-methyl-L-valyl-N-[(3R,4S,5S)-1-{(2S)-2-[(1R,2R)-3-{[(2S)-1-(benzylsulphonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

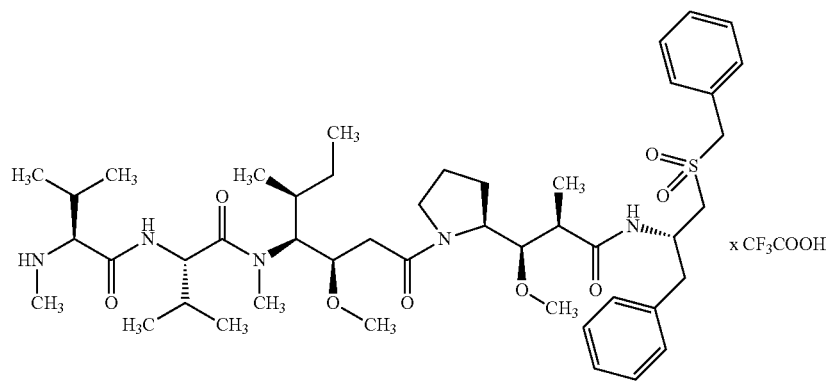 [SMILES: CC[C@H](C)[C@@H]([C@@H](CC(=O)N1CCC[C@H]1[C@H](OC)[C@@H](C)C(=O)N[C@@H](Cc1ccccc1)CS(=O)(=O)Cc1ccccc1)OC)N(C)C(=O)[C@@H](NC(=O)[C@@H](NC)C(C)C)C(C)C]

N-(tert-Butoxycarbonyl)-N-methyl-L-valyl-N-[(3R,4S,5S)-1-{(2S)-2-[(1R,2R)-3-{[(2S)-1-(benzylsulphonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared in analogy to the synthesis of Intermediate 55, by reaction of 20 mg (29 μmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide with 9.3 mg (20 μmol) of (2S)-1-(benzylsulphonyl)-3-phenylpropan-2-amine Yield: 19.2 mg (68% of theory)

HPLC (Method 10): $R_t$=3.5 min;

LC-MS (Method 12): $R_t$=1.41 min; MS (ESIpos): m/z=957 (M+H)$^+$

By subsequently detaching the BOC protecting group with trifluoroacetic acid, 19.3 mg (99% of theory) of the title compound were then obtained.

HPLC (Method 10): $R_t$=2.52 min;

LC-MS (Method 1): $R_t$=0.86 min; MS (ESIpos): m/z=857 (M+H)$^+$

Intermediate 58

N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

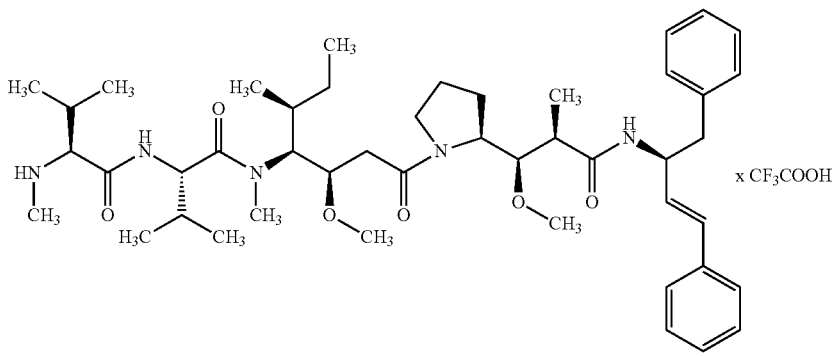 [SMILES: CC[C@H](C)[C@@H]([C@@H](CC(=O)N1CCC[C@H]1[C@H](OC)[C@@H](C)C(=O)N[C@H](/C=C/c1ccccc1)Cc1ccccc1)OC)N(C)C(=O)[C@@H](NC(=O)[C@@H](NC)C(C)C)C(C)C]

N-(tert-Butoxycarbonyl)-N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared in analogy to the synthesis of Intermediate 55, by reaction of 20 mg (29 μmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide with 7.1 mg (32 μmol) of (2S,3E)-1,4-diphenylbut-3-en-2-amine.

Yield: 15.1 mg (58% of theory)
HPLC (Method 10): $R_t$=4.2 min;
LC-MS (Method 12): $R_t$=1.51 min; MS (ESIpos): m/z=891 (M+H)$^+$ By subsequently detaching the BOC protecting group with trifluoroacetic acid, 15.7 mg (99% of theory) of the title compound were then obtained.
HPLC (Method 10): $R_t$=2.62 min;
LC-MS (Method 12): $R_t$=0.97 min; MS (ESIpos): m/z=791 (M+H)$^+$ Intermediate 61

N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

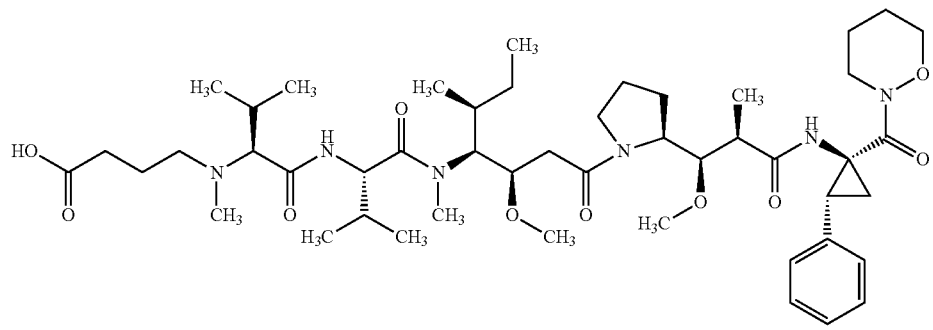 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)O)C(C)C]

50 mg (0.054 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide trifluoroacetate (Intermediate 16) were dissolved in 8 ml of dioxane/water, and 70 ml (0.108 mmol) of a 15% solution of 4-oxobutanoic acid in water were added. The reaction mixture was subsequently stirred at 100° C. for 1 h. After cooling to RT, 3.7 mg (0.059 mmol) of sodium cyanoborohydride were added and the mixture was adjusted to a pH of 3 by adding about 300 μl of 0.1 N hydrochloric acid. The reaction mixture was then stirred at 100° C. for a further 2 h. After cooling, another 70 ml (0.108 mmol) of the 15% 4-oxobutanoic acid solution were added and the reaction mixture was again stirred at 100° C. for 1 h. Then a further 3.7 mg (0.059 mmol) of sodium cyanoborohydride were added and about 300 μl of 0.1 N hydrochloric acid were subsequently used to adjust the pH back to 3. The reaction mixture was then stirred at 100° C. for another 2 h. In the event of conversion still being incomplete, this procedure was repeated for a third time. The reaction mixture was finally concentrated and the residue was purified by means of preparative HPLC. In this way, 32 mg (65% of theory) of the title compound were obtained in the form of a colourless foam.

HPLC (Method 5): $R_t$=1.64 min;
LC-MS (Method 9): $R_t$=4.76 min; MS (ESIpos): m/z=899 (M+H)$^+$ $^1$H NMR (500 MHz, DMSO-$d_6$): δ=8.95 and 8.8 (2m, 1H), 8.88 and 8.65 (2s, 1H), 7.4-7.1 (m, 5H), 5.0, 4.78, 4.65 and 4.55 (4m, 2H), 4.1-3.7 (m, 5H), 3.32, 3.29, 3.20, 3.12, 3.1 and 3.0 (6s, 9H), 2.75 (m, 2H), 2.63 (t, 1H), 2.4-2.2 (m, 4H), 2.1-1.2 (m, 12H), 1.2-0.8 (m, 16H), 0.75 (m, 3H) [further signals hidden under H$_2$O and DMSO peaks].

Intermediate 62

N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

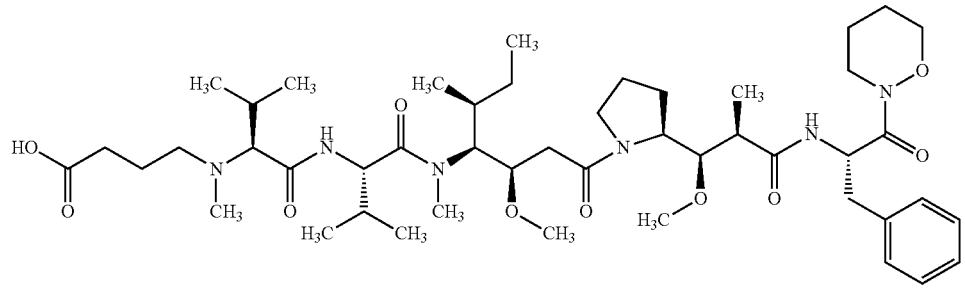 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCC(=O)O)C(C)C]

The title compound was prepared in analogy to the synthesis of Intermediate 61, by reaction of 50 mg of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide trifluoroacetate (Intermediate 14) with 4-oxobutanoic acid.

Yield: 34 mg (70% of theory)
HPLC (Method 5): $R_t$=1.64 min;
LC-MS (Method 9): $R_t$=4.77 min; MS (ESIpos): m/z=887 (M+H)$^+$.

Intermediate 63

N-(4-carboxybenzyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

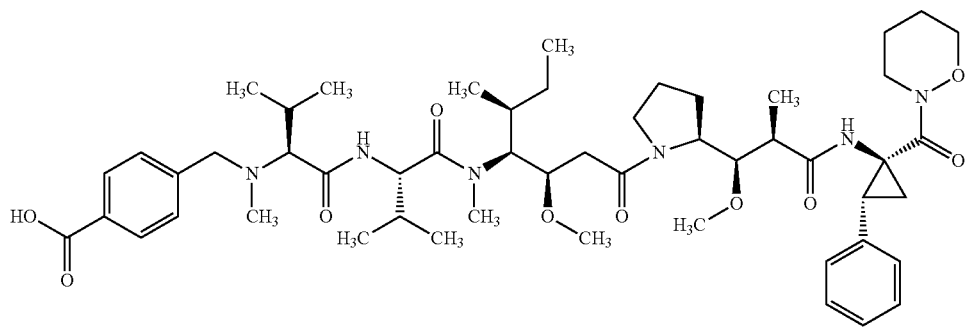 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)Cc1ccc(C(=O)O)cc1)C(C)C]

The title compound was prepared in analogy to the synthesis of Intermediate 61, by reaction of 15 mg of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide trifluoroacetate (Intermediate 16) with 4-formylbenzoic acid.

Yield: 7.5 mg (48% of theory)
HPLC (Method 5): $R_t$=1.75 min;
LC-MS (Method 1): $R_t$=0.97 min; MS (ESIpos): m/z=947 (M+H)$^+$.

Intermediate 64

N-(5-carboxypentyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

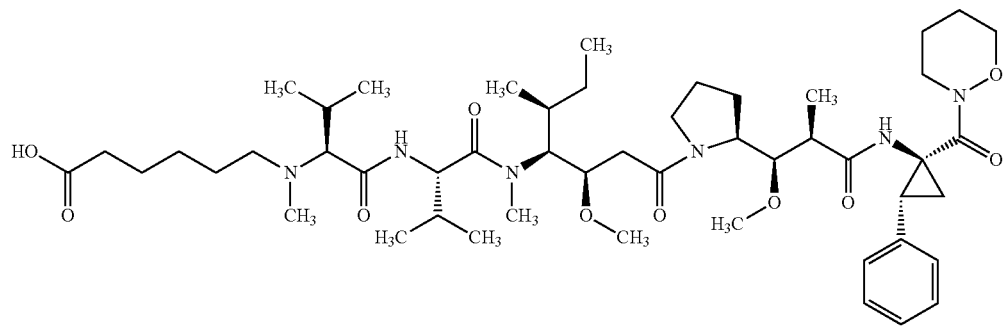 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCC(=O)O)C(C)C]

10 mg (0.011 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide trifluoroacetate (Intermediate 16) were dissolved in 2 ml of dioxane/water, and 2.8 mg (0.022 mmol) of 6-oxohexanoic acid were added. The reaction mixture was subsequently stirred at 100° C. for 1 h. After cooling to RT, 0.75 mg (0.012 mmol) of sodium cyanoborohydride was added and the mixture was adjusted to a pH of 3 by adding 0.1 N hydrochloric acid. The reaction mixture was then stirred at 100° C. for a further hour. After cooling, another 2.8 mg (0.022 mmol) of 6-oxohexanoic acid were added and the reaction mixture was again stirred at 100° C. for 1 h. A further 0.75 mg (0.012 mmol) of sodium cyanoborohydride was added and 0.1 N hydrochloric acid was subsequently used to adjust the pH back to 3. The reaction mixture was then stirred at 100° C. for another 1 h. This procedure was then repeated for a third time. The reaction mixture was finally concentrated and the crude product was purified by means of preparative HPLC. This gave 6.4 mg (64% of theory) of the title compound in the form of a colourless foam.

HPLC (Method 5): $R_t$=1.68 min;
LC-MS (Method 9): $R_t$=4.86 min; MS (ESIpos): m/z=927 (M+H)$^+$.

Intermediate 65

N-(2-aminoethyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide bistrifluoroacetate

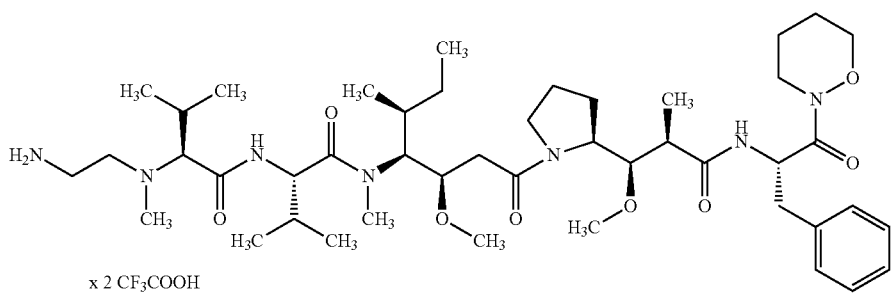 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCN)C(C)C]

x 2 CF$_3$COOH

The title compound was prepared by reaction of 68 mg of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide trifluoroacetate (Intermediate 14) with tert-butyl 2-oxoethyl carbamate and subsequent detachment of the Boc protecting group with trifluoroacetic acid.

Yield: 49 mg (62% of theory over two stages)
HPLC (Method 5): R$_t$=1.58 min;
LC-MS (Method 2): R$_t$=1.05 min; MS (ESIpos): m/z=844 (M+H)$^+$ $^1$H NMR (600 MHz, DMSO-d$_6$): δ=8.25 (m, 1H), 8.45 and 8.15 (2d, 1H), 7.65-7.55 (m, 3H), 7.23-7.1 (m, 5H), 5.12 and 4.95 (2m, 1H), 4.72 and 4.62 (2m, 1H), 4.6 and 4.52 (2t, 1H), 4.2-3.8 (m, 4H), 3.7 (d, 1H), 3.23, 3.20, 3.19, 3.18, 3.03 and 2.98 (6s, 9H), 3.0-2.7 (m, 6H), 2.4-1.2 (m, 15H), 1.05, 1.0, 0.88 and 0.82 (4d, 6H), 0.92 (m, 6H), 0.73 (m, 6H) [further signals hidden under H$_2$O peak].

Intermediate 66

N-(3-aminopropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

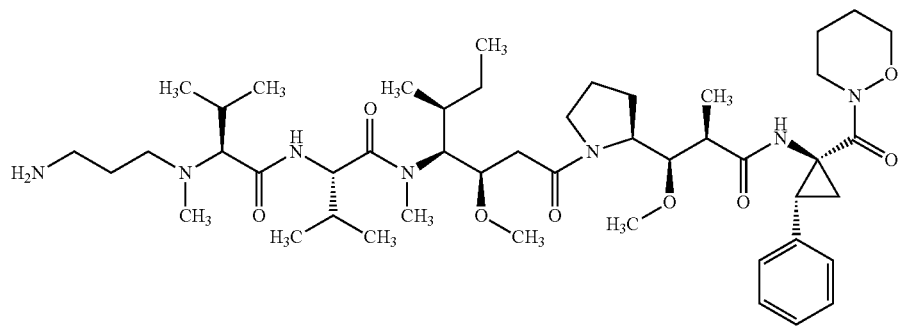 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCN)C(C)C]

The title compound was prepared in analogy to the synthesis of Intermediate 65, by reaction of 25 mg (0.027 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide trifluoroacetate (Intermediate 16) with benzyl 3-oxopropyl carbamate and subsequent hydrogenolytic detachment of the Z protecting group (with 10% palladium on charcoal as a catalyst, in ethanol as a solvent).

Yield: 11 mg (41% of theory over two stages)
HPLC (Method 5): R$_t$=1.53 min;
LC-MS (Method 1): R$_t$=0.72 min; MS (ESIpos): m/z=870 (M+H)$^+$.

Intermediate 67

N-(3-carboxypropyl)-N-methyl-L-valyl-N-[(3R,4S,5S)-1-{(2S)-2-[(1R,2R)-3-{[(2S)-1-(adamantan-1-ylmethoxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

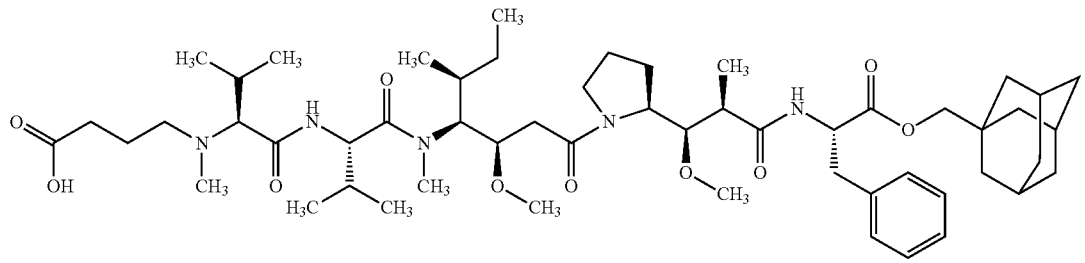 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCC12CC3CC(CC(C3)C1)C2)OC)N(C)C(=O)[C@@H](NC(=O)[C@H](C(C)C)N(C)CCCC(=O)O)C(C)C]

26 mg (26 µmol) of N-methyl-L-valyl-N-[(3R,4S,5S)-1-{(2S)-2-[(1R,2R)-3-{[(2S)-1-(adamantan-1-ylmethoxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate and 33.9 µl of a 15% aqueous succinaldehydic acid solution (53 µmol) were dissolved in 957 µl of a 1:1-dioxane/water mixture and heated to 100° C. for 1 h. After brief cooling, 1.81 mg (29 µmol) of sodium cyanoborohydride were added. The reaction mixture was adjusted to pH 3 by adding 0.1 N hydrochloric acid and the mixture was heated to 100° C. for a further 2 h. After again adding the same amounts of succinaldehydic acid solution, sodium cyanoborohydride and hydrochloric acid, the mixture was heated once again to 100° C. for 2 h. The reaction mixture was then separated directly into its components by means of preparative HPLC. 18.5 mg (73% of theory) of the title compound were thus obtained.

LC-MS (Method 1): $R_t$=1.17 min; m/z=967 (M+H)$^+$.

Intermediate 68

N-(3-carboxypropyl)-N-methyl-L-valyl-N-[(3R,4S,5S)-1-{(2S)-2-[(1R,2R)-3-{[(2S)-1-(benzyloxy)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

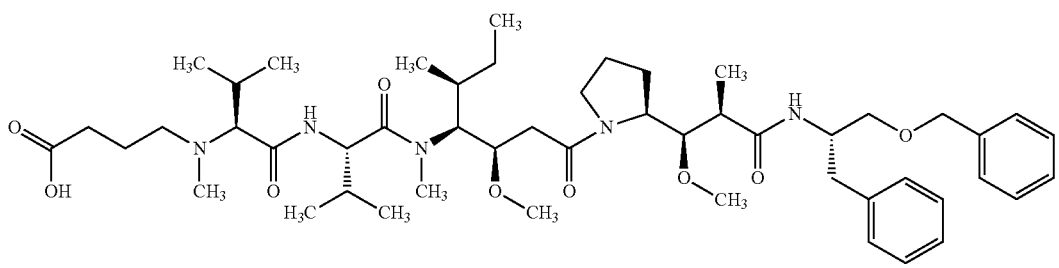 [SMILES: CC[C@H](C)[C@@H]([C@@H](CC(=O)N1CCC[C@H]1[C@H](OC)[C@@H](C)C(=O)N[C@H](COCc1ccccc1)Cc1ccccc1)OC)N(C)C(=O)[C@@H](NC(=O)[C@H](C(C)C)N(C)CCCC(=O)O)C(C)C]

24 mg (26 µmol) of N-methyl-L-valyl-N-[(3R,4S,5S)-1-{(2S)-2-[(1R,2R)-3-{[(2S)-1-(benzyloxy)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate and 33.7 µl of a 15% aqueous succinaldehydic acid solution (52 µmol) were dissolved in 953 µl of a 1:1-dioxane/water mixture and heated to 100° C. for 1 h. After brief cooling, 1.80 mg (29 µmol) of sodium cyanoborohydride were added. The reaction mixture was adjusted to pH 3 by adding 0.1 N hydrochloric acid and the mixture was heated to 100° C. for a further 2 h. After again adding the same amounts of succinaldehydic acid solution, sodium cyanoborohydride and hydrochloric acid, the mixture was heated once again to 100° C. for 2 h. The reaction mixture was then separated directly into its components by means of preparative HPLC. 15.2 mg (65% of theory) of the title compound were thus obtained.

LC-MS (Method 1): $R_t$=1.01 min; m/z=895 (M+H)$^+$

Intermediate 69

N-(3-carboxypropyl)-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

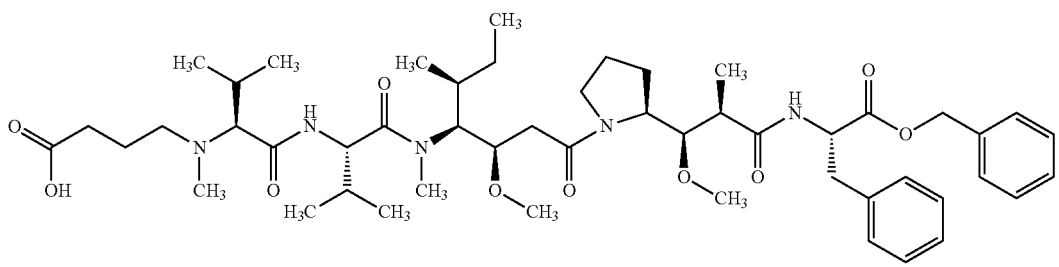 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1ccccc1)OC)N(C)C(=O)[C@@H](NC(=O)[C@H](C(C)C)N(C)CCCC(=O)O)C(C)C]

53 mg (84 µmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) and 45 mg (84 µmol) of benzyl N-{(2R,3R)-3-methoxy-2-methyl-3-[(2S)-pyrrolidin-2-yl]propanoyl}-L-phenylalaninate trifluoroacetate (Intermediate 12) were taken up in 2 ml of DMF, 19 µl of N,N-diisopropylethylamine, 14 mg (92 µmol) of HOBt and 17.6 mg (92 µmol) of EDC were added and then the mixture was stirred at RT overnight. Subsequently, the reaction mixture was concentrated and the residue was purified by means of preparative HPLC. This gave 59 mg (68% of theory) of the Fmoc-protected intermediate N-[(9H-fluoren-9-ylmethoxy)carbonyl]-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide LC-MS (Method 1): $R_t$=1.55 min; m/z=1044 (M+H)$^+$.

57 mg (0.055 mmol) of this intermediate were treated with 1.2 ml of piperidine in 5 ml of DMF to detach the Fmoc protecting group. After concentration and purification by means of preparative HPLC, 39 mg (76% of theory) of the free amine intermediate N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained as the trifluoroacetate.

HPLC (Method 5): $R_t$=1.9 min;
LC-MS (Method 1): $R_t$=1.01 min; m/z=822 (M+H)$^+$.

37 mg (0.045 mmol) of this intermediate were dissolved in 5 ml of dioxane/water and, analogously to the preparation of the compound in Intermediate 66, reacted with a 15% aqueous solution of 4-oxobutanoic acid in the presence of sodium cyanoborohydride. 16 mg (39% of theory) of the title compound were obtained in the form of a colourless foam.

HPLC (Method 6): $R_t$=2.1 min;
LC-MS (Method 1): $R_t$=1.01 min; MS (ESIpos): m/z=908 (M+H)$^+$.

Intermediate 70

N-(3-carboxypropyl)-N-methyl-L-valyl-N-[(3R,4S,5S)-1-{(2S)-2-[(1R,2R)-3-{[(2S,3S)-1-(benzyloxy)-1-oxo-3-phenylbutan-2-yl]amino}-1-methoxy-2-methyl-3-oxopropyl]pyrrolidin-1-yl}-3-methoxy-5-methyl-1-oxoheptan-4-yl]-N-methyl-L-valinamide

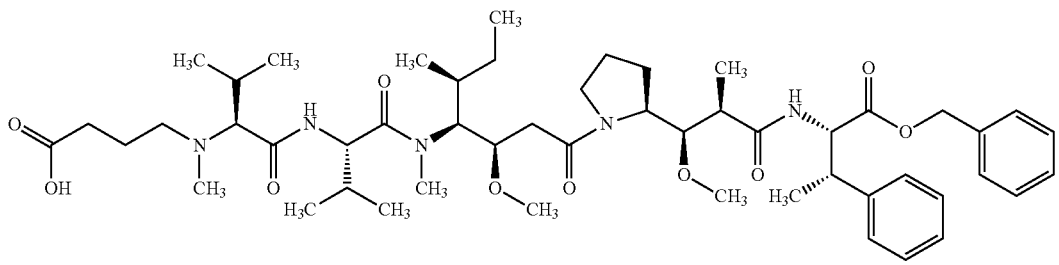 [SMILES: CC[C@H](C)[C@@H]([C@@H](CC(=O)N1CCC[C@H]1[C@H](OC)[C@@H](C)C(=O)N[C@H](C(=O)OCc1ccccc1)[C@@H](C)c1ccccc1)OC)N(C)C(=O)[C@@H](NC(=O)[C@H](C(C)C)N(C)CCCC(=O)O)C(C)C]

First, in analogy to the synthesis described in Intermediate 14, proceeding from Intermediates 4 and 26, the amine compound N-methyl-L-valyl-N-[(3R,4S,5S)-1-{(2S)-2-[(1R,2R)-3-{[(2S,3S)-1-(benzyloxy)-1-oxo-3-phenylbutan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared.

30 mg (0.032 mmol) of this compound were dissolved in 6 ml of dioxane/water, and 41 µl (0.063 mmol) of a 15% aqueous solution of 4-oxobutanoic acid were added. The reaction mixture was subsequently stirred at 100° C. for 1 h. After cooling to RT, 2.2 mg (0.035 mmol) of sodium cyanoborohydride were added and the mixture was adjusted to a pH of 3 by adding about 300 µl of 0.1 N hydrochloric acid. The reaction mixture was then stirred at 100° C. for a further 2 h. After cooling, another 41 µl (0.063 mmol) of the 15% 4-oxobutanoic acid solution were added and the reaction mixture was again stirred at 100° C. for 1 h. Then a further 2.2 mg (0.035 mmol) of sodium cyanoborohydride were added and about 300 µl of 0.1 N hydrochloric acid were subsequently used to adjust the pH back to 3. The reaction mixture was then stirred at 100° C. for another 2 h. In the event of conversion still being incomplete, this procedure was repeated for a third time. The reaction mixture was finally concentrated and the crude product was purified by means of preparative HPLC. This gave 24 mg (82% of theory) of the title compound in the form of a colourless foam.

HPLC (Method 5): $R_t$=1.9 min;
LC-MS (Method 9): $R_t$=5.15 min; MS (ESIpos): m/z=922 (M+H)$^+$.

Intermediate 71

N-(3-carboxypropyl)-N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide

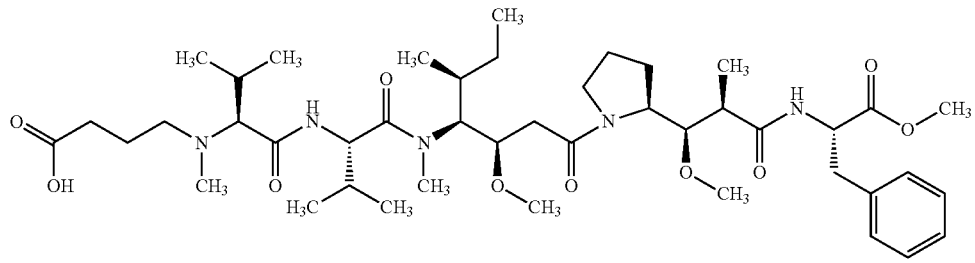 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCCC(=O)O)C(C)C]

First, in analogy to the synthesis described in Intermediate 14, proceeding from Intermediates 4 and 39, the amine compound N-methyl-L-valyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide was prepared. 7 mg (0.009 mmol) of this compound were then used, in analogy to the preparation of Intermediate 61, by reaction with 4-oxobutanoic acid in the presence of sodium cyanoborohydride, to obtain 2 mg (22% of theory) of the title compound in the form of a colourless foam.

HPLC (Method 6): $R_t$=1.9 min;

LC-MS (Method 2): $R_t$=1.06 min; MS (ESIpos): m/z=832 $(M+H)^+$.

Intermediate 72

N-(3-carboxypropyl)-N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

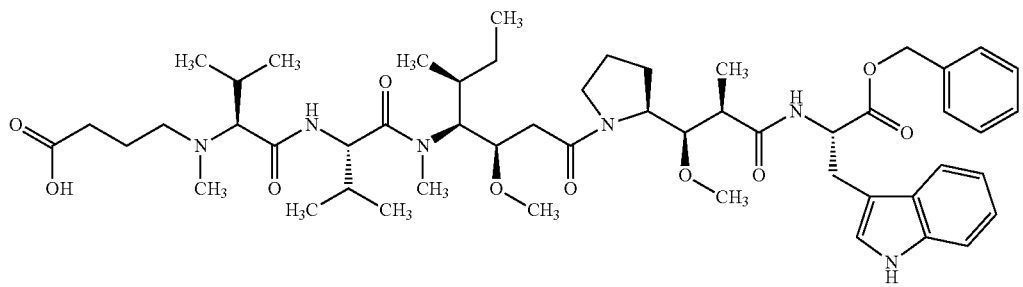 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OCc1ccccc1)OC)N(C)C(=O)[C@@H](NC(=O)[C@H](C(C)C)N(C)CCCC(=O)O)C(C)C]

212 mg (411 μmol) of N-(tert-butoxycarbonyl)-N-methyl-L-valyl-N-[(2R,3S,4S)-1-carboxy-2-methoxy-4-methyl-hexan-3-yl]-N-methyl-L-valinamide (Intermediate 8) and 237 mg (411 μmol) of benzyl-N-{(2R,3R)-3-methoxy-2-methyl-3-[(2S)-pyrrolidin-2-yl]propanoyl}-L-tryptophanate trifluoroacetate (Intermediate 20) were taken up in 30 ml of DMF, and 188 mg (493 μmol) of O-(7-azabenzotriazol-1-yl)-N,N,N',N'-tetramethyluronium hexafluorophosphate and 215 μl N,N-diisopropylethylamine were added. The reaction mixture was stirred at RT for 20 h, then concentrated under reduced pressure, and the residue was purified by means of preparative HPLC. The product fractions were combined and concentrated, and the residue was dried under high vacuum. This gave 315 mg (80% of theory) of the Boc-protected intermediate N-(tert-butoxycarbonyl)-N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide as a colourless foam.

LC-MS (Method 1): $R_t$=1.45 min; m/z=961 $(M+H)^+$.

50 mg (52 μmol) of this intermediate were treated with 1 ml of trifluoroacetic acid in 9 ml of dichloromethane to detach the Boc protecting group. After concentration and purification by means of preparative HPLC, 29 mg (57% of theory) of the free amine intermediate N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained as the trifluoroacetate.

LC-MS (Method 1): $R_t$=0.99 min; m/z=861 (M+H)$^+$.

29 mg (0.03 mmol) of this intermediate were dissolved in 6 ml of dioxane/water, and 39 μl (0.059 mmol) of a 15% aqueous solution of 4-oxobutanoic acid were added. The reaction mixture was subsequently stirred at 100° C. for 1 h. After cooling to RT, 2 mg (0.033 mmol) of sodium cyanoborohydride were added and the mixture was adjusted to a pH of 3 by adding about 300 μl of 0.1 N hydrochloric acid. The reaction mixture was then stirred at 100° C. for a further 2 h. After cooling, another 39 μl (0.059 mmol) of the 15% 4-oxobutanoic acid solution were added and the reaction mixture was again stirred at 100° C. for 1 h. Then a further 2 mg (0.033 mmol) of sodium cyanoborohydride were added and about 300 μl of 0.1 N hydrochloric acid were subsequently used to adjust the pH back to 3. The mixture was then stirred at 100° C. for another 2 h. Thereafter, the reaction mixture was poured onto a 1:1 mixture of semisaturated aqueous ammonium chloride solution and ethyl acetate. The organic phase was removed, washed with saturated sodium chloride solution, dried over sodium sulphate and concentrated. The residue was freeze-dried from water/acetonitrile. This gave 27 mg (94% of theory) of the title compound in the form of a colourless foam.

HPLC (Method 5): $R_t$=2.2 min;
LC-MS (Method 9): $R_t$=5.04 min; MS (ESIpos): m/z=947 (M+H)$^+$.

Intermediate 73

N-(3-carboxypropyl)-N-methyl-L-valyl-N-[(3R,4S,5S)-1-{(2S)-2-[(1R,2R)-3-({(2S)-1-[benzyl(methyl)amino]-1-oxo-3-phenylpropan-2-yl}amino)-1-methoxy-2-methyl-3-oxopropyl]pyrrolidin-1-yl}-3-methoxy-5-methyl-1-oxoheptan-4-yl]-N-methyl-L-valinamide

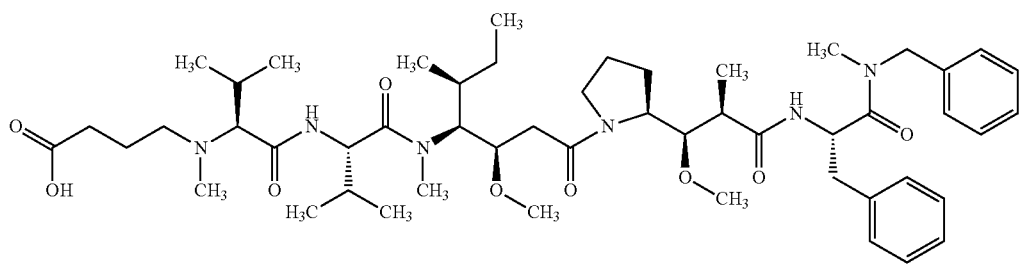 [SMILES: CC[C@H](C)[C@@H]([C@@H](CC(=O)N1CCC[C@H]1[C@H](OC)[C@@H](C)C(=O)N[C@@H](Cc1ccccc1)C(=O)N(C)Cc1ccccc1)OC)N(C)C(=O)[C@@H](NC(=O)[C@H](C(C)C)N(C)CCCC(=O)O)C(C)C]

First, in analogy to the synthesis described in Intermediate 14, proceeding from Intermediates 4 and 38, the amine compound N-methyl-L-valyl-N-[(3R,4S,5S)-1-{(2S)-2-[(1R,2R)-3-({(2S)-1-[benzyl(methyl)amino]-1-oxo-3-phenylpropan-2-yl}amino)-1-methoxy-2-methyl-3-oxopropyl]pyrrolidin-1-yl}-3-methoxy-5-methyl-1-oxoheptan-4-yl]-N-methyl-L-valinamide was prepared. 25 mg (0.026 mmol) of this compound were then used, in analogy to the preparation of Intermediate 61, by reaction with 4-oxobutanoic acid in the presence of sodium cyanoborohydride, to obtain 13 mg (54% of theory) of the title compound in the form of a colourless foam.

HPLC (Method 12): $R_t$=2.2 min;

LC-MS (Method 9): $R_t$=5.01 min; MS (ESIpos): m/z=921 (M+H)$^+$.

Intermediate 74

N-(3-carboxypropyl)-N-methyl-L-valyl-N-[(3R,4S, 5S)-1-{(2S)-2-[(1R,2R)-3-({(1S,2R)-1-[(benzyloxy)carbonyl]-2-phenylcyclopropyl}amino)-1-methoxy-2-methyl-3-oxopropyl]pyrrolidin-1-yl}-3-methoxy-5-methyl-1-oxoheptan-4-yl]-N-methyl-L-valinamide

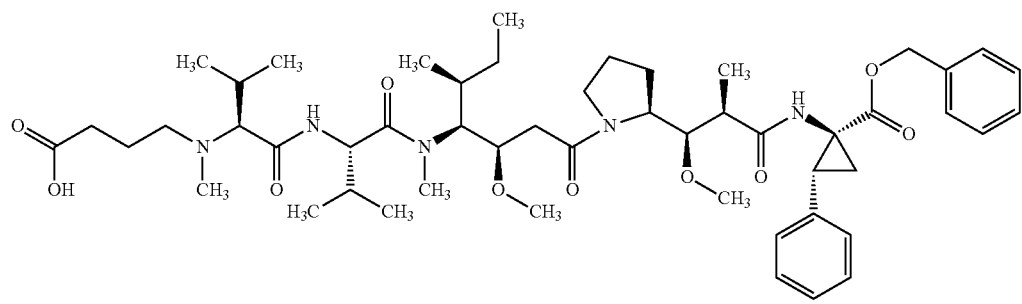 [SMILES: CC[C@H](C)[C@@H]([C@@H](CC(=O)N1CCC[C@H]1[C@H](OC)[C@@H](C)C(=O)N[C@@]1(C(=O)OCc2ccccc2)C[C@@H]1c1ccccc1)OC)N(C)C(=O)[C@@H](NC(=O)[C@H](C(C)C)N(C)CCCC(=O)O)C(C)C]

50 mg (73 µmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and 28 mg (73 µmol) of benzyl(1S,2R)-1-amino-2-phenylcyclopropanecarboxylate trifluoroacetate (Intermediate 45) were taken up in 5 ml of DMF, and 42 mg (110 µmol) of O-(7-azabenzotriazol-1-yl)-N,N,N',N'-tetramethyluronium hexafluorophosphate and 38 µl of N,N-diisopropylethylamine were added. The reaction mixture was stirred at RT for 5 h, then concentrated under reduced pressure, and the residue was purified by means of preparative HPLC. The product fractions were combined and concentrated. After lyophilization from dioxane/water, 35 mg (51% of theory) of the Boc-protected intermediate N-(tert-butoxycarbonyl)-N-methyl-L-valyl-N-[(3R,4S,5S)-1-{(2S)-2-[(1R,2R)-3-({(1S,2R)-1-[(benzyloxy)carbonyl]-2-phenylcyclopropyl}amino)-1-methoxy-2-methyl-3-oxopropyl]pyrrolidin-1-yl}-3-methoxy-5-methyl-1-oxoheptan-4-yl]-N-methyl-L-valinamide were obtained as a colourless foam.

LC-MS (Method 1): $R_t$=1.52 min; m/z=934 (M+H)$^+$.

35 mg of this intermediate were treated with 1 ml of trifluoroacetic acid in 5 ml of dichloromethane to detach the Boc protecting group. After concentration and lyophilization from dioxane/water, 34 mg (97% of theory) of the free amine intermediate N-methyl-L-valyl-N-[(3R,4S,5S)-1-{(2S)-2-[(1R,2R)-3-({(1S,2R)-1-[(benzyloxy)carbonyl]-2-phenylcyclopropyl}amino)-1-methoxy-2-methyl-3-oxopropyl]pyrrolidin-1-yl}-3-methoxy-5-methyl-1-oxoheptan-4-yl]-N-methyl-L-valinamide were obtained as the trifluoroacetate.

LC-MS (Method 1): $R_t$=0.91 min; m/z=834 (M+H)$^+$.

11 mg (0.011 mmol) of this intermediate were then used, in analogy to the preparation of Intermediate 66, by reaction with 4-oxobutanoic acid in the presence of sodium cyanoborohydride, to obtain 2.5 mg (24% of theory) of the title compound in the form of a colourless foam.

HPLC (Method 12): $R_t$=2.2 min;
LC-MS (Method 9): $R_t$=5.1 min; MS (ESIpos): m/z=920 (M+H)$^+$.

Intermediate 75

N-(3-carboxypropyl)-N-methyl-L-valyl-N-[(3R,4S, 5S)-3-methoxy-1-{(2S)-2-[(1R,2R)-1-methoxy-2-methyl-3-oxo-3-{[(1S,2R)-2-phenyl-1-(propylcarbamoyl)cyclopropyl]amino}propyl]pyrrolidin-1-yl}-5-methyl-1-oxoheptan-4-yl]-N-methyl-L-valinamide

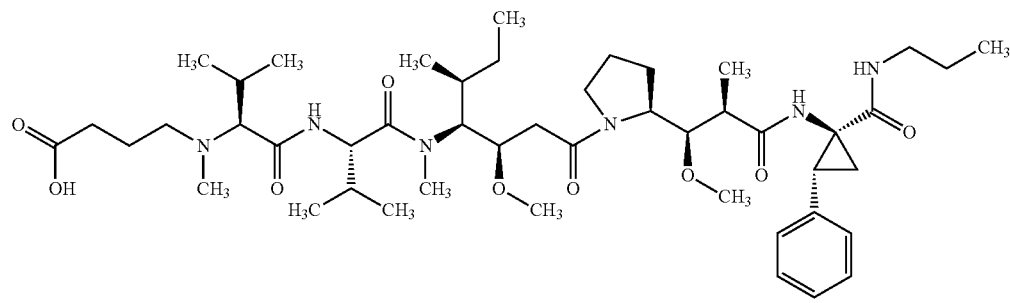 [SMILES: CCCNC(=O)[C@]1(NC(=O)[C@H](C)[C@@H](OC)[C@@H]2CCCN2C(=O)C[C@@H](OC)[C@H]([C@@H](C)CC)N(C)C(=O)[C@@H](NC(=O)[C@H](C(C)C)N(C)CCCC(=O)O)C(C)C)C[C@@H]1c1ccccc1]

First, in analogy to the synthesis described in Intermediate 74, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and (1S,2R)-1-amino-2-phenyl-N-propylcyclopropanecarboxamide trifluoroacetate (Intermediate 27) in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-[(3R,4S,5S)-3-methoxy-1-{(2S)-2-[(1R,2R)-1-methoxy-2-methyl-3-oxo-3-{[(1S,2R)-2-phenyl-1-(propylcarbamoyl)cyclopropyl]amino}propyl]pyrrolidin-1-yl}-5-methyl-1-oxoheptan-4-yl]-N-methyl-L-valinamide was prepared as the trifluoroacetate. 14 mg (0.016 mmol) of this compound were then used, in analogy to the preparation of Intermediate 61, by reaction with 4-oxobutanoic acid in the presence of sodium cyanoborohydride, to obtain 11.3 mg (83% of theory) of the title compound.

HPLC (Method 6): $R_t$=1.9 min;
LC-MS (Method 2): $R_t$=1.27 min; MS (ESIpos): m/z=871 $(M+H)^+$.

Intermediate 76

N-(3-carboxypropyl)-N-methyl-L-valyl-N-[(3R,4S,5S)-1-{(2S)-2-[(1R,2R)-3-{[(1S,2R)-1-(ethoxycarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

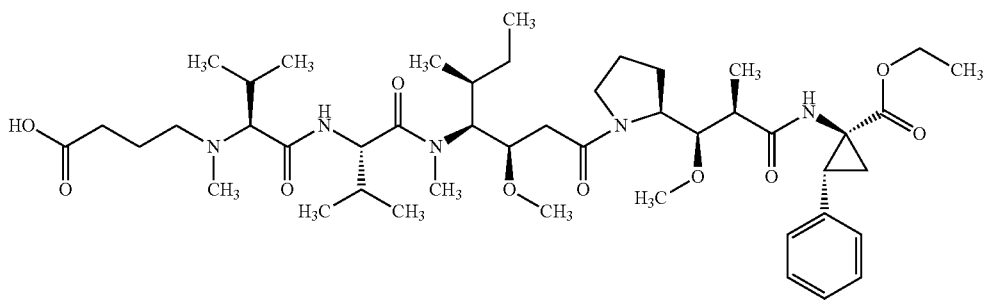 [SMILES: CCOC(=O)[C@]1(NC(=O)[C@H](C)[C@@H](OC)[C@@H]2CCCN2C(=O)C[C@@H](OC)[C@H]([C@@H](C)CC)N(C)C(=O)[C@@H](NC(=O)[C@H](C(C)C)N(C)CCCC(=O)O)C(C)C)C[C@@H]1c1ccccc1]

First, by coupling of Intermediate 46 (N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide) with Intermediate 48 (ethyl (1S,2R)-1-amino-2-phenylcyclopropanecarboxylate trifluoroacetate) in the presence of O-(7-azabenzotriazol-1-yl)-N,N,N',N'-tetramethyluronium hexafluorophosphate and subsequent Boc detachment, the starting compound N-methyl-L-valyl-N-[(3R,4S,5S)-1-{(2S)-2-[(1R,2R)-3-{[(1S,2R)-1-(ethoxycarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate was prepared. 70 mg (0.079 mmol) of this starting material were then used, by reaction with 4-oxobutanoic acid, in analogy to Intermediate 61, to obtain 46 mg (68% of theory) of the title compound.

HPLC (Method 6): $R_t$=1.9 min;
LC-MS (Method 2): $R_t$=1.28 min; MS (ESIpos): m/z=858 $(M+H)^+$ Intermediate 77

N-(3-carboxypropyl)-N-methyl-L-valyl-N-[(3R,4S,5S)-1-{(2S)-2-[(1R,2R)-3-{[(2S)-1-amino-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

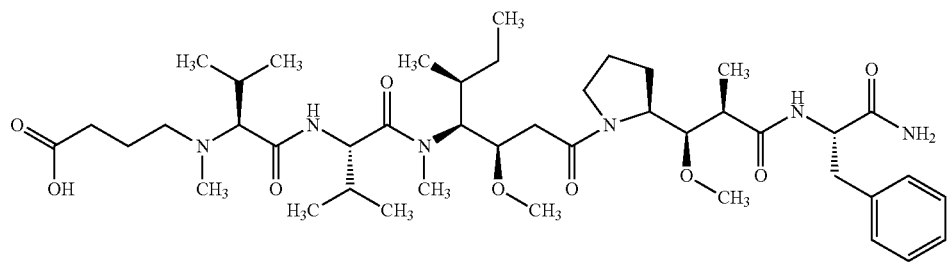 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](C(C)C)N(C)CCCC(=O)O)C(C)C]

First, in analogy to the synthesis described in Intermediate 75, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and L-phenylalaninamide hydrochloride in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-[(3R,4S,5S)-1-{(2S)-2-[(1R,2R)-3-{[(2S)-1-amino-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 47 mg (0.049 mmol) of this compound were then used, in analogy to the preparation of Intermediate 61, by reaction with 4-oxobutanoic acid in the presence of sodium cyanoborohydride, to obtain 39 mg (96% of theory) of the title compound.

HPLC (Method 6): $R_t$=1.7 min;
LC-MS (Method 9): $R_t$=4.44 min; MS (ESIpos): m/z=817 (M+H)$^+$
$^1$H NMR (500 MHz, DMSO-d$_6$): δ=8.95 and 8.8 (2m, 1H), 8.25 and 8.0 (2d, 1H), 7.45, 7.35 and 7.0 (3s, broad, 2H), 7.3-7.1 (m, 5H), 4.8-4.4 (2m, 3H), 3.95 (m, 1H), 3.82 (m, 1H), 3.72 (d, 1H), 3.22, 3.18, 3.15, 3.05 and 3.00 (5s, 9H), 2.85-2.7 (m, 4H), 2.45-1.6 (m, 12H), 1.5-1.2 (m, 3H), 1.1-0.7 (m, 21H) [further signals hidden under solvent peaks].

Intermediate 78

N-(6-aminohexyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

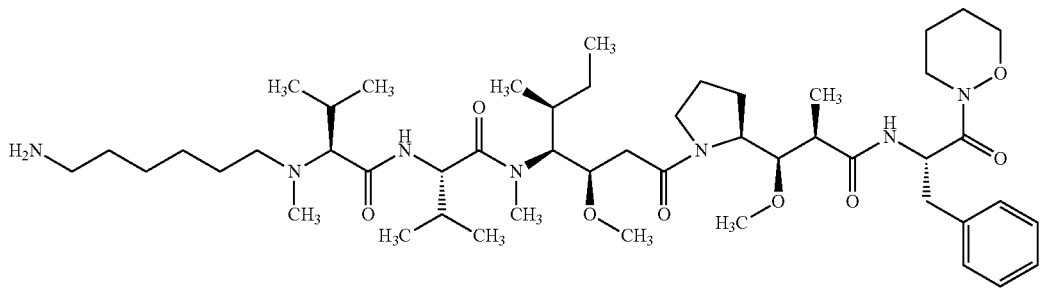 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCCCCN)C(C)C]

This compound was prepared in analogy to Intermediate 66 over 2 stages, proceeding from 20 mg (16 µmol) of the compound from Intermediate 14 and benzyl 6-oxohexyl carbamate, and the hydrogenation was performed in methanol as the solvent.

Yield: 7.6 mg (55% of theory over 2 stages)
HPLC (Method 6): $R_t$=1.8 min;
LC-MS (Method 1): $R_t$=0.7 min; MS (ESIpos): m/z=901 (M+H)$^+$.

Intermediate 79

N-(3-carboxypropyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

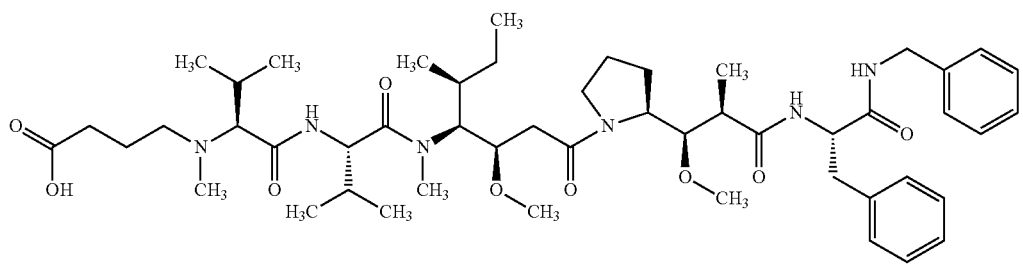 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCc1ccccc1)OC)N(C)C(=O)[C@@H](NC(=O)[C@H](C(C)C)N(C)CCCC(=O)O)C(C)C]

36 mg (43 µmol) of N-(tert-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (Intermediate 46) and 4.6 mg (43 µmol) of benzylamine were taken up in 5 ml of DMF, 7.5 µl (88 µmol) of N,N-diisopropylethylamine, 10 mg (65 µmol) of HOBt and 10 mg (52 µmol) of EDC were added, and then the mixture was stirred at RT overnight. Subsequently, the reaction mixture was concentrated and the residue was purified by means of preparative HPLC. 29 mg (73% of theory) of the Boc-protected intermediate N-(tert-butoxycarbonyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained.

LC-MS (Method 1): $R_t$=1.43 min; m/z=921 (M+H)$^+$.

29 mg of this intermediate were treated with 1 ml of trifluoroacetic acid in 6 ml of dichloromethane to detach the Boc protecting group. After concentration and lyophilization from dioxane/water, 30 mg (quant.) of the free amine intermediate N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained as the trifluoroacetate.

LC-MS (Method 1): $R_t$=0.95 min; m/z=821 (M+H)$^+$.

17 mg (0.018 mmol) of this intermediate were then used, in analogy to the preparation of Intermediate 61, by reaction with 4-oxobutanoic acid in the presence of sodium cyanoborohydride, to obtain 13 mg (80% of theory) of the title compound in the form of a colourless foam.

HPLC (Method 5): $R_t$=1.7 min;

LC-MS (Method 9): $R_t$=4.97 min; MS (ESIpos): m/z=907 (M+H)$^+$.

Intermediate 80

N-(3-carboxypropyl)-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

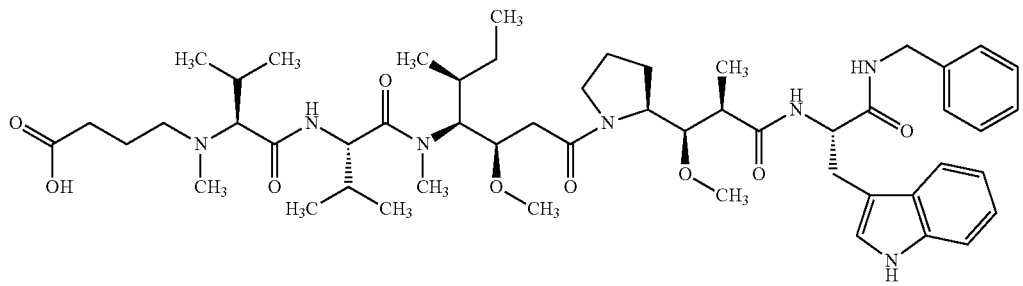 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)NCc1ccccc1)OC)N(C)C(=O)[C@@H](NC(=O)[C@H](C(C)C)N(C)CCCC(=O)O)C(C)C]

First, in analogy to the synthesis described in Intermediate 74, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and N-benzyl-L-tryptophanamide trifluoroacetate (Intermediate 47) in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 10 mg (0.01 mmol) of this compound were then used, in analogy to the preparation of Intermediate 61, by reaction with 4-oxobutanoic acid in the presence of sodium cyanoborohydride, to obtain 2.5 mg (26% of theory) of the title compound.

HPLC (Method 5): $R_t$=1.7 min;

LC-MS (Method 2): $R_t$=1.13 min; MS (ESIpos): m/z=946 (M+H)$^+$.

Intermediate 81

N-(3-carboxypropyl)-N-methyl-L-valyl-N-[(3R,4S,5S)-1-{(2S)-2-[(1R,2R)-3-{[(1S,2R)-1-carbamoyl-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

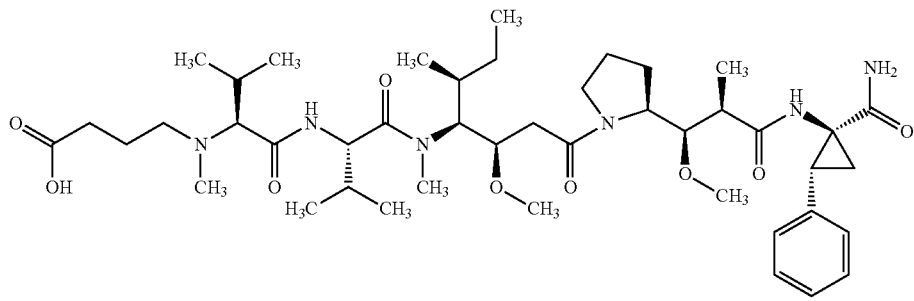 [SMILES: CC[C@H](C)[C@@H]([C@@H](CC(=O)N1CCC[C@H]1[C@H](OC)[C@@H](C)C(=O)N[C@@]1(C(N)=O)C[C@@H]1c1ccccc1)OC)N(C)C(=O)[C@@H](NC(=O)[C@H](C(C)C)N(C)CCCC(=O)O)C(C)C]

First, in analogy to the synthesis described in Intermediate 74, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and (1S,2R)-1-amino-2-phenylcyclopropanecarboxamide trifluoroacetate (Intermediate 48) in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-[(3R,4S,5S)-1-{(2S)-2-[(1R,2R)-3-{[(1S,2R)-1-carbamoyl-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 14 mg (0.0163 mmol) of this compound were then used, in analogy to the preparation of Intermediate 61, by reaction with 4-oxobutanoic acid in the presence of sodium cyanoborohydride, to obtain 8 mg (57% of theory) of the title compound.

HPLC (Method 5): $R_t$=1.6 min;

LC-MS (Method 9): $R_t$=4.64 min; MS (ESIpos): m/z=829 (M+H)$^+$.

Intermediate 82

N-(3-carboxypropyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

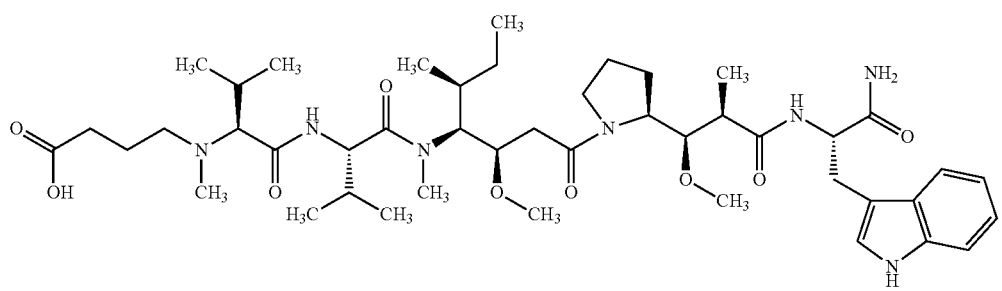 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)O)C(C)C]

First, in analogy to the synthesis described in Intermediate 69, by coupling of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) and N$^\alpha$-{(2R,3R)-3-methoxy-2-methyl-3-[(2S)-pyrrolidin-2-yl]propanoyl}-L-tryptophanamide trifluoroacetate (Intermediate 49) in the presence of O-(7-azabenzotriazol-1-yl)-N,N,N',N'-tetramethyluronium hexafluorophosphate and subsequent detachment of the Fmoc protecting group by means of piperidine, the amine compound N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 78 mg (0.088 mmol) of this compound were then used, in analogy to the preparation of Intermediate 61, by reaction with 4-oxobutanoic acid in the presence of sodium cyanoborohydride, to obtain 68 mg (90% of theory) of the title compound.

HPLC (Method 5): $R_t$=1.8 min;

LC-MS (Method 9): $R_t$=4.49 min; MS (ESIpos): m/z=856 (M+H)$^+$.

Intermediate 83

N-(5-carboxypentyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

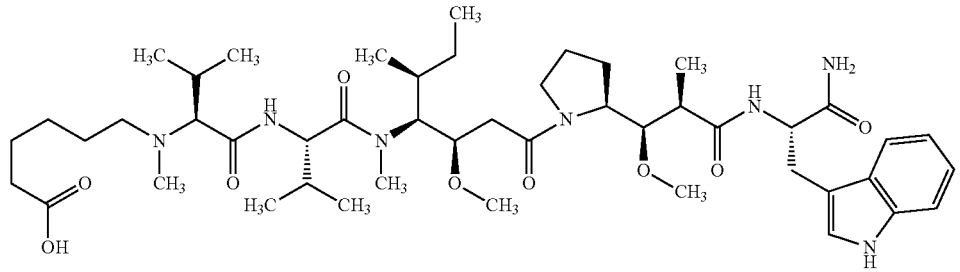 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCCCC(=O)O)C(C)C]

This compound was prepared in analogy to the compound in Intermediate 82, proceeding from 20 mg (26 μmol) of N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate, by reaction with 4-oxobutanoic acid in the presence of sodium cyanoborohydride prepared.

Yield: 5 mg (25% of theory)

HPLC (Method 5): $R_t$=1.6 min;

LC-MS (Method 11): $R_t$=0.72 min; MS (ESIpos): m/z=884 (M+H)$^+$.

Intermediate 84

N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(morpholin-4-yl)-1-oxo-3-phenyl-propan-2-yl]amino}-3-oxopropyl]pyrrolidin-1-yl}-5-methyl-1-oxoheptan-4-yl]-N-methyl-L-valinamide

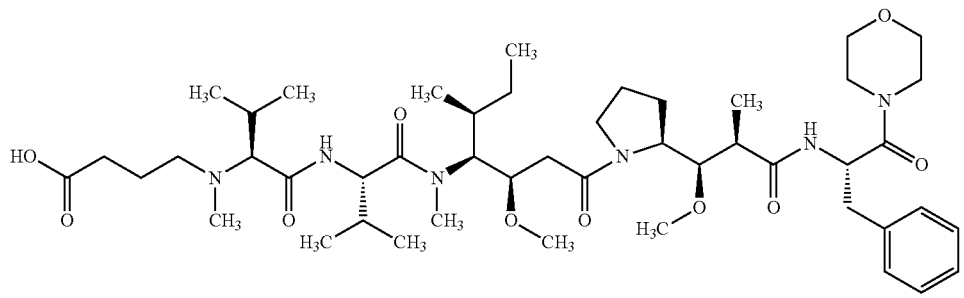 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCOCC1)OC)N(C)C(=O)[C@@H](NC(=O)[C@H](C(C)C)N(C)CCCC(=O)O)C(C)C]

First, in analogy to the synthesis described in Intermediate 79, by coupling of N-(tert-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (Intermediate 46) and morpholine in the presence of EDC and HOBT and subsequent detachment of the Boc protecting group by means of trifluoroacetic acid, the amine compound N-methyl-L-valyl-N-[(3R,4S,5S)-3-methoxy-1-{(2S)-2-[(1R,2R)-1-methoxy-2-methyl-3-{[(2S)-1-(morpholin-4-yl)-1-oxo-3-phenylpropan-2-yl]

amino}-3-oxopropyl]pyrrolidin-1-yl}-5-methyl-1-oxoheptan-4-yl]-N-methyl-L-valinamide was prepared as the trifluoroacetate. 30 mg (0.033 mmol) of this compound were then used, in analogy to the preparation of Intermediate 61, by reaction with 4-oxobutanoic acid in the presence of sodium cyanoborohydride, to obtain 22 mg (76% of theory) of the title compound.

HPLC (Method 5): $R_t$=1.6 min;
LC-MS (Method 9): $R_t$=4.58 min; MS (ESIpos): m/z=887 (M+H)$^+$.

Intermediate 85

N-(3-carboxypropyl)-N-methyl-L-valyl-N-[(3R,4S,5S)-1-{(2S)-2-[(1R,2R)-3-{[(2S,3R)-1-(benzylamino)-3-hydroxy-1-oxobutan-2-yl]amino}-1-methoxy-2-methyl-3-oxopropyl]pyrrolidin-1-yl}-3-methoxy-5-methyl-1-oxoheptan-4-yl]-N-methyl-L-valinamide

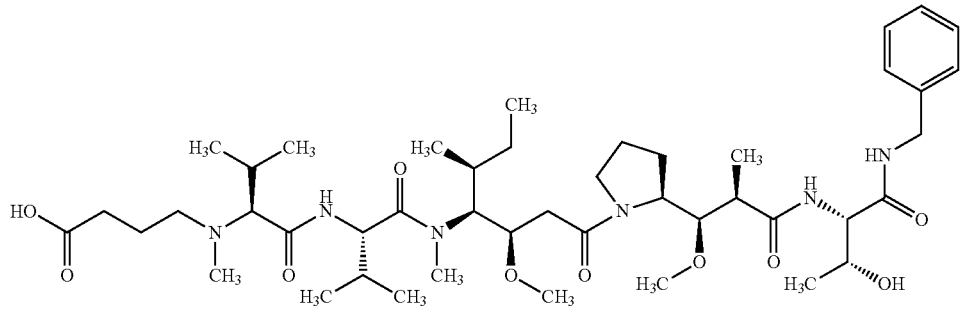 [SMILES: CC[C@H](C)[C@@H]([C@@H](CC(=O)N1CCC[C@H]1[C@H](OC)[C@@H](C)C(=O)N[C@H](C(=O)NCc1ccccc1)[C@@H](C)O)OC)N(C)C(=O)[C@@H](NC(=O)[C@H](C(C)C)N(C)CCCC(=O)O)C(C)C]

First, in analogy to the synthesis described in Intermediate 79, by coupling of N-(tert-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (Intermediate 46) and N-benzyl-L-threoninamide trifluoroacetate in the presence of HATU and subsequent detachment of the Boc protecting group by means of trifluoroacetic acid, the amine compound N-methyl-L-valyl-N-[(3R,4S,5S)-1-{(2S)-2-[(1R,2R)-3-{[(2S,3R)-1-(benzylamino)-3-hydroxy-1-oxobutan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 21 mg (0.024 mmol) of this compound were then used, in analogy to the preparation of Intermediate 61, by reaction with 4-oxobutanoic acid in the presence of sodium cyanoborohydride, to obtain 20 mg (97% of theory) of the title compound.

HPLC (Method 5): $R_t$=1.54 min;
LC-MS (Method 9): $R_t$=4.49 min; MS (ESIpos): m/z=861 (M+H)$^+$.

Intermediate 86

N-(3-carboxypropyl)-N-methyl-L-valyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

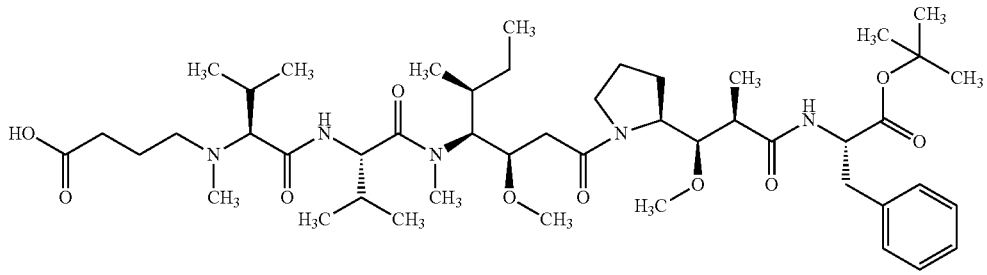 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)[C@H](C(C)C)N(C)CCCC(=O)O)C(C)C]

First, in analogy to the synthesis described in Intermediate 74, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and tert-butyl-L-phenylalaninate hydrochloride in the presence of O-(7-azabenzotriazol-1-yl)-N,N,N',N'-tetramethyluronium hexafluorophosphate and subsequent detachment of the Boc protecting group by means of trifluoroacetic acid to obtain the tert-butyl ester (stirring with trifluoroacetic acid in dichloromethane for 40 minutes), the amine compound N-methyl-L-valyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 22 mg (0.02 mmol) of this compound were then used, in analogy to the preparation of Intermediate 61, by reaction with 4-oxobutanoic acid in the presence of sodium cyanoborohydride, to obtain 16 mg (94% of theory) of the title compound.

HPLC (Method 5): $R_t$=2.0 min;
LC-MS (Method 9): $R_t$=5.05 min; MS (ESIpos): m/z=874 (M+H)$^+$.

Intermediate 87

N-(3-carboxypropyl)-N-methyl-L-valyl-N-[(3R,4S,5S)-1-{(2S)-2-[(1R,2R)-3-{[(2S)-1-tert-butoxy-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

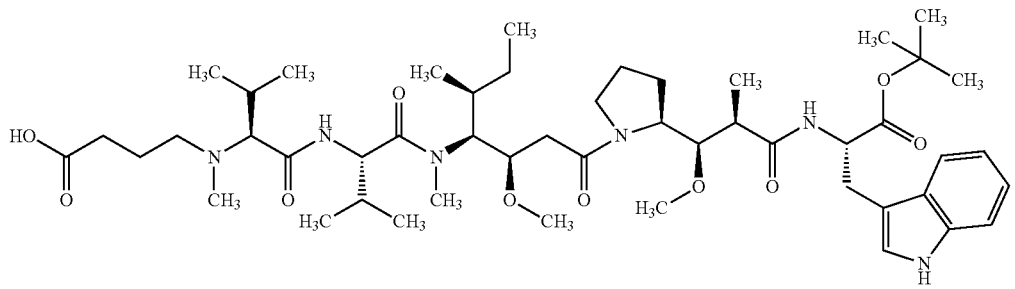 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OC(C)(C)C)OC)N(C)C(=O)[C@@H](NC(=O)[C@H](C(C)C)N(C)CCCC(=O)O)C(C)C]

This compound was prepared in analogy to the synthesis described in Intermediate 86, proceeding from 230 mg (336 µmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and tert-butyl-L-tryptophanate hydrochloride over 3 stages.

Yield: 95 mg (31% of theory over 3 stages)
HPLC (Method 5): $R_t$=2.0 min;
LC-MS (Method 9): $R_t$=5.05 min; MS (ESIpos): m/z=913 (M+H)$^+$.

Intermediate 88

N-(6-aminohexyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

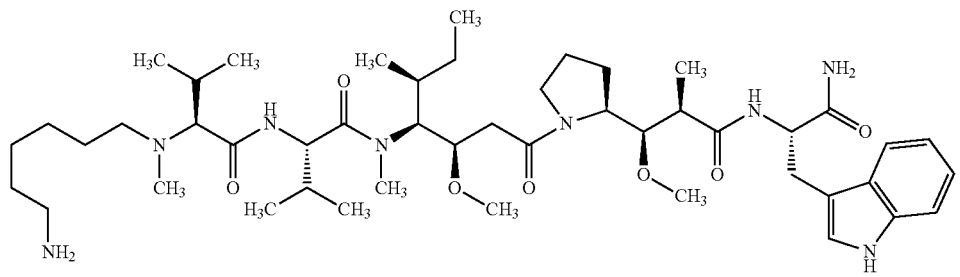 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCCCCN)C(C)C]

First, in analogy to the syntheses described in Intermediate 69, by coupling of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) and N$^{\alpha}$-{(2R,3R)-3-methoxy-2-methyl-3-[(2S)-pyrrolidin-2-yl]propanoyl}-L-tryptophanamide trifluoroacetate (Intermediate 49) in the presence of O-(7-azabenzotriazol-1-yl)-N,N,N',N'-tetramethyluronium hexafluorophosphate and subsequent detachment of the Fmoc protecting group by means of piperidine, the amine compound N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 30 mg (0.03 mmol) of this compound were then used, in analogy to the preparation of the compound of Intermediate 61, by reaction with benzyl 6-oxohexyl carbamate, which had been obtained beforehand by oxidation of benzyl 6-hydroxyhexyl carbamate, in the presence of sodium cyanoborohydride, to obtain 17 mg (45% of theory) of the Z-protected compound. Subsequently, hydrogenolysis in methanol over 10% palladium/activated carbon afforded the title compound.

Yield: 14 mg (95% of theory)
HPLC (Method 5): R$_t$=1.5 min;
LC-MS (Method 1): R$_t$=0.73 min; MS (ESIpos): m/z=869 (M+H)$^+$.

Intermediate 89

N-(6-aminohexyl)-N-methyl-L-valyl-N-[(3R,4S,5S)-1-{(2S)-2-[(1R,2R)-3-{[(2S)-1-tert-butoxy-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

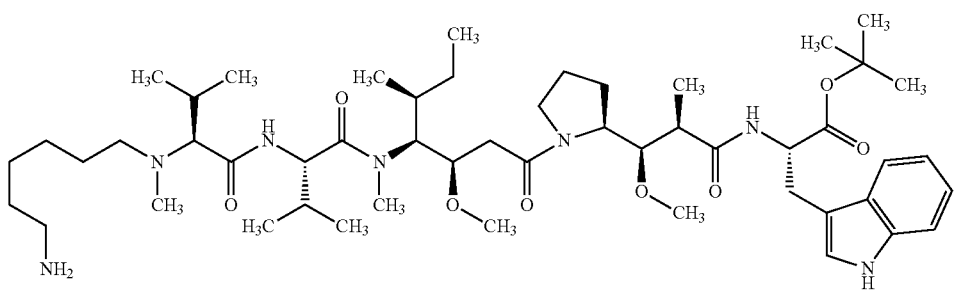 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OC(C)(C)C)OC)N(C)C(=O)[C@@H](NC(=O)[C@H](C(C)C)N(C)CCCCCCN)C(C)C]

First, in analogy to the synthesis described in Intermediate 86, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and tert-butyl-L-tryptophanate hydrochloride in the presence of O-(7-azabenzotriazol-1-yl)-N,N,N',N'-tetramethyluronium hexafluorophosphate and subsequent detachment of the Boc protecting group by means of trifluoroacetic acid to obtain the tert-butyl ester (stirring with 1:10 trifluoroacetic acid/dichloromethane for 30 min), the amine compound N-methyl-L-valyl-N-[(3R,4S,5S)-1-{(2S)-2-[(1R,2R)-3-{[(2S)-1-tert-butoxy-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 71 mg (0.075 mmol) of this compound were then used, in analogy to the preparation of the compound of Intermediate 61, by reaction with benzyl 6-oxohexyl carbamate, which had been obtained beforehand by oxidation of benzyl 6-hydroxyhexyl carbamate, in the presence of sodium cyanoborohydride, to obtain 35 mg (44% of theory) of the Z-protected compound. Subsequently, hydrogenolysis in methanol over 10% palladium/activated carbon afforded the title compound.

Yield: 30 mg (98% of theory)
HPLC (Method 5): R$_t$=1.9 min;
LC-MS (Method 1): R$_t$=0.77 min; MS (ESIpos): m/z=926 (M+H)+.

Intermediate 90

N-(3-carboxypropyl)-N-methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

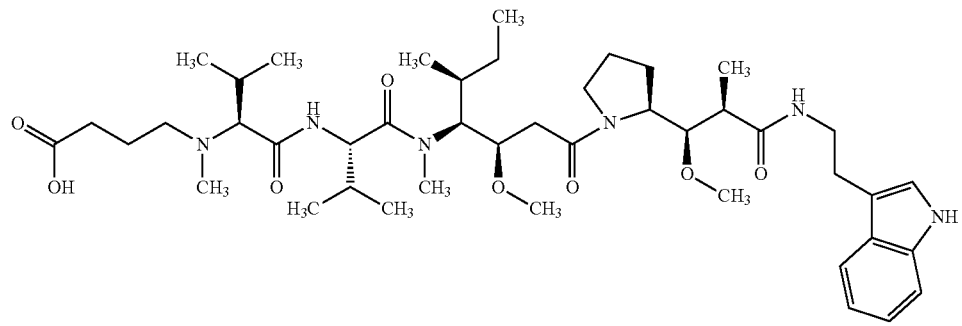 [SMILES: CC[C@H](C)[C@@H]([C@@H](CC(=O)N1CCC[C@H]1[C@H](OC)[C@@H](C)C(=O)NCCc1c[nH]c2ccccc12)OC)N(C)C(=O)[C@@H](NC(=O)[C@H](C(C)C)N(C)CCCC(=O)O)C(C)C]

First, in analogy to the synthesis described in Intermediate 74, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and 2-(1H-indol-3-yl)ethanamine in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate. 100 mg (0.119 mmol) of this compound were then used, in analogy to the preparation of Intermediate 61, by reaction with 4-oxobutanoic acid in the presence of sodium cyanoborohydride, to obtain 50 mg (49% of theory) of the title compound. The title compound was purified here by flash chromatography on silica gel with dichloromethane/methanol/17% ammonia as the eluent, in the course of which the mixing ratio was switched from initially 15/2/02 to 15/4/0.5.

HPLC (Method 6): $R_t$=1.8 min;

LC-MS (Method 1): $R_t$=0.87 min; MS (ESIpos): m/z=813 (M+H)$^+$.

Intermediate 91

N-(3-carboxypropyl)-N-methyl-L-valyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide

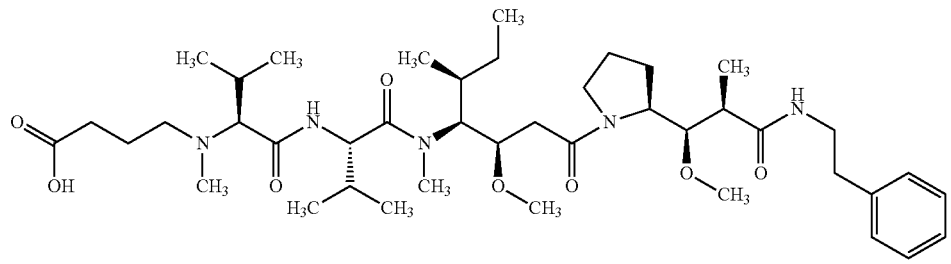 [SMILES: CC[C@H](C)[C@@H]([C@@H](CC(=O)N1CCC[C@H]1[C@H](OC)[C@@H](C)C(=O)NCCc1ccccc1)OC)N(C)C(=O)[C@@H](NC(=O)[C@H](C(C)C)N(C)CCCC(=O)O)C(C)C]

First, in analogy to the synthesis described in Intermediate 74, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and phenylethylamine in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide was prepared as the trifluoroacetate. 57 mg (0.071 mmol) of this compound were then used, in analogy to the preparation of Intermediate 61, by reaction with 4-oxobutanoic acid in the presence of sodium cyanoborohydride, to obtain 44 mg (80% of theory) of the title compound. The title compound can also be purified here by flash chromatography on silica gel with dichloromethane/methanol/17% ammonia as the eluent (15/2/02→15/4/0.5).

HPLC (Method 5): $R_t$=1.7 min;
LC-MS (Method 9): $R_t$=4.64 min; MS (ESIpos): m/z=774 (M+H)$^+$.

Intermediate 92

N-(3-carboxypropyl)-N-methyl-L-valyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

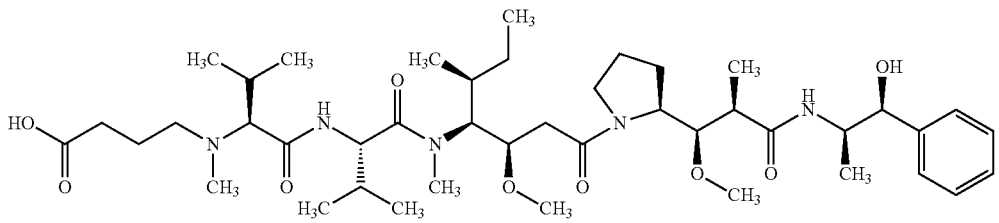 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)CCCC(=O)O)C(C)C]

100 mg (0.139 mmol) of N-methyl-L-valyl-N-[(3R,4S,5S)-1-{(2S)-2-[(1R,2R)-3-{[(1S,2R)-1-hydroxy-1-phenyl-propan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 40) were used, in analogy to the preparation of Intermediate 61, by reaction with 4-oxobutanoic acid in the presence of sodium cyanoborohydride, to obtain 94 mg (84% of theory) of the title compound. The title compound was purified by preparative HPLC.

HPLC (Method 5): $R_t$=1.5 min;
LC-MS (Method 9): $R_t$=4.46 min; MS (ESIpos): m/z=804 (M+H)$^+$.

Intermediate 93

N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

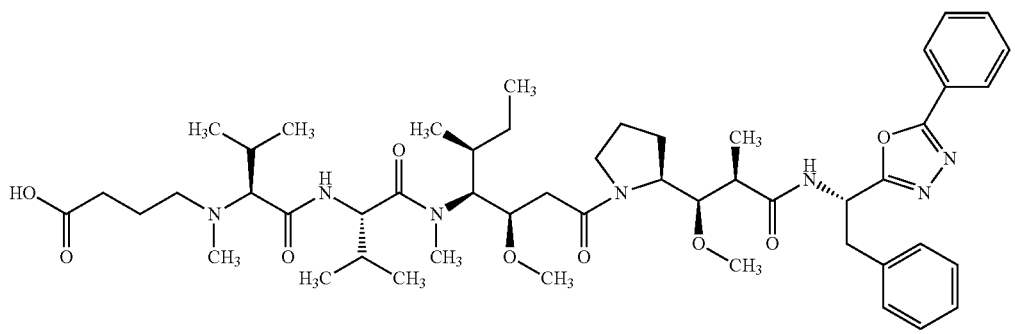 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@H](C(C)C)N(C)CCCC(=O)O)C(C)C]

22.4 mg (24 μmol) of N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetate were dissolved in 1.4 ml of dioxane/water and, analogously to the preparation of Intermediate 61, reacted with 15% aqueous solution of 4-oxobutanoic acid in the presence of sodium cyanoborohy dride. After lyophilization from dioxane, 8.2 mg (38% of theory) of the title compound were obtained in the form of a white solid.

HPLC (Method 10): $R_t$=2.54 min

LC-MS (Method 12): $R_t$=0.94 min; MS (ESIpos): m/z=919 (M+H)$^+$

Intermediate 94

N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

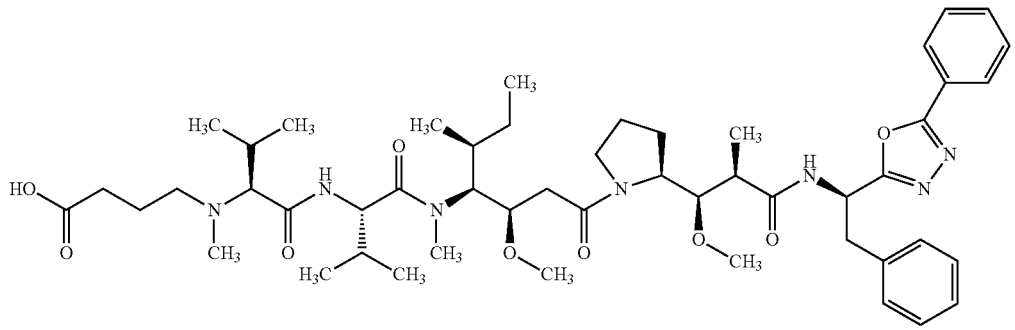 [SMILES: CC[C@H](C)[C@@H]([C@@H](CC(=O)N1CCC[C@H]1[C@H](OC)[C@@H](C)C(=O)N[C@H](Cc1ccccc1)c1nnc(-c2ccccc2)o1)OC)N(C)C(=O)[C@@H](NC(=O)[C@H](C(C)C)N(C)CCCC(=O)O)C(C)C]

17.1 mg (18 µmol) of N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetate were dissolved in 1.1 ml of dioxane/water and, analogously to the preparation of Intermediate 61, reacted with 15% aqueous solution of 4-oxobutanoic acid in the presence of sodium cyanoborohydride. After lyophilization from dioxane, 14.8 mg (89% of theory) of the title compound were obtained in the form of a white solid.

HPLC (Method 10): $R_t$=2.54 min;

LC-MS (Method 12): $R_t$=0.92 min; MS (ESIpos): m/z=919 (M+H)$^+$

Intermediate 95

N-(3-carboxypropyl)-N-methyl-L-valyl-N-[(3R,4S,5S)-1-{(2S)-2-[(1R,2R)-3-{[(2S)-1-(benzylsulphonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

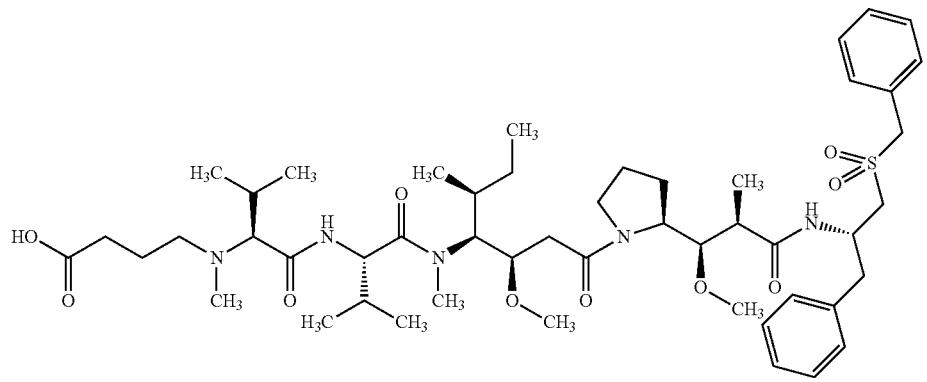 [SMILES: CC[C@H](C)[C@@H]([C@@H](CC(=O)N1CCC[C@H]1[C@H](OC)[C@@H](C)C(=O)N[C@@H](Cc1ccccc1)CS(=O)(=O)Cc1ccccc1)OC)N(C)C(=O)[C@@H](NC(=O)[C@H](C(C)C)N(C)CCCC(=O)O)C(C)C]

19.3 mg (20 μmol) N-methyl-L-valyl-N-[(3R,4S,5S)-1-{(2S)-2-[(1R,2R)-3-{[(2S)-1-(benzylsulphonyl)-3-phenyl-propan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate were dissolved in 1.2 ml of dioxane/water and, analogously to the preparation of Intermediate 61, reacted with 15% aqueous solution of 4-oxobutanoic acid in the presence of sodium cyanoborohydride. After lyophilization from dioxane, 8.6 mg (45% of theory) of the title compound were obtained in the form of a solid.

LC-MS (Method 11): R$_t$=0.85 min; MS (ESIpos): m/z=943 (M+H)$^+$

Intermediate 96

N-(3-carboxypropyl)-N-methyl-L-valyl-N-[(3R,4S,5S)-1-{(2S)-2-[(1R,2R)-3-{[(2S,3E)-1,4-diphenyl-but-3-en-2-yl]amino}-1-methoxy-2-methyl-3-oxo-propyl]pyrrolidin-1-yl}-3-methoxy-5-methyl-1-oxoheptan-4-yl]-N-methyl-L-valinamide

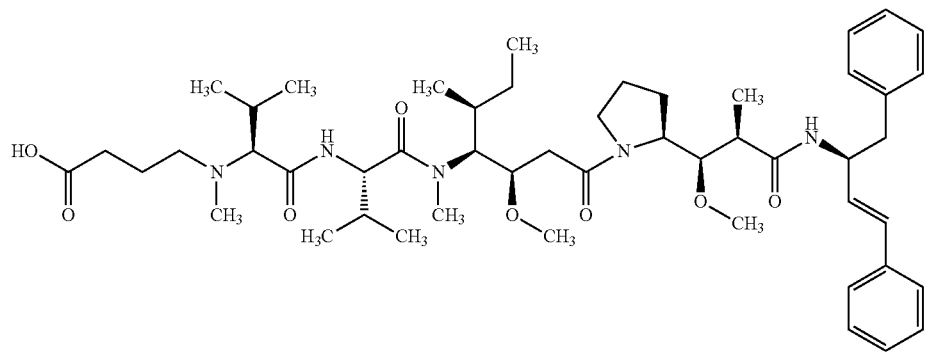 [SMILES: CC[C@H](C)[C@@H]([C@@H](CC(=O)N1CCC[C@H]1[C@H](OC)[C@@H](C)C(=O)N[C@H](/C=C/c1ccccc1)Cc1ccccc1)OC)N(C)C(=O)[C@@H](NC(=O)[C@H](C(C)C)N(C)CCCC(=O)O)C(C)C]

15.5 mg (10 μmol) of N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate were dissolved in 1.0 ml of dioxane/water and, analogously to the preparation of Intermediate 61, reacted with 15% aqueous solution of 4-oxobutanoic acid in the presence of sodium cyanoborohydride. After lyophilization from dioxane, 10.3 mg (68% of theory) of the title compound were obtained in the form of a white solid.

HPLC (Method 10): R$_t$=2.59 min;
LC-MS (Method 11): R$_t$=0.94 min; MS (ESIpos): m/z=877 (M+H)

Intermediate 97

N-(6-aminohexyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

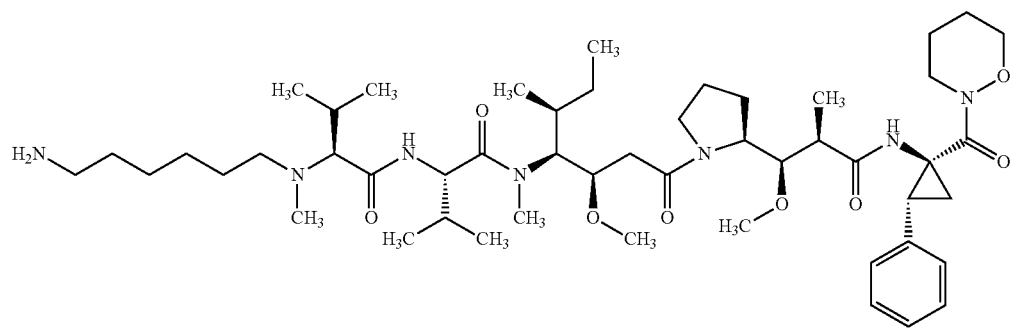 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCCN)C(C)C]

The title compound was prepared in analogy to the synthesis of Intermediate 66, by reaction of 200 mg (0.108 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide trifluoroacetate (Intermediate 16) with benzyl 6-oxohexyl carbamate and subsequent hydrogenolytic detachment of the Z protecting group (with 5% palladium on charcoal as a catalyst, in methanol as a solvent).

Yield: 69 mg (65% of theory over two stages)
HPLC (Method 5): $R_t$=1.7 min;
LC-MS (Method 1): $R_t$=0.76 min; MS (ESIpos): m/z=912 (M+H)$^+$.

Intermediate 98

N-(5-carboxypentyl)-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

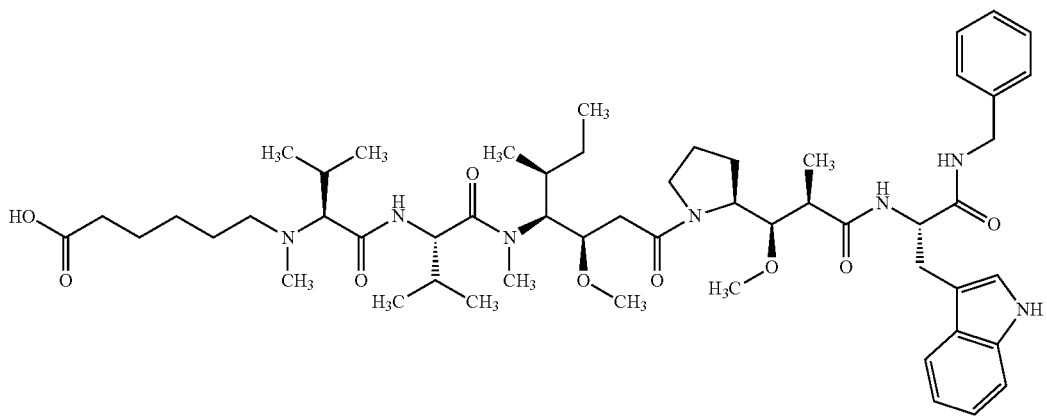 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)NCc1ccccc1)OC)N(C)C(=O)[C@@H](NC(=O)[C@H](C(C)C)N(C)CCCCCC(=O)O)C(C)C]

This compound was prepared in analogy to the synthesis described in Intermediate 80. The purification was effected by preparative HPLC.

Yield: 40 mg (29% of theory over 3 stages)
HPLC (Method 5): $R_t$=1.9 min;
LC-MS (Method 1): $R_t$=0.92 min; MS (ESIpos): m/z=974 (M+H)$^+$.

Intermediate 99

(2S)-2-amino-3-(1H-indol-3-yl)-1-(1,2-oxazinan-2-yl)propan-1-one trifluoroacetate

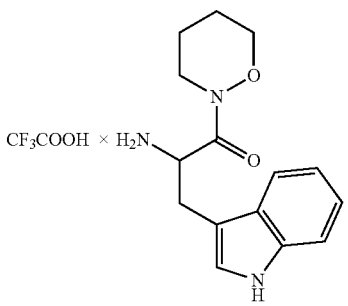

324 mg (0.81 mmol) of 2,5-dioxopyrrolidin-1-yl N-(tert-butoxycarbonyl)-L-tryptophanate were dissolved in 20 ml of DMF, and 200 mg (1.62 mmol) of 1,2-oxazinane hydrochloride (Starting Compound 5) and 850 µl of N,N-diisopropylethylamine were added. The reaction mixture was stirred at 50° C. overnight and then concentrated under reduced pressure. The residue was taken up in dichloromethane and extracted with water. The organic phase was dried over magnesium sulphate and concentrated. The residue was purified by flash chromatography on silica gel with 4:1 dichloromethane/ethyl acetate as the eluent. The product fractions were concentrated and the residue was dried under high vacuum. This gave 147.5 mg (48% of theory) of the Boc-protected intermediate.

HPLC (Method 12): $R_t$=1.9 min;

LC-MS (Method 1): $R_t$=1.03 min; MS (ESIpos): m/z=374 (M+H)$^+$.

Using 166 mg (444.5 μmol) of this intermediate, under standard conditions with 3 ml of trifluoroacetic acid in 20 ml of dichloromethane, the Boc protecting group was detached and, after HPLC purification, 155 mg (86% of theory) of the title compound were obtained.

HPLC (Method 12): $R_t$=1.43 min;

LC-MS (Method 11): $R_t$=0.56 min; MS (ESIpos): m/z=274 (M+H)$^+$.

Intermediate 100

N-(6-{[(benzyloxy)carbonyl]amino}hexyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

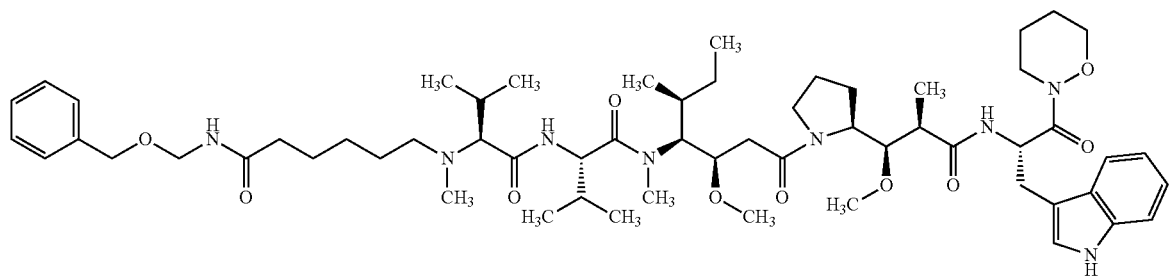 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCC(=O)NCOCc1ccccc1)C(C)C]

177 mg (260 μmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and 100 mg (260 μmol) of (2S)-2-amino-3-(1H-indol-3-yl)-1-(1,2-oxazinan-2-yl)propan-1-one trifluoroacetate (Intermediate 99) were taken up in 15 ml of DMF, and 118 mg (310 μmol) of O-(7-azabenzotriazol-1-yl)-N,N,N',N'-tetramethyluronium hexafluorophosphate and 140 μl of N,N-diisopropylethylamine were added. The reaction mixture was stirred at RT for 30 min, then concentrated under reduced pressure, and the residue was purified by means of preparative HPLC. The product fractions were combined and concentrated. After lyophilization from dioxane, 170 mg (68% of theory) of the Boc-protected intermediate were obtained.

LC-MS (Method 1): $R_t$=1.36 min; m/z=940 (M+H)$^+$.

170 mg of this intermediate were treated with 3 ml of trifluoroacetic acid in 30 ml of dichloromethane for 30 min to detach the Boc protecting group. Then the reaction mixture was concentrated under reduced pressure and the residue was purified by means of preparative HPLC to obtain 155 mg (86% of theory) of the deprotected N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide intermediate.

HPLC (Method 12): $R_t$=1.85 min;

LC-MS (Method 1): $R_t$=0.86 min; MS (ESIpos): m/z=840 (M+H)$^+$.

50 mg (0.052 mmol) of this intermediate were then used, in analogy to the preparation of Intermediate 97, with benzyl 6-oxohexyl carbamate in the presence of sodium cyanoborohydride and subsequent hydrogenolytic detachment of the Z protecting group (with 5% palladium on charcoal as a catalyst, in methanol as a solvent), prepared to prepare the title compound.

Yield: 21 mg (37% of theory)

HPLC (Method 12): $R_t$=2.1 min;

LC-MS (Method 1): $R_t$=1.02 min; MS (ESIpos): m/z=1073 (M+H)$^+$.

Intermediate 101

N-(6-aminohexyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

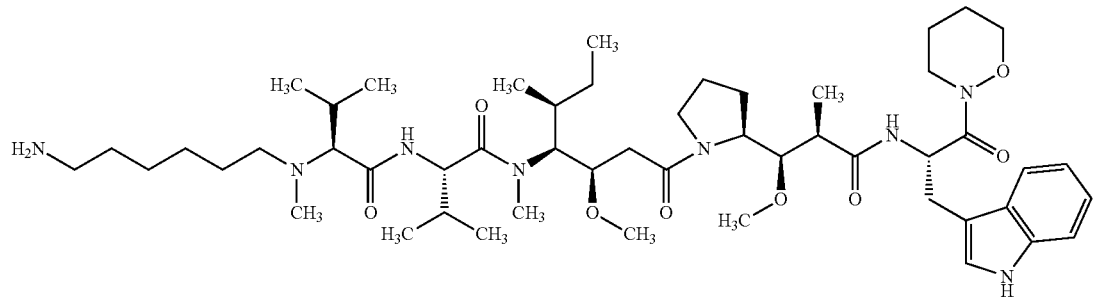 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCCN)C(C)C]

26.7 mg (24.87 μmol) of Intermediate 100 were dissolved in 10 ml of methanol and hydrogenated over palladium/activated carbon (5%) under standard hydrogen pressure for 30 min. The catalyst was filtered off and the solvent was evaporated off under reduced pressure. After the residue had been dried under high vacuum, 22.5 mg (96% of theory) of the title compound were obtained.

HPLC (Method 5): $R_t$=1.7 min;
LC-MS (Method 1): $R_t$=0.76 min; MS (ESIpos): m/z=939 (M+H)$^+$.

Intermediate 102

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-{[(2S)-1-(morpholin-4-yl)-1-oxo-3-phenylpropan-2-yl]amino}-3-oxopropyl]pyrrolidin-1-yl}-5-methyl-1-oxoheptan-4-yl]-N-methyl-L-valinamide

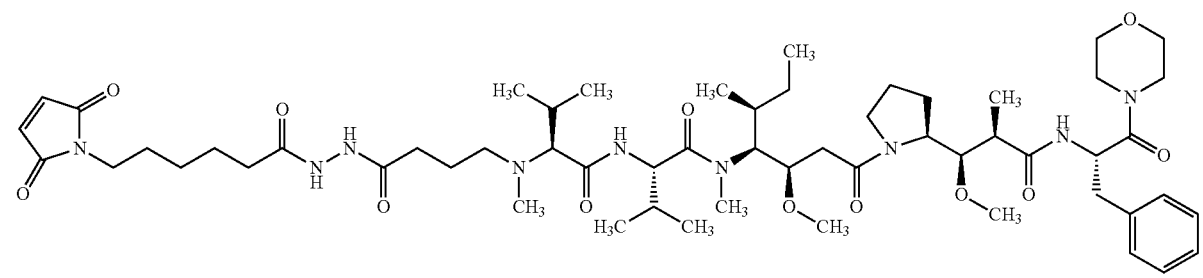 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCOCC1)OC)N(C)C(=O)[C@@H](NC(=O)[C@H](C(C)C)N(C)CCCC(=O)NNC(=O)CCCCCN1C(=O)C=CC1=O)C(C)C]

This compound was prepared in analogy to the synthesis described in Intermediate 157 from N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(morpholin-4-yl)-1-oxo-3-phenylpropan-2-yl]amino}-3-oxopropyl]pyrrolidin-1-yl}-5-methyl-1-oxoheptan-4-yl]-N-methyl-L-valinamide and commercially available 6-(2,5-dioxo-2,5-dihydro-1H-pyrrol-1-yl)hexanehydrazide.

Yield: 8 mg (71% of theory)

HPLC (Method 12): $R_t$=1.9 min;
LC-MS (Method 1): $R_t$=0.87 min; MS (ESIpos): m/z=1094 (M+H)$^+$.

Intermediate 103

N-(4-{2-[6-(2,5-dioxo-2,5-dihydro-1H-pyrrol-1-yl)
hexanoyl]hydrazino}-4-oxobutyl)-N-methyl-L-valyl-
N-[(3R,4S,5S)-1-{(2S)-2-[(1R,2R)-3-{[(2S,3R)-1-
(benzylamino)-3-hydroxy-1-oxobutan-2-yl]amino}-
1-methoxy-2-methyl-3-oxopropyl]pyrrolidin-1-yl}-
3-methoxy-5-methyl-1-oxoheptan-4-yl]-N-methyl-L-
valinamide

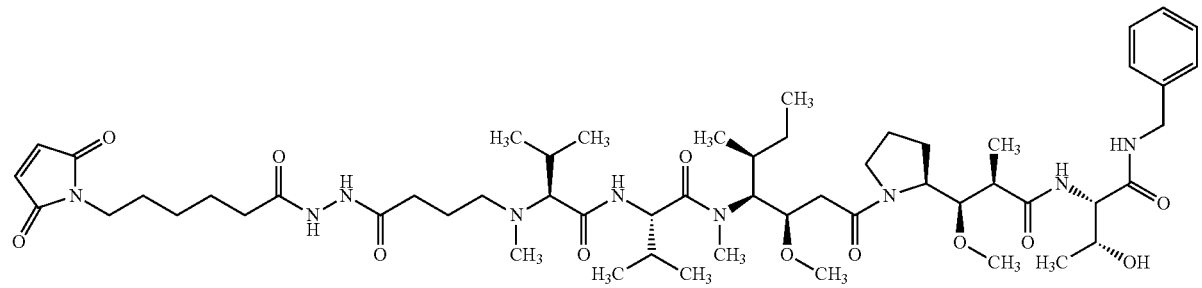 [SMILES: CC[C@H](C)[C@@H]([C@@H](CC(=O)N1CCC[C@H]1[C@H](OC)[C@@H](C)C(=O)N[C@H](C(=O)NCc1ccccc1)[C@@H](C)O)OC)N(C)C(=O)[C@@H](NC(=O)[C@H](C(C)C)N(C)CCCC(=O)NNC(=O)CCCCCN1C(=O)C=CC1=O)C(C)C]

This compound was prepared in analogy to the synthesis described in Intermediate 157 from N-(3-carboxypropyl)-N-methyl-L-valyl-N-[(3R,4S,5S)-1-{(2S)-2-[(1R,2R)-3-{[(2S,3R)-1-(benzylamino)-3-hydroxy-1-oxobutan-2-yl]amino}-1-methoxy-2-methyl-3-oxopropyl]pyrrolidin-1-yl}-3-methoxy-5-methyl-1-oxoheptan-4-yl]-N-methyl-L-valinamide and commercially available 6-(2,5-dioxo-2,5-dihydro-1H-pyrrol-1-yl)hexanehydrazide.

Yield: 3 mg (22% of theory)
HPLC (Method 5): $R_t$=1.6 min;
LC-MS (Method 1): $R_t$=0.78 min; MS (ESIpos): m/z=1069 (M+H)$^+$.

Intermediate 104

N-{4-[(trans-4-{[(2,5-dioxopyrrolidin-1-yl)oxy]
carbonyl}cyclohexyl)amino]-4-oxobutyl}-N-methyl-
L-valyl-N-[(3R,4S,5S)-1-{(2S)-2-[(1R,2R)-3-{[(2S)-
1-amino-3-(1H-indol-3-yl)-1-oxopropan-2-yl]
amino}-1-methoxy-2-methyl-3-oxopropyl]
pyrrolidin-1-yl}-3-methoxy-5-methyl-1-oxoheptan-
4-yl]-N-methyl-L-valinamide

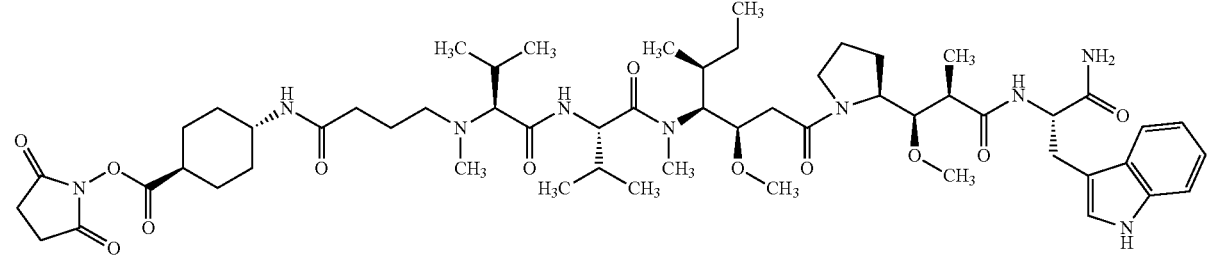 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)N[C@H]1CC[C@H](C(=O)ON2C(=O)CCC2=O)CC1)C(C)C]

First, benzyl trans-4-aminocyclohexanecarboxylate trifluoroacetate was prepared from trans-4-aminocyclohexanecarboxylic acid by introducing the Boc protecting group, then introducing the benzyl ester protecting group and subsequently detaching the Boc protecting group by conventional peptide chemistry methods.

15 mg (18 µmol) of N-(3-carboxypropyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide were then dissolved in 5 ml of dimethylformamide and subsequently admixed with 13 mg (35 µmol) of O-(7-azabenzotriazol-1-yl)-N,N,N',N'-tetramethyluronium hexafluorophosphate, 9 µl of N,N-diisopropylethylamine and with 15 mg (44 µmol) of benzyl trans-4-aminocyclohexanecarboxylate trifluoroacetate. The mixture was stirred at RT for 1 h and then concentrated under reduced pressure. The remaining residue was purified by means of preparative HPLC. The corresponding fractions were combined and the solvent was evaporated off under reduced pressure. After the residue had been dried under high vacuum, 14.7 mg (78% of theory) of the protected intermediate were obtained as a colourless foam.

HPLC (Method 6): $R_t$=2.0 min;
LC-MS (Method 1): $R_t$=0.95 min; MS (ESIpos): m/z=1072 (M+H)$^+$.

From this protected intermediate, the benzyl ester was first removed by hydrogenolytic means and the free carboxyl component was obtained in quantitative yield. 14 mg (14 µmol; 1 equiv.) of the deprotected compound were taken up in 5 ml of DMF and admixed with 3.3 mg (29 µmol; 2.1 equiv.) of N-hydroxysuccinimide in the presence of 4.1 mg (21 µmol; 1.5 equiv.) of 1-(3-dimethylaminopropyl)-3-ethylcarbodiimide hydrochloride, 7.5 µl (44 µmol; 3.1 equiv.) of N,N-diisopropylethylamine and 0.9 mg (7 µmol; 0.5 equiv.) of 4-dimethylaminopyridine, and the mixture was stirred at RT overnight. Then another 10 equiv. of N-hydroxysuccinimide, 5 equiv. of 1-(3-dimethylaminopropyl)-3-ethylcarbodiimide hydrochloride, 5 equiv. of N,N-diisopropylethylamine and 0.5 equiv. of 4-dimethylaminopyridine were added and the reaction mixture was treated in an ultrasound bath for 5 h. Subsequently, the solvent was evaporated off, the residue was purified by means of preparative HPLC and the corresponding fractions were combined and concentrated. After lyophilization of the residue from dioxane, 9.7 mg (62% of theory) of the title compound were obtained as a colourless foam.

HPLC (Method 6): $R_t$=1.8 min;
LC-MS (Method 11): $R_t$=0.77 min; MS (ESIpos): m/z=1078 (M+H)$^+$.

Intermediate 105

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide

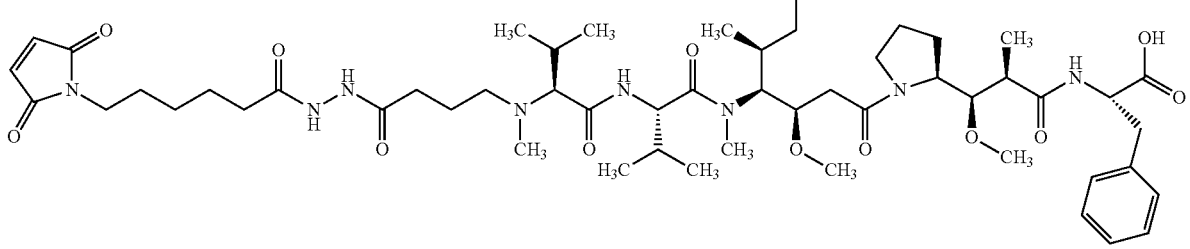

This compound was prepared in analogy to the synthesis described in Intermediate 157, proceeding from 4-{[(2S)-1-{[(2S)-1-{(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl](methyl)amino}-3-methylbutan-2-yl]amino}-3-methyl-1-oxobutan-2-yl](methyl)amino}butanoic acid and commercially available 6-(2,5-dioxo-2,5-dihydro-1H-pyrrol-1-yl)hexanehydrazide. The ester intermediate was obtained in 42% yield. In a second step, 6 mg (6 µmol) of this intermediate were cleaved with trifluoroacetic acid the tert-butyl ester. After HPLC purification, 3.4 mg (48% of theory) of the title compound were obtained.

HPLC (Method 5): $R_t$=1.66 min;
LC-MS (Method 2): $R_t$=1.04 min; MS (ESIpos): m/z=1025 (M+H)$^+$.

Intermediate 106

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

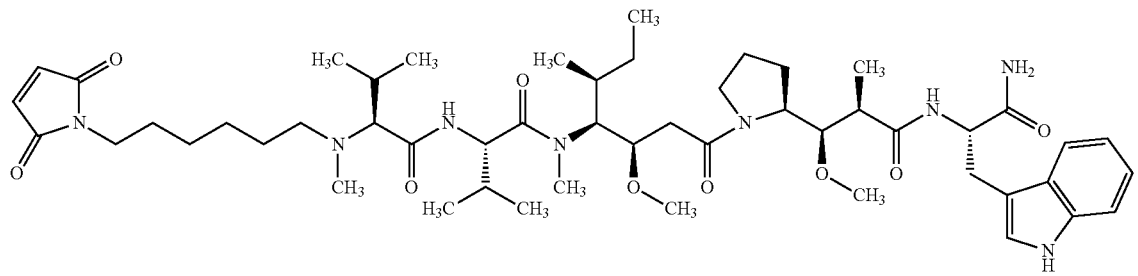

14 mg (16 μmol) of N-(6-aminohexyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 88) were taken up in 750 μl of dioxane and admixed with 1.5 ml of saturated sodium hydrogencarbonate solution and then with 3.2 mg (21 μmol) of methyl 2,5-dioxo-2,5-dihydro-1H-pyrrole-1-carboxylate. The reaction mixture was stirred at RT for 1 h and then concentrated under reduced pressure. The remaining residue was purified by means of preparative HPLC. After lyophilization, 5.5 mg (36% of theory) of the title compound were obtained.

HPLC (Method 5): $R_t$=1.7 min;
LC-MS (Method 1): $R_t$=0.84 min; MS (ESIpos): m/z=949 (M+H)$^+$.

Intermediate 107

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

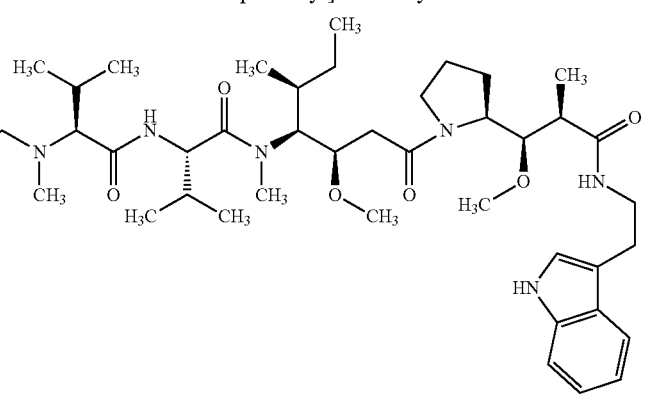

38 mg (47 μmol) of N-(3-carboxypropyl)-N-methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide were dissolved in 37 ml of DMF and then admixed with 71 mg (187 μmol) of O-(7-azabenzotriazol-1-yl)-N,N,N',N'-tetramethyluronium hexafluorophosphate, 33 μl of N,N-diisopropylethylamine and with 37 mg (140 μmol) of commercially available 6-(2,5-dioxo-2,5-dihydro-1H-pyrrol-1-yl)hexanehydrazide. The mixture was stirred at RT for 1 h. This was followed by concentration under high vacuum and purification of the remaining residue by means of preparative HPLC. Thus, 12.2 mg (26% of theory) of the title compound were obtained as a colourless foam.

HPLC (Method 5): $R_t$=1.6 min;
LC-MS (Method 1): $R_t$=0.85 min; MS (ESIpos): m/z=1020 (M+H)$^+$.

Intermediate 108

N-(4-{2-[6-(2,5-dioxo-2,5-dihydro-1H-pyrrol-1-yl)hexanoyl]hydrazino}-4-oxobutyl)-N-methyl-L-valyl-N-{(3R,4S,5S)-3-methoxy-1-[(2S)-2-{(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide

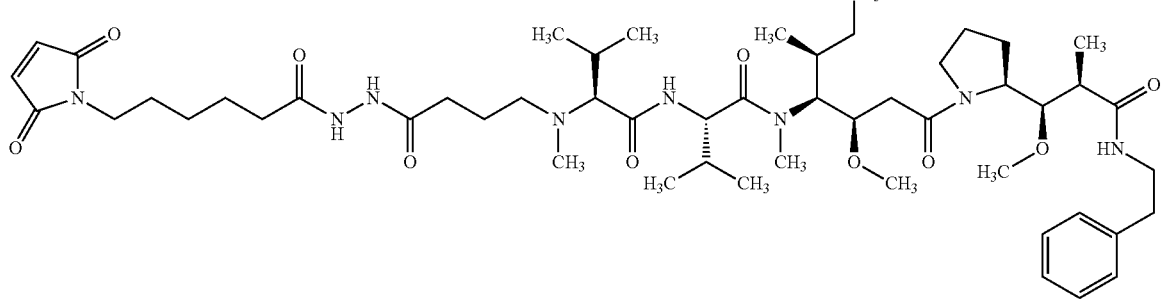

The compound was prepared in analogy to Intermediate 107.
Yield: 2.5 mg (30% of theory)
HPLC (Method 12): $R_t$=1.9 min;
LC-MS (Method 1): $R_t$=0.9 min; MS (ESIpos): m/z=981 $(M+H)^+$.

Intermediate 109

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

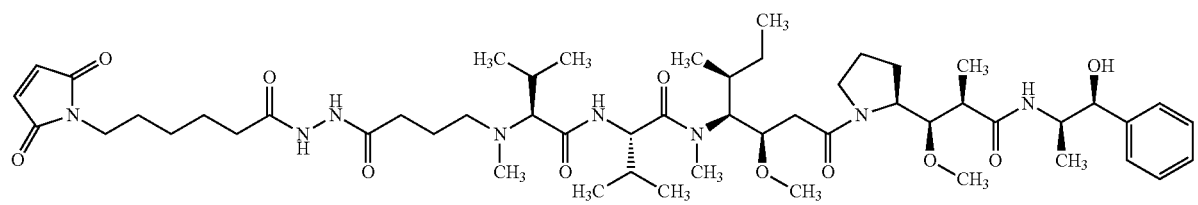 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)CCCC(=O)NNC(=O)CCCCCN1C(=O)C=CC1=O)C(C)C]

The compound was prepared in analogy to Intermediate 107 from the compound in Intermediate 92.
Yield: 35 mg (65% of theory)
HPLC (Method 5): $R_t$=1.9 min;
LC-MS (Method 11): $R_t$=0.76 min; MS (ESIpos): m/z=1011 $(M+H)^+$.

Intermediate 110

N-{6-[(2,5-dioxopyrrolidin-1-yl)oxy]-6-oxohexyl}-N-methyl-L-valyl-N-[(3R,4S,5S)-1-(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

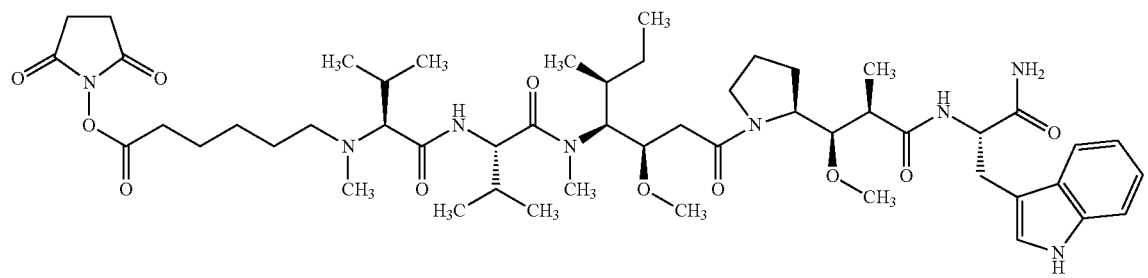 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCCCC(=O)ON1C(=O)CCC1=O)C(C)C]

This compound was prepared in analogy to Intermediate 147 from the compound in Intermediate 83.
Yield: 2.4 mg (24% of theory)
HPLC (Method 6): $R_t$=1.8 min;
LC-MS (Method 1): $R_t$=0.87 min; MS (ESIpos): m/z=981 $(M+H)^+$.

Intermediate 111

N-(4-{2-[6-(2,5-dioxo-2,5-dihydro-1H-pyrrol-1-yl)hexanoyl]-1-methylhydrazino}-4-oxobutyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

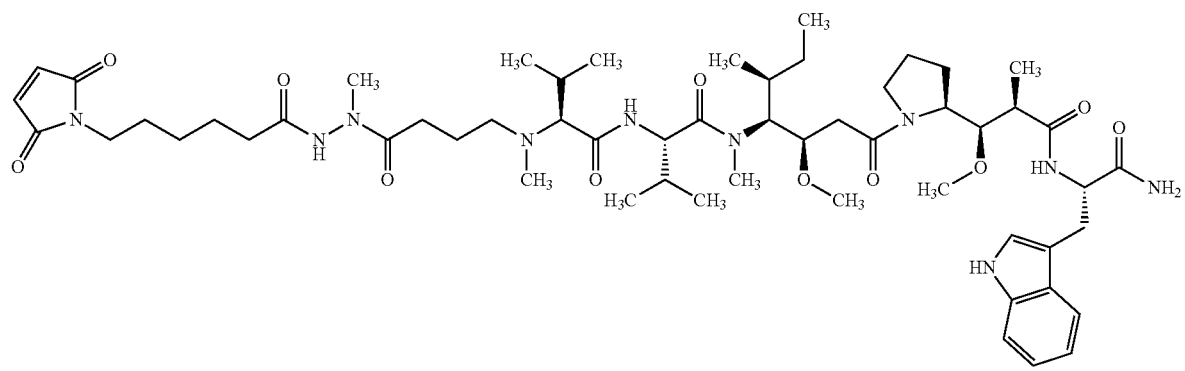 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)N(C)NC(=O)CCCCCN1C(=O)C=CC1=O)C(C)C]

This compound was prepared in analogy to Intermediate 140 from Intermediate 82 and Intermediate 22.

Yield: 6.5 mg (51% of theory)

HPLC (Method 6): $R_t$=1.8 min;

LC-MS (Method 1): $R_t$=4.71 min; MS (ESIpos): m/z=1077 (M+H)$^+$.

Intermediate 112

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(1S,2R)-1-carbamoyl-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

This compound was prepared in analogy to Intermediate 157 from the compound in Intermediate 81.

Yield: 5.7 mg (57% of theory)

HPLC (Method 5): $R_t$=1.6 min;

LC-MS (Method 1): $R_t$=0.87 min; MS (ESIpos): m/z=1036 (M+H)$^+$.

Intermediate 113

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

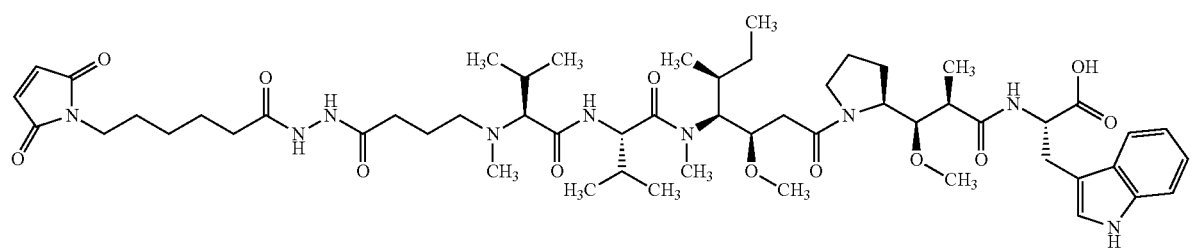 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)O)OC)N(C)C(=O)[C@@H](NC(=O)[C@H](C(C)C)N(C)CCCC(=O)NNC(=O)CCCCCN1C(=O)C=CC1=O)C(C)C]

95 mg (104 µmol) of 4-{[(2S)-1-{[(2S)-1-{[(3R,4S,5S)-1-{(2S)-2-[(1R,2R)-3-{[(2S)-1-tert-butoxy-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl](methyl)amino}-3-methylbutan-2-yl]amino}-3-methyl-1-oxobutan-2-yl](methyl)amino}butanoic acid were dissolved in DMF and then admixed with 79.5 mg (209 µmol) of O-(7-azabenzotriazol-1-yl)-N,N,N',N'-tetramethyluronium hexafluorophosphate, 73 µl of N,N-diisopropylethylamine and with 68 mg (261 µmol) of commercially available 6-(2,5-dioxo-2,5-dihydro-1H-pyrrol-1-yl)hexanehydrazide. The mixture was stirred at RT for 2 h. This was followed by concentration under high vacuum and purification of the remaining residue by means of preparative HPLC. Thus, 104 mg (89% of theory) of the tert-butyl ester of the title compound were obtained as a colourless foam.

HPLC (Method 5): $R_t$=2.0 min;
LC-MS (Method 1): $R_t$=0.93 min; MS (ESIpos): m/z=1121 (M+H)$^+$.

The intermediate was taken up in 33.4 ml of dichloromethane, 17 ml of trifluoroacetic acid were added, and the mixture was stirred at RT for 1 h. Subsequently, the reaction mixture was concentrated under reduced pressure and the residue was purified by preparative HPLC.

Thus, 61 mg (62% of theory) of the title compound were obtained as a colourless foam.

HPLC (Method 5): $R_t$=1.7 min;
LC-MS (Method 1): $R_t$=0.86 min; MS (ESIpos): m/z=1064 (M+H)$^+$.

Intermediate 114

N-[6-({[2-(2,5-dioxo-2,5-dihydro-1H-pyrrol-1-yl)ethyl]carbamoyl}amino)hexyl]-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

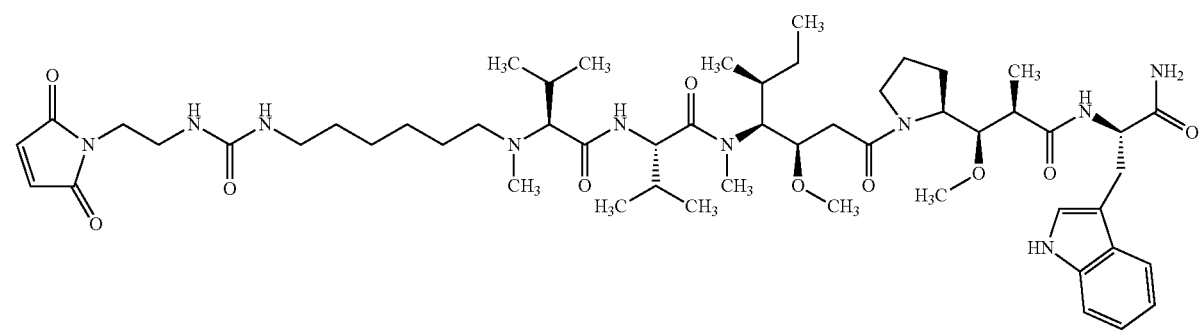

5 mg (5 μmol) of N-(6-aminohexyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide were taken up in 885 μl of DMF and admixed with 5.3 mg (8 μmol) of 4-nitrophenyl 2-(2,5-dioxo-2,5-dihydro-1H-pyrrol-1-yl)ethyl carbamate and 2.8 μl of N,N-diisopropylethylamine. The reaction mixture was stirred at RT for 2 h and then concentrated to dryness. The residue was purified by means of preparative HPLC.

Yield: 0.58 mg (11% of theory) of a colourless foam
HPLC (Method 5): $R_t$=1.6 min;

LC-MS (Method 1): $R_t$=0.83 min; MS (ESIpos): m/z=1035 (M+H)⁺.

Intermediate 115

N-{4-[(2,5-dioxopyrrolidin-1-yl)oxy]-4-oxobutyl}-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

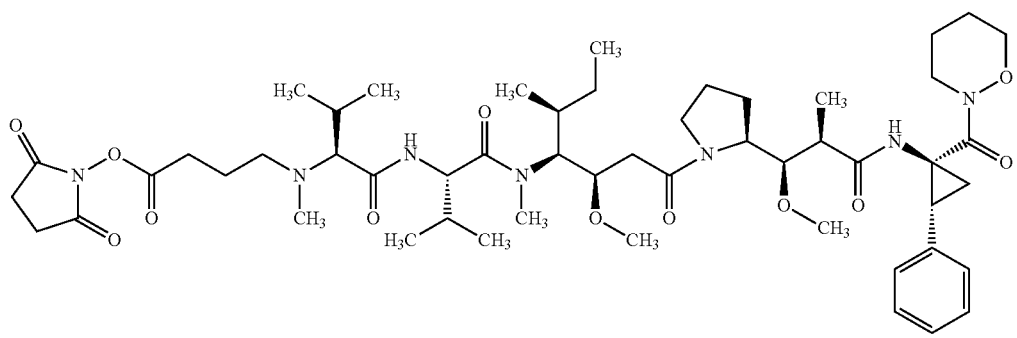 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)ON1C(=O)CCC1=O)C(C)C]

This compound was prepared in analogy to the compound in Intermediate 147, proceeding from 8 mg (9 μmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide. After concentration, the activated ester was purified by means of preparative HPLC and, after removal of the solvent under reduced pressure, reacted immediately with the antibody.

Yield: 3 mg (27% of theory) (hydrolysis-sensitive)
HPLC (Method 5): $R_t$=1.7 min;
LC-MS (Method 1): $R_t$=0.87 min; MS (ESIpos): m/z=996 (M+H)⁺.

Intermediate 116

N-{4-[(2,5-dioxopyrrolidin-1-yl)oxy]-4-oxobutyl}-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

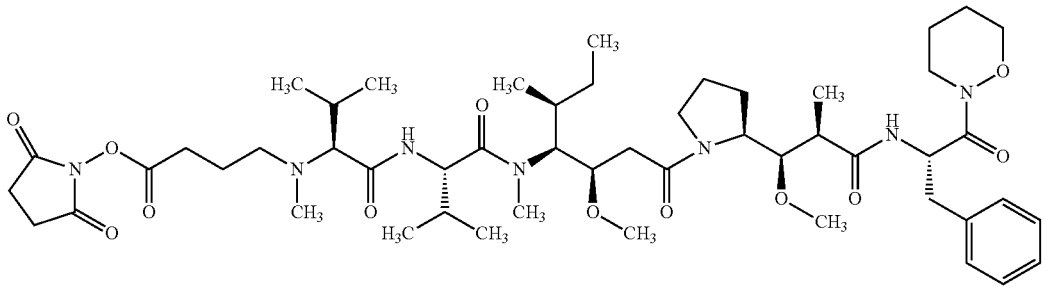 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCC(=O)ON1C(=O)CCC1=O)C(C)C]

This compound was prepared in analogy to the compound in Intermediate 147, proceeding from 5 mg (6 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide. After concentration, the activated ester was purified by means of preparative HPLC and, after removal of the solvent under reduced pressure, reacted immediately with the antibody.

Yield: 3.2 mg (43% of theory) (hydrolysis-sensitive)

HPLC (Method 5): $R_t$=1.7 min;

LC-MS (Method 1): $R_t$=0.92 min; MS (ESIpos): m/z=984 (M+H)$^+$.

Intermediate 117

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

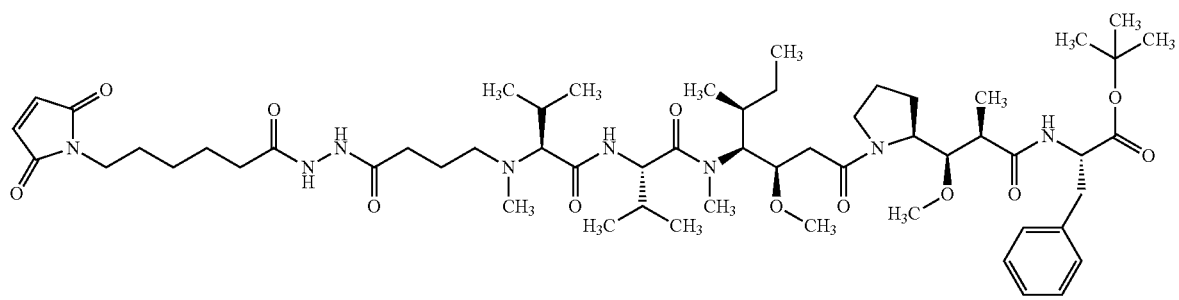 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)[C@H](C(C)C)N(C)CCCC(=O)NNC(=O)CCCCCN1C(=O)C=CC1=O)C(C)C]

This compound was prepared in analogy to Intermediate 157 from the compound in Intermediate 86.

Yield: 7 mg (42% of theory)

HPLC (Method 5): $R_t$=1.6 min;

LC-MS (Method 1): $R_t$=0.94 min; MS (ESIpos): m/z=1081 (M+H)$^+$.

Intermediate 118

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2R)-1-(benzyloxy)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

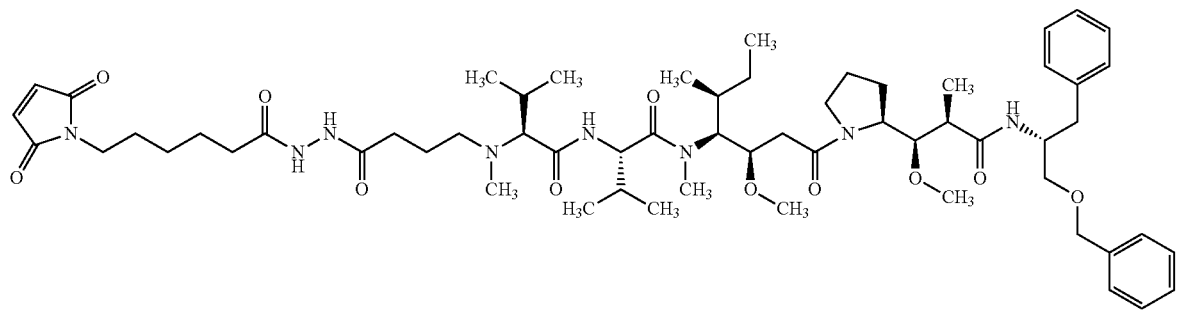 [SMILES: CC[C@H](C)[C@@H]([C@@H](CC(=O)N1CCC[C@H]1[C@H](OC)[C@@H](C)C(=O)N[C@@H](COCc1ccccc1)Cc1ccccc1)OC)N(C)C(=O)[C@@H](NC(=O)[C@H](C(C)C)N(C)CCCC(=O)NNC(=O)CCCCCN1C(=O)C=CC1=O)C(C)C]

The target compound was prepared analogously to Intermediate 157 from 7 mg (7.8 µmol) of the compound in Intermediate 68. Yield: 6.3 mg (53% of theory)

LC-MS (Method 1): $R_t$=1.00 min; MS (ESIpos): m/z=1102 (M+H)$^+$.

Intermediate 119

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

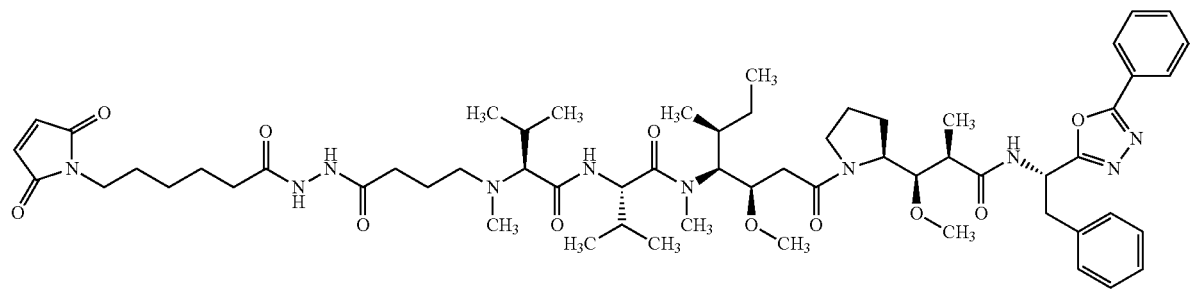 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@H](C(C)C)N(C)CCCC(=O)NNC(=O)CCCCCN1C(=O)C=CC1=O)C(C)C]

7.4 mg (8.1 mmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide and 6.3 mg (24.2 mmol) of 6-(2,5-dioxo-2,5-dihydro-1H-pyrrol-1-yl)hexanehydrazide hydrochloride were coupled and worked up in analogy to Intermediate 157. 1.6 mg (13% of theory) of the title compound were obtained as a solid.

LC-MS (Method 11): $R_t$=0.89 min; MS (ESIpos): m/z=1126 (M+H)$^+$

Intermediate 120

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

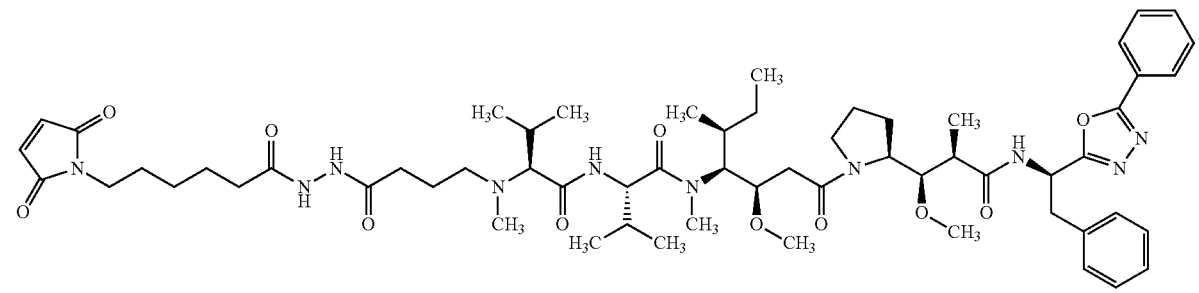 [SMILES: CC[C@H](C)[C@@H]([C@@H](CC(=O)N1CCC[C@H]1[C@H](OC)[C@@H](C)C(=O)N[C@H](Cc1ccccc1)c1nnc(-c2ccccc2)o1)OC)N(C)C(=O)[C@@H](NC(=O)[C@H](C(C)C)N(C)CCCC(=O)NNC(=O)CCCCCN1C(=O)C=CC1=O)C(C)C]

12.8 mg (13.9 mmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide and 10.9 mg (41.8 mmol) of 6-(2,5-dioxo-2,5-dihydro-1H-pyrrol-1-yl)hexanehydrazide hydrochloride were coupled and worked up in analogy to Intermediate 157. 10.8 mg (59% of theory) of the title compound were obtained as a solid.

LC-MS (Method 11): $R_t$=0.90 min; MS (ESIpos): m/z=1126 (M+H)$^+$

Intermediate 121

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-(benzylsulphonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

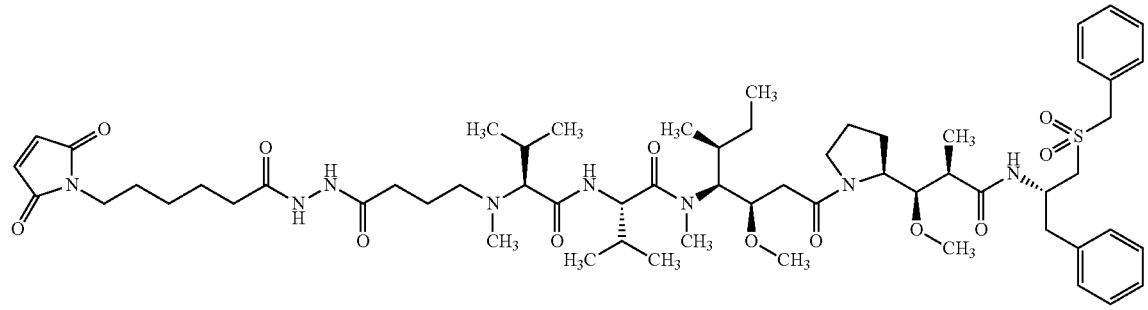 [SMILES: CC[C@H](C)[C@@H]([C@@H](CC(=O)N1CCC[C@H]1[C@H](OC)[C@@H](C)C(=O)N[C@@H](Cc1ccccc1)CS(=O)(=O)Cc1ccccc1)OC)N(C)C(=O)[C@@H](NC(=O)[C@H](C(C)C)N(C)CCCC(=O)NNC(=O)CCCCCN1C(=O)C=CC1=O)C(C)C]

7.4 mg (7.9 mmol) of N-(3-carboxypropyl)-N-methyl-L-valyl-N-[(3R,4S,5S)-1-{(2S)-2-[(1R,2R)-3-{[(2S)-1-(benzylsulphonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide and 6.2 mg (23.5 mmol) of 6-(2,5-dioxo-2,5-dihydro-1H-pyrrol-1-yl)hexanehydrazide hydrochloride were coupled and worked up in analogy to Intermediate 157. 6.9 mg (74% of theory) of the title compound were obtained as a solid.

LC-MS (Method 11): $R_t$=0.87 min; MS (ESIpos): m/z=1150 (M+H)$^+$

Intermediate 122

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide

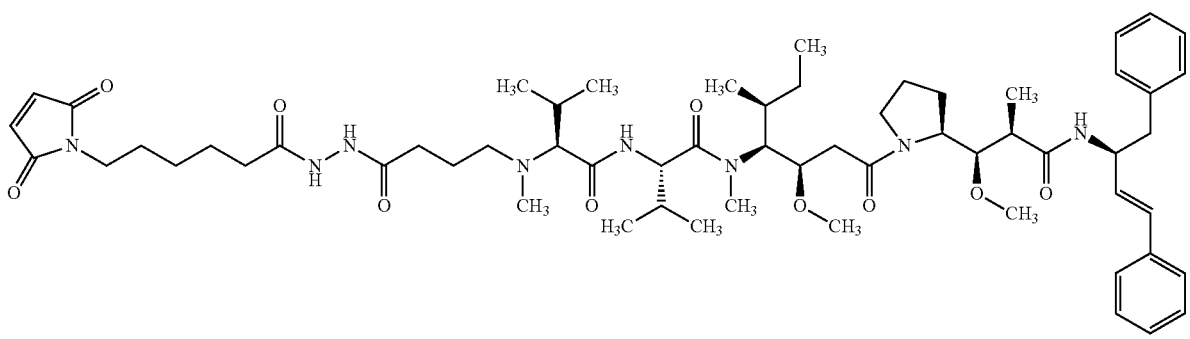 [SMILES: CC[C@H](C)[C@@H]([C@@H](CC(=O)N1CCC[C@H]1[C@H](OC)[C@@H](C)C(=O)N[C@H](/C=C/c1ccccc1)Cc1ccccc1)OC)N(C)C(=O)[C@@H](NC(=O)[C@H](C(C)C)N(C)CCCC(=O)NNC(=O)CCCCCN1C(=O)C=CC1=O)C(C)C]

8 mg (9.1 mmol) of N-(3-carboxypropyl)-N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide and 7.2 mg (27.4 mmol) of 6-(2,5-dioxo-2,5-dihydro-1H-pyrrol-1-yl)hexanehydrazide hydrochloride were coupled and worked up in analogy to Intermediate 157. 8.2 mg (82% of theory) of the title compound were obtained as a white solid.

LC-MS (Method 11): $R_t$=0.95 min; MS (ESIpos): m/z=1083 (M+H)$^+$

Intermediate 123

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(2S)-1-tert-butoxy-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

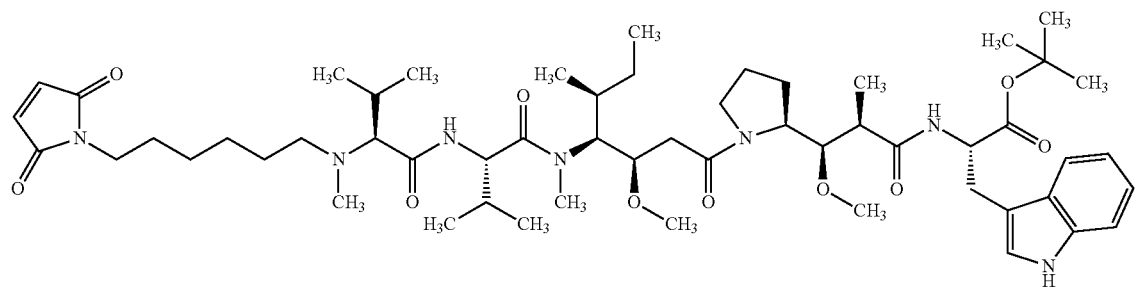 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OC(C)(C)C)OC)N(C)C(=O)[C@@H](NC(=O)[C@H](C(C)C)N(C)CCCCCCN1C(=O)C=CC1=O)C(C)C]

30 mg (30 μmol) of Intermediate 89 were taken up in 2 ml of 1,4-dioxane and admixed with 4 ml of saturated sodium hydrogencarbonate solution and then with 7.5 mg (50 μmol) of methyl 2,5-dioxo-2,5-dihydro-1H-pyrrole-1-carboxylate. The reaction mixture was stirred at RT for 1 h and then concentrated under reduced pressure. The remaining residue was purified by means of preparative HPLC. After lyophilization, 24 mg (74% of theory) of the title compound were obtained.

HPLC (Method 5): $R_t$=2.2 min;

LC-MS (Method 1): $R_t$=1.01 min; MS (ESIpos): m/z=1006 (M+H)$^+$.

Intermediate 124

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

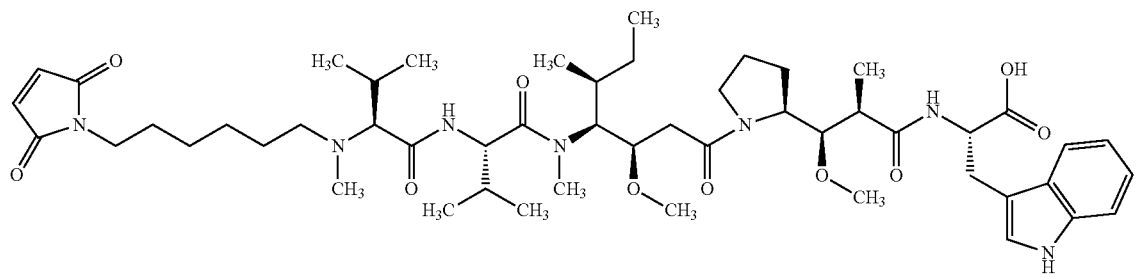

22 mg (20 μmol) of Intermediate 123 were reacted with 4 ml of trifluoroacetic acid in 8 ml of dichloromethane at RT for 1 h. Thereafter, the reaction mixture was concentrated under reduced pressure. The remaining residue was purified by means of preparative HPLC. After lyophilization, 11 mg (54% of theory) of the title compound were obtained.

HPLC (Method 5): $R_t$=1.8 min;

LC-MS (Method 11): $R_t$=0.85 min; MS (ESIpos): m/z=950 (M+H)$^+$.

Intermediate 125

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

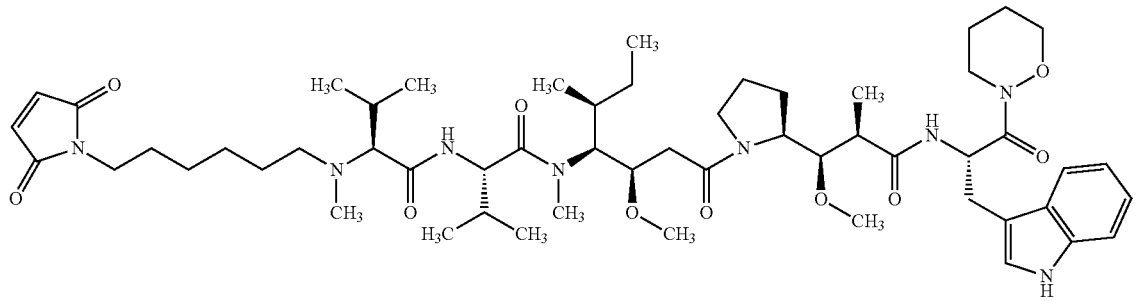 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCCN1C(=O)C=CC1=O)C(C)C]

22.5 mg (20 µmol) of Intermediate 101 were taken up in 2 ml of 1:1 dioxane/water and then admixed with 5.6 mg (40 µmol) of methyl 2,5-dioxo-2,5-dihydro-1H-pyrrole-1-carboxylate and with 0.25 ml of saturated sodium hydrogencarbonate solution. The reaction mixture was stirred at RT for 30 min. Then another 0.25 ml of the saturated sodium hydrogencarbonate solution was added and the reaction mixture was stirred at RT for a further 15 min and then concentrated under reduced pressure. The remaining residue was purified by means of preparative HPLC. After lyophilization, 12.8 mg (50% of theory) of the title compound were obtained as a colourless foam.

HPLC (Method 5): $R_t$=1.9 min;
LC-MS (Method 1): $R_t$=0.95 min; MS (ESIpos): m/z=1019 (M+H)$^+$.

Intermediate 126

N-[6-(2,5-dioxo-2,5-dihydro-1H-pyrrol-1-yl)hexyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

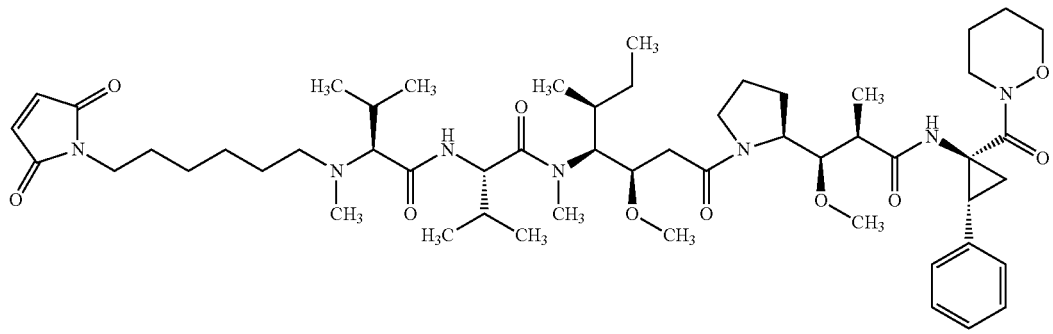 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCCN1C(=O)C=CC1=O)C(C)C]

64 mg (70 µmol) of N-(6-aminohexyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide (Intermediate 97) were taken up in 3 ml of 1:1 dioxane/water, then adjusted to pH 9 with 4 ml of saturated sodium hydrogencarbonate solution and subsequently admixed with 16.3 mg (110 µmol) of methyl 2,5-dioxo-2,5-dihydro-1H-pyrrole-1-carboxylate. The reaction mixture was stirred at RT for 1 h and then concentrated under reduced pressure. Then another 8 mg (55 µmol) of methyl 2,5-dioxo-2,5-dihydro-1H-pyrrole-1-carboxylate were added, and the reaction mixture was adjusted again to pH 9 and stirred at RT for a further hour. This was followed by concentration and purification of the remaining residue by means of preparative HPLC. At first, 31 mg of an as yet uncyclized intermediate were obtained. 27 mg of this intermediate were taken up again in 2 ml of 1:1 dioxane/water and then admixed with 250 µl of saturated sodium hydrogencarbonate solution. After stirring at RT for 2 hours, the reaction mixture was concentrated and the residue was purified by means of preparative HPLC. After lyophilization, 20 mg (29% of theory) of the title compound were obtained.

HPLC (Method 5): $R_t$=1.96 min;

LC-MS (Method 1): $R_t$=0.97 min; MS (ESIpos): m/z=992 (M+H)$^+$.

Intermediate 127

N-[6-[(2,5-dioxopyrrolidin-1-yl)oxy]-6-oxohexyl]-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

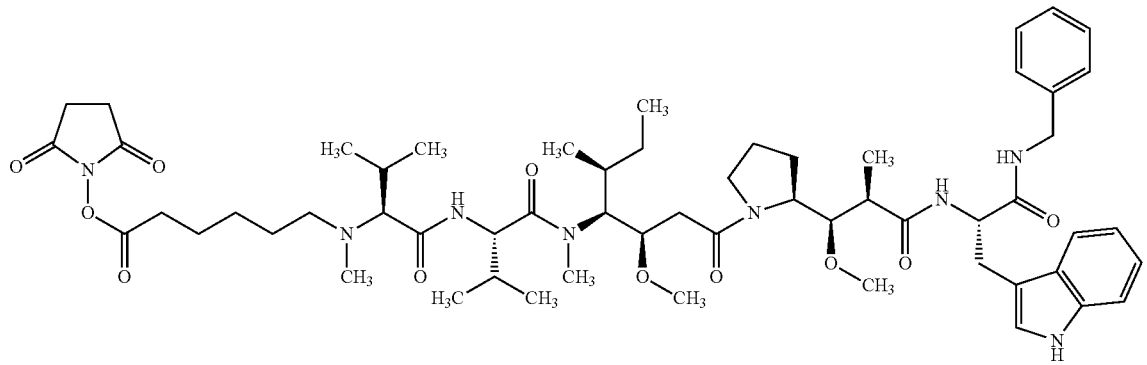 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)NCc1ccccc1)OC)N(C)C(=O)[C@@H](NC(=O)[C@H](C(C)C)N(C)CCCCCC(=O)ON1C(=O)CCC1=O)C(C)C]

17 mg (18 µmol) of N-(5-carboxypentyl)-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 98) were dissolved in 2.8 ml of dichloromethane and admixed with 20 mg (174 mmol) of 1-hydroxypyrrolidine-2,5-dione and then with 10 mg (52 µmol) of 1-(3-dimethylaminopropyl)-3-ethylcarbodiimide hydrochloride and 0.21 mg (0.17 µmol) of DMAP. After stirring at RT for 4 h, the reaction mixture was concentrated under reduced pressure. The remaining residue was purified by means of preparative HPLC. After lyophilization, 8.2 mg (43% of theory) of the title compound were obtained.

HPLC (Method 5): $R_t$=2.0 min;
LC-MS (Method 1): $R_t$=0.98 min; MS (ESIpos): m/z=1071 (M+H)$^+$.

Intermediate 128

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

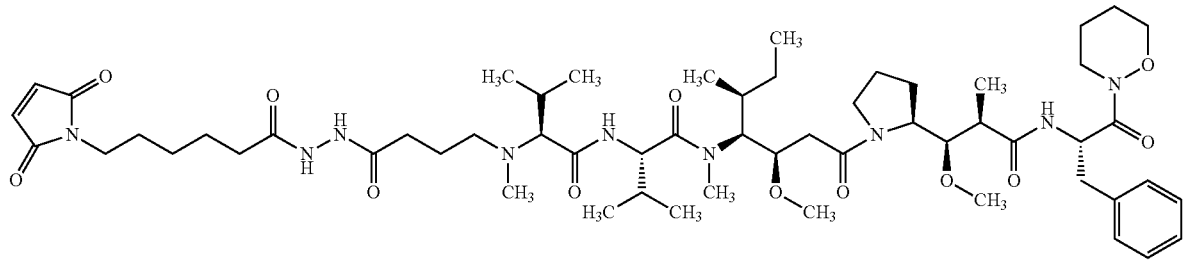 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCC(=O)NNC(=O)CCCCCN1C(=O)C=CC1=O)C(C)C]

5 mg (5.6 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide were dissolved in 845 µl of DMF and then admixed with 3.2 mg (17 µmol) of 1-(3-dimethylaminopropyl)-3-ethylcarbodiimide hydrochloride, 2.6 mg (17 µmol) of 1-hydroxy-1H-benzotriazole hydrate, 1.96 µl of N,N-diisopropylethylamine and with 5.9 mg (22.5 µmol) of commercially available 6-(2,5-dioxo-2,5-dihydro-1H-pyrrol-1-yl)hexanehydrazide. The mixture was stirred at RT overnight and then concentrated under high vacuum. The remaining residue was purified by means of preparative HPLC. Thus, 2.2 mg (36% of theory) of the title compound were obtained as a colourless foam.

HPLC (Method 5): $R_t$=1.7 min;
LC-MS (Method 1): $R_t$=0.88 min; MS (ESIpos): m/z=1094 (M+H)$^+$.

Intermediate 129

N-(6-{2-[6-(2,5-dioxo-2,5-dihydro-1H-pyrrol-1-yl)hexanoyl]hydrazino}-6-oxohexyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

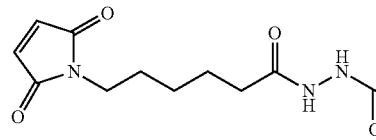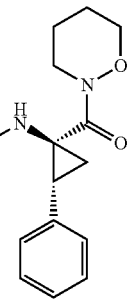

4 mg (4.3 µmol) of N-(5-carboxypentyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 646 µl of DMF and then admixed with 2.5 mg (13 µmol) of 1-(3-dimethylaminopropyl)-3-ethylcarbodiimide hydrochloride, 2.0 mg (13 µmol) of 1-hydroxy-1H-benzotriazole hydrate, 2.25 µl of N,N-diisopropylethylamine and with 4.5 mg (17 µmol) of commercially available 6-(2,5-dioxo-2,5-dihydro-1H-pyrrol-1-yl)hexanehydrazide. The mixture was stirred at RT for 3 h and then concentrated under high vacuum. The remaining residue was purified by means of preparative HPLC. Thus, 1.9 mg (39% of theory) of the title compound were obtained as a colourless foam.

HPLC (Method 5): $R_t$=1.7 min;
LC-MS (Method 9): $R_t$=4.9 min; MS (ESIpos): m/z=1134 (M+H)$^+$.

Intermediate 130

N-(4-{[(2R)-1-({5-[(2,5-dioxopyrrolidin-1-yl)oxy]-5-oxopentanoyl}amino)propan-2-yl]oxy}-4-oxobutyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

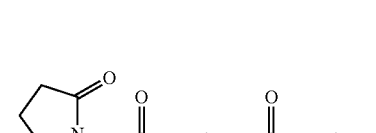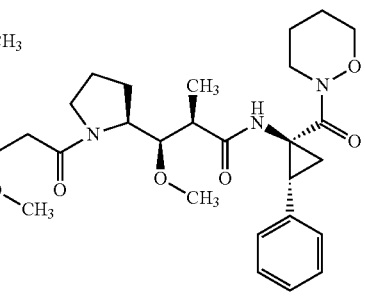

10.5 mg (11.7 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 3.7 ml of dichloromethane and then admixed with 6.7 mg (35 µmol) of 1-(3-dimethylaminopropyl)-3-ethylcarbodiimide hydrochloride, 0.7 mg (5.8 µmol) of 4-dimethylaminopyridine and with 8.2 mg (47 µmol) of commercially available tert-butyl (2R)-2-hydroxypropyl carbamate. The mixture was stirred at RT overnight and then concentrated under high vacuum. The remaining residue was purified by means of preparative HPLC. Thus, 7.5 mg (61% of theory) of the Boc-protected intermediate were obtained as a colourless foam.

HPLC (Method 5): $R_t$=2.0 min;
LC-MS (Method 1): $R_t$=1.03 min; MS (ESIpos): m/z=1056 (M+H)$^+$.

Subsequently, the Boc protecting group was detached with trifluoroacetic acid. 4.9 mg (0.005 mmol) of the deprotected crude product were then, without further purification, taken up in 1.8 ml of dichloromethane and admixed with 3.7 mg (0.011 mmol) of 1,1'-[(1,5-dioxopentane-1,5-diyl)bis(oxy)]dipyrrolidine-2,5-dione, 2.4 µl (0.014 mmol) of N,N-diisopropylethylamine and 0.6 mg (5 µmol) of 4-dimethylaminopyridine. The mixture was stirred at RT for 2 h and then concentrated under high vacuum. The remaining residue was purified by means of preparative HPLC. Thus, 0.77 mg (15% of theory) of the title compound were obtained as a colourless foam.

HPLC (Method 5): $R_t$=1.8 min;
LC-MS (Method 1): $R_t$=0.93 min; MS (ESIpos): m/z=1167 (M+H)$^+$.

Intermediate 131

N-{4-[(1-{5-[(2,5-dioxopyrrolidin-1-yl)oxy]-5-oxopentanoyl}piperidin-4-yl)oxy]-4-oxobutyl}-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

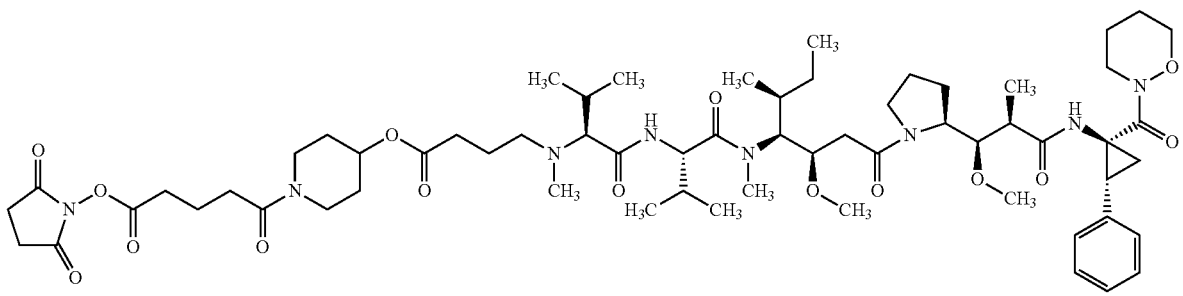 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)OC1CCN(C(=O)CCCC(=O)ON2C(=O)CCC2=O)CC1)C(C)C]

10 mg (11 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 2 ml of dichloromethane and then admixed with 4.3 mg (22 µmol) of 1-(3-dimethylaminopropyl)-3-ethylcarbodiimide hydrochloride, 0.88 mg (6 µmol) of 4-dimethylaminopyridine and with 5.2 mg (22 µmol) of commercially available benzyl 4-hydroxypiperidine-1-carboxylate. The mixture was stirred at RT overnight and then concentrated under high vacuum. The remaining residue was purified by means of preparative HPLC. Thus, 5 mg (40% of theory) of the Z-protected intermediate were obtained as a colourless foam.

HPLC (Method 5): $R_t$=2.1 min;
LC-MS (Method 1): $R_t$=1.04 min; MS (ESIpos): m/z=1116 (M+H)$^+$.

Subsequently, the Z protecting group was detached by hydrogenolytic means in ethanol over palladium/activated carbon. 4.6 mg (0.005 mmol) of the deprotected crude product were then, without further purification, taken up in 1.8 ml of dichloromethane and admixed with 3.8 mg (0.012 mmol) of 1,1'-[(1,5-dioxopentane-1,5-diyl)bis(oxy)]dipyrrolidine-2,5-dione, 0.8 µl (0.005 mmol) of N,N-diisopropylethylamine and 0.6 mg (5 µmol) of 4-dimethylaminopyridine. The mixture was stirred at RT overnight and then concentrated under high vacuum. The remaining residue was purified by means of preparative HPLC. Thus, 0.96 mg (16% of theory) of the title compound were obtained as a colourless foam.

HPLC (Method 5): $R_t$=1.8 min;
LC-MS (Method 1): $R_t$=0.94 min; MS (ESIpos): m/z=1193 (M+H)$^+$.

Intermediate 132

N-(4-{2-[6-(2,5-dioxo-2,5-dihydro-1H-pyrrol-1-yl)hexanoyl]hydrazinyl}-4-oxobutyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

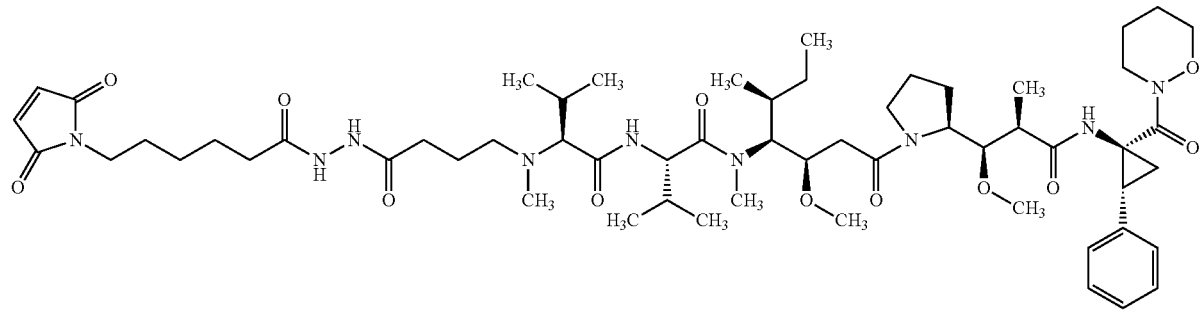 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)NNC(=O)CCCCCN1C(=O)C=CC1=O)C(C)C]

15 mg (16.7 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 2500 µl of DMF and then admixed with 9.6 mg (50 µmol) of 1-(3-dimethylaminopropyl)-3-ethylcarbodiimide hydrochloride, 7.6 mg (50 µmol) of 1-hydroxy-1H-benzotriazole hydrate, 5.8 µl of N,N-diisopropylethylamine and with 17.4 mg (67 µmol) of commercially available 6-(2,5-dioxo-2,5-dihydro-1H-pyrrol-1-yl)hexanehydrazide. The mixture was stirred at RT overnight and then concentrated under high vacuum. The remaining residue was purified by means of preparative HPLC. Thus, 11.2 mg (52% of theory) of the title compound were obtained as a colourless foam.

HPLC (Method 5): $R_t$=1.7 min;

LC-MS (Method 2): $R_t$=1.09 min; MS (ESIpos): m/z=1106 (M+H)$^+$.

Intermediate 133

N-(4-{2-[6-(2,5-dioxo-2,5-dihydro-1H-pyrrol-1-yl)hexanoyl]hydrazinyl}-4-oxobutyl)-N-methyl-L-valyl-N-[(3R,4S,5S)-1-{(2S)-2-[(1R,2R)-3-{[(2S,3S)-1-(benzyloxy)-1-oxo-3-phenylbutan-2-yl]amino}-1-methoxy-2-methyl-3-oxopropyl]pyrrolidin-1-yl}-3-methoxy-5-methyl-1-oxoheptan-4-yl]-N-methyl-L-valinamide

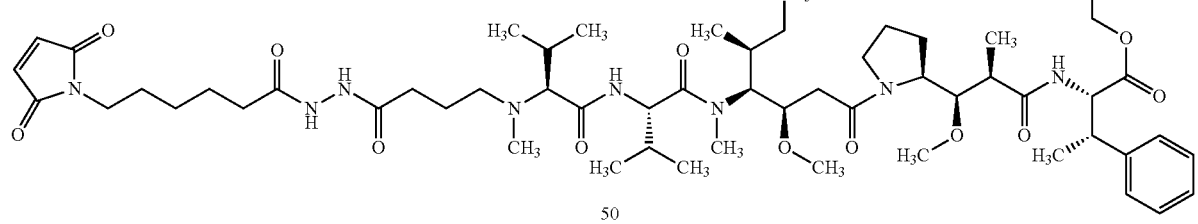

5.8 mg (6.3 µmol) of N-(3-carboxypropyl)-N-methyl-L-valyl-N-[(3R,4S,5S)-1-{(2S)-2-[(1R,2R)-3-{[(2S,3S)-1-(benzyloxy)-1-oxo-3-phenylbutan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 943 µl of DMF and then admixed with 3.6 mg (19 µmol) of 1-(3-dimethylaminopropyl)-3-ethylcarbodiimide hydrochloride, 2.9 mg (19 µmol) of 1-hydroxy-1H-benzotriazole hydrate, 2.2 µl of N,N-diisopropylethylamine and with 6.6 mg (25 µmol) of commercially available 6-(2,5-dioxo-2,5-dihydro-1H-pyrrol-1-yl)hexanehydrazide. The mixture was stirred at RT overnight and then concentrated under high vacuum. The remaining residue was purified by means of preparative HPLC. Thus, 4.5 mg (64% of theory) of the title compound were obtained as a colourless foam.

HPLC (Method 5): $R_t$=2.0 min;

LC-MS (Method 1): $R_t$=1.03 min; MS (ESIpos): m/z=1129 (M+H)$^+$.

Intermediate 134

N-[3-({[2-(2,5-dioxo-2,5-dihydro-1H-pyrrol-1-yl)ethyl]carbamoyl}amino)propyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

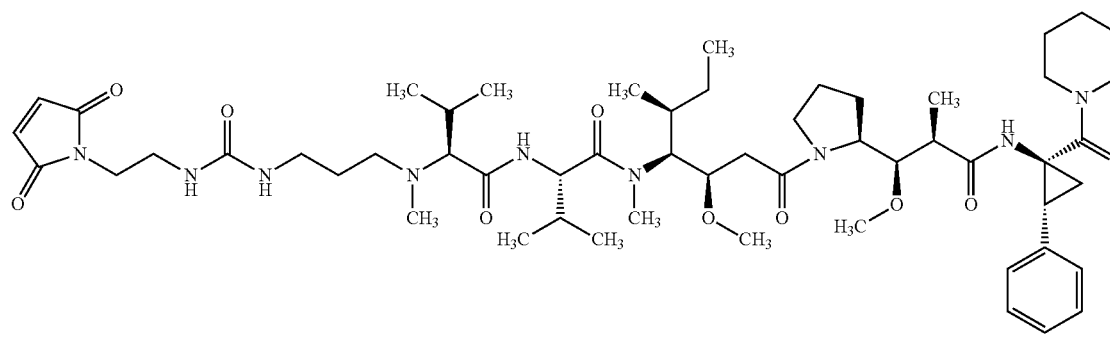

First, 4-nitrophenyl 2-(2,5-dioxo-2,5-dihydro-1H-pyrrol-1-yl)ethyl carbamate was prepared under standard conditions, proceeding from commercially available 1-(2-aminoethyl)-1H-pyrrole-2,5-dione trifluoroacetate and 4-nitrophenyl chlorocarbonate.

5 mg (6 μmol) of N-(3-aminopropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 1000 μl of DMF and then admixed with 2 μl of N,N-diisopropylethylamine and with 2.2 mg (9 μmol) of 4-nitrophenyl 2-(2,5-dioxo-2,5-dihydro-1H-pyrrol-1-yl)ethyl carbamate. The mixture was stirred at RT for 1 h and then concentrated under high vacuum. The remaining residue was purified by means of preparative HPLC. Thus, 1.6 mg (23% of theory) of the title compound were obtained as a colourless foam.

HPLC (Method 5): $R_t$=1.7 min;

LC-MS (Method 2): $R_t$=1.09 min; MS (ESIpos): m/z=1036 (M+H)$^+$.

Intermediate 135

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

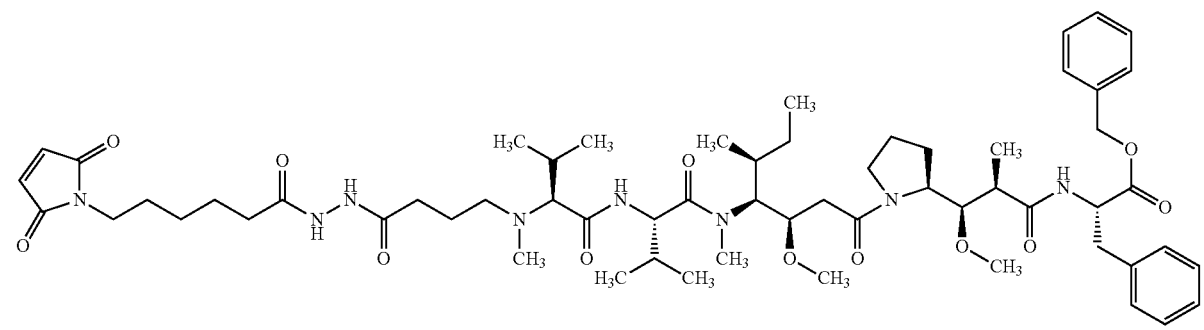 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1ccccc1)OC)N(C)C(=O)[C@@H](NC(=O)[C@H](C(C)C)N(C)CCCC(=O)NNC(=O)CCCCCN1C(=O)C=CC1=O)C(C)C]

10 mg (11 µmol) of N-(3-carboxypropyl)-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 4000 µl of DMF and then admixed with 6.3 mg (33 µmol) of 1-(3-dimethylaminopropyl)-3-ethylcarbodiimide hydrochloride, 4.5 mg (33 µmol) of 1-hydroxy-1H-benzotriazole hydrate, 5.7 µl of N,N-diisopropylethylamine and with 11.5 mg (44 µmol) of commercially available 6-(2,5-dioxo-2,5-dihydro-1H-pyrrol-1-yl)hexanehydrazide. The mixture was stirred at RT overnight and then concentrated under high vacuum. The remaining residue was purified by means of preparative HPLC. Thus, 2.6 mg (14% of theory) of the title compound were obtained as a colourless foam.

HPLC (Method 6): $R_t$=2.1 min;

LC-MS (Method 1): $R_t$=1.01 min; MS (ESIpos): m/z=1115 (M+H)$^+$.

Intermediate 136

N-(4-{4-[4-(2,5-dioxo-2,5-dihydro-1H-pyrrol-1-yl)butanoyl]piperazin-1-yl}-4-oxobutyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

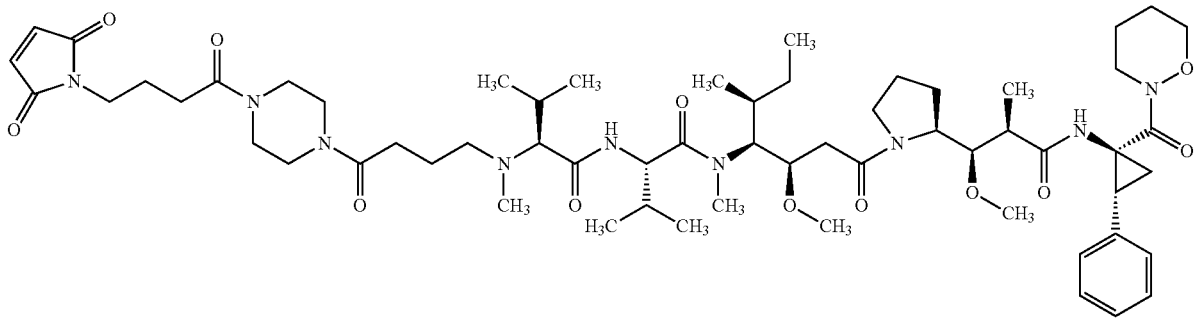 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)N1CCN(C(=O)CCCN2C(=O)C=CC2=O)CC1)C(C)C]

First, 1-[4-oxo-4-(piperazin-1-yl)butyl]-1H-pyrrole-2,5-dione trifluoroacetate was prepared under standard conditions, proceeding from tert-butyl piperazine-1-carboxylate and 4-(2,5-dioxo-2,5-dihydro-1H-pyrrol-1-yl)butanoic acid over 2 stages.

5 mg (5.6 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 1000 µl of DMF and then admixed with 2.1 mg (11 µmol) of 1-(3-dimethylaminopropyl)-3-ethylcarbodiimide hydrochloride, 1.7 mg (11 µmol) of 1-hydroxy-1H-benzotriazole hydrate, 2 µl of N,N-diisopropylethylamine and with 3.5 mg (5.6 µmol) of 1-[4-oxo-4-(piperazin-1-yl)butyl]-1H-pyrrole-2,5-dione trifluoroacetate. The mixture was stirred at RT overnight. Then 2.1 mg (5.6 µmol) of O-(7-azabenzotriazol-1-yl)-N,N,N',N'-tetramethyluronium hexafluorophosphate were added and the reaction mixture was stirred at RT for a further 3 h. Subsequently, the solvent was removed under reduced pressure and the remaining residue was purified by means of preparative HPLC. The corresponding fractions were concentrated and, by lyophilization from water, 0.6 mg (10% of theory) of the title compound was obtained as a colourless foam.

HPLC (Method 6): $R_t$=1.9 min;
LC-MS (Method 1): $R_t$=0.9 min; MS (ESIpos): m/z=1132 (M+H)$^+$.

Intermediate 137

N-(4-{2-[6-(2,5-dioxo-2,5-dihydro-1H-pyrrol-1-yl)hexanoyl]-1-methylhydrazino}-4-oxobutyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

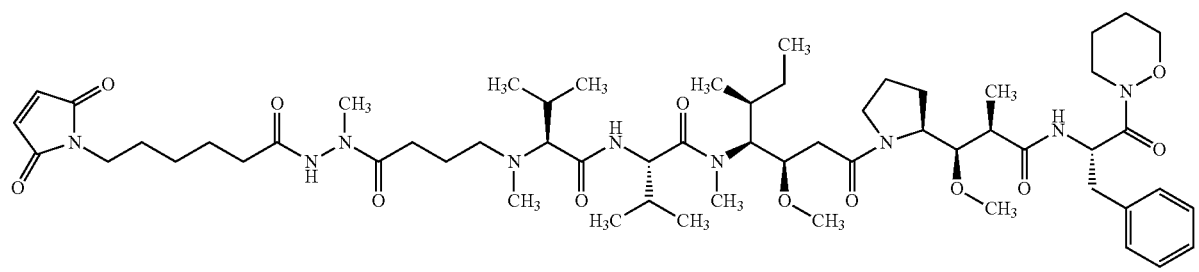 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCC(=O)N(C)NC(=O)CCCCCN1C(=O)C=CC1=O)C(C)C]

First, 6-(2,5-dioxo-2,5-dihydro-1H-pyrrol-1-yl)-N'-methylhexanehydrazide trifluoroacetate was prepared under standard conditions, proceeding from commercially available 6-(2,5-dioxo-2,5-dihydro-1H-pyrrol-1-yl)hexanoic acid and tert-butyl 1-methylhydrazinecarboxylate over 2 stages.

6.9 mg (8 μmol) of N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide were dissolved in 2540 μl of DMF and then admixed with 3.6 mg (9 μmol) of O-(7-azabenzotriazol-1-yl)-N,N,N',N'-tetramethyluronium hexafluorophosphate, 3 μl of N,N-diisopropylethylamine and with 4.1 mg (12 μmol) of 6-(2,5-dioxo-2,5-dihydro-1H-pyrrol-1-yl)-N'-methylhexanehydrazide trifluoroacetate. The mixture was stirred at RT overnight. Subsequently, the solvent was removed under reduced pressure and the remaining residue was purified by means of preparative HPLC. Thus, 3.9 mg (45% of theory) of the title compound were obtained as a colourless foam.

HPLC (Method 5): $R_t$=1.8 min;

LC-MS (Method 1): $R_t$=0.93 min; MS (ESIpos): m/z=1108 (M+H)$^+$.

Intermediate 138

N-{4-[(2-{[4-(2,5-dioxo-2,5-dihydro-1H-pyrrol-1-yl)butanoyl](methyl)amino}ethyl)(methyl)amino]-4-oxobutyl}-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

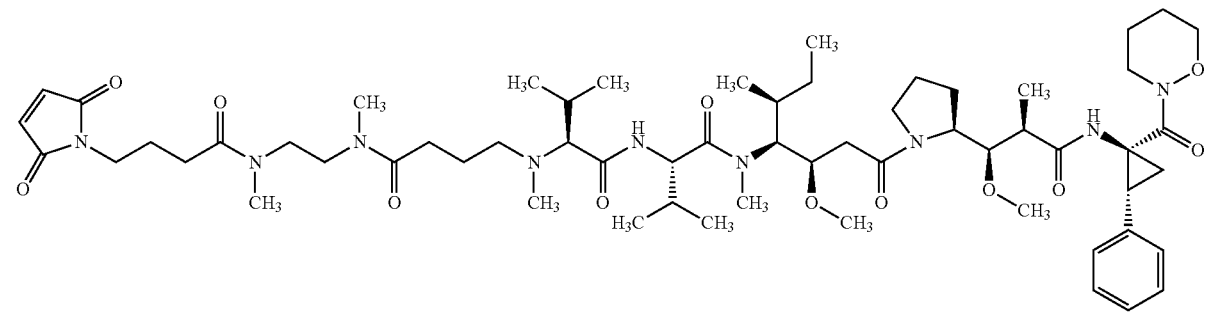 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)N(C)CCN(C)C(=O)CCCN1C(=O)C=CC1=O)C(C)C]

Proceeding from tert-butylmethyl 2-(methylamino)ethyl carbamate and 4-(2,5-dioxo-2,5-dihydro-1H-pyrrol-1-yl)butanoic acid, over 2 stages, 4-(2,5-dioxo-2,5-dihydro-1H-pyrrol-1-yl)-N-methyl-N-[2-(methylamino)ethyl]butanamide trifluoroacetate was first prepared by.

6.6 mg (7.3 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 2000 µl of DMF and then admixed with 5.6 mg (14.7 µmol) of O-(7-azabenzotriazol-1-yl)-N,N,N',N'-tetramethyluronium hexafluorophosphate, 2.6 µl of N,N-diisopropylethylamine and with 4.1 mg (9 µmol) of 4-(2,5-dioxo-2,5-dihydro-1H-pyrrol-1-yl)-N-methyl-N-[2-(methylamino)ethyl]butanamide trifluoroacetate. After stirring at RT for 3 h, the same amounts of HATU and N,N-diisopropylethylamine were added once again, and the reaction mixture was then stirred at RT overnight. Subsequently, the solvent was removed under reduced pressure and the remaining residue was purified by means of preparative HPLC. Thus, 4 mg (44% of theory) of the title compound were obtained as a colourless foam.

HPLC (Method 6): $R_t$=2.0 min;

LC-MS (Method 1): $R_t$=0.91 min; MS (ESIpos): m/z=1134 (M+H)$^+$.

Intermediate 139

(2R,3S)-3-amino-4-{2-[6-(2,5-dioxo-2,5-dihydro-1H-pyrrol-1-yl)hexanoyl]hydrazino}-4-oxobutan-2-yl (3R,4S,7S,10S)-4-[(2S)-butan-2-yl]-7,10-diisopropyl-3-(2-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-2-oxoethyl)-5,11-dimethyl-6,9-dioxo-2-oxa-5,8,11-triazapentadecan-15-oate

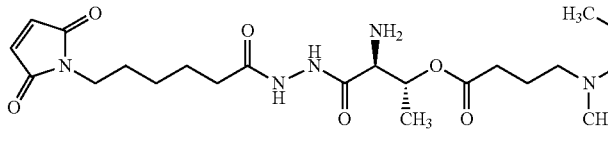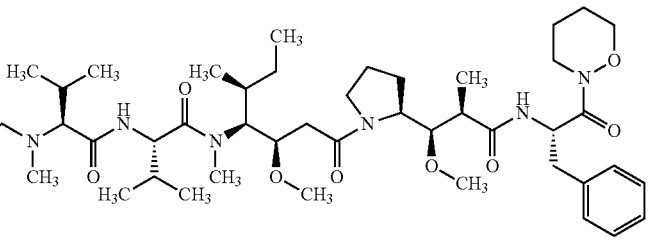

13 mg (14.7 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide were dissolved in 10 ml of dichloromethane and then admixed with 8.4 mg (44 µmol) of 1-(3-dimethylaminopropyl)-3-ethylcarbodiimide hydrochloride, 5.4 mg (44 µmol) of 4-dimethylaminopyridine and with 9 mg (29.3 µmol) of commercially available benzyl N-(tert-butoxycarbonyl)-L-threoninate. The mixture was stirred at RT for 5 h. Subsequently, the reaction mixture was twice extracted by shaking with water and the organic phase was dried over sodium sulphate and concentrated under reduced pressure. The remaining residue was purified by means of preparative HPLC. After lyophilization from dioxane/water, 14 mg (81% of theory) of the protected intermediate were obtained as a colourless foam.

HPLC (Method 12): $R_t$=2.3 min;

LC-MS (Method 1): $R_t$=1.13 min; MS (ESIpos): m/z=1178 (M+H)$^+$.

Subsequently, the Z protecting group was detached by hydrogenolytic means in methanol over 10% palladium/activated carbon. 9.5 mg (0.0087 mmol) of the deprotected crude product were then, without further purification, taken up in 5 ml of DMF, and admixed 5 mg (26.2 µmol) of 1-(3-dimethylaminopropyl)-3-ethylcarbodiimide hydrochloride, 4 mg (26.2 µmol) of 1-hydroxy-1H-benzotriazole hydrate, 54.6 µl of N,N-diisopropylethylamine and with 9.1 mg (34.9 µmol) of commercially available 6-(2,5-dioxo-2,5-dihydro-1H-pyrrol-1-yl)hexanehydrazide. The mixture was stirred at RT for 1 h and then concentrated under high vacuum. The remaining residue was purified by means of preparative HPLC. After lyophilization from dioxane, 9.5 mg (84% of theory) of the Boc-protected intermediate were obtained.

HPLC (Method 12): $R_t$=2.1 min;

LC-MS (Method 1): $R_t$=0.97 min; MS (ESIpos): m/z=1295 (M+H)$^+$.

Subsequently, 9.5 mg (7.3 µmol) were deprotected with 0.5 ml of trifluoroacetic acid in 2 ml of dichloromethane of the Boc-protected intermediate and, after lyophilization from dioxane, 9 mg (82% of theory) of the title compound were obtained as a colourless foam.

HPLC (Method 12): $R_t$=2.1 min;

LC-MS (Method 1): $R_t$=0.84 min; MS (ESIpos): m/z=1195 (M+H)$^+$.

Intermediate 140

N-(4-{2-[6-(2,5-dioxo-2,5-dihydro-1H-pyrrol-1-yl)hexanoyl]-1-methylhydrazino}-4-oxobutyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

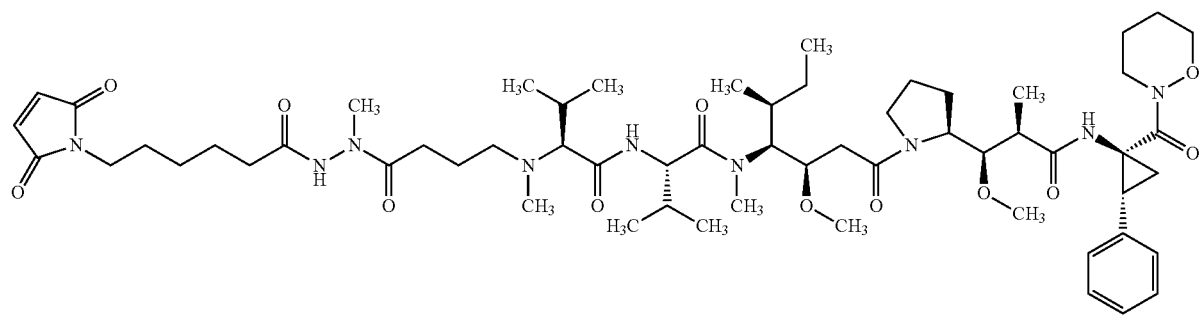 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)N(C)NC(=O)CCCCCN1C(=O)C=CC1=O)C(C)C]

4.1 mg (12 µmol) of 6-(2,5-dioxo-2,5-dihydro-1H-pyrrol-1-yl)-N'-methylhexanehydrazide trifluoroacetate (Intermediate 22) were dissolved together with 6.9 mg (8 µmol) of the compound from Intermediate 61 in 2.5 ml of DMF and then admixed with 3.5 mg (9 µmol) of O-(7-azabenzotriazol-1-yl)-N,N,N',N'-tetramethyluronium hexafluorophosphate and 3 µl of N,N-diisopropylethylamine. The mixture was stirred at RT overnight and then concentrated under high vacuum. The remaining residue was purified by means of preparative HPLC. After lyophilization from dioxane, 2.6 mg (30% of theory) of the title compound were obtained.

HPLC (Method 5): $R_t$=1.8 min;

LC-MS (Method 1): $R_t$=0.90 and 0.91 min; MS (ESIpos): m/z=1120 (M+H)$^+$.

Intermediate 141

N-[4-({1-[4-(2,5-dioxo-2,5-dihydro-1H-pyrrol-1-yl)butanoyl]piperidin-4-yl}oxy)-4-oxobutyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

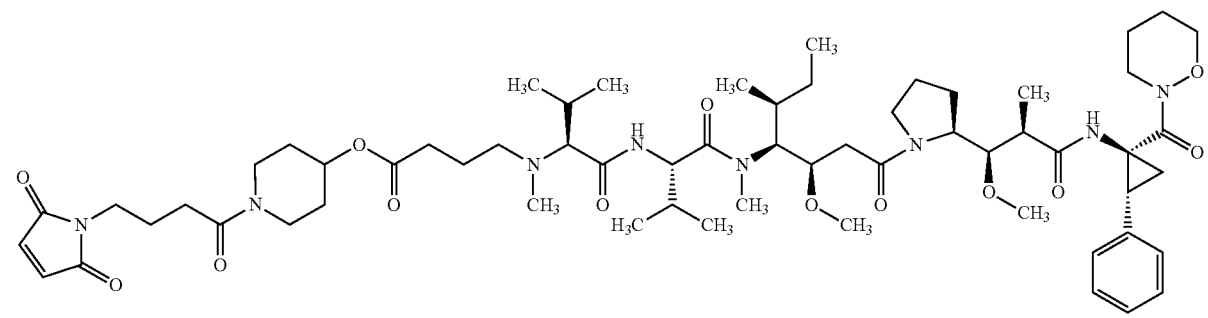 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)OC1CCN(C(=O)CCCN2C(=O)C=CC2=O)CC1)C(C)C]

44 mg (49 μmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide were dissolved in 2 ml of dichloromethane and then admixed with 18.8 mg (98 μmol) of 1-(3-dimethylaminopropyl)-3-ethylcarbodiimide hydrochloride, 3.8 mg (24 μmol) of 4-dimethylaminopyridine and with 23 mg (98 μmol) of commercially available benzyl 4-hydroxypiperidine-1-carboxylate. The mixture was stirred at RT overnight and then concentrated under high vacuum. The remaining residue was purified by means of preparative HPLC. Thus, 22 mg (40% of theory) of the Z-protected intermediate were obtained as a colourless foam.

HPLC (Method 5): $R_t$=2.1 min;
LC-MS (Method 1): $R_t$=1.04 min; MS (ESIpos): m/z=1116 (M+H)$^+$.

Subsequently, the Z protecting group was detached by hydrogenolytic means in ethanol over palladium/activated carbon.

19 mg (19 μmol) of the deprotected crude product were then, without further purification, taken up in 4 ml of DMF and admixed with 7 mg (39 μmol) of 4-(2,5-dioxo-2,5-dihydro-1H-pyrrol-1-yl)butanoic acid, 11 mg (29 μmol) of O-(7-azabenzotriazol-1-yl)-N,N,N',N'-tetramethyluronium hexafluorophosphate and 5 μl of N,N-diisopropylethylamine. The mixture was stirred at RT for 1 h and then concentrated under high vacuum. The remaining residue was purified by means of preparative HPLC. After lyophilization from dioxane, 7.5 mg (34% of theory) of the title compound were obtained.

HPLC (Method 5): $R_t$=1.8 min;
LC-MS (Method 1): $R_t$=0.94 min; MS (ESIpos): m/z=1147 (M+H)$^+$.

Intermediate 142

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

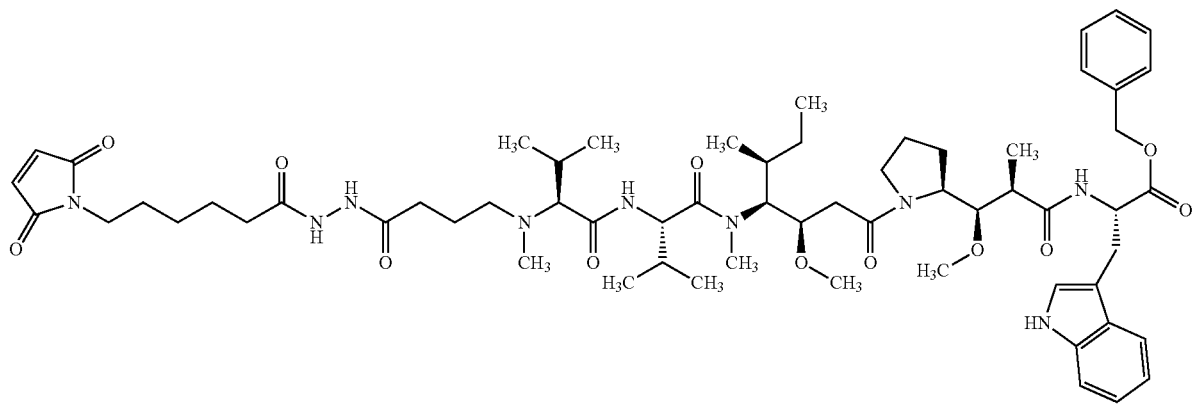 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OCc1ccccc1)OC)N(C)C(=O)[C@@H](NC(=O)[C@H](C(C)C)N(C)CCCC(=O)NNC(=O)CCCCCN1C(=O)C=CC1=O)C(C)C]

9 mg (9.5 μmol) of N-(3-carboxypropyl)-N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 72) were dissolved in 1000 μl of DMF and then admixed with 10 mg (38 μmol) of commercially available 6-(2,5-dioxo-2,5-dihydro-1H-pyrrol-1-yl)hexanehydrazide, 7.2 mg (19 μmol) of O-(7-azabenzotriazol-1-yl)-N,N,N',N'-tetramethyluronium hexafluorophosphate and 8 μl of N,N-diisopropylethylamine, and the reaction mixture was stirred at RT for 1 h. Subsequently, the solvent was removed under reduced pressure and the remaining residue was purified by means of preparative HPLC. The corresponding fractions were concentrated and, by lyophilization, 6.4 mg (58% of theory) of the title compound were obtained as a colourless foam.

HPLC (Method 5): $R_t$=1.9 min;
LC-MS (Method 1): $R_t$=0.99 min; MS (ESIpos): m/z=1154 (M+H)$^+$.

Intermediate 143

N-(4-{2-[4-(2,5-dioxo-2,5-dihydro-1H-pyrrol-1-yl)-2,2-dimethylbutanoyl]hydrazino}-4-oxobutyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

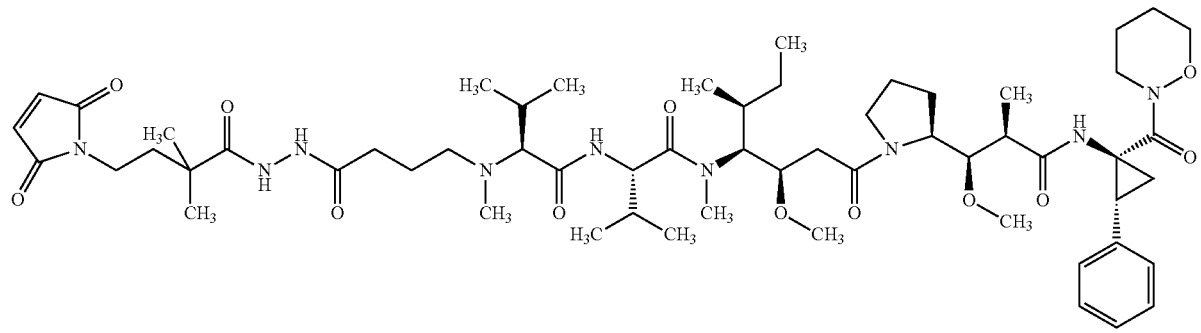 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)NNC(=O)C(C)(C)CCN1C(=O)C=CC1=O)C(C)C]

6 mg (6.7 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide (Intermediate 61) were reacted with 3 mg (8.7 µmol) of 4-(2,5-dioxo-2,5-dihydro-1H-pyrrol-1-yl)-2,2-dimethylbutanehydrazide trifluoroacetate in analogy to Intermediate 142 to give 2 mg (27% of theory) of the title compound.

HPLC (Method 12): $R_t$=2.1 min;

LC-MS (Method 3): $R_t$=1.92 min; MS (ESIpos): m/z=1106 (M+H)$^+$.

Intermediate 144

N-(4-{2-[4-(2,5-dioxo-2,5-dihydro-1H-pyrrol-1-yl)-2,2-dimethylbutanoyl]hydrazino}-4-oxobutyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

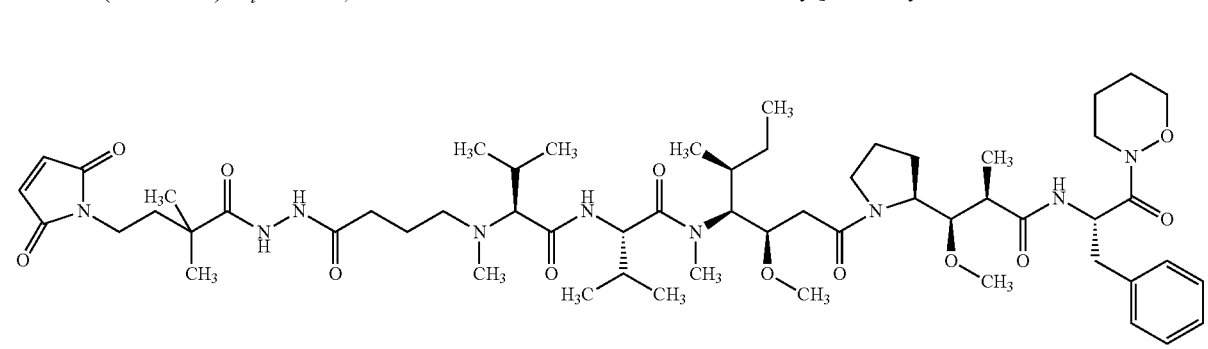

To a solution of 5 mg (5.6 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide in 1 ml of DMF were added 7.65 mg (22.5 µmol) of 4-(2,5-dioxo-2,5-dihydro-1H-pyrrol-1-yl)-2,2-dimethylbutanehydrazide trifluoroacetate, 3.2 mg (16.9 µmol) of EDC, 1.96 µl (11.3 µmol) of diisopropylethylamine and 2.6 mg (16.9 µmol) of HOBT. The reaction mixture was stirred at RT for 3 h. Subsequently, a further 0.95 mg (2.8 µmol) of 4-(2,5-dioxo-2,5-dihydro-1H-pyrrol-1-yl)-2,2-dimethylbutanehydrazide trifluoroacetate was added. After stirring overnight, the reaction mixture was concentrated and purified by preparative HPLC. 3.5 mg (85% purity, 48% of theory) of the title compound were obtained.

LC-MS (Method 3): $R_t$=1.86 min; m/z=1094 (M+H)$^+$.

Intermediate 145

N-[3-(2,5-dioxo-2,5-dihydro-1H-pyrrol-1-yl)propyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenyl cyclopropyl]amino}-3-oxopropyl]pyrrolidin-1-yl}-5-methyl-1-oxoheptan-4-yl]-N-methyl-L-valinamide

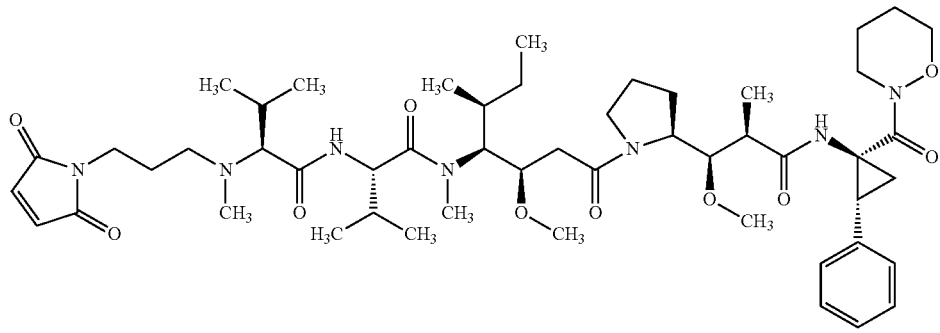 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCN1C(=O)C=CC1=O)C(C)C]

12 mg (14 μmol) of N-(3-aminopropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide (Intermediate 66) were taken up in 750 μl of dioxane and admixed with 1.5 ml of saturated sodium hydrogencarbonate solution and then with 3.2 mg (21 μmol) of methyl 2,5-dioxo-2,5-dihydro-1H-pyrrole-1-carboxylate. The reaction mixture was stirred at RT for 1 h and then concentrated under reduced pressure. The remaining residue was purified by means of preparative HPLC. After lyophilization, 4.2 mg (32% of theory) of the title compound were obtained.

HPLC (Method 5): $R_t$=1.7 min;
LC-MS (Method 1): $R_t$=0.94 min; MS (ESIpos): m/z=950 (M+H)$^+$.

Intermediate 146

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-({(2S)-1-[benzyl(methyl)amino]-1-oxo-3-phenylpropan-2-yl}amino)-1-methoxy-2-methyl-3-oxopropyl]pyrrolidin-1-yl}-3-methoxy-5-methyl-1-oxoheptan-4-yl]-N-methyl-L-valinamide

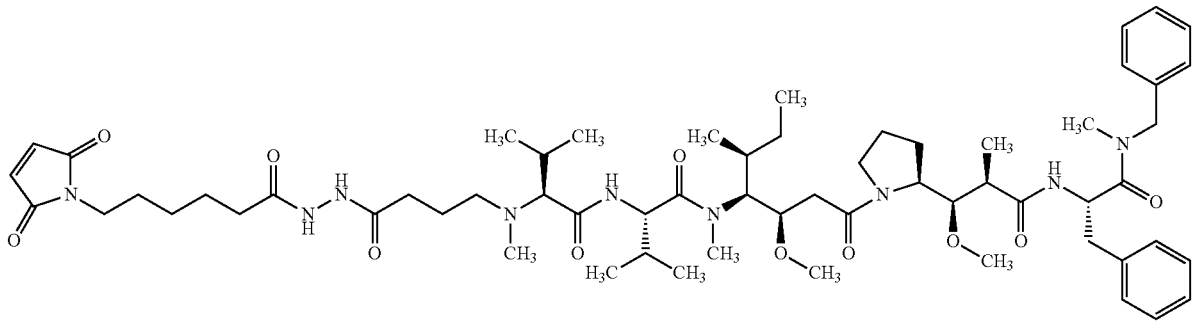 [SMILES: CC[C@H](C)[C@@H]([C@@H](CC(=O)N1CCC[C@H]1[C@H](OC)[C@@H](C)C(=O)N[C@@H](Cc1ccccc1)C(=O)N(C)Cc1ccccc1)OC)N(C)C(=O)[C@@H](NC(=O)[C@H](C(C)C)N(C)CCCC(=O)NNC(=O)CCCCCN1C(=O)C=CC1=O)C(C)C]

9 mg (9.8 μmol) of N-(3-carboxypropyl)-N-methyl-L-valyl-N-[(3R,4S,5S)-1-{(2S)-2-[(1R,2R)-3-({(2S)-1-[benzyl(methyl)amino]-1-oxo-3-phenylpropan-2-yl}amino)-1-methoxy-2-methyl-3-oxopropyl]pyrrolidin-1-yl}-3-methoxy-5-methyl-1-oxoheptan-4-yl]-N-methyl-L-valinamide (Intermediate 73) were reacted in analogy to Intermediate 133 with 10 mg (39 μmol) of 6-(2,5-dioxo-2,5-dihydro-1H-pyrrol-1-yl)hexanehydrazide to give 1.8 mg (15% of theory) of the title compound.

HPLC (Method 12): $R_t$=2.2 min;
LC-MS (Method 9): $R_t$=5.11 min; MS (ESIpos): m/z=1128 (M+H)$^+$.

Intermediate 147

N-{4-[(2,5-dioxopyrrolidin-1-yl)oxy]-4-oxobutyl}-N-methyl-L-valyl-N-[(3R,4S,5S)-1-{(2S)-2-[(1R,2R)-3-{[(2S,3S)-1-(benzyloxy)-1-oxo-3-phenylbutan-2-yl]amino}-1-methoxy-2-methyl-3-oxopropyl]pyrrolidin-1-yl}-3-methoxy-5-methyl-1-oxoheptan-4-yl]-N-methyl-L-valinamide

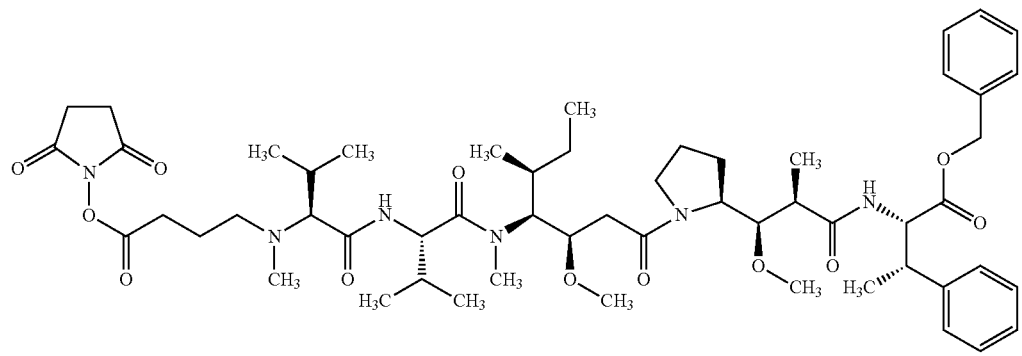 [SMILES: CC[C@H](C)[C@@H]([C@@H](CC(=O)N1CCC[C@H]1[C@H](OC)[C@@H](C)C(=O)N[C@H](C(=O)OCc1ccccc1)[C@@H](C)c1ccccc1)OC)N(C)C(=O)[C@@H](NC(=O)[C@H](C(C)C)N(C)CCCC(=O)ON1C(=O)CCC1=O)C(C)C]

16 mg (17 μmol) of N-(3-carboxypropyl)-N-methyl-L-valyl-N-[(3R,4S,5S)-1-{(2S)-2-[(1R,2R)-3-{[(2S,3S)-1-(benzyloxy)-1-oxo-3-phenylbutan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 70) were dissolved in 2 ml of dichloromethane and admixed with 2.6 mg (23 mmol) of 1-hydroxypyrrolidine-2,5-dione and then with 4 mg (21 μmol) of 1-(3-dimethylaminopropyl)-3-ethylcarbodiimide hydrochloride. After stirring at RT for 2 h, the same amounts of 1-hydroxypyrrolidine-2,5-dione and 1-(3-dimethylaminopropyl)-3-ethylcarbodiimide hydrochloride were added once again. Then stirring at RT overnight, the reaction mixture was concentrated under reduced pressure. The remaining residue was purified by means of preparative HPLC. After lyophilization, 10 mg (56% of theory) of the title compound were obtained.

HPLC (Method 5): $R_t$=2.0 min;

Intermediate 148

N-{4-[(2-{[4-(2,5-dioxo-2,5-dihydro-1H-pyrrol-1-yl)butanoyl](methyl)amino}ethyl)amino]-4-oxobutyl}-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

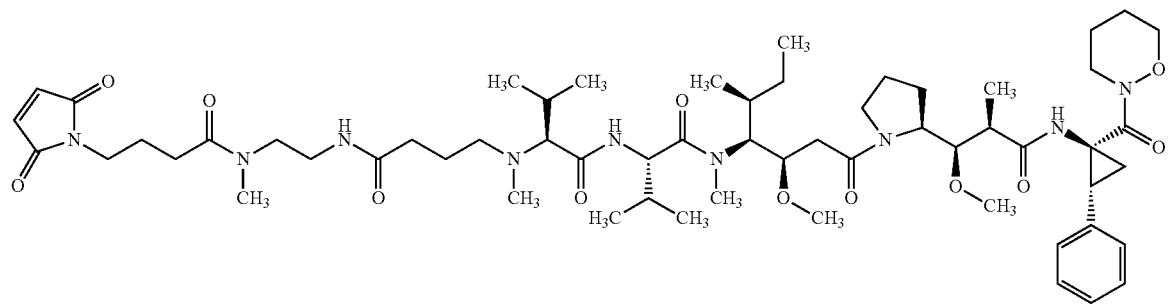 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)NCCN(C)C(=O)CCCN1C(=O)C=CC1=O)C(C)C]

6 mg (7 μmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide (Intermediate 61) were combined with 2.8 mg (8 μmol) of N-(2-aminoethyl)-4-(2,5-dioxo-2,5-dihydro-1H-pyrrol-1-yl)-N-methylbutanamide trifluoroacetate, 10.1 mg (27 μmol) of O-(7-azabenzotriazol-1-yl)-N,N,N',N'-tetramethyluronium hexafluorophosphate and 5 μl of N,N-diisopropylethylamine in 2 ml of DMF and stirred at RT overnight. Then another 5 mg (23.5 μmol) of O-(7-azabenzotriazol-1-yl)-N,N,N',N'-tetramethyluronium hexafluorophosphate and 3 μl of N,N-diisopropylethylamine were added. After stirring at RT for a further 5 h, the solvent was removed under reduced pressure and the remaining residue was purified by means of preparative HPLC. The corresponding fractions were concentrated and, by lyophilization from dioxane, 1.3 mg (15% of theory) of the title compound were obtained.

HPLC (Method 12): $R_f$=2.1 min;
LC-MS (Method 2): $R_t$=1.21 min; MS (ESIpos): m/z=1120 (M+H)$^+$.

Intermediate 149

N-{4-[(2-{[4-(2,5-dioxo-2,5-dihydro-1H-pyrrol-1-yl)butanoyl]amino}ethyl)(methyl)amino]-4-oxobutyl}-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

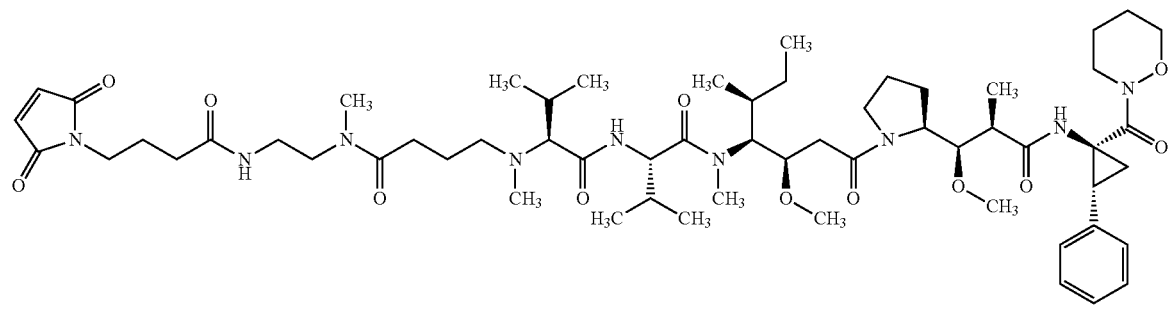 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)N(C)CCNC(=O)CCCN1C(=O)C=CC1=O)C(C)C]

6 mg (7 μmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide (Intermediate 61) were combined with 3.1 mg (9 μmol) of 4-(2,5-dioxo-2,5-dihydro-1H-pyrrol-1-yl)-N-[2-(methylamino)ethyl]butanamide trifluoroacetate, 10.1 mg (27 μmol) of O-(7-azabenzotriazol-1-yl)-N,N,N',N'-tetramethyluronium hexafluorophosphate and 5 μl of N,N-diisopropylethylamine in 2 ml of DMF, and the mixture was stirred at RT for 4 h. Then the solvent was removed under reduced pressure and the remaining residue was purified by means of preparative HPLC. The corresponding fractions were concentrated and, by lyophilization from dioxane, 1 mg (13.4% of theory) of the title compound were obtained.

HPLC (Method 12): $R_f$=2.1 min;
LC-MS (Method 1): $R_t$=0.89 min; MS (ESIpos): m/z=1121 (M+H)$^+$.

Intermediate 150

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-oxo-3-{[(1S,2R)-2-phenyl-1-(propylcarbamoyl)cyclopropyl]amino}propyl]pyrrolidin-1-yl}-5-methyl-1-oxoheptan-4-yl]-N-methyl-L-valinamide

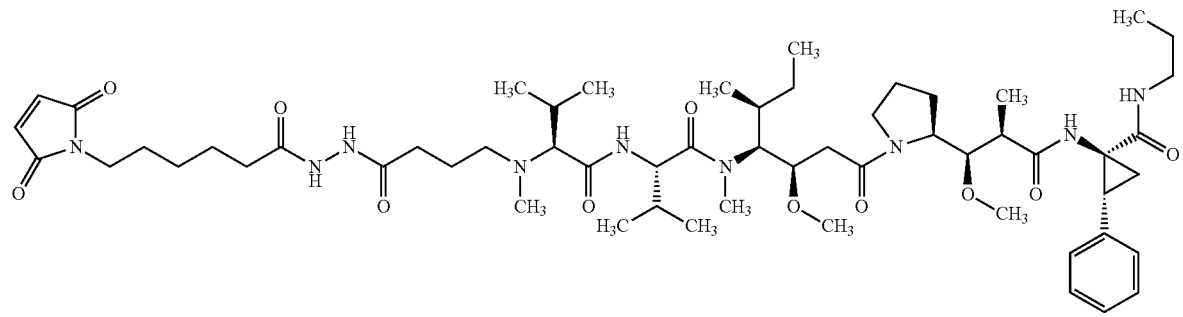 [SMILES: CCCNC(=O)[C@]1(NC(=O)[C@H](C)[C@@H](OC)[C@@H]2CCCN2C(=O)C[C@@H](OC)[C@H]([C@@H](C)CC)N(C)C(=O)[C@@H](NC(=O)[C@H](C(C)C)N(C)CCCC(=O)NNC(=O)CCCCCN2C(=O)C=CC2=O)C(C)C)C[C@@H]1c1ccccc1]

7.9 mg (9 μmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(1S,2R)-2-phenyl-1-(propylcarbamoyl)cyclopropyl]amino}propyl]pyrrolidin-1-yl}-5-methyl-1-oxoheptan-4-yl]-N-methyl-L-valinamide were dissolved in 3 ml of DMF and then admixed with 10.4 mg (54 μmol) of 1-(3-dimethylaminopropyl)-3-ethylcarbodiimide hydrochloride, 8.3 mg (54 μmol) of 1-hydroxy-1H-benzotriazole hydrate, 9 μl of N,N-diisopropylethylamine and with 9.5 mg (36 μmol) of commercially available 6-(2,5-dioxo-2,5-dihydro-1H-pyrrol-1-yl)hexanehydrazide. The mixture was stirred at RT overnight and then concentrated under high vacuum. The remaining residue was purified by means of preparative HPLC. Thus, 4.3 mg (22% of theory) of the title compound were obtained as a colourless foam.

HPLC (Method 6): $R_t$=1.9 min;
LC-MS (Method 9): $R_t$=4.93 min; MS (ESIpos): m/z=1078 (M+H)⁺.

Intermediate 151

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(1S,2R)-1-carbamoyl-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

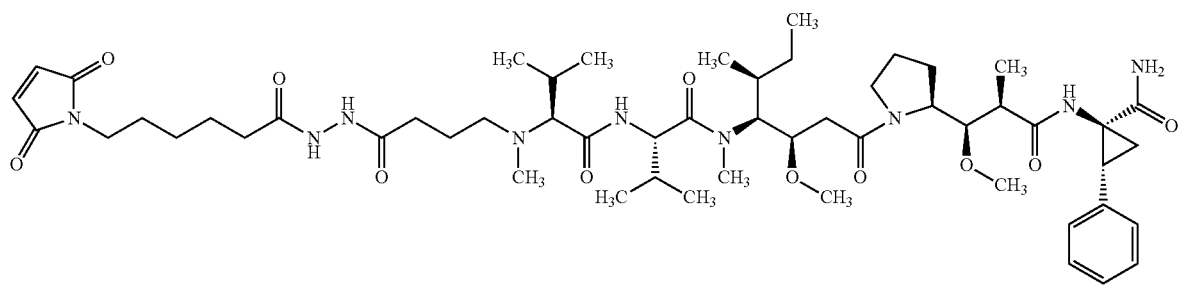 [SMILES: CC[C@H](C)[C@@H]([C@@H](CC(=O)N1CCC[C@H]1[C@H](OC)[C@@H](C)C(=O)N[C@@]1(C(N)=O)C[C@@H]1c1ccccc1)OC)N(C)C(=O)[C@@H](NC(=O)[C@H](C(C)C)N(C)CCCC(=O)NNC(=O)CCCCCN1C(=O)C=CC1=O)C(C)C]

The compound was prepared analogously to Intermediate 150, proceeding from the compound in Intermediate 81.
HPLC (Method 5): $R_t$=1.7 min;
LC-MS (Method 1): $R_t$=0.87 min; MS (ESIpos): m/z=1036 (M+H)⁺.

Intermediate 152

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(1S,2R)-1-(ethoxycarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

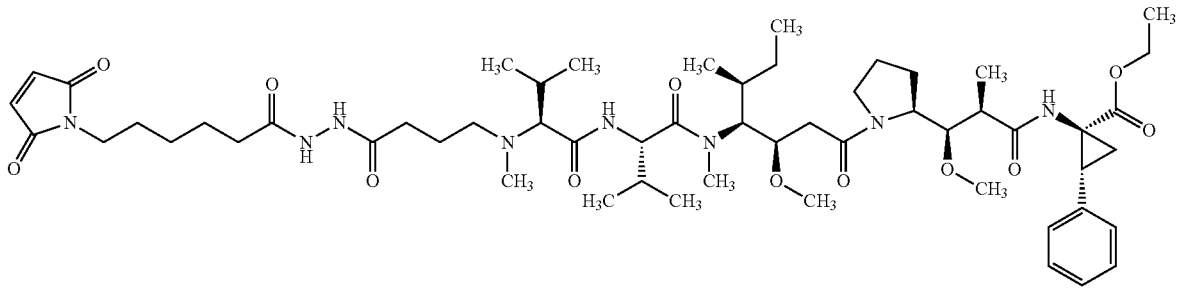 [SMILES: CCOC(=O)[C@]1(NC(=O)[C@H](C)[C@@H](OC)[C@@H]2CCCN2C(=O)C[C@@H](OC)[C@H]([C@@H](C)CC)N(C)C(=O)[C@@H](NC(=O)[C@H](C(C)C)N(C)CCCC(=O)NNC(=O)CCCCCN2C(=O)C=CC2=O)C(C)C)C[C@@H]1c1ccccc1]

10 mg (12 µmol) of N-(3-carboxypropyl)-N-methyl-L-valyl-N-[(3R,4S,5S)-1-{(2S)-2-[(1R,2R)-3-{[(1S,2R)-1-(ethoxycarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide were dissolved in 3 ml of DMF and then admixed with 8.9 mg (23 µmol) of O-(7-azabenzotriazol-1-yl)-N,N,N',N'-tetramethyluronium hexafluorophosphate, 10 µl of N,N-diisopropylethylamine and with 12 mg (47 µmol) of commercially available 6-(2,5-dioxo-2,5-dihydro-1H-pyrrol-1-yl)hexanehydrazide. The mixture was stirred at RT for 1 h. This was followed by concentration under high vacuum and purification of the remaining residue by means of preparative HPLC. Thus, 5.8 mg (37% of theory) of the title compound were obtained as a colourless foam.

HPLC (Method 6): $R_t$=2.0 min;

LC-MS (Method 9): $R_t$=4.99 min; MS (ESIpos): m/z=1066 (M+H)$^+$.

Intermediate 153

N-[1-(2,5-dioxo-2,5-dihydro-1H-pyrrol-1-yl)-12,15-dioxo-3,6,9-trioxa-13,14-diazaoctadecan-18-yl]-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

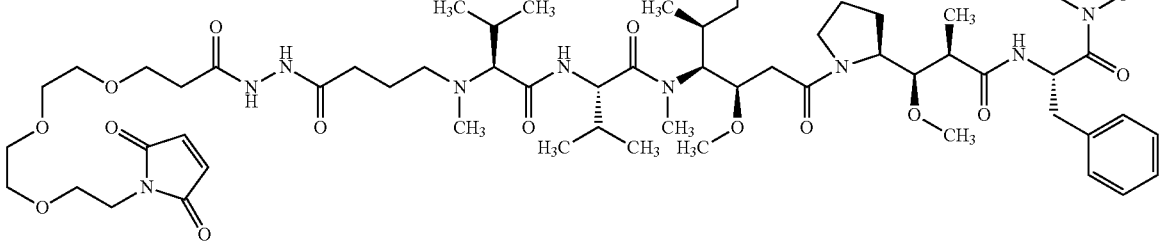

To a solution of 5 mg (5.6 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide in 1 ml of DMF were added 9.7 mg (22.5 µmol) of 3-(2-{2-[2-(2,5-dioxo-2,5-dihydro-1H-pyrrol-1-yl)ethoxy]ethoxy}ethoxy)propanehydrazide trifluoroacetate, 3.2 mg (16.9 µmol) of EDC, 1.96 µl (11.3 µmol) of N,N-diisopropylethylamine and 2.6 mg (16.9 mmol) of HOBT. The reaction mixture was stirred at RT for 3 h. Subsequently, a further 1.2 mg (2.8 µmol) of 3-(2-{2-[2-(2,5-dioxo-2,5-dihydro-1H-pyrrol-1-yl)ethoxy]ethoxy}ethoxy)propanehydrazide trifluoroacetate were added. The reaction mixture was stirred at RT overnight and then purified by preparative HPLC.

3.6 mg (51% of theory) of the title compound were obtained.

LC-MS (Method 1): $R_t$=0.90 min; m/z=1185 (M+H)$^+$.

Intermediate 154

(2R,3S)-3-amino-4-{2-[6-(2,5-dioxo-2,5-dihydro-1H-pyrrol-1-yl)hexanoyl]hydrazino}-4-oxobutan-2-yl (3R,4S,7S,10S)-4-[(2S)-butan-2-yl]-7,10-diisopropyl-3-(2-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-2-oxoethyl)-5,11-dimethyl-6,9-dioxo-2-oxa-5,8,11-triazapentadecan-15-oate

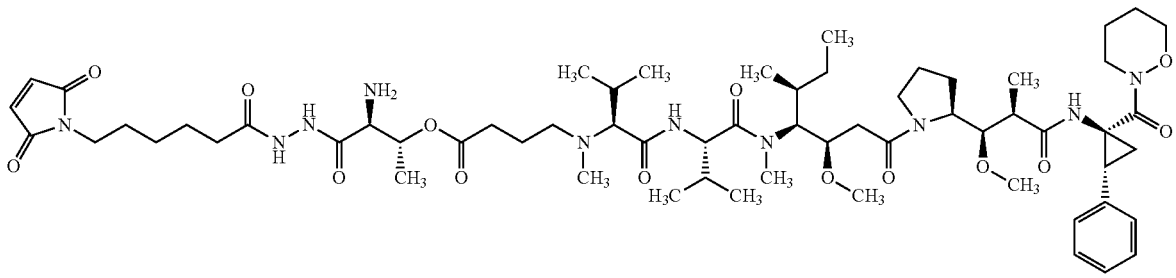 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)O[C@H](C)[C@H](N)C(=O)NNC(=O)CCCCCN1C(=O)C=CC1=O)C(C)C]

15 mg (17 µmol) of N-(3-carboxypropyl)-N-methyl-L-valyl-N-[(3R,4S,5S)-3-methoxy-1-{(2S)-2-[(1R,2R)-1-methoxy-2-methyl-3-{[(1S)-1-(1,2-oxazinan-2-yl)-2-phenylcyclopropyl]amino}-3-oxopropyl]pyrrolidin-1-yl}-5-methyl-1-oxoheptan-4-yl]-N-methyl-L-valinamide were dissolved in 10 ml of dichloromethane and then admixed with 12.8 mg (67 µmol) of 1-(3-dimethylaminopropyl)-3-ethylcarbodiimide hydrochloride, 10 mg (83 µmol) of 4-dimethylaminopyridine and with 10.3 mg (33 µmol) of commercially available benzyl N-(tert-butoxycarbonyl)-L-threoninate. The mixture was heated to reflux for 4 h. Then the same amounts of coupling reagent and 4-dimethylaminopyridine were added again and the reaction mixture was heated under reflux overnight. Subsequently, the reaction mixture was diluted with dichloromethane and extracted by shaking once with water, and the organic phase was removed and concentrated under high vacuum. The remaining residue was purified by means of preparative HPLC. Thus, 7.7 mg (37% of theory) of the protected intermediate were obtained as a colourless foam.

HPLC (Method 12): $R_t$=2.5 min;

LC-MS (Method 1): $R_t$=1.13 min; MS (ESIpos): m/z=1190 (M+H)$^+$.

Subsequently, the benzyl ester protecting group was removed by hydrogenation under standard hydrogen pressure in methanol over 10% palladium/activated carbon, and the acid thus obtained, as described in Intermediate 151, was joined to 6-(2,5-dioxo-2,5-dihydro-1H-pyrrol-1-yl)hexanehydrazide. In a last step, the Boc protecting group was detached with trifluoroacetic acid. The remaining residue was purified by means of preparative HPLC. Thus, 0.22 mg (2.5% of theory over 3 stages) of the title compound was obtained as a colourless foam.

HPLC (Method 12): $R_t$=2.0 min;

LC-MS (Method 1): $R_t$=0.81 min; MS (ESIpos): m/z=1207 (M+H)$^+$.

Intermediate 155

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-amino-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

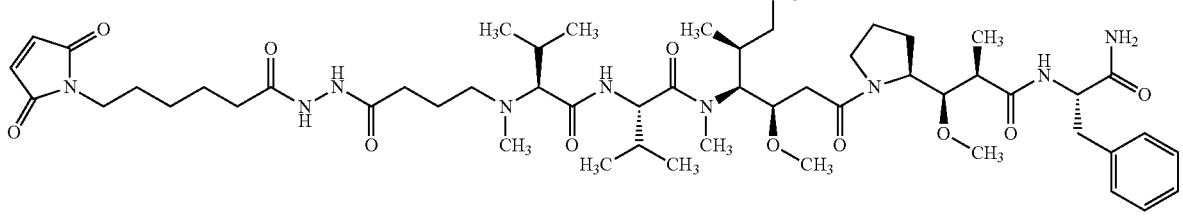

This compound was prepared in analogy to the synthesis described in Intermediate 152, from N-(3-carboxypropyl)-N-methyl-L-valyl-N-[(3R,4S,5S)-1-{(2S)-2-[(1R,2R)-3-{[(2S)-1-amino-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide and commercially available 6-(2,5-dioxo-2,5-dihydro-1H-pyrrol-1-yl)hexanehydrazide.

HPLC (Method 5): $R_t$=1.6 min;

LC-MS (Method 1): $R_t$=0.82 min; MS (ESIpos): m/z=1024 (M+H)$^+$.

Intermediate 156

N-(3-{[(1-{[(2,5-dioxopyrrolidin-1-yl)oxy]carbonyl}cyclopropyl)carbonyl]amino}propyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

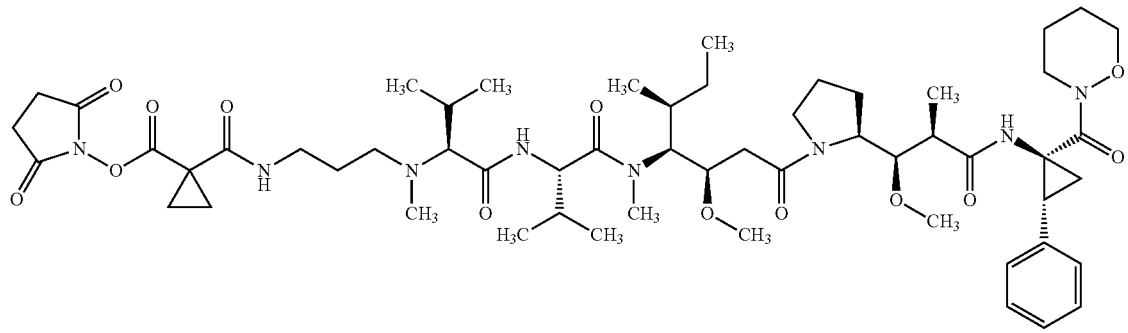 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCNC(=O)C1(C(=O)ON2C(=O)CCC2=O)CC1)C(C)C]

This compound was prepared in analogy to the synthesis described in the last stage of Intermediate 131, from N-(3-aminopropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide and 1,1'-[cyclopropane-1,1-diylbis(carbonyloxy)]dipyrrolidine-2,5-dione, which had been obtained from the corresponding dicarboxylic acid beforehand.

HPLC (Method 12): $R_t$=2.0 min;

LC-MS (Method 1): $R_t$=0.92 min; MS (ESIpos): m/z=1080 (M+H)⁺.

Intermediate 157

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

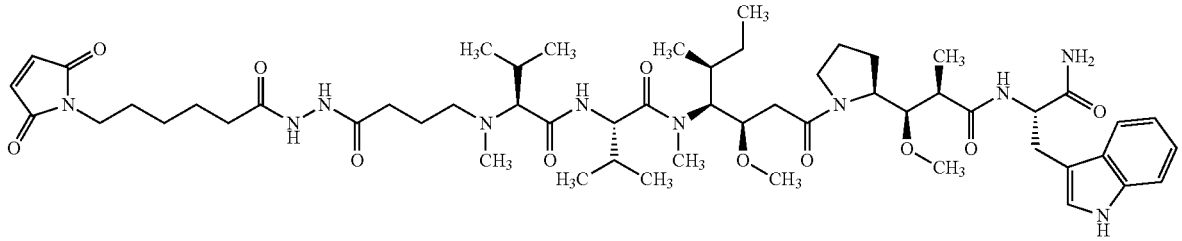

15 mg (18 μmol) of (N-(3-carboxypropyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 3.8 ml of DMF and then admixed with 27 mg (70 μmol) of O-(7-azabenzotriazol-1-yl)-N,N,N',N'-tetramethyluronium hexafluorophosphate, 12 μl of N,N-diisopropylethylamine and with 14 mg (53 μmol) of commercially available 6-(2,5-dioxo-2,5-dihydro-1H-pyrrol-1-yl)hexanehydrazide. The reaction mixture was stirred at RT for 1 h. This was followed by concentration under high vacuum and purification of the remaining residue by means of preparative HPLC. Thus, 6.2 mg (33% of theory) of the title compound were obtained as a colourless foam.

HPLC (Method 5): $R_t$=1.6 min;
LC-MS (Method 1): $R_t$=0.85 min; MS (ESIpos): m/z=1063 (M+H)⁺.
¹H-NMR (500 MHz, DMSO-$d_6$, characteristic signals): δ=10.8 (d, 1H), 9.8-9.7 (m, 2H), 9.6 and 9.4 (2m, 1H), 8.9, 8.88, 8.78 and 8.75 (4d, 1H), 8.08 and 7.85 (2d, 1H), 7.6-6.9 (m, 9H), 4.7-4.4 (m, 3H), 3.4 (t, 2H), 3.23, 3.2, 3.18, 3.0, and 2.99 (5s, 9H), 2.8 (m, 3H), 2.1 (t, 2H), 1.06 and 1.01 (2d, 3H), 0.95-0.8 (m, 15H), 0.8-0.75 (dd, 3H).

Intermediate 158

N-[4-({(2R)-1-[(2,5-dioxopyrrolidin-1-yl)oxy]-4-methyl-1-oxopentan-2-yl}amino)-4-oxobutyl]-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

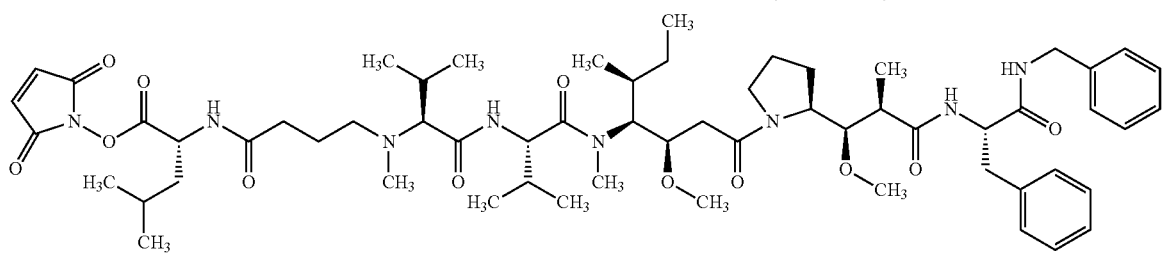 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCc1ccccc1)OC)N(C)C(=O)[C@@H](NC(=O)[C@H](C(C)C)N(C)CCCC(=O)N[C@H](CC(C)C)C(=O)ON1C(=O)C=CC1=O)C(C)C]

13 mg (14.7 µmol) of N-(3-carboxypropyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 4 ml of dimethylformamide and then admixed with 9.4 mg (25 µmol) of O-(7-azabenzotriazol-1-yl)-N,N,N',N'-tetramethyluronium hexafluorophosphate, 6 µl of N,N-diisopropylethylamine and with 7 mg (31 µmol) of commercially available tert-butyl D-leucinate hydrochloride. The mixture was stirred at RT for 5 h and then concentrated under reduced pressure. The remaining residue was purified by means of preparative HPLC. After lyophilization from dioxane/water, 6.5 mg (49% of theory) of the protected intermediate were obtained as a colourless foam.

HPLC (Method 5): $R_t$=2.2 min;

LC-MS (Method 1): $R_t$=1.21 min; MS (ESIpos): m/z=1076 (M+H)$^+$.

Trifluoroacetic acid in dichloromethane was first used to detach the Boc protecting group from this protected intermediate, giving 6.2 mg (99% of theory) of the deprotected compound. 5.2 mg (5 µmol) of this intermediate were taken up in 1.5 ml of dichloromethane and reacted with 0.8 mg (7 µmol) of N-hydroxysuccinimide in the presence of 1.2 mg (6 µmol) of 1-(3-dimethylaminopropyl)-3-ethylcarbodiimide hydrochloride and 0.16 mg (1 µmol) of 4-dimethylaminopyridine. After stirring at RT for 2 h, the reaction mixture was concentrated and purified by means of preparative HPLC. 1.3 mg of the title compound were obtained, some of which was hydrolysed to the reactant.

Intermediate 159

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

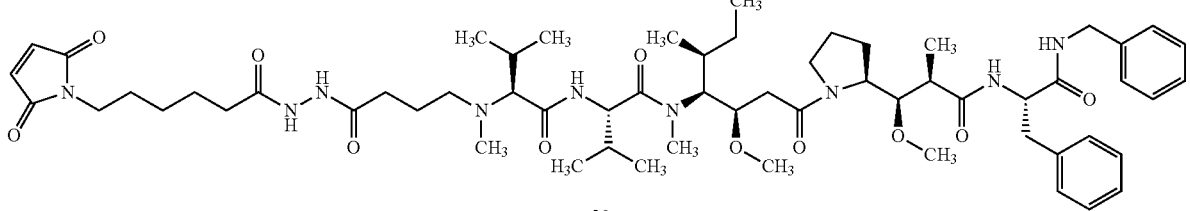

This compound was prepared in analogy to the synthesis described in Intermediate 157, from N-(3-carboxypropyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide and commercially available 6-(2,5-dioxo-2,5-dihydro-1H-pyrrol-1-yl)hexanehydrazide.

Yield: 6 mg (53% of theory)

HPLC (Method 5): $R_t$=1.9 min;

LC-MS (Method 1): $R_t$=0.94 min; MS (ESIpos): m/z=1114 (M+H)$^+$.

Intermediate 160

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

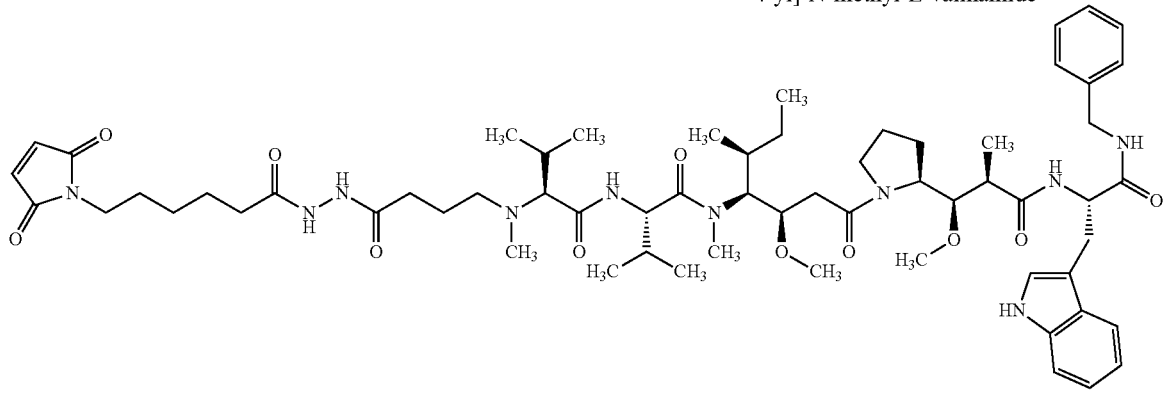

This compound was prepared in analogy to the synthesis described in Intermediate 157, from 20 mg (21 μmol) of N-(3-carboxypropyl)-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide and commercially available 6-(2,5-dioxo-2,5-dihydro-1H-pyrrol-1-yl)hexanehydrazide.

Yield: 13 mg (52% of theory)
HPLC (Method 5): $R_t$=1.9 min;
LC-MS (Method 1): $R_t$=0.92 min; MS (ESIpos): m/z=1153 (M+H)⁺.

Intermediate 161

N-(6-{2-[6-(2,5-dioxo-2,5-dihydro-1H-pyrrol-1-yl)hexanoyl]hydrazino}-6-oxohexyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

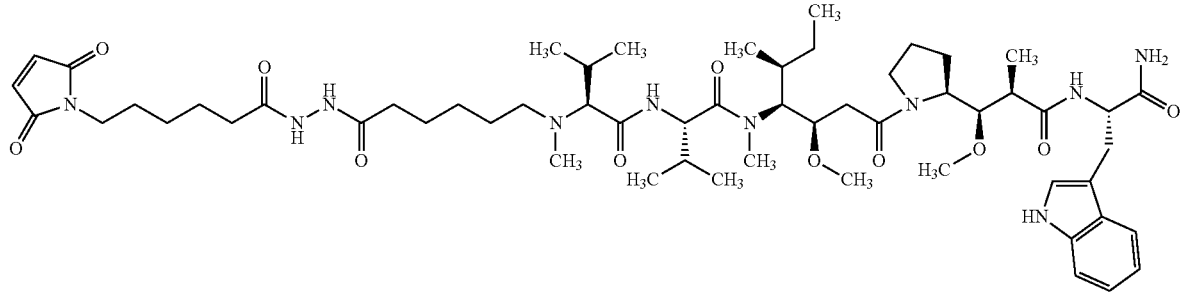 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCCCC(=O)NNC(=O)CCCCCN1C(=O)C=CC1=O)C(C)C]

This compound was prepared in analogy to the synthesis described in Intermediate 157, from N-(5-carboxypentyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide and commercially available 6-(2,5-dioxo-2,5-dihydro-1H-pyrrol-1-yl)hexanehydrazide.

Yield: 0.8 mg (16% of theory)
HPLC (Method 5): $R_t$=1.6 min;
LC-MS (Method 1): $R_t$=0.78 min; MS (ESIpos): m/z=1092 (M+H)⁺.

Intermediate 162

N-{6-[(2,5-dioxopyrrolidin-1-yl)oxy]-6-oxohexyl}-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

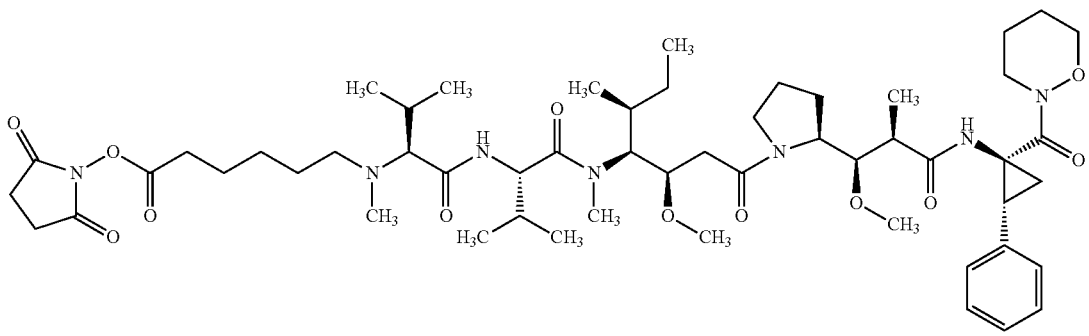 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCC(=O)ON1C(=O)CCC1=O)C(C)C]

18 mg (20 μmol) of N-(5-carboxypentyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide (Intermediate 64) were dissolved in 3.2 ml of dichloromethane and admixed with 22 mg (190 mmol) of 1-hydroxypyrrolidine-2,5-dione and then with 11 mg (60 μmol) of 1-(3-dimethylaminopropyl)-3-ethylcarbodiimide hydrochloride and 0.24 mg (0.17 μmol) of DMAP. After stirring at RT for 2 h, another 22 mg (190 mmol) of 1-hydroxypyrrolidine-2,5-dione, 11 mg (60 μmol) of 1-(3-dimethylaminopropyl)-3-ethylcarbodiimide hydrochloride and 0.24 mg (0.17 mol) of DMAP were added and the reaction mixture was stirred at RT for a further hour. This was followed by concentration under reduced pressure. The remaining residue was purified by means of preparative HPLC. After lyophilization, 8.2 mg (41% of theory) of the title compound were obtained.

HPLC (Method 5): $R_t$=2.0 min;
LC-MS (Method 11): $R_t$=0.9 min; MS (ESIpos): m/z=1024 (M+H)$^+$.

Intermediate 163

[(1S,2R)-1-amino-2-phenylcyclopropyl](1,4-dihydro-3H-2,3-benzoxazin-3-yl)methanone trifluoroacetate

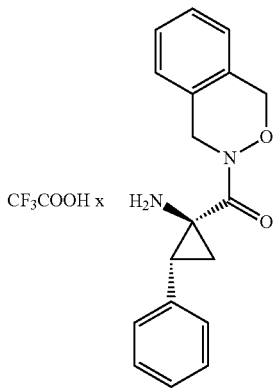 [SMILES: N[C@@]1(C(=O)N2Cc3ccccc3CO2)C[C@@H]1c1ccccc1]

First, proceeding from 265 mg (0.82 mmol) of tert-butyl (1S,2R)-1-(hydroxycarbamoyl)-2-phenylcyclopropyl carbamate (Starting Compound 7), by reaction with 1,2-bis(bromomethyl)benzene, analogously to a literature method (see H. King, J. Chem. Soc. 1942, 432), the Boc-protected tert-butyl (1S,2R)-1-(1,4-dihydro-3H-2,3-benzoxazin-3-ylcarbonyl)-2-phenylcyclopropyl carbamate intermediate was prepared.

Yield: 108 mg (34% of theory)
LC-MS (Method 2): $R_t$=1.3 min; MS (ESIpos): m/z=395 (M+H)$^+$.

108 mg (0.27 mmol) of this intermediate were taken up in 3.7 ml of dichloromethane, 1.8 ml of trifluoroacetic acid were added, and the mixture was stirred at RT for 15 min. This was followed by concentration under reduced pressure and lyophilization of the remaining residue from dioxane. 112 mg of the title compound were obtained in quantitative yield as a colourless foam LC-MS (Method 1): $R_t$=0.7 min; MS (ESIpos): m/z=295 (M+H)$^+$..

Intermediate 164

N-methyl-L-valyl-N-[(3R,4S,5S)-1-{(2S)-2-[(1R,2R)-3-{[(1S,2R)-1-(1,4-dihydro-3H-2,3-benzoxazin-3-ylcarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

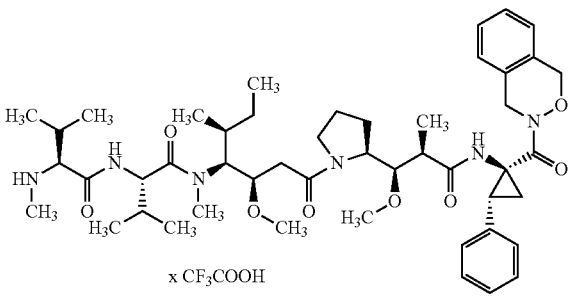 [SMILES: CC[C@H](C)[C@@H]([C@@H](CC(=O)N1CCC[C@H]1[C@H](OC)[C@@H](C)C(=O)N[C@@]1(C(=O)N2Cc3ccccc3CO2)C[C@@H]1c1ccccc1)OC)N(C)C(=O)[C@@H](NC(=O)[C@@H](NC)C(C)C)C(C)C]

166 mg (0.196 mmol) of N-[(9H-fluoren-9-ylmethoxy)carbonyl]-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 10) were taken up in 40 ml of DMF and admixed successively with 80 mg (0.196 mmol) of [(1S,2R)-1-amino-2-phenylcyclopropyl](1,4-dihydro-3H-2,3-benzoxazin-3-yl)methanone trifluoroacetate (Intermediate 163), 112 mg (0.294 mmol) of O-(7-azabenzotriazol-1-yl)-N,N,N',N'-tetramethyluronium hexafluorophosphate (HATU) and 682 μl (3.9 mmol) of N,N-diisopropylethylamine. The mixture was subsequently stirred at RT overnight. The reaction mixture was then concentrated under reduced pressure, the residue was taken up in ethyl acetate and the solution was washed with saturated aqueous sodium chloride solution. The organic phase was dried over magnesium sulphate, filtered and concentrated. The residue was finally purified by preparative HPLC. In this way, 19 mg (9% of theory) of the Fmoc-protected intermediate N-[(9H-fluoren-9-ylmethoxy)carbonyl]-N-methyl-L-valyl-N-[(3R,4S,5S)-1-{(2S)-2-[(1R,2R)-3-{[(1S,2R)-1-(1,4-dihydro-3H-2,3-benzoxazin-3-ylcarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide were obtained.

HPLC (Method 5): $R_t$=1.68 min;
LC-MS (Method 1): $R_t$=1.51 min; MS (ESIpos): m/z=1083 (M+H)$^+$.

19 mg (0.015 mmol) of this intermediate were dissolved in 4 ml of DMF. After 817 μl of piperidine had been added, the reaction mixture was stirred at RT for 5 min. This was followed by concentration under reduced pressure, and the residue was first digested with diethyl ether and then purified by means of preparative HPLC (eluent: acetonitrile+0.1% TFA/0.1% aq. TFA). The corresponding fractions were combined, the solvent was removed under reduced pressure and then the residue was lyophilized from dioxane/water. 12 mg (92% of theory) of the title compound were obtained as a colourless foam.

HPLC (Method 6): $R_t$=2.0 min;
LC-MS (Method 1): $R_t$=0.94 min; MS (ESIpos): m/z=861 (M+H)$^+$.

Intermediate 165

N-(6-aminohexyl)-N-methyl-L-valyl-N-[(3R,4S,5S)-1-{(2S)-2-[(1R,2R)-3-{[(1S,2R)-1-(1,4-dihydro-3H-2,3-benzoxazin-3-ylcarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

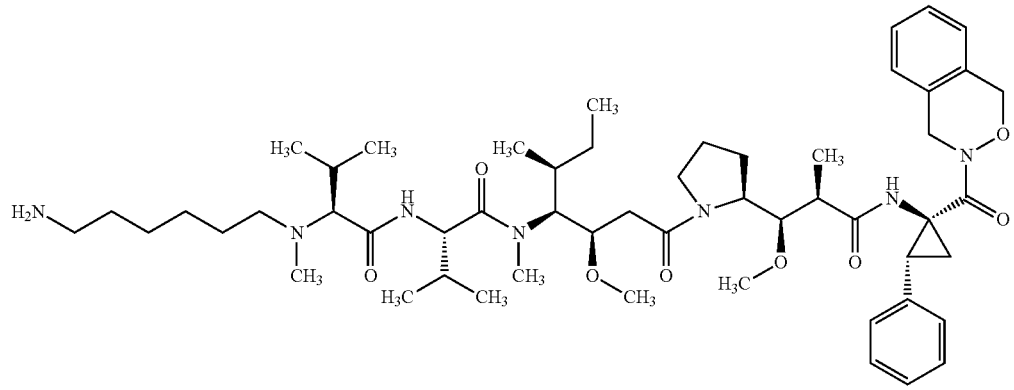 [SMILES: CC[C@H](C)[C@@H]([C@@H](CC(=O)N1CCC[C@H]1[C@H](OC)[C@@H](C)C(=O)N[C@@]1(C(=O)N2Cc3ccccc3CO2)C[C@@H]1c1ccccc1)OC)N(C)C(=O)[C@@H](NC(=O)[C@H](C(C)C)N(C)CCCCCCN)C(C)C]

20 mg (0.021 mmol) of Intermediate 164 were used, in analogy to the preparation of Intermediate 97, with benzyl 6-oxohexyl carbamate in the presence of sodium cyanoborohydride and subsequent hydrogenolytic detachment of the Z protecting group (with 5% palladium on charcoal as a catalyst, in methanol as a solvent), to prepare the title compound.

Yield: 4.5 mg (23% of theory over 2 stages)

HPLC (Method 12): $R_t$=1.9 min;

LC-MS (Method 1): $R_t$=0.9 min; MS (ESIpos): m/z=960 (M+H)$^+$.

Intermediate 166

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(1S,2R)-1-(1,4-dihydro-3H-2,3-benzoxazin-3-ylcarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

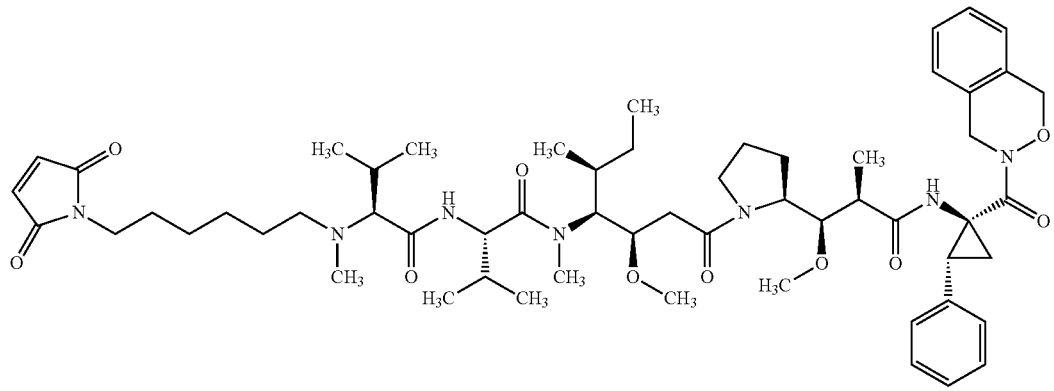 [SMILES: CC[C@H](C)[C@@H]([C@@H](CC(=O)N1CCC[C@H]1[C@H](OC)[C@@H](C)C(=O)N[C@@]1(C(=O)N2Cc3ccccc3CO2)C[C@@H]1c1ccccc1)OC)N(C)C(=O)[C@@H](NC(=O)[C@H](C(C)C)N(C)CCCCCCN1C(=O)C=CC1=O)C(C)C]

4.4 mg (4.5 µmol) of Intermediate 165 were taken up in 1 ml of 1:1 dioxane/water and then admixed with 1 mg (6.8 µmol) of methyl 2,5-dioxo-2,5-dihydro-1H-pyrrole-1-carboxylate and with 50 µl of saturated aqueous sodium hydrogencarbonate solution. The reaction mixture was stirred at RT for 30 min. Then another 50 µl of the saturated aqueous sodium hydrogencarbonate solution were added and the reaction mixture was stirred at RT for a further 15 min and then concentrated under reduced pressure. The remaining residue was purified by means of preparative HPLC. After lyophilization, 1 mg (21% of theory) of the title compound were obtained as a colourless foam.

HPLC (Method 12): $R_t$=2.1 min;

LC-MS (Method 1): $R_t$=1.08 min; MS (ESIpos): m/z=1040 (M+H)$^+$.

Intermediate 167 benzyl 3-{2-[2-(2-oxoethoxy)ethoxy]ethoxy}propanoate

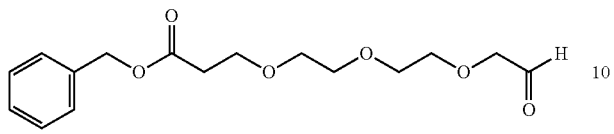

The title compound was prepared from 6 g (21.55 mmol) of commercially available 3-{2-[2-(2-hydroxyethoxy)ethoxy]ethoxy}propanoic acid under standard conditions, first by esterification with benzyl chloride and caesium carbonate and subsequent oxidation with sulphur trioxide-pyridine complex.

Yield: 611 mg (10% of theory over 2 stages)

LC-MS (Method 2): $R_t$=1.69 min; MS (ESIpos): m/z=311 $(M+H)^+$.

Intermediate 168

N-(2-{2-[2-(2-carboxyethoxy)ethoxy]ethoxy}ethyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

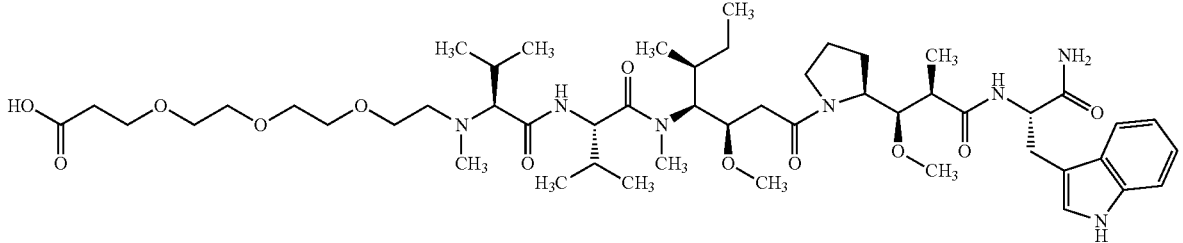 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCOCCOCCOCCC(=O)O)C(C)C]

First, in analogy to the synthesis described in Intermediate 69, by coupling of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) and $N^\alpha$-{(2R,3R)-3-methoxy-2-methyl-3-[(2S)-pyrrolidin-2-yl]propanoyl}-L-tryptophanamide trifluoroacetate (Intermediate 49) in the presence of O-(7-azabenzotriazol-1-yl)-N,N,N',N'-tetramethyluronium hexafluorophosphate and subsequent detachment of the Fmoc protecting group by means of piperidine, the amine compound N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate.

25 mg (0.028 mmol) of this compound and 17.5 mg (0.06 mmol) of Intermediate 167 were combined in 2 ml of methanol and admixed with 12.6 mg (0.14 mmol) of borane-pyridine complex and 2.5 ml of acetic acid. The reaction mixture was stirred at RT overnight. Then the same amounts of borane-pyridine complex and acetic acid were added once again and the reaction mixture was stirred at RT for a further 24 h. This was followed by concentration under reduced pressure, and the residue was purified by means of preparative HPLC. After concentration of the corresponding fractions and lyophilization from 1:1 dioxane/water, 26.5 mg (88% of theory) of the Z-protected title compound were obtained.

HPLC (Method 12): $R_t$=2.04 min;
LC-MS (Method 1): $R_t$=0.97 min; MS (ESIpos): m/z=1064 $(M+H)^+$.

25 mg (0.024 mmol) of this intermediate were taken up in 10 ml of methanol and hydrogenated over 10% palladium on activated carbon under standard hydrogen pressure at RT for 45 min. The catalyst was then filtered off and the solvent was removed under reduced pressure. After lyophilization from dioxane, 19.7 mg (85% of theory) of the title compound were obtained.

HPLC (Method 12): $R_t$=1.8 min;
LC-MS (Method 1): $R_t$=0.83 min; MS (ESIpos): m/z=974 $(M+H)^+$.

Intermediate 169

N-{2-[2-(2-{3-[(2,5-dioxopyrrolidin-1-yl)oxy]-3-oxopropoxy}ethoxy)ethoxy]ethyl}-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

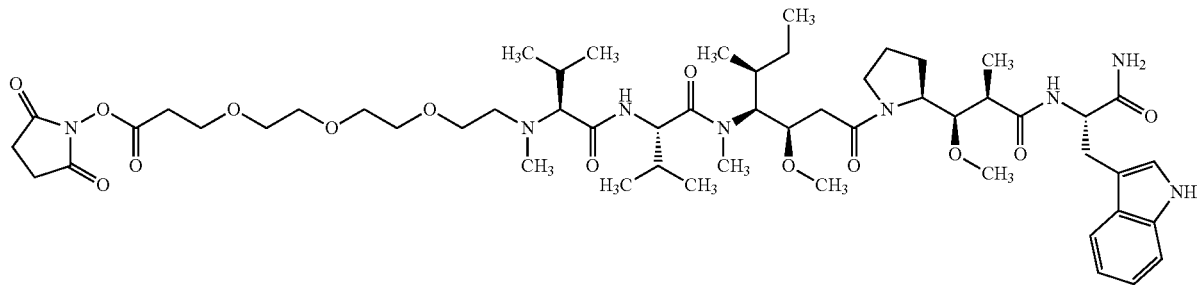 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCOCCOCCOCCC(=O)ON1C(=O)CCC1=O)C(C)C]

10 mg (10 μmol) of Intermediate 168 were dissolved in 3 ml of DMF and admixed with 3.5 mg (30 mmol) of 1-hydroxypyrrolidine-2,5-dione and then with 2.4 mg (10 μmol) of 1-(3-dimethylaminopropyl)-3-ethylcarbodiimide hydrochloride and 5 μl of N,N-diisopropylethylamine. After stirring at RT for 20 h, 8 mg (0.02 mmol) of HATU were added and the reaction mixture was stirred once again at RT overnight and then concentrated under reduced pressure. The remaining residue was purified by means of preparative HPLC. After lyophilization from dioxane, 8.6 mg (64% of theory) of the title compound were obtained.

HPLC (Method 12): Rt=1.9 min;
LC-MS (Method 11): Rt=0.81 min; MS (ESIpos): m/z=1071 (M+H)+.

Intermediate 170

N-(6-aminohexyl)-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide

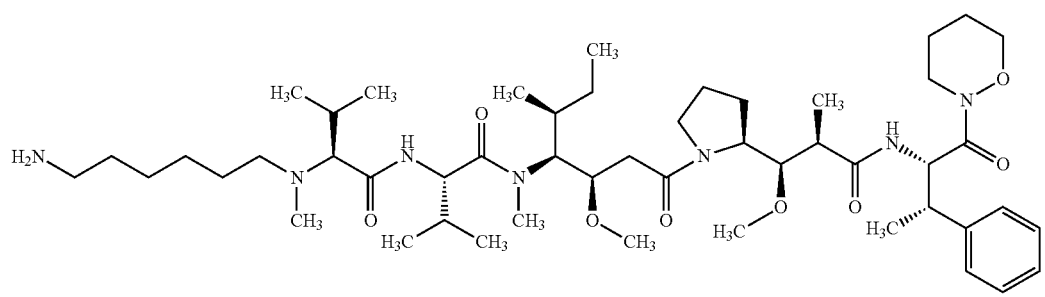 [SMILES: CC[C@H](C)[C@@H]([C@@H](CC(=O)N1CCC[C@H]1[C@H](OC)[C@@H](C)C(=O)N[C@H](C(=O)N1CCCCO1)[C@@H](C)c1ccccc1)OC)N(C)C(=O)[C@@H](NC(=O)[C@H](C(C)C)N(C)CCCCCCN)C(C)C]

This compound was prepared in analogy to Intermediate 101 over 2 stages, proceeding from 26 mg (0.028 mmol) of Intermediate 15.

Yield: 16.7 mg (63% of theory over 2 stages)
HPLC (Method 12): $R_t$=1.9 min;
LC-MS (Method 1): $R_t$=0.81 min; MS (ESIpos): m/z=914 (M+H)+.

Intermediate 171

N-(6-{[4-(2,5-dioxo-2,5-dihydro-1H-pyrrol-1-yl)butanoyl]amino}hexyl)-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide

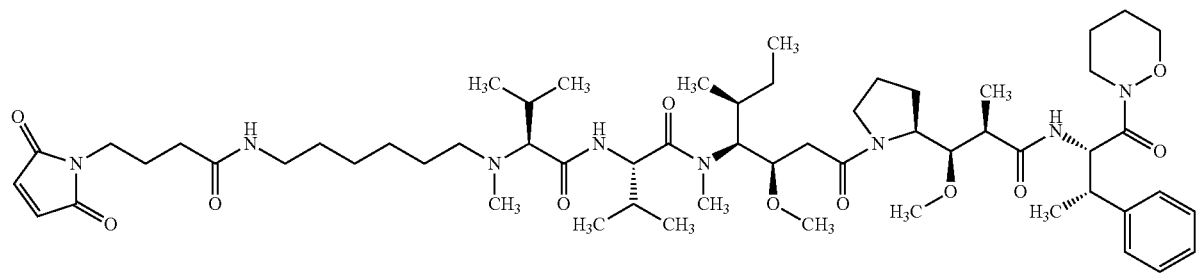 [SMILES: CC[C@H](C)[C@@H]([C@@H](CC(=O)N1CCC[C@H]1[C@H](OC)[C@@H](C)C(=O)N[C@H](C(=O)N1CCCCO1)[C@@H](C)c1ccccc1)OC)N(C)C(=O)[C@@H](NC(=O)[C@H](C(C)C)N(C)CCCCCCNC(=O)CCCN1C(=O)C=CC1=O)C(C)C]

6.7 mg (7.3 μmol) of the compound formed from Intermediate 170 and 3 mg (14.7 μmol) of commercially available 4-(2,5-dioxo-2,5-dihydro-1H-pyrrol-1-yl)butanoic acid were taken up in 2 ml of DMF and admixed with 5.6 mg (14.7 μmol) of O-(7-azabenzotriazol-1-yl)-N,N,N',N'-tetramethyluronium hexafluorophosphate (HATU) and 2 μl of N,N-diisopropylethylamine. The mixture was stirred at RT for 30 min. The reaction mixture was concentrated and the residue was purified by means of preparative HPLC. The corresponding fractions were combined, the solvent was removed under reduced pressure and then the residue was lyophilized from dioxane. Thus, 4.5 mg (56% of theory) of the title compound were obtained.

HPLC (Method 12): $R_t$=2.0 min;
LC-MS (Method 1): $R_t$=1.12 min; MS (ESIpos): m/z=1079 (M+H)$^+$.

Intermediate 172 benzyl 2-{2-[2-(2-oxoethoxy)ethoxy]ethoxy}ethyl carbamate

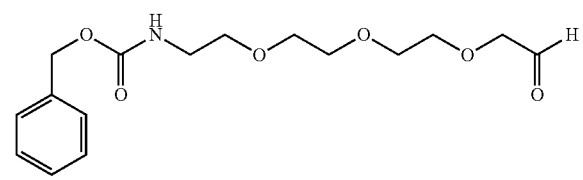 [SMILES: O=CCOCCOCCOCCNC(=O)OCc1ccccc1]

The title compound was prepared from commercially available 2-{2-[2-(2-aminoethoxy)ethoxy]ethoxy}ethanol under standard conditions, by first introducing the Z protecting group and then oxidizing with sulphur trioxide-pyridine complex.

HPLC (Method 12): $R_t$=1.4 min;
LC-MS (Method 11): $R_t$=0.65 min; MS (ESIpos): m/z=326 (M+H)$^+$.

Intermediate 173 benzyl {2-[2-(2-oxoethoxy)ethoxy]ethyl carbamate

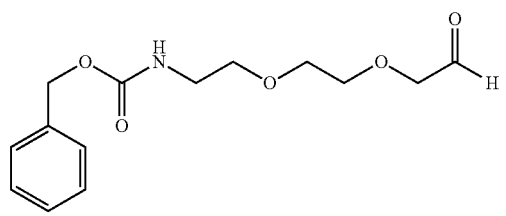 [SMILES: O=CCOCCOCCNC(=O)OCc1ccccc1]

The title compound was prepared analogously to Intermediate 172 from commercially available 2-[2-(2-aminoethoxy)ethoxy]ethanol under standard conditions, by first introducing the Z protecting group and then oxidizing with sulphur trioxide-pyridine complex.

HPLC (Method 12): $R_t$=1.3 min;
LC-MS (Method 11): $R_t$=0.68 min; MS (ESIpos): m/z=282 (M+H)$^+$.

Intermediate 174

N-(2-{2-[2-(2-aminoethoxy)ethoxy]ethoxy}ethyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenyl cyclopropyl]amino}-3-oxopropyl]pyrrolidin-1-yl}-5-methyl-1-oxoheptan-4-yl]-N-methyl-L-valinamide

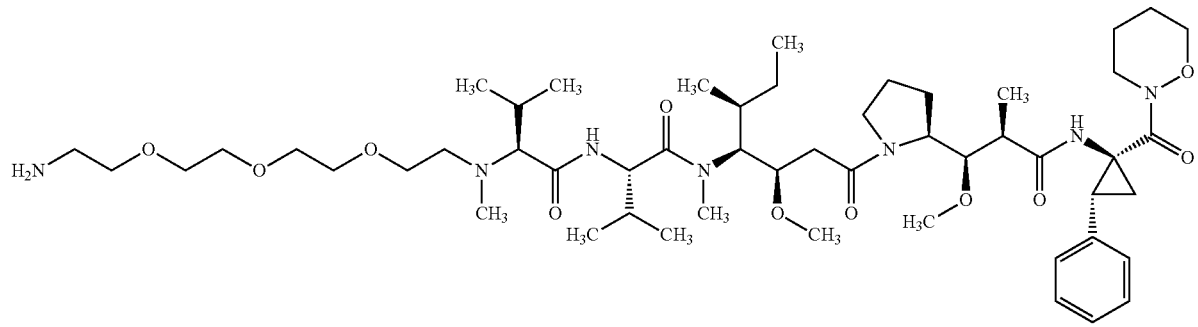 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCOCCOCCOCCN)C(C)C]

47 mg (0.05 mmol) of Intermediate 16 were reductively aminated in analogy to the preparation of Intermediate 167 with benzyl 2-{2-[2-(2-oxoethoxy)ethoxy]ethoxy}ethyl carbamate in the presence of borane-pyridine complex. Subsequently, the Z protecting group was removed by hydrogenolytic means with 5% palladium on charcoal as a catalyst and in methanol as a solvent, and 38 mg (66% of theory over 2 stages) of the title compound were prepared.

HPLC (Method 5): $R_t$=1.7 min;
LC-MS (Method 1): $R_t$=0.8 min; MS (ESIpos): m/z=988 (M+H)$^+$.

Intermediate 175

N-[2-(2-{2-[2-(2,5-dioxo-2,5-dihydro-1H-pyrrol-1-yl)ethoxy]ethoxy}ethoxy)ethyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

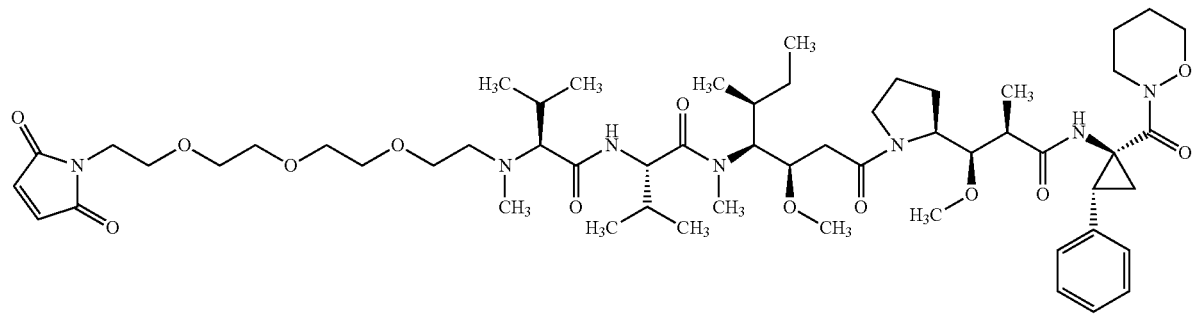 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCOCCOCCOCCN1C(=O)C=CC1=O)C(C)C]

The preparation was effected in analogy zu Intermediate 166, proceeding from 34 mg (0.03 mmol) of Intermediate 174.

Yield: 8.3 mg (23% of theory)
HPLC (Method 5): $R_t$=1.9 min;
LC-MS (Method 1): $R_t$=0.97 min; MS (ESIpos): m/z=1068 (M+H)$^+$.

Intermediate 176

N-(2-{2-[2-(2,5-dioxo-2,5-dihydro-1H-pyrrol-1-yl)ethoxy]ethoxy}ethyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

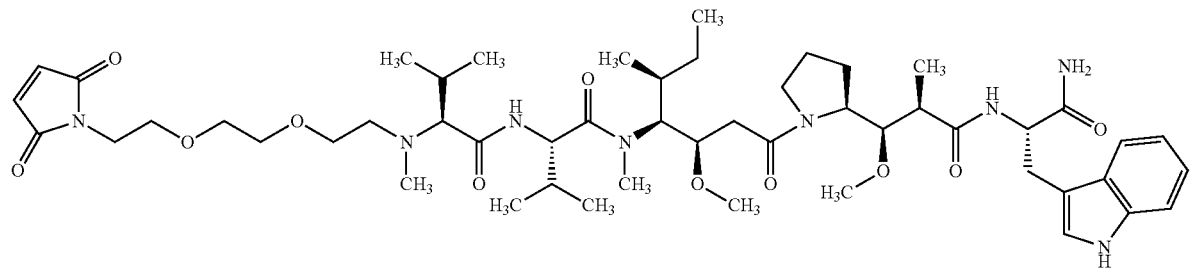 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCOCCOCCN1C(=O)C=CC1=O)C(C)C]

The preparation was effected in analogy to Intermediates 174 and 175, commencing with the reductive amination of Intermediate 16 with Intermediate 173, subsequent deprotection and formation of the maleimide.

HPLC (Method 12): $R_t$=1.8 min;
LC-MS (Method 11): $R_t$=0.8 min; MS (ESIpos): m/z=981 (M+H)$^+$.

Intermediate 177

N-[2-(2-{2-[2-(2,5-dioxo-2,5-dihydro-1H-pyrrol-1-yl)ethoxy]ethoxy}ethoxy)ethyl]-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

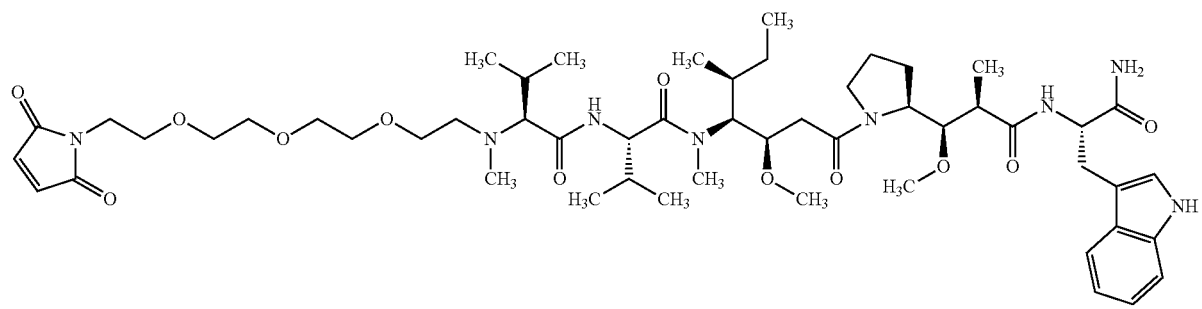 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCOCCOCCOCCN1C(=O)C=CC1=O)C(C)C]

The preparation was effected in analogy to Intermediates 174 and 175, commencing with the reductive amination of Intermediate 16 with Intermediate 172, subsequent deprotection and formation of the maleimide.

HPLC (Method 12): $R_t$=1.9 min;
LC-MS (Method 1): $R_t$=0.86 min; MS (ESIpos): m/z=1025 (M+H)$^+$.

Intermediate 178

N-{4-[(2,5-dioxopyrrolidin-1-yl)oxy]-4-oxobutyl}-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

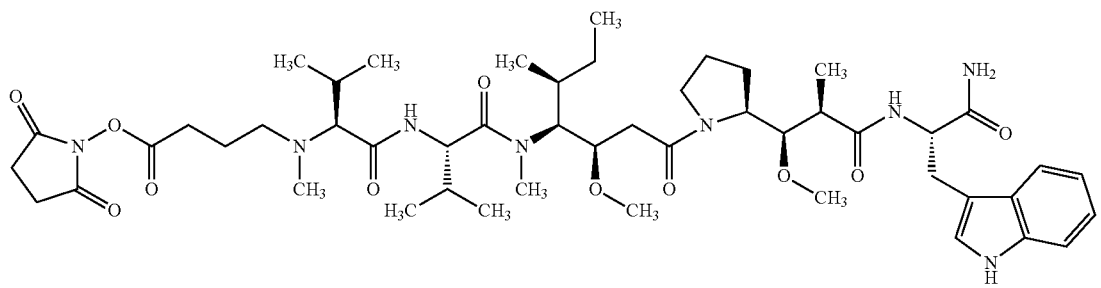 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)ON1C(=O)CCC1=O)C(C)C]

The preparation was effected in analogy to Intermediates 162, proceeding from 6 mg of Intermediate 82.

LC-MS (Method 1): $R_t$=0.82 min; MS (ESIpos): m/z=953 (M+H)$^+$.

stirred at RT for 20 h. After concentrating under reduced pressure, the residue was stirred with diethyl ether, and the precipitate formed was filtered off with suction and washed with diethyl ether. This gave 200 mg (62% of theory) of the title compound.

LC-MS (Method 11): $R_t$=0.44 min; MS (ESIpos): m/z=304 (M+H)$^+$.

Intermediate 179

4-[(1E,3S)-3-amino-4-phenylbut-1-en-1-yl]benzenesulphonic acid trifluoroacetate

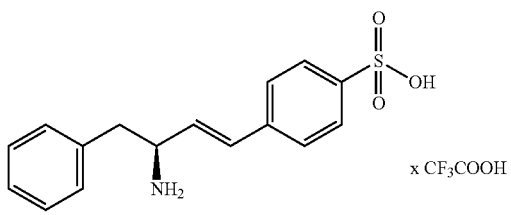 [SMILES: N[C@H](/C=C/c1ccc(S(=O)(=O)O)cc1)Cc1ccccc1]

Intermediate 180

4-[(3R)-3-amino-4-phenylbutyl]benzenesulphonic acid

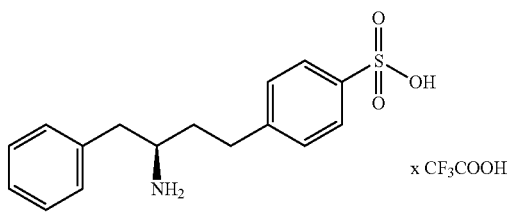 [SMILES: N[C@H](CCc1ccc(S(=O)(=O)O)cc1)Cc1ccccc1]

A mixture of 13.6 mg (0.06 mmol) of palladium(II) acetate, 469 mg (1.46 mmol) of potassium 4-iodobenzenesulphonate, 300 mg (1.21 mmol) of (S)-tert-butyl 1-phenylbut-3-en-2-yl carbamate, 16.5 mg (0.12 mmol) of phenylurea and 167.6 mg (1.21 mmol) of potassium carbonate in 7.5 ml of DMF was heated to 160° C. in a microwave for 15 min. The crude product was subsequently purified directly by preparative HPLC. This gave 312 mg of a mixture of 31% of the BOC-protected compound and 69% of the free amine.

This mixture was subsequently taken up in 30 ml of dichloromethane, admixed with 1 ml of trifluoroacetic acid and 100 mg (0.25 mmol) of 4-[(1E,3S)-3-amino-4-phenylbut-1-en-1-yl]benzenesulphonic acid trifluoroacetate were suspended in 10 ml of acetic acid and a few drops of DMF and water, admixed with 70 mg (0.07 mmol) of palladium on charcoal (10%) and hydrogenated at hydrogen pressure 2.2 bar for 24 h. The solution was filtered and the filtrate purified by prep. HPLC.

29 mg (76% purity, 21% of theory) of product were obtained.

LC-MS (Method 1): $R_t$=0.46 min; MS (ESIpos): m/z=306 (M+H)$^+$.

Intermediate 181

N-(tert-butoxycarbonyl)-N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide

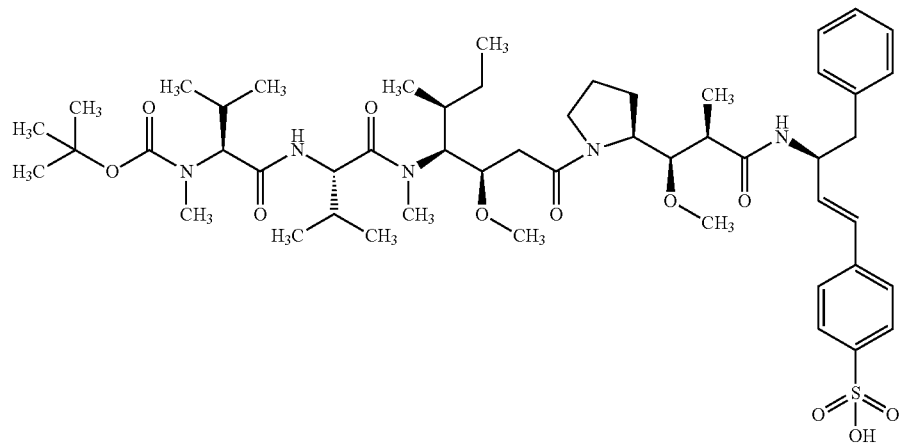 [SMILES: CC[C@H](C)[C@@H]([C@@H](CC(=O)N1CCC[C@H]1[C@H](OC)[C@@H](C)C(=O)N[C@H](/C=C/c1ccc(S(=O)(=O)O)cc1)Cc1ccccc1)OC)N(C)C(=O)[C@@H](NC(=O)[C@H](C(C)C)N(C)C(=O)OC(C)(C)C)C(C)C]

To a solution of 90 mg (0.13 mmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide in 4 ml of DMF were added 60 mg (0.16 mmol) of HATU and 69 µl of (0.39 mmol) HüNig's base. The reaction mixture was stirred at RT for 30 min and then admixed with 60 mg (0.15 mmol) 60.3 mg (0.13 mmol) of 4-[(1E,3S)-3-amino-4-phenylbut-1-en-1-yl]benzenesulphonic acid trifluoroacetate. After stirring overnight, the reaction mixture was purified by prep. HPLC. This gave 127 mg of a 44:56 mixture of the title compound and of the already deprotected amine.

LC-MS (Method 1): $R_t$=1.21 min; MS (ESIpos): m/z=971 (M+H)$^+$; Rt=0.84 min; MS (ESIpos): m/z=871 (M+H)$^+$ for the deprotected compound.

Intermediate 182

N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide trifluoroacetate 90 mg of Intermediate 180 were dissolved in 4.6 ml of dichloromethane, and 0.92 ml of trifluoroacetic acid was added. The reaction mixture was stirred at RT for 30 min and then concentrated. The crude product obtained was purified by prep. HPLC.

91 mg (98% of theory) of the target compound were obtained.

LC-MS (Method 1): $R_t$=0.85 min; MS (ESIpos): m/z=871 (M+H)$^+$

Intermediate 183

N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide

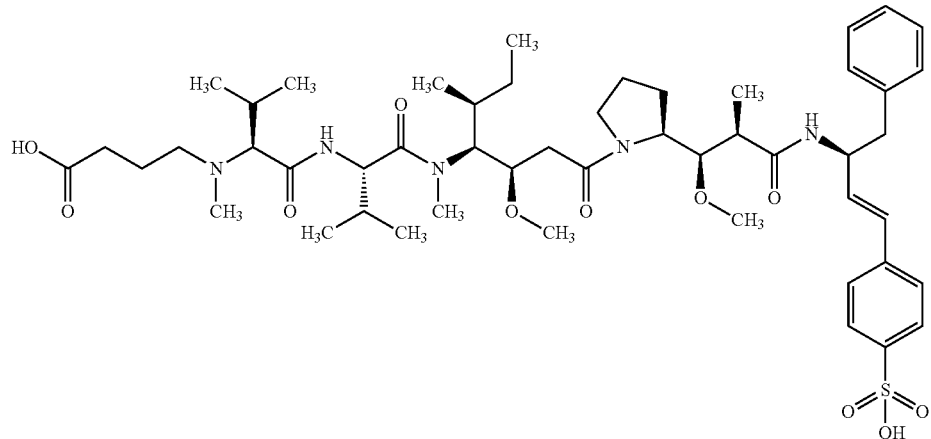 [SMILES: CC[C@H](C)[C@@H]([C@@H](CC(=O)N1CCC[C@H]1[C@H](OC)[C@@H](C)C(=O)N[C@H](/C=C/c1ccc(S(=O)(=O)O)cc1)Cc1ccccc1)OC)N(C)C(=O)[C@@H](NC(=O)[C@H](C(C)C)N(C)CCCC(=O)O)C(C)C]

16.7 µl (0.03 mmol) of a 15% aqueous succinaldehyde solution were initially charged in 943 µl of methanol and admixed with 17 mg (0.02 mmol) of N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide trifluoroacetate (Intermediate 181) and 1.1 µl (0.02 mmol) of acetic acid. The reaction mixture was stirred for 5 min at RT and then 2.9 µl (0.02 mmol) of borane-pyridine complex were added. After 1 h, a further 2 equivalents each of succinaldehyde, acetic acid and borane-pyridine complex were added and the mixture was stirred at RT for 20 h. The reaction mixture was then purified by prep. HPLC.

This gave 20 mg (83% purity, 80% of theory) of the title compound.

LC-MS (Method 1): $R_t$=0.87 min; MS (ESIpos): m/z=957 (M+H)$^+$

Intermediate 184

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide

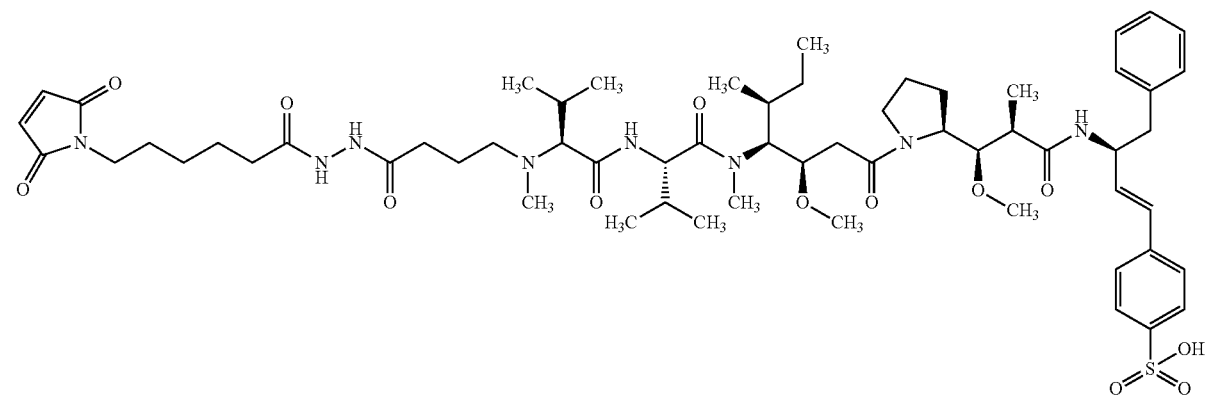 [SMILES: CC[C@H](C)[C@@H]([C@@H](CC(=O)N1CCC[C@H]1[C@H](OC)[C@@H](C)C(=O)N[C@H](/C=C/c1ccc(S(=O)(=O)O)cc1)Cc1ccccc1)OC)N(C)C(=O)[C@@H](NC(=O)[C@H](C(C)C)N(C)CCCC(=O)NNC(=O)CCCCCN1C(=O)C=CC1=O)C(C)C]

8 mg (7.5 μmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide, 2.8 mg (8.2 μmol) of 6-(2,5-dioxo-2,5-dihydro-1H-pyrrol-1-yl)hexanehydrazide trifluoroacetate, 3.4 mg (9 μmol) of HATU and 3.9 μl of Hünig's base were stirred in 0.77 ml of DMF at RT for 20 h.

Subsequently, the reaction mixture was purified by prep. HPLC.

3 mg (31% of theory) of the title compound were obtained.
LC-MS (Method 1): $R_t$=0.90 min; MS (ESIpos): m/z=1164 (M+H)$^+$ Intermediate 185

N-{4-[(2,5-dioxopyrrolidin-1-yl)oxy]-4-oxobutyl}-N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide

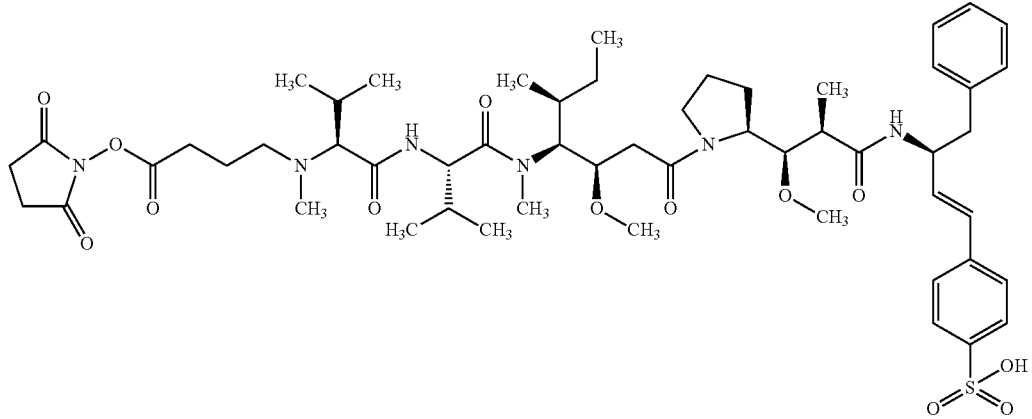 [SMILES: CC[C@H](C)[C@@H]([C@@H](CC(=O)N1CCC[C@H]1[C@H](OC)[C@@H](C)C(=O)N[C@H](/C=C/c1ccc(S(=O)(=O)O)cc1)Cc1ccccc1)OC)N(C)C(=O)[C@@H](NC(=O)[C@H](C(C)C)N(C)CCCC(=O)ON1C(=O)CCC1=O)C(C)C]

To a solution of 8 mg (7.5 μmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(2S,3E)-1-phenyl-4-(4-sulphophenyl)but-3-en-2-yl]amino}propyl]pyrrolidin-1-yl}-5-methyl-1-oxoheptan-4-yl]-N-methyl-L-valinamide in 2 ml of DMF were added 8.6 mg (74.8 μmol) of N-hydroxysuccinimide, 8.5 mg (22.4 μmol) of EDCI and 0.1 mg (0.75 μmol) of DMAP. The reaction mixture was stirred at RT for 20 h. Subsequently, 1.3 μl (7.5 μmol) of Hünig's base were added and the mixture was stirred for 1 h. The reaction mixture was then purified by prep. HPLC. 2.6 mg (72% purity, 21% of theory) of the title compound were obtained.
LC-MS (Method 1): $R_t$=0.89 min; MS (ESIpos): m/z=1054 (M+H)$^+$ Intermediate 186

N-(tert-butoxycarbonyl)-N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide

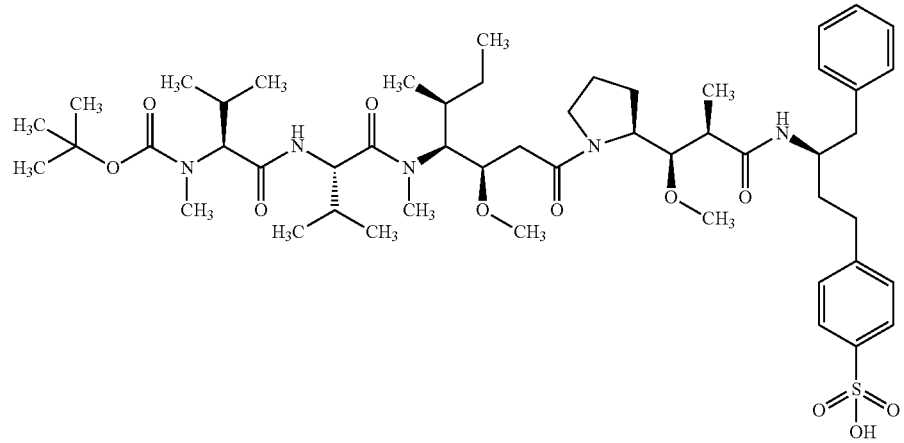 [SMILES: CC[C@H](C)[C@@H]([C@@H](CC(=O)N1CCC[C@H]1[C@H](OC)[C@@H](C)C(=O)N[C@H](CCc1ccc(S(=O)(=O)O)cc1)Cc1ccccc1)OC)N(C)C(=O)[C@@H](NC(=O)[C@H](C(C)C)N(C)C(=O)OC(C)(C)C)C(C)C]

To a solution of 43 mg (0.06 mmol) of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide in 1.9 ml of DMF were added 29 mg (0.07 mmol) of HATU and 33 μl (0.19 mmol) of Hünig's base. The reaction mixture was stirred at RT for 30 min and then admixed with 29 mg (0.07 mmol) of 4-[(3R)-3-amino-4-phenylbutyl]benzenesulphonic acid trifluoroacetate. After stirring overnight, the reaction mixture was purified by prep. HPLC. This gave 58 mg of a 45:55 mixture of the title compound and of the already deprotected amine.

LC-MS (Method 1): $R_t$=1.09 min; MS (ESIpos): m/z=973 (M+H)$^+$; Rt=0.87 min; MS (ESIpos): m/z=873 (M+H)$^+$ for the deprotected compound.

Intermediate 187

N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide trifluoroacetate

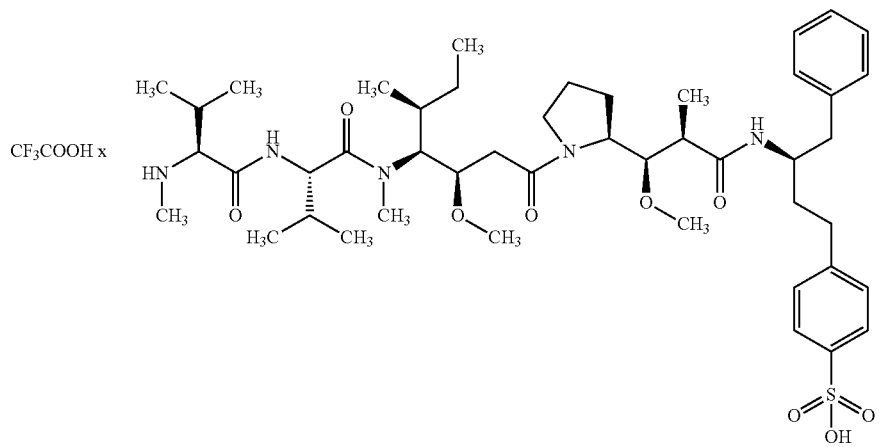 [SMILES: CC[C@H](C)[C@@H]([C@@H](CC(=O)N1CCC[C@H]1[C@H](OC)[C@@H](C)C(=O)N[C@H](CCc1ccc(S(=O)(=O)O)cc1)Cc1ccccc1)OC)N(C)C(=O)[C@@H](NC(=O)[C@@H](NC)C(C)C)C(C)C]

58 mg of Intermediate 186 were dissolved in 4.1 ml of dichloromethane, 0.41 ml of trifluoroacetic acid was added and the mixture was stirred at RT for 30 min. After concentration under reduced pressure, the crude product was purified by prep. HPLC.

50 mg (90% purity, 85% of theory) of the title compound were obtained.

LC-MS (Method 1): $R_t$=0.87 min; MS (ESIpos): m/z=873 (M+H)$^+$

Intermediate 188

N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide

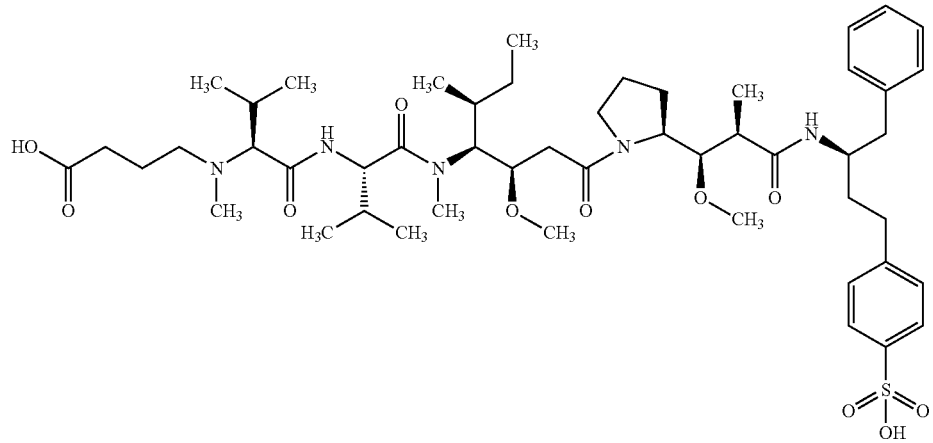 [SMILES: CC[C@H](C)[C@@H]([C@@H](CC(=O)N1CCC[C@H]1[C@H](OC)[C@@H](C)C(=O)N[C@H](CCc1ccc(S(=O)(=O)O)cc1)Cc1ccccc1)OC)N(C)C(=O)[C@@H](NC(=O)[C@H](C(C)C)N(C)CCCC(=O)O)C(C)C]

171 μl (0.26 mmol) of a 15% aqueous succinaldehyde solution were initially charged in 2.5 ml of methanol and admixed with 50 mg (0.05 mmol) of N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide trifluoroacetate and 11.6 μl (0.2 mmol) of acetic acid. The reaction mixture was stirred for 5 min at RT and then 30 μl (0.24 mmol) of borane-pyridine complex were added. After stirring for 24 hours, a further equivalent of borane-pyridine complex was added and the mixture was stirred for a further 2 h. The reaction mixture was then purified by prep. HPLC.

40 mg (90% purity, 66% of theory) of the title compound were obtained.

LC-MS (Method 1): $R_t$=0.91 min; MS (ESIpos): m/z=959 (M+H)$^+$

Intermediate 189

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide

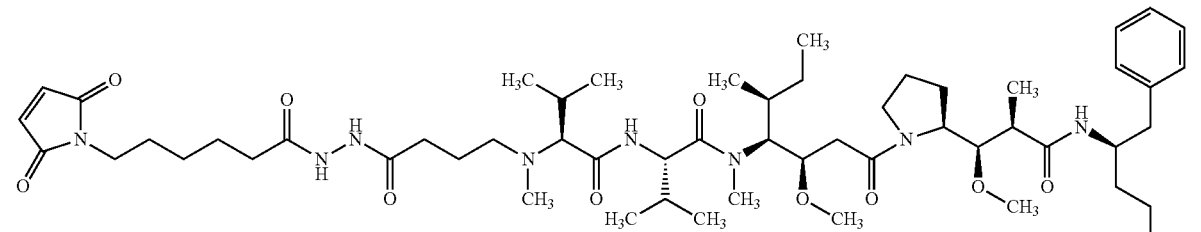

10 mg (9.3 μmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide, 3.5 mg (10.3 μmol) of 6-(2,5-dioxo-2,5-dihydro-1H-pyrrol-1-yl)hexanehydrazide trifluoroacetate, 4.3 mg (11.2 μmol) of HATU and 4.9 μl (28 μmol) of Hünig's base were stirred in 1 ml of DMF at RT for 20 h. Subsequently, the reaction mixture was purified by prep. HPLC.

4.2 mg (92% purity, 33% of theory) of the title compound were obtained.

LC-MS (Method 1): $R_t$=0.91 min; MS (ESIpos): m/z=1166 (M+H)$^+$

Intermediate 190

N-{4-[(2,5-dioxopyrrolidin-1-yl)oxy]-4-oxobutyl}-N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide

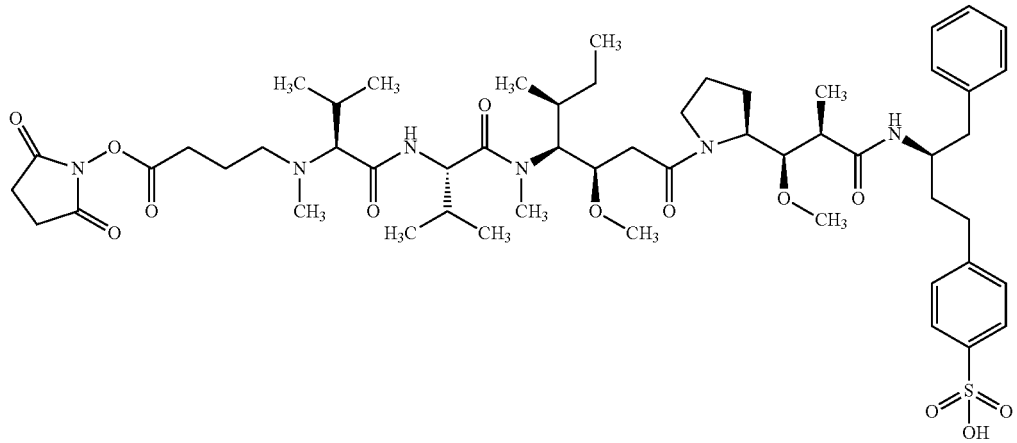 [SMILES: CC[C@H](C)[C@@H]([C@@H](CC(=O)N1CCC[C@H]1[C@H](OC)[C@@H](C)C(=O)N[C@H](CCc1ccc(S(=O)(=O)O)cc1)Cc1ccccc1)OC)N(C)C(=O)[C@@H](NC(=O)[C@H](C(C)C)N(C)CCCC(=O)ON1C(=O)CCC1=O)C(C)C]

To a solution of 10 mg (9.3 µmol) of N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(2R)-1-phenyl-4-(4-sulphophenyl)butan-2-yl]amino}propyl]pyrrolidin-1-yl}-5-methyl-1-oxoheptan-4-yl]-N-methyl-L-valinamide in 2.5 ml of DMF were added 10.7 mg (93 µmol) of N-hydroxysuccinimide, 10.6 mg (28 µmol) of EDCI and 0.12 mg (0.9 µmol) of DMAP. The reaction mixture was stirred at RT for 20 h and then purified by prep. HPLC.

3.8 mg (72% purity, 25% of theory) of the title compound were obtained.

LC-MS (Method 1): $R_t$=0.90 min; MS (ESIpos): m/z=1055 (M+H)$^+$

Intermediate 191

(2R,3R)—N-[(2S)-3-(1H-indol-3-yl)-1-(1,2-oxazinan-2-yl)-1-oxopropan-2-yl]-3-methoxy-2-methyl-3-[(2S)-pyrrolidin-2-yl]propanamide trifluoroacetate

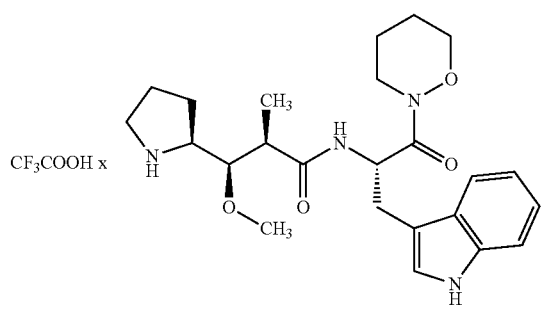 [SMILES: CO[C@@H]([C@@H]1CCCN1)[C@@H](C)C(=O)N[C@@H](Cc1c[nH]c2ccccc12)C(=O)N1CCCCO1]

The title compound was prepared in analogy to the synthesis of Intermediate 7 over two stages from Starting Compound 1 and (2S)-2-amino-3-(1H-indol-3-yl)-1-(1,2-oxazinan-2-yl)propan-1-one trifluoroacetate (Intermediate 99).

Yield over 2 stages: 62 mg (67% of theory)

HPLC (Method 6): $R_t$=1.65 min;

LC-MS (Method 1): $R_t$=0.7 min; MS (ESIpos): m/z=443 (M+H)$^+$.

Intermediate 192

N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

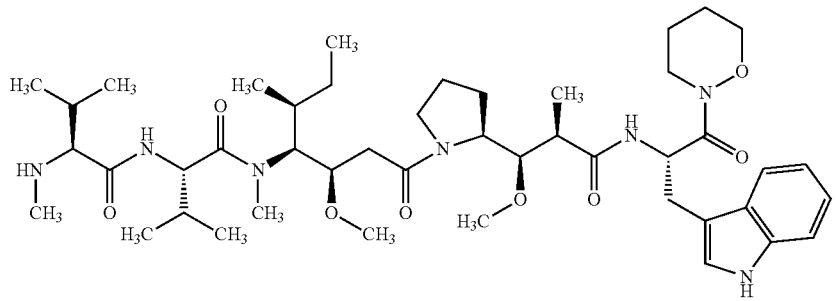 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@@H](NC)C(C)C)C(C)C]

1015 mg (1.59 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 50 ml of DMF, admixed with 654 mg (2.39 mmol) of 2-bromo-1-ethylpyridinium tetrafluoroborate (BEP) and 2.8 ml of N,N-diisopropylethylamine, and stirred at RT for 10 min. Then 1083 mg (1.75 mmol) of (2R,3R)—N-[(2S)-3-(1H-indol-3-yl)-1-(1,2-oxazinan-2-yl)-1-oxopropan-2-yl]-3-methoxy-2-methyl-3-[(2S)-pyrrolidin-2-yl]propanamide trifluoroacetate (Intermediate 191) were added and then the mixture was treated in an ultrasound bath at RT for 30 min. The reaction mixture was then concentrated under reduced pressure and the residue was taken up in 300 ml of ethyl acetate. The organic phase was washed successively with 5% aqueous citric acid solution and 5% aqueous sodium hydrogencarbonate solution, dried over magnesium sulphate, filtered and concentrated. The crude product thus obtained (1684 mg), without further purification, was taken up in 20 ml of acetonitrile, 2 ml of piperidine were added and the reaction mixture was then stirred at RT for 10 min. Then the mixture was concentrated under reduced pressure and the residue was admixed with diethyl ether. The solvent was concentrated by evaporation again and the residue was purified by flash chromatography on silica gel (eluent: 15:1:0.1→15:2:0.2 dichloromethane/methanol/17% aqueous ammonia solution). The corresponding fractions were combined, the solvent was removed under reduced pressure and the residue was lyophilized from acetonitrile/water. Thus, 895 mg (67% over 2 stages) of the title compound were obtained.

HPLC (Method 12): $R_t$=1.8 min;
LC-MS (Method 1): $R_t$=0.84 min; MS (ESIpos): m/z=840 (M+H)$^+$.
$^1$H NMR (500 MHz, DMSO-d$_6$): δ=10.8 (d, 1H), 8.3 and 8.05 (2d, 1H), 8.0 (d, 1H), 7.5 (m, 1H), 7.3 (m, 1H), 7.15 and 7.08 (2s, 1H) 7.05-6.9 (m, 2H), 5.12 and 4.95 (2m, 1H), 4.65 (m, 1H), 4.55 (m, 1H), 4.1-3.8 (m, 4H), 3.75 (d, 1H), 3.23, 3.18, 3.17, 3.12, 2.95 and 2.88 (6s, 9H), 3.1-3.0 and 2.85 (2m, 2H), 2.65 (d, 1H), 2.4-2.2 (m, 3H), 2.15 (m, 3H), 1.95 (br. m, 2H), 1.85-0.8 (br. m, 11H), 1.08 and 1.04 (2d, 3H), 0.9-0.75 (m, 15H), 0.75-0.65 (dd, 3H) [further signals hidden under H$_2$O peak].

Intermediate 193

N-(3-carboxypropyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

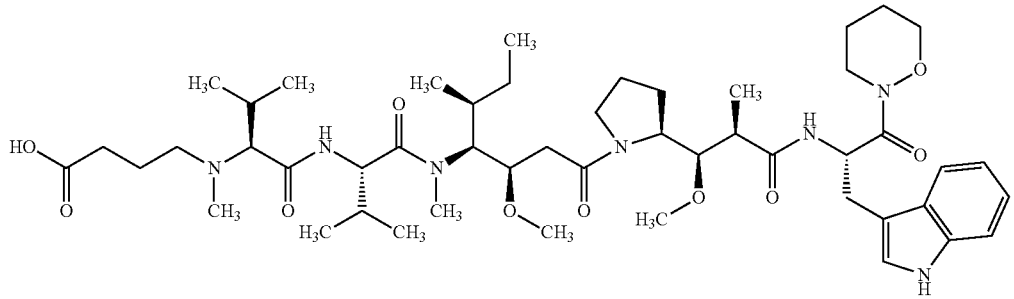 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCC(=O)O)C(C)C]

50 mg (0.052 mmol) of N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 192) and 204 µl einer of a 15% aqueous solution of 4-oxobutanoic acid were combined in 2 ml of methanol and admixed with 23.4 mg (0.252 mmol) of borane-pyridine complex and 6 µl of acetic acid. The reaction mixture was stirred at RT overnight. This was followed by concentration under reduced pressure, and the residue was purified by means of preparative HPLC. After concentration of the corresponding fractions, 38 mg (78% of theory) of the title compound were obtained.

HPLC (Method 5): $R_t$=1.7 min;
LC-MS (Method 9): $R_t$=4.7 min; MS (ESIpos): m/z=926 (M+H)$^+$.

Intermediate 194

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

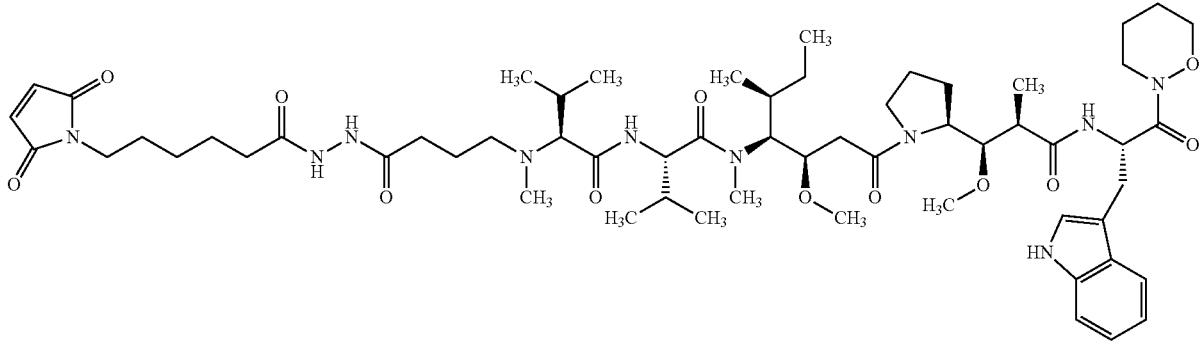 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCC(=O)NNC(=O)CCCCCN1C(=O)C=CC1=O)C(C)C]

This compound was prepared in analogy to the synthesis described in Intermediate 157 from 10 mg (11 μmol) of N-(3-carboxypropyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide and commercially available 6-(2,5-dioxo-2,5-dihydro-1H-pyrrol-1-yl)hexane-hydrazide.

Yield: 4.4 mg (35% of theory)
HPLC (Method 5): $R_t$=1.8 min;
LC-MS (Method 1): $R_t$=0.90 min; MS (ESIpos): m/z=1133 (M+H)⁺.

Intermediate 195

N-[6-(2,5-dioxo-2,5-dihydro-1H-pyrrol-1-yl)hexyl]-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide

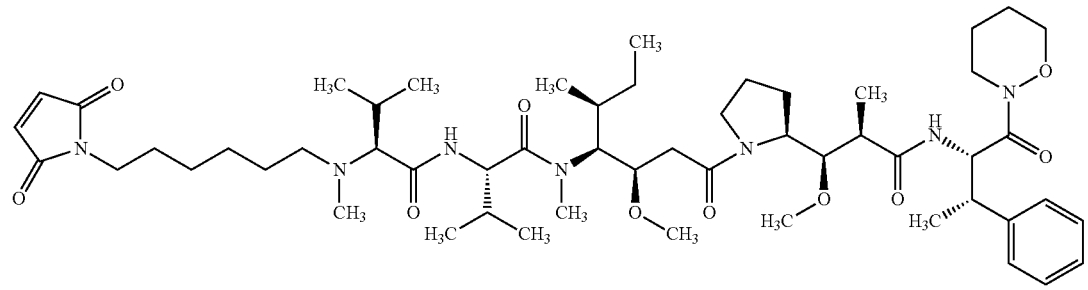 [SMILES: CC[C@H](C)[C@@H]([C@@H](CC(=O)N1CCC[C@H]1[C@H](OC)[C@@H](C)C(=O)N[C@H](C(=O)N1CCCCO1)[C@@H](C)c1ccccc1)OC)N(C)C(=O)[C@@H](NC(=O)[C@H](C(C)C)N(C)CCCCCCN1C(=O)C=CC1=O)C(C)C]

This compound was prepared in analogy to Intermediate 166, proceeding from 9 mg (0.010 mmol) of Intermediate 170.

Yield: 1.1 mg (10% of theory)
HPLC (Method 12): $R_t$=2.0 min;
LC-MS (Method 1): $R_t$=0.99 min; MS (ESIpos): m/z=994 (M+H)⁺.

Intermediate 196

(2S)-2-amino-1-(2-oxa-3-azabicyclo[2.2.2]oct-5-en-3-yl)-3-phenylpropan-1-one trifluoroacetate

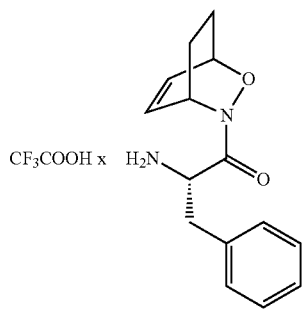

41 mg (0.37 mmol) of 2,5-dioxopyrrolidin-1-yl N-(tert-butoxycarbonyl)-L-phenylalaninate were taken up in 10 ml of DMF and admixed with 149 mg (0.41 mmol) of 2-oxa-3-azabicyclo[2.2.2]oct-5-ene (Starting Compound 6) and 72 μl (0.41 mmol) of N,N-diisopropylethylamine. The mixture was stirred at RT for 1 h. The solvent was removed under reduced pressure, and the residue was taken up in ethyl acetate and extracted by shaking with 5% aqueous citric acid solution and then with 5% aqueous sodium hydrogencarbonate solution. The organic phase was concentrated and the residue was purified by flash chromatography on silica gel with 10:1 toluene/ethanol as the eluent. The corresponding fractions were combined and the solvent was removed under reduced pressure. After the residue had been dried under high vacuum, 69 mg (47% of theory) of the Boc-protected intermediate tert-butyl (2S)-1-(2-oxa-3-azabicyclo[2.2.2]oct-5-en-3-yl)-1-oxo-3-phenylpropan-2-yl carbamate were thus obtained as a diastereomer mixture.

LC-MS (Method 1): $R_t$=1.1 min; MS (ESIpos): m/z=359 (M+H)⁺.

64 mg (0.18 mmol) of this intermediate were taken up in 10 ml of dichloromethane, 1 ml of trifluoroacetic acid was added, and the mixture was stirred at RT for 30 min. This was followed by concentration under reduced pressure and lyophilization of the remaining residue from water/dioxane. In this way, 66 mg (quant.) of the title compound were obtained as a foam.

HPLC (Method 6): $R_t$=1.45 min;
LC-MS (Method 3): $R_t$=1.12 min; MS (ESIpos): m/z=259 (M+H)⁺.

Intermediate 197

(2R,3R)-3-methoxy-2-methyl-N-[(2S)-1-(2-oxa-3-azabicyclo[2.2.2]oct-5-en-3-yl)-1-oxo-3-phenylpropan-2-yl]-3-[(2S)-pyrrolidin-2-yl]propanamide trifluoroacetate

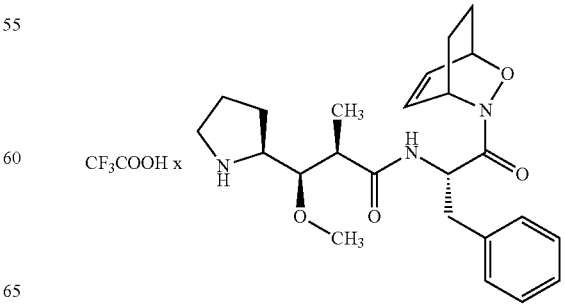

First, (2R,3R)-3-[(2S)-1-(tert-butoxycarbonyl)pyrrolidin-2-yl]-3-methoxy-2-methylpropanoic acid (Starting Compound 1) was released from 83 mg (0.18 mmol) of its dicyclohexylamine salt by taking it up in ethyl acetate and extractive shaking with 5% aqueous potassium hydrogensulphate solution. The organic phase was dried over magnesium sulphate, filtered and concentrated. The residue was taken up in 10 ml of DMF and admixed successively with 66 mg (0.18 mmol) of (2S)-2-amino-1-(2-oxa-3-azabicyclo[2.2.2]oct-5-en-3-yl)-3-phenylpropan-1-one trifluoroacetate (Intermediate 196), 101 mg (0.266 mmol) of O-(7-azabenzotriazol-1-yl)-N,N,N',N'-tetramethyluronium hexafluorophosphate (HATU) and 93 μl (0.53 mmol) of N,N-diisopropylethylamine. The mixture was stirred at RT for 30 min. The reaction mixture was then concentrated and the residue was purified by preparative HPLC. This gave 52 mg (56% of theory) of the Boc-protected intermediate tert-butyl (2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidine-1-carboxylate.

HPLC (Method 6): $R_t$=2.13 min;
LC-MS (Method 1): $R_t$=1.13 min; MS (ESIpos): m/z=528 (M+H)$^+$.

52 mg (0.1 mmol) of this intermediate were taken up in 10 ml of dichloromethane, 1 ml of trifluoroacetic acid was added, and the mixture was stirred at RT for 20 min. This was followed by concentration under reduced pressure and stirring of the remaining residue with 20 ml of diethyl ether. After 10 min, the mixture was filtered and the filter residue was dried under high vacuum. In this way, 39 mg (72% of theory) of the title compound were obtained.

HPLC (Method 6): $R_t$=1.62 min;
LC-MS (Method 1): $R_t$=0.68 min; MS (ESIpos): m/z=428 (M+H)$^+$.

Intermediate 198

N-methyl-L-valyl-N-[(3R,4S,5S)-3-methoxy-1-{(2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidin-1-yl}-5-methyl-1-oxoheptan-4-yl]-N-methyl-L-valinamide trifluoroacetate 44.5 mg (0.071 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 10 ml of DMF and admixed successively with 38.6 mg (0.071 mmol) of (2R,3R)-3-methoxy-2-methyl-N-[(2S)-1-(2-oxa-3-azabicyclo[2.2.2]oct-5-en-3-yl)-1-oxo-3-phenylpropan-2-yl]-3-[(2S)-pyrrolidin-2-yl]propanamide trifluoroacetate (Intermediate 197), 32.5 mg (0.086 mmol) of O-7-azabenzotriazol-1-yl)-N,N,N',N'-tetramethyluronium hexafluorophosphate (HATU) and 41 μl (0.235 mmol) of N,N-diisopropylethylamine. The mixture was stirred at RT for 1 h. The reaction mixture was then concentrated under reduced pressure and the residue was taken up in ethyl acetate. The organic phase was washed successively with 5% aqueous citric acid solution and 5% aqueous sodium hydrogencarbonate solution, dried over magnesium sulphate, filtered and concentrated. This gave 73 mg (98% of theory) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidin-1-yl}-5-methyl-1-oxoheptan-4-yl]-N-methyl-L-valinamide HPLC (Method 6): $R_t$=2.78 min;
LC-MS (Method 3): $R_t$=2.96 min; MS (ESIpos): m/z=1047 (M+H)$^+$.

73 mg (0.071 mmol) of this intermediate were dissolved in 5 ml of DMF. After 0.5 ml of piperidine had been added, the reaction mixture was stirred at RT for 10 min. This was followed by concentration under reduced pressure, and the residue was digested repeatedly with diethyl ether. After the diethyl ether had been decanted off, the residue was purified by preparative HPLC (eluent: acetonitrile/0.1% aq. TFA). 16 mg (26% of theory) of the title compound were obtained as a foam.

HPLC (Method 6): $R_t$=1.94 min;
LC-MS (Method 3): $R_t$=1.71 min; MS (ESIpos): m/z=825 (M+H)$^+$ $^1$H NMR (400 MHz, DMSO-d$_6$): δ=8.9-8.6 (m, 3H), 8.4, 8.3, 8.1 and 8.0 (4d, 1H), 7.3-7.1 (m, 5H), 6.7-6.5 (m, 2H), 5.2-4.8 (m, 3H), 4.75-4.55 (m, 3H), 4.05-3.95 (m, 1H), 3.7-3.4 (m, 4H), 3.22, 3.17, 3.15, 3.05, 3.02 and 2.95 (6s, 9H), 3.0 and 2.7 (2 br. m, 2H), 2.46 (m, 3H), 2.4-1.2 (br. m, 13H), 1.1-0.85 (m, 18H), 0.75 (m, 3H) [further signals hidden under H$_2$O peak].

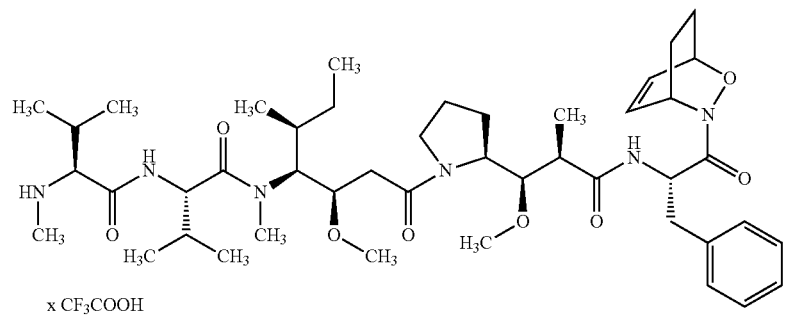 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1OC2C=CC1CC2)OC)N(C)C(=O)[C@@H](NC(=O)[C@@H](NC)C(C)C)C(C)C]

x CF$_3$COOH

Intermediate 199

N-(4-{2-[6-(2,5-dioxo-2,5-dihydro-1H-pyrrol-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidin-1-yl}-5-methyl-1-oxoheptan-4-yl]-N-methyl-L-valinamide

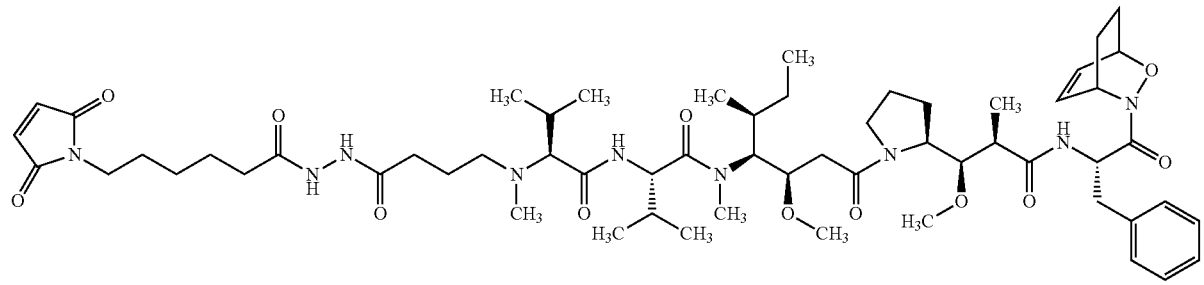 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1OC2C=CC1CC2)OC)N(C)C(=O)[C@@H](NC(=O)[C@H](C(C)C)N(C)CCCC(=O)NNC(=O)CCCCCN1C(=O)C=CC1=O)C(C)C]

The title compound was prepared in analogy to Intermediates 193 and 194, proceeding from 23 mg (24 μmol) of N-methyl-L-valyl-N-[(3R,4S,5S)-3-methoxy-1-{(2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidin-1-yl}-5-methyl-1-oxoheptan-4-yl]-N-methyl-L-valinamide trifluoroacetate (Intermediate 198).

HPLC (Method 12): Rt=1.9 min;
LC-MS (Method 2): Rt=2.1 min; MS (ESIpos): m/z=1118 (M+H)+.

Intermediate 200

N-[2-(2-{2-[2-(2,5-dioxo-2,5-dihydro-1H-pyrrol-1-yl)ethoxy]ethoxy}ethoxy)ethyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

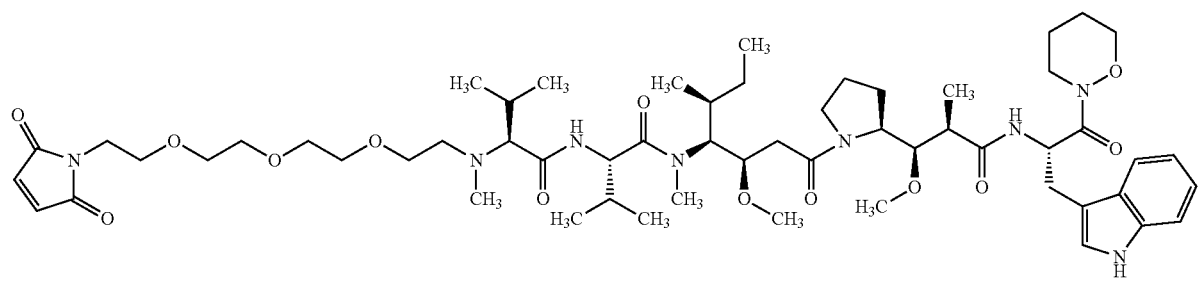 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCOCCOCCOCCN1C(=O)C=CC1=O)C(C)C]

The preparation was effected in analogy to Intermediates 174 and 175, commencing with the reductive alkylation of Intermediate 192 with Intermediate 172, subsequent deprotection and formation of the maleimide.

HPLC (Method 12): Rt=1.9 min;
LC-MS (Method 1): Rt=0.86 min; MS (ESIpos): m/z=1025 (M+H)+.

Intermediate 201

N-{6-[(bromoacetyl)amino]hexyl}-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

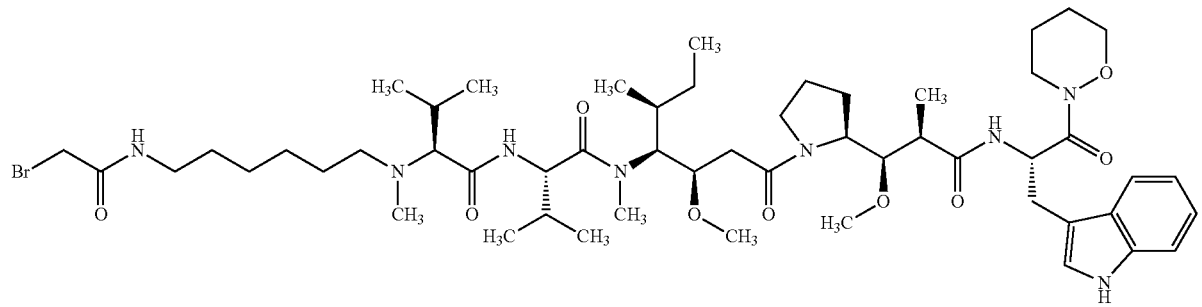 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCCNC(=O)CBr)C(C)C]

22 mg (0.023 mmol) of N-(6-aminohexyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 101) were dissolved in 9.5 ml of THF and admixed at 0° C. with 4.2 µl of triethylamine. A solution of bromoacetyl chloride in THF was added dropwise and the reaction mixture was stirred at 0° C. for 30 min. The reaction mixture was concentrated and the residue was purified by preparative HPLC. Thus, 6.9 mg (26% of theory) of the title compound were obtained as a foam.

HPLC (Method 5): $R_t$=1.8 min;

LC-MS (Method 11): $R_t$=0.9 min; MS (ESIpos): m/z=1059 and 1061 (M+H)$^+$.

Intermediate 202

N-{2-[2-(2-{3-[(2,5-dioxopyrrolidin-1-yl)oxy]-3-oxopropoxy}ethoxy)ethoxy]ethyl}-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

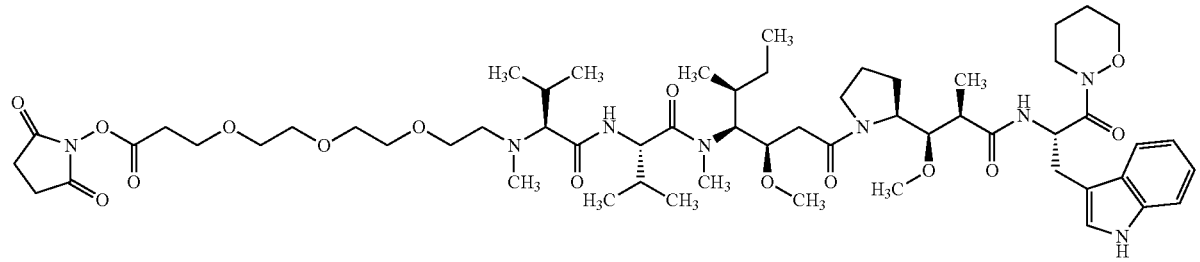 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCOCCOCCOCCC(=O)ON1C(=O)CCC1=O)C(C)C]

The preparation was at first effected in analogy to Intermediate 168, commencing with the reductive alkylation of Intermediate 192 with Intermediate 167 and subsequent hydrogenolytic cleavage of the benzyl ester of N-(2-{2-[2-(2-carboxyethoxy)ethoxy]ethoxy}ethyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide.

13 mg (10 µmol) of this intermediate were dissolved in 5 ml of DMF and admixed with 2.1 mg (20 mmol) of 1-hydroxypyrrolidine-2,5-dione, 6.5 µl of N,N-diisopropylethylamine and 7.1 mg (0.02 mmol) of HATU. The reaction mixture was stirred at RT overnight and then concentrated under reduced pressure. The remaining residue was purified by means of preparative HPLC. After lyophilization from acetonitrile/water, 9.2 mg (62% of theory) of the title compound were obtained.

HPLC (Method 12): $R_t$=2.0 min;
LC-MS (Method 2): $R_t$=2.1 min; MS (ESIpos): m/z=1141 (M+H)$^+$.

Intermediate 203 tert-butyl 6-hydrazino-6-oxohexyl carbamate

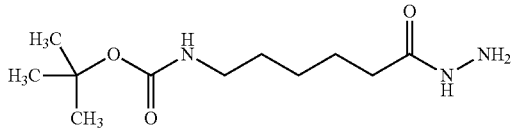 [SMILES: CC(C)(C)OC(=O)NCCCCCC(=O)NN]

This compound was prepared by standard peptide chemistry methods, by coupling of 6-[(tert-butoxycarbonyl)amino]hexanoic acid with benzyl hydrazinecarboxylate in the presence of EDCI and HOBT, and subsequent hydrogenolytic cleavage of the benzyloxycarbonyl protecting group.

LC-MS (Method 11): $R_t$=0.59 min; MS (ESIpos): m/z=246 (M+H)$^+$.

Intermediate 204

N-{4-[2-(6-aminohexanoyl)hydrazino]-4-oxobutyl}-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

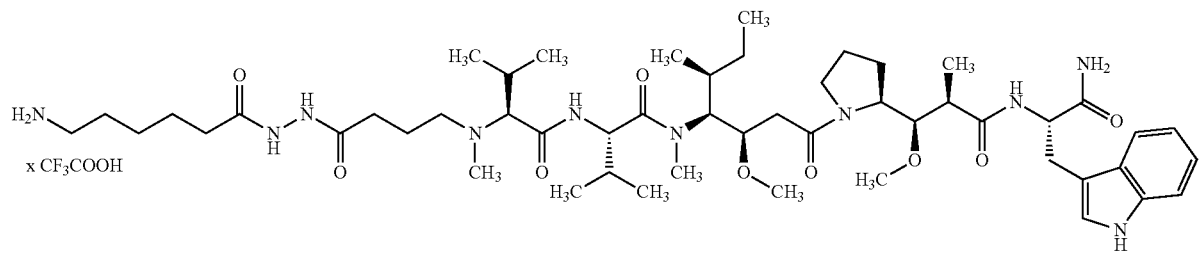 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)NNC(=O)CCCCCN)C(C)C]

146 mg (50 µmol) of (N-(3-carboxypropyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide were dissolved in 5 ml of DMF and then admixed with 30.6 mg (80 µmol) of O-(7-azabenzotriazol-1-yl)-N,N,N',N'-tetramethyluronium hexafluorophosphate, 19 µl of N,N-diisopropylethylamine and with 22.4 mg (60 µmol) of tert-butyl 6-hydrazino-6-oxohexyl carbamate. The reaction mixture was stirred at RT for 1.5 h. This was followed by concentration under high vacuum and purification of the remaining residue by means of preparative HPLC. Thus, 43 mg (68% of theory) of the protected intermediate were obtained, which were then taken up in 10 ml of dichloromethane and deprotected with 1 ml of trifluoroacetic acid. The reaction mixture was concentrated and the residue was stirred with dichloromethane, and the solvent was removed again under reduced pressure. Thus, 45 mg (68% of theory over 2 stages) of the title compound were obtained.

HPLC (Method 12): $R_t$=1.6 min;
LC-MS (Method 11): $R_t$=0.66 min; MS (ESIpos): m/z=983 (M+H)$^+$.

Intermediate 205

N-(4-{2-[6-({[2-(2,5-dioxo-2,5-dihydro-1H-pyrrol-1-yl)ethyl]carbamoyl}amino)hexanoyl]hydrazino}-4-oxobutyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

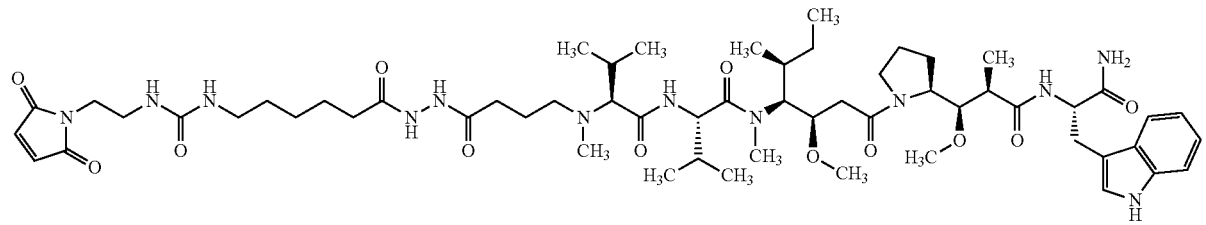 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)NNC(=O)CCCCCNC(=O)NCCN1C(=O)C=CC1=O)C(C)C]

This compound was prepared in analogy to Intermediate 114, proceeding from Intermediates 50 and 204.

Yield: 4 mg (78% of theory)

HPLC (Method 12): $R_t$=1.7 min;

LC-MS (Method 11): $R_t$=0.73 min; MS (ESIpos): m/z=1149 (M+H)⁺.

Intermediate 206

N-(6-{[3-({3-[(2,5-dioxopyrrolidin-1-yl)oxy]-3-oxopropyl}disulphanyl)propanoyl]amino}hexyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

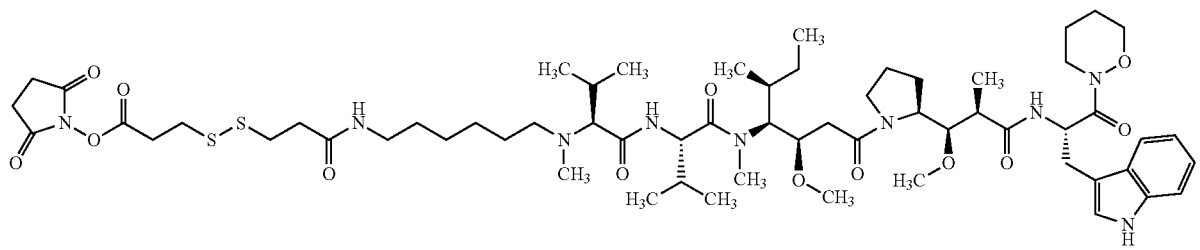 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCCNC(=O)CCSSCCC(=O)ON1C(=O)CCC1=O)C(C)C]

8 mg (10 µmol) of Intermediate 101 were dissolved in 2 ml of DMF and admixed with 8.6 mg (20 µmol) of 1,1'-{disulphanediylbis[(1-oxopropane-3,1-diyl)oxy]}dipyrrolidine-2,5-dione and 3.7 µl of N,N-diisopropylethylamine. The reaction mixture was stirred at RT for 2 h and then the solvent was evaporated off under reduced pressure and the residue was purified by preparative HPLC. 7.2 mg (68% of theory) of the title compound were obtained.

HPLC (Method 5): $R_t$=1.9 min;

LC-MS (Method 11): $R_t$=0.94 min; MS (ESIpos): m/z=615 [½ (M+2H⁺]

Intermediate 207

(1S,2R)-1-amino-2-phenylcyclopropanecarboxylic acid trifluoroacetate

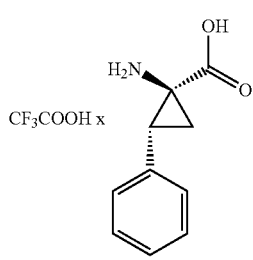 [SMILES: N[C@@]1(C(=O)O)C[C@@H]1c1ccccc1]

The title compound was obtained in quantitative yield by deprotecting 210 mg (0.76 mmol) of commercially available (1S,2R)-1-[(tert-butoxycarbonyl)amino]-2-phenylcyclopropanecarboxylic acid with trifluoroacetic acid.

LC-MS (Method 1): $R_t$=0.23 min; MS (ESIpos): m/z=178 (M+H)⁺.

Intermediate 208

9H-fluoren-9-ylmethyl 6-oxohexyl carbamate

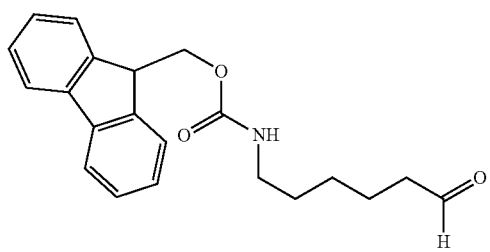 [SMILES: O=CCCCCCNC(=O)OCC1c2ccccc2-c2ccccc21]

The title compound was prepared from 1 g (2.95 mmol) of commercially available 9H-fluoren-9-ylmethyl 6-hydroxyhexyl carbamate under standard conditions, by oxidation with sulphur trioxide-pyridine complex. 840 mg (85% of theory) of the title compound were obtained.

HPLC (Method 12): $R_t$=2.0 min;

LC-MS (Method 1): $R_t$=1.1 min; MS (ESIpos): m/z=338 (M+H)⁺.

Intermediate 209

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(1S,2R)-1-carboxy-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

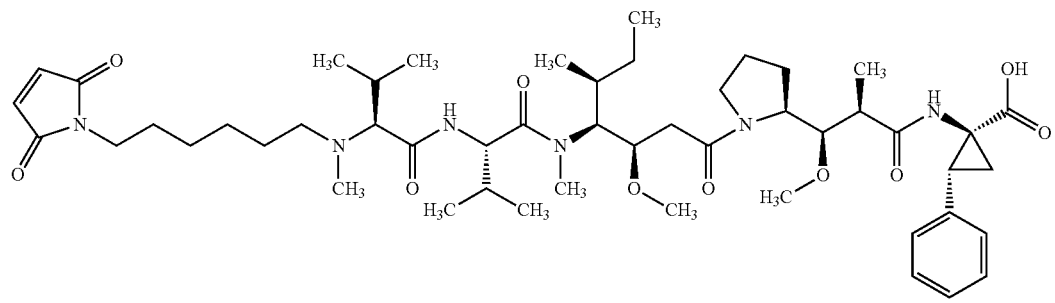 [SMILES: CC[C@H](C)[C@@H]([C@@H](CC(=O)N1CCC[C@H]1[C@H](OC)[C@@H](C)C(=O)N[C@@]1(C(=O)O)C[C@@H]1c1ccccc1)OC)N(C)C(=O)[C@@H](NC(=O)[C@H](C(C)C)N(C)CCCCCCN1C(=O)C=CC1=O)C(C)C]

First, in analogy to the synthesis described in Intermediate 75, by coupling of N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and (1S,2R)-1-amino-2-phenylcyclopropanecarboxylic acid trifluoroacetate (Intermediate 207) in the presence of O-(7-azabenzotriazol-1-yl)-N,N,N',N'-tetramethyluronium hexafluorophosphate and subsequent detachment of the Boc protecting group by means of trifluoroacetic acid, the amine compound N-methyl-L-valyl-N-[(3R,4S,5S)-1-{(2S)-2-[(1R,2R)-3-{[(1S,2R)-1-carboxy-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide was prepared as the trifluoroacetate.

To 22 mg (0.026 mmol) of this compound in 10 ml of methanol were then added 17 mg (0.05 mmol) of 9H-fluoren-9-ylmethyl 6-oxohexyl carbamate (Intermediate 208) and 2.3 mg of acetic acid, and also 11.4 mg (0.12 mmol) of borane-pyridine complex. The reaction mixture was stirred at RT overnight. Then the same amounts of borane-pyridine complex and acetic acid, and also 8 mg of fluoren-9-ylmethyl 6-oxohexyl carbamate, were added once again and the reaction mixture was stirred at RT for a further 24 h. This was followed by concentration under reduced pressure, and the residue was purified by means of preparative HPLC. After concentration of the corresponding fractions, the product was used immediately in the next stage.

33 mg of the still contaminated intermediate were taken up in 5 ml of DMF, and 1 ml of piperidine was added. After stirring at RT for 15 min, the reaction mixture was concentrated and the resulting residue was purified by preparative HPLC. Thus, 11 mg (55% of theory over 2 stages) of the aminocarboxylic acid intermediate were obtained.

HPLC (Method 12): $R_t$=1.7 min;

LC-MS (Method 11): $R_t$=0.7 min; MS (ESIpos): m/z=843 (M+H)$^+$.

6 mg (7.12 μmol) of this intermediate were taken up in 1 ml of dioxane and then admixed with 6.6 mg (42.7 μmol) of methyl 2,5-dioxo-2,5-dihydro-1H-pyrrole-1-carboxylate and with 5 μl of saturated aqueous sodium hydrogencarbonate solution. The reaction mixture was stirred at RT for 1 h. Then another 3 portions each of 50 μl of the saturated aqueous sodium hydrogencarbonate solution were added and the reaction mixture was stirred at RT for a further 30 min. Then the reaction mixture was acidified to pH 2 with trifluoroacetic acid and subsequently concentrated under reduced pressure. The remaining residue was purified by means of preparative HPLC. After lyophilization from acetonitrile/water, 4 mg (60% of theory) of the title compound were obtained as a foam.

HPLC (Method 12): $R_t$=1.9 min;

LC-MS (Method 11): $R_t$=0.88 min; MS (ESIpos): m/z=923 (M+H)$^+$.

Intermediate 210

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

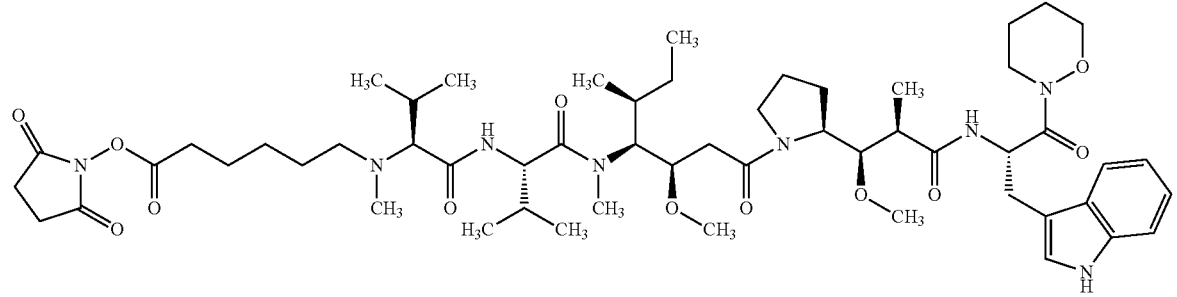 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCC(=O)ON1C(=O)CCC1=O)C(C)C]

First, 6-oxohexanoic acid was prepared by a literature method (J. Org. Chem. 58, 1993, 2196-2200).

80 mg (0.08 mmol) of N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 192) and 65.4 mg (0.5 mmol) of 6-oxohexanoic acid were combined in 9 ml of methanol and admixed with 10 µl of acetic acid and 37.4 mg (0.4 mmol) of borane-pyridine complex. The reaction mixture was stirred at RT overnight. This was followed by concentration under reduced pressure, and the residue was taken up in 1:1 acetonitrile/water and adjusted to pH 2 with trifluoroacetic acid. The reaction mixture was concentrated again and the residue was purified by means of preparative HPLC. After concentration of the corresponding fractions, 70 mg (86% of theory) of N-(5-carboxypentyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained as the trifluoroacetate.

HPLC (Method 12): $R_t$=1.9 min;
LC-MS (Method 1): $R_t$=0.87 min; MS (ESIpos): m/z=955 (M+H)$^+$.
$^1$H NMR (500 MHz, DMSO-d$_6$, characteristic signals): δ=12.0 (br. M, 1H), 10.8 (s, 1H), 9.4 (m, 1H), 8.9 and 8.8 (2d, 1H), 8.3 and 8.02 (2d, 1H), 7.5 (m, 1H), 7.3 (m, 1H), 7.15 and 7.1 (2s, 1H) 7.05-6.9 (m, 2H), 5.12 and 4.95 (2m, 1H), 4.7-4.5 (m, 2H), 4.1-3.8 (m, 4H), 3.75 (d, 1H), 3.25, 3.2, 3.18, 3.13, 2.98 and 2.88 (6s, 9H), 2.8 (m, 3H), 1.08 and 1.04 (2d, 3H), 0.95-0.8 (m, 15H), 0.8-0.65 (dd, 3H).

22 mg (23 µmol) of this intermediate were dissolved in 1.8 ml of dichloromethane and admixed with 13.2 mg (70 µmol) of 1-(3-dimethylaminopropyl)-3-ethylcarbodiimide hydrochloride, 26.5 mg (230 µmol) of 1-hydroxypyrrolidine-2,5-dione and 0.28 mg (2 µmol) of dimethylaminopyridine, and the reaction mixture was stirred at RT for 2 h. Subsequently, the reaction mixture was concentrated under reduced pressure and the remaining residue was purified by means of preparative HPLC. After lyophilization from acetonitrile/water, 21.3 mg (88% of theory) of the title compound were obtained.

HPLC (Method 12): $R_t$=1.9 min;
LC-MS (Method 1): $R_t$=0.94 min; MS (ESIpos): m/z=1052 (M+H)$^+$.

Intermediate 211

N-{6-[(2,5-dioxopyrrolidin-1-yl)oxy]-6-oxohexyl}-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide

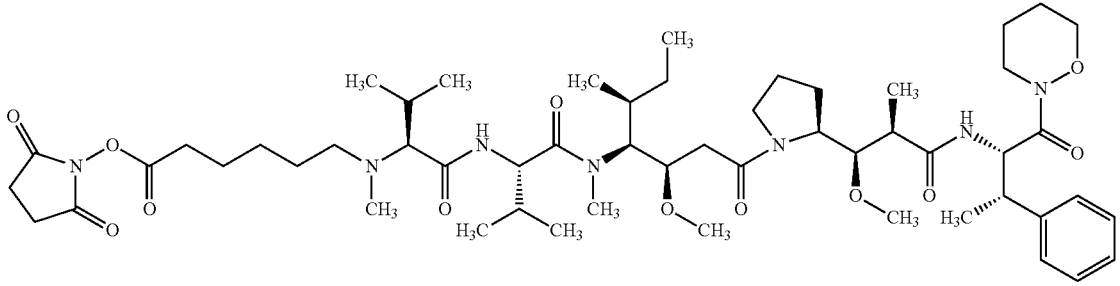 [SMILES: CC[C@H](C)[C@@H]([C@@H](CC(=O)N1CCC[C@H]1[C@H](OC)[C@@H](C)C(=O)N[C@H](C(=O)N1CCCCO1)[C@@H](C)c1ccccc1)OC)N(C)C(=O)[C@@H](NC(=O)[C@H](C(C)C)N(C)CCCCCC(=O)ON1C(=O)CCC1=O)C(C)C]

15 mg (20 µmol) of N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-yl}-5-methyl-1-oxoheptan-4-yl]-N-methyl-L-valinamide trifluoroacetate (Intermediate 15) were reductively alkylated with 6-oxohexanoic acid, in analogy to Intermediate 210.

Yield: 9.2 mg (61% of theory)
HPLC (Method 12): $R_t$=1.9 min;
LC-MS (Method 1): $R_t$=0.87 min; MS (ESIpos): m/z=929 (M+H)$^+$.

9 mg (10 µmol) of this intermediate were dissolved in 3 ml of DMF and admixed with 5.6 mg (48 µmol) of 1-hydroxypyrrolidine-2,5-dione, 5 µl of N,N-diisopropylethylamine and 5.5 mg (0.015 mmol) of HATU, and the reaction mixture was treated in an ultrasound bath for 6 h. In the course of this, 5.5 mg of HATU were added every hour. Subsequently, the reaction mixture was concentrated under reduced pressure, and the residue was taken up in acetonitrile/water and adjusted to pH 2 with trifluoroacetic acid. After concentrating again under reduced pressure, the remaining residue was purified by means of preparative HPLC. After lyophilization from acetonitrile/water, 5.8 mg (57% of theory) of the title compound were obtained.

HPLC (Method 12): $R_t$=2.0 min;
LC-MS (Method 1): $R_t$=0.95 min; MS (ESIpos): m/z=1027 (M+H)$^+$.

Intermediate 212

N-{2-[2-(2-{3-[(2,5-dioxopyrrolidin-1-yl)oxy]-3-oxopropoxy}ethoxy)ethoxy]ethyl}-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide

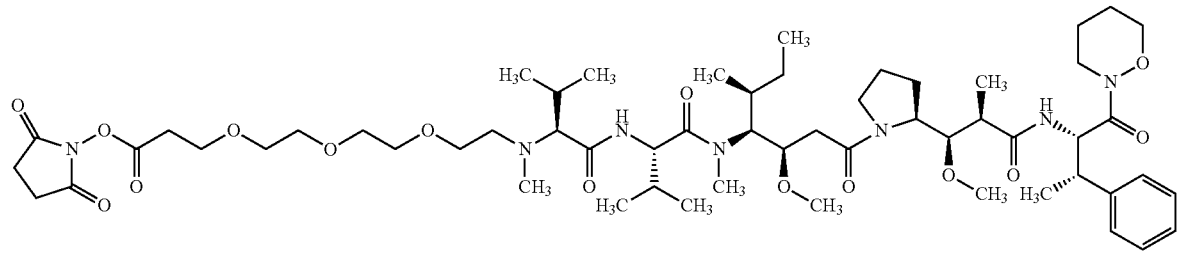 [SMILES: CC[C@H](C)[C@@H]([C@@H](CC(=O)N1CCC[C@H]1[C@H](OC)[C@@H](C)C(=O)N[C@H](C(=O)N1CCCCO1)[C@@H](C)c1ccccc1)OC)N(C)C(=O)[C@@H](NC(=O)[C@H](C(C)C)N(C)CCOCCOCCOCCC(=O)ON1C(=O)CCC1=O)C(C)C]

The preparation was at first effected in analogy to Intermediate 168, commencing with the reductive alkylation of Intermediate 15 with Intermediate 167 and subsequent hydrogenolytic cleavage of the benzyl ester of N-(2-{2-[2-(2-carboxyethoxy)ethoxy]ethoxy}ethyl)-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide.

8.4 mg (8 μmol) of this intermediate were dissolved in 3 ml of DMF and admixed with 9.5 mg (80 μmol) of 1-hydroxypyrrolidine-2,5-dione, 10 μl of N,N-diisopropylethylamine and 9.4 mg (25 μmol) of HATU, and the reaction mixture was stirred at RT overnight and then concentrated under reduced pressure. Subsequently, the reaction mixture was concentrated under reduced pressure, and the residue was taken up in acetonitrile/water and adjusted to pH 2 with trifluoroacetic acid. After concentrating again under reduced pressure, the remaining residue was purified by means of preparative HPLC. After lyophilization from acetonitrile/water, 4 mg (32% of theory) of the title compound were obtained.

HPLC (Method 12): $R_t$=2.0 min;

LC-MS (Method 1): $R_t$=0.96 min; MS (ESIpos): m/z=1117 (M+H)$^+$.

Intermediate 213

N-{6-[(trans-4-{[(2,5-dioxopyrrolidin-1-yl)oxy]carbonyl}cyclohexyl)amino]-6-oxohexyl}-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

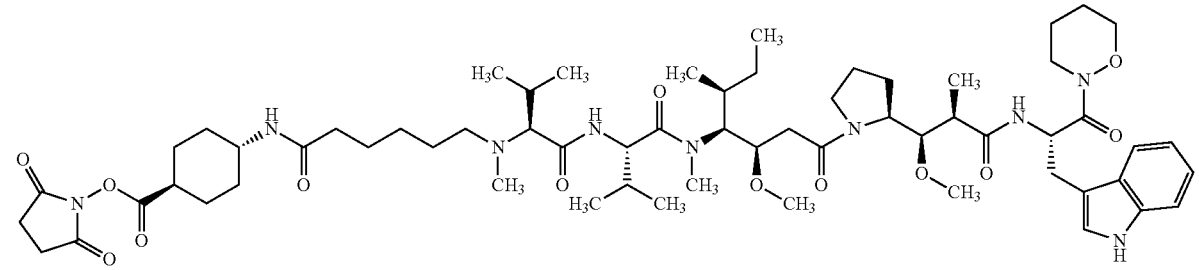 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCC(=O)N[C@H]1CC[C@H](C(=O)ON2C(=O)CCC2=O)CC1)C(C)C]

This compound was prepared in analogy to Intermediate 104, proceeding from N-(5-carboxypentyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, the synthesis of which was described under Intermediate 210. 9.3 mg of the title compound (37% of theory over 3 stages) were obtained.

HPLC (Method 12): $R_t$=1.9 min;

LC-MS (Method 1): $R_t$=0.9 min; MS (ESIpos): m/z=1177 (M+H)$^+$.

Intermediate 214

N-{4-[(2,5-dioxopyrrolidin-1-yl)oxy]-4-oxobutyl}-
N-methyl-L-valyl-N-[(3R,4S,5S)-1-{(2S)-2-[(1R,
2R)-3-{[(1S,2R)-1-hydroxy-1-phenylpropan-2-yl]
amino}-1-methoxy-2-methyl-3-oxopropyl]
pyrrolidin-1-yl}-3-methoxy-5-methyl-1-oxoheptan-
4-yl]-N-methyl-L-valinamide

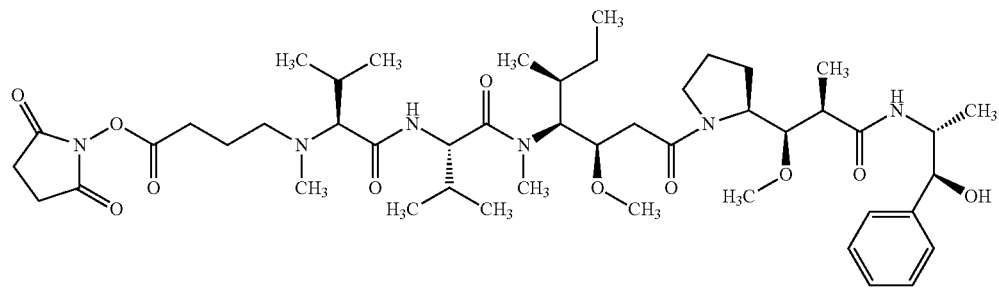 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)CCCC(=O)ON1C(=O)CCC1=O)C(C)C]

This compound was prepared in analogy to Intermediate 210, by conversion of Intermediate 92 to the active ester.
HPLC (Method 5): $R_t$=1.6 min;
LC-MS (Method 11): $R_t$=0.82 min; MS (ESIpos): m/z=901 (M+H)$^+$.

Intermediate 215

N-{6-[(2,5-dioxopyrrolidin-1-yl)oxy]-6-oxohexyl}-
N-methyl-L-valyl-N-[(3R,4S,5S)-1-{(2S)-2-[(1R,
2R)-3-{[(1S,2R)-1-hydroxy-1-phenylpropan-2-yl]
amino}-1-methoxy-2-methyl-3-oxopropyl]
pyrrolidin-1-yl}-3-methoxy-5-methyl-1-oxoheptan-
4-yl]-N-methyl-L-valinamide

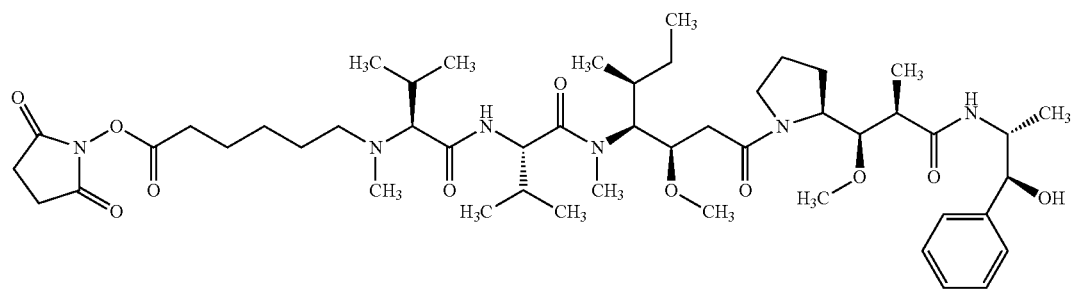 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)CCCCCC(=O)ON1C(=O)CCC1=O)C(C)C]

First, Intermediate 40, in analogy to Intermediate 183, was used with borane-pyridine complex to prepare N-(5-carboxypentyl)-N-methyl-L-valyl-N-[(3R,4S,5S)-1-{(2S)-2-[(1R, 2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide. From this compound, in analogy to Intermediate 210, the active ester was then generated. 34 mg (36% of theory over 2 stages) of the title compound were obtained.

HPLC (Method 5): $R_t$=1.6 min;
LC-MS (Method 1): $R_t$=0.85 min; MS (ESIpos): m/z=930 (M+H)$^+$.

Intermediate 216

N-(4-{[(2,5-dioxopyrrolidin-1-yl)oxy]carbonyl}benzyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

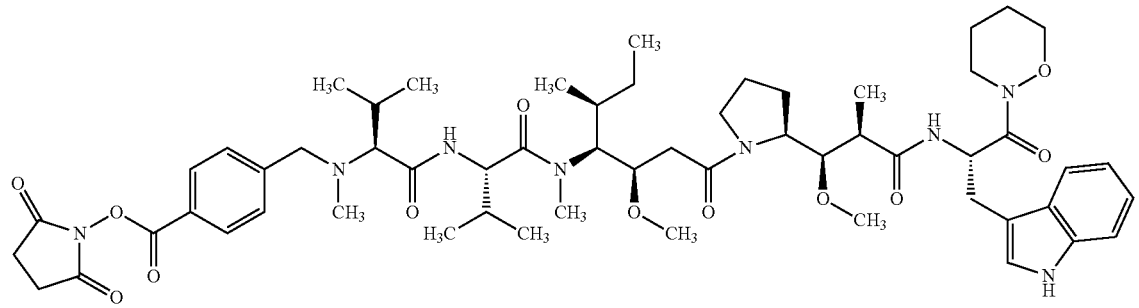 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)Cc1ccc(C(=O)ON2C(=O)CCC2=O)cc1)C(C)C]

First, in analogy to the preparation of Intermediate 183, Intermediate 192 was reacted with 4-formylbenzoic acid with borane-pyridine complex to give N-(4-carboxybenzyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide. This compound was then used, in analogy to Intermediate 210, to generate 11 mg (68% of theory) of the title compound.

HPLC (Method 5): $R_t$=1.8 min;

LC-MS (Method 1): $R_t$=1.13 min; MS (ESIpos): m/z=1072 (M+H)$^+$.

Intermediate 217

N-(5-carboxypentyl)-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

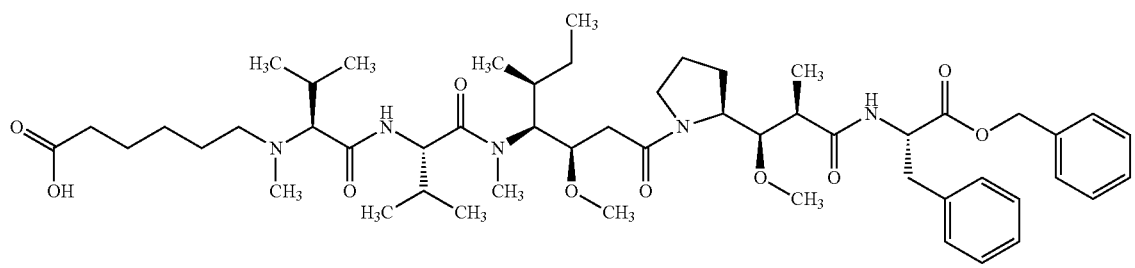 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1ccccc1)OC)N(C)C(=O)[C@@H](NC(=O)[C@H](C(C)C)N(C)CCCCCC(=O)O)C(C)C]

53 mg (84 µmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) and 45 mg (84 µmol) of benzyl N-{(2R,3R)-3-methoxy-2-methyl-3-[(2S)-pyrrolidin-2-yl]propanoyl}-L-phenylalaninate trifluoroacetate (Intermediate 12) were taken up in 2 ml of DMF, 19 µl of N,N-diisopropylethylamine, 14 mg (92 µmol) of HOBt and 17.6 mg (92 µmol) of EDC were added and then the mixture was stirred at RT overnight. Subsequently, the reaction mixture was concentrated and the residue was purified by means of preparative HPLC. This gave 59 mg (68% of theory) of the Fmoc-protected intermediate N-[(9H-fluoren-9-ylmethoxy)carbonyl]-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide LC-MS (Method 1): $R_t$=1.55 min; m/z=1044 (M+H)$^+$.

57 mg (0.055 mmol) of this intermediate were treated with 1.2 ml of piperidine in 5 ml of DMF to detach the Fmoc protecting group. After concentration and purification by means of preparative HPLC, 39 mg (76% of theory) of the free amine intermediate N-methyl-L-valyl-N-[(3R,4S,5S)-1-{(2S)-2-[(1R,2R)-3-{[(2S)-1-(benzyloxy)-1-oxo-3-phenyl-propan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained as the trifluoroacetate.

HPLC (Method 5): $R_t$=1.9 min;

LC-MS (Method 1): $R_t$=1.01 min; m/z=822 (M+H)$^+$.

60 mg (0.06 mmol) of this intermediate were reacted, in analogy to Intermediate 210, with 6-oxohexanoic acid in the presence of borane-pyridine complex. 45 mg (75% of theory) of the title compound were obtained as a foam.

HPLC (Method 5): $R_t$=1.9 min;

LC-MS (Method 1): $R_t$=0.97 min; MS (ESIpos): m/z=9936 (M+H)$^+$.

Intermediate 218

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

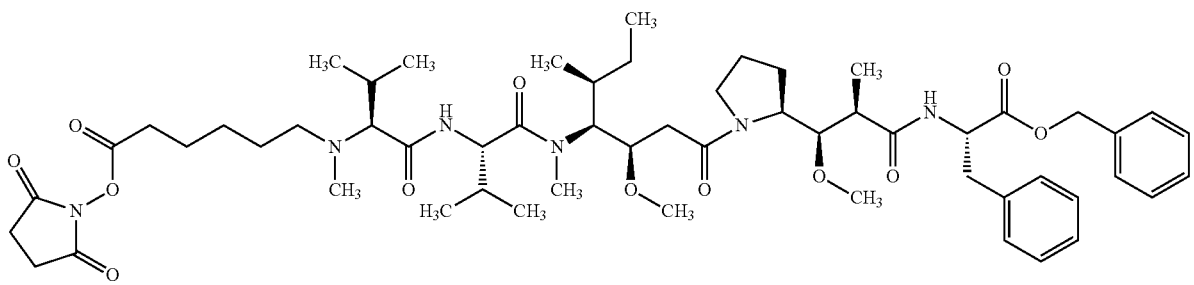 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1ccccc1)OC)N(C)C(=O)[C@@H](NC(=O)[C@H](C(C)C)N(C)CCCCCC(=O)ON1C(=O)CCC1=O)C(C)C]

This compound was prepared by conversion of 42 mg (0.05 mmol) of Intermediate 217 to the active ester.

Yield: 26 mg (54%)

HPLC (Method 5): $R_t$=2.1 min;

LC-MS (Method 1): $R_t$=1.01 min; MS (ESIpos): m/z=1034 (M+H)$^+$.

Intermediate 219

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide

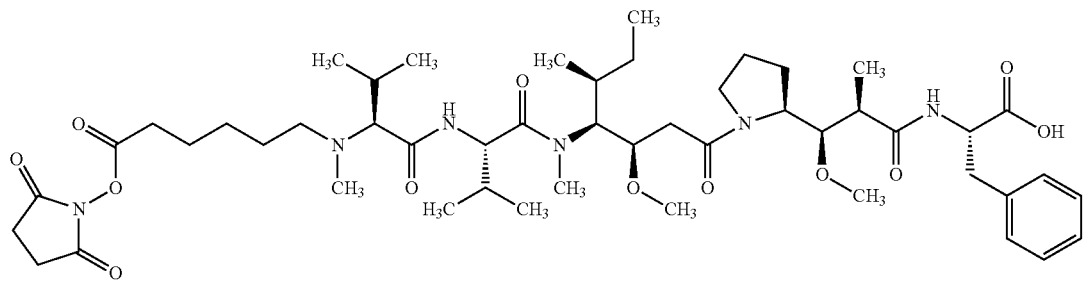 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCCCC(=O)ON1C(=O)CCC1=O)C(C)C]

20 mg (0.02 μmol) of the compound from Intermediate 218 were taken up in 2.4 ml of methanol and hydrogenated over 5% palladium on activated carbon under standard hydrogen pressure at RT for 30 min. The catalyst was then filtered off and the solvent was removed under reduced pressure. The residue was lyophilized from 1:1 acetonitrile/water. This gave 14 mg (92% of theory) of the title compound as a colourless foam.

HPLC (Method 5): $R_t$=1.7 min;

Intermediate 220

N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

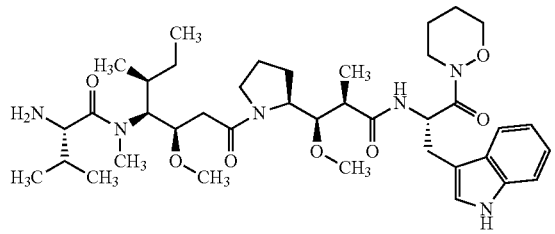 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](N)C(C)C]

0.5 g (1.01 mmol) of Intermediate 1 in 10 ml of dichloromethane were admixed with 1 ml of trifluoroacetic acid. After treatment in an ultrasound bath for 30 min, the mixture was concentrated and redistilled first with DCM and then with diethyl ether, and dried under high vacuum. The oily residue was used in the next stage, without further purification.

500 mg of this intermediate were dissolved in 20 ml of DMF and admixed with 466 mg (3.8 mmol) of Intermediate 191, 382 mg (1.01 mmol) of O-(7-azabenzotriazol-1-yl)-N,N,N',N'-tetramethyluronium hexafluorophosphate (HATU) and 440 µl (2.5 mmol) of N,N-diisopropylethylamine. The mixture was stirred at RT for 1 h and then concentrated. The residue was taken up in dichloromethane and extracted by shaking first twice with 5% aqueous citric acid solution and then with saturated aqueous sodium hydrogencarbonate solution. The organic phase was concentrated and the residue was purified by flash chromatography on silica gel with 95:5 dichloromethane/methanol as the eluent. The corresponding fractions were combined and the solvent was removed under reduced pressure. After the residue had been dried under high vacuum, 562 mg (65% of theory over both stages) of the Z-protected intermediate were obtained.

562 mg (0.57 mmol) of this intermediate were taken up in 50 ml of methanol and hydrogenated with 155 mg of 10% palladium on activated carbon under standard hydrogen pressure at RT for 20 min. The catalyst was then filtered off and the solvent was removed under reduced pressure. The residue was purified by preparative HPLC. The corresponding fractions were combined, the solvent was evaporated off under reduced pressure and the residue was lyophilized from dioxane. This gave 361 mg (87% of theory) of the title compound as a foam.

HPLC (Method 5): double peak with $R_t$=1.75 and 1.86 min;
LC-MS (Method 1): double peak at $R_t$=0.84 min and 0.91 min with the same mass; MS (ESIpos): m/z=944 (M+H)$^+$.

Intermediate 221

N-{(2S)-2-[(tert-butoxycarbonyl)amino]-3-phenylpropyl}-N-methyl-L-valine

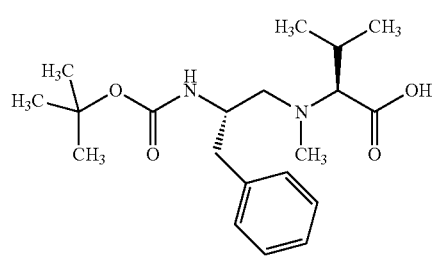 [SMILES: CC(C)[C@@H](C(=O)O)N(C)C[C@H](Cc1ccccc1)NC(=O)OC(C)(C)C]

100 mg (0.76 mmol) of commercially available N-methyl-L-valine and 285 mg (1.14 mmol) of commercially available tert-butyl (2S)-1-oxo-3-phenylpropan-2-yl carbamate were combined in 22 ml of methanol and admixed with 340 mg (3.66 mmol) of borane-pyridine complex and 70 µl of acetic acid. The reaction mixture was stirred at RT overnight. This was followed by concentration under reduced pressure, and the residue was purified by flash chromatography on silica gel with dichloromethane/methanol/17% aqueous ammonia solution as the eluent. After concentration of the corresponding fractions and lyophilization from 1:1 dioxane/water, 259 mg (93% of theory) of the title compound were obtained.

HPLC (Method 12): $R_t$=1.6 min;
LC-MS (Method 11): $R_t$=0.76 min; MS (ESIpos): m/z=365 (M+H)$^+$.

Intermediate 222

N-[(2S)-2-amino-3-phenylpropyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

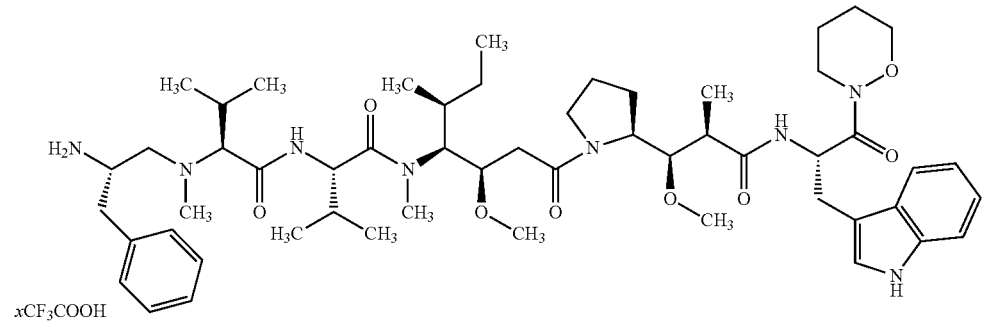 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)C[C@@H](N)Cc1ccccc1)C(C)C]

40 mg (0.11 mmol) of N-{(2S)-2-[(tert-butoxycarbonyl)amino]-3-phenylpropyl}-N-methyl-L-valine (Intermediate 221) were dissolved in 5 ml of DMF and admixed with 80 mg (0.11 mmol) of N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 220), 50 mg (0.13 mmol) of O-(7-azabenzotriazol-1-yl)-N,N,N',N'-tetramethyluronium hexafluorophosphate (HATU) and 57 µl (2.5 mmol) of N,N-diisopropylethylamine. The mixture was stirred at RT for 1 h and then concentrated. The residue was taken up in ethyl acetate and washed first with 5% aqueous citric acid solution and then with water. The organic phase was concentrated and the residue was purified by means of preparative HPLC. The corresponding fractions were combined and the solvent was removed under reduced pressure. After lyophilization from dioxane, 60 mg (50% of theory) of the protected intermediate were obtained.

HPLC (Method 12): R$_t$=2.2 min;
LC-MS (Method 1): R$_t$=1.17 min; MS (ESIpos): m/z=1073 (M+H)$^+$.

60 mg (0.05 mmol) of this intermediate were taken up in 10 ml of dichloromethane, 2 ml of trifluoroacetic acid were added, and the reaction mixture was stirred at RT for 1.5 h. Subsequently, the reaction mixture was concentrated under reduced pressure and the remaining residue was purified by means of preparative HPLC. The corresponding fractions were combined, the solvent was removed under reduced pressure and the residue was lyophilized from dioxane/water. In this way, 25 mg (42% of theory) of the title compound were obtained as a foam.

HPLC (Method 12): R$_t$=1.9 min;
LC-MS (Method 1): R$_t$=0.95 min; MS (ESIpos): m/z=974 (M+H)$^+$.

Intermediate 223

N-[(2S)-2-({[2-(2,5-dioxo-2,5-dihydro-1H-pyrrol-1-yl)ethyl]carbamoyl}amino)-3-phenylpropyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

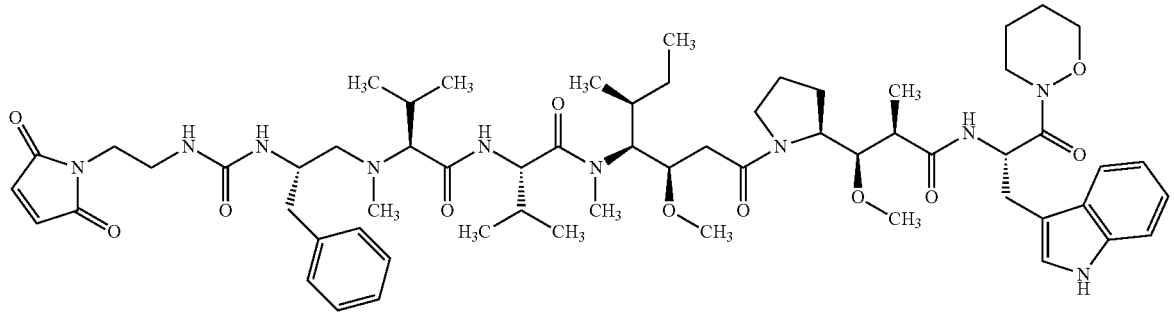 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)C[C@H](Cc1ccccc1)NC(=O)NCCN1C(=O)C=CC1=O)C(C)C]

The preparation was effected in analogy to Intermediate 134, proceeding from 5 mg (4.6 µmol) of Intermediate 222. 3.4 mg (65% of theory) of the title compound were obtained.

HPLC (Method 12): R$_t$=2.0 min;
LC-MS (Method 1): R$_t$=0.99 min; MS (ESIpos): m/z=1140 (M+H)$^+$.

Intermediate 224

N-[(2S)-2-({[2-(2,5-dioxo-2,5-dihydro-1H-pyrrol-1-yl)ethyl]carbamoyl}amino)propyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

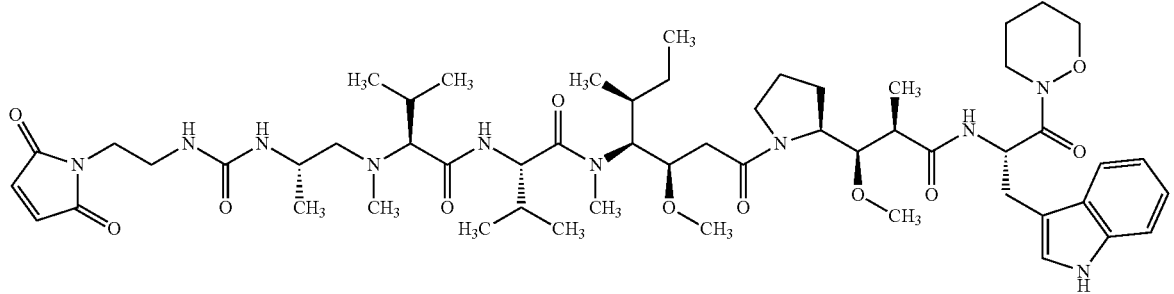 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)C[C@H](C)NC(=O)NCCN1C(=O)C=CC1=O)C(C)C]

The preparation was effected in analogy to the synthesis of Intermediate 223.

HPLC (Method 12): R$_t$=1.9 min;
LC-MS (Method 1): R$_t$=0.92 min; MS (ESIpos): m/z=1064 (M+H)$^+$.

Intermediate 225

N-(2-aminoethyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

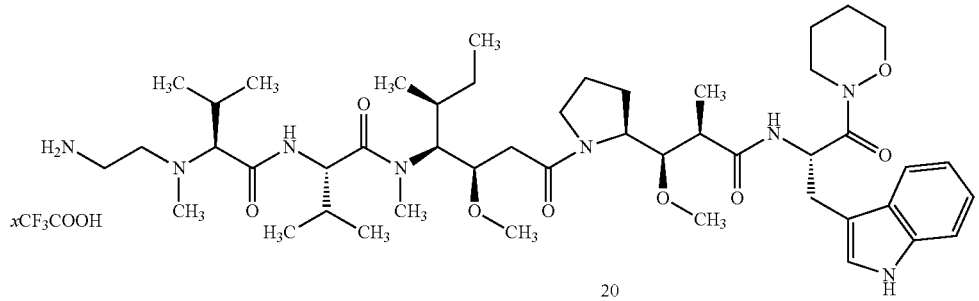 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCN)C(C)C]

100 mg (0.76 mmol) of commercially available N-methyl-L-valine and 182 mg (1.14 mmol) of commercially available tert-butyl 2-oxoethyl carbamate were combined in 20 ml of methanol and admixed with 340 mg (3.66 mmol) of borane-pyridine complex and 65 µl of acetic acid. The reaction mixture was stirred at RT overnight. This was followed by concentration under reduced pressure, and the residue was purified by flash chromatography on silica gel with dichloromethane/methanol/17% aqueous ammonia solution (15/4/0.5) as the eluent. After concentration of the corresponding fractions and lyophilization from 1:1 dioxane/water, 190 mg in 39% purity (35% of theory) of the intermediate were obtained, which were converted further without further purification.

50 mg (0.07 mmol) of this intermediate were dissolved in 10 ml of DMF and admixed with 52 mg (0.07 mmol) of N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Intermediate 220), 32 mg (0.09 mmol) of O-7-azabenzotriazol-1-yl)-N,N,N',N'-tetramethyluronium hexafluorophosphate (HATU) and 37 µl (0.2 mmol) of N,N-diisopropylethylamine. The mixture was stirred at RT overnight and then concentrated. The residue was taken up in ethyl acetate and extracted by shaking first with 5% aqueous citric acid solution and then with water. The organic phase was concentrated and the residue was purified by means of preparative HPLC. The corresponding fractions were combined and the solvent was removed under reduced pressure. After lyophilization from dioxane, 53 mg (76% of theory) of the protected intermediate were obtained.

HPLC (Method 12): $R_t$=2.0 min;
LC-MS (Method 1): $R_t$=1.02 min; MS (ESIpos): m/z=984 (M+H)$^+$.

53 mg (0.05 mmol) of this intermediate were taken up in 10 ml of dichloromethane, 2 ml of trifluoroacetic acid were added, and the reaction mixture was stirred at RT for 30 min. Subsequently, the reaction mixture was concentrated under reduced pressure and the remaining residue was purified by means of preparative HPLC. The corresponding fractions were combined, the solvent was removed under reduced pressure and the residue was lyophilized from dioxane/water. In this way, 21 mg (40% of theory) of the title compound were obtained in 65% purity.

HPLC (Method 12): $R_t$=1.7 min;
LC-MS (Method 1): $R_t$=0.87 min; MS (ESIpos): m/z=884 (M+H)$^+$.

Intermediate 226

N-[2-({[2-(2,5-dioxo-2,5-dihydro-1H-pyrrol-1-yl)ethyl]carbamoyl}amino)ethyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

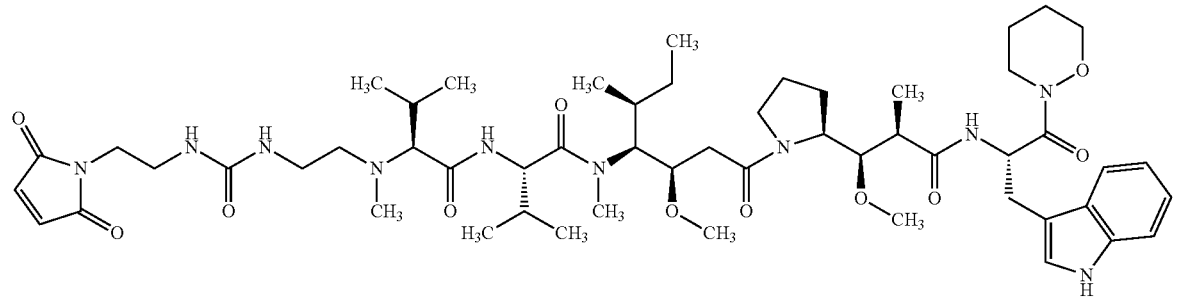 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCNC(=O)NCCN1C(=O)C=CC1=O)C(C)C]

The preparation was effected proceeding from Intermediate 225, in analogy to the synthesis of Intermediate 134. 11.6 mg (59% of theory) of the title compound were obtained.

HPLC (Method 12): $R_t$=1.9 min;
LC-MS (Method 1): $R_t$=0.90 min; MS (ESIpos): m/z=1050 (M+H)$^+$.

Intermediate 227

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

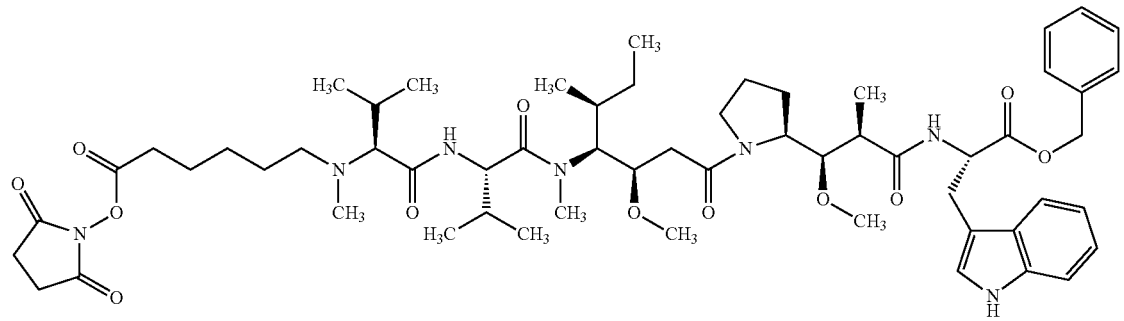 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OCc1ccccc1)OC)N(C)C(=O)[C@@H](NC(=O)[C@H](C(C)C)N(C)CCCCCC(=O)ON1C(=O)CCC1=O)C(C)C]

This compound was prepared analogously to Intermediate 218, by conversion to the active ester.
Yield: 18 mg (51% of theory)
HPLC (Method 5): $R_t$=2.1 min;
LC-MS (Method 1): $R_t$=0.98 min; MS (ESIpos): m/z=1073 (M+H)$^+$.

Intermediate 228

(2R,3S)-3-[(tert-butoxycarbonyl)amino]-4-{2-[6-(2,5-dioxo-2,5-dihydro-1H-pyrrol-1-yl)hexanoyl]hydrazino}-4-oxobutan-2-yl(3R,4S,7S,10S)-4-[(2S)-butan-2-yl]-7,10-diisopropyl-3-(2-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-2-oxoethyl)-5,11-dimethyl-6,9-dioxo-2-oxa-5,8,11-triazapentadecan-15-oate

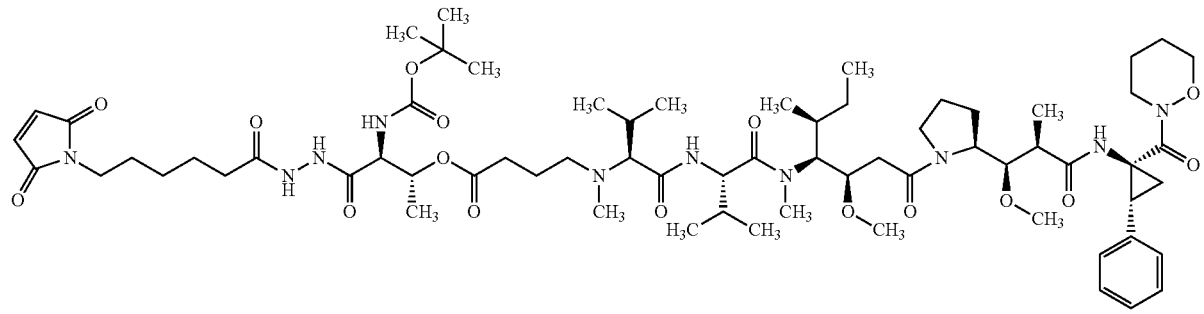 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)O[C@H](C)[C@H](NC(=O)OC(C)(C)C)C(=O)NNC(=O)CCCCCN1C(=O)C=CC1=O)C(C)C]

The title compound was prepared by coupling the Boc-protected intermediate obtained in the synthesis of Intermediate 154 with commercially available 6-(2,5-dioxo-2,5-dihydro-1H-pyrrol-1-yl)hexanehydrazide.

HPLC (Method 12): $R_t$=2.1 min;
LC-MS (Method 1): $R_t$=0.97 min; MS (ESIpos): m/z=1308 (M+H)$^+$.

Intermediate 229

(2R,3S)-3-acetamido-4-{2-[6-(2,5-dioxo-2,5-dihydro-1H-pyrrol-1-yl)hexanoyl]hydrazino}-4-oxobutan-2-yl (3R,4S,7S,10S)-4-[(2S)-butan-2-yl]-7,10-diisopropyl-3-(2-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-2-oxoethyl)-5,11-dimethyl-6,9-dioxo-2-oxa-5,8,11-triazapentadecan-15-oate

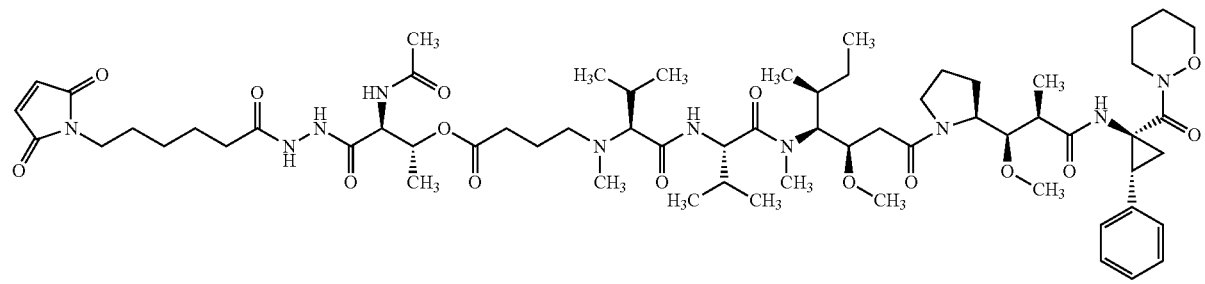 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)O[C@H](C)[C@H](NC(C)=O)C(=O)NNC(=O)CCCCCN1C(=O)C=CC1=O)C(C)C]

The title compound was prepared from 7.5 mg (2.5 µmol) of Intermediate 154 by acetylation with 2.3 µl of acetic anhydride in 1 ml of DMF in the presence of 0.4 µl of N,N-diisopropylethylamine Yield: 1.4 mg (40% of theory)

HPLC (Method 12): $R_t$=1.9 min;

LC-MS (Method 1): $R_t$=0.86 min; MS (ESIpos): m/z=1250 (M+H)$^+$.

Intermediate 230

(2R,3S)-3-[(tert-butoxycarbonyl)amino]-4-{2-[6-(2,5-dioxo-2,5-dihydro-1H-pyrrol-1-yl)hexanoyl]hydrazino}-4-oxobutan-2-yl (3R,4S,7S,10S)-4-[(2S)-butan-2-yl]-3-(2-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-2-oxoethyl)-7,10-diisopropyl-5,11-dimethyl-6,9-dioxo-2-oxa-5,8,11-triazapentadecan-15-oate

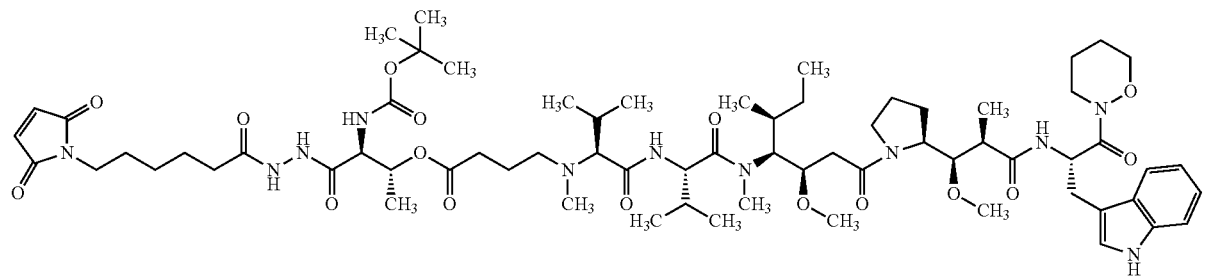 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCC(=O)O[C@H](C)[C@H](NC(=O)OC(C)(C)C)C(=O)NNC(=O)CCCCCN1C(=O)C=CC1=O)C(C)C]

This compound was prepared in analogy to Intermediate 228, proceeding from Intermediate 193. 16 mg (30% of theory over 3 stages) of the title compound were obtained.

HPLC (Method 12): $R_t$=2.0 min;

LC-MS (Method 1): $R_t$=1.02 min; MS (ESIpos): m/z=1335 (M+H)$^+$.

Intermediate 231

(2R,3S)-3-acetamido-4-{2-[6-(2,5-dioxo-2,5-dihydro-1H-pyrrol-1-yl)hexanoyl]hydrazino}-4-oxobutan-2-yl (3R,4S,7S,10S)-4-[(2S)-butan-2-yl]-3-(2-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-2-oxoethyl)-7,10-diisopropyl-5,11-dimethyl-6,9-dioxo-2-oxa-5,8,11-triazapentadecan-15-oate

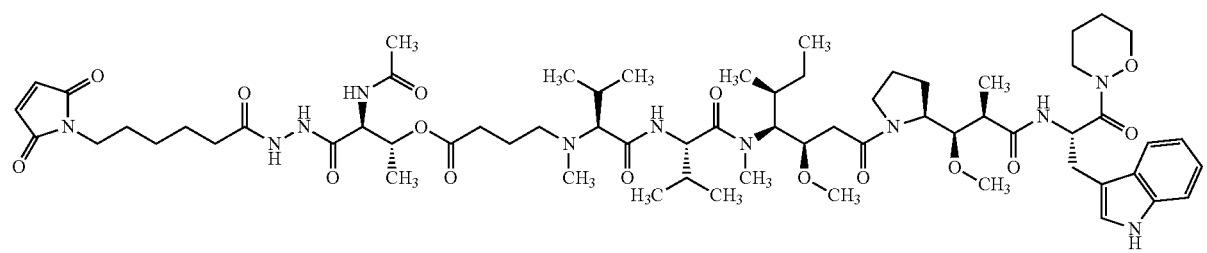 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCC(=O)O[C@H](C)[C@H](NC(C)=O)C(=O)NNC(=O)CCCCCN1C(=O)C=CC1=O)C(C)C]

This compound was prepared from 8 mg (6 μmol) of Intermediate 230, first by deprotection with trifluoroacetic acid and subsequent acetylation with acetic anhydride in DMF in the presence of N,N-diisopropylethylamine. 2 mg (37% of theory over 2 stages) of the title compound were obtained.

HPLC (Method 12): $R_t$=1.9 min;
LC-MS (Method 1): $R_t$=0.88 min; MS (ESIpos): m/z=1277 (M+H)$^+$.

Intermediate 232 benzyl N-[(4-nitrophenoxy)carbonyl]-beta-alaninate

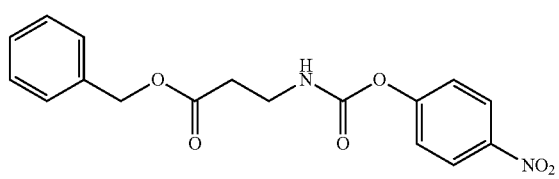 [SMILES: O=C(CCNC(=O)Oc1ccc([N+](=O)[O-])cc1)OCc1ccccc1]

200 mg (0.57 mmol) of commercially available 4-methylbenzenesulphonic acid-benzyl beta-alaninate and 229 mg (1.14 mmol) of 4-nitrophenyl chlorocarbonate were taken up in 15 ml of tetrahydrofuran and the reaction mixture was then heated to reflux for 30 min. Subsequently, the reaction mixture was concentrated under reduced pressure and the residue was purified by means of preparative HPLC. After concentration of the corresponding fractions and drying of the residue under high vacuum, 86 mg (44% of theory) of the title compound were obtained.

HPLC (Method 12): $R_t$=1.8 min;
LC-MS (Method 1): $R_t$=1.07 min; MS (ESIpos): m/z=345 (M+H)$^+$.

Intermediate 233

N-{2-[({3-[(2,5-dioxopyrrolidin-1-yl)oxy]-3-oxopropyl}carbamoyl)amino]ethyl}-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

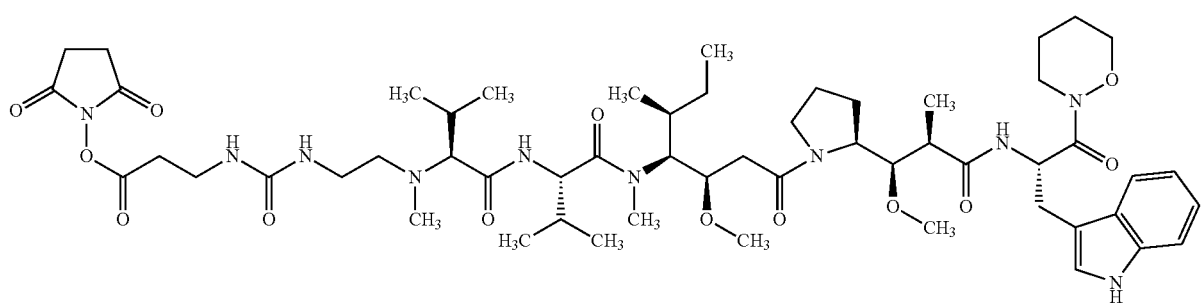 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCNC(=O)NCCC(=O)ON1C(=O)CCC1=O)C(C)C]

13 mg (10 µmol) of Intermediate 225 and 6.7 mg (20 µmol) of Intermediate 232 were dissolved in 3 ml of DMF, and then 7 µl of N,N-diisopropylethylamine were added. The mixture was stirred at RT overnight and then concentrated under high vacuum. The remaining residue was purified by means of preparative HPLC. After concentration of the corresponding fractions and drying of the residue under high vacuum, 5.4 mg (38% of theory) of the protected intermediate were obtained.

HPLC (Method 5): $R_t$=2.1 min;
LC-MS (Method 1): $R_t$=0.6 in; MS (ESIpos): m/z=1089 (M+H)$^+$.

5.4 mg (5 µmol) of this intermediate were dissolved in 5 ml of methanol and, after addition of 2 mg of 10% palladium on activated carbon, hydrogenated under standard hydrogen pressure at RT for 20 min. The catalyst was then filtered off and the solvent was removed under reduced pressure. After the residue had been dried under high vacuum, 5 mg (quant.) of the acid intermediate were obtained.

HPLC (Method 12): $R_t$=1.8 min;
LC-MS (Method 1): $R_t$=0.84 min; MS (ESIpos): m/z=999 (M+H)$^+$.

5 mg (10 µmol) of this intermediate were dissolved in 1 ml of DMF and admixed with 5.8 mg (50 mmol) of 1-hydroxy-pyrrolidine-2,5-dione and then with 2.6 µl of N,N-diisopropylethylamine and 3.8 mg (10 µmol) of HATU. After stirring at RT for 20 h, the reaction mixture was concentrated under reduced pressure. The remaining residue was purified by means of preparative HPLC. After lyophilization from 1:1 dioxane/water, 1.1 mg (20% of theory) of the title compound were obtained.

HPLC (Method 12): $R_t$=1.9 min;
LC-MS (Method 1): $R_t$=0.87 min; MS (ESIpos): m/z=1096 (M+H)$^+$.

Intermediate 234

N-(6-{[(benzyloxy)carbonyl]amino}hexyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

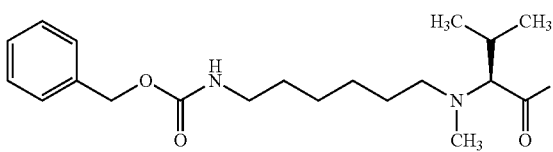
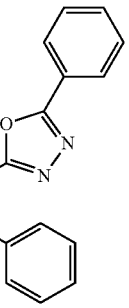

25 mg (30 µmol) of N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide (Intermediate 55) and 45 mg (180 µmol) of benzyl 6-oxohexyl carbamate were taken up in 3 ml of methanol and acidified with acetic acid. At room temperature, 15 µl (144 µmol; 9.4M) of borane-pyridine complex were subsequently added. The mixture was subsequently stirred at RT for 24 h, and acetic acid and 15 µl (144 µmol; 9.4M) of borane-pyridine complex were added again after 8 h. The reaction mixture was subsequently adjusted to pH 2 with TFA and purified by means of preparative HPLC. The product fractions were combined and concentrated, and the residue was dried under high vacuum. This gave 15 mg (46% of theory) of the title compound as a foam.

LC-MS (Method 1): $R_t$=1.03 min; m/z=1066 (M+H)$^+$.

Intermediate 235

N-(6-aminohexyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

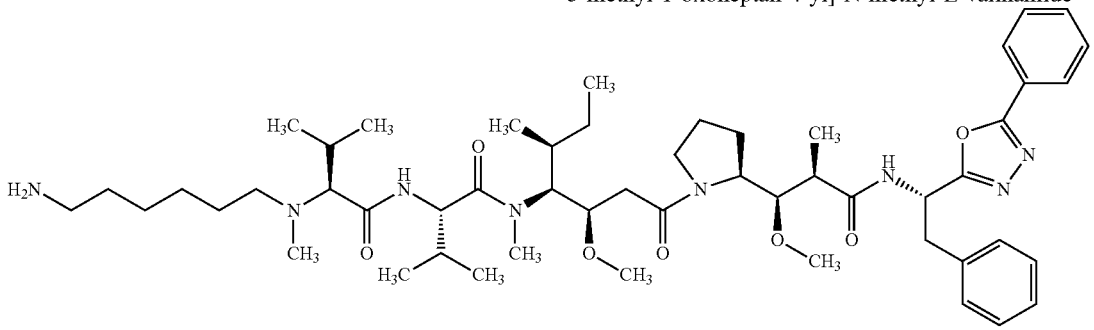

15 mg (14 µmol) of N-(6-{[(benzyloxy)carbonyl]amino}hexyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide (Intermediate 234) were taken up in 3 ml of methanol, and 1.8 mg of palladium on charcoal (5%) were added. The reaction mixture was subsequently hydrogenated under standard hydrogen pressure at RT for 2 h. The catalyst was then filtered off and the solvent was removed under reduced pressure. The residue was lyophilized from 1:1 acetonitrile/water. 11 mg (86% of theory) of the title compound were obtained as a foam.

LC-MS (Method 1): $R_t$=0.81 min; m/z=932 (M+H)$^+$.

Intermediate 236

N-[6-(2,5-dioxo-2,5-dihydro-1H-pyrrol-1-yl)hexyl]-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

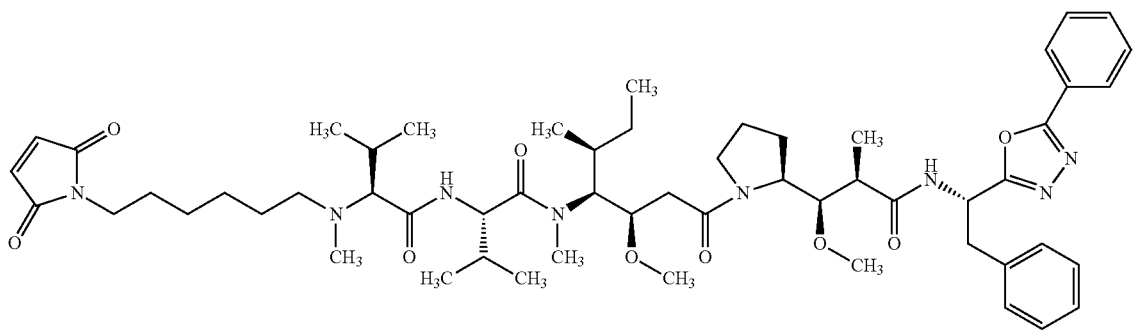 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@H](C(C)C)N(C)CCCCCCN1C(=O)C=CC1=O)C(C)C]

11 mg (12 µmol) of N-(6-aminohexyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide (Intermediate 235) were taken up in 500 µl of 1:1 dioxane/water and admixed with 253 µl of 1M aqueous sodium hydrogencarbonate solution and then with 2.8 mg (18 µmol) of methyl 2,5-dioxo-2,5-dihydro-1H-pyrrole-1-carboxylate. The reaction mixture was stirred at RT for 30 min and then acidified with trifluoroacetic acid. The reaction mixture was purified by means of preparative HPLC. After lyophilization, 0.8 mg (7% of theory) of the title compound was obtained.

LC-MS (Method 1): $R_t$=1.01 min; m/z=1012 (M+H)$^+$.

Intermediate 237

N-(5-carboxypentyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

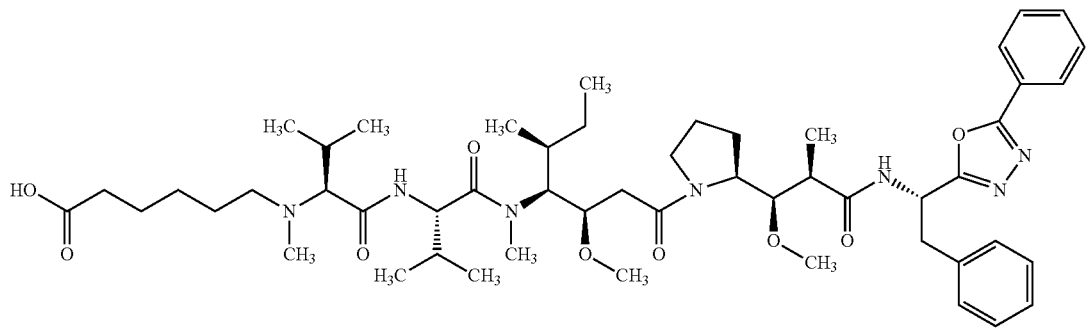 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@H](C(C)C)N(C)CCCCCC(=O)O)C(C)C]

25 mg (30 µmol) of N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide (Intermediate 55) and 23 mg (180 µmol) of 6-oxohexanoic acid were taken up in 3 ml of methanol and acidified with acetic acid. At room temperature, 15 µl (144 µmol; 9.4M) of borane-pyridine complex were subsequently added. The reaction mixture was subsequently stirred at RT for 20 h, and acetic acid and 15 µl (144 µmol; 9.4M) of borane-pyridine complex were added again after 8 h. The reaction mixture was subsequently adjusted to pH 2 with trifluoroacetic acid and purified by means of preparative HPLC. The product fractions were combined and concentrated, and the residue was lyophilized. 21 mg (74% of theory) of the title compound were thus obtained as a foam.

LC-MS (Method 1): $R_t$=0.91 min; m/z=947 (M+H)$^+$.

Intermediate 238

N-{6-[(2,5-dioxopyrrolidin-1-yl)oxy]-6-oxohexyl}-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

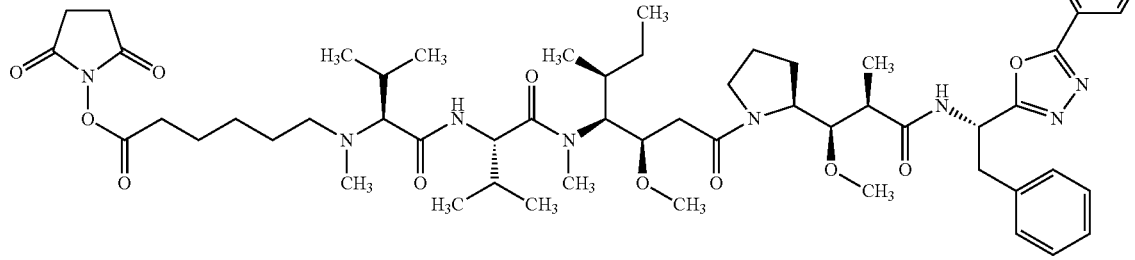

21 mg (22 µmol) of Intermediate 237 were dissolved in 1 ml of DMF and admixed with 38 mg (333 µmol) of 1-hydroxypyrrolidine-2,5-dione and then with 2.4 mg (10 µmol) of O-(7-azabenzotriazol-1-yl)-N,N,N',N'-tetramethyluronium hexafluorophosphate (HATU) and 19 µl of N,N-diisopropylethylamine. After stirring at RT for 2 h, the reaction mixture was purified by means of preparative HPLC. After lyophilization from dioxane, 22 mg (96% of theory) of the title compound were obtained.

LC-MS (Method 1): $R_t$=0.95 min; m/z=1044 (M+H)$^+$.

Intermediate 239

N-methyl-L-threonyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

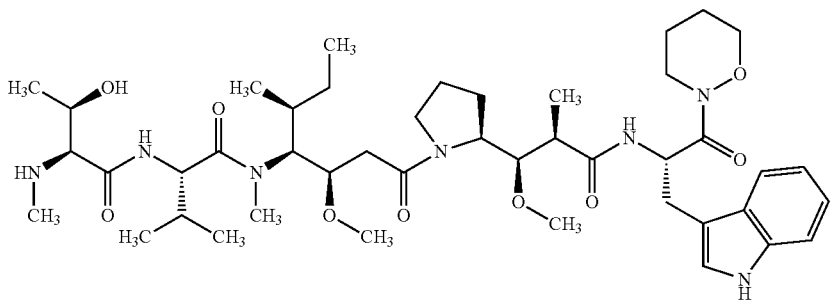 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@@H](NC)[C@@H](C)O)C(C)C]

First, N-[(benzyloxy)carbonyl]-N-methyl-L-threonine was released from 237 mg (0.887 mmol) of its dicyclohexylamine salt by taking it up in ethyl acetate and extractive shaking with 5% aqueous sulphuric acid. The organic phase was dried over magnesium sulphate, filtered and concentrated. 14.7 mg (0.055 mmol) of N-[(benzyloxy)carbonyl]-N-methyl-L-threonine were taken up in 3 ml of DMF and admixed successively with 40 mg (0.055 mmol) of Intermediate 220, 12.7 mg (0.066 mmol) of 1-(3-dimethylaminopropyl)-3-ethylcarbodiimide hydrochloride and 10 mg (0.066 mmol) of 1-hydroxy-1H-benzotriazole hydrate. The mixture was subsequently stirred at RT for 2 h. The solvent was then removed under reduced pressure and the residue purified by preparative HPLC. 29 mg (54% of theory) of the Z-protected intermediate were thus obtained.

LC-MS (Method 1): $R_t$=1.15 min; MS (ESIpos): m/z=976 (M+H)$^+$.

29 mg (0.003 mmol) of this intermediate were dissolved in 5 ml of methanol and hydrogenated over 5 mg of 5% palladium/charcoal at RT and standard pressure for 1 h. The catalyst was subsequently filtered off and the solvent was evaporated off. The remaining residue was purified by preparative HPLC. 17 mg (54% of theory) of the title compound were obtained.

LC-MS (Method 1): $R_t$=0.77 min; MS (ESIpos): m/z=842 (M+H)$^+$.

Intermediate 240

N-{6-[(2,5-dioxopyrrolidin-1-yl)oxy]-6-oxohexyl}-N-methyl-L-threonyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

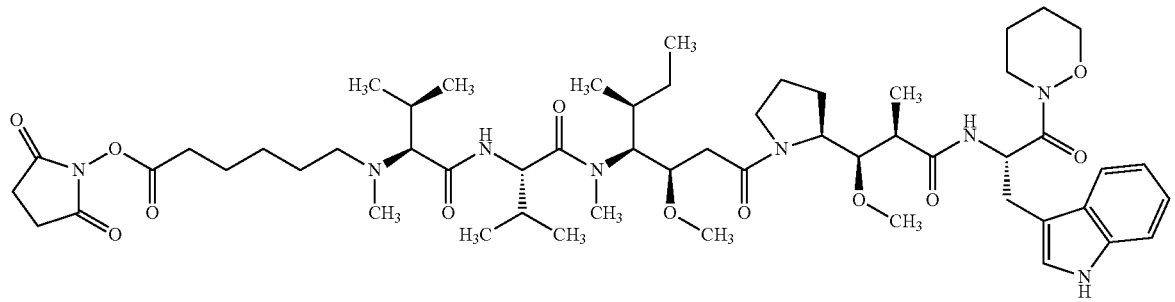

This compound was prepared in analogy to Intermediate 210 from 15.6 mg (0.016 mmol) of Intermediate 239. 10.8 mg (67% of theory over 2 stages) of the title compound were obtained.

HPLC (Method 5): $R_t$=1.7 min;
LC-MS (Method 1): $R_t$=0.85 min; MS (ESIpos): m/z=1053 (M+H)$^+$.

Intermediate 241

N-methyl-L-valyl-N-[(3R,4S,5S)-1-{(2S)-2-[(1R,2R)-3-{[(2S)-3-(4-hydroxyphenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

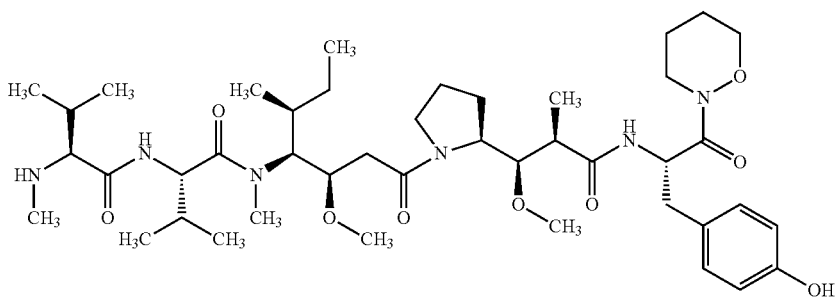 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)N1CCCCO1)OC)N(C)C(=O)[C@@H](NC(=O)[C@@H](NC)C(C)C)C(C)C]

First, in analogy to Intermediate 5, trifluoroacetic acid-(2S)-2-amino-3-(4-hydroxyphenyl)-1-(1,2-oxazinan-2-yl)propan-1-one (1:1) was prepared. This reagent was then used, in analogy to the synthesis described in Intermediate 75, by coupling with N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) in the presence of O-(7-azabenzotriazol-1-yl)-N,N,N',N'-tetramethyluronium hexafluorophosphate and subsequent detachment of the Boc protecting group by means of trifluoroacetic acid, to prepare the title compound.

HPLC (Method 12): $R_t$=1.7 min;

LC-MS (Method 1): $R_t$=0.85 min; MS (ESIpos): m/z=817 (M+H)$^+$.

Intermediate 242

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(2S)-3-(4-hydroxyphenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

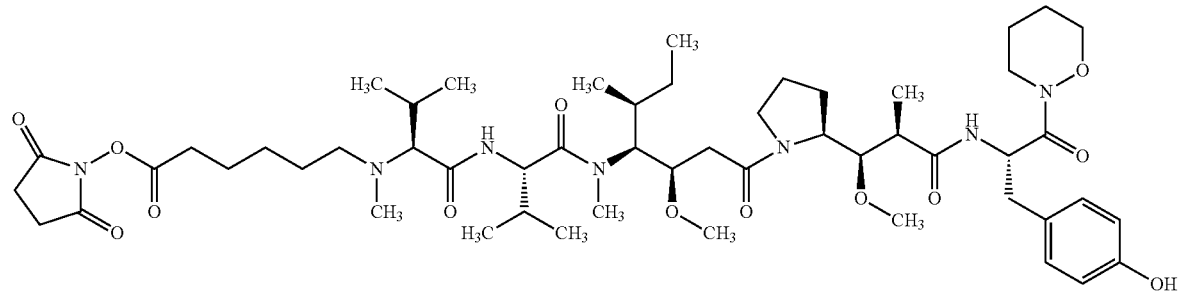 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)N1CCCCO1)OC)N(C)C(=O)[C@@H](NC(=O)[C@H](C(C)C)N(C)CCCCCC(=O)ON1C(=O)CCC1=O)C(C)C]

50 mg (0.05 mmol) of Intermediate 241 were reacted, in analogy to Intermediate 210, with 6-oxohexanoic acid in the presence of borane-pyridine complex. Subsequently, 22.5 mg (0.02 mmol) of the resulting acid were converted to the activated ester. 13.5 mg (36% of theory over 2 stages) of the title compound were obtained.

HPLC (Method 12): $R_t$=1.8 min;
LC-MS (Method 1): $R_t$=0.86 min; MS (ESIpos): m/z=1028 (M+H)$^+$.

Intermediate 243

N-(6-aminohexyl)-N-methyl-L-valyl-N-[(3R,4S,5S)-1-{(2S)-2-[(1R,2R)-3-{[(2S)-3-(4-hydroxyphenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

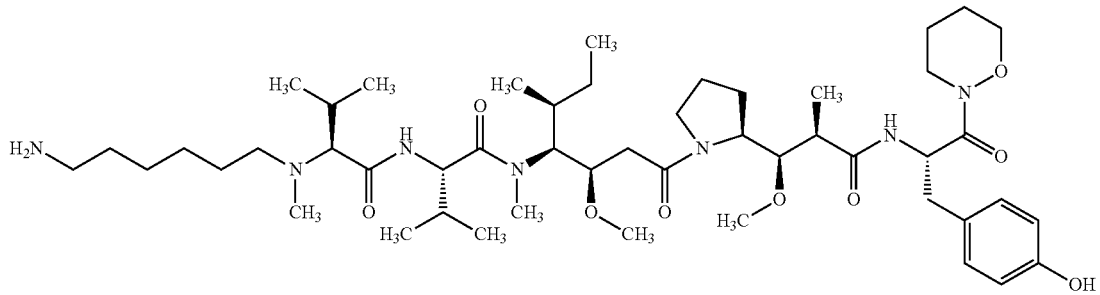 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)N1CCCCO1)OC)N(C)C(=O)[C@@H](NC(=O)[C@H](C(C)C)N(C)CCCCCCN)C(C)C]

The preparation was effected in analogy to Intermediate 78, by reductive alkylation of Intermediate 241 with benzyl 6-oxohexyl carbamate and borane-pyridine complex and subsequent hydrogenation in methanol as the solvent.

Yield: 17.5 mg (34% of theory over 2 stages)
HPLC (Method 12): $R_t$=1.7 min;
LC-MS (Method 1): $R_t$=0.63 min; MS (ESIpos): m/z=916 (M+H)$^+$.

Intermediate 244

N-[6-(2,5-dioxo-2,5-dihydro-1H-pyrrol-1-yl)hexyl]-N-methyl-L-valyl-N-[(3R,4S,5S)-1-{(2S)-2-[(1R,2R)-3-{[(2S)-3-(4-hydroxyphenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

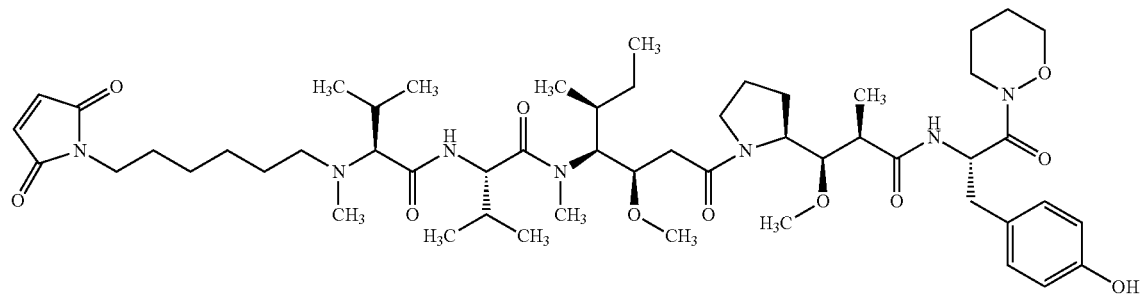 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)N1CCCCO1)OC)N(C)C(=O)[C@@H](NC(=O)[C@H](C(C)C)N(C)CCCCCCN1C(=O)C=CC1=O)C(C)C]

The preparation was effected in analogy to Intermediate 166, proceeding from Intermediate 243.

Yield: 1.3 mg (12% of theory)
HPLC (Method 12): $R_t$=1.9 min;
LC-MS (Method 1): $R_t$=0.89 min; MS (ESIpos): m/z=996 $(M+H)^+$.

Intermediate 245

2,5-dioxopyrrolidin-1-yl O-[(3R,4S,7S,10S)-4-[(2S)-butan-2-yl]-3-(2-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-2-oxoethyl)-7,10-diisopropyl-5,11-dimethyl-6,9,15-trioxo-2-oxa-5,8,11-triazapentadecan-15-yl]-N-(tert-butoxycarbonyl)-L-threonyl-beta-alaninate

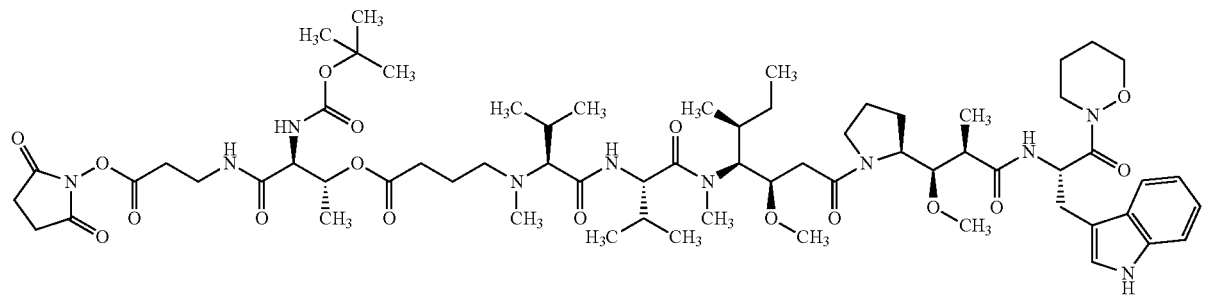 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCC(=O)O[C@H](C)[C@H](NC(=O)OC(C)(C)C)C(=O)NCCC(=O)ON1C(=O)CCC1=O)C(C)C]

First, Intermediate 193, as described for Intermediate 154, was reacted with benzyl N-(tert-butoxycarbonyl)-L-threoninate and then the benzyl ester was removed by hydrogenolysis. 30 mg (0.027 mmol) of the N-[4-({(1S,2R)-1-[(tert-butoxycarbonyl)amino]-1-carboxypropan-2-yl}oxy)-4-oxobutyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide thus obtained were then coupled with 4-methylbenzenesulphonic acid-benzyl beta-alaninate in the presence of HATU and the benzyl ester was removed again by hydrogenolysis (yield: 24 mg (71% of theory over 2 stages)). Finally, 10 mg (0.008 mmol) of the resulting acid were converted to the activated ester. After HPLC purification, 2.7 mg (23% of theory) of the title compound were obtained.

HPLC (Method 5): $R_t$=1.9 min;

LC-MS (Method 1): $R_t$=1.01 min; MS (ESIpos): m/z=1295 (M+H)$^+$

Intermediate 246a

2S)-2-amino-1-(4-hydroxy-1,2-oxazolidin-2-yl)-3-(1H-indol-3-yl)propan-1-one trifluoroacetate (Diastereomer 1

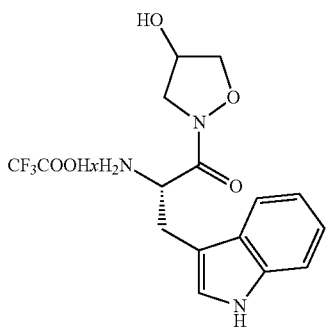

1.6 g (3.982 mmol) of 2,5-dioxopyrrolidin-1-yl N-(tert-butoxycarbonyl)-L-tryptophanate were dissolved in 15 ml of DMF and admixed with 500 mg (3.982 mmol) of 1,2-oxazolidin-4-ol and 100 µl of N,N-diisopropylethylamine. The reaction mixture was stirred at RT overnight. Then another 100 µl of N,N-diisopropylethylamine were added, and the mixture was first treated in an ultrasound bath for 5 h, then stirred at RT overnight, and subsequently concentrated under reduced pressure. The remaining residue was taken up in ethyl acetate and extracted first twice with 5% aqueous citric acid solution, then with saturated aqueous sodium hydrogencarbonate solution and finally with water. The organic phase was concentrated and the residue was separated into the diastereomers by flash chromatography on silica gel with 95:5 dichloromethane/methanol as the eluent. The corresponding fractions of both diastereomers were combined and the solvent was removed under reduced pressure. After the residues had been dried under high vacuum, 272 mg (18% of theory) of Diastereomer 1 ($R_f$=0.18 (95:5 dichloromethane/methanol) and 236 mg (16% of theory) of Diastereomer 2 ($R_f$=0.13 (95:5 dichloromethane/methanol), and also 333 mg (22% of theory) of a mixed fraction of the Boc-protected intermediates were obtained.

Under standard conditions, 5 ml of trifluoroacetic acid in 20 ml of dichloromethane were used to detach the Boc protecting group from 272 mg (725 µmol) of Diastereomer 1 of this intermediate and, after lyophilization from dioxane/water, 290 mg (quant) of the title compound were obtained in 75% purity and used in the next stage without further purification.

HPLC (Method 12): $R_t$=1.1 min;
LC-MS (Method 13): $R_t$=1.80 min; MS (ESIpos): m/z=276 (M+H)$^+$ Intermediate 246b 2S)-2-amino-1-(4-hydroxy-1,2-oxazolidin-2-yl)-3-(1H-indol-3-yl)propan-1-one trifluoroacetate (Diastereomer 2

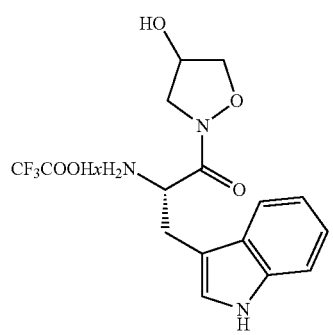

Under standard conditions, 5 ml of trifluoroacetic acid in 20 ml of dichloromethane were used to detach the Boc protecting group from 236 mg (630 µmol) of Diastereomer 2 of the intermediate described in 246a and, after concentration, stirring with diethyl ether and drying of the residue under high vacuum, 214 mg (76%) of the title compound were obtained.

LC-MS (Method 13): $R_t$=1.84 min; MS (ESIpos): m/z=276 (M+H)$^+$

Intermediate 247a

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(2S)-1-(4-hydroxy-1,2-oxazolidin-2-yl)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Diastereomer 1)

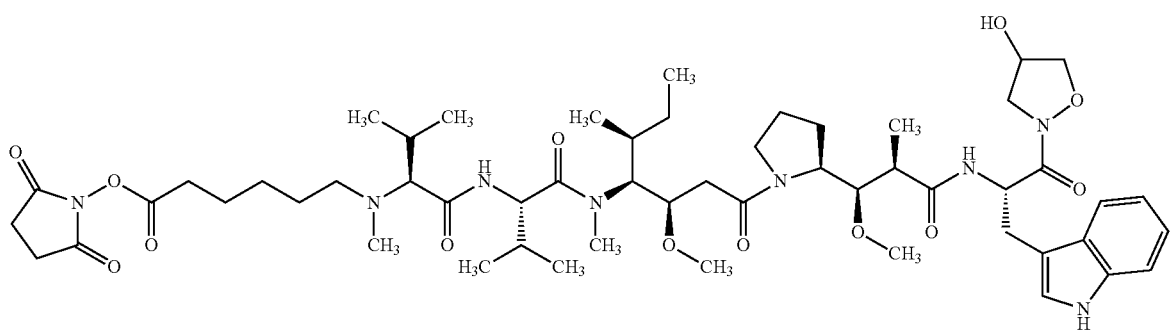 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CC(O)CO1)OC)N(C)C(=O)[C@@H](NC(=O)[C@H](C(C)C)N(C)CCCCCC(=O)ON1C(=O)CCC1=O)C(C)C]

To synthesize this compound, the coupling of Intermediates 26 and 246a with subsequent detachment of the Boc protecting group was first performed as described for Intermediate 74. Subsequently, the alkylation with 6-oxohexanoic acid in the presence of borane-pyridine complex and subsequent conversion of the acid to the active ester were performed as described for Intermediate 210. The title compound was purified by preparative HPLC.

HPLC (Method 12): R$_t$=1.8 min;

LC-MS (Method 1): R$_t$=0.86 min; MS (ESIpos): m/z=1053 (M+H)$^+$

Intermediate 247b

N-{6-[(2,5-dioxopyrrolidin-1-yl)oxy]-6-oxohexyl}-N-methyl-L-valyl-N-[(3R,4S,5S)-1-{(2S)-2-[(1R,2R)-3-{[(2S)-1-(4-hydroxy-1,2-oxazolidin-2-yl)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Diastereomer 2)

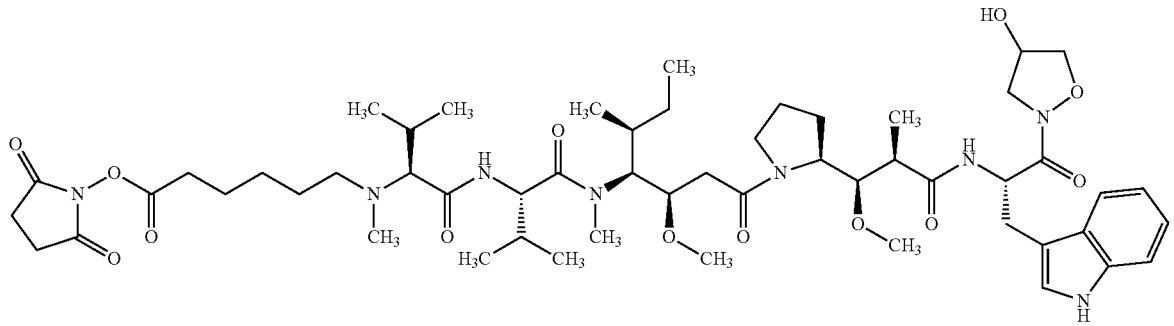 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CC(O)CO1)OC)N(C)C(=O)[C@@H](NC(=O)[C@H](C(C)C)N(C)CCCCCC(=O)ON1C(=O)CCC1=O)C(C)C]

To synthesize this compound, the coupling of Intermediates 26 and 246b with subsequent detachment of the Boc protecting group was first performed as described for Intermediate 74. Subsequently, the alkylation with 6-oxohexanoic acid in the presence of borane-pyridine complex and subsequent conversion of the acid to the active ester were performed as described for Intermediate 210. The title compound was purified by preparative HPLC.

HPLC (Method 12): R$_t$=1.8 min;

LC-MS (Method 1): R$_t$=0.86 min; MS (ESIpos): m/z=1053 (M+H)$^+$

Intermediate 248

N-(5-carboxypentyl)-N-methyl-L-valyl-N-[(3R,4S,5S)-1-{(2S)-2-[(1R,2R)-3-{[(2S)-1-tert-butoxy-3-(4-hydroxyphenyl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

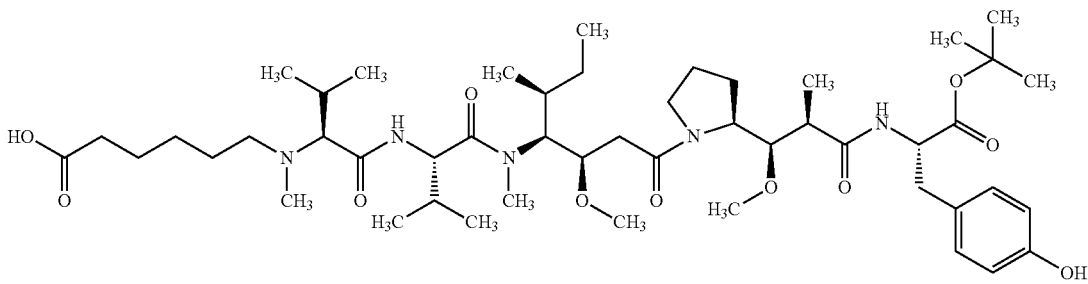 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)OC(C)(C)C)OC)N(C)C(=O)[C@@H](NC(=O)[C@H](C(C)C)N(C)CCCCCC(=O)O)C(C)C]

irst, in analogy to the synthesis described in Intermediate 86, by coupling N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 26) and tert-butyl L-tyrosinate in the presence of O-(7-azabenzotriazol- 1-yl)-N,N,N',N'-tetramethyluronium hexafluorophosphate and subsequent detachment of the Boc protecting group by means of trifluoroacetic acid to obtain the tert-butyl ester (stirring with trifluoroacetic acid in dichloromethane for 40 min), the amine compound tert-butyl N-[(2R,3R)-3-methoxy-3-{(2S)-1-[(3R,4S,5S)-3-methoxy-5-methyl-4-(methyl{(2S)-3-methyl-2-[(N-methyl-L-valyl)amino]butyl}amino)heptanoyl]pyrrolidin-2-yl}-2-methylpropanoyl]-L-tyrosinate was prepared as the trifluoroacetate. 38 mg (0.04 mmol) of this compound were then used, in analogy to the preparation of Intermediate 210, by reaction with 6-oxohexanoic acid in the presence of borane-pyridine complex, to obtain 31 mg (99% of theory) of the title compound.

HPLC (Method 12): $R_t$=1.8 min;

LC-MS (Method 1): $R_t$=0.88 min; MS (ESIpos): m/z=918 $(M+H)^+$.

B: PREPARATION OF ANTIBODY-DRUG CONJUGATES (ADCs)

B-1. General Process for Generating Anti-C4.4a Antibodies

The anti-C4.4a antibodies described by the sequences of Table 1 and Table 2 were generated by screening a phage display library for recombinant human C4.4a SEQ ID NO: 1 and murine C4.4a SEQ ID NO: 2 and for cells expressing C4.4a. The antibodies obtained in this way were reformatted to the human IgG1 format and used for the working examples described here.

B-2. General Process for Expressing Anti-C4.4a Antibodies in Mammalian Cells

The antibodies, for example M31-B01 (light chain SEQ ID NO: 346 and heavy chain SEQ ID NO: 347) or further antibodies of Table 2 were produced in a mammalian cell culture. For this purpose, HEK293 6E cells were transiently transfected with a suitable CMV promotor based expression plasmid. The heavy and light chains of the antibodies were cloned either together into a one-vector system, or separately into a two-vector system. The cell culture scale was either up to 1.5 L in a shake flask or 10 L in a "wave-bag". Expression took place at 37° C. for 5-6 days in F17 Medium (Invitrogen) supplemented with Tryptone TN1 (Organotechnie) with 1% "FCS ultra low IgG" (Invitrogen) and 0.5 mM valproic acid. The expression yields were between 100 and 600 mg/l.

B-3. General Process for Purifying Antibodies from Cell Supernatants

The antibodies, for example M31-B01 (light chain SEQ ID NO: 346 and heavy chain SEQ ID NO: 347) or further antibodies of Table 2 were obtained from the cell culture supernatants. The cell supernatants were clarified by centrifugation to remove cells. Subsequently the cell supernatant was purified by affinity chromatography on a MabSelect Sure (GE Healthcare) chromatography column. For this purpose the column was equilibrated in DPBS pH 7.4 (Sigma/Aldrich), the cell supernatant was applied, and the column was washed with about 10 column volumes of DPBS pH 7.4+500 mM sodium chloride. The antibodies were eluted in 50 mM sodium acetate pH 3.5+500 mM sodium chloride and subsequently purified further by gel filtration chromatography on a Superdex 200 column (GE Healthcare) in DPBS pH 7.4.

B-4. General Process for Coupling to Cysteine Side Chains

The antibodies used in the coupling reactions were as follows:
anti-C4.4a M31-B01
anti-C4.4a B01-3
anti-C4.4a B01-10
anti-C4.4a B01-7
anti-C4.4a D02-4
anti-C4.4a D02-6
anti-C4.4a D02-7

Added to a solution of the corresponding antibody in PBS buffer in the concentration range between 1 mg/ml and 15 mg/ml were 3 equivalents of tris(2-carboxyethyl)phosphine hydrochloride (TCEP), in solution in PBS buffer, and the mixture was stirred at RT for 1 hour. Subsequently, depending on the desired loading, between 2 and 10 equivalents of the maleimide precursor compound or halide precursor compound for coupling (Intermediate 102, 103, 105-109, 111-114, 117-126, 128, 129, 132-146, 148-155, 157, 159-161, 166, 171, 175-177, 184, 189, 194-195, 199-201, 205, 209, 223-224, 226, 228-231, 236 and 244) were added as a solution in DMSO. The amount of DMSO here ought not to exceed 10% of the overall volume. The batch was stirred at RT for 60-120 minutes and then applied to PD 10 columns (Sephadex® G-25, GE Healthcare) equilibrated with PBS, and eluted with PBS buffer. Optionally a concentration procedure was carried out additionally by means of ultracentrifugation. If necessary, for more effective removal of low molecular mass constituents, the concentration by ultrafiltration was repeated after re-dilution with PBS buffer.

Normally, unless otherwise indicated, 5 mg of the corresponding antibody in PBS buffer were used for the reduction and the subsequent coupling. Following purification via the PD10 column, this gave, in each case, solutions of the corresponding ADC in 3.5 ml of PBS buffer. The particular protein concentration indicated was then determined for these solutions. Furthermore, the loading of the antibody (drug/mAb ratio) was determined in accordance with the methods described below.

This process was used to prepare the immunoconjugates represented in Examples 1-3, 5-30, 32-36, 38-59, 61-66, 68-70, 80, 82-85, 87, 88, 92-95, 97, 98, 107, 109-114, 119 and 122.

In the structural formulae illustrated, the definition of $AK_{1A}$-$AK_{1G}$ is as follows $AK_{1A}$=anti-C4.4a antibody M31-B01 (partially reduced)-S§$^1$
$AK_{1B}$=anti-C4.4a antibody B01-3 (partially reduced)-S§$^1$
$AK_{1C}$=anti-C4.4a antibody B01-10 (partially reduced)-S§$^1$
$AK_{1D}$=anti-C4.4a antibody B01-7 (partially reduced)-S§$^1$
$AK_{1E}$=anti-C4.4a antibody D02-4 (partially reduced)-S§$^1$
$AK_{1F}$=anti-C4.4a antibody D02-6 (partially reduced)-S§$^1$
$AK_{1G}$=anti-C4.4a antibody D02-7 (partially reduced)-S§$^1$
where
§$^1$ denotes the link with the succinimide group,
and
S stands for the sulphur atom of a cysteine residue of the partially reduced antibody.

B-5. General Process for Coupling to Lysine Side Chains

The antibodies used in the coupling reactions were as follows:
anti-C4.4a antibody M31-B01
anti-C4.4a antibody B01-3

Added to a solution of the corresponding antibody in PBS buffer in the concentration range between 1 mg/ml and 15 mg/ml were, depending on the desired loading, between 2 and 5 equivalents of the precursor compound for coupling (Intermediate 104, 110, 115, 116, 127, 130, 131, 147, 156, 158, 162, 169, 178, 185, 190, 202, 206, 210-216, 218, 219, 227, 233, 238, 240, 242, 245, 247a and 247b)) as a solution in DMSO. After 30 minutes of stirring at RT, the same amount of precursor compound in DMSO was added again. Alternatively it was possible to add 4-10 equivalents of the precursor compound for coupling, in one go. The amount of DMSO here ought not to exceed 10% of the overall volume. After a further 30 minutes of stirring at RT, the batch was applied to PD 10 columns (Sephadex® G-25, GE Healthcare) equilibrated with PBS, and eluted with PBS buffer. Optionally a concentration procedure was carried out additionally by means of ultracentrifugation. If necessary, for more effective removal of low molecular mass constituents, the concentration by ultrafiltration was repeated after re-dilution with PBS buffer.

Normally, unless otherwise indicated, 5 mg of the corresponding antibody in PBS buffer were used for the coupling. Following purification via the PD10 column, this gave, in each case, solutions of the corresponding ADC in 3.5 ml of PBS buffer. The particular protein concentration indicated was then determined for these solutions and the loading of the antibody (drug/mAb ratio) was determined in accordance with the methods described below.

This process was used to prepare the immunoconjugates represented in Examples 4, 31, 37, 60, 67, 81, 86, 89-91, 96, 99-106, 108, 118, 120, 121 and 123-125.

In the structural formulae illustrated, the definition of $AK_{2A}$ and $A_{2B}$ is as follows $AK_{2A}$=anti-C4.4a antibody M31-B01—NH$§^2$
$AK_{2B}$=anti-C4.4a antibody B01-3—NH$§^2$
where
$§^2$ denotes the link with the carbonyl group,
and
NH stands for the side chain amino group of a lysine residue of the antibody.

B-6. General Process for Preparing Cysteine Adducts:

10 µmol of the above-described maleimide precursor compounds were taken up in 3 ml of DMF and admixed with 2.1 mg (20 µmol) of L-cysteine. The reaction mixture was stirred at RT for 2 hours, then concentrated under reduced pressure and subsequently purified by preparative HPLC.

In the structural formulae illustrated, the definition of Cys is as follows

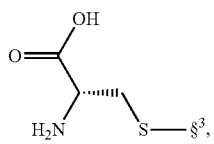

where
$§^3$ denotes the link with the linker-toxophore unit.

Further Purification and Characterization of the Conjugates of the Invention

After reaction had taken place, in certain cases the reaction mixture was concentrated, by ultrafiltration, for example, and then desalted and purified by means of chromatography, for example using a Sephadex® G-25. Elution took place with, for example, phosphate-buffered saline (PBS). The solution was subsequently subjected to sterile filtration and freezing. An alternative option is to lyophilize the conjugate.

B-7. Determination of the Toxophore Loading

The toxophore loading of the resultant solutions of the conjugates described in the working examples, in PBS buffer, was determined as follows:

The toxophore loading of lysine-linked ADCs was determined by mass-spectrometric determination of the molecular weights of the individual conjugate species. In this case, to start with, the antibody conjugates were deglycosylated by means of PNGaseF, and the sample was acidified and, following HPLC separation, was analysed by mass spectrometry using an ESI-MicroTofQ (Bruker Daltonik). All of the spectra were added via the signal in the TIC (Total Ion Chromatogram), and the molecular weight of the various conjugate species was calculated on the basis of MaxEnt Deconvolution. Following signal integration of the different species, the DAR (Drug/Antibody Ratio) was then calculated.

For protein identification, in addition to the molecular weight determination, a tryptic digestion was carried out after deglycosylation and/or denaturing, and this digestion, after denaturing, reduction and derivatization, confirmed the identity of the protein on the basis of the tryptic peptides detected.

The toxophore loading of cysteine-linked conjugates was determined via reversed-phase chromatography of the reduced and denatured ADC. The ADC solution (1 mg/mL, 50 µL) was admixed with guanidinium hydrochloride (Gu-HCl) (28.6 mg) and with a solution of DL-dithiothreitol (DTT) (500 mM, 3 µL). The mixture was incubated at 55° C. for an hour and analysed by HPLC.

The HPLC analysis was carried out on an Agilent 1260 HPLC System with detection at 220 nm. The column used was a Polymer Laboratories PLRP-S Polymeric Reversed Phase column (catalogue number PL1912-3802) (2.1×150 mm, 8 µm particle size, 1000 Å) with a flow rate of 1 mL/min, using the following gradient: 0 min, 25% B; 3 min, 25% B; 28 min, 50% B. Eluent A consisted of 0.05% trifluoroacetic acid (TFA) in water, eluent B of 0.05% trifluoroacetic acid in acetonitrile.

The peaks detected were assigned by retention time comparison with the light chain (L0) and the heavy chain (H0) of the unconjugated antibody. Peaks which were detected exclusively in the conjugated sample were assigned to the light chain, with a toxophore (L1), and to the heavy chains, with one, two and three toxophores (H1, H2, H3).

The average loading of the antibody with toxophores was calculated as follows: first of all, the light-chain loading was calculated from the peak areas—determined by integration—of the peaks L0 and L1 belonging to the light chains, as the sum of the toxophore number weighted integration results of L0 and L1, divided by the sum of the singularly weighted integration results of L0 and L1. In the same way, the heavy-chain loading was calculated from the peak areas—determined by integration—of the peaks H0, H1, H2 and H3, belonging to the heavy chains, as the sum of the toxophore number weighted integration results of H0, H1, H2 and H3, divided by the sum of the singularly weighted integration results of H0, H1, H2 and H3. The DAR is given by the light-chain loading and the heavy-chain loading, as the two-fold sum of light-chain loading and heavy-chain loading. The factor 2 takes account of the fact that an antibody consists of two light chains and two heavy chains. In certain individual cases it may be impossible exactly to determine the toxophore loading, owing to co-elutions of certain peaks.

B-8. Testing of the Antigen Binding of the ADC

The binding capacity of the binder to the target molecule was tested after coupling had taken place. The skilled worker knows of diverse methods for achieving this—for example, the affinity of the conjugate can be tested by means of ELISA technology or surface plasmon resonance analysis (BJAcore™ measurements). The conjugate concentration can be measured by the skilled person using common methods—for example, for antibody conjugates, by means of protein determination (see also Doronina et al.; Nature Biotechnol. 2003; 21:778-784 and Polson et al., Blood 2007; 1102:616-623).

WORKING EXAMPLES

Immunoconjugates

Example 1

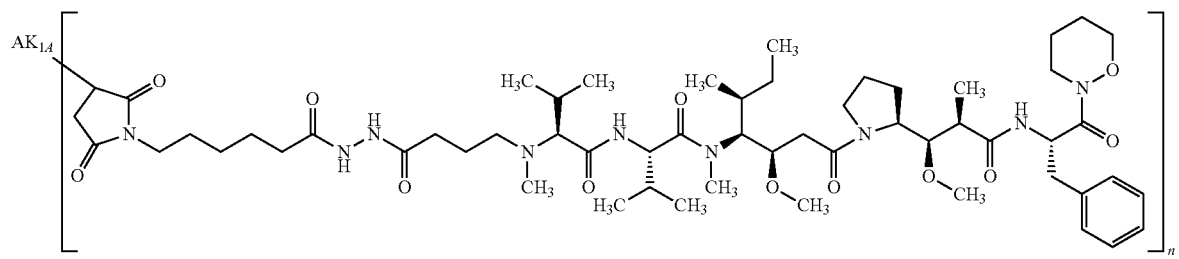

In this case coupling was carried out using 70 mg of anti-C4.4a M31-B01 in DPBS pH 7.4 and following the Sephadex purification the batch was concentrated by ultracentifugation.
Protein concentration: 12.2 mg/ml
Drug/mAb Ratio: 1.5

Example 2

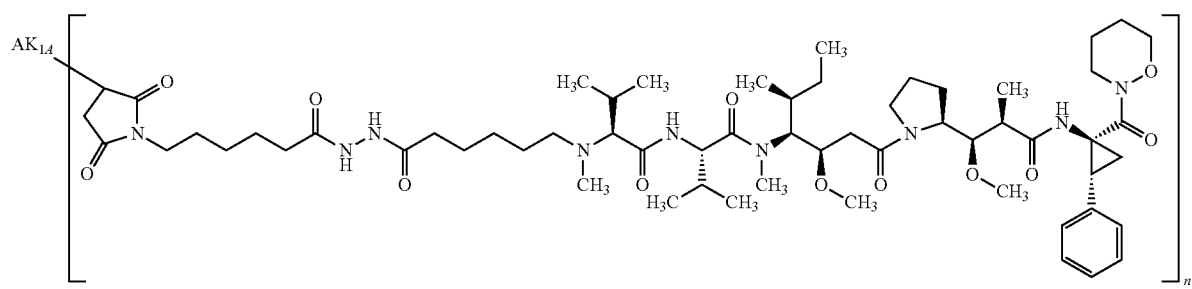

Protein concentration: 0.87 mg/ml
Drug/mAb Ratio: 5.8

Example 3

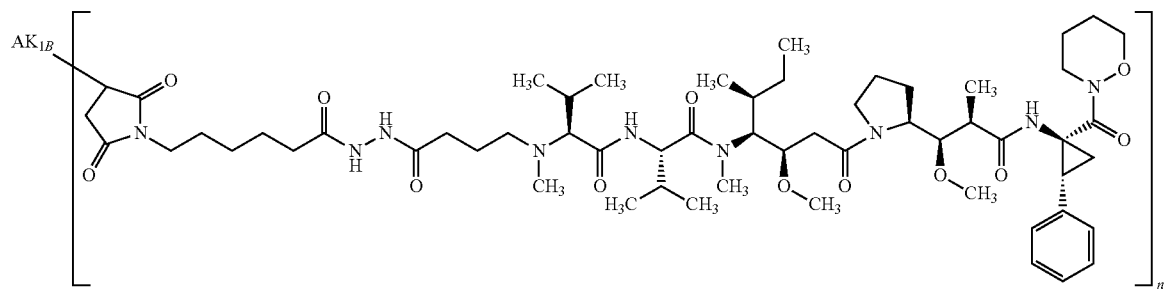

Protein concentration: 1.16 mg/ml
Drug/mAb Ratio: 3.1

Example 4
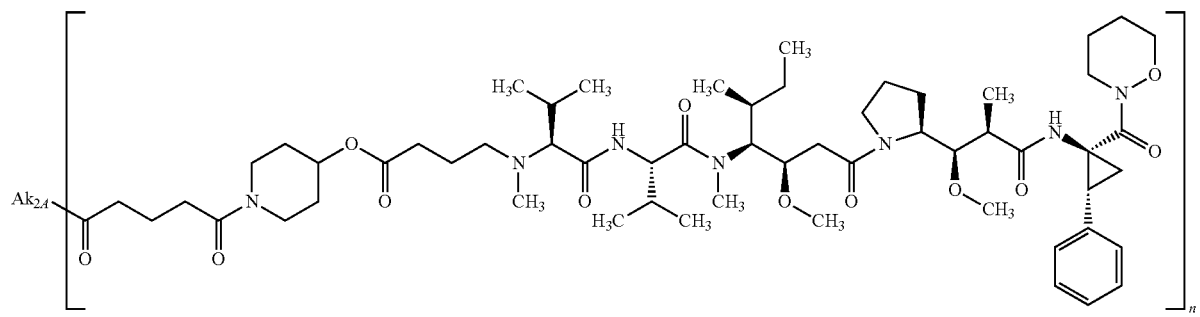
Protein concentration: 1.24 mg/ml
Drug/mAb Ratio: 1.6
Example 5
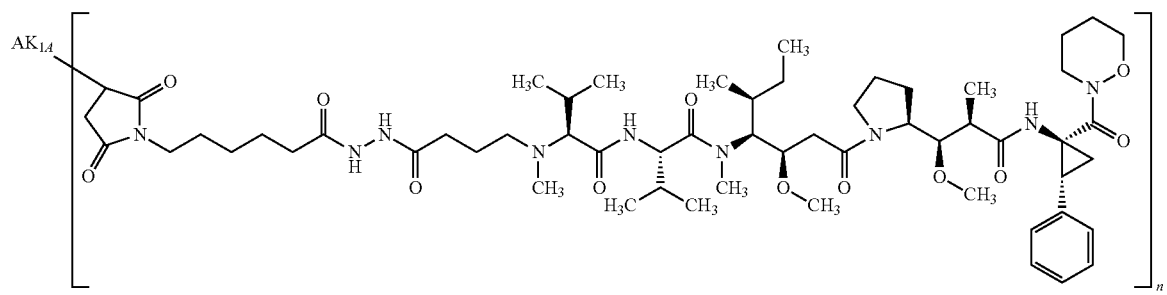
Protein concentration: 0.88 mg/ml
Drug/mAb Ratio: 6.9
Example 6
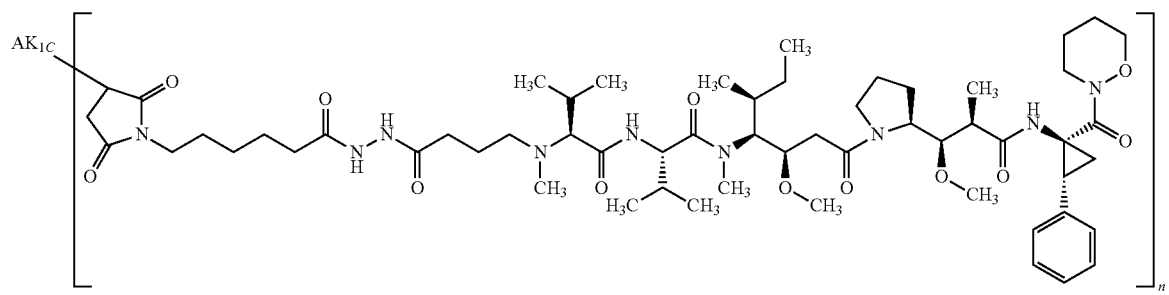
Protein concentration: 1.2 mg/ml
Drug/mAb Ratio: 2.8

Example 7
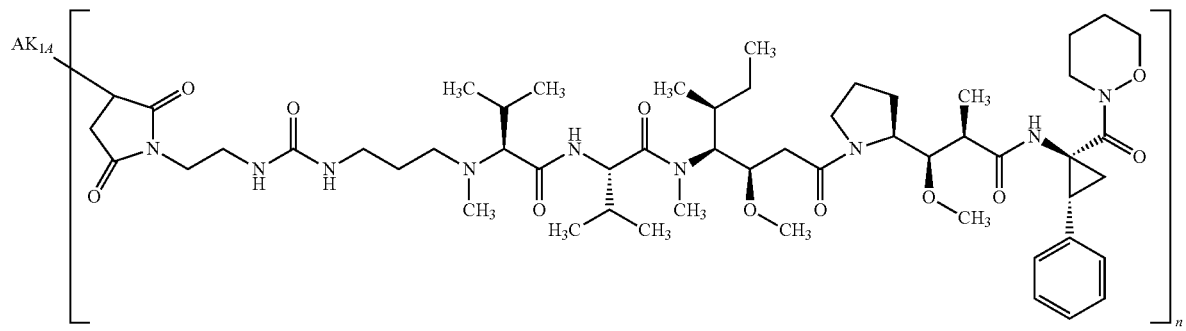
Protein concentration: 0.9 mg/ml
Drug/mAb Ratio: 3.9
Example 8ke
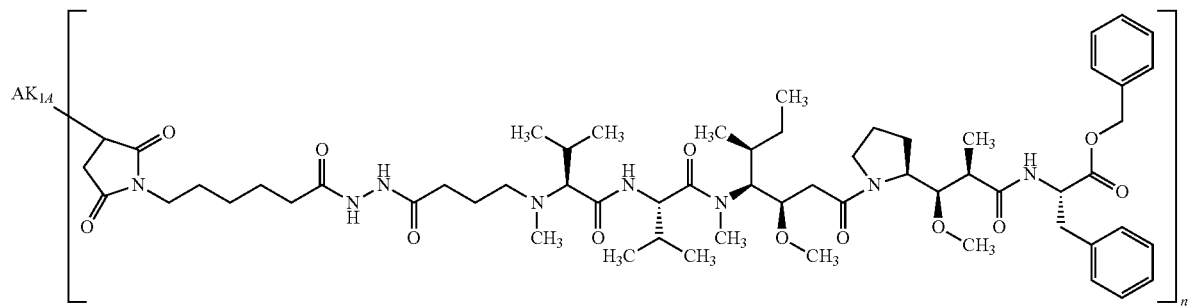
Protein concentration: 0.52 mg/ml
Drug/mAb Ratio: 1.6
Example 9
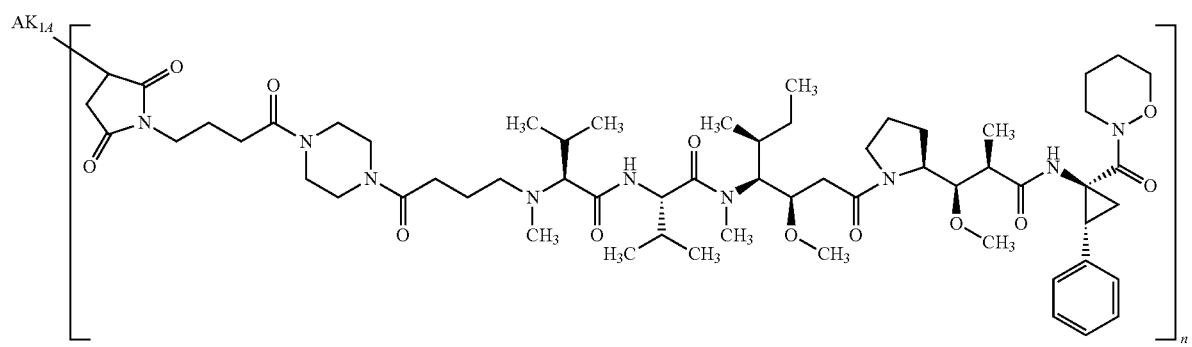
Protein concentration: 0.47 mg/ml
Drug/mAb Ratio: 6.6

Example 10
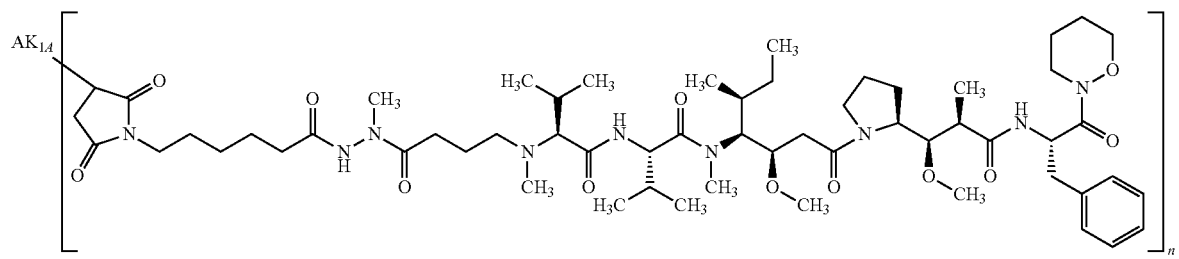
Protein concentration: 0.77 mg/ml
Drug/mAb Ratio: 6.9
Example 11
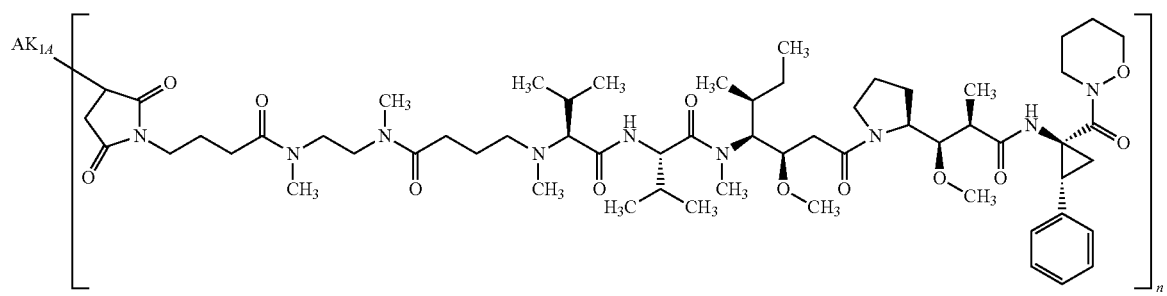
Protein concentration: 0.47 mg/ml
Drug/mAb Ratio: 4.0
Example 12
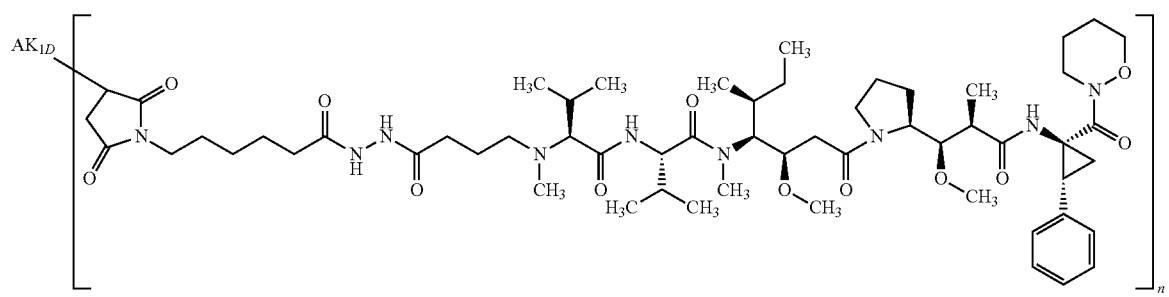
Protein concentration: 1.46 mg/ml
Drug/mAb Ratio: 2.5

Example 13
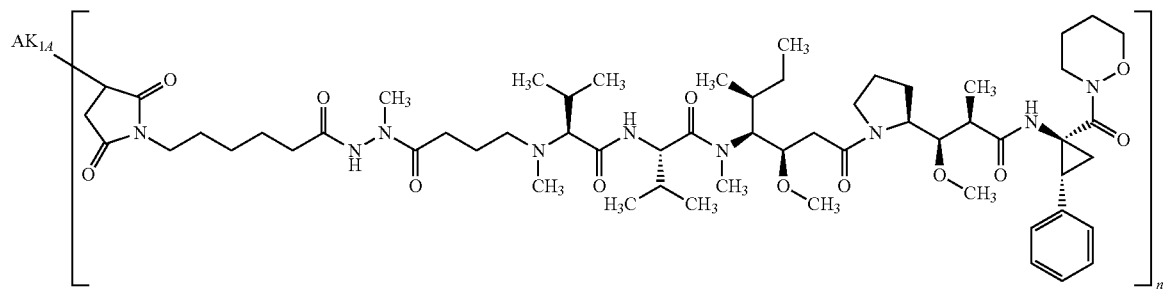
Protein concentration: 0.45 mg/ml
Drug/mAb Ratio: 3.3
Example 14
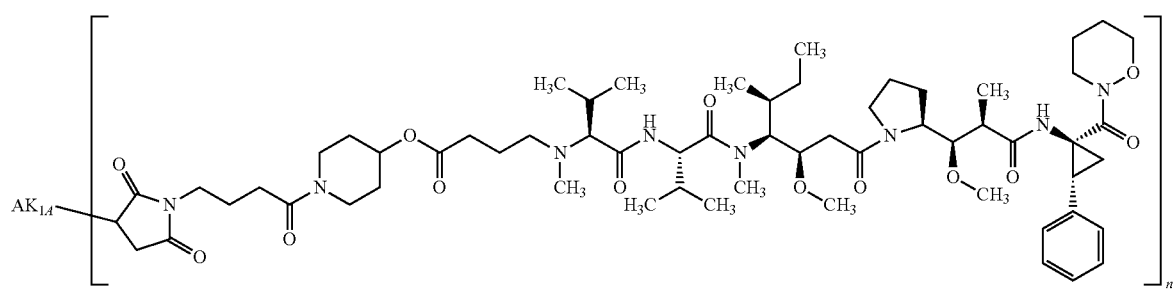
Protein concentration: 0.98 mg/ml
Drug/mAb Ratio: 3.6
Example 15
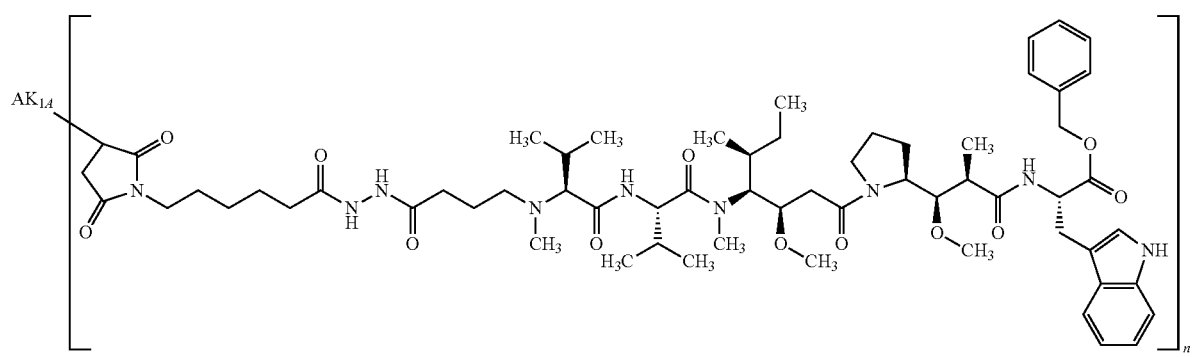
Coupling here was carried out using 70 mg of anti-C4.4a M31-B01 in DPBS pH 7.4, and following the Sephadex purification the batch was concentrated by ultracentifugation.
Protein concentration: 9.42 mg/ml
Drug/mAb Ratio: 4.1

Example 16
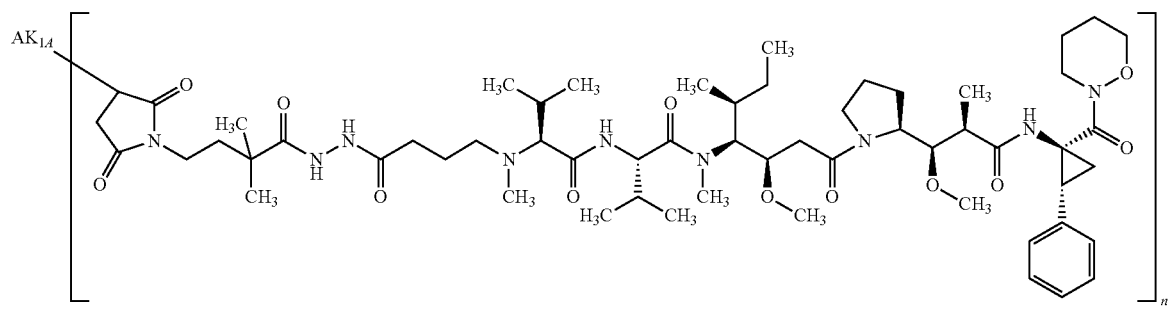
Protein concentration: 0.65 mg/ml
Drug/mAb Ratio: 1.8
Example 17
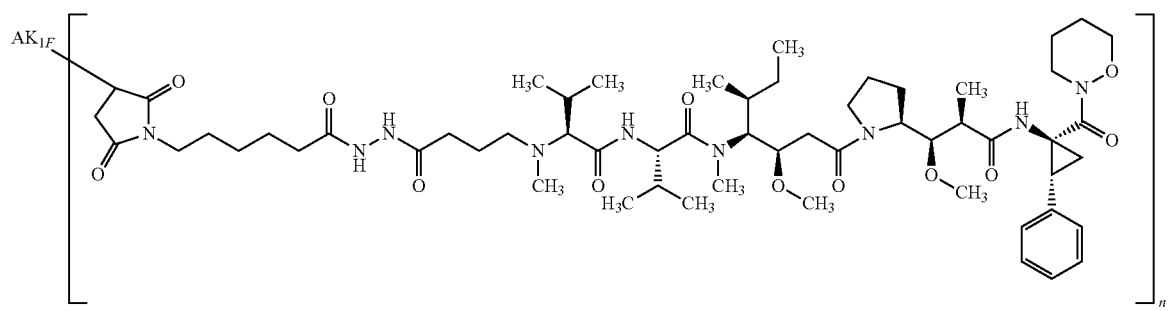
Protein concentration: 1.07 mg/ml
Drug/mAb Ratio: not determinable
Example 18
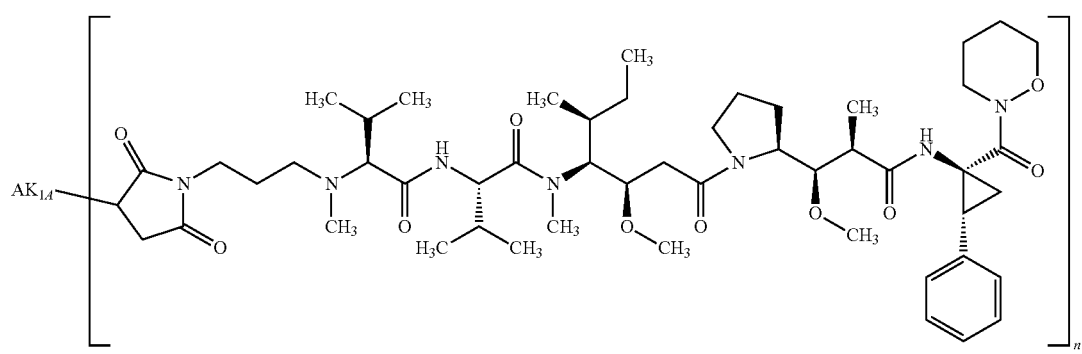
Protein concentration: 0.47 mg/ml
Drug/mAb Ratio: 4.4

Example 19
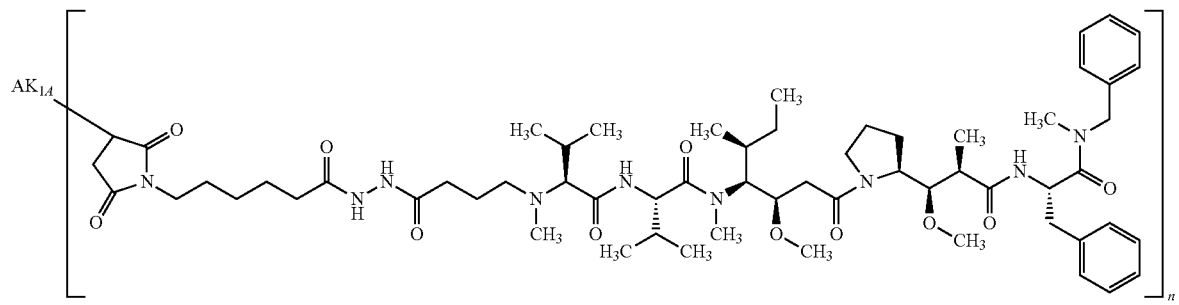
Protein concentration: 0.43 mg/ml
Drug/mAb Ratio: 4.8
Example 20
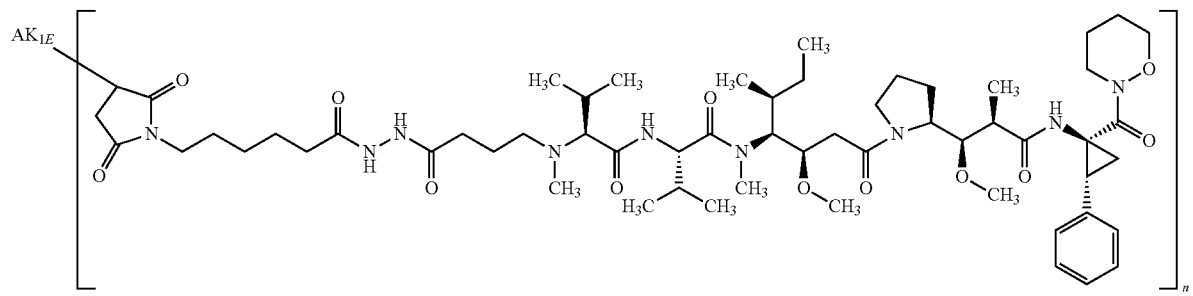
Protein concentration: 1.01 mg/ml
Drug/mAb Ratio: 2.6
Example 21
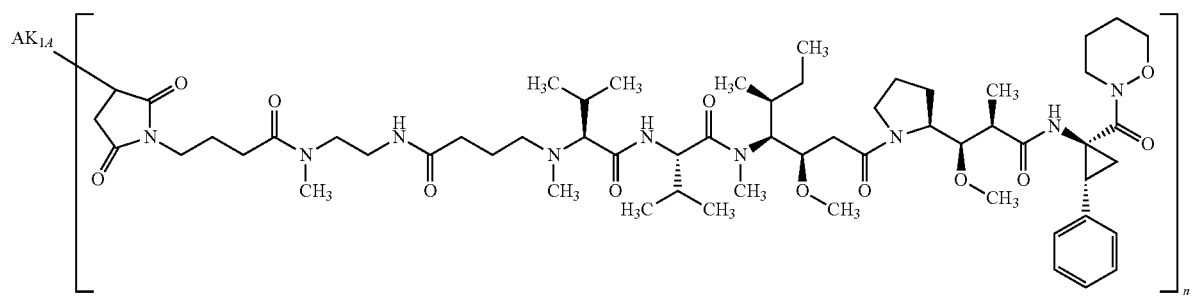
Protein concentration: 0.53 mg/ml
Drug/mAb Ratio: 0.6

Example 22
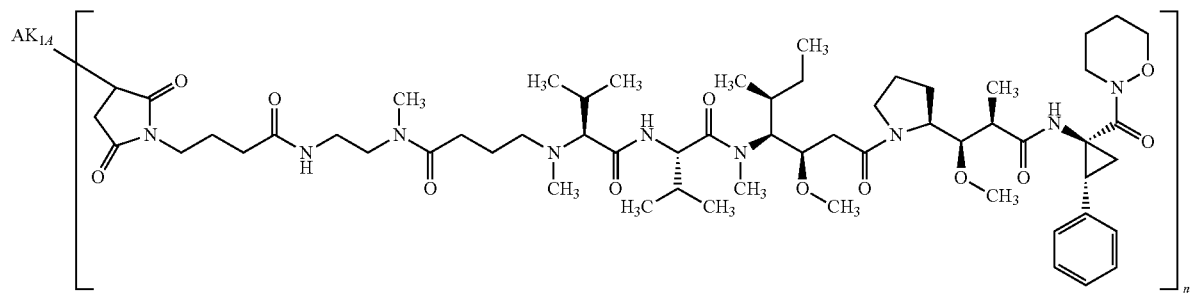
Protein concentration: 0.55 mg/ml
Drug/mAb Ratio: 1.3
Example 23
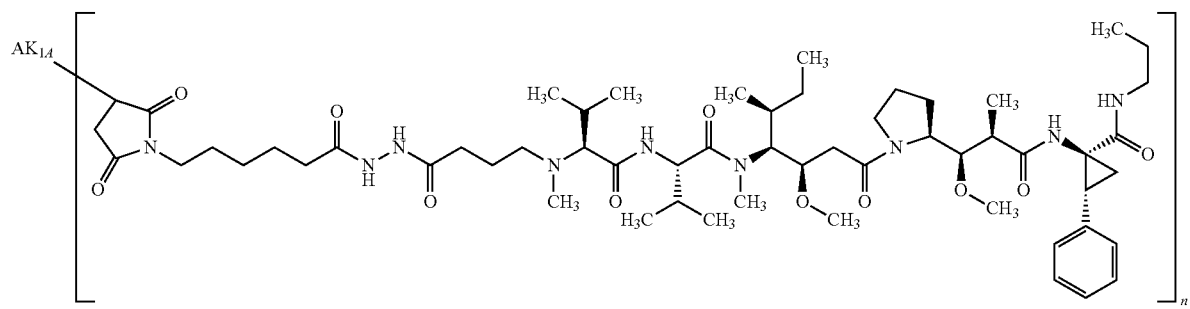
Protein concentration: 0.65 mg/ml
Drug/mAb Ratio: 1.1
Example 24
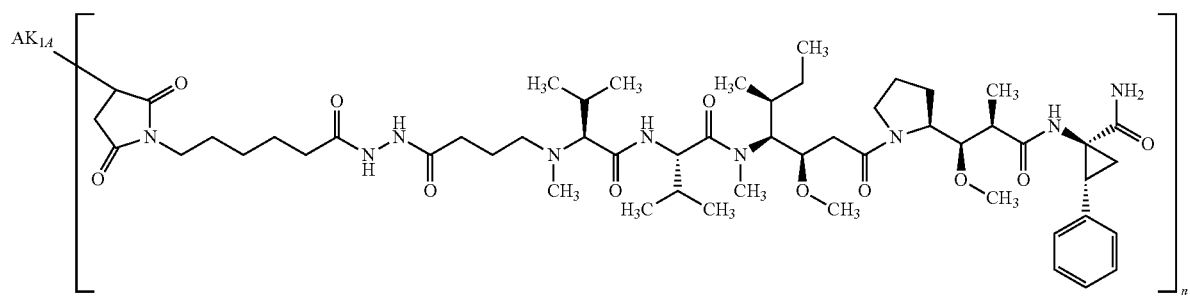
Protein concentration: 1.04
Drug/mAb Ratio: 3.5

Example 25
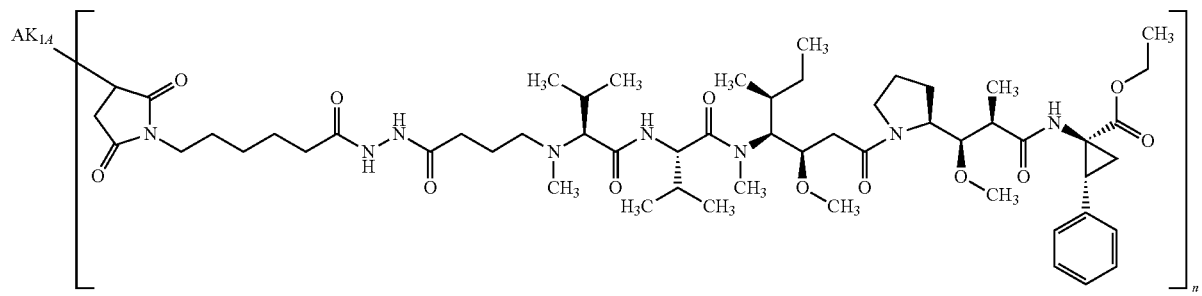
Protein concentration: 0.62 mg/ml
Drug/mAb Ratio: 2.4
Example 26
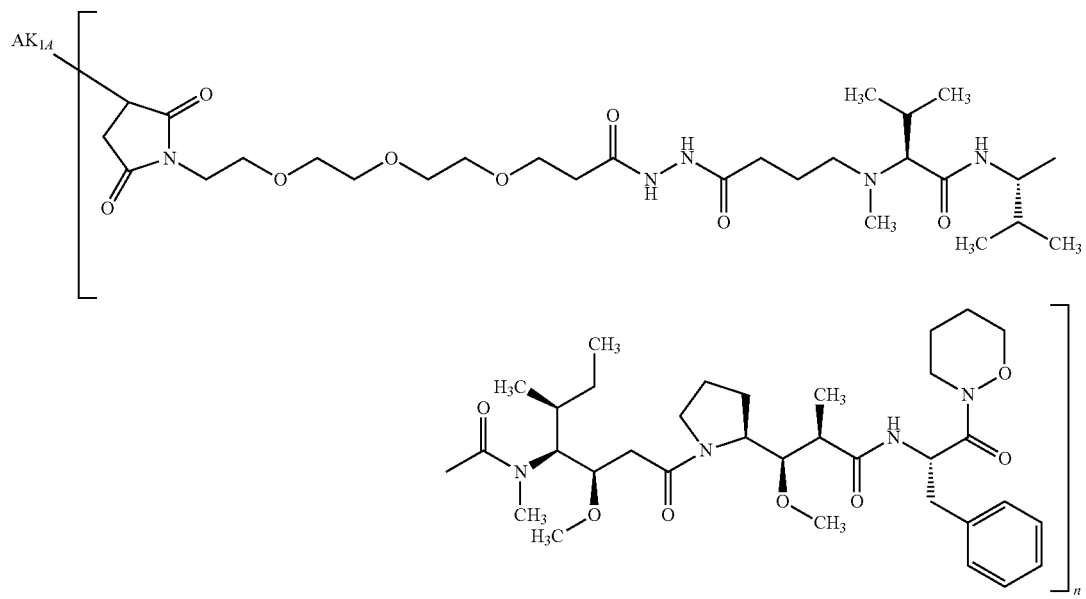
Coupling here was carried out using 90 mg of anti-C4.4a M31-B01 in DPBS pH 7.4 and following the Sephadex purification the batch was concentrated by ultracentifugation.
Protein concentration: 11.2 mg/ml
Drug/mAb-Ratio: 2.3
Example 27
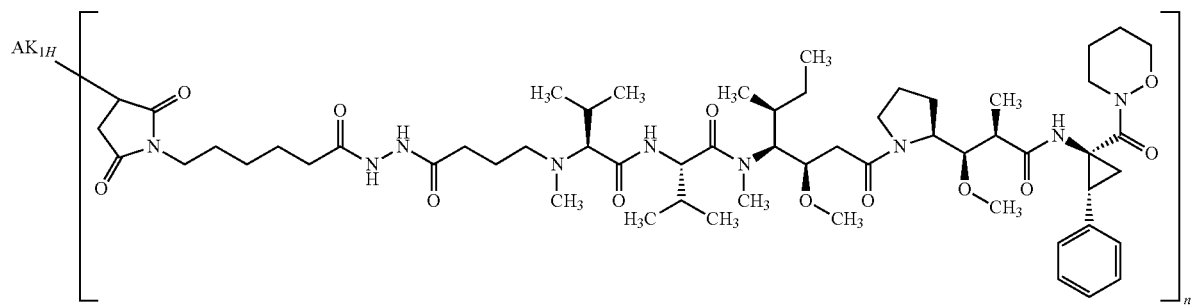

Protein concentration: 1.11 mg/ml
Drug/mAb-Ratio: 2.4

Example 28

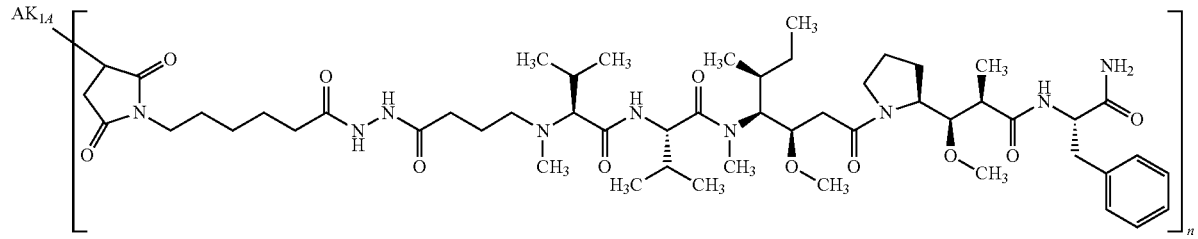

Coupling here was carried out using 70 mg of anti-C4.4a M31-B01 in DPBS pH 7.4 and following the Sephadex purification the batch was concentrated by ultracentifugation.
Protein concentration: 10.7 mg/ml
Drug/mAb Ratio: 2.2

Example 29

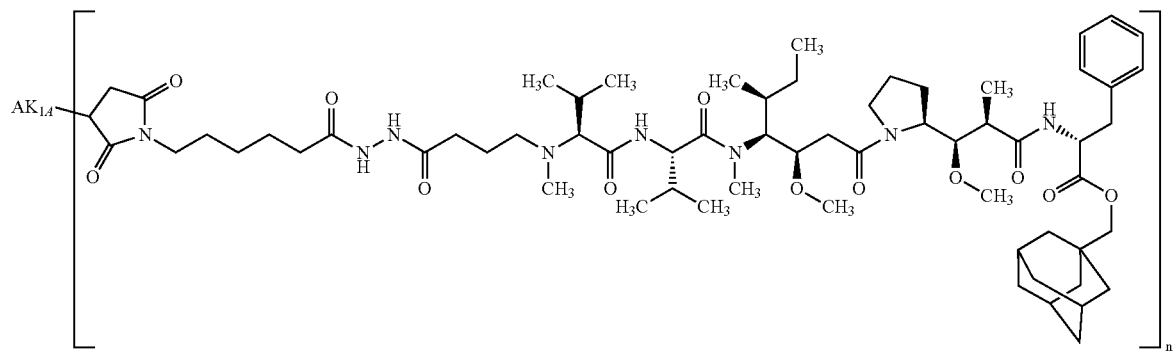

Protein concentration: 0.87 mg/ml
Drug/mAb Ratio: 1.8

Example 30

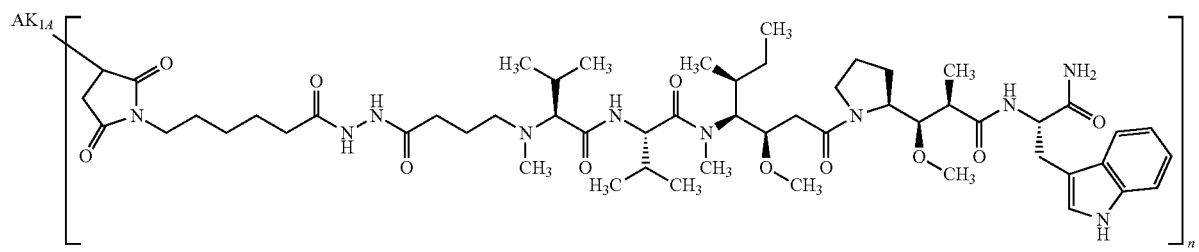

Protein concentration: 1.3 mg/ml
Drug/mAb Ratio: 2.1

Example 31

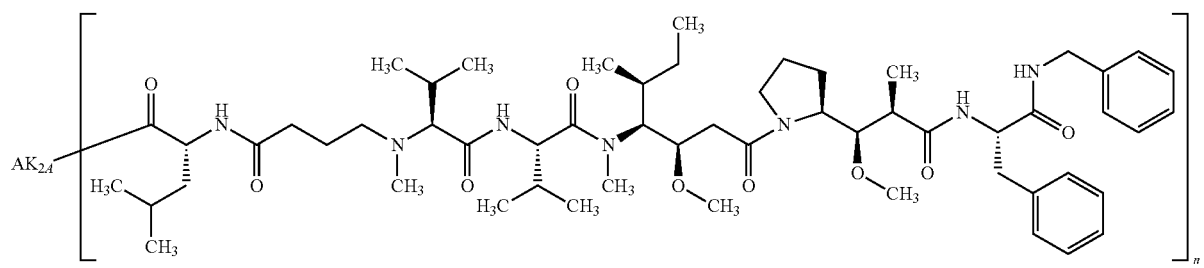

Protein concentration: 1.3 mg/ml
Drug/mAb Ratio: 0.3

Example 32

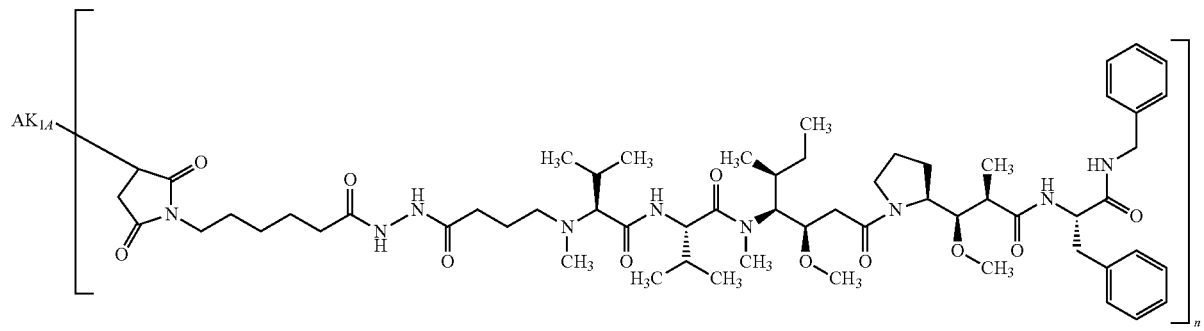

Coupling here was carried out using 70 mg of anti-C4.4a M31-B01 in DPBS pH 7.4 and following the Sephadex purification the batch was concentrated by ultracentifugation.
Protein concentration: 12.0 mg/ml
Drug/mAb Ratio: 3.2

Example 33

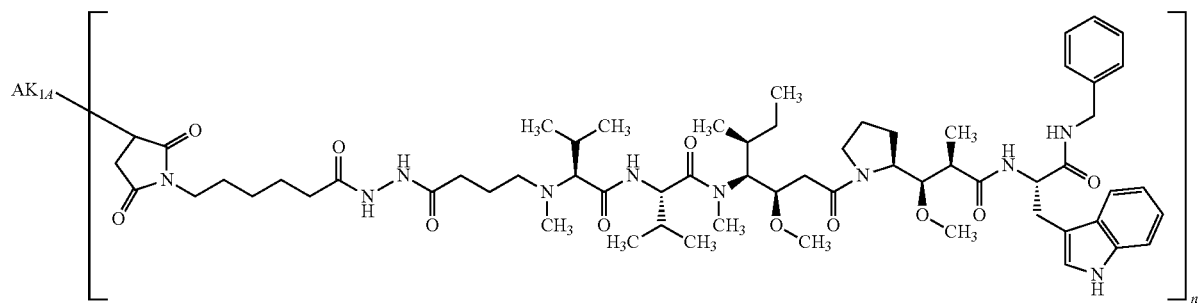

Coupling here was carried out using 90 mg of anti-C4.4a M31-B01 in DPBS pH 7.4 and following the Sephadex purification the batch was concentrated by ultracentifugation.
Protein concentration: 10.2 mg/ml
Drug/mAb Ratio: 4.3

Example 34
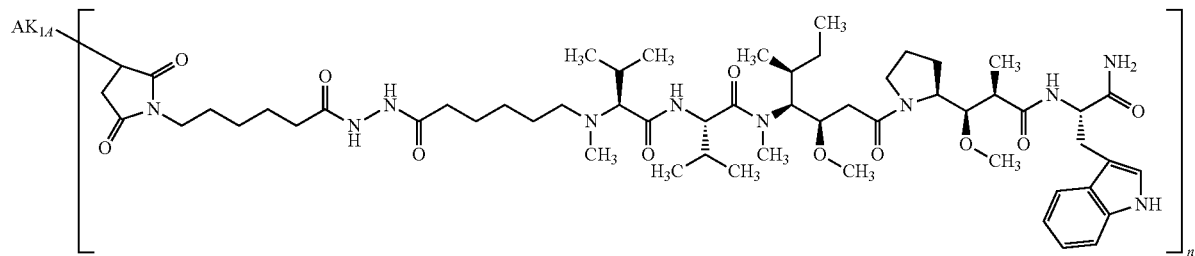
Protein concentration: 1.37 mg/ml
Drug/mAb Ratio: 2.6
Example 35
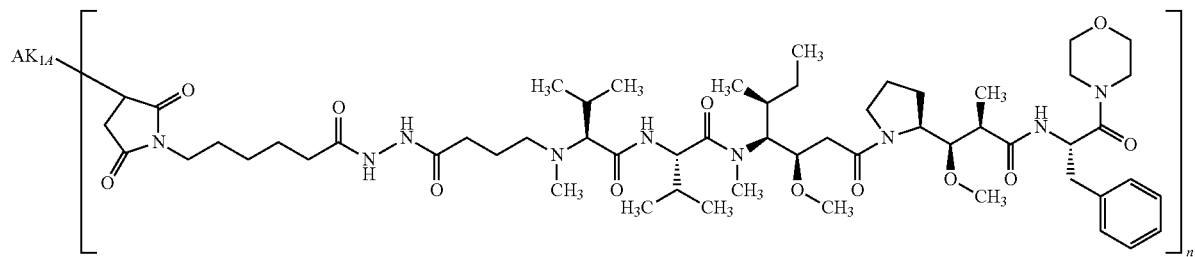
Protein concentration: 1.14 mg/ml
Drug/mAb Ratio: 2.0
Example 36
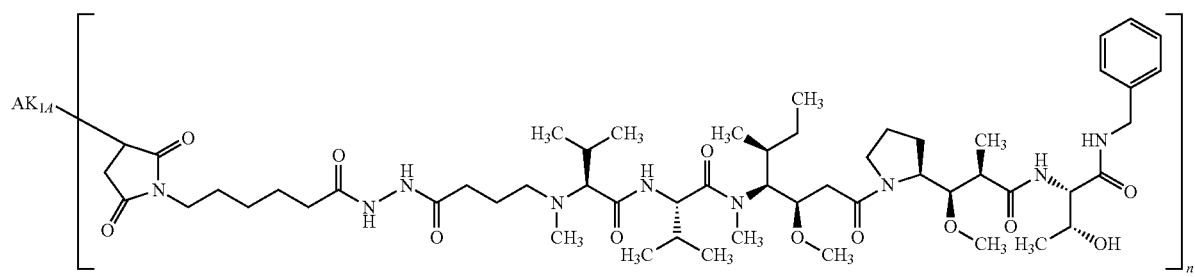
Protein concentration: 1.07 mg/ml
Drug/mAb Ratio: 3.5

Example 37
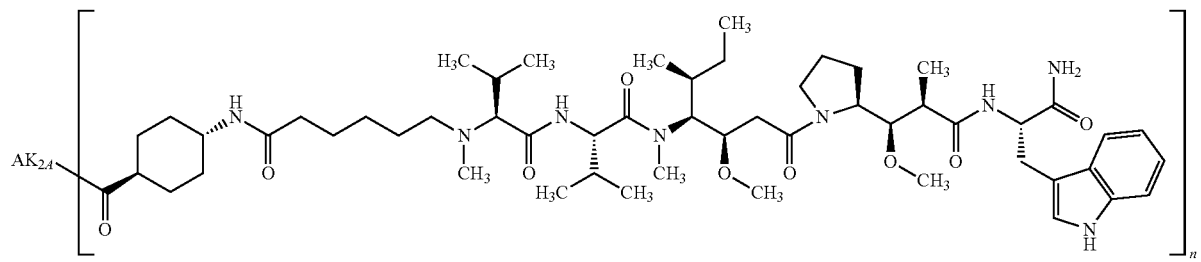
Protein concentration: 1.14 mg/ml
Drug/mAb Ratio: 1.9
Example 38
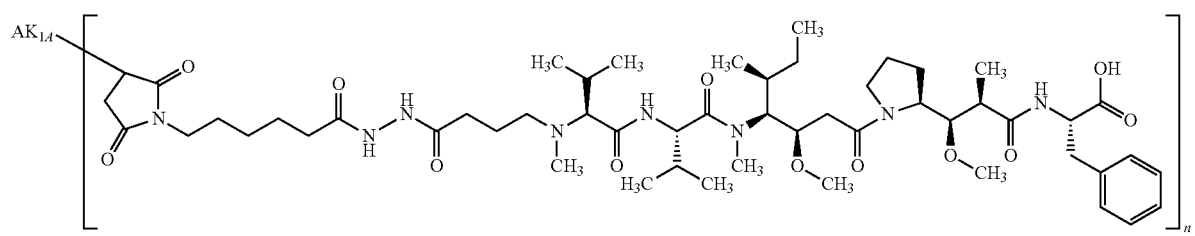
Protein concentration: 1.22 mg/ml
Drug/mAb Ratio: 3.3
Example 39
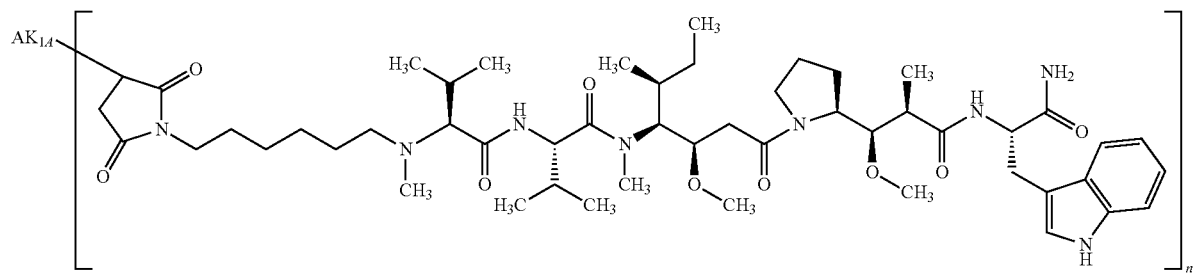
Protein concentration: 1.3 mg/ml
Drug/mAb Ratio: 3.2

Example 40
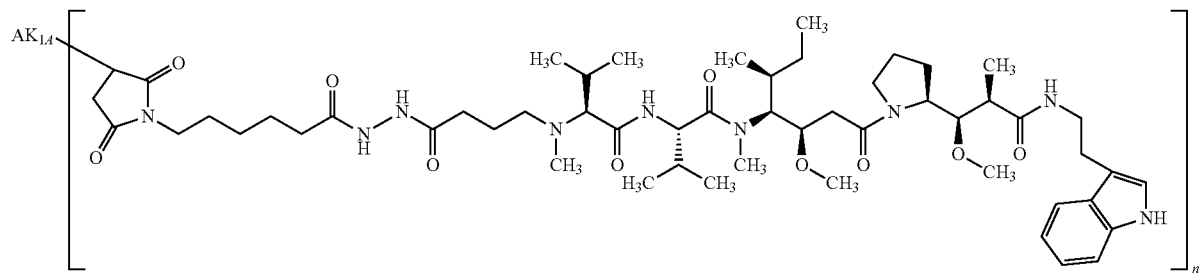
Protein concentration: 1.23 mg/ml
Drug/mAb Ratio: 3.3
Example 41
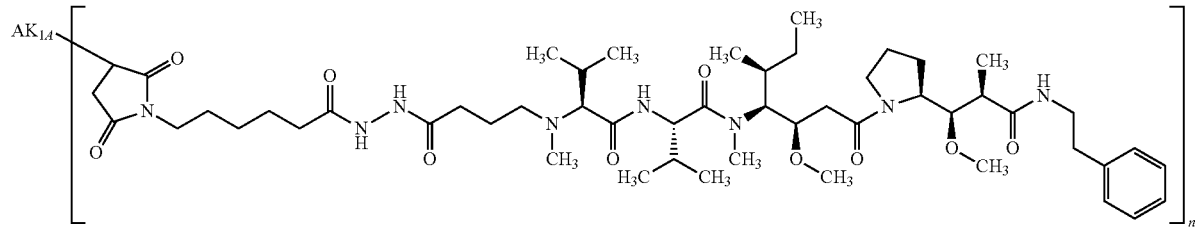
Protein concentration: 1.64 mg/ml
Drug/mAb Ratio: 1.8
Example 42
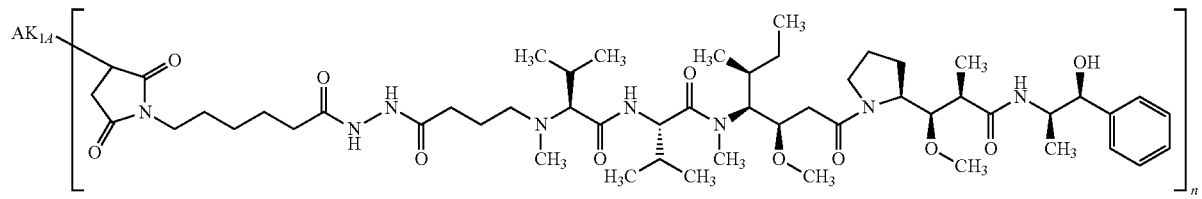
Protein concentration: 1.07 mg/ml
Drug/mAb Ratio: 3.1

Example 43
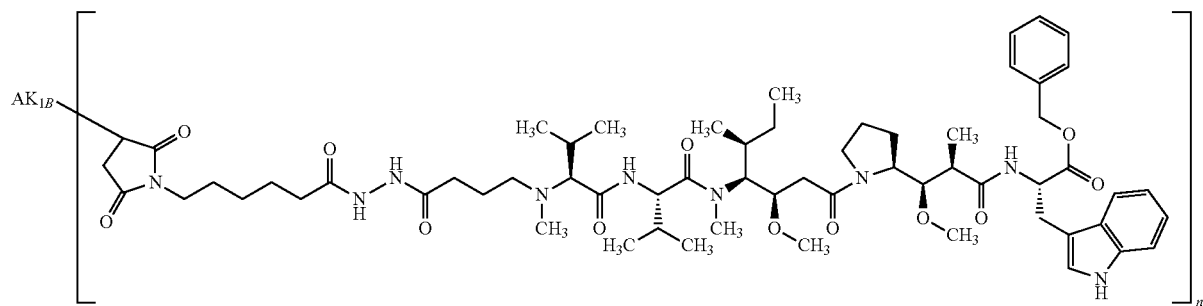
Protein concentration: 1.14 mg/ml
Drug/mAb Ratio: 2.3
Example 44
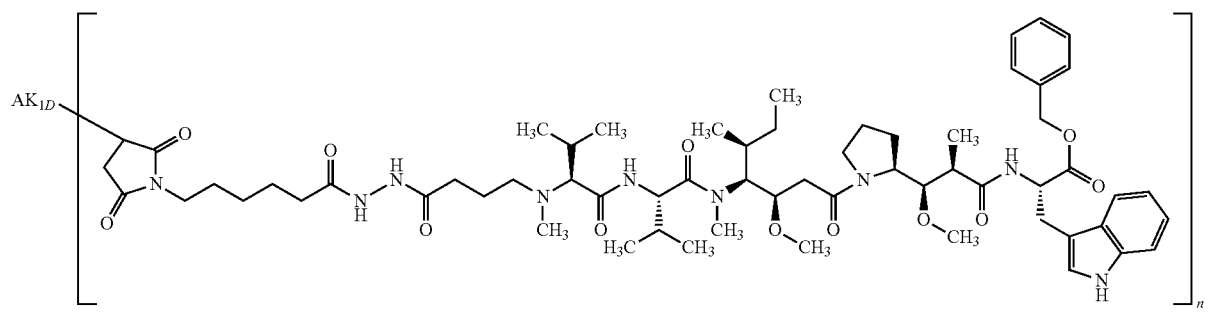
Protein concentration: 1.23 mg/ml
Drug/mAb Ratio: 3.4
Example 45
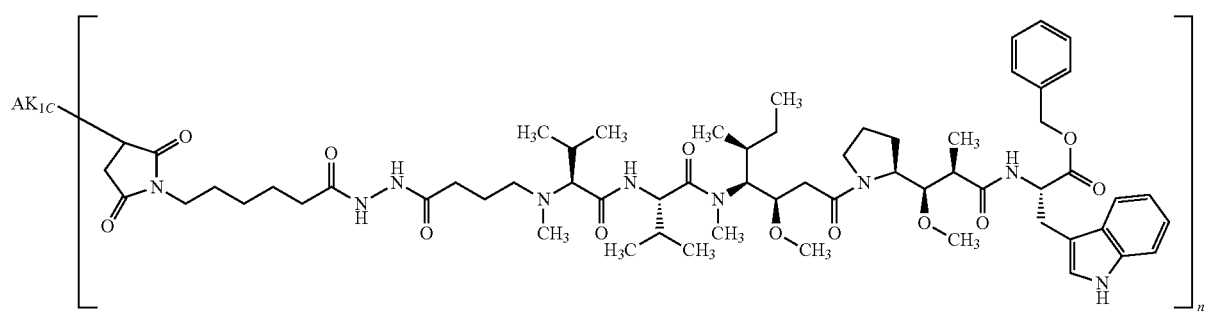
Protein concentration: 1.22 mg/ml
Drug/mAb Ratio: 2.5

Example 46
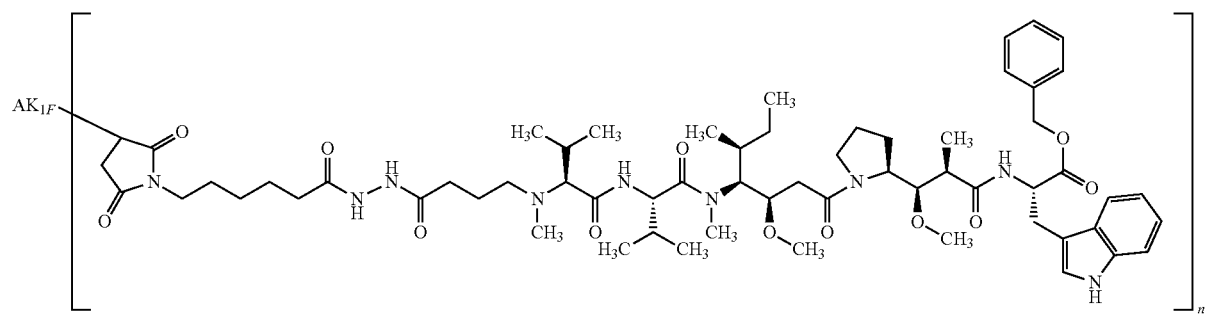
Protein concentration: 1.22 mg/ml
Drug/mAb Ratio: 2.4
Example 47
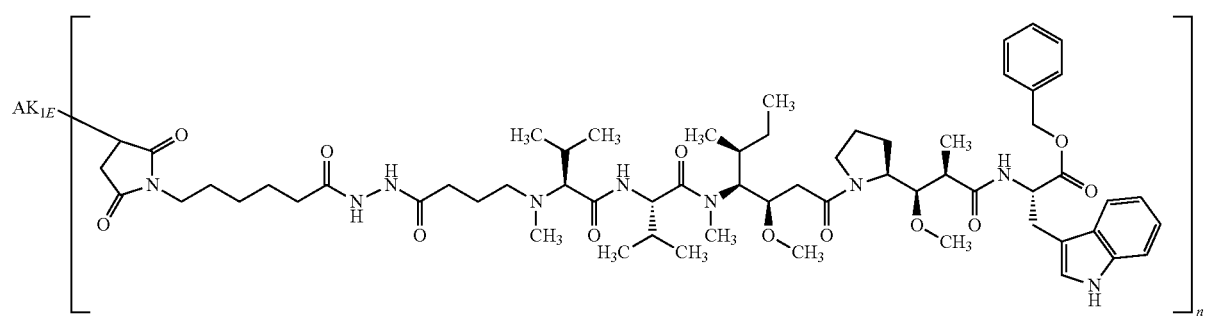
Protein concentration: 1.32 mg/ml
Drug/mAb Ratio: not determinable
Example 48
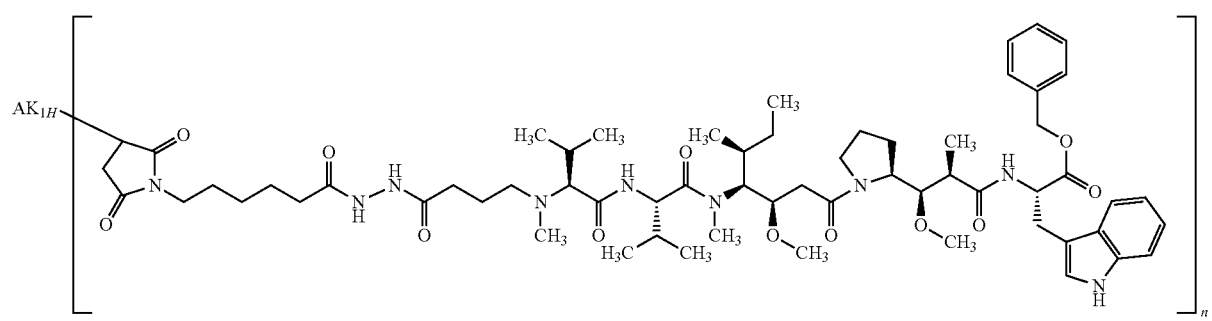
Protein concentration: 1.44 mg/ml
Drug/mAb Ratio: 2.3

Example 49

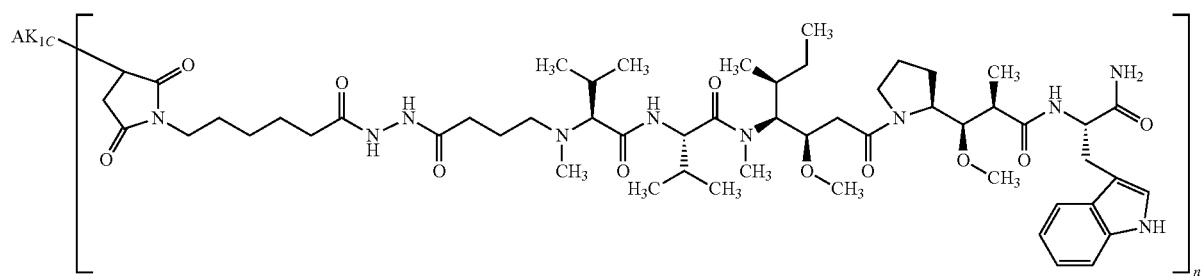

Coupling here was carried out using 250 mg of anti-C4.4a B01-10 in DPBS pH 7.4 and following the Sephadex purification the batch was concentrated by ultracentifugation.
Protein concentration: 12.8 mg/ml
Drug/mAb Ratio: 5.2

Example 50

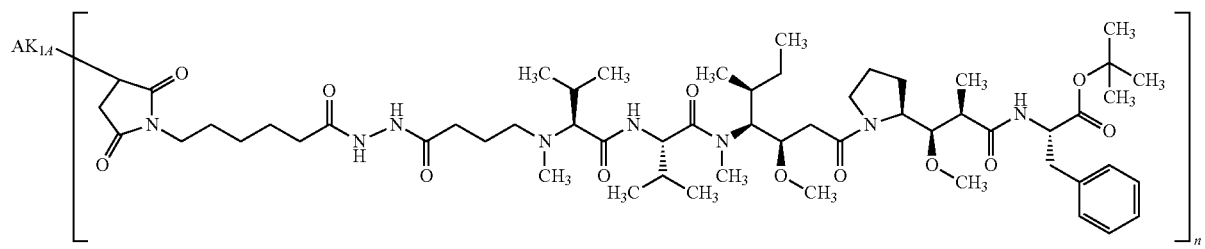

Protein concentration: 0.9 mg/ml
Drug/mAb Ratio: 2

Example 51

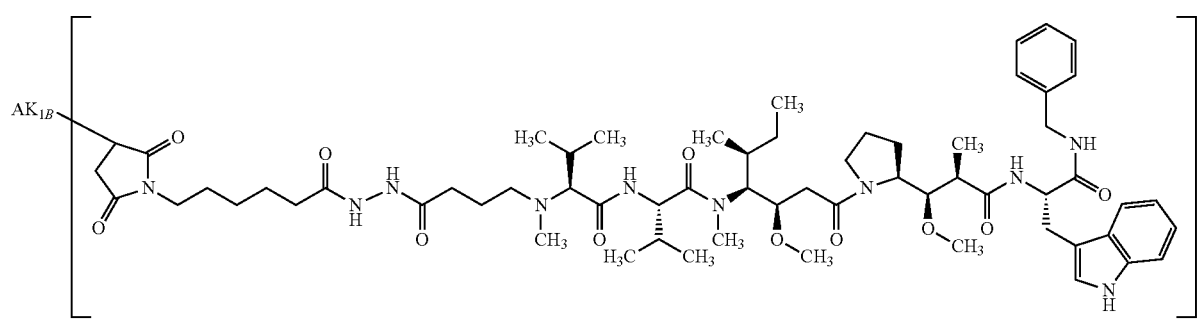

Coupling here was carried out using 250 mg of anti-C4.4a B01-3 in DPBS PH 7.4 and following the Sephadex purification the batch was concentrated by ultracentifugation.
Protein concentration: 8.0 mg/ml
Drug/mAb Ratio: 4.5

Example 52

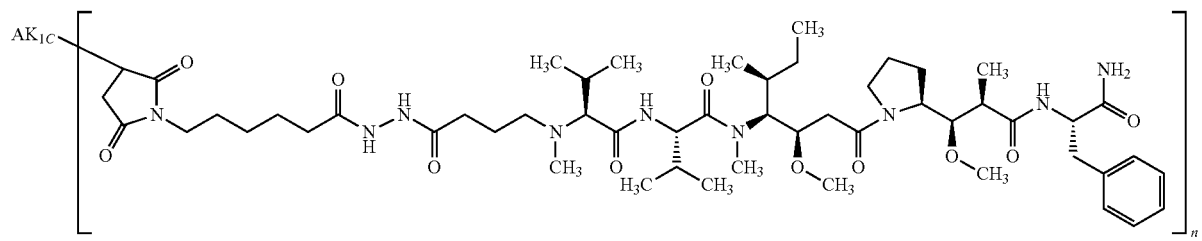

Coupling here was carried out using 250 mg of anti-C4.4a B01-10 in DPBS pH 7.4 and following the Sephadex purification the batch was concentrated by ultracentifugation.
Protein concentration: 12.3 mg/ml
Drug/mAb Ratio: 5.2

Example 53

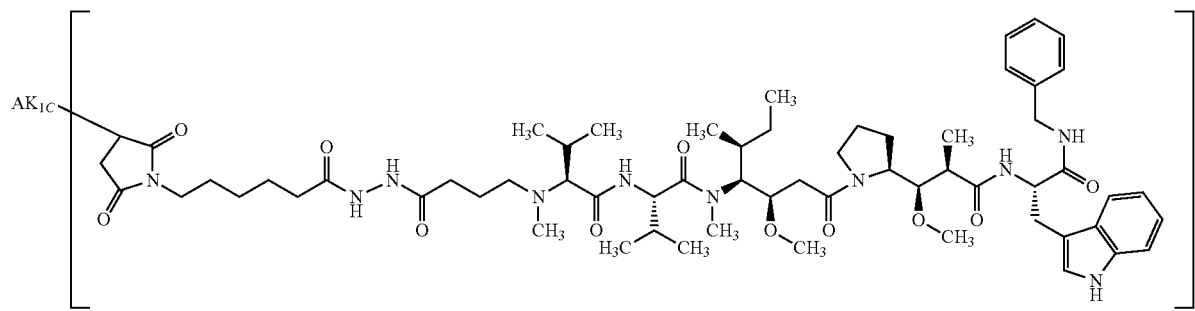

Coupling here was carried out using 250 mg of anti-C4.4a B01-10 in DPBS pH 7.4 and following the Sephadex purification the batch was concentrated by ultracentifugation.
Protein concentration: 10.2 mg/ml
Drug/mAb Ratio: 4.4

Example 54

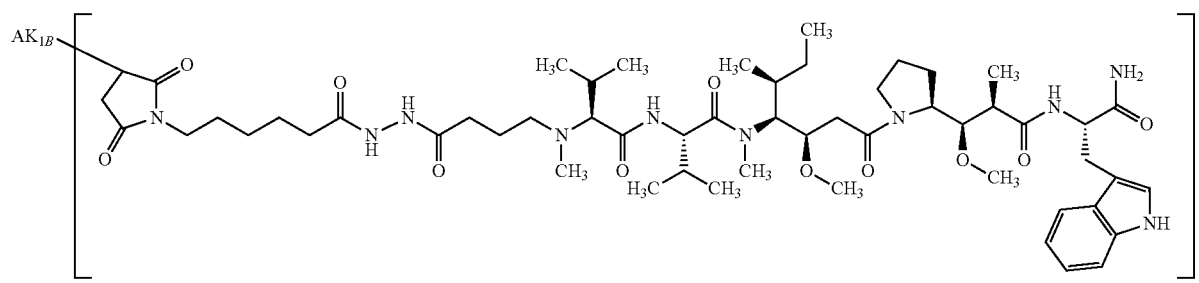

Coupling here was carried out using 50 mg of anti-C4.4a B01-3 in DPBS pH 7.4 and following the Sephadex purification the batch was concentrated by ultracentifugation.
Protein concentration: 11.5 mg/ml
Drug/mAb Ratio: 5.2

Example 55

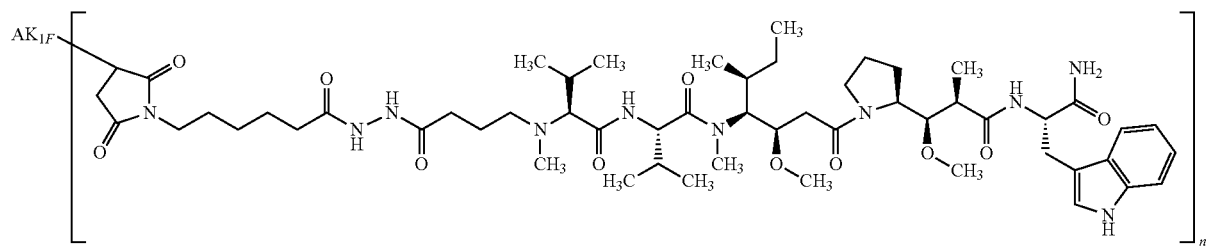

Coupling here was carried out using 250 mg of anti-C4.4a D02-6 in DPBS pH 7.4 and following the Sephadex purification the batch was concentrated by ultracentifugation.
Protein concentration: 13 mg/ml
Drug/mAb Ratio: 5.2

Example 56

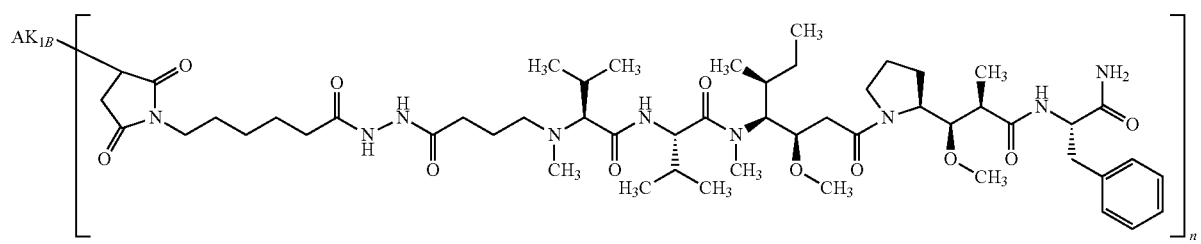

Coupling here was carried out using 250 mg of anti-C4.4a B01-3 in DPBS pH 7.4 and following the Sephadex purification the batch was concentrated by ultracentifugation.
Protein concentration: 10.3 mg/ml
Drug/mAb Ratio: 4.9

Example 57

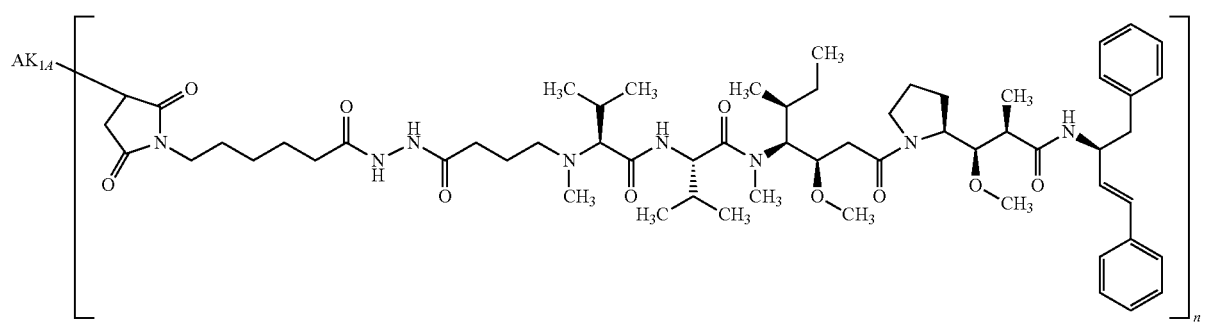

Protein concentration: 0.88 mg/ml
Drug/mAb Ratio: 3.2

Example 58
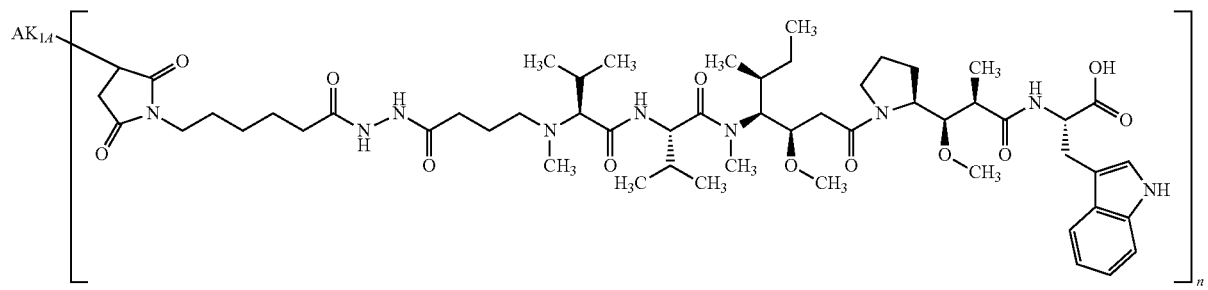
Protein concentration: 1.18 mg/ml
Drug/mAb Ratio: 3.4
Example 59
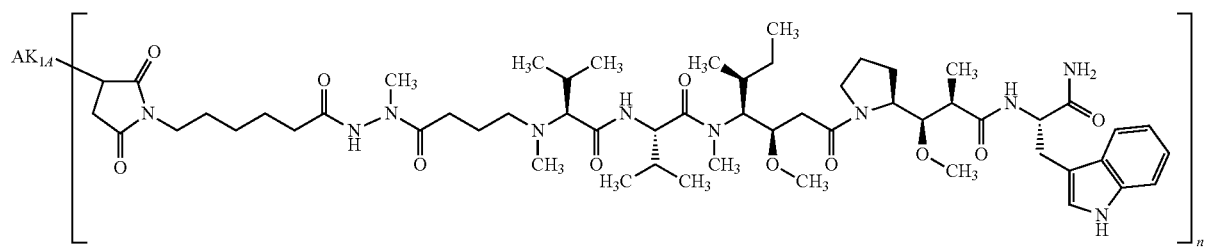
Protein concentration: 1.23 mg/ml
Drug/mAb Ratio: 3.0
Example 60
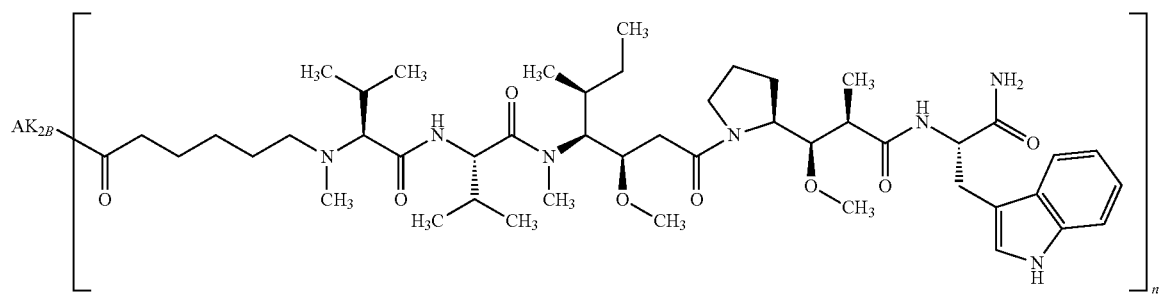
Protein concentration: 1.3 mg/ml
Drug/mAb Ratio: 3.3

Example 61
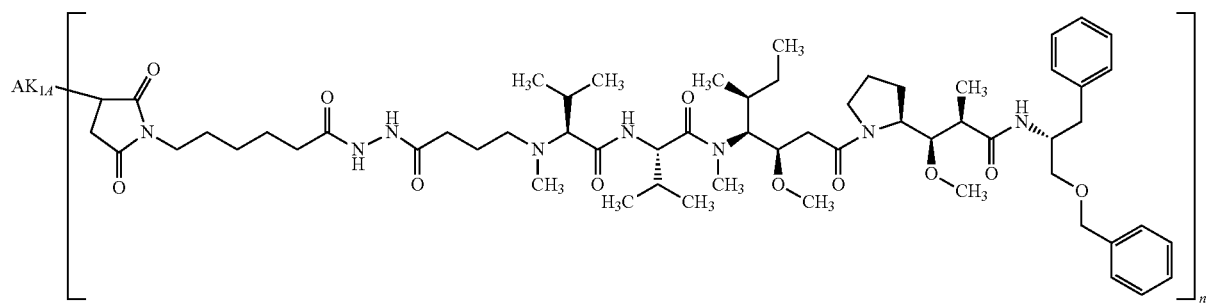
Protein concentration: 1.11 mg/ml
Drug/mAb Ratio: not determinable
Example 62
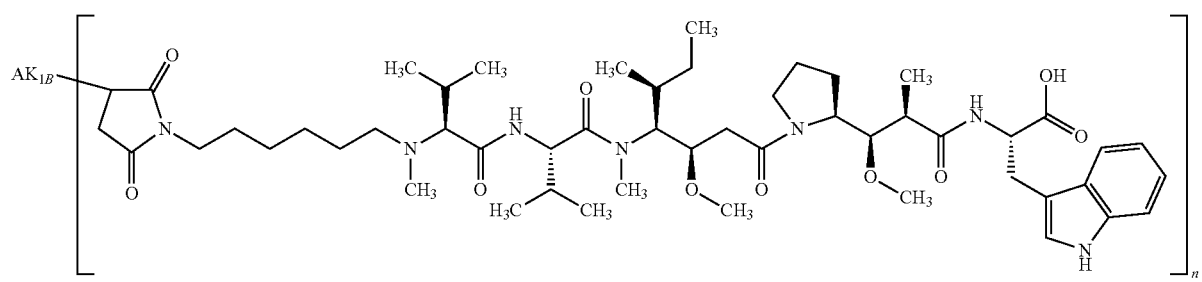
Protein concentration: 1.25 mg/ml
Drug/mAb Ratio: 2.4
Example 63
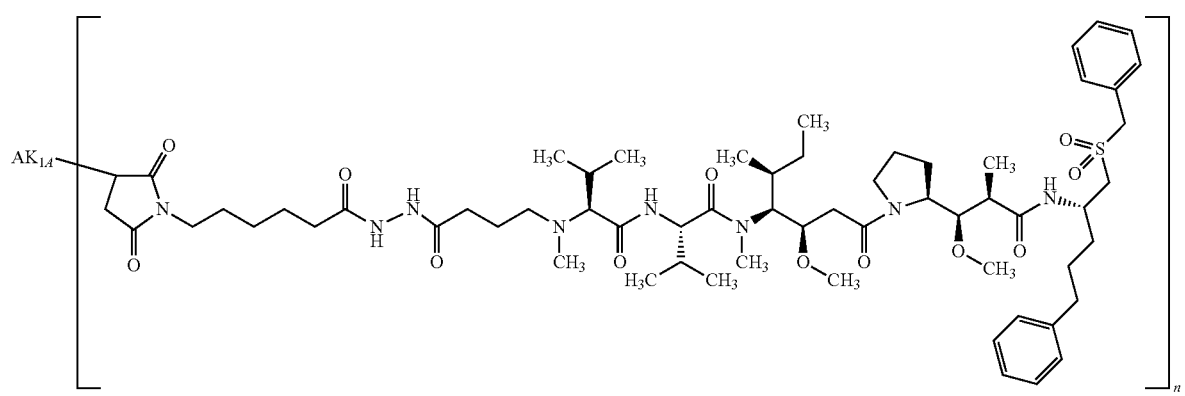
Protein concentration: 0.88 mg/ml
Drug/mAb Ratio: 5.0

Example 64
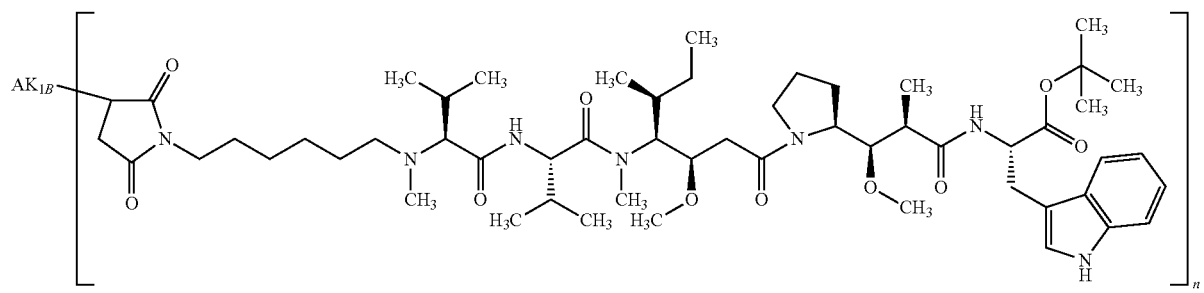
Protein concentration: 1.23 mg/ml
Drug/mAb Ratio: 3.3
Example 65
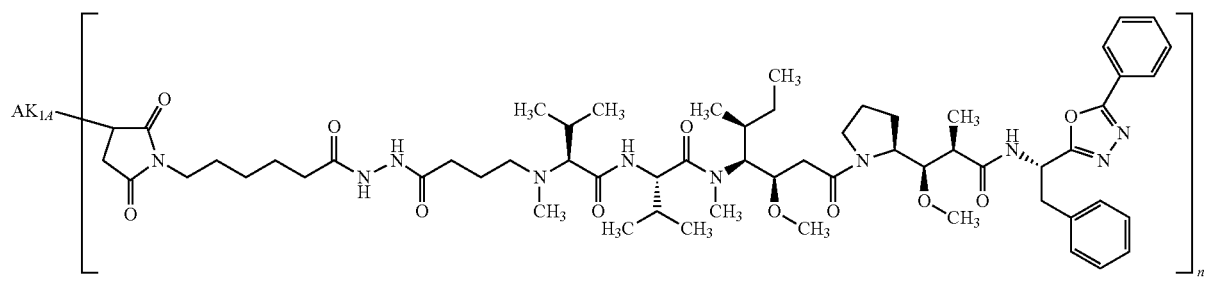
Protein concentration: 0.93 mg/ml
Drug/mAb Ratio: 1.8
Example 66
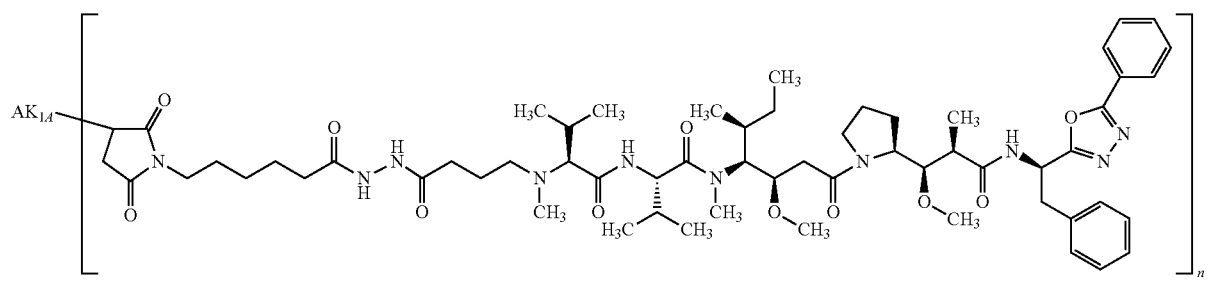
Protein concentration: 0.85 mg/ml
Drug/mAb Ratio: 5.3

Example 67
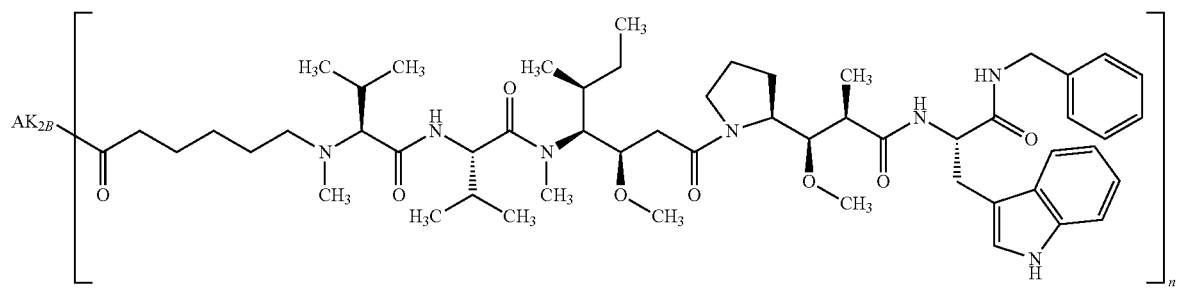
Protein concentration: 1.51 mg/ml
Drug/mAb Ratio: 1.4
Example 68
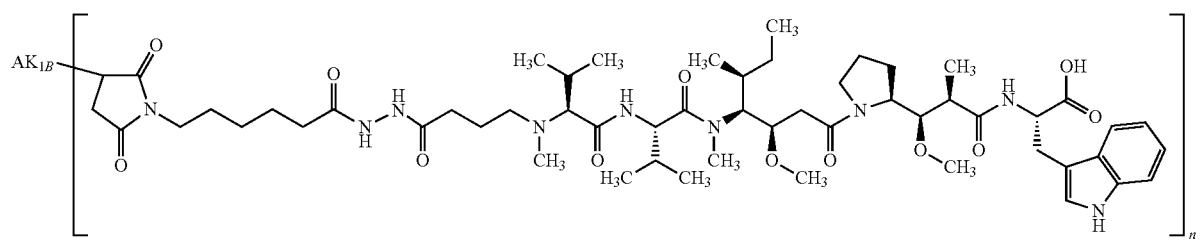
Coupling here was carried out using 150 mg of anti-C4.4a B01-3 in DPBS PH 7.4 and following the Sephadex purification the batch was concentrated by ultracentifugation.
Protein concentration: 11.0 mg/ml
Drug/mAb Ratio: 4.5
Example 69
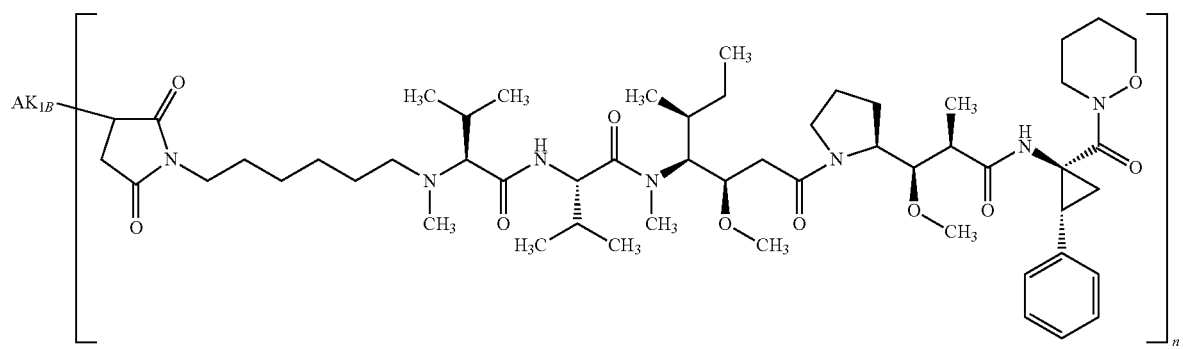
Protein concentration: 1.2 mg/ml
Drug/mAb Ratio: 3.3

Example 70

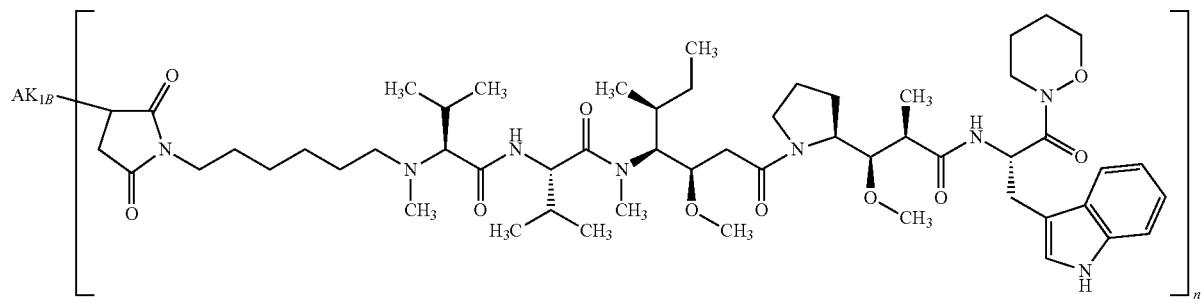

Protein concentration: 1.25 mg/ml
Drug/mAb Ratio: 3.1

Example 71

N-(4-{2-[6-(3-{[(2R)-2-Amino-2-carboxyethyl]sulphanyl}-2,5-dioxopyrrolidin-1-yl)hexanoyl]hydrazino}-4-oxobutyl)-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

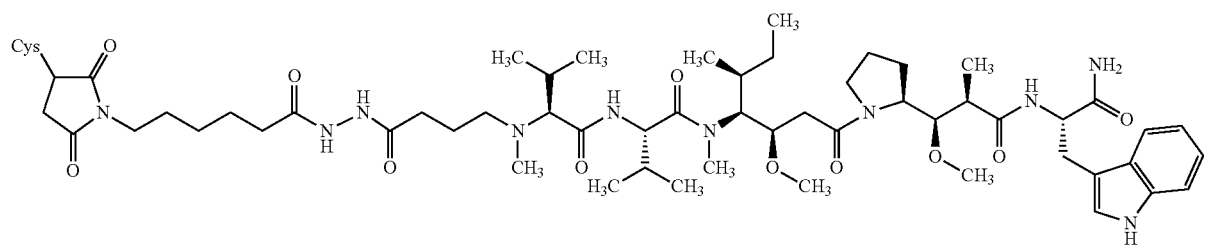

10 mg (10 μmol) of Intermediate 157 were taken up in 5.2 ml of DMF and admixed with 2.28 mg (20 μmol) of L-cysteine. The reaction mixture was stirred at RT for 2 hours, then concentrated under reduced pressure and subsequently purified by preparative HPLC. This gave 5.8 mg (48% of theory) of the title compound.

HPLC (Method 5): $R_t$=1.45 min;

LC-MS (Method 1): $R_t$=0.74 min; MS (ESIpos): m/z=1184 (M+H)$^+$.

Example 72

N-(4-{2-[6-(3-{[(2R)-2-Amino-2-carboxyethyl]sulphanyl}-2,5-dioxopyrrolidin-1-yl)hexanoyl]hydrazino}-4-oxobutyl)-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

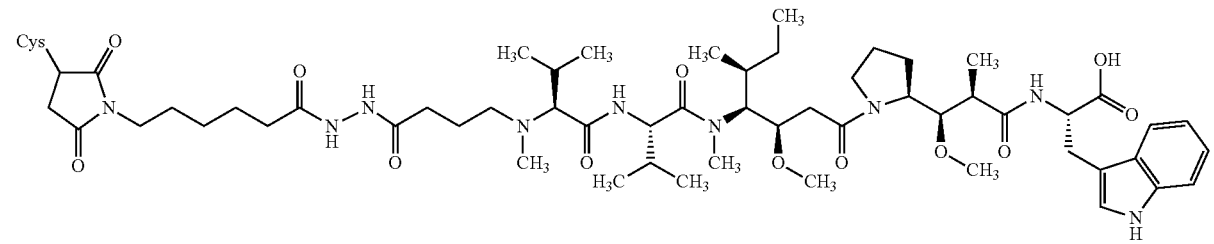

10 mg (10 µmol) of Intermediate 113 were taken up in 5.2 ml of DMF and admixed with 2.28 mg (20 µmol) of L-cysteine. The reaction mixture was stirred at RT for 2 hours, then concentrated under reduced pressure and subsequently purified by preparative HPLC. This gave 6 mg (54% of theory) of the title compound.

HPLC (Method 5): $R_t$=1.5 min;

LC-MS (Method 1): $R_t$=0.77 min; MS (ESIpos): m/z=1185 (M+H)$^+$.

Example 73

N-(4-{2-[6-(3-{[(2R)-2-Amino-2-carboxyethyl]sulphanyl}-2,5-dioxopyrrolidin-1-yl)hexanoyl]hydrazino}-4-oxobutyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

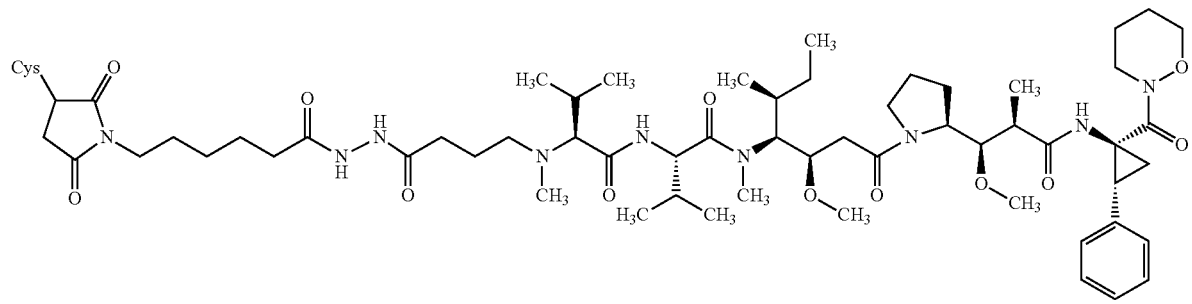

9 mg (8.3 µmol) of Intermediate 132 were taken up in 4 ml of DMF and admixed with 3 mg (24.4 µmol) of L-cysteine. The reaction mixture was stirred at RT overnight, then concentrated under reduced pressure and subsequently purified by preparative HPLC. This gave 6.8 mg (68% of theory) of the title compound.

HPLC (Method 12): $R_t$=1.8 min;

LC-MS (Method 1): $R_t$=0.78 min; MS (ESIpos): m/z=1227 (M+H)$^+$.

Example 74

N-[6-(3-{[(2R)-2-Amino-2-carboxyethyl]sulphanyl}-2,5-dioxopyrrolidin-1-yl)hexyl]-N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

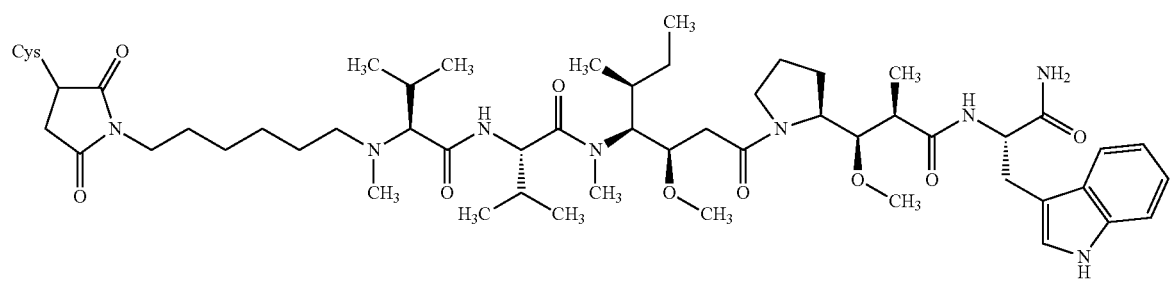

10 mg (10 µmol) of Intermediate 106 were taken up in 5.8 ml of DMF and admixed with 2.5 mg (20 µmol) of L-cysteine. The reaction mixture was stirred at RT for 2 hours, then concentrated under reduced pressure and subsequently purified by preparative HPLC. This gave 5.2 mg (46% of theory of the title compound.

HPLC (Method 5): $R_t$=1.5 min;

LC-MS (Method 11): $R_t$=0.71 min; MS (ESIpos): m/z=1070 (M+H)$^+$.

Example 75

N-[6-(3-{[(2R)-2-Amino-2-carboxyethyl]sulpha-nyl}-2,5-dioxopyrrolidin-1-yl)hexyl]-N-methyl-L-valyl-N-[(3R,4S,5S)-1-{(2S)-2-[(1R,2R)-3-{R1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

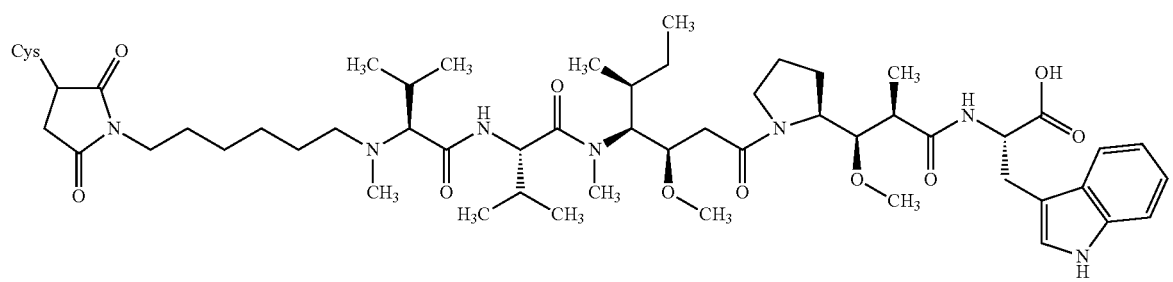

10 mg (10 µmol) of Intermediate 124 were taken up in 4 ml of DMF and admixed with 2.5 mg (20 µmol) of L-cysteine. The reaction mixture was stirred at RT for 2 hours, then concentrated under reduced pressure and subsequently purified by preparative HPLC. This gave 7.2 mg (64% of theory of the title compound.

HPLC (Method 5): $R_t$=1.6 min;

LC-MS (Method 1): $R_t$=0.8 min; MS (ESIpos): m/z=1071 (M+H)$^+$.

Example 76

N-[6-(3-{[(2R)-2-Amino-2-carboxyethyl]sulpha-nyl}-2,5-dioxopyrrolidin-1-yl)hexyl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

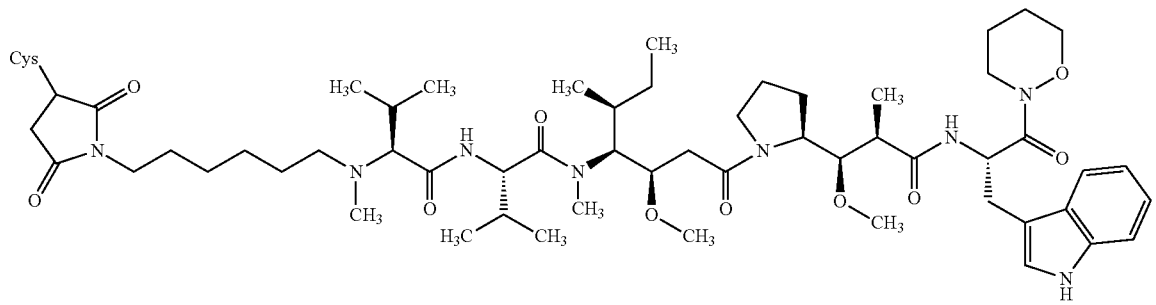

10 mg (10 µmol) of Intermediate 125 were taken up in 4 ml of DMF and admixed with 2.4 mg (20 µmol) of L-cysteine. The reaction mixture was stirred at RT for 2 hours, then concentrated under reduced pressure and subsequently purified by preparative HPLC. This gave 7.7 mg (69% of theory of the title compound.

HPLC (Method 5): $R_t$=1.7 min;

LC-MS (Method 2): $R_t$=1.91 min; MS (ESIpos): m/z=1140 (M+H)$^+$.

Example 77

N-(4-{2-[6-(3-{[(2R)-2-Amino-2-carboxyethyl]sulphanyl}-2,5-dioxopyrrolidin-1-yl)hexanoyl]hydrazino}-4-oxobutyl)-N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide

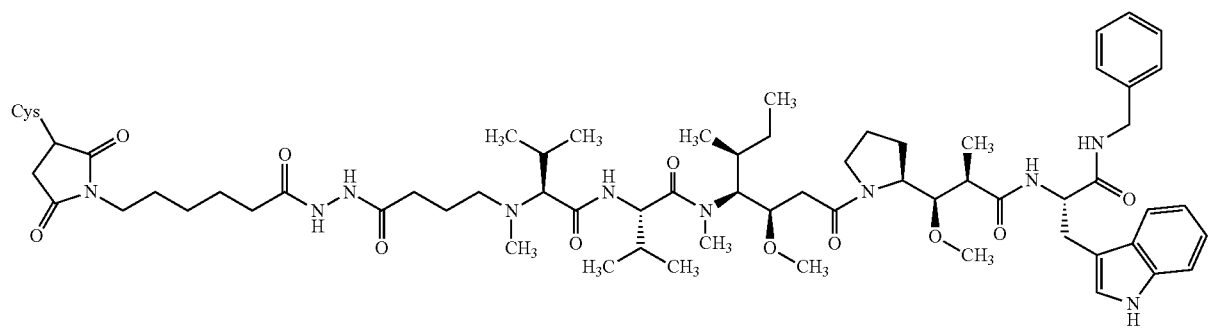

10 mg (10 µmol) of Intermediate 160 were taken up in 3 ml of DMF and admixed with 2.1 mg (20 µmol) of L-cysteine. The reaction mixture was stirred at RT for 2 hours, then concentrated under reduced pressure and subsequently purified by preparative HPLC. This gave 8.1 mg (73% of theory of the title compound.

HPLC (Method 5): $R_t$=1.7 min;

LC-MS (Method 1): $R_t$=0.86 min; MS (ESIpos): m/z=1274 (M+H)$^+$.

Example 78

N-(4-{2-[6-(3-{[(2R)-2-Amino-2-carboxyethyl]sulphanyl}-2,5-dioxopyrrolidin-1-yl)hexanoyl]hydrazino}-4-oxobutyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

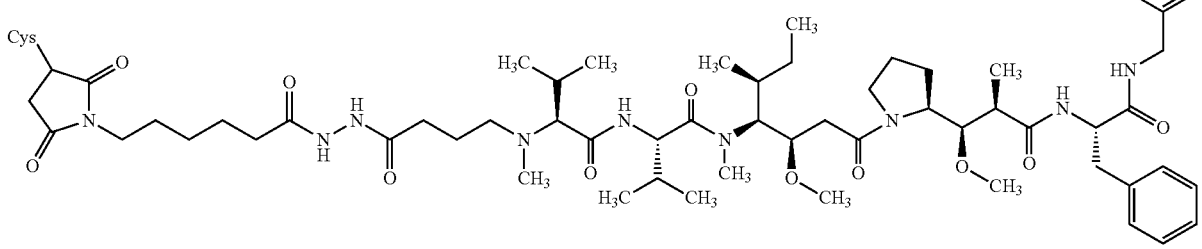

3.5 mg (3 µmol) of Intermediate 159 were taken up in 1 ml of DMF and admixed with 0.76 mg (6 µmol) of L-cysteine. The reaction mixture was stirred at RT for 2 hours, then concentrated under reduced pressure and subsequently purified by preparative HPLC. This gave 2.6 mg (65% of theory of the title compound.

HPLC (Method 5): $R_t$=1.75 min;

LC-MS (Method 1): $R_t$=0.85 min; MS (ESIpos): m/z=1235 (M+H)$^+$.

Example 79

N-(6-{2-[6-(3-{[(2R)-2-Amino-2-carboxyethyl]sulphanyl}-2,5-dioxopyrrolidin-1-yl)hexanoyl]hydrazino}-6-oxohexyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide

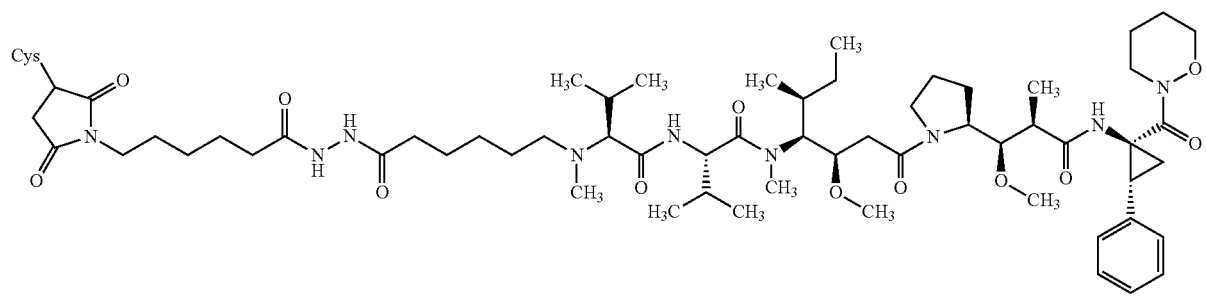

3.6 mg (3 µmol) of Intermediate 129 were taken up in 1 ml of DMF and admixed with 0.77 mg (6 µmol) of L-cysteine. The reaction mixture was stirred at RT for 2 hours, then concentrated under reduced pressure and subsequently purified by preparative HPLC. This gave 1.55 mg (39% of theory of the title compound.

HPLC (Method 5): $R_t$=1.6 min;
LC-MS (Method 1): $R_t$=0.87 min; MS (ESIpos): m/z=1255 (M+H)$^+$.

Example 80

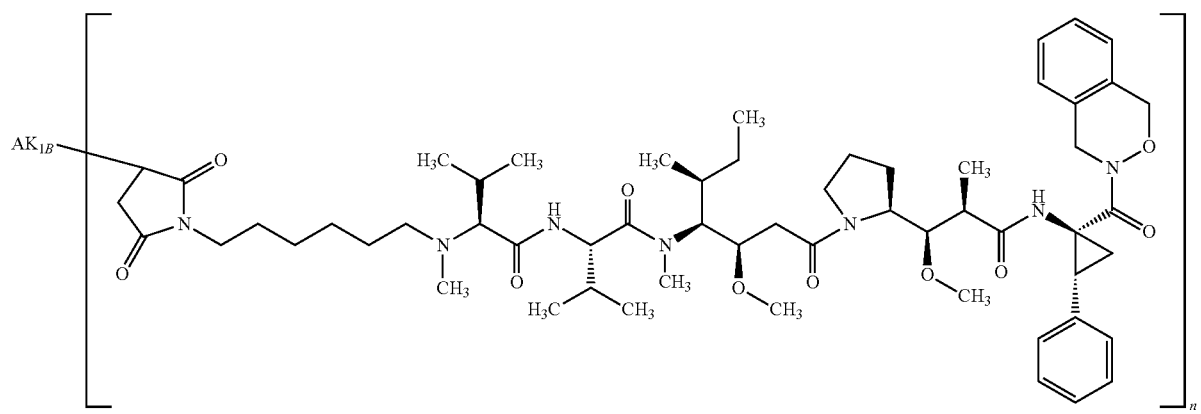

Coupling here was carried out using 5 mg of anti-C4.4a B01-3 in PBS and the batch, following Sephadex purification, was concentrated by ultracentrifugation and re-diluted.
Protein concentration: 0.83 mg/ml
Drug/mAb Ratio: 1.6

Example 81

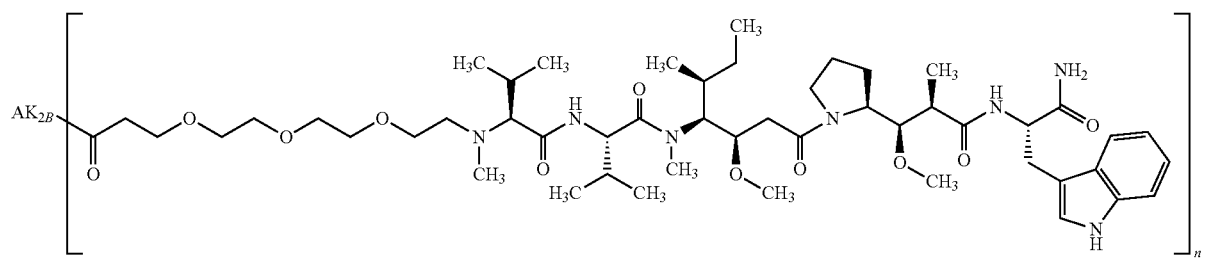

Coupling here was carried out using 5 mg of anti-C4.4a B01-3 in PBS and the batch, following Sephadex purification, was concentrated by ultracentrifugation and re-diluted.
Protein concentration: 1.59 mg/ml
Drug/mAb Ratio: 3.1
Drug/mAb Ratio: 2.9

Example 82

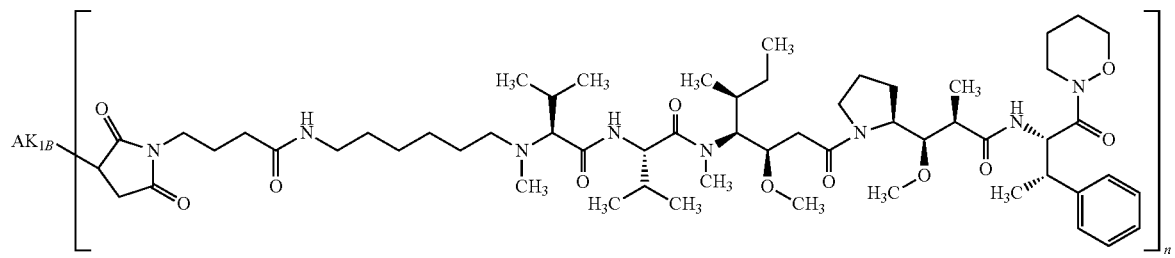

Coupling here was carried out using 5 mg of anti-C4.4a B01-3 in PBS and the batch, following Sephadex purification, was concentrated by ultracentrifugation and re-diluted.
Protein concentration: 1.25 mg/ml
Drug/mAb Ratio: 4.0

Example 83

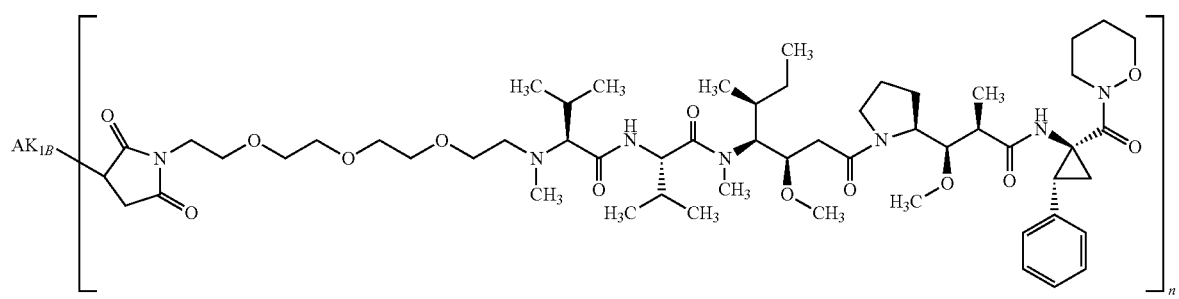

Coupling here was carried out using 5 mg of anti-C4.4a B01-3 in PBS and the batch, following Sephadex purification, was concentrated by ultracentrifugation and re-diluted.
Protein concentration: 1.27 mg/ml
Drug/mAb Ratio: 3.6

Example 84

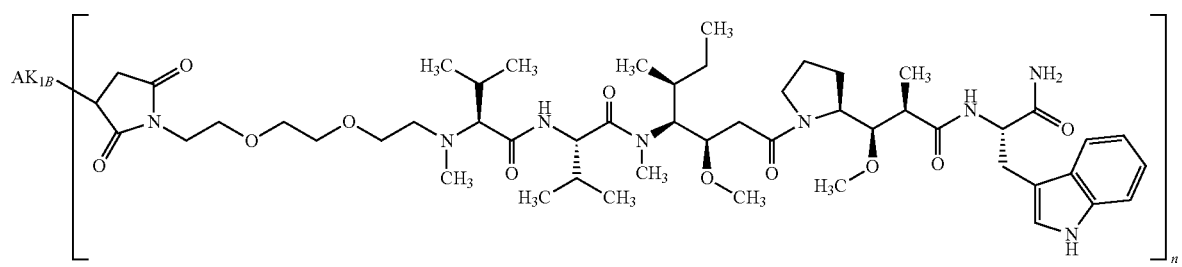

Coupling here was carried out using 5 mg of anti-C4.4a B01-3 in PBS and the batch, following Sephadex purification, was concentrated by ultracentrifugation and re-diluted.
Protein concentration: 1.54 mg/ml
Drug/mAb Ratio: 4.7

Example 85

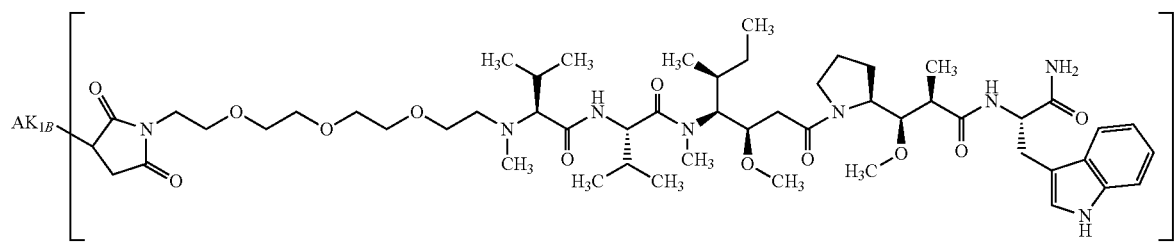

Coupling here was carried out using 5 mg of anti-C4.4a B01-3 in PBS and the batch, following Sephadex purification, was concentrated by ultracentrifugation and re-diluted.
Protein concentration: 1.73 mg/ml
Drug/mAb Ratio: 4.7

Example 86

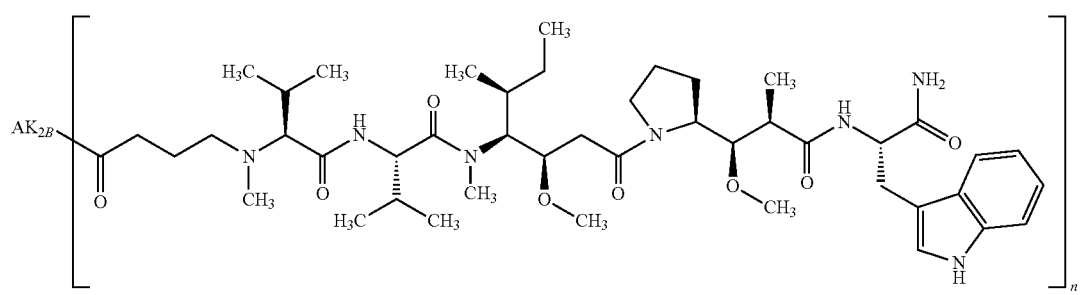

Coupling here was carried out using 5 mg of anti-C4.4a B01-3 in PBS and the batch, following Sephadex purification, was concentrated by ultracentrifugation and re-diluted.
Protein concentration: 1.66 mg/ml
Drug/mAb Ratio: 1.3

Example 87
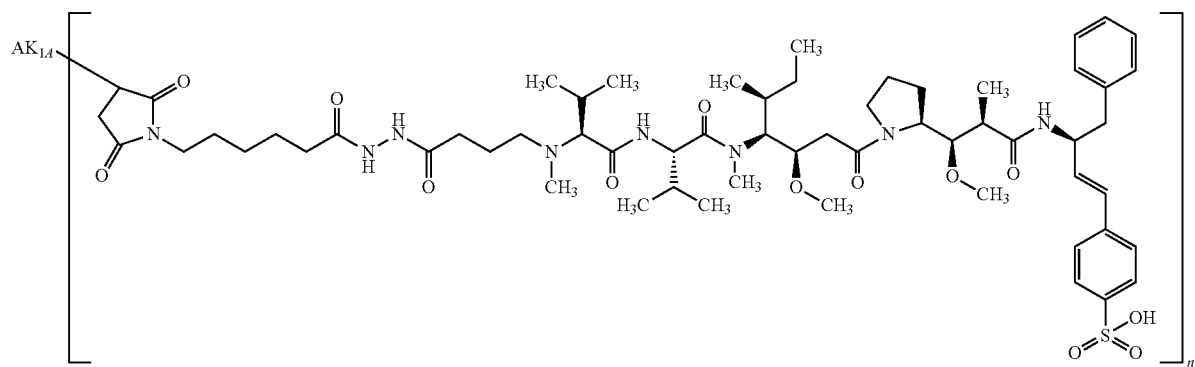
Protein concentration: 2.11 mg/ml
Drug/mAb Ratio: 5.5
Example 88
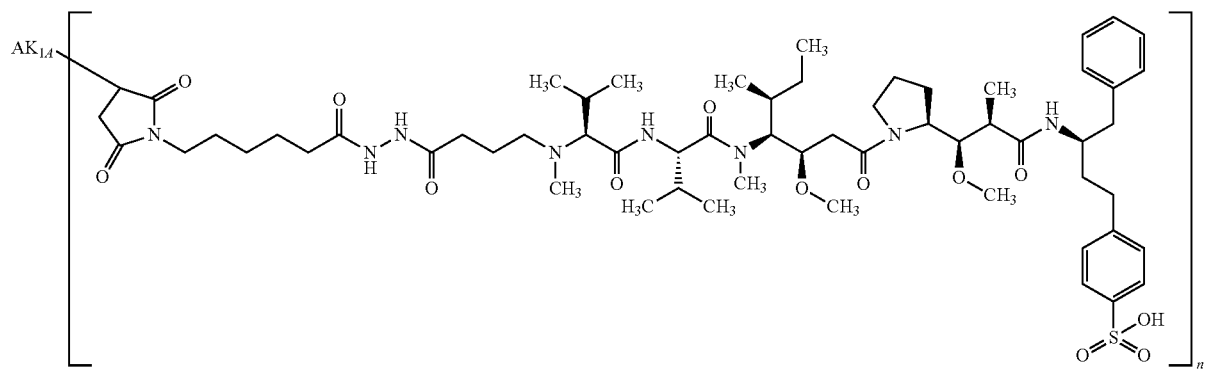
Protein concentration: 1.53 mg/ml
Drug/mAb Ratio: 3.4
Example 89
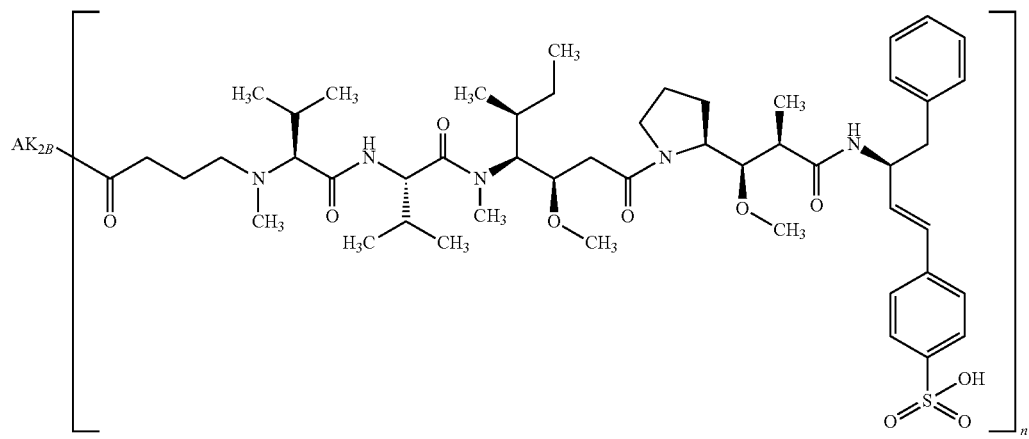
Protein concentration: 1.5 mg/ml
Drug/mAb Ratio: 0.2

Example 90

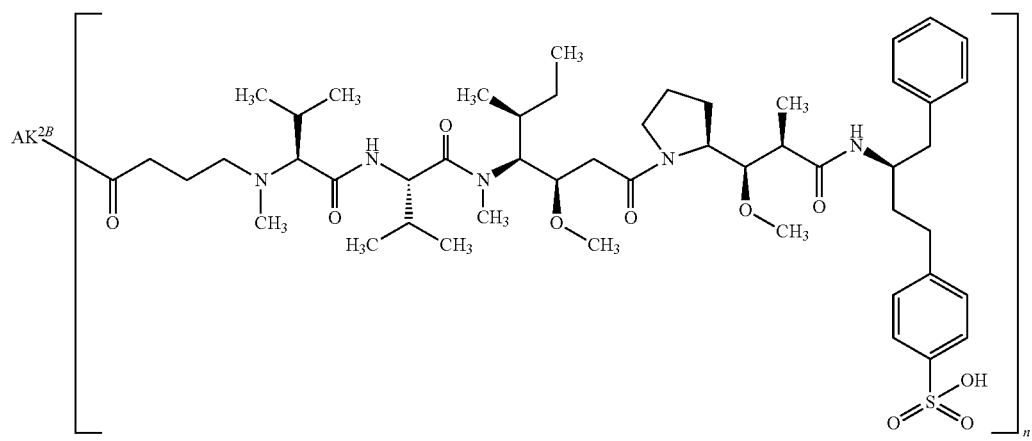

Protein concentration: 1.32 mg/ml
Drug/mAb Ratio: 0.1

Example 91

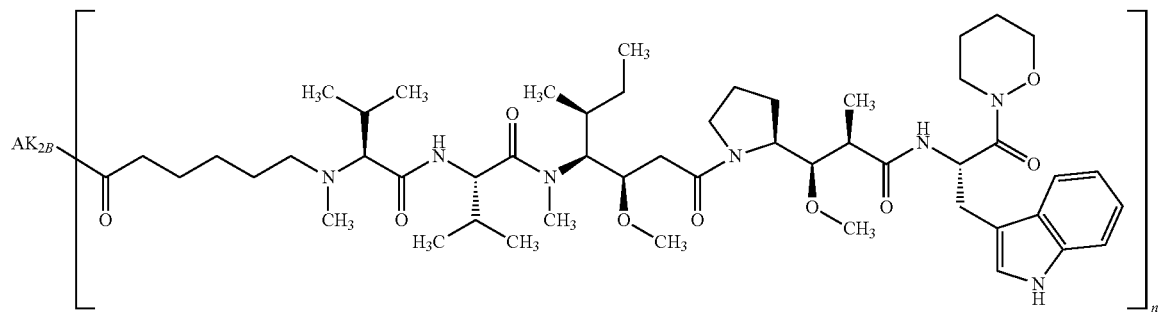

Coupling here was carried out using 80 mg of anti-C4.4a B01-3 in PBS and the batch, following Sephadex purification, was concentrated by ultracentrifugation, re-diluted with PBS and concentrated again.
Protein concentration: 10.3 mg/ml
Drug/mAb Ratio: 3.1

Example 92

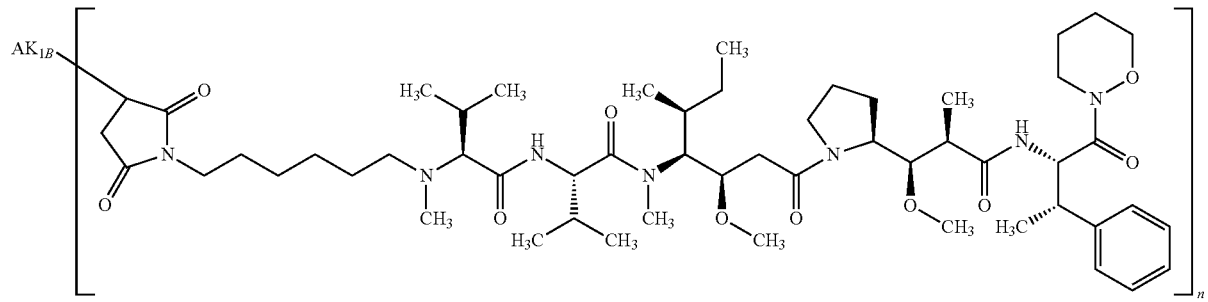

Coupling here was carried out using 5 mg of anti-C4.4a B01-3 in PBS and the batch, following Sephadex purification, was concentrated by ultracentrifugation and re-diluted.
Protein concentration: 1.09 mg/ml
Drug/mAb Ratio: 1.8

Example 93

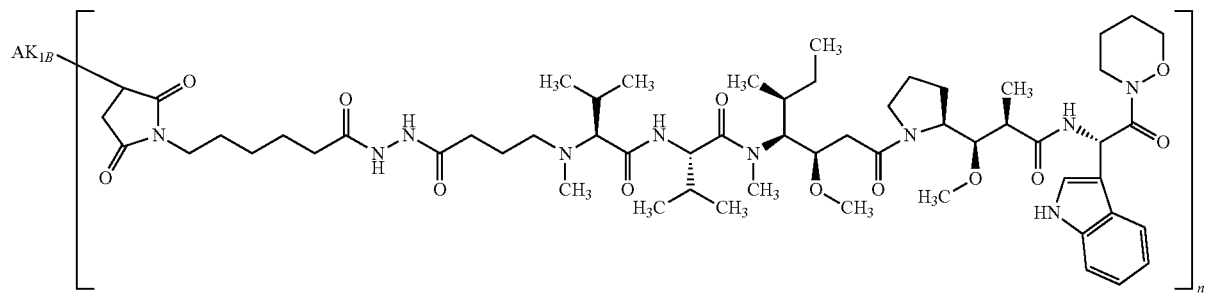

Coupling here was carried out using 5 mg of anti-C4.4a B01-3 in PBS and the batch, following Sephadex purification, was concentrated by ultracentrifugation and re-diluted.
Protein concentration: 1.52 mg/ml
Drug/mAb Ratio: 4.2

Example 94

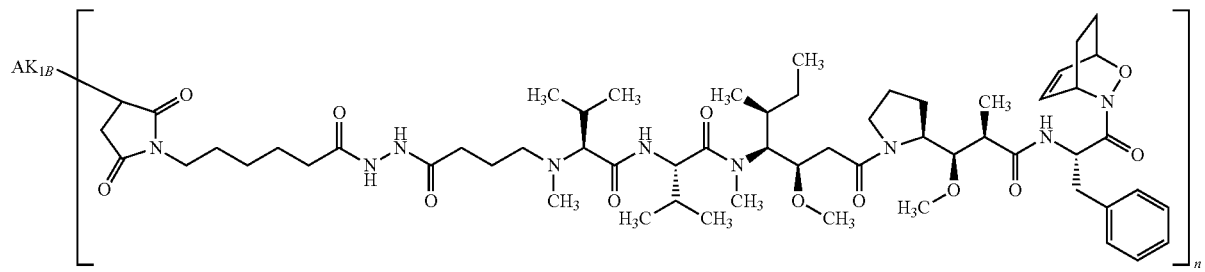

Coupling here was carried out using 5 mg of anti-C4.4a B01-3 in PBS and the batch, following Sephadex purification, was concentrated by ultracentrifugation and re-diluted.
Protein concentration: 1.1 mg/ml
Drug/mAb Ratio: 3.3

Example 95

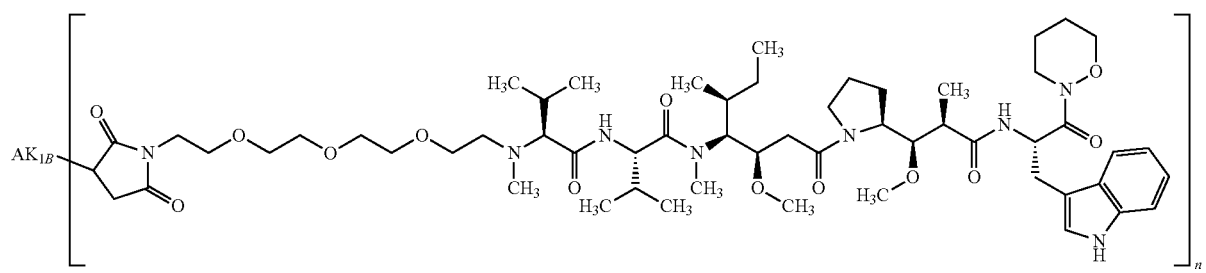

Coupling here was carried out using 5 mg of anti-C4.4a B01-3 in PBS and the batch, following Sephadex purification, was concentrated by ultracentrifugation and re-diluted.
Protein concentration: 1.43 mg/ml
Drug/mAb Ratio: 4.8

Example 96

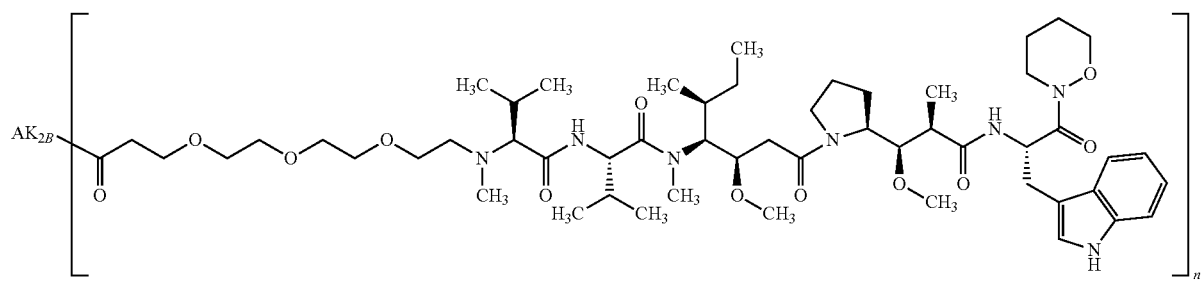

Coupling here was carried out using 5 mg of anti-C4.4a B01-3 in PBS and the batch, following Sephadex purification, was concentrated by ultracentrifugation, re-diluted with PBS and concentrated again.
Protein concentration: 1.36 mg/ml
Drug/mAb Ratio: 4.6

Example 97

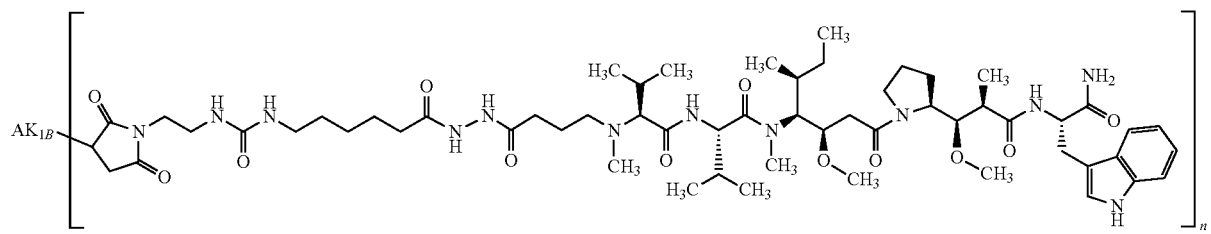

Coupling here was carried out using 5 mg of anti-C4.4a B01-3 in PBS and the batch, following Sephadex purification, was concentrated by ultracentrifugation and re-diluted.
Protein concentration: 1.33 mg/ml
Drug/mAb Ratio: 4.0

Example 98

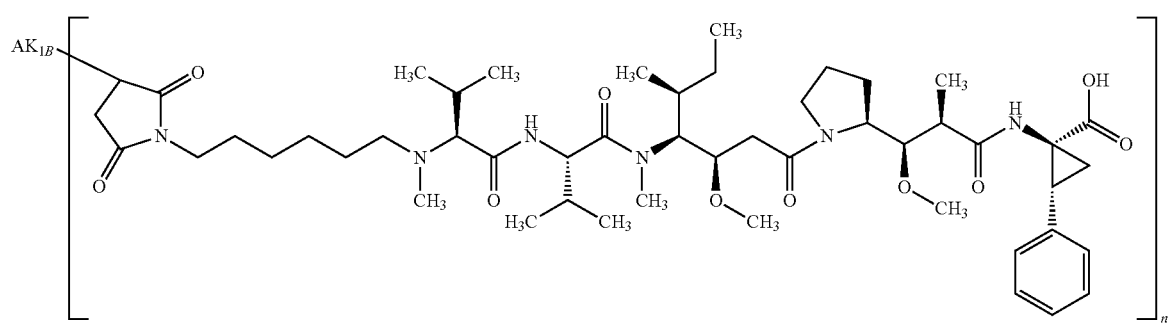

Coupling here was carried out using 5 mg of anti-C4.4a B01-3 in PBS and the batch, following Sephadex purification, was concentrated by ultracentrifugation and re-diluted.
Protein concentration: 1.33 mg/ml
Drug/mAb Ratio: 4.6

Example 99

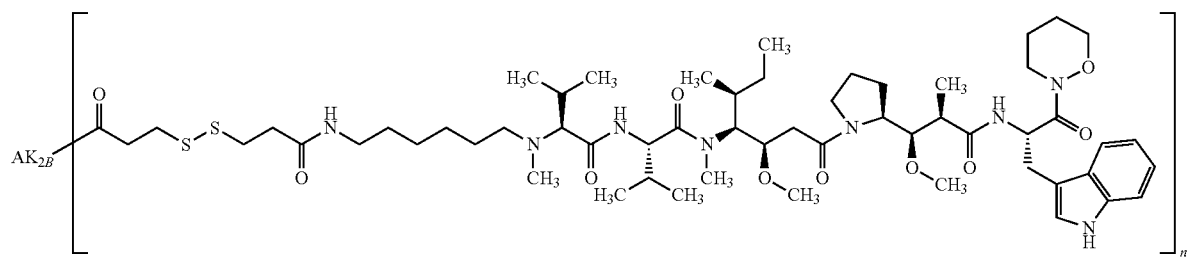

Coupling here was carried out using 5 mg of anti-C4.4a B01-3 in PBS and the batch, following Sephadex purification, was concentrated by ultracentrifugation and re-diluted.
Protein concentration: 1.47 mg/ml
Drug/mAb Ratio: 1.6

Example 100

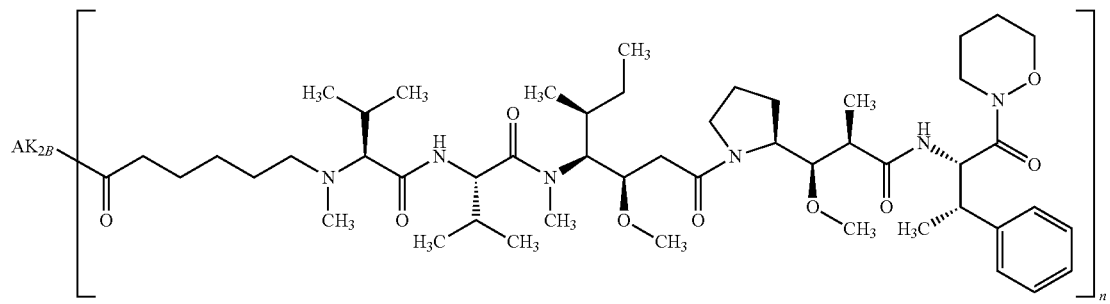

Coupling here was carried out using 5 mg of anti-C4.4a B01-3 in PBS and the batch, following Sephadex purification, was concentrated by ultracentrifugation and re-diluted.
Protein concentration: 1.49 mg/ml
Drug/mAb Ratio: 4.5

Example 101

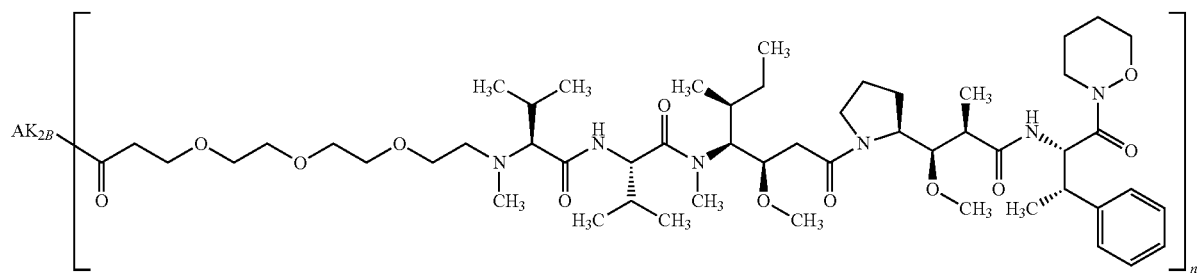

Coupling here was carried out using 5 mg of anti-C4.4a B01-3 in PBS and the batch, following Sephadex purification, was concentrated by ultracentrifugation and re-diluted.
Protein concentration: 1.29 mg/ml
Drug/mAb Ratio: 3.3

Example 102

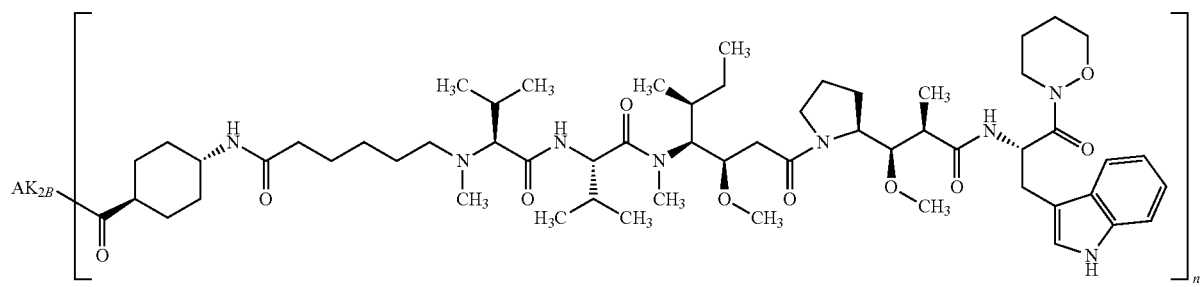

Coupling here was carried out using 5 mg of anti-C4.4a B01-3 in PBS and the batch, following Sephadex purification, was concentrated by ultracentrifugation and re-diluted.
Protein concentration: 1.74 mg/ml
Drug/mAb Ratio: 3.5

Example 103

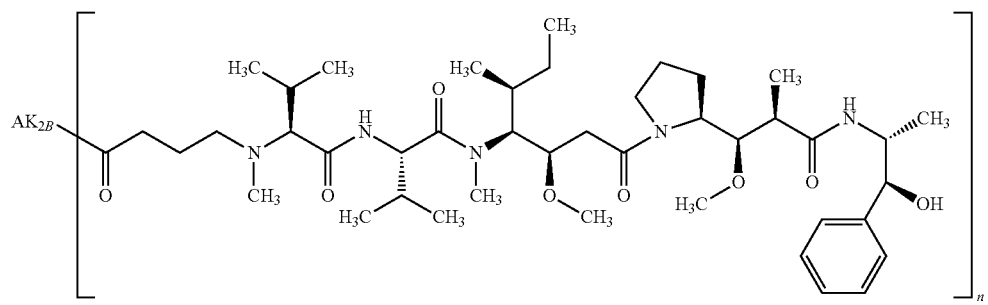

Coupling here was carried out using 5 mg of anti-C4.4a B01-3 in PBS and the batch, following Sephadex purification, was concentrated by ultracentrifugation and re-diluted.
Protein concentration: 1.09 mg/ml
Drug/mAb Ratio: 3.2

Example 104

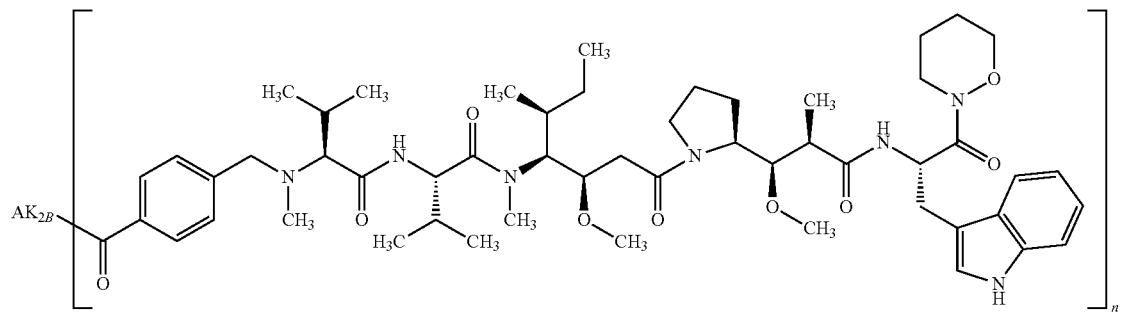

Coupling here was carried out using 5 mg of anti-C4.4a B01-3 in PBS and the batch, following Sephadex purification, was concentrated by ultracentrifugation and re-diluted.
Protein concentration: 1.63 mg/ml
Drug/mAb Ratio: 0.2

Example 105

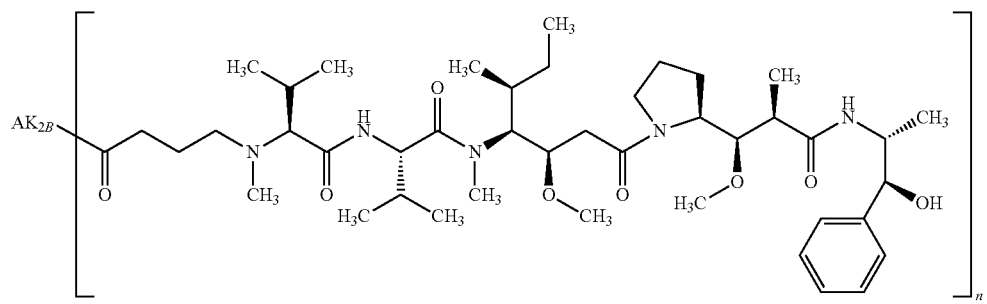

Coupling here was carried out using 5 mg of anti-C4.4a B01-3 in PBS and the batch, following Sephadex purification, was concentrated by ultracentrifugation and re-diluted.
Protein concentration: 1.41 mg/ml
Drug/mAb Ratio: 7.6

Example 106

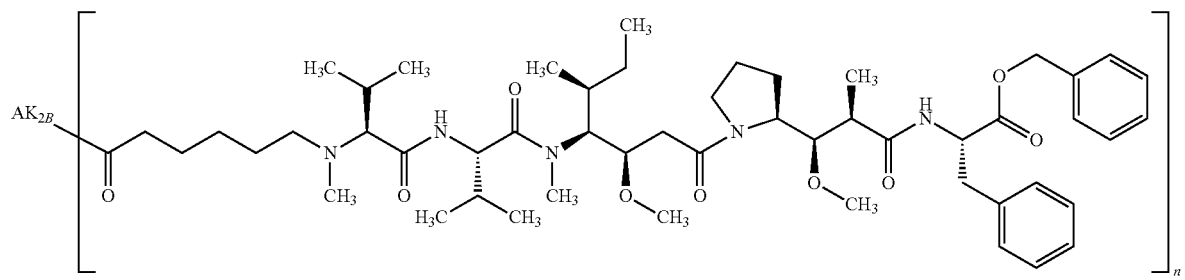

Coupling here was carried out using 5 mg of anti-C4.4a B01-3 in PBS and the batch, following Sephadex purification, was concentrated by ultracentrifugation and re-diluted.
Protein concentration: 2.0 mg/ml
Drug/mAb Ratio: 1.6

Example 107

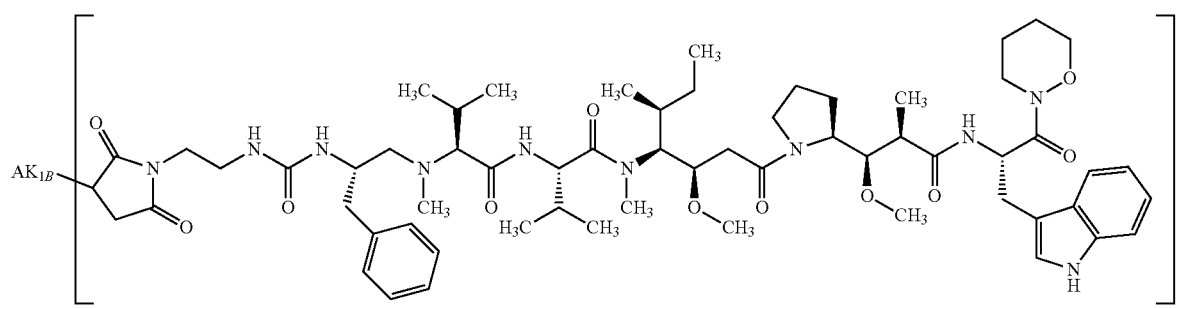

Coupling here was carried out using 5 mg of anti-C4.4a B01-3 in PBS and the batch, following Sephadex purification, was concentrated by ultracentrifugation and re-diluted.
Protein concentration: 1.67 mg/ml
Drug/mAb Ratio: 2.8

Example 108

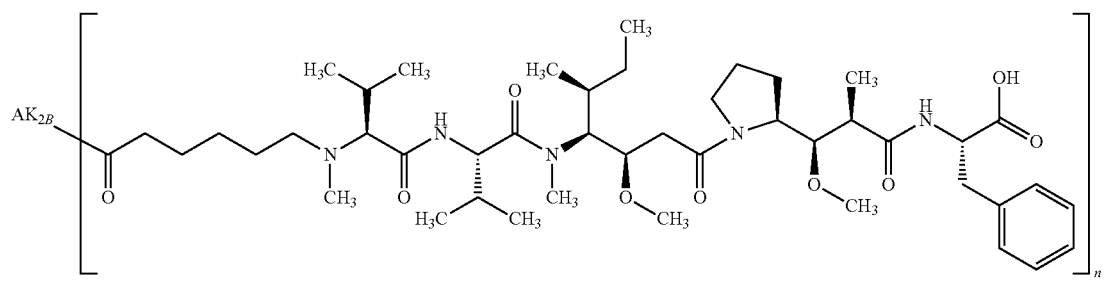

Coupling here was carried out using 5 mg of anti-C4.4a B01-3 in PBS and the batch, following Sephadex purification, was concentrated by ultracentrifugation and re-diluted.
Protein concentration: 1.91 mg/ml
Drug/mAb Ratio: 5.3

Example 109

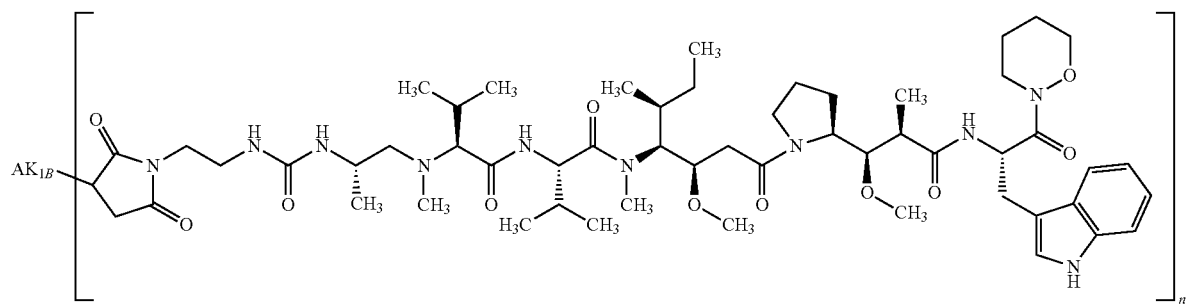

Coupling here was carried out using 5 mg of anti-C4.4a B01-3 in PBS and the batch, following Sephadex purification, was concentrated by ultracentrifugation and re-diluted.
Protein concentration: 1.82 mg/ml
Drug/mAb Ratio: 4.6

Example 110

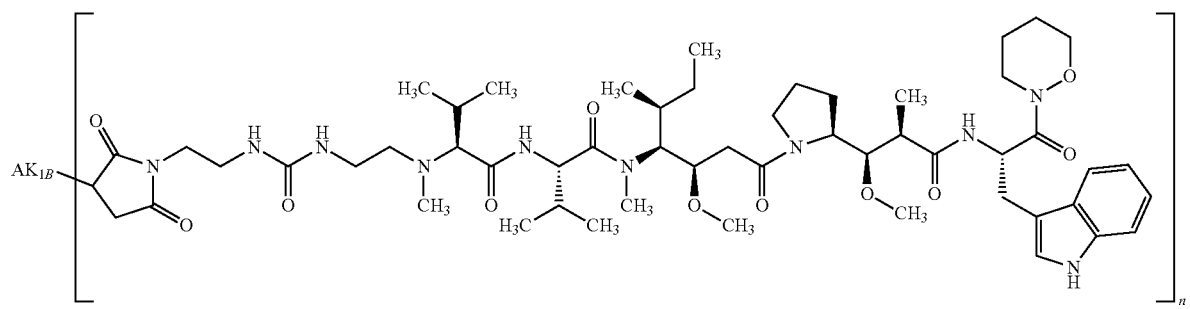

Coupling here was carried out using 5 mg of anti-C4.4a B01-3 in PBS and the batch, following Sephadex purification, was concentrated by ultracentrifugation and re-diluted.
Protein concentration: 1.9 mg/ml
Drug/mAb Ratio: 4.2

Example 111
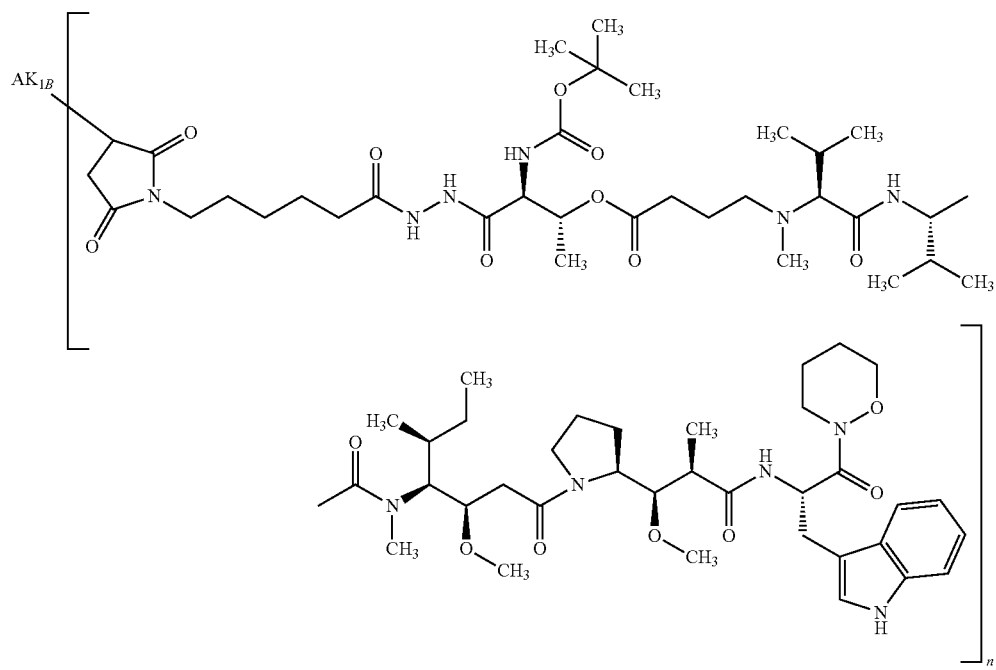
Coupling here was carried out using 5 mg of anti-C4.4a B01-3 in PBS and the batch, following Sephadex purification, was concentrated by ultracentrifugation and re-diluted.
Protein concentration: 1.89 mg/ml
Drug/mAb-Ratio: 2.7
Example 112
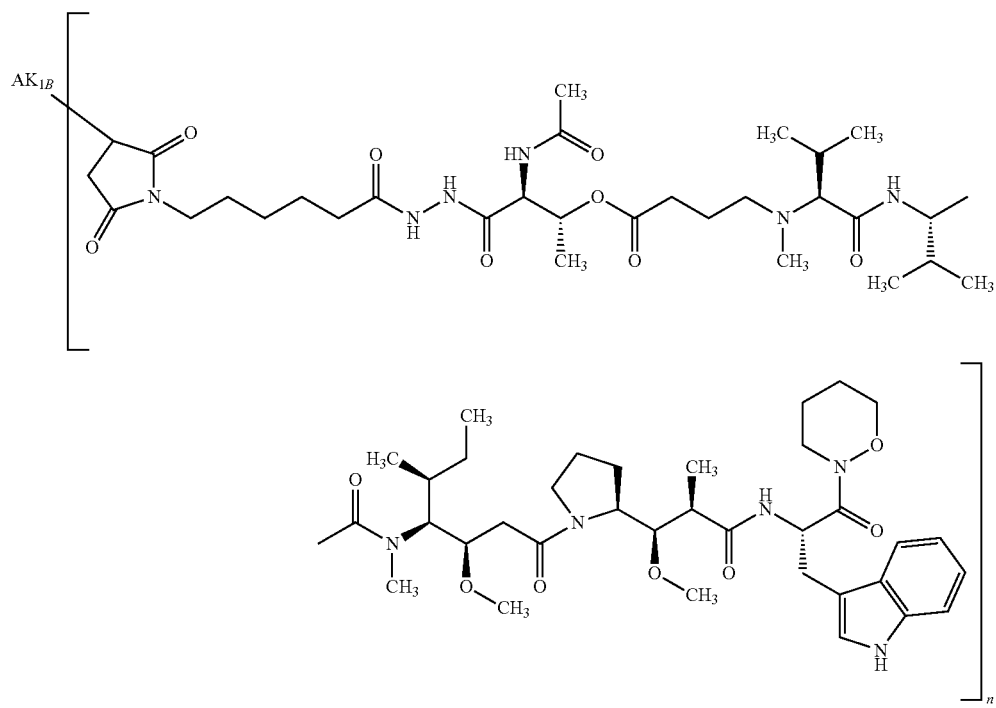

Coupling here was carried out using 5 mg of anti-C4.4a B01-3 in PBS and the batch, following Sephadex purification, was concentrated by ultracentrifugation and re-diluted.
Protein concentration: 1.73 mg/ml
Drug/mAb-Ratio: 2.3

Example 113

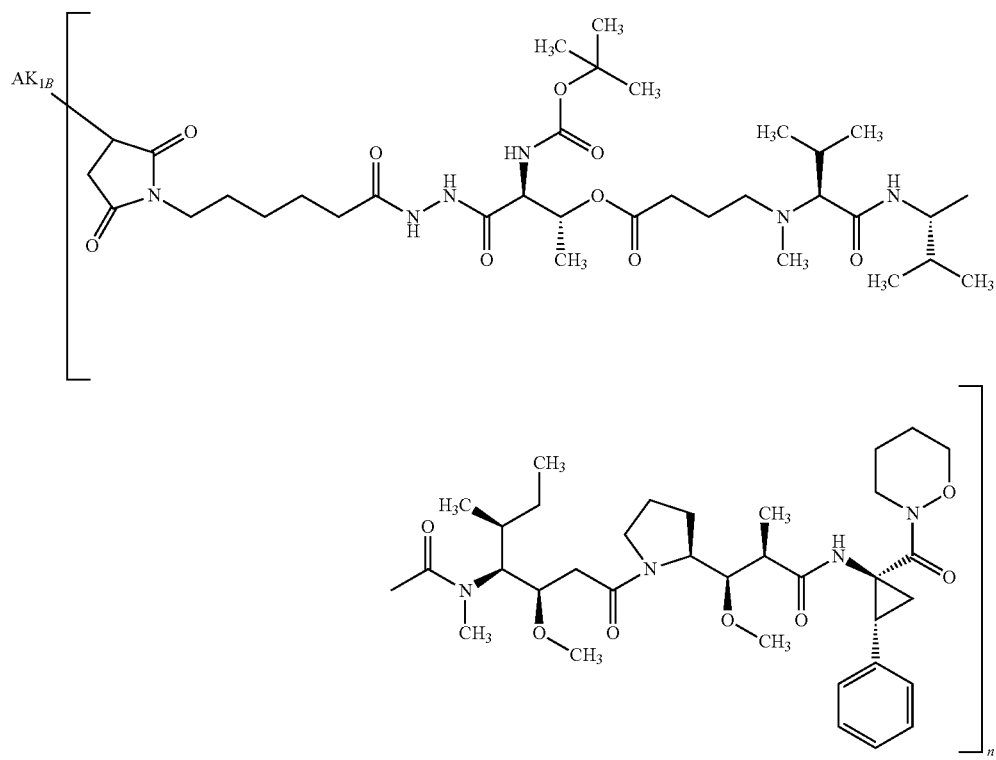

Coupling here was carried out using 5 mg of anti-C4.4a B01-3 in PBS and the batch, following Sephadex purification, was concentrated by ultracentrifugation and re-diluted.
Protein concentration: 1.71 mg/ml
Drug/mAb-Ratio: 3.3

Example 114

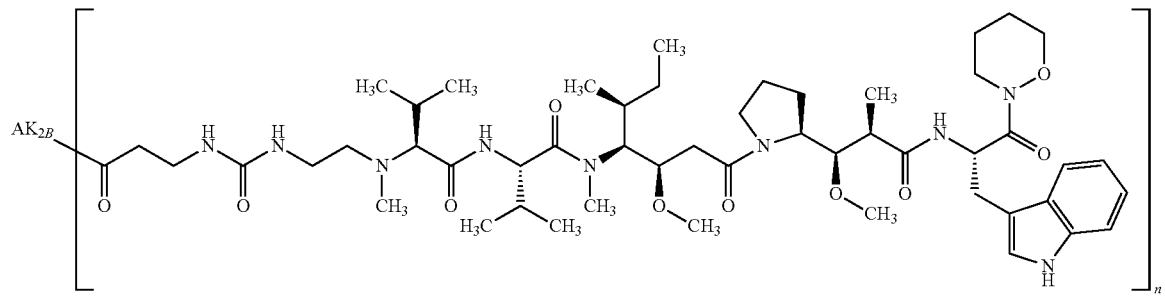

Coupling here was carried out using 5 mg of anti-C4.4a B01-3 in PBS and the batch, following Sephadex purification, was concentrated by ultracentrifugation and re-diluted.
Protein concentration: 1.47 mg/ml
Drug/mAb Ratio: 3.9

Example 115

N-(6-{[(5S)-5-Amino-5-carboxypentyl]amino}-6-oxohexyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

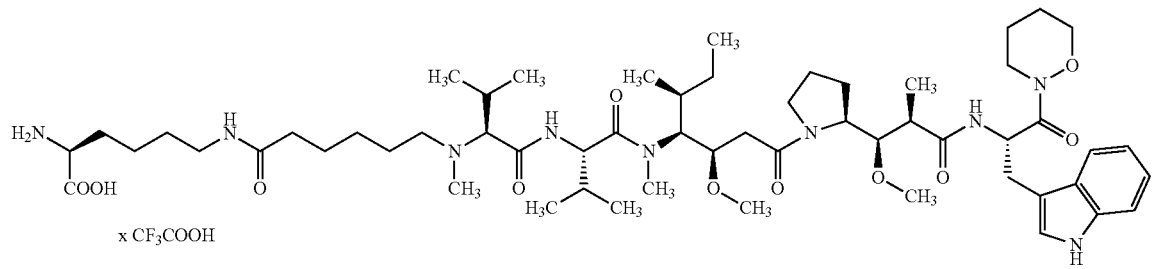 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCC(=O)NCCCC[C@H](N)C(=O)O)C(C)C]

15.5 mg (15 μmol) of Intermediate 210 were taken up in 5 ml of DMF and admixed with 4.4 mg (18 μmol) of $N^2$-(tert-butoxycarbonyl)-L-lysine and also 7.7 μL (44 μmol of N,N-diisopropylethylamine. The reaction mixture was stirred at RT overnight and then concentrated under reduced pressure. The residue was subsequently purified by preparative HPLC. This gave 14 mg (81% of theory) of the protected intermediate of the title compound, which was subsequently taken up in 1 ml of dichloromethane and deprotected with 1 ml of trifluoroacetic acid. The batch was concentrated and, following lyophilization of the residue from acetonitrile/water (1:1), 15 mg (97% of theory) of the title compound were obtained.

HPLC (Method 12): $R_t$=1.8 min;

LC-MS (Method 1): $R_t$=0.79 min; MS (ESIpos): m/z=1083 (M+H)$^+$.

Example 116

N-(6-{[(5S)-5-Amino-5-carboxypentyl]amino}-6-oxohexyl)-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

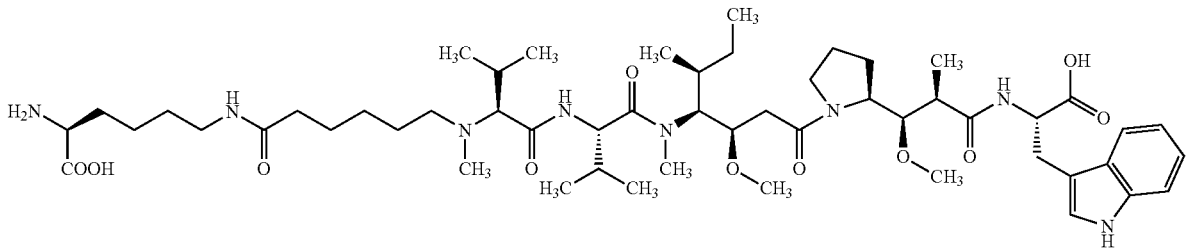 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)O)OC)N(C)C(=O)[C@@H](NC(=O)[C@H](C(C)C)N(C)CCCCCC(=O)NCCCC[C@H](N)C(=O)O)C(C)C]

40 mg (40 μmol) of Intermediate 227 were taken up in 5 ml of DMF and admixed with 11.5 mg (40 μmol) of $N^2$-[(benzyloxy)carbonyl]-L-lysine and also 13 μL (80 μmol) of N,N-diisopropylethylamine. The reaction mixture was stirred at RT overnight, then concentrated under reduced pressure and subsequently purified by preparative HPLC. This gave 32.5 mg (70% of theory) of the protected intermediate of the title compound.

32.5 mg of this intermediate were dissolved in 10 ml of methanol and, following addition of 2 mg of 10% palladium on activated carbon, were hydrogenated under standard hydrogen pressure at RT for 30 minutes. The catalyst was then removed by filtration and the solvent was removed under reduced pressure. Lyophilization of the residue from dioxane/water 1:1 gave 26 mg (99% of theory) of the title compound.

HPLC (Method 12): $R_t$=1.7 min;
LC-MS (Method 1): $R_t$=0.76 min; MS (ESIpos): m/z=1014 (M+14)$^+$.

Example 117

N-[(18S)-18-Amino-18-carboxy-12-oxo-3,6,9-tri-oxa-13-azaoctadec-1-yl]-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

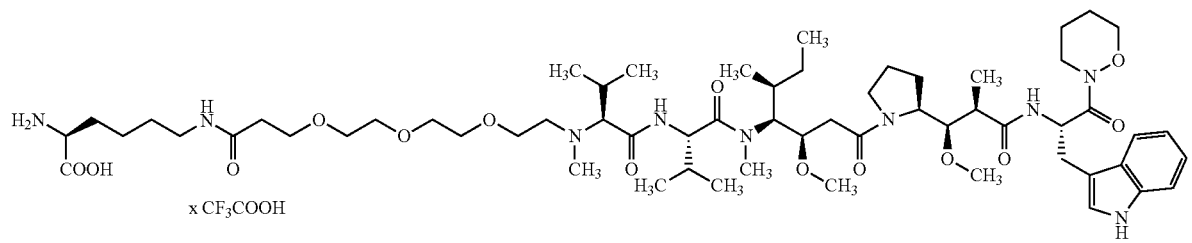 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCOCCOCCOCCC(=O)NCCCC[C@H](N)C(=O)O)C(C)C]

3.5 mg (3 μmol) of Intermediate 202 were taken up in 2 ml of DMF and admixed with 0.8 mg (3 μmol) of $N^2$-(tert-butoxycarbonyl)-L-lysine and also 1.6 μL (10 μmol) of N,N-diisopropylethylamine. The reaction mixture was stirred at RT overnight and then concentrated under reduced pressure. The residue was taken up in acetonitrile/water: (1:1), brought to a pH of 2 with trifluoroacetic acid and then purified by preparative HPLC. This gave 1 mg (25% of theory) of the protected intermediate of the title compound, which was subsequently taken up in 500 μl of dichloromethane and deprotected with 500 μl of trifluoroacetic acid. The batch was concentrated and, following lyophilization of the residue from acetonitrile/water (1:1), 1 mg (89% of theory) of the title compound was obtained.

HPLC (Method 12): $R_t$=1.9 min;
LC-MS (Method 1): $R_t$=0.82 min; MS (ESIpos): m/z=1173 (M+H)$^+$.

Example 118

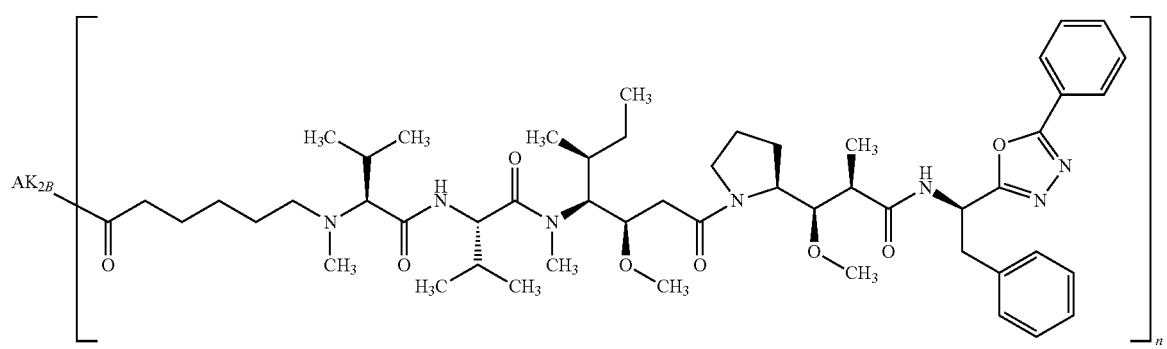

Coupling here was carried out using 5 mg of anti-C4.4a B01-3 in PBS, and the batch, following Sephadex purification, was concentrated by ultracentrifugation and re-diluted.
Protein concentration: 0.89 mg/ml
Drug/mAb Ratio: 1.8

Example 119

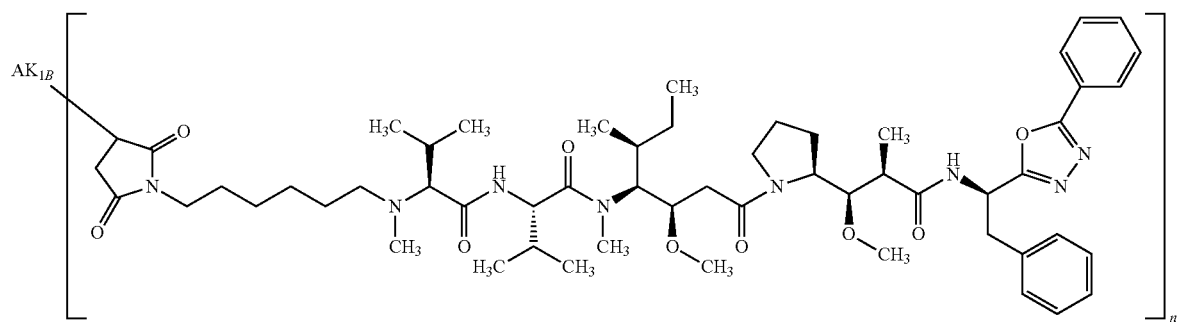

Coupling here was carried out using 5 mg of anti-C4.4a B01-3 and the batch, following Sephadex purification, was concentrated by ultracentrifugation and re-diluted.
Protein concentration: 0.57 mg/ml
Drug/mAb Ratio: 1.5

Example 120

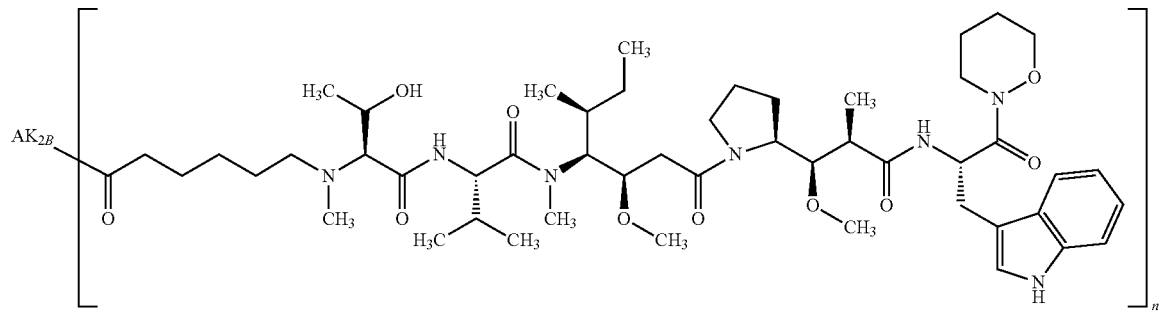

Coupling here was carried out using 5 mg of anti-C4.4a B01-3 and the reaction mixture, following Sephadex purification, was concentrated by ultracentrifugation and re-diluted with PBS.
Protein concentration: 1.39 mg/ml
Drug/mAb Ratio: 7.1

Example 121

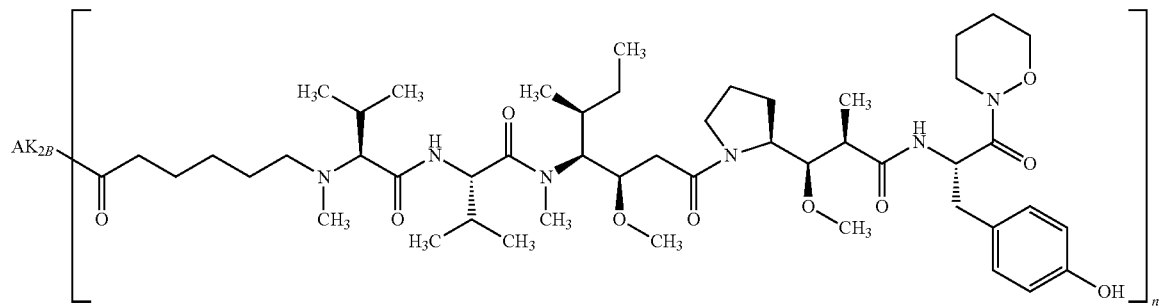

Coupling here was carried out using 5 mg of anti-C4.4a B01-3 and the reaction mixture, following Sephadex purification, was concentrated by ultracentrifugation and re-diluted with PBS.

Protein concentration: 1.54 mg/ml
Drug/mAb Ratio: 2.4

Example 122

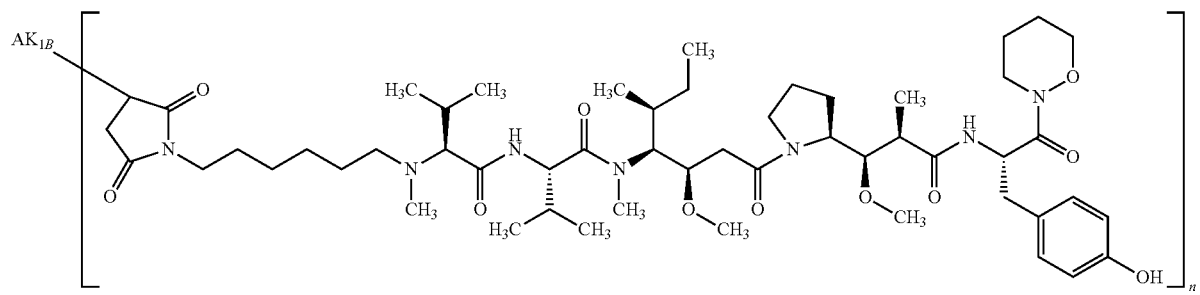

Coupling here was carried out using 5 mg of anti-C4.4a B01-3 in PBS, and the batch, following Sephadex purification, was concentrated by ultracentrifugation and re-diluted.

Protein concentration: 1.48 mg/ml
Drug/mAb Ratio: 2.4

Example 123

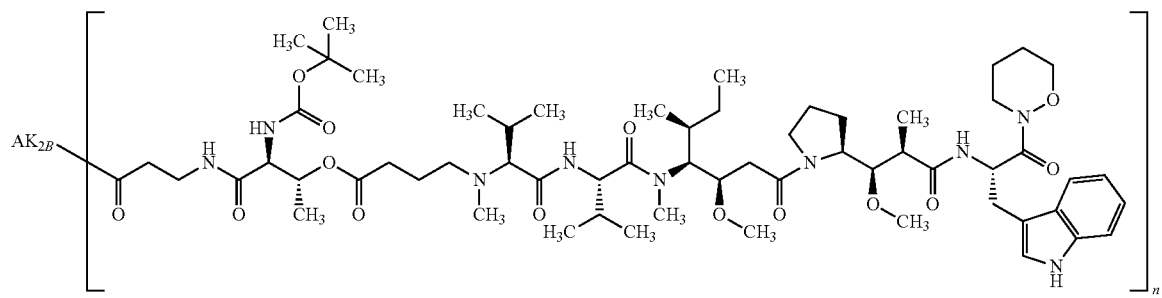

Coupling here was carried out using 5 mg of anti-C4.4a B01-3 in PBS, and the batch, following Sephadex purification, was concentrated by ultracentrifugation and re-diluted.

Protein concentration: 1.43 mg/ml
Drug/mAb-Ratio: 3.6

Example 124

Diastereomer 1

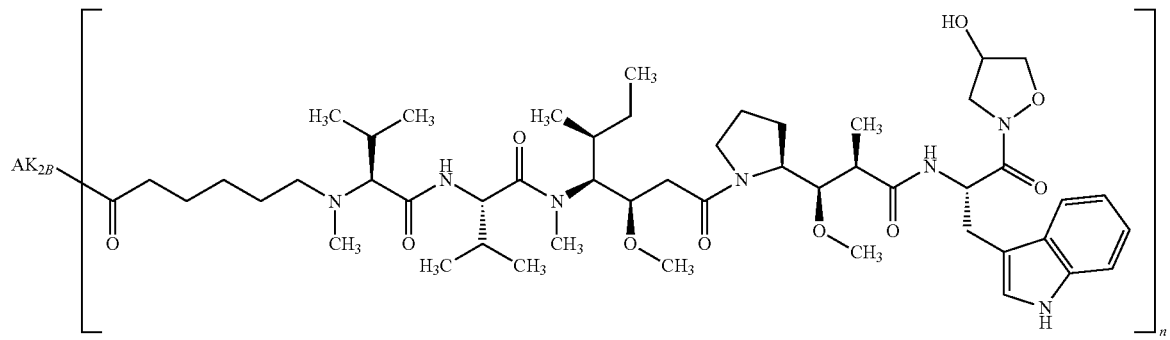

Coupling here was carried out using Intermediate 247a and 5 mg of anti-C4.4a B01-3 in PBS, and the batch, following Sephadex purification, was concentrated by ultracentrifugation and re-diluted with PBS.

Protein concentration: 1.45 mg/ml
Drug/mAb Ratio: 3.8

Example 125

Diastereomer 2

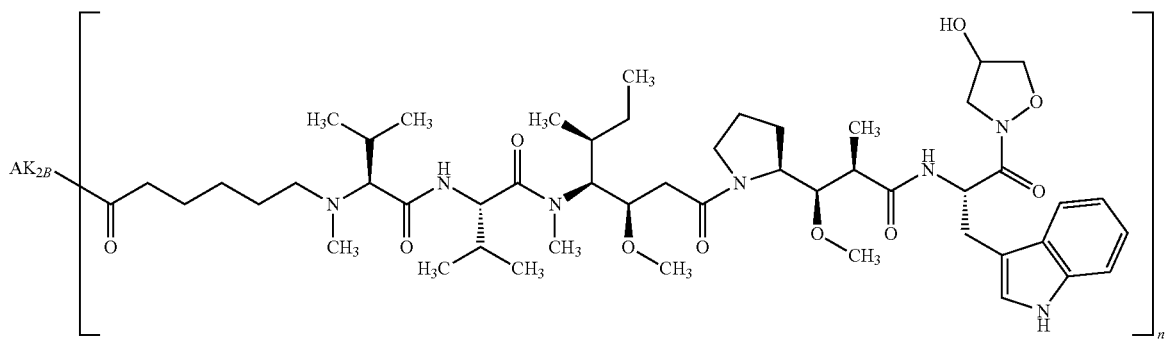

Coupling here was carried out using Intermediate 247a and 5 mg of anti-C4.4a B01-3 in PBS, and the batch, following Sephadex purification, was concentrated by ultracentrifugation and re-diluted with PBS.

Protein concentration: 1.42 mg/ml
Drug/mAb Ratio: 4.0

Example 126

N-(6-{[(55)-5-Amino-5-carboxypentl]amino}-6-oxohexyl)-N-methyl-L-threonyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino]-1-methoxy-2-methyl-3-oxopropyl]pyrrolidin-1-yl}-3-methoxy-5-methyl-1-oxoheptan-4-yl]-N-methyl-L-valinamide trifluoroacetate

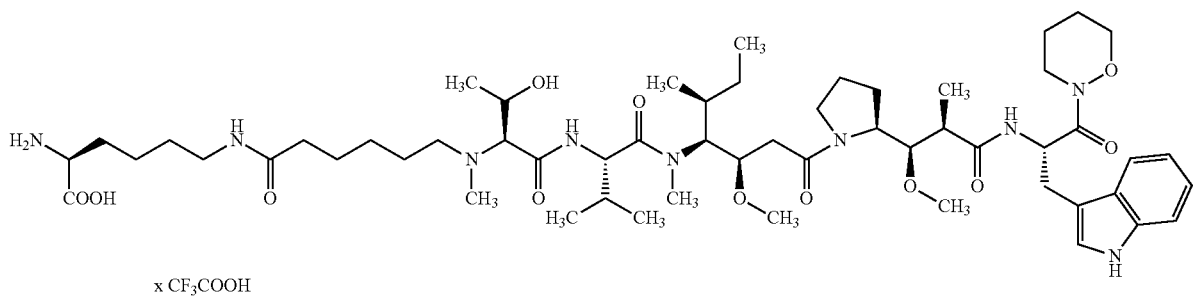 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)O)N(C)CCCCCC(=O)NCCCC[C@H](N)C(=O)O)C(C)C]

x CF₃COOH 8.6 mg (8 µmol) of Intermediate 240 were taken up in 5 ml of DMF and admixed with 4.0 mg (16 µmol) of N²-(tert-butoxycarbonyl)-L-lysine and also 2 µL (16 µmol) of N,N-diisopropylethylamine. The reaction mixture was stirred at RT for 4 hours, then admixed again with the same amounts of N²-(tert-butoxycarbonyl)-L-lysine and N,N-diisopropylethylamine, and stirred at RT overnight. The reaction mixture was subsequently concentrated under reduced pressure. The residue was then purified by preparative HPLC. This gave 7 mg (72% of theory) of the protected intermediate of the title compound, which was subsequently taken up in 1 ml of dichloromethane and deprotected with 0.5 ml of trifluoroacetic acid. The reaction mixture was concentrated and the residue was purified by preparative HPLC. Drying under a high vacuum gave 3.3 mg (47% of theory) of the title compound.

HPLC (Method 5): $R_t$=1.5 min;

LC-MS (Method 1): $R_t$=0.8 min; MS (ESIpos): m/z=1084 (M+H)⁺.

Example 127

N-(6-{[(5S)-5-Amino-5-carboxypentyl]amino}-6-oxohexyl)-N-methyl-L-valyl-N-[(3R,4S,5S)-1-{(2S)-2-[(1R,2R)-3-{[(2S)-3-(4-hydroxyphenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

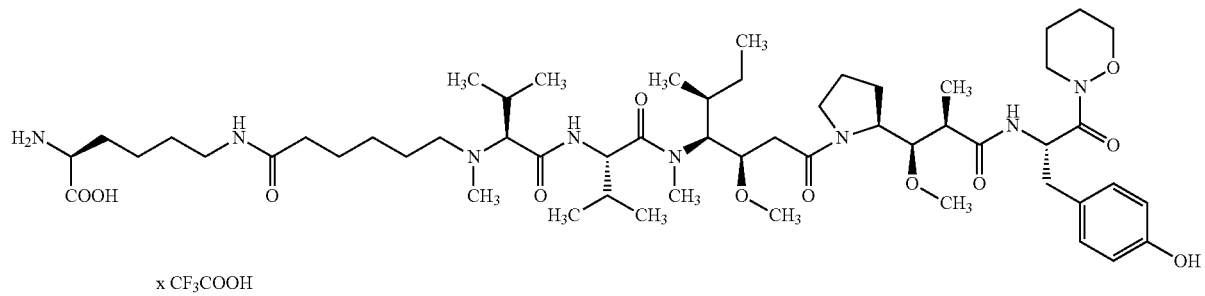 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)N1CCCCO1)OC)N(C)C(=O)[C@@H](NC(=O)[C@H](C(C)C)N(C)CCCCCC(=O)NCCCC[C@H](N)C(=O)O)C(C)C]

x CF₃COOH 8 mg (8 μmol) of Intermediate 242 were taken up in 3 ml of DMF and admixed with 2.9 mg (12 μmol) of N²-(tert-butoxycarbonyl)-L-lysine and also 2.7 μL (16 μmol) of N,N-diisopropylethylamine. The reaction mixture was stirred at RT overnight, then admixed again with the same amounts of N²-(tert-butoxycarbonyl)-L-lysine and N,N-diisopropylethylamine, and stirred at RT for a further 4 hours. The reaction mixture was subsequently concentrated under reduced pressure. The residue was then purified by preparative HPLC. Lyophilization from acetonitrile/water gave 6.5 mg (72% of theory) of the protected intermediate of the title compound, which was subsequently taken up in 5 ml of dichloromethane and deprotected with 0.75 ml of trifluoroacetic acid. The batch was concentrated, and lyophilization of the residue from dioxane/water gave 5 mg (76% of theory) of the title compound.

HPLC (Method 12): $R_t$=1.7 min;

LC-MS (Method 1): $R_t$=0.69 min; MS (ESIpos): m/z=1059 (M+H)⁺.

Example 128

N-(6-{[(5S)-5-Amino-5-carboxypentyl]amino}-6-oxohexyl)-N-methyl-L-valyl-N-[(3R,4S,5S)-1-{(2S)-2-[(1R,2R)-3-{[(1S)-1-carboxy-2-(4-hydroxyphenyl)ethyl]amino}-1-methoxy-2-methyl-3-oxopropyl]pyrrolidin-1-yl}-3-methoxy-5-methyl-1-oxoheptan-4-yl]-N-methyl-L-valinamide trifluoroacetate

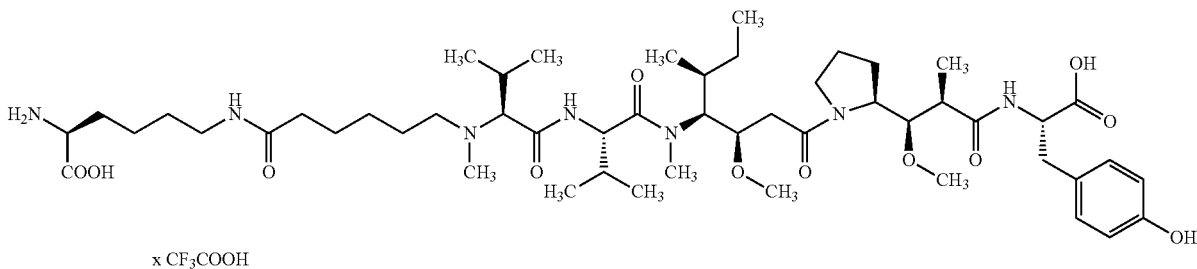 [SMILES: CC[C@H](C)[C@@H]([C@@H](CC(=O)N1CCC[C@H]1[C@H](OC)[C@@H](C)C(=O)N[C@@H](Cc1ccc(O)cc1)C(=O)O)OC)N(C)C(=O)[C@@H](NC(=O)[C@H](C(C)C)N(C)CCCCCC(=O)NCCCC[C@H](N)C(=O)O)C(C)C]

x CF₃COOH 38 mg (41 μmol) of Intermediate 248 were first converted into the N-hydroxysuccinimide ester. 72 mg of the crude product obtained were taken up in 5 ml of DMF and admixed with 24 mg (100 μmol) of N²-(tert-butoxycarbonyl)-L-lysine and 23 μL of N,N-diisopropylethylamine. The reaction mixture was stirred at RT overnight, and then admixed again with 16 mg of N²-(tert-butoxycarbonyl)-L-lysine and 12 μL of N,N-diisopropylethylamine, and subsequently treated in an ultrasound bath for a further 2 hours. The batch was then concentrated under reduced pressure and the residue was purified by preparative HPLC. Lyophilization from acetonitrile/water gave 20 mg (50% of theory) of the protected intermediate of the title compound.

15 mg (12 µmol) of this intermediate were subsequently taken up in 3 ml of dichloromethane and admixed with 1 ml of trifluoroacetic acid. After 40 minutes of stirring at RT, a further 1.5 ml of trifluoroacetic acid were added and the batch was treated in an ultrasound bath for 1 hour. Thereafter the reaction mixture was concentrated, and lyophilization of the residue from dioxane/water gave 13 mg (90% of theory) of the title compound.

HPLC (Method 12): $R_t$=1.5 min;

LC-MS (Method 1): $R_t$=0.68 min; MS (ESIpos): m/z=990 $(M+H)^+$.

C: EVALUATION OF BIOLOGICAL ACTIVITY

The biological effect of the compounds of the invention was demonstrated in the assays described below

C-1. Analysis of the Cytotoxic Effect of the ADCs Directed Against C4.4a

The cytotoxic effect of the anti-C4.4a ADCs is analysed in different cell lines:

- A549 (CCL-185, ATCC), transfected with the sequence for the complete C4.4a receptor,
- A549, Mock transfected
- A549 Wildtype (DSMZ, lot 11)
- NCI-H292, endogenously C4.4a expressing lung cancer cell line (CRL-1848, ATCC)
- SCC-4 endogenously C4.4a expressing squamous epithelial carcinoma cell line (CRL-1624, ATCC)
- SCC-9 endogenously C4.4a expressing squamous epithelial carcinoma cell line (CRL-1629, ATCC)
- HCT-116 endogenously C4.4a expressing colonic carcinoma cell line (CCL-247, ATCC)
- HCT-116/VM46, HCT-116 transfected with VM46
- A431NS(CRL-2592, ATCC)

The cells are cultivated by a standard method, as indicated in the American Tissue Type Collection (ATCC) for the respective cell lines. For the procedure, the cells are detached using a solution of trypsin (0.05%) and EDTA (0.02%) in PBS (Biochrom AG #L2143), pelletized, resuspended in culture medium, counted and seeded out into a 96-well culture plate with a white base (Costar $\#^{3610}$) (2500 cells in 100 µl/well) and incubated in an incubator at 37° C. with 5% carbon dioxide. After 24 hours, the antibody-drug conjugates in 100 µl of culture medium are applied to the cells at concentrations of $10^{-7}$M to $10^{-11}$M (duplicate values), and were incubated in the incubator at 37° C. with 5% carbon dioxide. After 72 hours, cell viability is determined using the Cell Titer Glow Luminescent Cell Viability Assay (Promega #G7573 and #G7571). For this purpose, 100 µl of the substrate are added per cell batch, and the plates are subsequently covered with aluminium foil, shaken at 180 rpm in a plate shaker for 2 minutes, left to stand on the laboratory bench for 8 minutes, and then measured using a Victor X2 (Perkin Elmer). The substrate detects the ATP content of the living cells, producing a luminescence signal whose extent is directly proportional to the vitality of the cells. The data measured is used for calculating the $IC_{50}$ using the Graph Pad Prism Laboratory software.

Table 3 lists the $IC_{50}$ values[1]) of representative working examples from this assay:

TABLE 3

| Example | $IC_{50}$ [nM] A549: C4.4a | $IC_{50}$ [nM] A549 Mock |
|---|---|---|
| 1 | 0.081 | 11.15 |
| 2 | 0.7 | 50 |
| 3 | 0.47 | 4.75 |
| 4 | 0.6 | 100 |
| 5 | 0.4 | 20 |
|  | 0.2 | 26 |
|  | 0.1 | 17 |
| 6 | 0.53 | 4.50 |
| 7 | 0.39 | 32 |
| 8 | 0.01 | 0.15 |
| 9 | 0.43 | 10 |
| 10 | 0.01 | 25 |
| 11 | 4 | >100 |
| 12 | 0.58 | 6.36 |
| 13 | 0.7 | 14.9 |
| 14 | 0.1 | 65.5 |
| 15 | 0.030 | 9.53 |
| 16 | 3.8 | 21 |
| 17 | 0.62 | 4.19 |
| 18 | 0.4 | >100 |
| 19 | 1.2 | 66.1 |
| 20 | 0.46 | 4.20 |
| 21 | 4.5 | 12.7 |
| 22 | 5 | 16 |
| 23 | 0.4 | 0.7 |
| 24 | 0.3 | 23 |
| 25 | 5.4 | 53 |
| 26 | 0.052 | 11.27 |
| 27 | 0.65 | 6.70 |
| 28 | 0.062 | >100 |
| 29 | 0.02 | 2.5 |
| 30 | 0.1 | 71 |
| 31 | 0.32 | 9 |
| 32 | 0.035 | 6.19 |
| 33 | 0.037 | ~30 |
| 34 |  |  |
| 35 | 0.3 | 20 |
| 36 | 0.08 | >100 |
| 37 | 0.1 | kH |
| 38 | 0.03 | 50 |
| 39 | 0.04 | 1.5 |
| 40 | 0.6 | 50 |
| 41 | 0.4 | 2 |
| 42 | 0.1 | 14 |
| 43 | 0.062 | 6.33 |
| 44 | 0.044 | 6.93 |
| 45 | 0.058 | 4.01 |
| 46 | 0.062 | 7.74 |
| 47 | 0.066 | 9.11 |
| 48 | 0.061 | 6.78 |
| 49 | 0.076 | 100 |
| 50 | 0.02 | 0.02 |
| 51 | 0.044 | 44 |
| 52 | 0.04 | 45 |
| 53 | 0.046 | 26 |
| 54 | 0.074 | >100 |
| 55 | 0.053 | >100 |
| 56 | 0.037 | 60 |
| 57 | 0.3 | 1 |
| 58 | 0.04 | >100 |
| 59 | 0.1 | >100 |
| 60 | 0.04 | >100 |
| 61 | 0.44 | 6.8 |
| 62 | 0.09 | 50 |
| 63 | 0.1 | 0.4 |
| 64 | 0.04 | 0.52 |
| 65 | 0.03 | 0.04 |
| 66 | 0.03 | 0.04 |
| 67 | 0.08 | 26 |
| 68 | 0.02 | >100 |
| 69 | 0.17 | 0.27 |
| 70 | 0.06 | 7 |
| 80 | 3.0 | >100 |
| 81 | 0.045 | >100 |
| 82 | 0.06 | >100 |

TABLE 3-continued

| Example | IC$_{50}$ [nM] A549: C4.4a | IC$_{50}$ [nM] A549 Mock |
|---|---|---|
| 83 | 0.27 | >100 |
| 84 | 0.13 | >100 |
| 85 | 0.14 | >100 |
| 86 | 0.17 | >100 |
| 87 | 0.28 | >100 |
| 88 | 1.1 | >100 |
| 89 | 1.3 | >100 |
| 90 | >100 | >100 |
| 91 | 0.15 | kH |
| 92 | 0.29 | >100 |
| 93 | 0.04 | >100 |
| 94 | 0.035 | 100 |
| 95 | 0.036 | >100 |
| 96 | 0.018 | >100 |
| 97 | 0.062 | >100 |
| 98 | 0.06 | >100 |
| 99 | 0.1 | 80 |
| 100 | 0.1 | kH |
| 101 | 0.3 | kH |
| 102 | 0.1 | kH |
| 103 | 0.2 | 30 |
| 104 | 3 | kH |
| 105 | 0.03 | 50 |
| 106 | 0.05 | 20 |
| 107 | >100 | kH |
| 108 | 0.03 | >100 |
| 109 | 1 | >100 |
| 110 | 0.2 | kH |
| 112 | 0.27 | >100 |
| 113 | 3 | >100 |
| 114 | 0.05 | >100 |
| 118 | 0.29 | 20 |
| 119 | 0.32 | 15 |
| 120 | 0.07 | >100 |
| 121 | 0.03 | 7 |
| 122 | 0.04 | >100 |
| 123 | 0.02 | >100 |
| 124 | 0.04 | >100 |
| 125 | 0.04 | >100 |

[1] The activity data reported relate to the working examples described in the present experimental section, with the drug/mAB ratios indicated. The values may possibly deviate for different drug/mAB ratios.

C-2. Determination of the Effect on Tubulin Polymerization

Cancer cells are denatured cells which frequently lead to the formation of tumours also as a result of increased cell division. Microtubuli form the spindle fibres of the spindle apparatus and are an essential constituent of the cell cycle. The regulated construction and breakdown of microtubuli allows the precise division of the chromosomes among the daughter cells, and constitutes a continuously dynamic process. Disruption to this dynamic process results in incorrect cell division and ultimately in cell death. The increased cell division of cancer cells, however, also makes them particularly sensitive towards spindle fibre poisons, which constitute a fixed constituent of chemotherapy. Spindle fibre poisons such as paclitaxel or epothilone lead to a sharply increased polymerization rate of the microtubuli, while vinca alkaloids or else monomethylauristatin E (MMAE) lead to a sharply reduced polymerization rate of the microtubuli. In both cases, the necessary dynamism of the cell cycle is critically disrupted. The compounds investigated in the context of the present invention result in a reduced polymerization rate of the microtubuli.

Tubulin polymerization was investigated using the "Fluorescence-based Microtubule Polymerisation Assay Kit" from Cytoskeleton (Denver, Colo., USA; order number: BK011). With this assay, GTP is added to unpolymerized tubulin, allowing polymerization to take place spontaneously. The assay is based on the binding of the fluorophore 4',6-diamidino-2-phenylindole (DAPI) to tubulin. Free and bound DAPI can be differentiated on the basis of different emission spectra. Since DAPI exhibits a significantly high affinity for polymerized tubulin in comparison to non-polymerized tubulin, the tubulin polymerization can be followed via the increase in the fluorescence of bound DAPI fluorophores.

For the implementation of this assay, the compounds of the invention, in solution in DMSO, were diluted from their initial concentration of 10 mM to 1 µM in water. In addition to the buffer control, paclitaxel, with a polymerization-increasing effect, and vinblastin, with a polymerization inhibiting effect, were run additionally as assay controls. Measurement was carried out using 96-well plates with a half base area. The kinetics of the tubulin polymerization were monitored in a Fluorimeter at 37° C. for 1 hour. The excitation wavelength was 355 nm, and emission was monitored at 460 nm. For the region of linear increase within the first 10 minutes, a calculation was made of the change in fluorescence per minute (ΔF/min), which represents the polymerization rate of the microtubuli. The potency of the test substances was quantified on the basis of their respective reduction of the polymerization rate.

The value for the inhibition of MMAF at a concentration of 1 µM is set as being 100%.

Table 4 gives data for the inhibition of tubulin polymerization by representative working examples.

TABLE 4

| Working example | Concentration of toxophore [µM] | Tubulin polymerization in the presence of toxophore in [%]. Tubulin polymerization rate at 1 µM MMAF set at 100% |
|---|---|---|
| MMAF | 1 | 100 |
| MMAF | 10 | 34 |
| MMAF | 100 | 0 |
| 115 | 1 | 45 |
| 115 | 10 | 1 |
| 116 | 1 | 80 |
| 116 | 10 | 14 |
| 117 | 1 | 60 |
| 117 | 10 | 0 |
| 71 | 1 | 88 |
| 71 | 10 | 25 |
| 72 | 1 | 109 |
| 72 | 10 | 27 |
| 73 | 1 | 120 |
| 74 | 1 | 117 |
| 74 | 10 | 64 |
| 75 | 1 | 107 |
| 75 | 10 | 25 |
| 76 | 1 | 121 |
| 76 | 10 | 35 |
| 77 | 1 | 111 |
| 77 | 10 | 45 |
| 78 | 1 | 110 |
| 117 | 1 | 78 |
| 117 | 10 | 24 |
| 126 | 1 | 102 |
| 126 | 10 | 31 |
| 127 | 1 | 88 |
| 127 | 10 | 21 |
| 128 | 1 | 90 |
| 128 | 10 | 17 |

The MMAF toxophore and the working examples inhibit tubulin polymerization as a function of their concentration. At 100 µM MMAF, the tubulin polymerization is inhibited completely. Working Example 115 inhibits the tubulin polymerization rate at 1 µM to 45% of the value measured for 1 µM MMAF.

C-3. In Vitro Tests for Determining Cell Permeability

The cell permeability of a substance can be investigated by means of in vitro testing in a flux assay using Caco-2 cells [M. D. Troutman and D R Thakker, Pharm. Res. 20 (8), 1210-1224 (2003)]. For this purpose, the cells were cultured for 15-16 days on 24-well filter plates. For the determination of permeation, the respective working example was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Boblingen, Germany) using reverse phase columns. The HPLC system was coupled via a Turbo Ion Spray Interface to a Triple Quadropol mass spectrometer API 4000 (Applied Biosystems Applera, Darmstadt, Germany). The permeability was evaluated on the basis of a $P_{app}$ value, which was calculated using the formula published by Schwab et al. [D. Schwab et al., J. Med. Chem. 46, 1716-1725 (2003)].

Of critical importance for toxophores which are released intracellularly is the permeability from B to A [$P_{app}$ (B-A)]: the lower this permeability, the longer the residence time of the working example in the cell following intracellular release, and hence also the longer the time available for interaction with the biochemical target (in this case: tubulin).

Table 5 below sets out permeability data for representative working examples from this assay:

TABLE 5

| Working example | $P_{app}$ (B-A) [nm/s] |
|---|---|
| 71 | 2 |
| 72 | 1.6 |
| 73 | 2.5 |
| 74 | 5 |
| 75 | 1 |
| 77 | 7 |
| 115 | 2 |
| 116 | 1 |
| 126 | 1.8 |
| 127 | 1.5 |

The working examples exhibit a low permeability from B to A [$P_{app}$ (B-A) and therefore have a long residence time in the CaCo-2 cells. In comparison, monomethylauristatin E (MMAE) and monomethylauristatin F (MMAF) in this test exhibit a $P_{app}$ (B-A) value of 73 nm/s, and therefore have a significantly shorter residence time in the Caco-2 cells.

C-4. In Vitro Tests for Determining the Substrate Properties for P-Glycoprotein (P-gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., J. Clin. Invest. 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as Ivermectin or Verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany). The permeability was evaluated on the basis of a $P_{app}$ value which was calculated using the formula published by Schwab et al. [D. Schwab et al., J. Med. Chem. 46, 1716-1725 (2003)].

Of critical importance for toxophores which are released intracellularly is the permeability from B to A [$P_{app}$ (B-A)]: the lower this permeability, the longer the residence time of the working example in the cell following intracellular release, and hence also the longer the time available for interaction with the biochemical target (in this case: tubulin).

Table 6 below lists permeability data for representative working examples from this assay, which was carried out in L-MDR1 cells:

TABLE 6

| Working example | $P_{app}$ (B-A) [nm/s] |
|---|---|
| 71 | 3 |
| 72 | 3.6 |
| 73 | 2.1 |
| 74 | 3.6 |
| 75 | 4 |
| 77 | 2 |
| 115 | 6 |
| 116 | 4 |

The working examples exhibit a low permeability from B to A [$P_{app}$ (B-A) and therefore have a long residence time in the L-MDR1 cells.

C-5. Activity Test In Vivo

The activity of the conjugates of the invention was tested in vivo by means, for example, of xenograft models. The skilled person knows of methods in the prior art for testing the activity of a conjugate of the invention (see, for example, WO 2005/081711; Polson et al., Cancer Res. 2009 Mar. 15; 69(6): 2358-64). For this purpose, for example, rodents (e.g. mice) were implanted with a tumour cell line which expresses the target molecule of the binder. These tumour-bearing rodents were subsequently administered either a conjugate of the invention or a control antibody conjugate, or isotonic salt solution. Administration took place singularly or more often. Tumour growth was determined twice weekly with the aid of a sliding calliper. After tumour growth for several weeks, the tumour size of conjugate-treated animals was compared with that of the control group. The conjugate-treated animals showed a significantly smaller tumour size.

C-5a. Testing of ADCs in Experimental Tumours in the Mouse

The predictive force of mice xenograft tumour models, relative to the clinical situation in the case of immunotoxin therapies, is often limited, on the one hand by the deficient cross-reactivity of the therapeutic antibodies with the murine species, and on the other hand by the incidence of anti-drug antibodies (ADAs) in the human body on administration of murine or chimeric antibodies. In order to utilize the full potential of the specific C4.4a expression for cancer therapy, for an immunoconjugate approach, for example, there is a need for human antibodies which are of high affinity, are selective and exhibit species cross-reactivity, of the kind employed preferably in accordance with the invention. With such antibodies, mice xenograft tumour models yield meaningful findings relative to the clinical situation.

Human tumour cells which express C4.4a are inoculated subcutaneously into the flank of immunosuppressed mice, such as nude mice or SCID mice. 1-10 million cells are detached from the cell culture, centrifuged and resuspended with 100 µl of medium or 50% medium/50% Matrigel. The cell suspension is injected beneath the skin of the mouse.

Within a few days, a tumour grows. Treatment begins no earlier than after tumour establishment with a tumour size of 25 mm².

Treatment with ADCs takes place by the intravenous route into the caudal vein of the mouse. The ADC is dissolved in PBS and is administered with a volume of 10 ml/kg.

The treatment scheme is governed by the pharmacokinetics of the antibody. As a standard, the treatment takes place three times following every fourth day. Treatment, however, may also be continued further, or a second cycle with three days of treatment may follow at a later point in time.

As a standard basis, 8 animals are used per treatment group. This number may be higher if particularly strong fluctuations in tumour growth or after treatment are anticipated. As well as the groups which receive the active substances, one group, as a control group, is treated only with the buffer, in accordance with the same scheme.

In the course of the experiment, the area of the tumour is measured regularly using a sliding calliper in two dimensions (length/width).

At the end of the experiment, the tumours are removed and weighed. The ratio of the average tumour weights for the therapy group (T) to the control group (C) is expressed as T/C. Where control groups and treatment groups are ended at different times, the T/C value is calculated on the basis of the tumour areas of the last joint measurement of all the treatment groups and control groups.

1 million SCC-4 cells are inoculated subcutaneously into the flank of female NMRI nude mice.

Intravenous treatment with the ADCs is commenced at an average tumour size of 30-35 mm². When the control groups have reached the maximum allowed size, the experiment is ended and the tumours are removed and weighed. All of the ADCs tested that target C4.4a have inhibited tumour growth in a dose-dependent manner. At a dose of 30 mg/kg, Example 54, Example 49, Example 51 and Example 53 each reached a T/C of <0.1. Significant anti-tumour activity in comparison to the control was achieved for Examples 49, 52, 53, 54 and 56 at a dose of down to 15 mg/kg, achieving T/C values of ≤0.29.

1 million NCI-H292 cells were inoculated subcutaneously into the flank of female NMRI nude mice.

Intravenous treatment with the ADCs is commenced at an average tumour size of 30-35 mm². Control groups and treatment groups are each ended when the maximum allowable tumour size is reached. In this way, differences in the further growth of tumours after the end of treatment may contribute to further characterization of the ADCs. Consequently, the tumour areas at the last joint point in time of measurement was employed for determining the anti-tumour activity in comparison to the control (T/C). In the NCI-H292 mouse model used, it is shown that all of the ADCs tested reduce tumour growth dose-dependently in comparison to the control. A significant anti-tumour effect was obtained for Example 54 at a dose of down to 1.9 mg/kg, and for Example 49 at a dose of down to 3.75 mg/kg. The minimum T/C values obtained in this model are a T/C of 0.16 at 30 mg/kg for Example 54, a T/C of 0.17 at 30 mg/kg for Example 49, a T/C of 0.16 at 30 mg/kg for Example 53, a T/C of 0.17 at 15 mg/kg for Example 51, and a T/C of 0.19 at 3.75 mg/kg for Example 70. On comparative administration of the ADCs with a constant dose of 7.5 mg/kg, it was possible to achieve a T/C of 0.20 with each of Examples 49 and 54, a T/C of 0.27 with Example 51, a T/C of 0.22 with Example 52, a T/C of 0.23 with Example 53, a T/C of 0.24 with Example 55, a T/C of 0.21 with Example 56 and a T/C of 0.17 with Example 70.

C-6. Pharmacokinetics in the A549 Tumour Model with C4.4a-Transfected and Non-Transfected A549 Cells Following intravenous administration of 7-30 mg/kg of various ADCs, the plasma concentrations and tumour concentrations of ADC and also of potential metabolites were measured, and the pharmacokinetic parameters such as clearance (CL), area under the curve (AUC) and half-life ($t_{1/2}$) were calculated.

Analysis for Quantifying the Potential Metabolites

The measurement of the compounds in plasma and tumour took place following precipitation of the proteins with methanol, by means of high-pressure liquid chromatography (HPLC) coupled to a tandem mass spectrometer (MS).

For the processing of 100 µL of plasma, it was admixed with 400 µL of methanol and 10 µL of internal standard (ISTD, 50 ng/mL in methanol) and shaken for 10 seconds. After centrifuging for 5 minutes at 16 000 g, 250 µL of supernatant were transferred to an autosampler vial, which was made up with 250 µL of ammonium acetate buffer (AAC, 10 mM, pH 6.8) and shaken again.

For the processing of a tumour, it was admixed with 4 times the amount of methanol. In a Tissuelyser II (Quiagen), the sample was comminuted at 30 impacts per minute for 6 minutes and then centrifuged off at 16 000 g for 5 minutes. 50 µL of the supernatant were transferred to an autosampler vial and made up with 50 µL of ammonium acetate buffer (10 mM, pH 6.8) and with 5 µL of ISTD. After again being shaken, the tumour sample was ready for measurement.

The measurement of both matrix samples took place, lastly, on the HPLC-coupled, atmospheric pressure ionization/tandem mass spectrometer by means of a Turbo Ion Spray Interface (TISP) on an API4000 instrument from SCIEX.

HPLC/LC-MSMS (TISP) analysis ran on an HP1100 pump (Agilent) with a Gemini column (5 µm C18 110 A, 50×3 mm, Phenomenex).

For calibration, plasma samples were admixed with concentrations of 0.5-2000 µg/L. The detection limit (LOQ) was about 2 µg/L. The linear range extended from 2 to 1000 µg/L For the calibration of the tumour samples, the supernatant of untreated tumours was admixed with concentrations of 0.5-200 µg/L. The detection limit was 5 µg/L. The linear range extended from to 200 µg/L.

Quality controls for validity testing contained 5 and 50 µg/L, with an additional 500 µg/L in plasma. The concentrations found for these samples deviated by up to 20% from the intended value (data not attached).

D. WORKING EXAMPLES FOR PHARMACEUTICAL COMPOSITIONS

The compounds of the invention can be converted as follows into pharmaceutical preparations:

i.v. Solution:

The compound of the invention is dissolved at a concentration below the saturation solubility in a physiologically tolerated solvent (e.g. isotonic saline solution, D-PBS, or a formulation with glycine and sodium chloride in citrate buffer with addition of polysorbate 80). The solution is subjected to sterile filtration and dispensed into sterile and pyrogen-free injection containers.

i.v. Solution:

The compounds of the invention can be converted into the administration forms cited. This can be accomplished in a known way by "mixing with" or "dissolving in" inert, non-toxic, pharmaceutically suitable excipients (e.g. buffer substances, stabilizers, solubilizers, preservatives). The following, for example, may be present: amino acids (glycine, histidine, methionine, arginine, lysine, leucine, isoleucine, threonine, glutamic acid, phenylalanine and others), sugars and related compounds (glucose, saccharose, mannitol, trehalose, sucrose, mannose, lactose, sorbitol), glycerol, sodium salts, potassium, ammonium salts and calcium salts (e.g. sodium chloride, potassium chloride or disodiumhydrogenphosphate and many others), acetate/acetic acid buffer systems, phosphate buffer systems, citric acid and citrate buffer systems, trometamol (TRIS and TRIS salts), Polysorbates (e.g. Polysorbate 80 and Polysorbate 20), Poloxamers (e.g. Poloxamer 188 and Poloxamer 171), Macrogols (PEG derivatives, e.g. 3350), Triton X-100, EDTA salts, glutathione, albumins (e.g. human), urea, benzyl alcohol, phenol, chlorocresol, metacresol, benzalkonium chloride and many others.

Lyophilizate for Subsequent Conversion into an i.v., s.c. or i.m. Solution:

Alternatively the compounds of the invention may be converted into a stable lyophilizate (possibly with the aid of abovementioned excipients) and, before being administered, reconstituted with a suitable solvent (e.g. injection-grade water, isotonic saline solution) and administered.

---

The invention claimed is:

1. A binder-drug conjugate having the structure:

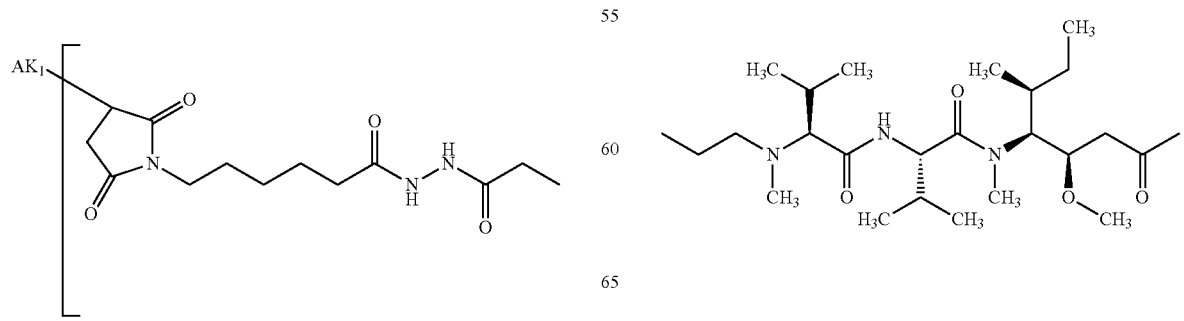

-continued

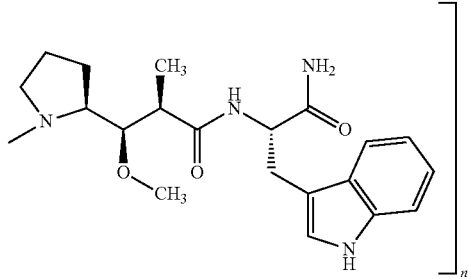

or a salt thereof, in which
n is a number from 1 to 20,
and
AK₁ is a human or humanized antibody or an antigen-binding antibody fragment which binds to C4.4a and is bonded via a cysteine residue to the toxophor-linker unit.

2. The binder-drug conjugate of claim 1, wherein n is a number from 1 to 10.

3. The binder-drug conjugate of claim 1, wherein n is a number from 2 to 8.

4. The binder-drug conjugate of claim 1, wherein the antibody or antigen-binding antibody fragment comprises three heavy chain CDR regions comprising the amino acid sequences of SEQ ID NOs: 45-47 and three light chain CDR regions comprising the amino acid sequences of SEQ ID NOs: 48-50.

5. The binder-drug conjugate of claim 1, wherein the antibody or antigen-binding antibody fragment comprises a heavy chain variable region comprising the amino acid sequence of SEQ ID NO: 51 and a light chain variable region comprising the amino acid sequence of SEQ ID NO: 52.

6. The binder-drug conjugate of claim 1, wherein AK₁ is an antibody comprising a heavy chain and a light chain, the heavy chain comprising the amino acid sequence of SEQ ID NO: 353 and the light chain comprising the amino acid sequence of SEQ ID NO: 352.

7. The binder-drug conjugate of claim 3, wherein the antibody or antigen-binding antibody fragment comprises three heavy chain CDR regions comprising the amino acid sequences of SEQ ID NOs: 45-47 and three light chain CDR regions comprising the amino acid sequences of SEQ ID NOs: 48-50.

8. The binder-drug conjugate of claim 3, wherein the antibody or antigen-binding antibody fragment comprises a heavy chain variable region comprising the amino acid sequence of SEQ ID NO: 51 and a light chain variable region comprising the amino acid sequence of SEQ ID NO: 52.

9. The binder-drug conjugate of claim 3, wherein AK₁ is an antibody comprising a heavy chain and a light chain, the heavy chain comprising the amino acid sequence of SEQ ID NO: 353 and the light chain comprising the amino acid sequence of SEQ ID NO: 352.

10. A medicament comprising the binder-drug conjugate of claim 1 in combination with a pharmaceutically acceptable excipient.

11. A medicament comprising the binder-drug conjugate of claim 4 in combination with a pharmaceutically acceptable excipient.

12. The medicament of claim 11, wherein n is a number from 2 to 8.

* * * * *

SEQUENCE LISTING

<160> NUMBER OF SEQ ID NOS: 446

<210> SEQ ID NO 1
<211> LENGTH: 278
<212> TYPE: PRT
<213> ORGANISM: Homo Sapiens

<400> SEQUENCE: 1

Leu Glu Cys Tyr Ser Cys Val Gln Lys Ala Asp Asp Gly Cys Ser Pro
1               5                   10                  15

Asn Lys Met Lys Thr Val Lys Cys Ala Pro Gly Val Asp Val Cys Thr
            20                  25                  30

Glu Ala Val Gly Ala Val Glu Thr Ile His Gly Gln Phe Ser Leu Ala
        35                  40                  45

Val Arg Gly Cys Gly Ser Gly Leu Pro Gly Lys Asn Asp Arg Gly Leu
    50                  55                  60

Asp Leu His Gly Leu Leu Ala Phe Ile Gln Leu Gln Gln Cys Ala Gln
65                  70                  75                  80

Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
            100                 105                 110

Cys Val Gly Leu Ser Arg Glu Ala Cys Gln Gly Thr Ser Pro Pro Val
        115                 120                 125

Val Ser Cys Tyr Asn Ala Ser Asp His Val Tyr Lys Gly Cys Phe Asp
    130                 135                 140

Gly Asn Val Thr Leu Thr Ala Ala Asn Val Thr Val Ser Leu Pro Val
145                 150                 155                 160

Arg Gly Cys Val Gln Asp Glu Phe Cys Thr Arg Asp Gly Val Thr Gly
                165                 170                 175

Pro Gly Phe Thr Leu Ser Gly Ser Cys Cys Gln Gly Ser Arg Cys Asn
            180                 185                 190

Ser Asp Leu Arg Asn Lys Thr Tyr Phe Ser Pro Arg Ile Pro Pro Leu
        195                 200                 205

Val Arg Leu Pro Pro Glu Pro Thr Thr Val Ala Ser Thr Thr Ser
    210                 215                 220

Val Thr Thr Ser Thr Ser Ala Pro Val Arg Pro Thr Ser Thr Thr Lys
225                 230                 235                 240

Pro Met Pro Ala Pro Thr Ser Gln Thr Pro Arg Gln Gly Val Glu His
                245                 250                 255

Glu Ala Ser Arg Asp Glu Glu Pro Arg Leu Thr Gly Gly Ala Ala Gly
            260                 265                 270

His Gln Asp Arg Ser Asn

<210> SEQ ID NO 2
<211> LENGTH: 293
<212> TYPE: PRT
<213> ORGANISM: Mus musculus

<400> SEQUENCE: 2

```
Leu Glu Cys Tyr Ser Cys Val Gln Lys Ala Asp Gly Cys Ser Pro
1               5                   10                  15

His Arg Met Lys Thr Val Lys Cys Gly Pro Gly Val Asp Val Cys Thr
            20                  25                  30

Glu Ala Val Gly Ala Val Glu Thr Ile His Gly Gln Phe Ser Val Ala
        35                  40                  45

Val Arg Gly Cys Gly Ser Gly Ile Pro Gly Lys Asn Asp Arg Gly Leu
    50                  55                  60

Asp Leu His Gly Leu Leu Ala Phe Phe Gln Leu Gln Gln Cys Ser Glu
65                  70                  75                  80

Asp Arg Cys Asn Ala Lys Leu Asn Leu Thr Leu Arg Gly Leu Asn Pro
                85                  90                  95

Ala Gly Asn Glu Ser Ala Tyr Glu Pro Asn Gly Ala Glu Cys Tyr Ser
            100                 105                 110

Cys Val Gly Leu Ser Arg Glu Lys Cys Gln Gly Ser Met Pro Pro Val
        115                 120                 125

Val Asn Cys Tyr Asn Ala Ser Gly Arg Val Tyr Lys Gly Cys Phe Asp
    130                 135                 140

Gly Asn Val Thr Leu Thr Ala Ala Asn Val Thr Val Ser Leu Pro Val
145                 150                 155                 160

Arg Gly Cys Val Gln Asp Glu Thr Cys Thr Arg Asp Gly Val Thr Gly
                165                 170                 175

Pro Gly Phe Thr Leu Ser Gly Ser Cys Cys Gln Gly Pro Arg Cys Asn
            180                 185                 190

Ala Asp Leu Arg Asn Lys Thr Tyr Phe Ser Pro Arg Ile Pro Pro Leu
        195                 200                 205

Val Leu Leu Pro Pro Thr Thr Ala Ala Pro Ser Thr Arg Ala Gln
    210                 215                 220

Asn Ser Ser Ser Thr Thr Ser Thr Ala Ala Pro Thr Thr Thr Thr Ser
225                 230                 235                 240

Ile Ile Lys Pro Thr Thr Ala Gln Ala Ser His Thr Ser Pro His Glu
                245                 250                 255

Met Asp Leu Glu Val Ile Gln Glu Glu Gly Ala Ser Leu Ser Gly Gly
            260                 265                 270

Ala Ala Gly His Gly Gly Thr Ala Gly His Gly Gly Ala Ala Gly His
        275                 280                 285

Gln Asp Arg Ser Asn
    290
```

<210> SEQ ID NO 3
<211> LENGTH: 346
<212> TYPE: PRT
<213> ORGANISM: Homo Sapiens

<400> SEQUENCE: 3

```
Met Asp Pro Ala Arg Lys Ala Gly Ala Gln Ala Met Ile Trp Thr Ala
1               5                   10                  15

Gly Trp Leu Leu Leu Leu Leu Leu Arg Gly Gly Ala Gln Ala Leu Glu
```

```
            20                  25                  30
Cys Tyr Ser Cys Val Gln Lys Ala Asp Asp Gly Cys Ser Pro Asn Lys
             35                  40                  45

Met Lys Thr Val Lys Cys Ala Pro Gly Val Asp Val Cys Thr Glu Ala
 50                  55                  60

Val Gly Ala Val Glu Thr Ile His Gly Gln Phe Ser Leu Ala Val Arg
 65                  70                  75                  80

Gly Cys Gly Ser Gly Leu Pro Gly Lys Asn Asp Arg Gly Leu Asp Leu
                 85                  90                  95

His Gly Leu Leu Ala Phe Ile Gln Leu Gln Gln Cys Ala Gln Asp Arg
                100                 105                 110

Cys Asn Ala Lys Leu Asn Leu Thr Ser Arg Ala Leu Asp Pro Ala Gly
            115                 120                 125

Asn Glu Ser Ala Tyr Pro Pro Asn Gly Val Glu Cys Tyr Ser Cys Val
        130                 135                 140

Gly Leu Ser Arg Glu Ala Cys Gln Gly Thr Ser Pro Pro Val Val Ser
145                 150                 155                 160

Cys Tyr Asn Ala Ser Asp His Val Tyr Lys Gly Cys Phe Asp Gly Asn
                165                 170                 175

Val Thr Leu Thr Ala Ala Asn Val Thr Val Ser Leu Pro Val Arg Gly
                180                 185                 190

Cys Val Gln Asp Glu Phe Cys Thr Arg Asp Gly Val Thr Gly Pro Gly
            195                 200                 205

Phe Thr Leu Ser Gly Ser Cys Cys Gln Gly Ser Arg Cys Asn Ser Asp
210                 215                 220

Leu Arg Asn Lys Thr Tyr Phe Ser Pro Arg Ile Pro Pro Leu Val Arg
225                 230                 235                 240

Leu Pro Pro Pro Glu Pro Thr Thr Val Ala Ser Thr Thr Ser Val Thr
                245                 250                 255

Thr Ser Thr Ser Ala Pro Val Arg Pro Thr Ser Thr Thr Lys Pro Met
                260                 265                 270

Pro Ala Pro Thr Ser Gln Thr Pro Arg Gln Gly Val Glu His Glu Ala
            275                 280                 285

Ser Arg Asp Glu Glu Pro Arg Leu Thr Gly Gly Ala Ala Gly His Gln
        290                 295                 300

Asp Arg Ser Asn Ser Gly Gln Tyr Pro Ala Lys Gly Pro Gln Gln
305                 310                 315                 320

Pro His Asn Lys Gly Cys Val Ala Pro Thr Ala Gly Leu Ala Ala Leu
                325                 330                 335

Leu Leu Ala Val Ala Ala Gly Val Leu Leu
                340                 345

<210> SEQ ID NO 4
<211> LENGTH: 363
<212> TYPE: PRT
<213> ORGANISM: Mus musculus

<400> SEQUENCE: 4

Met Asp Ala Ala Arg Arg Gly Asp Thr Gln Pro Val Met Trp Thr Thr
 1               5                  10                  15

Gly Trp Leu Leu Leu Leu Pro Leu Leu Leu Cys Glu Gly Ala Gln Ala
                 20                  25                  30

Leu Glu Cys Tyr Ser Cys Val Gln Lys Ala Asp Asp Gly Cys Ser Pro
             35                  40                  45
```

```
His Arg Met Lys Thr Val Lys Cys Gly Pro Gly Val Asp Val Cys Thr
 50                  55                  60

Glu Ala Val Gly Ala Val Glu Thr Ile His Gly Gln Phe Ser Val Ala
 65                  70                  75                  80

Val Arg Gly Cys Gly Ser Gly Ile Pro Gly Lys Asn Asp Arg Gly Leu
                 85                  90                  95

Asp Leu His Gly Leu Leu Ala Phe Phe Gln Leu Gln Gln Cys Ser Glu
            100                 105                 110

Asp Arg Cys Asn Ala Lys Leu Asn Leu Thr Leu Arg Gly Leu Asn Pro
        115                 120                 125

Ala Gly Asn Glu Ser Ala Tyr Glu Pro Asn Gly Ala Glu Cys Tyr Ser
    130                 135                 140

Cys Val Gly Leu Ser Arg Glu Lys Cys Gln Gly Ser Met Pro Pro Val
145                 150                 155                 160

Val Asn Cys Tyr Asn Ala Ser Gly Arg Val Tyr Lys Gly Cys Phe Asp
                165                 170                 175

Gly Asn Val Thr Leu Thr Ala Ala Asn Val Thr Val Ser Leu Pro Val
            180                 185                 190

Arg Gly Cys Val Gln Asp Glu Thr Cys Thr Arg Asp Gly Val Thr Gly
        195                 200                 205

Pro Gly Phe Thr Leu Ser Gly Ser Cys Cys Gln Gly Pro Arg Cys Asn
    210                 215                 220

Ala Asp Leu Arg Asn Lys Thr Tyr Phe Ser Pro Arg Ile Pro Pro Leu
225                 230                 235                 240

Val Leu Leu Pro Pro Thr Thr Ala Ala Pro Ser Thr Arg Ala Gln
                245                 250                 255

Asn Ser Ser Ser Thr Thr Ser Thr Ala Ala Pro Thr Thr Thr Thr Ser
            260                 265                 270

Ile Ile Lys Pro Thr Thr Ala Gln Ala Ser His Thr Ser Pro His Glu
        275                 280                 285

Met Asp Leu Glu Val Ile Gln Glu Gly Ala Ser Leu Ser Gly Gly
    290                 295                 300

Ala Ala Gly His Gly Gly Thr Ala Gly His Gly Gly Ala Ala Gly His
305                 310                 315                 320

Gln Asp Arg Ser Asn Met Glu Lys Tyr Pro Gly Lys Gly Ala Gln
                325                 330                 335

Ile Pro Ala Lys Gly Gly Ser Gly Thr Leu Gly Ser Trp Leu Ser Ala
            340                 345                 350

Val Leu Leu Thr Val Val Ala Gly Ala Met Leu
        355                 360

<210> SEQ ID NO 5
<211> LENGTH: 9
<212> TYPE: PRT
<213> ORGANISM: Artificial Sequence
<220> FEATURE:
<223> OTHER INFORMATION: C4.4a binder

<400> SEQUENCE: 5

Phe Ser Asn Ala Trp Met Ser Trp Val
1               5

<210> SEQ ID NO 6
<211> LENGTH: 9
<212> TYPE: PRT
<213> ORGANISM: Artificial Sequence
<220> FEATURE:
```

```
<223> OTHER INFORMATION: C4.4a binder

<400> SEQUENCE: 6

Phe Ser Asp Tyr Gln Met Thr Trp Ile
1               5

<210> SEQ ID NO 7
<211> LENGTH: 9
<212> TYPE: PRT
<213> ORGANISM: Artificial Sequence
<220> FEATURE:
<223> OTHER INFORMATION: C4.4a binder

<400> SEQUENCE: 7

Phe Gly His Tyr Tyr Met Phe Trp Ile
1               5

<210> SEQ ID NO 8
<211> LENGTH: 8
<212> TYPE: PRT
<213> ORGANISM: Artificial Sequence
<220> FEATURE:
<223> OTHER INFORMATION: C4.4a binder

<400> SEQUENCE: 8

Phe Ser Ser Asn Tyr Met Ser Trp
1               5

<210> SEQ ID NO 9
<211> LENGTH: 20
<212> TYPE: PRT
<213> ORGANISM: Artificial Sequence
<220> FEATURE:
<223> OTHER INFORMATION: C4.4a binder

<400> SEQUENCE: 9

Val Ser Tyr Ile Ser Ser Ser Gly Ser Thr Ile Tyr Tyr Ala Asp Ser
1               5                   10                  15

Val Lys Gly Arg
            20

<210> SEQ ID NO 10
<211> LENGTH: 20
<212> TYPE: PRT
<213> ORGANISM: Artificial Sequence
<220> FEATURE:
<223> OTHER INFORMATION: C4.4a binder

<400> SEQUENCE: 10

Val Ser Gly Val Ser Trp Asn Gly Ala Arg Thr His Tyr Ala Asp Ser
1               5                   10                  15

Val Lys Gly Arg
            20

<210> SEQ ID NO 11
<211> LENGTH: 20
<212> TYPE: PRT
<213> ORGANISM: Artificial Sequence
<220> FEATURE:
<223> OTHER INFORMATION: C4.4a binder

<400> SEQUENCE: 11

Val Ser Ala Ile Ser Gly Ser Gly Tyr Ser Thr His Tyr Ala Asp Ser
1               5                   10                  15

Val Lys Gly Arg
```

```
<210> SEQ ID NO 12
<211> LENGTH: 20
<212> TYPE: PRT
<213> ORGANISM: Artificial Sequence
<220> FEATURE:
<223> OTHER INFORMATION: C4.4a binder

<400> SEQUENCE: 12

Val Ser Ala Ile Ser Ser Ser Gly Ser Ser Thr Tyr Tyr Ala Asp Ser
1               5                   10                  15

Val Lys Gly Arg
            20

<210> SEQ ID NO 13
<211> LENGTH: 10
<212> TYPE: PRT
<213> ORGANISM: Artificial Sequence
<220> FEATURE:
<223> OTHER INFORMATION: C4.4a binder

<400> SEQUENCE: 13

Ala Arg Glu Gly Leu Trp Ala Phe Asp Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: C4.4a binder

<400> SEQUENCE: 14

Ala Lys Gly Asp Tyr Leu Val Tyr Ser Ala Tyr Tyr Phe Asp Ser
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: C4.4a binder

<400> SEQUENCE: 15

Ala Arg Leu Pro Tyr Gly Ser Gln Ser Gly Val Asp Tyr
1               5                   10

<210> SEQ ID NO 16
<211> LENGTH: 17
<212> TYPE: PRT
<213> ORGANISM: Artificial Sequence
<220> FEATURE:
<223> OTHER INFORMATION: C4.4a binder

<400> SEQUENCE: 16

Ala Arg Glu Ser Gly Gly Ser Gly Pro Asn Tyr Tyr Tyr Gly Met Asp
1               5                   10                  15

Val

<210> SEQ ID NO 17
<211> LENGTH: 14
<212> TYPE: PRT
<213> ORGANISM: Artificial Sequence
<220> FEATURE:
<223> OTHER INFORMATION: C4.4a binder
```

```
<400> SEQUENCE: 17

Thr Gly Ser Ser Ser Asn Ile Gly Ala Gly Tyr Val Val His
1               5                   10

<210> SEQ ID NO 18
<211> LENGTH: 13
<212> TYPE: PRT
<213> ORGANISM: Artificial Sequence
<220> FEATURE:
<223> OTHER INFORMATION: C4.4a binder

<400> SEQUENCE: 18

Ser Gly Ser Ser Ser Asn Val Gly Ser Asn Pro Val Asn
1               5                   10

<210> SEQ ID NO 19
<211> LENGTH: 14
<212> TYPE: PRT
<213> ORGANISM: Artificial Sequence
<220> FEATURE:
<223> OTHER INFORMATION: C4.4a binder

<400> SEQUENCE: 19

Thr Gly Ser Ser Ser Asn Ile Gly Ala Gly Tyr Val Val His
1               5                   10

<210> SEQ ID NO 20
<211> LENGTH: 14
<212> TYPE: PRT
<213> ORGANISM: Artificial Sequence
<220> FEATURE:
<223> OTHER INFORMATION: C4.4a binder

<400> SEQUENCE: 20

Thr Gly Ser Ser Ser Asn Ile Gly Ala Gly Tyr Val Val His
1               5                   10

<210> SEQ ID NO 21
<211> LENGTH: 7
<212> TYPE: PRT
<213> ORGANISM: Artificial Sequence
<220> FEATURE:
<223> OTHER INFORMATION: C4.4a binder

<400> SEQUENCE: 21

Asp Asn Asn Lys Arg Pro Ser
1               5

<210> SEQ ID NO 22
<211> LENGTH: 7
<212> TYPE: PRT
<213> ORGANISM: Artificial Sequence
<220> FEATURE:
<223> OTHER INFORMATION: C4.4a binder

<400> SEQUENCE: 22

Arg Asn Asn Gln Arg Pro Ser
1               5

<210> SEQ ID NO 23
<211> LENGTH: 7
<212> TYPE: PRT
<213> ORGANISM: Artificial Sequence
<220> FEATURE:
<223> OTHER INFORMATION: C4.4a binder
```

```
<400> SEQUENCE: 23

Ser Asn Asn Gln Arg Pro Ser
1               5

<210> SEQ ID NO 24
<211> LENGTH: 7
<212> TYPE: PRT
<213> ORGANISM: Artificial Sequence
<220> FEATURE:
<223> OTHER INFORMATION: C4.4a binder

<400> SEQUENCE: 24

Ser Asn Asn Gln Arg Pro Ser
1               5

<210> SEQ ID NO 25
<211> LENGTH: 12
<212> TYPE: PRT
<213> ORGANISM: Artificial Sequence
<220> FEATURE:
<223> OTHER INFORMATION: C4.4a binder

<400> SEQUENCE: 25

Cys Ala Ala Trp Asp Asp Arg Leu Asn Gly Pro Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: C4.4a binder

<400> SEQUENCE: 26

Cys Ala Ala Trp Asp Asp Arg Leu Asn Gly Trp Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: C4.4a binder

<400> SEQUENCE: 27

Cys Gln Ser Tyr Asp Ser Ser His Val Leu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: C4.4a binder

<400> SEQUENCE: 28

Cys Gln Ser Tyr Asp Arg Ser Leu Arg Gly Trp Val
1               5                   10

<210> SEQ ID NO 29
<211> LENGTH: 113
<212> TYPE: PRT
<213> ORGANISM: Artificial Sequence
<220> FEATURE:
<223> OTHER INFORMATION: C4.4a binder

<400> SEQUENCE: 29
```

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
50                  55                  60

Ser Gly Ser Lys Ser Gly Thr Ser Ala Ser Leu Ala Ile Ser Gly Leu
65              70                  75                  80

Arg Ser Glu Asp Glu Ala Asp Tyr Tyr Cys Ala Ala Trp Asp Asp Arg
                85                  90                  95

Leu Asn Gly Pro Val Phe Gly Gly Gly Thr Lys Leu Thr Val Leu Gly
            100                 105                 110

Gln
```

<210> SEQ ID NO 30
<211> LENGTH: 112
<212> TYPE: PRT
<213> ORGANISM: Artificial Sequence
<220> FEATURE:
<223> OTHER INFORMATION: C4.4a binder

<400> SEQUENCE: 30

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Val Gly Ser Asn
                20                  25                  30

Pro Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Arg Leu
                85                  90                  95

Asn Gly Trp Val Phe Gly Gly Gly Thr Lys Leu Thr Val Leu Gly Gln
            100                 105                 110
```

<210> SEQ ID NO 31
<211> LENGTH: 111
<212> TYPE: PRT
<213> ORGANISM: Artificial Sequence
<220> FEATURE:
<223> OTHER INFORMATION: C4.4a binder

<400> SEQUENCE: 31

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Ser Asn Asn Gln Arg Pro Ser Gly Val Pro Asp Arg Phe
50                  55                  60

Ser Gly Ser Lys Ser Gly Thr Ser Ala Ser Leu Ala Ile Ser Gly Leu
65              70                  75                  80
```

-continued

```
Arg Ser Glu Asp Glu Ala Asp Tyr Tyr Cys Gln Ser Tyr Asp Ser Ser
                 85                  90                  95

His Val Leu Phe Gly Gly Gly Thr Lys Leu Thr Val Leu Gly Gln
            100                 105                 110

<210> SEQ ID NO 32
<211> LENGTH: 113
<212> TYPE: PRT
<213> ORGANISM: Artificial Sequence
<220> FEATURE:
<223> OTHER INFORMATION: C4.4a binder

<400> SEQUENCE: 32

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Arg Ser
                85                  90                  95

Leu Arg Gly Trp Val Phe Gly Gly Gly Thr Lys Leu Thr Val Leu Gly
            100                 105                 110

Gln

<210> SEQ ID NO 33
<211> LENGTH: 117
<212> TYPE: PRT
<213> ORGANISM: Artificial Sequence
<220> FEATURE:
<223> OTHER INFORMATION: C4.4a binder

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Thr Ser
            115

<210> SEQ ID NO 34
<211> LENGTH: 122
<212> TYPE: PRT
<213> ORGANISM: Artificial Sequence
```

<220> FEATURE:
<223> OTHER INFORMATION: C4.4a binder

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Val Ser Trp Asn Gly Ala Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Thr Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: C4.4a binder

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly His Tyr
            20                  25                  30

Tyr Met Phe Trp Ile Arg Gln Ala Pro Gly Lys Gly Leu Glu Trp Val
        35                  40                  45

Ser Ala Ile Ser Gly Ser Gly Tyr Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Tyr Gly Ser Ser Gly Val Asp Tyr Trp Gly Gln
            100                 105                 110

Gly Thr Leu Val Thr Val Thr Ser
        115                 120

<210> SEQ ID NO 36
<211> LENGTH: 124
<212> TYPE: PRT
<213> ORGANISM: Artificial Sequence
<220> FEATURE:
<223> OTHER INFORMATION: C4.4a binder

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

```
Tyr Met Ser Trp Val Arg Gln Ala Pro Gly Lys Gly Leu Glu Trp Val
         35                  40                  45

Ser Ala Ile Ser Ser Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ser Gly Gly Ser Gly Pro Asn Tyr Tyr Gly Met Asp
             100                 105                 110

Val Trp Gly Gln Gly Thr Leu Val Thr Val Thr Ser
         115                 120

<210> SEQ ID NO 37
<211> LENGTH: 339
<212> TYPE: DNA
<213> ORGANISM: Artificial Sequence
<220> FEATURE:
<223> OTHER INFORMATION: C4.4a binder

<400> SEQUENCE: 37
cagtctgtgc tgactcagcc accctcagcg tctgggaccc ctgggcagag ggtcaccatc        60
tcctgcactg ggagcagctc caacattggg gcgggttatg ttgtacattg gtatcagcag       120
ctcccaggaa cggccccca actcctcatc tatgacaata taagcgacc ctcaggggtc        180 cctgaccgat tctctggctc caagtctggc acctcagcct ccctggccat cagtgggctc       240
cggtccgagg atgaggctga ttattactgt gcagcatggg atgacaggct gaatggtccg       300
gtgttcggcg gaggaaccaa gttaaccgtc ctaggtcag                              339

<210> SEQ ID NO 38
<211> LENGTH: 336
<212> TYPE: DNA
<213> ORGANISM: Artificial Sequence
<220> FEATURE:
<223> OTHER INFORMATION: C4.4a binder

<400> SEQUENCE: 38
cagtctgtgc tgactcagcc accctcagcg tctgggaccc ccgggcagag ggtcaccatc        60
tcttgttctg gaagcagctc caacgtcggg agtaatcctg taaactggta tcagcagctc       120
ccaggaacgg cccccaaact cctcatctat aggaataatc agcggccctc aggggtccct       180
gaccgattct ctggctccaa gtctggcacc tcagcctccc tggccatcag tgggctccgg       240
tccgaggatg aggctgatta ttactgtgca gcatgggatg acaggctgaa tggttgggtg       300
ttcggcggag gaaccaagct gaccgtccta ggtcag                                 336

<210> SEQ ID NO 39
<211> LENGTH: 333
<212> TYPE: DNA
<213> ORGANISM: Artificial Sequence
<220> FEATURE:
<223> OTHER INFORMATION: C4.4a binder

<400> SEQUENCE: 39
cagtctgtgc tgactcagcc accctcagcg tctgggaccc ccgggcagag ggtcaccatc        60
tcctgcactg ggagcagctc caacattggg gcgggttatg ttgtacattg gtatcagcag       120
ctcccaggaa cggccccca actcctcatc tatagtaata atcagcggcc ctcaggagtc       180
cctgaccgat tctctggctc caagtctggc acctcagcct ccctggccat cagtgggctc       240
```

```
cggtccgagg atgaggctga ttattactgc cagtcctatg acagcagcca tgttttattc    300
ggcggaggaa ccaagctgac ggtcctaggt cag                                 333
```

<210> SEQ ID NO 40
<211> LENGTH: 339
<212> TYPE: DNA
<213> ORGANISM: Artificial Sequence
<220> FEATURE:
<223> OTHER INFORMATION: C4.4a binder

<400> SEQUENCE: 40

```
cagtctgtgc tgactcagcc accctcagcg tctgggaccc ccgggcagag ggtcaccatc    60
tcctgcactg ggagcagctc aacattggg gcgggttatg ttgtacattg gtatcagcag    120
ctcccaggaa cggcccccaa actcctcatc tatagtaata atcagcggcc ctcaggggtc    180
cctgaccgat tctctggctc caagtctggc acctcagcct ccctggccat cagtgggctc    240
cggtccgagg atgaggctga ttattactgc cagtcctatg acagaagcct gcgtggttgg    300
gtgttcggcg gaggaaccaa gctgacggtc ctaggtcag                           339
```

<210> SEQ ID NO 41
<211> LENGTH: 351
<212> TYPE: DNA
<213> ORGANISM: Artificial Sequence
<220> FEATURE:
<223> OTHER INFORMATION: C4.4a binder

<400> SEQUENCE: 41

```
gaggtgcagc tgttggagtc tgggggaggc ttggtacagc ctggggggtc cctgagactc    60
tcctgtgcag cctctggatt caccttcagt aacgcctgga tgagctgggt ccgccaggct    120
ccagggaagg ggctggagtg ggtttcatac attagtagta gtggtagtac catatactac    180
gcagactctg tgaagggccg attcaccatc tccagagaca attccaagaa cacgctgtat    240
ctgcaaatga acagcctgag agccgaggac actgccgtgt attactgtgc gagagaaggg    300
ttatgggcct ttgactactg gggccagggt accctggtca ccgtgactag t             351
```

<210> SEQ ID NO 42
<211> LENGTH: 366
<212> TYPE: DNA
<213> ORGANISM: Artificial Sequence
<220> FEATURE:
<223> OTHER INFORMATION: C4.4a binder

<400> SEQUENCE: 42

```
gaggtgcagc tgttggagtc tgggggaggc ttggtacagc ctggggggtc cctgagactc    60
tcctgtgcag cctctggatt caccttcagt gactatcaga tgacctggat ccgccagact    120
ccagggaagg ggctggagtg ggtatcgggt gttagttgga atggcgctag gacgcactat    180
gcagactctg tgaagggccg attcaccatc tccagagaca attccaagaa cacgctgtat    240
ctacaaatga acagcctgag agccgaggac actgccgtgt attactgtgc gaagggcgac    300
tacctggttt actccgcata ctactttgac tcctggggcc agggtaccct ggtcaccgtg    360
actagt                                                               366
```

<210> SEQ ID NO 43
<211> LENGTH: 360
<212> TYPE: DNA
<213> ORGANISM: Artificial Sequence
<220> FEATURE:

<223> OTHER INFORMATION: C4.4a binder

<400> SEQUENCE: 43

```
gaggtgcagc tgttggagtc tgggggaggc ttggtacagc ctggggggtc cctgagactc    60
tcctgtgcag cctctggatt caccttcggt cactactata tgttctggat ccgtcaggct   120
ccagggaagg ggctggagtg ggtctcagct attagtggta gtggttatag cacacactac   180
gcagactccg tgaagggccg gttcaccatc tccagagaca attccaagaa cacgctgtat   240
ctgcaaatga acagcctgag agccgaggac actgccgtgt attactgtgc gagactgcca   300
tatggttcgc agagtggcgt tgactactgg ggccaggtca cctggtcac cgtgactagt    360
```

<210> SEQ ID NO 44
<211> LENGTH: 372
<212> TYPE: DNA
<213> ORGANISM: Artificial Sequence
<220> FEATURE:
<223> OTHER INFORMATION: C4.4a binder

<400> SEQUENCE: 44

```
gaggtgcagc tgttggagtc tgggggaggc ttggtacagc ctggggggtc cctgagactc    60
tcctgtgcag cctctggatt caccttcagt agcaactaca tgagctgggt ccgccaggct   120
ccagggaagg ggctggagtg ggtctcagct attagtagta gtggtagtag cacatactac   180
gcagactccg tgaagggccg gttcaccatc tccagagaca attccaagaa cacgctgtat   240
ctgcaaatga acagcctgag agccgaggac actgccgtgt attactgtgc gagagaatct   300
ggtgggagcg gaccgaacta ctactacggt atggacgtct ggggccaagg taccctggtc   360
accgtgacta gt                                                       372
```

<210> SEQ ID NO 45
<211> LENGTH: 9
<212> TYPE: PRT
<213> ORGANISM: Artificial Sequence
<220> FEATURE:
<223> OTHER INFORMATION: C4.4a binder

<400> SEQUENCE: 45

Phe Ser Asn Ala Trp Met Ser Trp Val
1               5

<210> SEQ ID NO 46
<211> LENGTH: 20
<212> TYPE: PRT
<213> ORGANISM: Artificial Sequence
<220> FEATURE:
<223> OTHER INFORMATION: C4.4a binder

<400> SEQUENCE: 46

Val Ser Tyr Ile Ser Ser Ser Gly Ser Thr Ile Tyr Tyr Ala Asp Ser
1               5                   10                  15

Val Lys Gly Arg
            20

<210> SEQ ID NO 47
<211> LENGTH: 10
<212> TYPE: PRT
<213> ORGANISM: Artificial Sequence
<220> FEATURE:
<223> OTHER INFORMATION: C4.4a binder

<400> SEQUENCE: 47

```
Ala Arg Glu Gly Leu Trp Ala Phe Asp Tyr
1               5                   10
```

<210> SEQ ID NO 48
<211> LENGTH: 14
<212> TYPE: PRT
<213> ORGANISM: Artificial Sequence
<220> FEATURE:
<223> OTHER INFORMATION: C4.4a binder

<400> SEQUENCE: 48

```
Thr Gly Ser Ser Ser Asn Ile Gly Ala Gly Tyr Val Val His
1               5                   10
```

<210> SEQ ID NO 49
<211> LENGTH: 7
<212> TYPE: PRT
<213> ORGANISM: Artificial Sequence
<220> FEATURE:
<223> OTHER INFORMATION: C4.4a binder

<400> SEQUENCE: 49

```
Asp Asn Asn Lys Arg Pro Ser
1               5
```

<210> SEQ ID NO 50
<211> LENGTH: 12
<212> TYPE: PRT
<213> ORGANISM: Artificial Sequence
<220> FEATURE:
<223> OTHER INFORMATION: C4.4a binder

<400> SEQUENCE: 50

```
Cys Ala Ala Trp Asp Asp Arg Leu Asn Gly Pro Val
1               5                   10
```

<210> SEQ ID NO 51
<211> LENGTH: 117
<212> TYPE: PRT
<213> ORGANISM: Artificial Sequence
<220> FEATURE:
<223> OTHER INFORMATION: C4.4a binder

<400> SEQUENCE: 51

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser
            115
```

<210> SEQ ID NO 52
<211> LENGTH: 113

```
<212> TYPE: PRT
<213> ORGANISM: Artificial Sequence
<220> FEATURE:
<223> OTHER INFORMATION: C4.4a binder

<400> SEQUENCE: 52

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Arg
                85                  90                  95

Leu Asn Gly Pro Val Phe Gly Gly Gly Thr Lys Leu Thr Val Leu Gly
            100                 105                 110

Gln

<210> SEQ ID NO 53
<211> LENGTH: 351
<212> TYPE: DNA
<213> ORGANISM: Artificial Sequence
<220> FEATURE:
<223> OTHER INFORMATION: C4.4a binder

<400> SEQUENCE: 53
gaggtgcagc tgctggaaag cggcggagga ctggtgcagc ctggaggcag cctgagactg      60
tcttgcgccg ccagcggctt caccttcagc aacgcctgga tgagctgggt ccgacaggct     120
cctggcaagg gcctggaatg ggtgtcctac atcagcagca gcggcagcac catctactac     180
gccgacagcg tgaagggccg gttcaccatc agccgggaca caagcaagaa caccctgtac     240
ctgcagatga acagcctgcg ggccgaggac accgccgtgt actactgcgc cagagaaggc     300
ctgtgggcct tcgactactg gggccagggc accctggtca ccgtgtctag c              351

<210> SEQ ID NO 54
<211> LENGTH: 339
<212> TYPE: DNA
<213> ORGANISM: Artificial Sequence
<220> FEATURE:
<223> OTHER INFORMATION: C4.4a binder

<400> SEQUENCE: 54
gagagcgtgc tgacccagcc tcctagcgtg tccggcgctc ctggccagag agtgaccatc      60
agctgcaccg gcagcagcag caacatcgga gccggctacg tggtgcactg gtatcagcag     120
ctgcccggca ccgccccaa gctgctgatc tacgacaaca caagcggcc tagcggcgtg      180 cccgacagat tcagcggcag caagagcggc accagcgcca gcctggccat cagcggcctg     240
agaagcgagg acgaggccga ctactactgc gccgcctggg acgacagact gaacggccct     300
gtgttcggcg gaggcaccaa gctgaccgtg ctgggacag                            339

<210> SEQ ID NO 55
<211> LENGTH: 9
<212> TYPE: PRT
<213> ORGANISM: Artificial Sequence
```

```
<220> FEATURE:
<223> OTHER INFORMATION: C4.4a binder

<400> SEQUENCE: 55

Phe Ser Asn Ala Trp Met Ser Trp Val
1               5

<210> SEQ ID NO 56
<211> LENGTH: 20
<212> TYPE: PRT
<213> ORGANISM: Artificial Sequence
<220> FEATURE:
<223> OTHER INFORMATION: C4.4a binder

<400> SEQUENCE: 56

Val Ser Tyr Ile Ser Ser Ser Gly Ser Thr Ile Tyr Tyr Ala Asp Ser
1               5                   10                  15

Val Lys Gly Arg
            20

<210> SEQ ID NO 57
<211> LENGTH: 10
<212> TYPE: PRT
<213> ORGANISM: Artificial Sequence
<220> FEATURE:
<223> OTHER INFORMATION: C4.4a binder

<400> SEQUENCE: 57

Ala Arg Glu Gly Leu Trp Ala Phe Asp Tyr
1               5                   10

<210> SEQ ID NO 58
<211> LENGTH: 14
<212> TYPE: PRT
<213> ORGANISM: Artificial Sequence
<220> FEATURE:
<223> OTHER INFORMATION: C4.4a binder

<400> SEQUENCE: 58

Thr Gly Ser Ser Ser Asn Ile Gly Ala Gly Tyr Val Val His
1               5                   10

<210> SEQ ID NO 59
<211> LENGTH: 7
<212> TYPE: PRT
<213> ORGANISM: Artificial Sequence
<220> FEATURE:
<223> OTHER INFORMATION: C4.4a binder

<400> SEQUENCE: 59

Asp Asn Asn Lys Arg Pro Ser
1               5

<210> SEQ ID NO 60
<211> LENGTH: 12
<212> TYPE: PRT
<213> ORGANISM: Artificial Sequence
<220> FEATURE:
<223> OTHER INFORMATION: C4.4a binder

<400> SEQUENCE: 60

Cys Ala Ala Tyr Asp Asp Ser Leu Ser Gly Pro Val
1               5                   10

<210> SEQ ID NO 61
<211> LENGTH: 117
```

<212> TYPE: PRT
<213> ORGANISM: Artificial Sequence
<220> FEATURE:
<223> OTHER INFORMATION: C4.4a binder

<400> SEQUENCE: 61

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Ala
            20                  25                  30
Trp Met Ser Trp Val Arg Gln Ala Pro Gly Lys Gly Leu Glu Trp Val
        35                  40                  45
Ser Tyr Ile Ser Ser Gly Ser Thr Ile Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Leu Trp Ala Phe Asp Tyr Trp Gly Gln Gly Thr Leu
            100                 105                 110
Val Thr Val Ser Ser
        115

<210> SEQ ID NO 62
<211> LENGTH: 113
<212> TYPE: PRT
<213> ORGANISM: Artificial Sequence
<220> FEATURE:
<223> OTHER INFORMATION: C4.4a binder

<400> SEQUENCE: 62

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Val Val His Trp Tyr Gln Gln Leu Pro Gly Thr Ala Pro Lys Leu
        35                  40                  45
Leu Ile Tyr Asp Asn Asn Lys Arg Pro Ser Gly Val Pro Asp Arg Phe
    50                  55                  60
Ser Gly Ser Lys Ser Gly Thr Ser Ala Ser Leu Ala Ile Ser Gly Leu
65                  70                  75                  80
Arg Ser Glu Asp Glu Ala Asp Tyr Tyr Cys Ala Ala Tyr Asp Ser
                85                  90                  95
Leu Ser Gly Pro Val Phe Gly Gly Gly Thr Lys Leu Thr Val Leu Gly
            100                 105                 110
Gln

<210> SEQ ID NO 63
<211> LENGTH: 351
<212> TYPE: DNA
<213> ORGANISM: Artificial Sequence
<220> FEATURE:
<223> OTHER INFORMATION: C4.4a binder

<400> SEQUENCE: 63
gaggtgcagc tgctggaatc cggcggaggc ctggtgcagc ctggcggatc tctgagactg      60
tcctgcgccg ccagcggctt taccttctcc aacgcctgga tgtcctgggt ccgacaggcc     120
cctggcaagg gactggaatg ggtgtcctac atctcctcct ccggctccac catctactac     180

```
gccgactccg tgaagggccg gttcaccatc tcccgggaca actccaagaa caccctgtac    240
ctgcagatga actccctgcg ggccgaggac accgccgtgt actactgcgc ccgagagggc    300
ctgtgggcct tcgattattg gggccagggc accctggtca ccgtcagctc a             351
```

```
<210> SEQ ID NO 64
<211> LENGTH: 339
<212> TYPE: DNA
<213> ORGANISM: Artificial Sequence
<220> FEATURE:
<223> OTHER INFORMATION: C4.4a binder

<400> SEQUENCE: 64
cagtccgtgc tgacccagcc cccttctgtg tctggcgccc ctggccagag agtgaccatc    60
tcttgcaccg ctcctccag caacatcggc gctggctacg tggtgcactg gtatcagcag    120
ctgcccggca ccgcccccaa gctgctgatc tacgacaaca acaagcggcc ctccggcgtg    180
cccgacagat ctccggctc caagtccggc acctccgcct ccctggccat ctccggcctg    240
agatctgagg acgaggccga ctactactgc gccgcctacg acgactccct gtccggccct    300
gtgttcggcg gaggcacaaa gttaaccgtg ctgggccag                           339
```

```
<210> SEQ ID NO 65
<211> LENGTH: 9
<212> TYPE: PRT
<213> ORGANISM: Artificial Sequence
<220> FEATURE:
<223> OTHER INFORMATION: C4.4a binder

<400> SEQUENCE: 65

Phe Ser Asn Ala Trp Met Ser Trp Val
1               5
```

```
<210> SEQ ID NO 66
<211> LENGTH: 20
<212> TYPE: PRT
<213> ORGANISM: Artificial Sequence
<220> FEATURE:
<223> OTHER INFORMATION: C4.4a binder

<400> SEQUENCE: 66

Val Ser Tyr Ile Ser Ser Ser Gly Ser Thr Ile Tyr Tyr Ala Asp Ser
1               5                   10                  15
Val Lys Gly Arg
            20
```

```
<210> SEQ ID NO 67
<211> LENGTH: 10
<212> TYPE: PRT
<213> ORGANISM: Artificial Sequence
<220> FEATURE:
<223> OTHER INFORMATION: C4.4a binder

<400> SEQUENCE: 67

Ala Arg Glu Gly Leu Trp Ala Phe Asp Tyr
1               5                   10
```

```
<210> SEQ ID NO 68
<211> LENGTH: 14
<212> TYPE: PRT
<213> ORGANISM: Artificial Sequence
<220> FEATURE:
<223> OTHER INFORMATION: C4.4a binder
```

```
<400> SEQUENCE: 68

Thr Gly Ser Ser Ser Asn Ile Gly Ala Gly Tyr Val Val His
1               5                   10

<210> SEQ ID NO 69
<211> LENGTH: 7
<212> TYPE: PRT
<213> ORGANISM: Artificial Sequence
<220> FEATURE:
<223> OTHER INFORMATION: C4.4a binder

<400> SEQUENCE: 69

Asp Asn Asn Lys Arg Pro Ser
1               5

<210> SEQ ID NO 70
<211> LENGTH: 12
<212> TYPE: PRT
<213> ORGANISM: Artificial Sequence
<220> FEATURE:
<223> OTHER INFORMATION: C4.4a binder

<400> SEQUENCE: 70

Cys Ala Ala Phe Asp Asp Ser Leu Asn Gly Pro Val
1               5                   10

<210> SEQ ID NO 71
<211> LENGTH: 117
<212> TYPE: PRT
<213> ORGANISM: Artificial Sequence
<220> FEATURE:
<223> OTHER INFORMATION: C4.4a binder

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Ser Ser
        115

<210> SEQ ID NO 72
<211> LENGTH: 113
<212> TYPE: PRT
<213> ORGANISM: Artificial Sequence
<220> FEATURE:
<223> OTHER INFORMATION: C4.4a binder

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
```

```
                20                  25                  30
Tyr Val Val His Trp Tyr Gln Gln Leu Pro Gly Thr Ala Pro Lys Leu
             35                  40                  45

Leu Ile Tyr Asp Asn Asn Lys Arg Pro Ser Gly Val Pro Asp Arg Phe
         50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Phe Asp Asp Arg
                 85                  90                  95

Leu Asn Gly Pro Val Phe Gly Gly Gly Thr Lys Leu Thr Val Leu Gly
            100                 105                 110

Gln

<210> SEQ ID NO 73
<211> LENGTH: 351
<212> TYPE: DNA
<213> ORGANISM: Artificial Sequence
<220> FEATURE:
<223> OTHER INFORMATION: C4.4a binder

<400> SEQUENCE: 73
gaggtgcagc tgctggaatc cggcggaggc ctggtgcagc tggcggatc tctgagactg       60 tcctgcgccg cctccggctt taccttctcc aacgcctgga tgtcctgggt ccgacaggct      120
cctggcaagg gcctggaatg ggtgtcctac atctcctcct ccggctccac catctactac      180
gccgactccg tgaagggccg gttcaccatc tcccgggaca actccaagaa cacccctgtac     240 ctgcagatga actccctgcg ggccgaggac accgccgtgt actactgcgc ccgagagggc      300
ctgtgggcct cgataagtg gggccagggc accctggtca ccgtcagctc a                351

<210> SEQ ID NO 74
<211> LENGTH: 339
<212> TYPE: DNA
<213> ORGANISM: Artificial Sequence
<220> FEATURE:
<223> OTHER INFORMATION: C4.4a binder

<400> SEQUENCE: 74
cagtccgtgc tgacccagcc tccttccgcc tctggcaccc ctggccagag agtgaccatc       60
tcctgcaccg gctcctccag caacatcggc gctggctacg tggtgcactg gtatcagcag      120
ctgcccggca cgcccccaa gctgctgatc tacgacaaca acaagcggcc ctccggcgtg       180
cccgacagat tctccggctc caagtccggc acctccgcct ccctggccat ctccggcctg      240
agatctgagg acgaggccga ctactactgc gccgccttcg acgaccggct gaacggccct      300
gtgttcggcg gaggcacaaa gttaaccgtg ctgggccag                             339

<210> SEQ ID NO 75
<211> LENGTH: 9
<212> TYPE: PRT
<213> ORGANISM: Artificial Sequence
<220> FEATURE:
<223> OTHER INFORMATION: C4.4a binder

<400> SEQUENCE: 75

Phe Ser Ser Ala Trp Met Ser Trp Val
 1               5

<210> SEQ ID NO 76
<211> LENGTH: 20
```

```
<212> TYPE: PRT
<213> ORGANISM: Artificial Sequence
<220> FEATURE:
<223> OTHER INFORMATION: C4.4a binder

<400> SEQUENCE: 76

Val Ser Tyr Ile Ser Ser Gly Ser Thr Ile Tyr Tyr Ala Asp Ser
1               5                   10                  15

Val Lys Gly Arg
            20

<210> SEQ ID NO 77
<211> LENGTH: 10
<212> TYPE: PRT
<213> ORGANISM: Artificial Sequence
<220> FEATURE:
<223> OTHER INFORMATION: C4.4a binder

<400> SEQUENCE: 77

Ala Arg Glu Gly Leu Trp Ala Phe Asp Tyr
1               5                   10

<210> SEQ ID NO 78
<211> LENGTH: 14
<212> TYPE: PRT
<213> ORGANISM: Artificial Sequence
<220> FEATURE:
<223> OTHER INFORMATION: C4.4a binder

<400> SEQUENCE: 78

Thr Gly Ser Ser Ser Asn Ile Gly Ala Gly Tyr Val Val His
1               5                   10

<210> SEQ ID NO 79
<211> LENGTH: 7
<212> TYPE: PRT
<213> ORGANISM: Artificial Sequence
<220> FEATURE:
<223> OTHER INFORMATION: C4.4a binder

<400> SEQUENCE: 79

Asp Asn Asn Lys Arg Pro Ser
1               5

<210> SEQ ID NO 80
<211> LENGTH: 12
<212> TYPE: PRT
<213> ORGANISM: Artificial Sequence
<220> FEATURE:
<223> OTHER INFORMATION: C4.4a binder

<400> SEQUENCE: 80

Cys Ala Ala Tyr Asp Asp Ser Leu Ser Gly Pro Val
1               5                   10

<210> SEQ ID NO 81
<211> LENGTH: 117
<212> TYPE: PRT
<213> ORGANISM: Artificial Sequence
<220> FEATURE:
<223> OTHER INFORMATION: C4.4a binder

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
```

```
                    20                   25                   30
Trp Met Ser Trp Val Arg Gln Ala Pro Gly Lys Gly Leu Glu Trp Val
            35                   40                   45

Ser Tyr Ile Ser Ser Gly Ser Thr Ile Tyr Tyr Ala Asp Ser Val
    50                   55                   60

Lys Gly Arg Phe Thr Ile Ser Arg Asp Asn Ser Lys Asn Thr Leu Tyr
65                   70                   75                   80

Leu Gln Met Asn Ser Leu Arg Ala Glu Asp Thr Ala Val Tyr Tyr Cys
                85                   90                   95

Ala Arg Glu Gly Leu Trp Ala Phe Asp Tyr Trp Gly Gln Gly Thr Leu
            100                  105                  110

Val Thr Val Ser Ser
        115

<210> SEQ ID NO 82
<211> LENGTH: 113
<212> TYPE: PRT
<213> ORGANISM: Artificial Sequence
<220> FEATURE:
<223> OTHER INFORMATION: C4.4a binder

<400> SEQUENCE: 82

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                   30

Tyr Val Val His Trp Tyr Gln Gln Leu Pro Gly Thr Ala Pro Lys Leu
        35                   40                   45

Leu Ile Tyr Asp Asn Asn Lys Arg Pro Ser Gly Val Pro Asp Arg Phe
    50                   55                   60

Ser Gly Ser Lys Ser Gly Thr Ser Ala Ser Leu Ala Ile Ser Gly Leu
65                   70                   75                   80

Arg Ser Glu Asp Glu Ala Asp Tyr Tyr Cys Ala Ala Tyr Asp Asp Ser
                85                   90                   95

Leu Ser Gly Pro Val Phe Gly Gly Gly Thr Lys Leu Thr Val Leu Gly
            100                  105                  110

Gln

<210> SEQ ID NO 83
<211> LENGTH: 351
<212> TYPE: DNA
<213> ORGANISM: Artificial Sequence
<220> FEATURE:
<223> OTHER INFORMATION: C4.4a binder

<400> SEQUENCE: 83
gaggtgcagc tgctggaatc cggcggaggc ctggtgcagc ctggcggatc tctgagactg      60
tcctgcgccg ccagcggctt taccttctcc agcgcctgga tgtcctgggt ccgacaggcc     120
cctggcaagg gactggaatg gtgtcctac atctcctcct ccggctccac catctactac     180
gccgactccg tgaagggccg gttcaccatc tcccgggaca actccaagaa caccctgtac     240
ctgcagatga actccctgcg ggccgaggac accgccgtgt actactgcgc ccgagagggc     300
ctgtgggcct tcgattattg gggccagggc accctggtca ccgtcagctc a              351

<210> SEQ ID NO 84
<211> LENGTH: 339
<212> TYPE: DNA
```

```
<213> ORGANISM: Artificial Sequence
<220> FEATURE:
<223> OTHER INFORMATION: C4.4a binder

<400> SEQUENCE: 84
cagtccgtgc tgacccagcc cccttctgtg tctggcgccc ctggccagag agtgaccatc    60
tcttgcaccg gctcctccag caacatcggc gctggctacg tggtgcactg gtatcagcag   120
ctgcccggca cgcccccaa gctgctgatc tacgacaaca acaagcggcc ctccggcgtg    180
cccgacagat tctccggctc aagtccggc acctccgcct ccctggccat ctccggcctg    240
agatctgagg acgaggccga ctactactgc gccgcctacg acgactccct gtccggccct   300
gtgttcggcg gaggcacaaa gttaaccgtg ctgggccag                          339

<210> SEQ ID NO 85
<211> LENGTH: 9
<212> TYPE: PRT
<213> ORGANISM: Artificial Sequence
<220> FEATURE:
<223> OTHER INFORMATION: C4.4a binder

<400> SEQUENCE: 85

Phe Ser Ser Ala Trp Met Ser Trp Val
1               5

<210> SEQ ID NO 86
<211> LENGTH: 20
<212> TYPE: PRT
<213> ORGANISM: Artificial Sequence
<220> FEATURE:
<223> OTHER INFORMATION: C4.4a binder

<400> SEQUENCE: 86

Val Ser Tyr Ile Ser Ser Ser Gly Ser Ser Thr Tyr Tyr Ala Asp Ser
1               5                   10                  15

Val Lys Gly Arg
            20

<210> SEQ ID NO 87
<211> LENGTH: 10
<212> TYPE: PRT
<213> ORGANISM: Artificial Sequence
<220> FEATURE:
<223> OTHER INFORMATION: C4.4a binder

<400> SEQUENCE: 87

Ala Arg Glu Gly Leu Trp Ala Phe Asp Lys
1               5                   10

<210> SEQ ID NO 88
<211> LENGTH: 14
<212> TYPE: PRT
<213> ORGANISM: Artificial Sequence
<220> FEATURE:
<223> OTHER INFORMATION: C4.4a binder

<400> SEQUENCE: 88

Ser Gly Ser Ser Ser Asn Ile Gly Ala Gly Tyr Val Val His
1               5                   10

<210> SEQ ID NO 89
<211> LENGTH: 7
<212> TYPE: PRT
<213> ORGANISM: Artificial Sequence
<220> FEATURE:
```

```
<223> OTHER INFORMATION: C4.4a binder

<400> SEQUENCE: 89

Asp Asn Asn Gln Arg Pro Ser
1               5

<210> SEQ ID NO 90
<211> LENGTH: 12
<212> TYPE: PRT
<213> ORGANISM: Artificial Sequence
<220> FEATURE:
<223> OTHER INFORMATION: C4.4a binder

<400> SEQUENCE: 90

Cys Ala Ala Phe Asp Asp Arg Leu Ser Gly Pro Val
1               5                   10

<210> SEQ ID NO 91
<211> LENGTH: 117
<212> TYPE: PRT
<213> ORGANISM: Artificial Sequence
<220> FEATURE:
<223> OTHER INFORMATION: C4.4a binder

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Ser Ser
        115

<210> SEQ ID NO 92
<211> LENGTH: 113
<212> TYPE: PRT
<213> ORGANISM: Artificial Sequence
<220> FEATURE:
<223> OTHER INFORMATION: C4.4a binder

<400> SEQUENCE: 92

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80
```

Arg Ser Glu Asp Glu Ala Asp Tyr Tyr Cys Ala Ala Phe Asp Asp Arg
                85                  90                  95

Leu Ser Gly Pro Val Phe Gly Gly Gly Thr Lys Leu Thr Val Leu Gly
            100                 105                 110

Gln

<210> SEQ ID NO 93
<211> LENGTH: 351
<212> TYPE: DNA
<213> ORGANISM: Artificial Sequence
<220> FEATURE:
<223> OTHER INFORMATION: C4.4a binder

<400> SEQUENCE: 93
gaggtgcagc tgctggaaag cggcggaggc ctggtgcagc ctggcggaag cctgagactg     60
agctgtgccg ccagcggctt caccttcagc agcgcctgga tgagctgggt ccgacaggcc    120
cctggcaagg gcctggaatg gtgtcctac atcagcagca gcggcagcag cacctactac     180
gccgacagcg tgaagggccg gttcaccatc agccgggaca cagcaagaa caccctgtac     240 ctgcagatga acagcctgcg ggccgaggac accgccgtgt actactgcgc cagagaaggc    300
ctgtgggcct cgataagtg gggccagggc accctggtca ccgtcagctc a              351

<210> SEQ ID NO 94
<211> LENGTH: 339
<212> TYPE: DNA
<213> ORGANISM: Artificial Sequence
<220> FEATURE:
<223> OTHER INFORMATION: C4.4a binder

<400> SEQUENCE: 94
cagagcgtgc tgacccagcc tcctagcgcc tctggcaccc ctggccagag agtgaccatc     60
agctgcagcg gcagcagcag caacatcgga gccggctacg tggtgcactg gtatcagcag    120
ctgcccggca ccgcccccaa gctgctgatc tacgacaaca accagcggcc cagcggcgtg    180
cccgacagat tttccggcag caagagcggc accagcgcca gcctggccat cagcggcctg    240
agaagcgagg acgaggccga ctactactgc gccgccttcg acgacagact gagcggccct    300
gtgttcggcg gaggcacaaa gttaaccgtg ctgggccag                           339

<210> SEQ ID NO 95
<211> LENGTH: 9
<212> TYPE: PRT
<213> ORGANISM: Artificial Sequence
<220> FEATURE:
<223> OTHER INFORMATION: C4.4a binder

<400> SEQUENCE: 95

Phe Ser Asp Tyr Gln Met Thr Trp Ile
1               5

<210> SEQ ID NO 96
<211> LENGTH: 20
<212> TYPE: PRT
<213> ORGANISM: Artificial Sequence
<220> FEATURE:
<223> OTHER INFORMATION: C4.4a binder

<400> SEQUENCE: 96

Val Ser Gly Val Ser Trp Asn Gly Ala Arg Thr His Tyr Ala Asp Ser
1               5                   10                  15

Val Lys Gly Arg

-continued

```
<210> SEQ ID NO 97
<211> LENGTH: 15
<212> TYPE: PRT
<213> ORGANISM: Artificial Sequence
<220> FEATURE:
<223> OTHER INFORMATION: C4.4a binder

<400> SEQUENCE: 97

Ala Lys Gly Asp Tyr Leu Val Tyr Ser Ala Tyr Tyr Phe Asp Ser
1               5                   10                  15

<210> SEQ ID NO 98
<211> LENGTH: 13
<212> TYPE: PRT
<213> ORGANISM: Artificial Sequence
<220> FEATURE:
<223> OTHER INFORMATION: C4.4a binder

<400> SEQUENCE: 98

Ser Gly Ser Ser Ser Asn Val Gly Ser Asn Pro Val Asn
1               5                   10

<210> SEQ ID NO 99
<211> LENGTH: 7
<212> TYPE: PRT
<213> ORGANISM: Artificial Sequence
<220> FEATURE:
<223> OTHER INFORMATION: C4.4a binder

<400> SEQUENCE: 99

Arg Asn Asn Gln Arg Pro Ser
1               5

<210> SEQ ID NO 100
<211> LENGTH: 12
<212> TYPE: PRT
<213> ORGANISM: Artificial Sequence
<220> FEATURE:
<223> OTHER INFORMATION: C4.4a binder

<400> SEQUENCE: 100

Cys Ala Ala Trp Asp Asp Arg Leu Asn Gly Trp Val
1               5                   10

<210> SEQ ID NO 101
<211> LENGTH: 122
<212> TYPE: PRT
<213> ORGANISM: Artificial Sequence
<220> FEATURE:
<223> OTHER INFORMATION: C4.4a binder

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Ser Ser
        115                 120
```

<210> SEQ ID NO 102
<211> LENGTH: 112
<212> TYPE: PRT
<213> ORGANISM: Artificial Sequence
<220> FEATURE:
<223> OTHER INFORMATION: C4.4a binder

<400> SEQUENCE: 102

```
Glu Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Gly Phe Gly Gly Gly Thr Lys Leu Thr Val Leu Gly Gln
            100                 105                 110
```

<210> SEQ ID NO 103
<211> LENGTH: 366
<212> TYPE: DNA
<213> ORGANISM: Artificial Sequence
<220> FEATURE:
<223> OTHER INFORMATION: C4.4a binder

<400> SEQUENCE: 103

```
gaggtgcagc tgctggaaag cggcggagga ctggtgcagc tggaggcag cctgagactg      60 tcttgcgccg ccagcggctt caccttcagc gactaccaga tgacctggat ccgacagacc    120
cctggcaagg gcctggaatg ggtgtccggc atcagctgga acggaggcag caccactac     180 gccgacagcg tgaagggccg gttcaccatc agccgggaca cagcaagaa cacccctgtac   240 ctgcagatga acagcctgcg ggccgaggac accgccgtgt actactgcgc caagggcgac    300
tacctggtgt acagcgccta ctacttcgac agctggggcc agggcaccct ggtcaccgtg    360
tctagc                                                              366
```

<210> SEQ ID NO 104
<211> LENGTH: 336
<212> TYPE: DNA
<213> ORGANISM: Artificial Sequence
<220> FEATURE:
<223> OTHER INFORMATION: C4.4a binder

<400> SEQUENCE: 104

```
gagagcgtgc tgacccagcc tcctagcgcc tctggcaccc ctggccagag agtgaccatc      60
agctgctctg gcagcagcag caacatcgga agcaaccccg tgaactggta tcagcagctg    120
cccggcaccg cccccaagct gctgatctac cggaacaacc agcggcctag cggcgtgccc    180
```

```
gacagattca gcggcagcaa gagcggcacc agcgccagcc tggccatcag cggcctgaga    240
agcgaggacg aggccgacta ctactgcgcc gcctgggacg acagactgaa cggctggggc    300
ttcggcggag caccaagct gaccgtgctg ggacag    336
```

<210> SEQ ID NO 105
<211> LENGTH: 9
<212> TYPE: PRT
<213> ORGANISM: Artificial Sequence
<220> FEATURE:
<223> OTHER INFORMATION: C4.4a binder

<400> SEQUENCE: 105

Phe Ser Asp Tyr Gln Met Thr Trp Ile
1               5

<210> SEQ ID NO 106
<211> LENGTH: 20
<212> TYPE: PRT
<213> ORGANISM: Artificial Sequence
<220> FEATURE:
<223> OTHER INFORMATION: C4.4a binder

<400> SEQUENCE: 106

Val Ser Gly Ile Ser Trp Asn Gly Gly Ser Thr His Tyr Ala Asp Ser
1               5                   10                  15

Val Lys Gly Arg
            20

<210> SEQ ID NO 107
<211> LENGTH: 15
<212> TYPE: PRT
<213> ORGANISM: Artificial Sequence
<220> FEATURE:
<223> OTHER INFORMATION: C4.4a binder

<400> SEQUENCE: 107

Ala Lys Gly Asp Tyr Leu Val Tyr Ser Ser Tyr Tyr Phe Lys Ser
1               5                   10                  15

<210> SEQ ID NO 108
<211> LENGTH: 13
<212> TYPE: PRT
<213> ORGANISM: Artificial Sequence
<220> FEATURE:
<223> OTHER INFORMATION: C4.4a binder

<400> SEQUENCE: 108

Ser Gly Ser Ser Ser Asn Ile Gly Ser Asn Pro Val Asn
1               5                   10

<210> SEQ ID NO 109
<211> LENGTH: 7
<212> TYPE: PRT
<213> ORGANISM: Artificial Sequence
<220> FEATURE:
<223> OTHER INFORMATION: C4.4a binder

<400> SEQUENCE: 109

Arg Asn Asn Gln Arg Pro Ser
1               5

<210> SEQ ID NO 110
<211> LENGTH: 12
<212> TYPE: PRT

<213> ORGANISM: Artificial Sequence
<220> FEATURE:
<223> OTHER INFORMATION: C4.4a binder

<400> SEQUENCE: 110

Cys Ala Ala Trp Asp Asp Arg Leu Ser Gly Trp Ala
1               5                   10

<210> SEQ ID NO 111
<211> LENGTH: 122
<212> TYPE: PRT
<213> ORGANISM: Artificial Sequence
<220> FEATURE:
<223> OTHER INFORMATION: C4.4a binder

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Ser Trp
            100                 105                 110

Gly Gln Gly Thr Leu Val Thr Val Ser Ser
        115                 120

<210> SEQ ID NO 112
<211> LENGTH: 112
<212> TYPE: PRT
<213> ORGANISM: Artificial Sequence
<220> FEATURE:
<223> OTHER INFORMATION: C4.4a binder

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Ala Phe Gly Gly Gly Thr Lys Leu Thr Val Leu Gly Gln
            100                 105                 110

<210> SEQ ID NO 113
<211> LENGTH: 366
<212> TYPE: DNA
<213> ORGANISM: Artificial Sequence

```
<220> FEATURE:
<223> OTHER INFORMATION: C4.4a binder

<400> SEQUENCE: 113
gaggtgcagc tgctggaatc cggcggaggc ctggtgcagc ctggcggatc tctgagactg      60
tcctgcgccg cctccggctt caccttctcc gactaccaga tgacctggat cagacagacc     120
cccggcaagg gcctggaatg ggtgtccggc atctcctgga acggcggctc cacccactac     180
gccgactctg tgaagggccg gttcaccatc tcccgggaca actccaagaa cacccctgta     240
ctgcagatga actccctgcg ggccgaggac accgccgtgt actactgcgc caagggcgac     300
tacctggtgt actcctccta ctacttcaag tcctggggcc agggcaccct ggtcaccgtc     360
agctca                                                                366

<210> SEQ ID NO 114
<211> LENGTH: 336
<212> TYPE: DNA
<213> ORGANISM: Artificial Sequence
<220> FEATURE:
<223> OTHER INFORMATION: C4.4a binder

<400> SEQUENCE: 114
cagtccgtgc tgacccagcc tccttccgcc tctggcaccc tggccagag agtgaccatc       60 tcctgctccg gctcctcctc caacatcggc tccaaccccg tgaactggta tcagcagctg     120
cccggcaccg cccccaagct gctgatctac cggaacaacc agcggccctc cggcgtgccc     180
gacagattct ccggctccaa gtccggcacc tccgcctccc tggccatctc cggcctgaga     240
tctgaggacg aggccgacta ctactgcgcc gcctgggacg accggctgtc tggctgggct     300
tttggcggcg gaacaaagtt aaccgtgctg ggccag                               336

<210> SEQ ID NO 115
<211> LENGTH: 9
<212> TYPE: PRT
<213> ORGANISM: Artificial Sequence
<220> FEATURE:
<223> OTHER INFORMATION: C4.4a binder

<400> SEQUENCE: 115

Phe Ser Asp Tyr Gln Met Thr Trp Ile
1               5

<210> SEQ ID NO 116
<211> LENGTH: 20
<212> TYPE: PRT
<213> ORGANISM: Artificial Sequence
<220> FEATURE:
<223> OTHER INFORMATION: C4.4a binder

<400> SEQUENCE: 116

Val Ser Gly Ile Ser Trp Asn Gly Gly Ser Thr His Tyr Ala Asp Ser
1               5                   10                  15
Val Lys Gly Arg
            20

<210> SEQ ID NO 117
<211> LENGTH: 15
<212> TYPE: PRT
<213> ORGANISM: Artificial Sequence
<220> FEATURE:
<223> OTHER INFORMATION: C4.4a binder

<400> SEQUENCE: 117
```

```
Ala Lys Gly Asp Tyr Leu Val Tyr Lys Ser Tyr Tyr Phe Lys Ser
1               5                   10                  15
```

<210> SEQ ID NO 118
<211> LENGTH: 13
<212> TYPE: PRT
<213> ORGANISM: Artificial Sequence
<220> FEATURE:
<223> OTHER INFORMATION: C4.4a binder

<400> SEQUENCE: 118

```
Ser Gly Ser Ser Ser Asn Ile Gly Ser Asn Pro Val Asn
1               5                   10
```

<210> SEQ ID NO 119
<211> LENGTH: 7
<212> TYPE: PRT
<213> ORGANISM: Artificial Sequence
<220> FEATURE:
<223> OTHER INFORMATION: C4.4a binder

<400> SEQUENCE: 119

```
Arg Asn Asn Gln Arg Pro Ser
1               5
```

<210> SEQ ID NO 120
<211> LENGTH: 12
<212> TYPE: PRT
<213> ORGANISM: Artificial Sequence
<220> FEATURE:
<223> OTHER INFORMATION: C4.4a binder

<400> SEQUENCE: 120

```
Cys Ala Ala Trp Asp Asp Ser Leu Ser Gly Trp Ala
1               5                   10
```

<210> SEQ ID NO 121
<211> LENGTH: 122
<212> TYPE: PRT
<213> ORGANISM: Artificial Sequence
<220> FEATURE:
<223> OTHER INFORMATION: C4.4a binder

<400> SEQUENCE: 121

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Tyr Phe Lys Ser Trp
                100                 105                 110

Gly Gln Gly Thr Leu Val Thr Val Ser Ser
            115                 120
```

<210> SEQ ID NO 122

<211> LENGTH: 112
<212> TYPE: PRT
<213> ORGANISM: Artificial Sequence
<220> FEATURE:
<223> OTHER INFORMATION: C4.4a binder

<400> SEQUENCE: 122

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Pro Val Asn Trp Tyr Gln Gln Leu Pro Gly Thr Ala Pro Lys Leu Leu
        35                  40                  45
Ile Tyr Arg Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ser Leu
                85                  90                  95
Ser Gly Trp Ala Phe Gly Gly Gly Thr Lys Leu Thr Val Leu Gly Gln
            100                 105                 110
```

<210> SEQ ID NO 123
<211> LENGTH: 366
<212> TYPE: DNA
<213> ORGANISM: Artificial Sequence
<220> FEATURE:
<223> OTHER INFORMATION: C4.4a binder

<400> SEQUENCE: 123

```
gaggtgcagc tgctggaatc cggcggaggc ctggtgcagc ctggcggatc tctgagactg      60
tcctgcgccg cctccggctt caccttctcc gactaccaga tgacctggat cagacagacc     120
cccggcaagg gcctggaatg ggtgtccggc atctcctgga acggcggctc cacccactac     180
gccgactctg tgaagggccg gttcaccatc tcccgggaca actccaagaa caccctgtac     240
ctgcagatga actccctgcg ggccgaggac accgccgtgt actactgcgc caagggcgac     300
tacctggtgt acaagtccta ctacttcaag tcctggggcc agggcaccct ggtcaccgtc     360
agctca                                                                366
```

<210> SEQ ID NO 124
<211> LENGTH: 336
<212> TYPE: DNA
<213> ORGANISM: Artificial Sequence
<220> FEATURE:
<223> OTHER INFORMATION: C4.4a binder

<400> SEQUENCE: 124

```
cagtccgtgc tgacccagcc tccttccgcc tctggcaccc tggccagag agtgaccatc       60
tcctgctccg gctcctcctc aacatcggc tccaaccccg tgaactggta tcagcagctg      120
cccggcaccg cccccaagct gctgatctac cggaacaacc agcggccctc cggcgtgccc     180
gacagattct ccggctccaa gtccggcacc tccgcctccc tggccatctc cggcctgaga     240
tctgaggacg aggccgacta ctactgcgcc gcctgggacg actccctgtc tggctgggct     300
tttggcggcg gaacaaagtt aaccgtgctg ggccag                               336
```

<210> SEQ ID NO 125
<211> LENGTH: 9
<212> TYPE: PRT

```
<213> ORGANISM: Artificial Sequence
<220> FEATURE:
<223> OTHER INFORMATION: C4.4a binder

<400> SEQUENCE: 125

Phe Ser Asp Tyr Gln Met Thr Trp Ile
1               5

<210> SEQ ID NO 126
<211> LENGTH: 20
<212> TYPE: PRT
<213> ORGANISM: Artificial Sequence
<220> FEATURE:
<223> OTHER INFORMATION: C4.4a binder

<400> SEQUENCE: 126

Val Ser Gly Ile Ser Trp Asn Gly Gly Ser Thr His Tyr Ala Asp Ser
1               5                   10                  15

Val Lys Gly Arg
            20

<210> SEQ ID NO 127
<211> LENGTH: 15
<212> TYPE: PRT
<213> ORGANISM: Artificial Sequence
<220> FEATURE:
<223> OTHER INFORMATION: C4.4a binder

<400> SEQUENCE: 127

Ala Lys Gly Asp Tyr Leu Val Tyr Ser Ser Tyr Tyr Phe Lys Ser
1               5                   10                  15

<210> SEQ ID NO 128
<211> LENGTH: 13
<212> TYPE: PRT
<213> ORGANISM: Artificial Sequence
<220> FEATURE:
<223> OTHER INFORMATION: C4.4a binder

<400> SEQUENCE: 128

Ser Gly Ser Ser Ser Asn Ile Gly Ser Asn Pro Val Asn
1               5                   10

<210> SEQ ID NO 129
<211> LENGTH: 7
<212> TYPE: PRT
<213> ORGANISM: Artificial Sequence
<220> FEATURE:
<223> OTHER INFORMATION: C4.4a binder

<400> SEQUENCE: 129

Arg Asn Asn Gln Arg Pro Ser
1               5

<210> SEQ ID NO 130
<211> LENGTH: 12
<212> TYPE: PRT
<213> ORGANISM: Artificial Sequence
<220> FEATURE:
<223> OTHER INFORMATION: C4.4a binder

<400> SEQUENCE: 130

Cys Ala Ala Trp Asp Asp Arg Leu Ser Gly Trp Gly
1               5                   10

<210> SEQ ID NO 131
```

```
<211> LENGTH: 122
<212> TYPE: PRT
<213> ORGANISM: Artificial Sequence
<220> FEATURE:
<223> OTHER INFORMATION: C4.4a binder

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Ser Trp
            100                 105                 110

Gly Gln Gly Thr Leu Val Thr Val Ser Ser
        115                 120

<210> SEQ ID NO 132
<211> LENGTH: 112
<212> TYPE: PRT
<213> ORGANISM: Artificial Sequence
<220> FEATURE:
<223> OTHER INFORMATION: C4.4a binder

<400> SEQUENCE: 132

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Gly Phe Gly Gly Gly Thr Lys Leu Thr Val Leu Gly Gln
            100                 105                 110

<210> SEQ ID NO 133
<211> LENGTH: 366
<212> TYPE: DNA
<213> ORGANISM: Artificial Sequence
<220> FEATURE:
<223> OTHER INFORMATION: C4.4a binder

<400> SEQUENCE: 133
gaggtgcagc tgctggaatc cggcggaggc ctggtgcagc ctggcggatc tctgagactg      60
tcctgcgccg cctccggctt caccttctcc gactaccaga tgacctggat cagacagacc     120
cccggcaagg gcctggaatg ggtgtccggc atctcctgga acggcggctc cacccactac     180
```

```
gccgactctg tgaagggccg gttcaccatc tccgggaca actccaagaa caccctgtac    240
ctgcagatga actccctgcg ggccgaggac accgccgtgt actactgcgc caagggcgac    300
tacctggtgt actcctccta ctacttcaag tcctggggcc agggcaccct ggtcaccgtc    360
agctca                                                               366

<210> SEQ ID NO 134
<211> LENGTH: 336
<212> TYPE: DNA
<213> ORGANISM: Artificial Sequence
<220> FEATURE:
<223> OTHER INFORMATION: C4.4a binder

<400> SEQUENCE: 134
cagtccgtgc tgacccagcc tccttccgcc tctggcaccc ctggccagag agtgaccatc     60
tcctgctccg gctcctcctc aacatcggc tccaaccccg tgaactggta tcagcagctg    120
cccggcaccg cccccaagct gctgatctac cggaacaacc agcggccctc cggcgtgccc    180
gacagattct ccggctccaa gtccggcacc tccgcctccc tggccatctc cggcctgaga    240
tctgaggacg aggccgacta ctactgcgcc gcctgggacg accggctgtc tggctgggga    300
tttggcggcg aacaaagtt aaccgtgctg ggccag                               336

<210> SEQ ID NO 135
<211> LENGTH: 9
<212> TYPE: PRT
<213> ORGANISM: Artificial Sequence
<220> FEATURE:
<223> OTHER INFORMATION: C4.4a binder

<400> SEQUENCE: 135

Phe Ser Ser Tyr Gln Met Thr Trp Ile
1               5

<210> SEQ ID NO 136
<211> LENGTH: 20
<212> TYPE: PRT
<213> ORGANISM: Artificial Sequence
<220> FEATURE:
<223> OTHER INFORMATION: C4.4a binder

<400> SEQUENCE: 136

Val Ser Gly Ile Ser Trp Asn Gly Gly Ser Thr His Tyr Ala Asp Ser
1               5                   10                  15

Val Lys Gly Arg
            20

<210> SEQ ID NO 137
<211> LENGTH: 15
<212> TYPE: PRT
<213> ORGANISM: Artificial Sequence
<220> FEATURE:
<223> OTHER INFORMATION: C4.4a binder

<400> SEQUENCE: 137

Ala Lys Gly Asp Tyr Leu Val Tyr Lys Ser Tyr Tyr Phe Lys Ser
1               5                   10                  15

<210> SEQ ID NO 138
<211> LENGTH: 13
<212> TYPE: PRT
<213> ORGANISM: Artificial Sequence
<220> FEATURE:
<223> OTHER INFORMATION: C4.4a binder
```

<400> SEQUENCE: 138

Ser Gly Ser Ser Ser Asn Ile Gly Ser Asn Pro Val Asn
1               5                   10

<210> SEQ ID NO 139
<211> LENGTH: 7
<212> TYPE: PRT
<213> ORGANISM: Artificial Sequence
<220> FEATURE:
<223> OTHER INFORMATION: C4.4a binder

<400> SEQUENCE: 139

Arg Asn Asn Gln Arg Pro Ser
1               5

<210> SEQ ID NO 140
<211> LENGTH: 12
<212> TYPE: PRT
<213> ORGANISM: Artificial Sequence
<220> FEATURE:
<223> OTHER INFORMATION: C4.4a binder

<400> SEQUENCE: 140

Cys Ala Ala Trp Asp Asp Ser Leu Ser Gly Trp Ala
1               5                   10

<210> SEQ ID NO 141
<211> LENGTH: 122
<212> TYPE: PRT
<213> ORGANISM: Artificial Sequence
<220> FEATURE:
<223> OTHER INFORMATION: C4.4a binder

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Thr Trp Ile Arg Gln Ala Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Tyr Phe Lys Ser Trp
            100                 105                 110

Gly Gln Gly Thr Leu Val Thr Val Ser Ser
        115                 120

<210> SEQ ID NO 142
<211> LENGTH: 112
<212> TYPE: PRT
<213> ORGANISM: Artificial Sequence
<220> FEATURE:
<223> OTHER INFORMATION: C4.4a binder

<400> SEQUENCE: 142

Gln Ser Val Leu Thr Gln Pro Pro Ser Ala Ser Gly Thr Pro Gly Gln
1               5                   10                  15

```
Arg Val Thr Ile Ser Cys Ser Gly Ser Ser Asn Ile Gly Ser Asn
             20                  25                  30

Pro Val Asn Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Ser Leu
                 85                  90                  95

Ser Gly Trp Ala Phe Gly Gly Gly Thr Lys Leu Thr Val Leu Gly Gln
            100                 105                 110
```

<210> SEQ ID NO 143
<211> LENGTH: 366
<212> TYPE: DNA
<213> ORGANISM: Artificial Sequence
<220> FEATURE:
<223> OTHER INFORMATION: C4.4a binder

<400> SEQUENCE: 143

```
gaggtgcagc tgctggaaag cggcggaggc ctggtgcagc ctggcggaag cctgagactg    60
agctgtgccg ccagcggctt cacctcagc agctaccaga tgacctggat cagacaggcc   120
cctggcaagg gcctggaatg ggtgtccggc atcagctgga acggcggcag cacccactac   180
gccgacagcg tgaagggccg gttcaccatc agccgggaca cagcaagaa caccctgtac   240
ctgcagatga acagcctgcg ggccgaggac accgccgtgt actactgcgc caagggcgac   300
tacctggtgt acaagagcta ctacttcaag agctggggcc agggcacact ggtcaccgtc   360
agctca                                                             366
```

<210> SEQ ID NO 144
<211> LENGTH: 336
<212> TYPE: DNA
<213> ORGANISM: Artificial Sequence
<220> FEATURE:
<223> OTHER INFORMATION: C4.4a binder

<400> SEQUENCE: 144

```
cagagcgtgc tgacccagcc tcctagcgcc tctggcaccc ctggccagag agtgaccatc    60
agctgcagcg gcagcagcag caacatcggc agcaaccccg tgaactggta tcagcagctg   120
cccggcaccg cccccaagct gctgatctac cggaacaacc agcggcccag cggcgtgccc   180
gacagattt ccggcagcaa gagcggcacc agcgccagcc tggccatcag cggcctgaga   240
agcgaggacg aggccgacta ctactgcgcc gcctgggacg atagcctgag cggctgggcc   300
tttggcggcg gaacaaagtt aaccgtgctg ggccag                             336
```

<210> SEQ ID NO 145
<211> LENGTH: 9
<212> TYPE: PRT
<213> ORGANISM: Artificial Sequence
<220> FEATURE:
<223> OTHER INFORMATION: C4.4a binder

<400> SEQUENCE: 145

```
Phe Ser Asn Ala Trp Met Ser Trp Val
 1               5
```

<210> SEQ ID NO 146

-continued

```
<211> LENGTH: 20
<212> TYPE: PRT
<213> ORGANISM: Artificial Sequence
<220> FEATURE:
<223> OTHER INFORMATION: C4.4a binder

<400> SEQUENCE: 146

Val Ser Tyr Ile Ser Ser Ser Gly Ser Thr Ile Tyr Tyr Ala Asp Ser
1               5                   10                  15

Val Lys Gly Arg
            20

<210> SEQ ID NO 147
<211> LENGTH: 10
<212> TYPE: PRT
<213> ORGANISM: Artificial Sequence
<220> FEATURE:
<223> OTHER INFORMATION: C4.4a binder

<400> SEQUENCE: 147

Ala Arg Glu Gly Leu Trp Ala Phe Asp Lys
1               5                   10

<210> SEQ ID NO 148
<211> LENGTH: 14
<212> TYPE: PRT
<213> ORGANISM: Artificial Sequence
<220> FEATURE:
<223> OTHER INFORMATION: C4.4a binder

<400> SEQUENCE: 148

Thr Gly Ser Ser Ser Asn Ile Gly Ala Gly Tyr Val Val His
1               5                   10

<210> SEQ ID NO 149
<211> LENGTH: 7
<212> TYPE: PRT
<213> ORGANISM: Artificial Sequence
<220> FEATURE:
<223> OTHER INFORMATION: C4.4a binder

<400> SEQUENCE: 149

Asp Asn Asn Lys Arg Pro Ser
1               5

<210> SEQ ID NO 150
<211> LENGTH: 12
<212> TYPE: PRT
<213> ORGANISM: Artificial Sequence
<220> FEATURE:
<223> OTHER INFORMATION: C4.4a binder

<400> SEQUENCE: 150

Cys Ala Ala Tyr Asp Asp Ser Leu Lys Gly Pro Val
1               5                   10

<210> SEQ ID NO 151
<211> LENGTH: 117
<212> TYPE: PRT
<213> ORGANISM: Artificial Sequence
<220> FEATURE:
<223> OTHER INFORMATION: C4.4a binder

<400> SEQUENCE: 151

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Thr Ser
        115

<210> SEQ ID NO 152
<211> LENGTH: 113
<212> TYPE: PRT
<213> ORGANISM: Artificial Sequence
<220> FEATURE:
<223> OTHER INFORMATION: C4.4a binder

<400> SEQUENCE: 152

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Ser
                85                  90                  95

Leu Lys Gly Pro Val Phe Gly Gly Gly Thr Lys Leu Thr Val Leu Gly
            100                 105                 110

Gln

<210> SEQ ID NO 153
<211> LENGTH: 9
<212> TYPE: PRT
<213> ORGANISM: Artificial Sequence
<220> FEATURE:
<223> OTHER INFORMATION: C4.4a binder

<400> SEQUENCE: 153

Phe Ser Asn Ala Trp Met Ser Trp Val
1               5

<210> SEQ ID NO 154
<211> LENGTH: 20
<212> TYPE: PRT
<213> ORGANISM: Artificial Sequence
<220> FEATURE:
<223> OTHER INFORMATION: C4.4a binder

<400> SEQUENCE: 154

Val Ser Tyr Ile Ser Ser Ser Gly Ser Thr Ile Tyr Tyr Ala Asp Ser
1               5                   10                  15
```

Val Lys Gly Arg
            20

<210> SEQ ID NO 155
<211> LENGTH: 10
<212> TYPE: PRT
<213> ORGANISM: Artificial Sequence
<220> FEATURE:
<223> OTHER INFORMATION: C4.4a binder

<400> SEQUENCE: 155

Ala Arg Glu Gly Leu Trp Ala Phe Asp Lys
1               5                   10

<210> SEQ ID NO 156
<211> LENGTH: 14
<212> TYPE: PRT
<213> ORGANISM: Artificial Sequence
<220> FEATURE:
<223> OTHER INFORMATION: C4.4a binder

<400> SEQUENCE: 156

Thr Gly Ser Ser Ser Asn Ile Gly Ala Gly Tyr Val Val His
1               5                   10

<210> SEQ ID NO 157
<211> LENGTH: 7
<212> TYPE: PRT
<213> ORGANISM: Artificial Sequence
<220> FEATURE:
<223> OTHER INFORMATION: C4.4a binder

<400> SEQUENCE: 157

Asp Asn Asn Lys Arg Pro Ser
1               5

<210> SEQ ID NO 158
<211> LENGTH: 12
<212> TYPE: PRT
<213> ORGANISM: Artificial Sequence
<220> FEATURE:
<223> OTHER INFORMATION: C4.4a binder

<400> SEQUENCE: 158

Cys Ala Ala Phe Asp Asp Ser Leu Asn Gly Pro Val
1               5                   10

<210> SEQ ID NO 159
<211> LENGTH: 117
<212> TYPE: PRT
<213> ORGANISM: Artificial Sequence
<220> FEATURE:
<223> OTHER INFORMATION: C4.4a binder

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr 65                  70                  75                  80
Leu Gln Met Asn Ser Leu Arg Ala Glu Asp Thr Ala Val Tyr Tyr Cys
                    85                  90                  95

Ala Arg Glu Gly Leu Trp Ala Phe Asp Lys Trp Gly Gln Gly Thr Leu
                100                 105                 110

Val Thr Val Thr Ser
            115

<210> SEQ ID NO 160
<211> LENGTH: 113
<212> TYPE: PRT
<213> ORGANISM: Artificial Sequence
<220> FEATURE:
<223> OTHER INFORMATION: C4.4a binder

<400> SEQUENCE: 160

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Ser
                85                  90                  95

Leu Asn Gly Pro Val Phe Gly Gly Gly Thr Lys Leu Thr Val Leu Gly
                100                 105                 110

Gln

<210> SEQ ID NO 161
<211> LENGTH: 9
<212> TYPE: PRT
<213> ORGANISM: Artificial Sequence
<220> FEATURE:
<223> OTHER INFORMATION: C4.4a binder

<400> SEQUENCE: 161

Phe Ser Asn Ala Trp Met Ser Trp Val
1               5

<210> SEQ ID NO 162
<211> LENGTH: 20
<212> TYPE: PRT
<213> ORGANISM: Artificial Sequence
<220> FEATURE:
<223> OTHER INFORMATION: C4.4a binder

<400> SEQUENCE: 162

Val Ser Tyr Ile Ser Ser Ser Gly Ser Thr Ile Tyr Tyr Ala Asp Ser
1               5                   10                  15

Val Lys Gly Arg
            20

<210> SEQ ID NO 163
<211> LENGTH: 10
<212> TYPE: PRT
<213> ORGANISM: Artificial Sequence
<220> FEATURE:

-continued

<223> OTHER INFORMATION: C4.4a binder

<400> SEQUENCE: 163

Ala Arg Glu Gly Leu Trp Ala Phe Asp Lys
1               5                   10

<210> SEQ ID NO 164
<211> LENGTH: 14
<212> TYPE: PRT
<213> ORGANISM: Artificial Sequence
<220> FEATURE:
<223> OTHER INFORMATION: C4.4a binder

<400> SEQUENCE: 164

Thr Gly Ser Ser Ser Asn Ile Gly Ala Gly Tyr Val Val His
1               5                   10

<210> SEQ ID NO 165
<211> LENGTH: 7
<212> TYPE: PRT
<213> ORGANISM: Artificial Sequence
<220> FEATURE:
<223> OTHER INFORMATION: C4.4a binder

<400> SEQUENCE: 165

Asp Asn Asn Lys Arg Pro Ser
1               5

<210> SEQ ID NO 166
<211> LENGTH: 12
<212> TYPE: PRT
<213> ORGANISM: Artificial Sequence
<220> FEATURE:
<223> OTHER INFORMATION: C4.4a binder

<400> SEQUENCE: 166

Cys Ala Ala Tyr Asp Asp Ser Leu Ser Gly Pro Val
1               5                   10

<210> SEQ ID NO 167
<211> LENGTH: 117
<212> TYPE: PRT
<213> ORGANISM: Artificial Sequence
<220> FEATURE:
<223> OTHER INFORMATION: C4.4a binder

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Thr Ser
            115

<210> SEQ ID NO 168
<211> LENGTH: 113
<212> TYPE: PRT
<213> ORGANISM: Artificial Sequence
<220> FEATURE:
<223> OTHER INFORMATION: C4.4a binder

<400> SEQUENCE: 168

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Ser
                85                  90                  95

Leu Asn Gly Pro Val Phe Gly Gly Gly Thr Lys Leu Thr Val Leu Gly
            100                 105                 110

Gln

<210> SEQ ID NO 169
<211> LENGTH: 9
<212> TYPE: PRT
<213> ORGANISM: Artificial Sequence
<220> FEATURE:
<223> OTHER INFORMATION: C4.4a binder

<400> SEQUENCE: 169

Phe Ser Ser Ala Trp Met Ser Trp Val
1               5

<210> SEQ ID NO 170
<211> LENGTH: 20
<212> TYPE: PRT
<213> ORGANISM: Artificial Sequence
<220> FEATURE:
<223> OTHER INFORMATION: C4.4a binder

<400> SEQUENCE: 170

Val Ser Tyr Ile Ser Ser Ser Gly Ser Ser Thr Tyr Tyr Ala Asp Ser
1               5                   10                  15

Val Lys Gly Arg
            20

<210> SEQ ID NO 171
<211> LENGTH: 10
<212> TYPE: PRT
<213> ORGANISM: Artificial Sequence
<220> FEATURE:
<223> OTHER INFORMATION: C4.4a binder

<400> SEQUENCE: 171

Ala Arg Glu Gly Leu Trp Ala Phe Asp Trp
1               5                   10

<210> SEQ ID NO 172
<211> LENGTH: 14

```
<212> TYPE: PRT
<213> ORGANISM: Artificial Sequence
<220> FEATURE:
<223> OTHER INFORMATION: C4.4a binder

<400> SEQUENCE: 172

Ser Gly Ser Ser Ser Asn Ile Gly Ala Gly Tyr Val Val His
1               5                   10

<210> SEQ ID NO 173
<211> LENGTH: 7
<212> TYPE: PRT
<213> ORGANISM: Artificial Sequence
<220> FEATURE:
<223> OTHER INFORMATION: C4.4a binder

<400> SEQUENCE: 173

Asp Asn Asn Gln Arg Pro Ser
1               5

<210> SEQ ID NO 174
<211> LENGTH: 12
<212> TYPE: PRT
<213> ORGANISM: Artificial Sequence
<220> FEATURE:
<223> OTHER INFORMATION: C4.4a binder

<400> SEQUENCE: 174

Cys Ala Ala Tyr Asp Asp Ser Leu Ser Gly Pro Val
1               5                   10

<210> SEQ ID NO 175
<211> LENGTH: 117
<212> TYPE: PRT
<213> ORGANISM: Artificial Sequence
<220> FEATURE:
<223> OTHER INFORMATION: C4.4a binder

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Trp Trp Gly Gln Gly Thr Leu
            100                 105                 110

Val Thr Val Thr Ser
        115

<210> SEQ ID NO 176
<211> LENGTH: 113
<212> TYPE: PRT
<213> ORGANISM: Artificial Sequence
<220> FEATURE:
<223> OTHER INFORMATION: C4.4a binder

<400> SEQUENCE: 176
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65              70                  75                  80

Arg Ser Glu Asp Glu Ala Asp Tyr Tyr Cys Ala Ala Tyr Asp Asp Ser
                85                  90                  95

Leu Ser Gly Pro Val Phe Gly Gly Gly Thr Lys Leu Thr Val Leu Gly
            100                 105                 110

Gln
```

<210> SEQ ID NO 177
<211> LENGTH: 9
<212> TYPE: PRT
<213> ORGANISM: Artificial Sequence
<220> FEATURE:
<223> OTHER INFORMATION: C4.4a binder

<400> SEQUENCE: 177

```
Phe Ser Ser Ala Trp Met Ser Trp Val
1               5
```

<210> SEQ ID NO 178
<211> LENGTH: 20
<212> TYPE: PRT
<213> ORGANISM: Artificial Sequence
<220> FEATURE:
<223> OTHER INFORMATION: C4.4a binder

<400> SEQUENCE: 178

```
Val Ser Tyr Ile Ser Ser Ser Gly Ser Ser Thr Tyr Tyr Ala Asp Ser
1               5                   10                  15

Val Lys Gly Arg
            20
```

<210> SEQ ID NO 179
<211> LENGTH: 10
<212> TYPE: PRT
<213> ORGANISM: Artificial Sequence
<220> FEATURE:
<223> OTHER INFORMATION: C4.4a binder

<400> SEQUENCE: 179

```
Ala Arg Glu Gly Leu Trp Ala Phe Asp Asn
1               5                   10
```

<210> SEQ ID NO 180
<211> LENGTH: 14
<212> TYPE: PRT
<213> ORGANISM: Artificial Sequence
<220> FEATURE:
<223> OTHER INFORMATION: C4.4a binder

<400> SEQUENCE: 180

```
Ser Gly Ser Ser Ser Asn Ile Gly Ala Gly Tyr Val Val His
1               5                   10
```

```
<210> SEQ ID NO 181
<211> LENGTH: 7
<212> TYPE: PRT
<213> ORGANISM: Artificial Sequence
<220> FEATURE:
<223> OTHER INFORMATION: C4.4a binder

<400> SEQUENCE: 181

Asp Asn Asn Gln Arg Pro Ser
1               5

<210> SEQ ID NO 182
<211> LENGTH: 12
<212> TYPE: PRT
<213> ORGANISM: Artificial Sequence
<220> FEATURE:
<223> OTHER INFORMATION: C4.4a binder

<400> SEQUENCE: 182

Cys Ala Ala Tyr Asp Asp Ser Leu Asn Gly Pro Val
1               5                  10

<210> SEQ ID NO 183
<211> LENGTH: 117
<212> TYPE: PRT
<213> ORGANISM: Artificial Sequence
<220> FEATURE:
<223> OTHER INFORMATION: C4.4a binder

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Thr Ser
        115

<210> SEQ ID NO 184
<211> LENGTH: 113
<212> TYPE: PRT
<213> ORGANISM: Artificial Sequence
<220> FEATURE:
<223> OTHER INFORMATION: C4.4a binder

<400> SEQUENCE: 184

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
        35                  40                  45
```

Leu Ile Tyr Asp Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Ser
                85                  90                  95

Leu Asn Gly Pro Val Phe Gly Gly Gly Thr Lys Leu Thr Val Leu Gly
            100                 105                 110

Gln

<210> SEQ ID NO 185
<211> LENGTH: 9
<212> TYPE: PRT
<213> ORGANISM: Artificial Sequence
<220> FEATURE:
<223> OTHER INFORMATION: C4.4a binder

<400> SEQUENCE: 185

Phe Ser Ser Ala Trp Met Ser Trp Val
1               5

<210> SEQ ID NO 186
<211> LENGTH: 20
<212> TYPE: PRT
<213> ORGANISM: Artificial Sequence
<220> FEATURE:
<223> OTHER INFORMATION: C4.4a binder

<400> SEQUENCE: 186

Val Ser Tyr Ile Ser Ser Ser Gly Ser Ser Thr Tyr Tyr Ala Asp Ser
1               5                   10                  15

Val Lys Gly Arg
            20

<210> SEQ ID NO 187
<211> LENGTH: 10
<212> TYPE: PRT
<213> ORGANISM: Artificial Sequence
<220> FEATURE:
<223> OTHER INFORMATION: C4.4a binder

<400> SEQUENCE: 187

Ala Arg Glu Gly Leu Trp Ala Phe Asp Tyr
1               5                   10

<210> SEQ ID NO 188
<211> LENGTH: 14
<212> TYPE: PRT
<213> ORGANISM: Artificial Sequence
<220> FEATURE:
<223> OTHER INFORMATION: C4.4a binder

<400> SEQUENCE: 188

Ser Gly Ser Ser Ser Asn Ile Gly Ala Gly Tyr Val Val His
1               5                   10

<210> SEQ ID NO 189
<211> LENGTH: 7
<212> TYPE: PRT
<213> ORGANISM: Artificial Sequence
<220> FEATURE:
<223> OTHER INFORMATION: C4.4a binder

<400> SEQUENCE: 189

Asp Asn Asn Gln Arg Pro Ser
1               5

<210> SEQ ID NO 190
<211> LENGTH: 12
<212> TYPE: PRT
<213> ORGANISM: Artificial Sequence
<220> FEATURE:
<223> OTHER INFORMATION: C4.4a binder

<400> SEQUENCE: 190

Cys Ala Ala Trp Asp Asp Arg Leu Asn Gly Pro Val
1               5                   10

<210> SEQ ID NO 191
<211> LENGTH: 117
<212> TYPE: PRT
<213> ORGANISM: Artificial Sequence
<220> FEATURE:
<223> OTHER INFORMATION: C4.4a binder

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser
        115

<210> SEQ ID NO 192
<211> LENGTH: 113
<212> TYPE: PRT
<213> ORGANISM: Artificial Sequence
<220> FEATURE:
<223> OTHER INFORMATION: C4.4a binder

<400> SEQUENCE: 192

Glu Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Arg
                85                  90                  95

Leu Asn Gly Pro Val Phe Gly Gly Gly Thr Lys Leu Thr Val Leu Gly

```
                100             105             110
Gln

<210> SEQ ID NO 193
<211> LENGTH: 11
<212> TYPE: PRT
<213> ORGANISM: Artificial Sequence
<220> FEATURE:
<223> OTHER INFORMATION: C4.4a binder

<400> SEQUENCE: 193

Phe Thr Phe Ser Asn Ala Trp Met Ser Trp Val
1               5                   10

<210> SEQ ID NO 194
<211> LENGTH: 20
<212> TYPE: PRT
<213> ORGANISM: Artificial Sequence
<220> FEATURE:
<223> OTHER INFORMATION: C4.4a binder

<400> SEQUENCE: 194

Val Ser Tyr Ile Ser Ser Ser Gly Ser Thr Ile Tyr Tyr Ala Asp Ser
1               5                   10                  15

Val Lys Gly Arg
            20

<210> SEQ ID NO 195
<211> LENGTH: 10
<212> TYPE: PRT
<213> ORGANISM: Artificial Sequence
<220> FEATURE:
<223> OTHER INFORMATION: C4.4a binder

<400> SEQUENCE: 195

Ala Arg Glu Gly Leu Trp Ala Phe Asp Tyr
1               5                   10

<210> SEQ ID NO 196
<211> LENGTH: 14
<212> TYPE: PRT
<213> ORGANISM: Artificial Sequence
<220> FEATURE:
<223> OTHER INFORMATION: C4.4a binder

<400> SEQUENCE: 196

Thr Gly Ser Ser Ser Asn Ile Gly Ala Gly Tyr Val Val His
1               5                   10

<210> SEQ ID NO 197
<211> LENGTH: 7
<212> TYPE: PRT
<213> ORGANISM: Artificial Sequence
<220> FEATURE:
<223> OTHER INFORMATION: C4.4a binder

<400> SEQUENCE: 197

Asp Asn Asn Lys Arg Pro Ser
1               5

<210> SEQ ID NO 198
<211> LENGTH: 12
<212> TYPE: PRT
<213> ORGANISM: Artificial Sequence
<220> FEATURE:
<223> OTHER INFORMATION: C4.4a binder
```

-continued

<400> SEQUENCE: 198

Cys Ala Ala Tyr Asp Asp Arg Leu Asn Gly Pro Val
1               5                   10

<210> SEQ ID NO 199
<211> LENGTH: 117
<212> TYPE: PRT
<213> ORGANISM: Artificial Sequence
<220> FEATURE:
<223> OTHER INFORMATION: C4.4a binder

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser
        115

<210> SEQ ID NO 200
<211> LENGTH: 113
<212> TYPE: PRT
<213> ORGANISM: Artificial Sequence
<220> FEATURE:
<223> OTHER INFORMATION: C4.4a binder

<400> SEQUENCE: 200

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Arg
                85                  90                  95

Leu Asn Gly Pro Val Phe Gly Gly Gly Thr Lys Leu Thr Val Leu Gly
            100                 105                 110

Gln

<210> SEQ ID NO 201
<211> LENGTH: 11
<212> TYPE: PRT
<213> ORGANISM: Artificial Sequence
<220> FEATURE:

<223> OTHER INFORMATION: C4.4a binder

<400> SEQUENCE: 201

Phe Thr Phe Ser Ser Ala Trp Met Ser Trp Val
1               5                   10

<210> SEQ ID NO 202
<211> LENGTH: 20
<212> TYPE: PRT
<213> ORGANISM: Artificial Sequence
<220> FEATURE:
<223> OTHER INFORMATION: C4.4a binder

<400> SEQUENCE: 202

Val Ser Tyr Ile Ser Ser Ser Gly Ser Ser Thr Tyr Tyr Ala Asp Ser
1               5                   10                  15

Val Lys Gly Arg
            20

<210> SEQ ID NO 203
<211> LENGTH: 10
<212> TYPE: PRT
<213> ORGANISM: Artificial Sequence
<220> FEATURE:
<223> OTHER INFORMATION: C4.4a binder

<400> SEQUENCE: 203

Ala Arg Glu Gly Leu Trp Ala Phe Asp Gly
1               5                   10

<210> SEQ ID NO 204
<211> LENGTH: 14
<212> TYPE: PRT
<213> ORGANISM: Artificial Sequence
<220> FEATURE:
<223> OTHER INFORMATION: C4.4a binder

<400> SEQUENCE: 204

Ser Gly Ser Ser Ser Asn Ile Gly Ala Gly Tyr Val Val His
1               5                   10

<210> SEQ ID NO 205
<211> LENGTH: 7
<212> TYPE: PRT
<213> ORGANISM: Artificial Sequence
<220> FEATURE:
<223> OTHER INFORMATION: C4.4a binder

<400> SEQUENCE: 205

Asp Asn Asn Gln Arg Pro Ser
1               5

<210> SEQ ID NO 206
<211> LENGTH: 12
<212> TYPE: PRT
<213> ORGANISM: Artificial Sequence
<220> FEATURE:
<223> OTHER INFORMATION: C4.4a binder

<400> SEQUENCE: 206

Cys Ala Ala Tyr Asp Asp Ser Leu Asn Arg Pro Val
1               5                   10

<210> SEQ ID NO 207
<211> LENGTH: 117
<212> TYPE: PRT

<213> ORGANISM: Artificial Sequence
<220> FEATURE:
<223> OTHER INFORMATION: C4.4a binder

<400> SEQUENCE: 207

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser | Ala |
| | | | 20 | | | | | 25 | | | | | 30 | |
| Trp | Met | Ser | Trp | Val | Arg | Gln | Ala | Pro | Gly | Lys | Gly | Leu | Glu | Trp | Val |
| | | | 35 | | | | | 40 | | | | | 45 | |
| Ser | Tyr | Ile | Ser | Ser | Ser | Gly | Ser | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Glu | Gly | Leu | Trp | Ala | Phe | Asp | Gly | Trp | Gly | Gln | Gly | Thr | Leu |
| | | | | 100 | | | | | 105 | | | | | 110 | |
| Val | Thr | Val | Ser | Ser | | | | | | | | | | | |
| | | | | 115 | | | | | | | | | | | |

<210> SEQ ID NO 208
<211> LENGTH: 113
<212> TYPE: PRT
<213> ORGANISM: Artificial Sequence
<220> FEATURE:
<223> OTHER INFORMATION: C4.4a binder

<400> SEQUENCE: 208

| | | | | | | | | | | | | | | |
|---|---|---|---|---|---|---|---|---|---|---|---|---|---|---|
| Gln | Ser | Val | Leu | Thr | Gln | Pro | Pro | Ser | Ala | Ser | Gly | Thr | Pro | Gly |
| 1 | | | | 5 | | | | | 10 | | | | | 15 |
| Arg | Val | Thr | Ile | Ser | Cys | Ser | Gly | Ser | Ser | Asn | Ile | Gly | Ala | Gly |
| | | | 20 | | | | | 25 | | | | | 30 | |
| Tyr | Val | Val | His | Trp | Tyr | Gln | Gln | Leu | Pro | Gly | Thr | Ala | Pro | Lys | Leu |
| | | | 35 | | | | | 40 | | | | | 45 | |
| Leu | Ile | Tyr | Asp | Asn | Asn | Gln | Arg | Pro | Ser | Gly | Val | Pro | Asp | Arg | Phe |
| | 50 | | | | | 55 | | | | | 60 | | | | |
| Ser | Gly | Ser | Lys | Ser | Gly | Thr | Ser | Ala | Ser | Leu | Ala | Ile | Ser | Gly | Leu |
| 65 | | | | | 70 | | | | | 75 | | | | | 80 |
| Arg | Ser | Glu | Asp | Glu | Ala | Asp | Tyr | Tyr | Cys | Ala | Ala | Tyr | Asp | Asp | Ser |
| | | | | 85 | | | | | 90 | | | | | 95 | |
| Leu | Asn | Arg | Pro | Val | Phe | Gly | Gly | Gly | Thr | Lys | Leu | Thr | Val | Leu | Gly |
| | | | | 100 | | | | | 105 | | | | | 110 | |
| Gln | | | | | | | | | | | | | | | |

<210> SEQ ID NO 209
<211> LENGTH: 11
<212> TYPE: PRT
<213> ORGANISM: Artificial Sequence
<220> FEATURE:
<223> OTHER INFORMATION: C4.4a binder

<400> SEQUENCE: 209

| | | | | | | | | | | |
|---|---|---|---|---|---|---|---|---|---|---|
| Phe | Thr | Phe | Ser | Asn | Ala | Trp | Met | Ser | Trp | Val |
| 1 | | | | 5 | | | | | 10 | |

<210> SEQ ID NO 210
<211> LENGTH: 20

```
<212> TYPE: PRT
<213> ORGANISM: Artificial Sequence
<220> FEATURE:
<223> OTHER INFORMATION: C4.4a binder

<400> SEQUENCE: 210

Val Ser Tyr Ile Ser Ser Gly Ser Thr Ile Tyr Tyr Ala Asp Ser
1               5                   10                  15

Val Lys Gly Arg
            20

<210> SEQ ID NO 211
<211> LENGTH: 10
<212> TYPE: PRT
<213> ORGANISM: Artificial Sequence
<220> FEATURE:
<223> OTHER INFORMATION: C4.4a binder

<400> SEQUENCE: 211

Ala Arg Glu Gly Leu Trp Ala Phe Asp Tyr
1               5                   10

<210> SEQ ID NO 212
<211> LENGTH: 14
<212> TYPE: PRT
<213> ORGANISM: Artificial Sequence
<220> FEATURE:
<223> OTHER INFORMATION: C4.4a binder

<400> SEQUENCE: 212

Thr Gly Ser Ser Ser Asn Ile Gly Ala Gly Tyr Val Val His
1               5                   10

<210> SEQ ID NO 213
<211> LENGTH: 7
<212> TYPE: PRT
<213> ORGANISM: Artificial Sequence
<220> FEATURE:
<223> OTHER INFORMATION: C4.4a binder

<400> SEQUENCE: 213

Asp Asn Asn Lys Arg Pro Ser
1               5

<210> SEQ ID NO 214
<211> LENGTH: 12
<212> TYPE: PRT
<213> ORGANISM: Artificial Sequence
<220> FEATURE:
<223> OTHER INFORMATION: C4.4a binder

<400> SEQUENCE: 214

Cys Ala Ala Phe Asp Asp Ser Leu Asn Gly Pro Val
1               5                   10

<210> SEQ ID NO 215
<211> LENGTH: 117
<212> TYPE: PRT
<213> ORGANISM: Artificial Sequence
<220> FEATURE:
<223> OTHER INFORMATION: C4.4a binder

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
```

```
                20                  25                  30
Trp Met Ser Trp Val Arg Gln Ala Pro Gly Lys Gly Leu Glu Trp Val
                35                  40                  45

Ser Tyr Ile Ser Ser Gly Ser Thr Ile Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
               100                 105                 110

Val Thr Val Ser Ser
               115

<210> SEQ ID NO 216
<211> LENGTH: 113
<212> TYPE: PRT
<213> ORGANISM: Artificial Sequence
<220> FEATURE:
<223> OTHER INFORMATION: C4.4a binder

<400> SEQUENCE: 216

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
                35                  40                  45

Leu Ile Tyr Asp Asn Asn Lys Arg Pro Ser Gly Val Pro Asp Arg Phe
                50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Phe Asp Asp Ser
                85                  90                  95

Leu Asn Gly Pro Val Phe Gly Gly Gly Thr Lys Leu Thr Val Leu Gly
               100                 105                 110

Gln

<210> SEQ ID NO 217
<211> LENGTH: 9
<212> TYPE: PRT
<213> ORGANISM: Artificial Sequence
<220> FEATURE:
<223> OTHER INFORMATION: C4.4a binder

<400> SEQUENCE: 217

Phe Ser Ser Ala Trp Met Ser Trp Val
 1               5

<210> SEQ ID NO 218
<211> LENGTH: 20
<212> TYPE: PRT
<213> ORGANISM: Artificial Sequence
<220> FEATURE:
<223> OTHER INFORMATION: C4.4a binder

<400> SEQUENCE: 218

Val Ser Tyr Ile Ser Ser Ser Gly Ser Ser Thr Tyr Tyr Ala Asp Ser
 1               5                  10                  15
```

```
Val Lys Gly Arg
            20

<210> SEQ ID NO 219
<211> LENGTH: 10
<212> TYPE: PRT
<213> ORGANISM: Artificial Sequence
<220> FEATURE:
<223> OTHER INFORMATION: C4.4a binder

<400> SEQUENCE: 219

Ala Arg Glu Gly Leu Trp Ala Phe Asp Lys
1               5                   10

<210> SEQ ID NO 220
<211> LENGTH: 14
<212> TYPE: PRT
<213> ORGANISM: Artificial Sequence
<220> FEATURE:
<223> OTHER INFORMATION: C4.4a binder

<400> SEQUENCE: 220

Thr Gly Ser Ser Ser Asn Ile Gly Ala Gly Tyr Val Val His
1               5                   10

<210> SEQ ID NO 221
<211> LENGTH: 7
<212> TYPE: PRT
<213> ORGANISM: Artificial Sequence
<220> FEATURE:
<223> OTHER INFORMATION: C4.4a binder

<400> SEQUENCE: 221

Asp Asn Asn Lys Arg Pro Ser
1               5

<210> SEQ ID NO 222
<211> LENGTH: 12
<212> TYPE: PRT
<213> ORGANISM: Artificial Sequence
<220> FEATURE:
<223> OTHER INFORMATION: C4.4a binder

<400> SEQUENCE: 222

Cys Ala Ala Phe Asp Asp Ser Leu Asn Gly Pro Val
1               5                   10

<210> SEQ ID NO 223
<211> LENGTH: 117
<212> TYPE: PRT
<213> ORGANISM: Artificial Sequence
<220> FEATURE:
<223> OTHER INFORMATION: C4.4a binder

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Thr Ser
        115

<210> SEQ ID NO 224
<211> LENGTH: 113
<212> TYPE: PRT
<213> ORGANISM: Artificial Sequence
<220> FEATURE:
<223> OTHER INFORMATION: C4.4a binder

<400> SEQUENCE: 224

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Ser
                85                  90                  95

Leu Asn Gly Pro Val Phe Gly Gly Gly Thr Lys Leu Thr Val Leu Gly
            100                 105                 110

Gln

<210> SEQ ID NO 225
<211> LENGTH: 11
<212> TYPE: PRT
<213> ORGANISM: Artificial Sequence
<220> FEATURE:
<223> OTHER INFORMATION: C4.4a binder

<400> SEQUENCE: 225

Phe Thr Phe Ser Ser Ala Trp Met Ser Trp Val
1               5                   10

<210> SEQ ID NO 226
<211> LENGTH: 20
<212> TYPE: PRT
<213> ORGANISM: Artificial Sequence
<220> FEATURE:
<223> OTHER INFORMATION: C4.4a binder

<400> SEQUENCE: 226

Val Ser Tyr Ile Ser Ser Ser Gly Ser Ser Thr Tyr Tyr Ala Asp Ser
1               5                   10                  15

Val Lys Gly Arg
            20

<210> SEQ ID NO 227
<211> LENGTH: 10
<212> TYPE: PRT
<213> ORGANISM: Artificial Sequence
<220> FEATURE:
<223> OTHER INFORMATION: C4.4a binder

<400> SEQUENCE: 227

Ala Arg Glu Gly Leu Trp Ala Phe Asp Lys
1               5                   10

<210> SEQ ID NO 228
<211> LENGTH: 14
<212> TYPE: PRT
<213> ORGANISM: Artificial Sequence
<220> FEATURE:
<223> OTHER INFORMATION: C4.4a binder

<400> SEQUENCE: 228

Ser Gly Ser Ser Ser Asn Ile Gly Ala Gly Tyr Val Val His
1               5                   10

<210> SEQ ID NO 229
<211> LENGTH: 7
<212> TYPE: PRT
<213> ORGANISM: Artificial Sequence
<220> FEATURE:
<223> OTHER INFORMATION: C4.4a binder

<400> SEQUENCE: 229

Asp Asn Asn Gln Arg Pro Ser
1               5

<210> SEQ ID NO 230
<211> LENGTH: 12
<212> TYPE: PRT
<213> ORGANISM: Artificial Sequence
<220> FEATURE:
<223> OTHER INFORMATION: C4.4a binder

<400> SEQUENCE: 230

Cys Ala Ala Phe Asp Asp Ser Leu Asn Gly Pro Val
1               5                   10

<210> SEQ ID NO 231
<211> LENGTH: 117
<212> TYPE: PRT
<213> ORGANISM: Artificial Sequence
<220> FEATURE:
<223> OTHER INFORMATION: C4.4a binder

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Ser Ser
        115

<210> SEQ ID NO 232
<211> LENGTH: 113
<212> TYPE: PRT
<213> ORGANISM: Artificial Sequence
<220> FEATURE:
<223> OTHER INFORMATION: C4.4a binder

<400> SEQUENCE: 232

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ala Gly
            20                  25                  30
Tyr Val His Trp Tyr Gln Gln Leu Pro Gly Thr Ala Pro Lys Leu
        35                  40                  45
Leu Ile Tyr Asp Asn Asn Gln Arg Pro Ser Gly Val Pro Asp Arg Phe
    50                  55                  60
Ser Gly Ser Lys Ser Gly Thr Ser Ala Ser Leu Ala Ile Ser Gly Leu
65              70                  75                  80
Arg Ser Glu Asp Glu Ala Asp Tyr Tyr Cys Ala Ala Phe Asp Asp Ser
                85                  90                  95
Leu Asn Gly Pro Val Phe Gly Gly Thr Lys Leu Thr Val Leu Gly
            100                 105                 110
Gln
```

<210> SEQ ID NO 233
<211> LENGTH: 11
<212> TYPE: PRT
<213> ORGANISM: Artificial Sequence
<220> FEATURE:
<223> OTHER INFORMATION: C4.4a binder

<400> SEQUENCE: 233

```
Phe Thr Phe Ser Ser Ala Trp Met Ser Trp Val
1               5                   10
```

<210> SEQ ID NO 234
<211> LENGTH: 20
<212> TYPE: PRT
<213> ORGANISM: Artificial Sequence
<220> FEATURE:
<223> OTHER INFORMATION: C4.4a binder

<400> SEQUENCE: 234

```
Val Ser Tyr Ile Ser Ser Ser Gly Ser Ser Thr Tyr Tyr Ala Asp Ser
1               5                   10                  15
Val Lys Gly Arg
            20
```

<210> SEQ ID NO 235
<211> LENGTH: 10
<212> TYPE: PRT
<213> ORGANISM: Artificial Sequence
<220> FEATURE:
<223> OTHER INFORMATION: C4.4a binder

<400> SEQUENCE: 235

```
Ala Arg Glu Gly Leu Trp Ala Phe Asp Lys
1               5                   10
```

<210> SEQ ID NO 236
<211> LENGTH: 14
<212> TYPE: PRT

<210> SEQ ID NO 236
<211> LENGTH: (not shown)
<212> TYPE: PRT
<213> ORGANISM: Artificial Sequence
<220> FEATURE:
<223> OTHER INFORMATION: C4.4a binder

<400> SEQUENCE: 236

Ser Gly Ser Ser Ser Asn Ile Gly Ala Gly Tyr Val Val His
1               5                   10

<210> SEQ ID NO 237
<211> LENGTH: 7
<212> TYPE: PRT
<213> ORGANISM: Artificial Sequence
<220> FEATURE:
<223> OTHER INFORMATION: C4.4a binder

<400> SEQUENCE: 237

Asp Asn Asn Gln Arg Pro Ser
1               5

<210> SEQ ID NO 238
<211> LENGTH: 12
<212> TYPE: PRT
<213> ORGANISM: Artificial Sequence
<220> FEATURE:
<223> OTHER INFORMATION: C4.4a binder

<400> SEQUENCE: 238

Cys Ala Ala Phe Asp Asp Arg Leu Ser Gly Pro Val
1               5                   10

<210> SEQ ID NO 239
<211> LENGTH: 117
<212> TYPE: PRT
<213> ORGANISM: Artificial Sequence
<220> FEATURE:
<223> OTHER INFORMATION: C4.4a binder

<400> SEQUENCE: 239

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Ser Ser
        115

<210> SEQ ID NO 240
<211> LENGTH: 113
<212> TYPE: PRT
<213> ORGANISM: Artificial Sequence
<220> FEATURE:
<223> OTHER INFORMATION: C4.4a binder

<400> SEQUENCE: 240

-continued

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
            35                  40                  45

Leu Ile Tyr Asp Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Arg
                85                  90                  95

Leu Ser Gly Pro Val Phe Gly Gly Gly Thr Lys Leu Thr Val Leu Gly
            100                 105                 110

Gln
```

<210> SEQ ID NO 241
<211> LENGTH: 9
<212> TYPE: PRT
<213> ORGANISM: Artificial Sequence
<220> FEATURE:
<223> OTHER INFORMATION: C4.4a binder

<400> SEQUENCE: 241

```
Phe Ser Asp Tyr Gln Met Thr Trp Ile
1               5
```

<210> SEQ ID NO 242
<211> LENGTH: 20
<212> TYPE: PRT
<213> ORGANISM: Artificial Sequence
<220> FEATURE:
<223> OTHER INFORMATION: C4.4a binder

<400> SEQUENCE: 242

```
Val Ser Gly Val Ser Trp Asn Gly Ala Arg Thr His Tyr Ala Asp Ser
1               5                   10                  15

Val Lys Gly Arg
            20
```

<210> SEQ ID NO 243
<211> LENGTH: 15
<212> TYPE: PRT
<213> ORGANISM: Artificial Sequence
<220> FEATURE:
<223> OTHER INFORMATION: C4.4a binder

<400> SEQUENCE: 243

```
Ala Lys Gly Asp Tyr Leu Val Tyr Ser Ser Tyr Tyr Phe Lys Ser
1               5                   10                  15
```

<210> SEQ ID NO 244
<211> LENGTH: 13
<212> TYPE: PRT
<213> ORGANISM: Artificial Sequence
<220> FEATURE:
<223> OTHER INFORMATION: C4.4a binder

<400> SEQUENCE: 244

```
Ser Gly Ser Ser Ser Asn Val Gly Ser Asn Pro Val Asn
1               5                   10
```

```
<210> SEQ ID NO 245
<211> LENGTH: 7
<212> TYPE: PRT
<213> ORGANISM: Artificial Sequence
<220> FEATURE:
<223> OTHER INFORMATION: C4.4a binder

<400> SEQUENCE: 245

Arg Asn Asn Gln Arg Pro Ser
1               5

<210> SEQ ID NO 246
<211> LENGTH: 13
<212> TYPE: PRT
<213> ORGANISM: Artificial Sequence
<220> FEATURE:
<223> OTHER INFORMATION: C4.4a binder

<400> SEQUENCE: 246

Cys Ala Ala Trp Asp Asp Arg Leu Asn Gly Trp Thr Gly
1               5                   10

<210> SEQ ID NO 247
<211> LENGTH: 122
<212> TYPE: PRT
<213> ORGANISM: Artificial Sequence
<220> FEATURE:
<223> OTHER INFORMATION: C4.4a binder

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Val Ser Trp Asn Gly Ala Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Ser Trp
            100                 105                 110

Gly Gln Gly Thr Leu Val Thr Val Thr Ser
        115                 120

<210> SEQ ID NO 248
<211> LENGTH: 112
<212> TYPE: PRT
<213> ORGANISM: Artificial Sequence
<220> FEATURE:
<223> OTHER INFORMATION: C4.4a binder

<400> SEQUENCE: 248

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Val Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
```

```
                   50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Arg Leu
                 85                  90                  95

Asn Gly Trp Gly Phe Gly Gly Gly Thr Lys Leu Thr Val Leu Gly Gln
            100                 105                 110
```

<210> SEQ ID NO 249
<211> LENGTH: 11
<212> TYPE: PRT
<213> ORGANISM: Artificial Sequence
<220> FEATURE:
<223> OTHER INFORMATION: C4.4a binder

<400> SEQUENCE: 249

```
Phe Thr Phe Ser Ser Tyr Gln Met Thr Trp Ile
 1               5                  10
```

<210> SEQ ID NO 250
<211> LENGTH: 20
<212> TYPE: PRT
<213> ORGANISM: Artificial Sequence
<220> FEATURE:
<223> OTHER INFORMATION: C4.4a binder

<400> SEQUENCE: 250

```
Val Ser Gly Ile Ser Trp Asn Gly Ser Thr His Tyr Ala Asp Ser
 1               5                  10                  15

Val Lys Gly Arg
         20
```

<210> SEQ ID NO 251
<211> LENGTH: 15
<212> TYPE: PRT
<213> ORGANISM: Artificial Sequence
<220> FEATURE:
<223> OTHER INFORMATION: C4.4a binder

<400> SEQUENCE: 251

```
Ala Lys Gly Asp Tyr Leu Val Tyr Ser Ala Tyr Tyr Phe Asp Ser
 1               5                  10                  15
```

<210> SEQ ID NO 252
<211> LENGTH: 13
<212> TYPE: PRT
<213> ORGANISM: Artificial Sequence
<220> FEATURE:
<223> OTHER INFORMATION: C4.4a binder

<400> SEQUENCE: 252

```
Ser Gly Ser Ser Ser Asn Ile Gly Ser Asn Pro Val Asn
 1               5                  10
```

<210> SEQ ID NO 253
<211> LENGTH: 7
<212> TYPE: PRT
<213> ORGANISM: Artificial Sequence
<220> FEATURE:
<223> OTHER INFORMATION: C4.4a binder

<400> SEQUENCE: 253

```
Arg Asn Asn Gln Arg Pro Ser
 1               5
```

<210> SEQ ID NO 254
<211> LENGTH: 12
<212> TYPE: PRT
<213> ORGANISM: Artificial Sequence
<220> FEATURE:
<223> OTHER INFORMATION: C4.4a binder

<400> SEQUENCE: 254

Cys Ala Ala Trp Asp Asp Arg Leu Asn Gly Trp Gly
1               5                   10

<210> SEQ ID NO 255
<211> LENGTH: 122
<212> TYPE: PRT
<213> ORGANISM: Artificial Sequence
<220> FEATURE:
<223> OTHER INFORMATION: C4.4a binder

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Ser Ser
        115                 120

<210> SEQ ID NO 256
<211> LENGTH: 112
<212> TYPE: PRT
<213> ORGANISM: Artificial Sequence
<220> FEATURE:
<223> OTHER INFORMATION: C4.4a binder

<400> SEQUENCE: 256

Glu Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Gly Phe Gly Gly Gly Thr Lys Leu Thr Val Leu Gly Gln
            100                 105                 110

```
<210> SEQ ID NO 257
<211> LENGTH: 11
<212> TYPE: PRT
<213> ORGANISM: Artificial Sequence
<220> FEATURE:
<223> OTHER INFORMATION: C4.4a binder

<400> SEQUENCE: 257

Phe Thr Phe Ser Asp Tyr Gln Met Thr Trp Ile
1               5                   10

<210> SEQ ID NO 258
<211> LENGTH: 20
<212> TYPE: PRT
<213> ORGANISM: Artificial Sequence
<220> FEATURE:
<223> OTHER INFORMATION: C4.4a binder

<400> SEQUENCE: 258

Val Ser Gly Ile Ser Trp Asn Gly Gly Ser Thr His Tyr Ala Asp Ser
1               5                   10                  15

Val Lys Gly Arg
            20

<210> SEQ ID NO 259
<211> LENGTH: 15
<212> TYPE: PRT
<213> ORGANISM: Artificial Sequence
<220> FEATURE:
<223> OTHER INFORMATION: C4.4a binder

<400> SEQUENCE: 259

Ala Lys Gly Asp Tyr Leu Val Tyr Ser Ser Tyr Tyr Phe Lys Tyr
1               5                   10                  15

<210> SEQ ID NO 260
<211> LENGTH: 13
<212> TYPE: PRT
<213> ORGANISM: Artificial Sequence
<220> FEATURE:
<223> OTHER INFORMATION: C4.4a binder

<400> SEQUENCE: 260

Ser Gly Ser Ser Ser Asn Ile Gly Ser Asn Pro Val Asn
1               5                   10

<210> SEQ ID NO 261
<211> LENGTH: 7
<212> TYPE: PRT
<213> ORGANISM: Artificial Sequence
<220> FEATURE:
<223> OTHER INFORMATION: C4.4a binder

<400> SEQUENCE: 261

Arg Asn Asn Gln Arg Pro Ser
1               5

<210> SEQ ID NO 262
<211> LENGTH: 12
<212> TYPE: PRT
<213> ORGANISM: Artificial Sequence
<220> FEATURE:
<223> OTHER INFORMATION: C4.4a binder

<400> SEQUENCE: 262

Cys Ala Ala Trp Asp Asp Arg Leu Asn Gly Trp Ala
1               5                   10
```

<210> SEQ ID NO 263
<211> LENGTH: 122
<212> TYPE: PRT
<213> ORGANISM: Artificial Sequence
<220> FEATURE:
<223> OTHER INFORMATION: C4.4a binder

<400> SEQUENCE: 263

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Tyr Trp
            100                 105                 110

Gly Gln Gly Thr Leu Val Thr Val Ser Ser
        115                 120
```

<210> SEQ ID NO 264
<211> LENGTH: 112
<212> TYPE: PRT
<213> ORGANISM: Artificial Sequence
<220> FEATURE:
<223> OTHER INFORMATION: C4.4a binder

<400> SEQUENCE: 264

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Ala Phe Gly Gly Gly Thr Lys Leu Thr Val Leu Gly Gln
            100                 105                 110
```

<210> SEQ ID NO 265
<211> LENGTH: 11
<212> TYPE: PRT
<213> ORGANISM: Artificial Sequence
<220> FEATURE:
<223> OTHER INFORMATION: C4.4a binder

<400> SEQUENCE: 265

```
Phe Thr Phe Ser Asp Tyr Gln Met Thr Trp Ile
1               5                   10
```

```
<210> SEQ ID NO 266
<211> LENGTH: 20
<212> TYPE: PRT
<213> ORGANISM: Artificial Sequence
<220> FEATURE:
<223> OTHER INFORMATION: C4.4a binder

<400> SEQUENCE: 266

Val Ser Gly Ile Ser Trp Asn Gly Gly Ser Thr His Tyr Ala Asp Ser
1               5                   10                  15

Val Lys Gly Arg
            20

<210> SEQ ID NO 267
<211> LENGTH: 15
<212> TYPE: PRT
<213> ORGANISM: Artificial Sequence
<220> FEATURE:
<223> OTHER INFORMATION: C4.4a binder

<400> SEQUENCE: 267

Ala Lys Gly Asp Tyr Leu Val Tyr Ser Ser Tyr Tyr Phe Lys Ser
1               5                   10                  15

<210> SEQ ID NO 268
<211> LENGTH: 13
<212> TYPE: PRT
<213> ORGANISM: Artificial Sequence
<220> FEATURE:
<223> OTHER INFORMATION: C4.4a binder

<400> SEQUENCE: 268

Ser Gly Ser Ser Ser Asn Ile Gly Ser Asn Pro Val Asn
1               5                   10

<210> SEQ ID NO 269
<211> LENGTH: 7
<212> TYPE: PRT
<213> ORGANISM: Artificial Sequence
<220> FEATURE:
<223> OTHER INFORMATION: C4.4a binder

<400> SEQUENCE: 269

Arg Asn Asn Gln Arg Pro Ser
1               5

<210> SEQ ID NO 270
<211> LENGTH: 12
<212> TYPE: PRT
<213> ORGANISM: Artificial Sequence
<220> FEATURE:
<223> OTHER INFORMATION: C4.4a binder

<400> SEQUENCE: 270

Cys Ala Ala Trp Asp Asp Ser Leu Asn Gly Trp Gly
1               5                   10

<210> SEQ ID NO 271
<211> LENGTH: 122
<212> TYPE: PRT
<213> ORGANISM: Artificial Sequence
<220> FEATURE:
<223> OTHER INFORMATION: C4.4a binder

<400> SEQUENCE: 271

Glu Val Gln Leu Leu Glu Ser Gly Gly Gly Leu Val Gln Pro Gly Gly
```

```
                1               5                   10                  15
            Ser Leu Arg Leu Ser Cys Ala Ala Ser Gly Phe Thr Phe Ser Asp Tyr
                            20                  25                  30

Gln Met Thr Trp Ile Arg Gln Thr Pro Gly Lys Gly Leu Glu Trp Val
                        35                  40                  45

Ser Gly Ile Ser Trp Asn Gly Ser Thr His Tyr Ala Asp Ser Val
                    50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Lys Gly Asp Tyr Leu Val Tyr Ser Ser Tyr Tyr Phe Lys Ser Trp
                            100                 105                 110

Gly Gln Gly Thr Leu Val Thr Val Ser Ser
                        115                 120
```

<210> SEQ ID NO 272
<211> LENGTH: 112
<212> TYPE: PRT
<213> ORGANISM: Artificial Sequence
<220> FEATURE:
<223> OTHER INFORMATION: C4.4a binder

<400> SEQUENCE: 272

```
            Gln Ser Val Leu Thr Gln Pro Pro Ser Ala Ser Gly Thr Pro Gly Gln
            1               5                   10                  15

Arg Val Thr Ile Ser Cys Ser Gly Ser Ser Ser Asn Ile Gly Ser Asn
                            20                  25                  30

Pro Val Asn Trp Tyr Gln Gln Leu Pro Gly Thr Ala Pro Lys Leu Leu
                        35                  40                  45

Ile Tyr Arg Asn Asn Gln Arg Pro Ser Gly Val Pro Asp Arg Phe Ser
                    50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ala Ala Trp Asp Asp Ser Leu
                            85                  90                  95

Asn Gly Trp Gly Phe Gly Gly Gly Thr Lys Leu Thr Val Leu Gly Gln
                            100                 105                 110
```

<210> SEQ ID NO 273
<211> LENGTH: 11
<212> TYPE: PRT
<213> ORGANISM: Artificial Sequence
<220> FEATURE:
<223> OTHER INFORMATION: C4.4a binder

<400> SEQUENCE: 273

```
            Phe Thr Phe Ser Asp Tyr Gln Met Thr Trp Ile
            1               5                   10
```

<210> SEQ ID NO 274
<211> LENGTH: 20
<212> TYPE: PRT
<213> ORGANISM: Artificial Sequence
<220> FEATURE:
<223> OTHER INFORMATION: C4.4a binder

<400> SEQUENCE: 274

```
            Val Ser Gly Ile Ser Trp Asn Gly Ser Thr His Tyr Ala Asp Ser
            1               5                   10                  15
```

Val Lys Gly Arg
            20

<210> SEQ ID NO 275
<211> LENGTH: 15
<212> TYPE: PRT
<213> ORGANISM: Artificial Sequence
<220> FEATURE:
<223> OTHER INFORMATION: C4.4a binder

<400> SEQUENCE: 275

Ala Lys Gly Asp Tyr Leu Val Tyr Lys Ser Tyr Tyr Phe Lys Ser
1               5                   10                  15

<210> SEQ ID NO 276
<211> LENGTH: 13
<212> TYPE: PRT
<213> ORGANISM: Artificial Sequence
<220> FEATURE:
<223> OTHER INFORMATION: C4.4a binder

<400> SEQUENCE: 276

Ser Gly Ser Ser Ser Asn Ile Gly Ser Asn Pro Val Asn
1               5                   10

<210> SEQ ID NO 277
<211> LENGTH: 7
<212> TYPE: PRT
<213> ORGANISM: Artificial Sequence
<220> FEATURE:
<223> OTHER INFORMATION: C4.4a binder

<400> SEQUENCE: 277

Arg Asn Asn Gln Arg Pro Ser
1               5

<210> SEQ ID NO 278
<211> LENGTH: 12
<212> TYPE: PRT
<213> ORGANISM: Artificial Sequence
<220> FEATURE:
<223> OTHER INFORMATION: C4.4a binder

<400> SEQUENCE: 278

Cys Ala Ala Trp Asp Asp Arg Leu Ser Gly Trp Gly
1               5                   10

<210> SEQ ID NO 279
<211> LENGTH: 122
<212> TYPE: PRT
<213> ORGANISM: Artificial Sequence
<220> FEATURE:
<223> OTHER INFORMATION: C4.4a binder

<400> SEQUENCE: 279

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr

```
                65                   70                  75                  80
Leu Gln Met Asn Ser Leu Arg Ala Glu Asp Thr Ala Val Tyr Tyr Cys
                    85                  90                  95
Ala Lys Gly Asp Tyr Leu Val Tyr Lys Ser Tyr Tyr Phe Lys Ser Trp
            100                 105                 110
Gly Gln Gly Thr Leu Val Thr Val Ser Ser
        115                 120

<210> SEQ ID NO 280
<211> LENGTH: 112
<212> TYPE: PRT
<213> ORGANISM: Artificial Sequence
<220> FEATURE:
<223> OTHER INFORMATION: C4.4a binder

<400> SEQUENCE: 280

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Gly Phe Gly Gly Gly Thr Lys Leu Thr Val Leu Gly Gln
            100                 105                 110

<210> SEQ ID NO 281
<211> LENGTH: 11
<212> TYPE: PRT
<213> ORGANISM: Artificial Sequence
<220> FEATURE:
<223> OTHER INFORMATION: C4.4a binder

<400> SEQUENCE: 281

Phe Thr Phe Ser Asp Tyr Gln Met Thr Trp Ile
1               5                   10

<210> SEQ ID NO 282
<211> LENGTH: 20
<212> TYPE: PRT
<213> ORGANISM: Artificial Sequence
<220> FEATURE:
<223> OTHER INFORMATION: C4.4a binder

<400> SEQUENCE: 282

Val Ser Gly Ile Ser Trp Asn Gly Gly Ser Thr His Tyr Ala Asp Ser
1               5                   10                  15

Val Lys Gly Arg
            20

<210> SEQ ID NO 283
<211> LENGTH: 15
<212> TYPE: PRT
<213> ORGANISM: Artificial Sequence
<220> FEATURE:
<223> OTHER INFORMATION: C4.4a binder
```

```
<400> SEQUENCE: 283

Ala Lys Gly Asp Tyr Leu Val Tyr Ser Ser Tyr Tyr Phe Lys Ser
1               5                   10                  15

<210> SEQ ID NO 284
<211> LENGTH: 13
<212> TYPE: PRT
<213> ORGANISM: Artificial Sequence
<220> FEATURE:
<223> OTHER INFORMATION: C4.4a binder

<400> SEQUENCE: 284

Ser Gly Ser Ser Ser Asn Ile Gly Ser Asn Pro Val Asn
1               5                   10

<210> SEQ ID NO 285
<211> LENGTH: 7
<212> TYPE: PRT
<213> ORGANISM: Artificial Sequence
<220> FEATURE:
<223> OTHER INFORMATION: C4.4a binder

<400> SEQUENCE: 285

Arg Asn Asn Gln Arg Pro Ser
1               5

<210> SEQ ID NO 286
<211> LENGTH: 12
<212> TYPE: PRT
<213> ORGANISM: Artificial Sequence
<220> FEATURE:
<223> OTHER INFORMATION: C4.4a binder

<400> SEQUENCE: 286

Cys Ala Ala Trp Asp Asp Arg Leu Ser Gly Trp Gly
1               5                   10

<210> SEQ ID NO 287
<211> LENGTH: 122
<212> TYPE: PRT
<213> ORGANISM: Artificial Sequence
<220> FEATURE:
<223> OTHER INFORMATION: C4.4a binder

<400> SEQUENCE: 287

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Ser Trp
            100                 105                 110

Gly Gln Gly Thr Leu Val Thr Val Ser Ser
        115                 120
```

<210> SEQ ID NO 288
<211> LENGTH: 112
<212> TYPE: PRT
<213> ORGANISM: Artificial Sequence
<220> FEATURE:
<223> OTHER INFORMATION: C4.4a binder

<400> SEQUENCE: 288

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Gly Phe Gly Gly Gly Thr Lys Leu Thr Val Leu Gly Gln
            100                 105                 110

<210> SEQ ID NO 289
<211> LENGTH: 11
<212> TYPE: PRT
<213> ORGANISM: Artificial Sequence
<220> FEATURE:
<223> OTHER INFORMATION: C4.4a binder

<400> SEQUENCE: 289

Phe Thr Phe Ser Asp Tyr Gln Met Thr Trp Ile
1               5                   10

<210> SEQ ID NO 290
<211> LENGTH: 20
<212> TYPE: PRT
<213> ORGANISM: Artificial Sequence
<220> FEATURE:
<223> OTHER INFORMATION: C4.4a binder

<400> SEQUENCE: 290

Val Ser Gly Ile Ser Trp Asn Gly Gly Ser Thr His Tyr Ala Asp Ser
1               5                   10                  15

Val Lys Gly Arg
            20

<210> SEQ ID NO 291
<211> LENGTH: 15
<212> TYPE: PRT
<213> ORGANISM: Artificial Sequence
<220> FEATURE:
<223> OTHER INFORMATION: C4.4a binder

<400> SEQUENCE: 291

Ala Lys Gly Asp Tyr Leu Val Tyr Lys Ser Tyr Tyr Phe Lys Ser
1               5                   10                  15

<210> SEQ ID NO 292
<211> LENGTH: 13
<212> TYPE: PRT
<213> ORGANISM: Artificial Sequence
<220> FEATURE:
<223> OTHER INFORMATION: C4.4a binder

<400> SEQUENCE: 292

Ser Gly Ser Ser Ser Asn Ile Gly Ser Asn Pro Val Asn
1               5                   10

<210> SEQ ID NO 293
<211> LENGTH: 7
<212> TYPE: PRT
<213> ORGANISM: Artificial Sequence
<220> FEATURE:
<223> OTHER INFORMATION: C4.4a binder

<400> SEQUENCE: 293

Arg Asn Asn Gln Arg Pro Ser
1               5

<210> SEQ ID NO 294
<211> LENGTH: 12
<212> TYPE: PRT
<213> ORGANISM: Artificial Sequence
<220> FEATURE:
<223> OTHER INFORMATION: C4.4a binder

<400> SEQUENCE: 294

Cys Ala Ala Trp Asp Asp Ser Leu Asn Gly Trp Gly
1               5                   10

<210> SEQ ID NO 295
<211> LENGTH: 122
<212> TYPE: PRT
<213> ORGANISM: Artificial Sequence
<220> FEATURE:
<223> OTHER INFORMATION: C4.4a binder

<400> SEQUENCE: 295

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Tyr Phe Lys Ser Trp
            100                 105                 110

Gly Gln Gly Thr Leu Val Thr Val Ser Ser
        115                 120

<210> SEQ ID NO 296
<211> LENGTH: 112
<212> TYPE: PRT
<213> ORGANISM: Artificial Sequence
<220> FEATURE:
<223> OTHER INFORMATION: C4.4a binder

<400> SEQUENCE: 296

Gln Ser Val Leu Thr Gln Pro Pro Ser Ala Ser Gly Thr Pro Gly Gln
1               5                   10                  15

-continued

```
Arg Val Thr Ile Ser Cys Ser Gly Ser Ser Asn Ile Gly Ser Asn
             20                  25                  30

Pro Val Asn Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                 85                  90                  95

Asn Gly Trp Gly Phe Gly Gly Gly Thr Lys Leu Thr Val Leu Gly Gln
            100                 105                 110

<210> SEQ ID NO 297
<211> LENGTH: 9
<212> TYPE: PRT
<213> ORGANISM: Artificial Sequence
<220> FEATURE:
<223> OTHER INFORMATION: consensus sequence for M20 D02 S-A derived
      CDRH1
<220> FEATURE:
<221> NAME/KEY: VARIANT
<222> LOCATION: (3)..(3)
<223> OTHER INFORMATION: X = D or S

<400> SEQUENCE: 297

Phe Ser Xaa Tyr Gln Met Thr Trp Ile
1               5

<210> SEQ ID NO 298
<211> LENGTH: 20
<212> TYPE: PRT
<213> ORGANISM: Artificial Sequence
<220> FEATURE:
<223> OTHER INFORMATION: consensus sequence for M20 D02 S-A derived
      CDRH2
<220> FEATURE:
<221> NAME/KEY: VARIANT
<222> LOCATION: (4)..(4)
<223> OTHER INFORMATION: X = V or I
<220> FEATURE:
<221> NAME/KEY: VARIANT
<222> LOCATION: (9)..(9)
<223> OTHER INFORMATION: X = A or G
<220> FEATURE:
<221> NAME/KEY: VARIANT
<222> LOCATION: (10)..(10)
<223> OTHER INFORMATION: X = R or S

<400> SEQUENCE: 298

Val Ser Gly Xaa Ser Trp Asn Gly Xaa Xaa Thr His Tyr Ala Asp Ser
1               5                   10                  15

Val Lys Gly Arg
            20

<210> SEQ ID NO 299
<211> LENGTH: 15
<212> TYPE: PRT
<213> ORGANISM: Artificial Sequence
<220> FEATURE:
<223> OTHER INFORMATION: consensus for M20 D02 S-A derived CDRH3
<220> FEATURE:
<221> NAME/KEY: VARIANT
<222> LOCATION: (9)..(9)
<223> OTHER INFORMATION: X = S, K, or R
<220> FEATURE:
<221> NAME/KEY: VARIANT
<222> LOCATION: (10)..(10)
```

```
<223> OTHER INFORMATION: X = A, S or R
<220> FEATURE:
<221> NAME/KEY: VARIANT
<222> LOCATION: (14)..(14)
<223> OTHER INFORMATION: X = D, K, E or R
<220> FEATURE:
<221> NAME/KEY: VARIANT
<222> LOCATION: (15)..(15)
<223> OTHER INFORMATION: X = S or Y

<400> SEQUENCE: 299

Ala Lys Gly Asp Tyr Leu Val Tyr Xaa Xaa Tyr Tyr Phe Xaa Xaa
1               5                   10                  15

<210> SEQ ID NO 300
<211> LENGTH: 13
<212> TYPE: PRT
<213> ORGANISM: Artificial Sequence
<220> FEATURE:
<223> OTHER INFORMATION: consensus seqeunce derived from M20 D02 S-A
      CDRL1
<220> FEATURE:
<221> NAME/KEY: VARIANT
<222> LOCATION: (7)..(7)
<223> OTHER INFORMATION: X = V or I

<400> SEQUENCE: 300

Ser Gly Ser Ser Ser Asn Xaa Gly Ser Asn Pro Val Asn
1               5                   10

<210> SEQ ID NO 301
<211> LENGTH: 12
<212> TYPE: PRT
<213> ORGANISM: Artificial Sequence
<220> FEATURE:
<223> OTHER INFORMATION: consensus sequence derived from M20 D02 S-A
      derived CDRL3
<220> FEATURE:
<221> NAME/KEY: VARIANT
<222> LOCATION: (3)..(3)
<223> OTHER INFORMATION: X = A, Q or R
<220> FEATURE:
<221> NAME/KEY: VARIANT
<222> LOCATION: (5)..(5)
<223> OTHER INFORMATION: X = D or G
<220> FEATURE:
<221> NAME/KEY: VARIANT
<222> LOCATION: (7)..(7)
<223> OTHER INFORMATION: X = R or S
<220> FEATURE:
<221> NAME/KEY: VARIANT
<222> LOCATION: (9)..(9)
<223> OTHER INFORMATION: X = N, W or S
<220> FEATURE:
<221> NAME/KEY: VARIANT
<222> LOCATION: (12)..(12)
<223> OTHER INFORMATION: X = V, A or G

<400> SEQUENCE: 301

Cys Ala Xaa Trp Xaa Asp Xaa Leu Xaa Gly Trp Xaa
1               5                   10

<210> SEQ ID NO 302
<211> LENGTH: 9
<212> TYPE: PRT
<213> ORGANISM: Artificial Sequence
<220> FEATURE:
<223> OTHER INFORMATION: consensus sequence derived from M31 B01 CDRH1
<220> FEATURE:
<221> NAME/KEY: VARIANT
<222> LOCATION: (3)..(3)
<223> OTHER INFORMATION: X = N or S
<220> FEATURE:
```

```
<221> NAME/KEY: VARIANT
<222> LOCATION: (4)..(4)
<223> OTHER INFORMATION: X = A or Y

<400> SEQUENCE: 302

Phe Ser Xaa Xaa Trp Met Ser Trp Val
1               5

<210> SEQ ID NO 303
<211> LENGTH: 20
<212> TYPE: PRT
<213> ORGANISM: Artificial Sequence
<220> FEATURE:
<223> OTHER INFORMATION: consensus sequence derived from M31 B01 CDRH2
<220> FEATURE:
<221> NAME/KEY: VARIANT
<222> LOCATION: (10)..(10)
<223> OTHER INFORMATION: X = T or S
<220> FEATURE:
<221> NAME/KEY: VARIANT
<222> LOCATION: (11)..(11)
<223> OTHER INFORMATION: X = I or T

<400> SEQUENCE: 303

Val Ser Tyr Ile Ser Ser Ser Gly Ser Xaa Xaa Tyr Tyr Ala Asp Ser
1               5                   10                  15

Val Lys Gly Arg
            20

<210> SEQ ID NO 304
<211> LENGTH: 10
<212> TYPE: PRT
<213> ORGANISM: Artificial Sequence
<220> FEATURE:
<223> OTHER INFORMATION: consensus sequence derived from M31 B01 CDRH3
<220> FEATURE:
<221> NAME/KEY: VARIANT
<222> LOCATION: (10)..(10)
<223> OTHER INFORMATION: X = Y, K, G, W or N

<400> SEQUENCE: 304

Ala Arg Glu Gly Leu Trp Ala Phe Asp Xaa
1               5                   10

<210> SEQ ID NO 305
<211> LENGTH: 14
<212> TYPE: PRT
<213> ORGANISM: Artificial Sequence
<220> FEATURE:
<223> OTHER INFORMATION: consensus sequence derived from M31 B01 CDRL1
<220> FEATURE:
<221> NAME/KEY: VARIANT
<222> LOCATION: (1)..(1)
<223> OTHER INFORMATION: X = T or S

<400> SEQUENCE: 305

Xaa Gly Ser Ser Ser Asn Ile Gly Ala Gly Tyr Val Val His
1               5                   10

<210> SEQ ID NO 306
<211> LENGTH: 7
<212> TYPE: PRT
<213> ORGANISM: Artificial Sequence
<220> FEATURE:
<223> OTHER INFORMATION: consensus sequence derived from M31 B01 CDRL2
<220> FEATURE:
<221> NAME/KEY: VARIANT
<222> LOCATION: (4)..(4)
<223> OTHER INFORMATION: X = K or Q
```

```
<400> SEQUENCE: 306

Asp Asn Asn Xaa Arg Pro Ser
1               5

<210> SEQ ID NO 307
<211> LENGTH: 12
<212> TYPE: PRT
<213> ORGANISM: Artificial Sequence
<220> FEATURE:
<223> OTHER INFORMATION: consensus sequence derived from M31 B01 CDRL3
<220> FEATURE:
<221> NAME/KEY: VARIANT
<222> LOCATION: (4)..(4)
<223> OTHER INFORMATION: X = W, E, F or Y
<220> FEATURE:
<221> NAME/KEY: VARIANT
<222> LOCATION: (7)..(7)
<223> OTHER INFORMATION: X = R, S or M
<220> FEATURE:
<221> NAME/KEY: VARIANT
<222> LOCATION: (9)..(9)
<223> OTHER INFORMATION: X = N, K or S
<220> FEATURE:
<221> NAME/KEY: VARIANT
<222> LOCATION: (10)..(10)
<223> OTHER INFORMATION: X = G or R
<220> FEATURE:
<221> NAME/KEY: VARIANT
<222> LOCATION: (11)..(11)
<223> OTHER INFORMATION: X = P or A

<400> SEQUENCE: 307

Cys Ala Ala Xaa Asp Asp Xaa Leu Xaa Xaa Xaa Val
1               5                   10

<210> SEQ ID NO 308
<211> LENGTH: 351
<212> TYPE: DNA
<213> ORGANISM: Artificial Sequence
<220> FEATURE:
<223> OTHER INFORMATION: C4.4a binder

<400> SEQUENCE: 308
gaggtgcagc tgctggagag cggggggggg ctggtgcagc cggggggggag cctgcgcctg      60 agctgcgcgg cgagcgggtt tacctttagc aacgcgtgga tgagctgggt cgccaggcg     120 ccggggaaag gctggagtg ggtgagctat attagcagca gcgggagcac catttattat     180
gcggatagcg tgaaagggcg ctttaccatt agccgcgata acagcaaaaa cacctgtat     240 ctgcagatga acagcctgcg cgcggaggat accgcggtgt attattgcgc gcgcgagggg     300
ctgtgggcgt ttgataaatg ggggcagggg accctggtga ccgtgaccag c              351

<210> SEQ ID NO 309
<211> LENGTH: 339
<212> TYPE: DNA
<213> ORGANISM: Artificial Sequence
<220> FEATURE:
<223> OTHER INFORMATION: C4.4a binder

<400> SEQUENCE: 309
cagagcgtgc tgacccagcc gccgagcgcg agcgggaccc cggggcagcg cgtgaccatt      60
agctgcaccg ggagcagcag caacattggg gcggggtatg tggtgcattg gtatcagcag     120
ctgccgggga ccgcgccgaa actgctgatt tatgataaca caaacgccc gagcggggtg     180 ccggatcgct ttagcgggag caaaagcggg accagcgcga gctggcgat tagcgggctg     240 cgcagcgagg atgaggcgga ttattattgc gcggcgtatg atgatagcct gaaagggccg     300
```

```
gtgtttgggg gggggaccaa actgaccgtg ctggggcag                          339
```

<210> SEQ ID NO 310
<211> LENGTH: 351
<212> TYPE: DNA
<213> ORGANISM: Artificial Sequence
<220> FEATURE:
<223> OTHER INFORMATION: C4.4a binder

<400> SEQUENCE: 310

```
gaggtgcagc tgctggagag cggggggggg ctggtgcagc cggggggggag cctgcgcctg    60
agctgcgcgg cgagcgggtt tacctttagc aacgcgtgga tgagctgggt gcgccaggcg   120
ccggggaaag gctggagtg ggtgagctat attagcagca gcgggagcac catttattat   180
gcggatagcg tgaaagggcg ctttaccatt agccgcgata acagcaaaaa caccctgtat   240
ctgcagatga acagcctgcg cgcggaggat accgcggtgt attattgcgc gcgcgagggg   300
ctgtgggcgt ttgataaatg ggggcagggg accctggtga ccgtgaccag c           351
```

<210> SEQ ID NO 311
<211> LENGTH: 339
<212> TYPE: DNA
<213> ORGANISM: Artificial Sequence
<220> FEATURE:
<223> OTHER INFORMATION: C4.4a binder

<400> SEQUENCE: 311

```
cagagcgtgc tgacccagcc gccgagcgtg agcggggcgc cggggcagcg cgtgaccatt    60
agctgcaccg ggagcagcag caacattggg gcggggtatg tggtgcattg gtatcagcag   120
ctgccgggga ccgcgccgaa actgctgatt tatgataaca caaaacgccc gagcggggtg   180
ccggatcgct ttagcgggag caaaagcggg accagcgcga gcctggcgat tagcgggctg   240
cgcagcgagg atgaggcgga ttattattgc gcggcgtttg atgatagcct gaacgggccg   300
gtgtttgggg ggggaccaa actgaccgtg ctggggcag                          339
```

<210> SEQ ID NO 312
<211> LENGTH: 351
<212> TYPE: DNA
<213> ORGANISM: Artificial Sequence
<220> FEATURE:
<223> OTHER INFORMATION: C4.4a binder

<400> SEQUENCE: 312

```
gaggtgcagc tgctggagag cggggggggg ctggtgcagc cggggggggag cctgcgcctg    60
agctgcgcgg cgagcgggtt tacctttagc aacgcgtgga tgagctgggt gcgccaggcg   120
ccggggaaag gctggagtg ggtgagctat attagcagca gcgggagcac catttattat   180
gcggatagcg tgaaagggcg ctttaccatt agccgcgata acagcaaaaa caccctgtat   240
ctgcagatga acagcctgcg cgcggaggat accgcggtgt attattgcgc gcgcgagggg   300
ctgtgggcgt ttgataaatg ggggcagggg accctggtga ccgtgaccag c           351
```

<210> SEQ ID NO 313
<211> LENGTH: 339
<212> TYPE: DNA
<213> ORGANISM: Artificial Sequence
<220> FEATURE:
<223> OTHER INFORMATION: C4.4a binder

<400> SEQUENCE: 313

```
cagagcgtgc tgacccagcc gccgagcgtg agcggggcgc cggggcagcg cgtgaccatt    60
agctgcaccg ggagcagcag caacattggg gcggggtatg tggtgcattg gtatcagcag   120
ctgccgggga ccgcgccgaa actgctgatt tatgataaca caaacgccc gagcggggtg    180 ccggatcgct ttagcgggag caaaagcggg accagcgcga gcctggcgat tagcgggctg   240
cgcagcgagg atgaggcgga ttattattgc gcggcgtttg atgatagcct gaacgggccg   300
gtgtttgggg gggggaccaa actgaccgtg ctggggcag                          339
```

<210> SEQ ID NO 314
<211> LENGTH: 351
<212> TYPE: DNA
<213> ORGANISM: Artificial Sequence
<220> FEATURE:
<223> OTHER INFORMATION: C4.4a binder

<400> SEQUENCE: 314

```
gaggtgcagc tgctggagag cggggggggg ctggtgcagc cggggggag cctgcgcctg     60 agctgcgcgg cgagcgggtt tacctttagc agcgcgtgga tgagctgggt gcgccaggcg   120
ccggggaaag gctggagtg ggtgagctat attagcagca gcgggagcag cacctattat    180
gcggatagcg tgaaagggcg ctttaccatt agccgcgata cagcaaaaa cacccctgtat   240 ctgcagatga acagcctgcg cgcggaggat accgcggtgt attattgcgc gcgcgagggg   300
ctgtgggcgt ttgattggtg ggggcagggg accctggtga ccgtgaccag c            351
```

<210> SEQ ID NO 315
<211> LENGTH: 339
<212> TYPE: DNA
<213> ORGANISM: Artificial Sequence
<220> FEATURE:
<223> OTHER INFORMATION: C4.4a binder

<400> SEQUENCE: 315

```
cagagcgtgc tgacccagcc gccgagcgcg agcgggaccc cggggcagcg cgtgaccatt    60
agctgcagcg ggagcagcag caacattggg gcggggtatg tggtgcattg gtatcagcag   120
ctgccgggga ccgcgccgaa actgctgatt tatgataaca accagcgccc gagcggggtg   180
ccggatcgct ttagcgggag caaaagcggg accagcgcga gcctggcgat tagcgggctg   240
cgcagcgagg atgaggcgga ttattattgc gcggcgtatg atgatagcct gagcgggccg   300
gtgtttgggg gggggaccaa actgaccgtg ctggggcag                          339
```

<210> SEQ ID NO 316
<211> LENGTH: 351
<212> TYPE: DNA
<213> ORGANISM: Artificial Sequence
<220> FEATURE:
<223> OTHER INFORMATION: C4.4a binder

<400> SEQUENCE: 316

```
gaggtgcagc tgctggagag cggggggggg ctggtgcagc cggggggag cctgcgcctg     60 agctgcgcgg cgagcgggtt tacctttagc aacgcgtgga tgagctgggt gcgccaggcg   120
ccggggaaag gctggagtg ggtgagctat attagcagca gcgggagcac catttattat    180
gcggatagcg tgaaagggcg ctttaccatt agccgcgata cagcaaaaa cacccctgtat   240 ctgcagatga acagcctgcg cgcggaggat accgcggtgt attattgcgc gcgcgagggg   300
ctgtgggcgt ttgattattg ggggcagggg accctggtga ccgtgaccag c            351
```

```
<210> SEQ ID NO 317
<211> LENGTH: 339
<212> TYPE: DNA
<213> ORGANISM: Artificial Sequence
<220> FEATURE:
<223> OTHER INFORMATION: C4.4a binder

<400> SEQUENCE: 317
cagagcgtgc tgacccagcc gccgagcgcg agcgggaccc cggggcagcg cgtgaccatt      60
agctgcagcg ggagcagcag caacattggg gcggggtatg tggtgcattg gtatcagcag     120
ctgccgggga ccgcgccgaa actgctgatt tatgataaca accagcgccc gagcggggtg     180
ccggatcgct ttagcgggag caaaagcggg accagcgcga gcctggcgat tagcgggctg     240
cgcagcgagg atgaggcgga ttattattgc gcggcgtatg atgatagcct gaacgggccg     300
gtgtttgggg ggggaccaa actgaccgtg ctggggcag                             339

<210> SEQ ID NO 318
<211> LENGTH: 351
<212> TYPE: DNA
<213> ORGANISM: Artificial Sequence
<220> FEATURE:
<223> OTHER INFORMATION: C4.4a binder

<400> SEQUENCE: 318
gaggtgcagc tgctggagag cggggggggg ctggtgcagc cggggggag cctgcgcctg       60 agctgcgcgg cgagcgggtt tacctttagc agcgcgtgga tgagctgggt gcgccaggcg     120
ccggggaaag gctggagtg ggtgagctat attagcagca gcgggagcag cacctattat      180
gcggatagcg tgaaagggcg ctttaccatt agccgcgata cagcaaaaaa caccctgtat     240
ctgcagatga acagcctgcg cgcggaggat accgcggtgt attattgcgc gcgcgagggg     300
ctgtgggcgt ttgattattg ggggcagggg accctggtga ccgtgagcag c              351

<210> SEQ ID NO 319
<211> LENGTH: 339
<212> TYPE: DNA
<213> ORGANISM: Artificial Sequence
<220> FEATURE:
<223> OTHER INFORMATION: C4.4a binder

<400> SEQUENCE: 319
gagagcgtgc tgacccagcc gccgagcgcg agcgggaccc cggggcagcg cgtgaccatt      60
agctgcagcg ggagcagcag caacattggg gcggggtatg tggtgcattg gtatcagcag     120
ctgccgggga ccgcgccgaa actgctgatt tatgataaca accagcgccc gagcggggtg     180
ccggatcgct ttagcgggag caaaagcggg accagcgcga gcctggcgat tagcgggctg     240
cgcagcgagg atgaggcgga ttattattgc gcggcgtggg atgatcgcct gaacgggccg     300
gtgtttgggg ggggaccaa actgaccgtg ctggggcag                             339

<210> SEQ ID NO 320
<211> LENGTH: 351
<212> TYPE: DNA
<213> ORGANISM: Artificial Sequence
<220> FEATURE:
<223> OTHER INFORMATION: C4.4a binder

<400> SEQUENCE: 320
gaggtgcagc tgctggagag cggggggggg ctggtgcagc cggggggag cctgcgcctg       60 agctgcgcgg cgagcgggtt tacctttagc aacgcgtgga tgagctgggt gcgccaggcg     120
```

| ccggggaaag | ggctggagtg | ggtgagctat | attagcagca | gcgggagcac | catttattat | 180 |

| gcggatagcg | tgaaagggcg | ctttaccatt | agccgcgata | acagcaaaaa | caccctgtat | 240 |

| ctgcagatga | acagcctgcg | cgcggaggat | accgcggtgt | attattgcgc | gcgcgagggg | 300 |

| ctgtgggcgt | tgattattg | ggggcagggg | accctggtga | ccgtgagcag | c | 351 |

```
<210> SEQ ID NO 321
<211> LENGTH: 339
<212> TYPE: DNA
<213> ORGANISM: Artificial Sequence
<220> FEATURE:
<223> OTHER INFORMATION: C4.4a binder

<400> SEQUENCE: 321
```

| gagagcgtgc | tgacccagcc | gccgagcgtg | agcggggcgc | cggggcagcg | cgtgaccatt | 60 |

| agctgcaccg | ggagcagcag | caacattggg | gcggggtatg | tggtgcattg | gtatcagcag | 120 |

| ctgccgggga | ccgcgccgaa | actgctgatt | tatgataaca | acaaacgccc | gagcggggtg | 180 |

| ccggatcgct | ttagcgggag | caaaagcggg | accagcgcga | gcctggcgat | tagcgggctg | 240 |

| cgcagcgagg | atgaggcgga | ttattattgc | gcggcgtatg | atgatcgcct | gaacgggccg | 300 |

| gtgtttgggg | gggggaccaa | actgaccgtg | ctggggcag | | | 339 |

```
<210> SEQ ID NO 322
<211> LENGTH: 351
<212> TYPE: DNA
<213> ORGANISM: Artificial Sequence
<220> FEATURE:
<223> OTHER INFORMATION: C4.4a binder

<400> SEQUENCE: 322
```

| gaggtgcagc | tgctggagag | cgggggggggg | ctggtgcagc | cggggggggag | cctgcgcctg | 60 |

| agctgcgcgg | cgagcgggtt | tacctttagc | agcgcgtgga | tgagctgggt | gcgccaggcg | 120 |

| ccggggaaag | ggctggagtg | ggtgagctat | attagcagca | gcgggagcag | cacctattat | 180 |

| gcggatagcg | tgaaagggcg | ctttaccatt | agccgcgata | acagcaaaaa | caccctgtat | 240 |

| ctgcagatga | acagcctgcg | cgcggaggat | accgcggtgt | attattgcgc | gcgcgagggg | 300 |

| ctgtgggcgt | tgatgggtg | ggggcagggg | accctggtga | ccgtgagcag | c | 351 |

```
<210> SEQ ID NO 323
<211> LENGTH: 339
<212> TYPE: DNA
<213> ORGANISM: Artificial Sequence
<220> FEATURE:
<223> OTHER INFORMATION: C4.4a binder

<400> SEQUENCE: 323
```

| cagagcgtgc | tgacccagcc | gccgagcgcg | agcgggaccc | cggggcagcg | cgtgaccatt | 60 |

| agctgcagcg | ggagcagcag | caacattggg | gcggggtatg | tggtgcattg | gtatcagcag | 120 |

| ctgccgggga | ccgcgccgaa | actgctgatt | tatgataaca | accagcgccc | gagcggggtg | 180 |

| ccggatcgct | ttagcgggag | caaaagcggg | accagcgcga | gcctggcgat | tagcgggctg | 240 |

| cgcagcgagg | atgaggcgga | ttattattgc | gcggcgtatg | atgatagcct | gaaccgcccg | 300 |

| gtgtttgggg | gggggaccaa | actgaccgtg | ctggggcag | | | 339 |

```
<210> SEQ ID NO 324
<211> LENGTH: 351
<212> TYPE: DNA
<213> ORGANISM: Artificial Sequence
```

```
<220> FEATURE:
<223> OTHER INFORMATION: C4.4a binder

<400> SEQUENCE: 324
gaggtgcagc tgctggagag cggggggggg ctggtgcagc cggggggag cctgcgcctg      60 agctgcgcgg cgagcgggtt tacctttagc aacgcgtgga tgagctgggt gcgccaggcg    120
ccggggaaag gctggagtg ggtgagctat attagcagca gcgggagcac catttattat    180
gcggatagcg tgaaagggcg ctttaccatt agccgcgata acagcaaaaa caccctgtat    240
ctgcagatga acagcctgcg cgcggaggat accgcggtgt attattgcgc gcgcgagggg    300
ctgtgggcgt ttgattattg ggggcagggg accctggtga ccgtgagcag c            351

<210> SEQ ID NO 325
<211> LENGTH: 339
<212> TYPE: DNA
<213> ORGANISM: Artificial Sequence
<220> FEATURE:
<223> OTHER INFORMATION: C4.4a binder

<400> SEQUENCE: 325
cagagcgtgc tgacccagcc gccgagcgtg agcggggcgc cggggcagcg cgtgaccatt     60
agctgcaccg ggagcagcag caacattggg gcggggtatg tggtgcattg gtatcagcag    120
ctgccgggga ccgcgccgaa actgctgatt tatgataaca acaaacgccc gagcggggtg    180
ccggatcgct ttagcgggag caaaagcggg accagcgcga gcctggcgat tagcgggctg    240
cgcagcgagg atgaggcgga ttattattgc gcggcgtttg atgatagcct gaacgggccg    300
gtgtttgggg gggggaccaa actgaccgtg ctggggcag                          339

<210> SEQ ID NO 326
<211> LENGTH: 351
<212> TYPE: DNA
<213> ORGANISM: Artificial Sequence
<220> FEATURE:
<223> OTHER INFORMATION: C4.4a binder

<400> SEQUENCE: 326
gaggtgcagc tgctggagag cggggggggg ctggtgcagc cggggggag cctgcgcctg      60 agctgcgcgg cgagcgggtt tacctttagc agcgcgtgga tgagctgggt gcgccaggcg    120
ccggggaaag gctggagtg ggtgagctat attagcagca gcgggagcag cacctattat    180
gcggatagcg tgaaagggcg ctttaccatt agccgcgata acagcaaaaa caccctgtat    240
ctgcagatga acagcctgcg cgcggaggat accgcggtgt attattgcgc gcgcgagggg    300
ctgtgggcgt ttgataaatg ggggcagggg accctggtga ccgtgaccag c            351

<210> SEQ ID NO 327
<211> LENGTH: 339
<212> TYPE: DNA
<213> ORGANISM: Artificial Sequence
<220> FEATURE:
<223> OTHER INFORMATION: C4.4a binder

<400> SEQUENCE: 327
cagagcgtgc tgacccagcc gccgagcgcg agcgggaccc cggggcagcg cgtgaccatt     60
agctgcaccg ggagcagcag caacattggg gcggggtatg tggtgcattg gtatcagcag    120
ctgccgggga ccgcgccgaa actgctgatt tatgataaca acaaacgccc gagcggggtg    180
ccggatcgct ttagcgggag caaaagcggg accagcgcga gcctggcgat tagcgggctg    240
```

```
cgcagcgagg atgaggcgga ttattattgc gcggcgtttg atgatagcct gaacgggccg    300
gtgtttgggg gggggaccaa actgaccgtg ctggggcag                           339
```

<210> SEQ ID NO 328
<211> LENGTH: 351
<212> TYPE: DNA
<213> ORGANISM: Artificial Sequence
<220> FEATURE:
<223> OTHER INFORMATION: C4.4a binder

<400> SEQUENCE: 328

```
gaggtgcagc tgctggagag cggggggggg ctggtgcagc cggggggggag cctgcgcctg    60 agctgcgcgg cgagcgggtt tacctttagc agcgcgtgga tgagctgggt gcgccaggcg    120
ccggggaaag gctggagtg gtgagctat attagcagca gcgggagcag cacctattat     180
gcggatagcg tgaaagggcg ctttaccatt agccgcgata acagcaaaaa caccctgtat   240
ctgcagatga acagcctgcg cgcggaggat accgcggtgt attattgcgc gcgcgagggg   300
ctgtgggcgt ttgataaatg ggggcagggg accctggtga ccgtgagcag c            351
```

<210> SEQ ID NO 329
<211> LENGTH: 339
<212> TYPE: DNA
<213> ORGANISM: Artificial Sequence
<220> FEATURE:
<223> OTHER INFORMATION: C4.4a

<400> SEQUENCE: 329

```
cagagcgtgc tgacccagcc gccgagcgcg agcgggaccc cggggcagcg cgtgaccatt    60
agctgcagcg ggagcagcag caacattggg gcggggtatg tggtgcattg gtatcagcag   120
ctgccgggga ccgcgccgaa actgctgatt tatgataaca accagcgccc gagcggggtg    180
ccggatcgct ttagcgggag caaaagcggg accagcgcga gcctggcgat tagcgggctg    240
cgcagcgagg atgaggcgga ttattattgc gcggcgtttg atgatagcct gaacgggccg    300
gtgtttgggg gggggaccaa actgaccgtg ctggggcag                           339
```

<210> SEQ ID NO 330
<211> LENGTH: 351
<212> TYPE: DNA
<213> ORGANISM: Artificial Sequence
<220> FEATURE:
<223> OTHER INFORMATION: C4.4a binder

<400> SEQUENCE: 330

```
gaggtgcagc tgctggagag cggggggggg ctggtgcagc cggggggggag cctgcgcctg    60 agctgcgcgg cgagcgggtt tacctttagc agcgcgtgga tgagctgggt gcgccaggcg    120
ccggggaaag gctggagtg gtgagctat attagcagca gcgggagcag cacctattat     180
gcggatagcg tgaaagggcg ctttaccatt agccgcgata acagcaaaaa caccctgtat   240
ctgcagatga acagcctgcg cgcggaggat accgcggtgt attattgcgc gcgcgagggg   300
ctgtgggcgt ttgataaatg ggggcagggg accctggtga ccgtgagcag c            351
```

<210> SEQ ID NO 331
<211> LENGTH: 339
<212> TYPE: DNA
<213> ORGANISM: Artificial Sequence
<220> FEATURE:
<223> OTHER INFORMATION: C4.4a binder

<400> SEQUENCE: 331

```
cagagcgtgc tgacccagcc gccgagcgcg agcgggaccc ggggcagcg cgtgaccatt      60 agctgcagcg ggagcagcag caacattggg cggggtatg tggtgcattg gtatcagcag     120
ctgccgggga ccgcgccgaa actgctgatt tatgataaca accagcgccc gagcggggtg     180
ccggatcgct ttagcgggag caaaagcggg accagcgcga gcctggcgat tagcgggctg     240
cgcagcgagg atgaggcgga ttattattgc gcggcgtttg atgatcgcct gagcgggccg     300
gtgtttgggg gggggaccaa actgaccgtg ctggggcag                            339
```

```
<210> SEQ ID NO 332
<211> LENGTH: 366
<212> TYPE: DNA
<213> ORGANISM: Artificial Sequence
<220> FEATURE:
<223> OTHER INFORMATION: C4.4a binder

<400> SEQUENCE: 332
gaggtgcagc tgctggagag cggggggggg ctggtgcagc cggggggggag cctgcgcctg      60 agctgcgcgg cgagcgggtt tacctttagc gattatcaga tgacctggat tcgccagacc     120
ccggggaaag gctggagtg gtgagcggg gtgagctgga acggggcgcg cacccattat     180
gcggatagcg tgaaagggcg ctttaccatt agccgcgata cagcaaaaa cacccctgtat     240 ctgcagatga acagcctgcg cgcggaggat ccgcggtgt attattgcgc gaaaggggat     300
tatctggtgt atagcagcta ttattttaaa agctggggc aggggaccct ggtgaccgtg     360
accagc                                                                366
```

```
<210> SEQ ID NO 333
<211> LENGTH: 336
<212> TYPE: DNA
<213> ORGANISM: Artificial Sequence
<220> FEATURE:
<223> OTHER INFORMATION: C4.4a binder

<400> SEQUENCE: 333
cagagcgtgc tgacccagcc gccgagcgcg agcgggaccc ggggcagcg cgtgaccatt      60 agctgcagcg ggagcagcag caacgtgggg agcaacccgg tgaactggta tcagcagctg     120
ccggggaccg cgccgaaact gctgatttat cgcaacaacc agcgcccgag cggggtgccg     180
gatcgcttta gcgggagcaa aagcgggacc agcgcgagcc tggcgattag cgggctgcgc     240
agcgaggatg aggcggatta ttattgcgcg gcgtgggatg atcgcctgaa cgggtggggg     300 tttgggggg ggaccaaaact gaccgtgctg gggcag                              336
```

```
<210> SEQ ID NO 334
<211> LENGTH: 363
<212> TYPE: DNA
<213> ORGANISM: Artificial Sequence
<220> FEATURE:
<223> OTHER INFORMATION: C4.4a binder

<400> SEQUENCE: 334
gagcagctgc tggagagcgg gggggggctg gtgcagccgg ggggggagcct gcgcctgagc      60 tgcgcggcga gcgggtttac ctttagcagc tatcagatga cctggattcg ccagaccccg     120
gggaaagggc tggagtgggt gagcgggatt agctggaacg ggggagcac ccattatgcg     180 gatagcgtga aagggcgctt taccattagc cgcgataaca gcaaaaacac cctgtatctg     240
cagatgaaca gcctgcgcgc ggaggatacc gcggtgtatt attgcgcgaa agggattat     300
```

```
ctggtgtata gcgcgtatta ttttgatagc tggggcagg ggaccctggt gaccgtgagc      360
agc                                                                   363

<210> SEQ ID NO 335
<211> LENGTH: 333
<212> TYPE: DNA
<213> ORGANISM: Artificial Sequence
<220> FEATURE:
<223> OTHER INFORMATION: C4.4a binder

<400> SEQUENCE: 335
caggtgctga cccagccgcc gagcgcgagc gggaccccgg ggcagcgcgt gaccattagc       60
tgcagcggga gcagcagcaa cattgggagc aacccggtga actggtatca gcagctgccg      120
gggaccgcgc cgaaactgct gatttatcgc aacaaccagc gcccgagcgg ggtgccggat      180
cgctttagcg ggagcaaaag cgggaccagc gcgagcctgg cgattagcgg gctgcgcagc      240
gaggatgagg cggattatta ttgcgcggcg tgggatgatc gcctgaacgg gtgggggttt      300
ggggggggga ccaaactgac cgtgctgggg cag                                  333

<210> SEQ ID NO 336
<211> LENGTH: 366
<212> TYPE: DNA
<213> ORGANISM: Artificial Sequence
<220> FEATURE:
<223> OTHER INFORMATION: C4.4a binder

<400> SEQUENCE: 336
gaggtgcagc tgctggagag cggggggggg ctggtgcagc cgggggggag cctgcgcctg       60
agctgcgcgg cgagcgggtt taccttagc gattatcaga tgacctggat tcgccagacc      120
ccggggaaag gctggagtg gtgagcggg attagctgga acgggggggag cacccattat      180 gcggatagcg tgaaagggcg ctttaccatt agccgcgata cagcaaaaa caccctgtat      240 ctgcagatga acagcctgcg cgcggaggat accgcggtgt attattgcgc gaaaggggat      300
tatctggtgt atagcagcta ttattttaaa tattggggc aggggaccct ggtgaccgtg      360
agcagc                                                                366

<210> SEQ ID NO 337
<211> LENGTH: 336
<212> TYPE: DNA
<213> ORGANISM: Artificial Sequence
<220> FEATURE:
<223> OTHER INFORMATION: C4.4a binder

<400> SEQUENCE: 337
cagagcgtgc tgacccagcc gccgagcgcg agcgggaccc cggggcagcg cgtgaccatt       60
agctgcagcg ggagcagcag caacattggg agcaacccgg tgaactggta tcagcagctg      120
ccggggaccg cgccgaaact gctgatttat cgcaacaacc agcgcccgag cggggtgccg      180
gatcgcttta gcgggagcaa aagcgggacc agcgcgagcc tggcgattag cgggctgcgc      240
agcgaggatg aggcggatta ttattgcgcg gcgtgggatg atcgcctgaa cgggtgggcg      300
tttggggggg ggaccaaact gaccgtgctg gggcag                               336

<210> SEQ ID NO 338
<211> LENGTH: 366
<212> TYPE: DNA
<213> ORGANISM: Artificial Sequence
<220> FEATURE:
<223> OTHER INFORMATION: C4.4a binder
```

<400> SEQUENCE: 338

```
gaggtgcagc tgctggagag cggggggggg ctggtgcagc cggggggag cctgcgcctg      60
agctgcgcgg cgagcgggtt tacctttagc gattatcaga tgacctggat tcgccagacc    120
ccggggaaag gctggagtg ggtgagcggg attagctgga acggggggag cacccattat     180
gcggatagcg tgaaagggcg ctttaccatt agccgcgata acagcaaaaa caccctgtat    240
ctgcagatga acagcctgcg cgcggaggat accgcggtgt attattgcgc gaaagggggat    300
tatctggtgt atagcagcta ttattttaaa agctgggggc aggggaccct ggtgaccgtg    360
agcagc                                                               366
```

<210> SEQ ID NO 339
<211> LENGTH: 336
<212> TYPE: DNA
<213> ORGANISM: Artificial Sequence
<220> FEATURE:
<223> OTHER INFORMATION: C4.4a binder

<400> SEQUENCE: 339

```
cagagcgtgc tgacccagcc gccgagcgcg agcgggaccc cggggcagcg cgtgaccatt     60
agctgcagcg ggagcagcag caacattggg agcaacccgg tgaactggta tcagcagctg    120
ccggggaccg cgccgaaact gctgatttat cgcaacaacc agcgcccgag cggggtgccg    180
gatcgcttta gcgggagcaa aagcgggacc agcgcgagcc tggcgattag cgggctgcgc    240
agcgaggatg aggcggatta ttattgcgcg gcgtgggatg atagcctgaa cgggtgggggg    300
tttggggggg ggaccaaact gaccgtgctg gggcag                              336
```

<210> SEQ ID NO 340
<211> LENGTH: 366
<212> TYPE: DNA
<213> ORGANISM: Artificial Sequence
<220> FEATURE:
<223> OTHER INFORMATION: C4.4a binder

<400> SEQUENCE: 340

```
gaggtgcagc tgctggagag cggggggggg ctggtgcagc cggggggag cctgcgcctg      60
agctgcgcgg cgagcgggtt tacctttagc gattatcaga tgacctggat tcgccagacc    120
ccggggaaag gctggagtg ggtgagcggg attagctgga acggggggag cacccattat     180
gcggatagcg tgaaagggcg ctttaccatt agccgcgata acagcaaaaa caccctgtat    240
ctgcagatga acagcctgcg cgcggaggat accgcggtgt attattgcgc gaaagggggat    300
tatctggtgt ataaaagcta ttattttaaa agctgggggc aggggaccct ggtgaccgtg    360
agcagc                                                               366
```

<210> SEQ ID NO 341
<211> LENGTH: 336
<212> TYPE: DNA
<213> ORGANISM: Artificial Sequence
<220> FEATURE:
<223> OTHER INFORMATION: C4.4a binder

<400> SEQUENCE: 341

```
cagagcgtgc tgacccagcc gccgagcgcg agcgggaccc cggggcagcg cgtgaccatt     60
agctgcagcg ggagcagcag caacattggg agcaacccgg tgaactggta tcagcagctg    120
ccggggaccg cgccgaaact gctgatttat cgcaacaacc agcgcccgag cggggtgccg    180
```

| | |
|---|---|
| gatcgcttta gcgggagcaa aagcgggacc agcgcgagcc tggcgattag cgggctgcgc | 240 |
| agcgaggatg aggcggatta ttattgcgcg gcgtgggatg atcgcctgag cgggtggggg | 300 |
| tttggggggg ggaccaaact gaccgtgctg gggcag | 336 |

<210> SEQ ID NO 342
<211> LENGTH: 366
<212> TYPE: DNA
<213> ORGANISM: Artificial Sequence
<220> FEATURE:
<223> OTHER INFORMATION: C4.4a binder

<400> SEQUENCE: 342

| | |
|---|---|
| gaggtgcagc tgctggagag cggggggggg ctggtgcagc cggggggggag cctgcgcctg | 60 |
| agctgcgcgg cgagcgggtt tacctttagc gattatcaga tgacctggat tcgccagacc | 120 |
| ccggggaaag gctggagtg gtgagcggg attagctgga acggggggag cacccattat | 180 |
| gcggatagcg tgaaagggcg ctttaccatt agccgcgata acagcaaaaa caccctgtat | 240 |
| ctgcagatga acagcctgcg cgcggaggat accgcgtgt attattgcgc gaaagggggat | 300 |
| tatctggtgt atagcagcta ttatttaaa agctggggggc aggggaccct ggtgaccgtg | 360 |
| agcagc | 366 |

<210> SEQ ID NO 343
<211> LENGTH: 336
<212> TYPE: DNA
<213> ORGANISM: Artificial Sequence
<220> FEATURE:
<223> OTHER INFORMATION: C4.4a binder

<400> SEQUENCE: 343

| | |
|---|---|
| cagagcgtgc tgacccagcc gccgagcgcg agcgggaccc cggggcagcg cgtgaccatt | 60 |
| agctgcagcg ggagcagcag caacattggg agcaacccgg tgaactggta tcagcagctg | 120 |
| ccggggaccg cgccgaaact gctgatttat cgcaacaacc agcgcccgag cggggtgccg | 180 |
| gatcgcttta gcgggagcaa aagcgggacc agcgcgagcc tggcgattag cgggctgcgc | 240 |
| agcgaggatg aggcggatta ttattgcgcg gcgtgggatg atcgcctgag cgggtggggg | 300 |
| tttggggggg ggaccaaact gaccgtgctg gggcag | 336 |

<210> SEQ ID NO 344
<211> LENGTH: 366
<212> TYPE: DNA
<213> ORGANISM: Artificial Sequence
<220> FEATURE:
<223> OTHER INFORMATION: C4.4a binder

<400> SEQUENCE: 344

| | |
|---|---|
| gaggtgcagc tgctggagag cggggggggg ctggtgcagc cggggggggag cctgcgcctg | 60 |
| agctgcgcgg cgagcgggtt tacctttagc gattatcaga tgacctggat tcgccagacc | 120 |
| ccggggaaag gctggagtg gtgagcggg attagctgga acggggggag cacccattat | 180 |
| gcggatagcg tgaaagggcg ctttaccatt agccgcgata acagcaaaaa caccctgtat | 240 |
| ctgcagatga acagcctgcg cgcggaggat accgcggtgt attattgcgc gaaagggggat | 300 |
| tatctggtgt ataaaagcta ttatttaaa agctggggggc aggggaccct ggtgaccgtg | 360 |
| agcagc | 366 |

<210> SEQ ID NO 345
<211> LENGTH: 336

```
<212> TYPE: DNA
<213> ORGANISM: Artificial Sequence
<220> FEATURE:
<223> OTHER INFORMATION: C4.4a binder

<400> SEQUENCE: 345
cagagcgtgc tgacccagcc gccgagcgcg agcgggaccc cggggcagcg cgtgaccatt      60
agctgcagcg ggagcagcag caacattggg agcaacccgg tgaactggta tcagcagctg     120
ccggggaccg cgccgaaact gctgatttat cgcaacaacc agcgcccgag cggggtgccg     180
gatcgcttta gcgggagcaa aagcgggacc agcgcgagcc tggcgattag cgggctgcgc     240
agcgaggatg aggcggatta ttattgcgcg gcgtgggatg atagcctgaa cgggtggggg     300
tttggggggg ggaccaaact gaccgtgctg gggcag                               336

<210> SEQ ID NO 346
<211> LENGTH: 217
<212> TYPE: PRT
<213> ORGANISM: Homo Sapiens

<400> SEQUENCE: 346

Asp Ile Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Arg
                85                  90                  95

Leu Asn Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Gly Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 347
<211> LENGTH: 447
<212> TYPE: PRT
<213> ORGANISM: Homo Sapiens

<400> SEQUENCE: 347

Gln Val Glu Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

```
His Asn His Tyr Thr Gln Lys Ser Leu Ser Leu Ser Pro Gly Lys
            435                 440                 445
```

<210> SEQ ID NO 348
<211> LENGTH: 217
<212> TYPE: PRT
<213> ORGANISM: Homo Sapiens
<400> SEQUENCE: 348

```
Glu Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp
                85                  90                  95

Leu Asn Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 349
<211> LENGTH: 446
<212> TYPE: PRT
<213> ORGANISM: Homo Sapiens
<400> SEQUENCE: 349

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Ser Tyr Ile Ser Ser Ser Gly Ser Thr Ile Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Glu Gly Leu Trp Ala Phe Asp Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 350
<211> LENGTH: 217
<212> TYPE: PRT
<213> ORGANISM: Homo Sapiens

<400> SEQUENCE: 350

Glu Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ala Gly
            20                  25                  30
```

Tyr Val Val His Trp Tyr Gln Gln Leu Pro Gly Thr Ala Pro Lys Leu
              35                  40                  45

Leu Ile Tyr Asp Asn Asn Gln Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Arg
                 85                  90                  95

Leu Asn Gly Pro Val Phe Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 351
<211> LENGTH: 446
<212> TYPE: PRT
<213> ORGANISM: Homo Sapiens

<400> SEQUENCE: 351

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ala
             20                  25                  30

Trp Met Ser Trp Val Arg Gln Ala Pro Gly Lys Gly Leu Glu Trp Val
         35                  40                  45

Ser Tyr Ile Ser Ser Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Leu Trp Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

```
            180                 185                 190
Leu Gly Thr Gln Thr Tyr Ile Cys Asn Val Asn His Lys Pro Ser Asn
        195                 200                 205
Thr Lys Val Asp Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 352
<211> LENGTH: 217
<212> TYPE: PRT
<213> ORGANISM: Homo Sapiens

<400> SEQUENCE: 352

Glu Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Val Val His Trp Tyr Gln Gln Leu Pro Gly Thr Ala Pro Lys Leu
        35                  40                  45
Leu Ile Tyr Asp Asn Asn Lys Arg Pro Ser Gly Val Pro Asp Arg Phe
    50                  55                  60
Ser Gly Ser Lys Ser Gly Thr Ser Ala Ser Leu Ala Ile Ser Gly Leu
65                  70                  75                  80
Arg Ser Glu Asp Glu Ala Asp Tyr Tyr Cys Ala Ala Trp Asp Asp Arg
                85                  90                  95
Leu Asn Gly Pro Val Phe Gly Gly Gly Thr Lys Leu Thr Val Leu Gly
            100                 105                 110
```

```
Gln Pro Lys Ala Ala Pro Ser Val Thr Leu Phe Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 353
<211> LENGTH: 446
<212> TYPE: PRT
<213> ORGANISM: Homo Sapiens

<400> SEQUENCE: 353

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 354
<211> LENGTH: 217
<212> TYPE: PRT
<213> ORGANISM: Homo Sapiens

<400> SEQUENCE: 354

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Arg
                85                  90                  95

Leu Asn Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
```

```
            195                 200                 205
Lys Thr Val Ala Pro Thr Glu Cys Ser
    210                 215
```

<210> SEQ ID NO 355
<211> LENGTH: 446
<212> TYPE: PRT
<213> ORGANISM: Homo Sapiens

<400> SEQUENCE: 355

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 356
<211> LENGTH: 217
<212> TYPE: PRT
<213> ORGANISM: Homo Sapiens

<400> SEQUENCE: 356

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Ser
                85                  90                  95

Leu Ser Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 357
<211> LENGTH: 446
<212> TYPE: PRT
<213> ORGANISM: Homo Sapiens

<400> SEQUENCE: 357

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
```

<210> SEQ ID NO 358
<211> LENGTH: 217
<212> TYPE: PRT
<213> ORGANISM: Homo Sapiens

<400> SEQUENCE: 358

Gln Ser Val Leu Thr Gln Pro Pro Ser Ala Gly Thr Pro Gly Gln
1               5                   10                  15

Arg Val Thr Ile Ser Cys Ser Gly Ser Ser Asn Ile Gly Ala Gly
                20                  25                  30

Tyr Val His Trp Tyr Gln Gln Leu Pro Gly Thr Ala Pro Lys Leu
            35                  40                  45

Leu Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Ser
                85                  90                  95

Leu Asn Arg Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 359
<211> LENGTH: 446
<212> TYPE: PRT
<213> ORGANISM: Homo Sapiens

<400> SEQUENCE: 359

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
                20                  25                  30

Trp Met Ser Trp Val Arg Gln Ala Pro Gly Lys Gly Leu Glu Trp Val
            35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Gly Trp Gly Gln Gly Thr Leu

```
            100                 105                 110
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 360
<211> LENGTH: 217
<212> TYPE: PRT
<213> ORGANISM: Homo Sapiens

<400> SEQUENCE: 360

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30
```

```
Tyr Val Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Phe Asp Asp Arg
                85                  90                  95

Leu Asn Gly Pro Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 361
<211> LENGTH: 446
<212> TYPE: PRT
<213> ORGANISM: Homo Sapiens

<400> SEQUENCE: 361

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190
```

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 362
<211> LENGTH: 217
<212> TYPE: PRT
<213> ORGANISM: Homo Sapiens

<400> SEQUENCE: 362

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Ser
                85                  90                  95

Leu Asn Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
```

```
            115                 120                 125
Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215

<210> SEQ ID NO 363
<211> LENGTH: 446
<212> TYPE: PRT
<213> ORGANISM: Homo Sapiens

<400> SEQUENCE: 363

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 364
<211> LENGTH: 217
<212> TYPE: PRT
<213> ORGANISM: Homo Sapiens

<400> SEQUENCE: 364

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Tyr Asp Asp Ser
                85                  90                  95

Leu Ser Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205
```

```
Lys Thr Val Ala Pro Thr Glu Cys Ser
    210             215

<210> SEQ ID NO 365
<211> LENGTH: 446
<212> TYPE: PRT
<213> ORGANISM: Homo Sapiens

<400> SEQUENCE: 365

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
```

```
                    355                 360                 365
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 366
<211> LENGTH: 217
<212> TYPE: PRT
<213> ORGANISM: Homo Sapiens

<400> SEQUENCE: 366

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Ser
                85                  90                  95

Leu Asn Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 367
<211> LENGTH: 446
<212> TYPE: PRT
<213> ORGANISM: Homo Sapiens

<400> SEQUENCE: 367

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
```

-continued

```
                20                  25                  30
Trp Met Ser Trp Val Arg Gln Ala Pro Gly Lys Gly Leu Glu Trp Val
            35                  40                  45
Ser Tyr Ile Ser Ser Gly Ser Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Glu Gly Leu Trp Ala Phe Asp Lys Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
            435                 440                 445
```

<210> SEQ ID NO 368
<211> LENGTH: 217
<212> TYPE: PRT
<213> ORGANISM: Homo Sapiens

<400> SEQUENCE: 368

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Phe Asp Asp Arg
                85                  90                  95

Leu Ser Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 369
<211> LENGTH: 446
<212> TYPE: PRT
<213> ORGANISM: Homo Sapiens

<400> SEQUENCE: 369

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Lys Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 370
<211> LENGTH: 216
<212> TYPE: PRT
<213> ORGANISM: Homo Sapiens

<400> SEQUENCE: 370

Asp Ile Val Leu Thr Gln Pro Pro Ser Ala Ser Gly Thr Pro Gly Gln
1               5                   10                  15

Arg Val Thr Ile Ser Cys Ser Gly Ser Ser Ser Asn Val Gly Ser Asn
            20                  25                  30

Pro Val Asn Trp Tyr Gln Gln Leu Pro Gly Thr Ala Pro Lys Leu Leu

```
            35                  40                  45
Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Trp Asp Asp Arg Leu
                 85                  90                  95

Asn Gly Trp Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Gly Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
210                 215

<210> SEQ ID NO 371
<211> LENGTH: 452
<212> TYPE: PRT
<213> ORGANISM: Homo Sapiens

<400> SEQUENCE: 371

Gln Val Glu Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Gln Met Thr Trp Ile Arg Gln Thr Pro Gly Lys Gly Leu Glu Trp Val
                 35                  40                  45

Ser Gly Val Ser Trp Asn Gly Ala Arg Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Asp Tyr Leu Val Tyr Ser Ala Tyr Tyr Phe Asp Ser Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190
```

```
Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 372
<211> LENGTH: 216
<212> TYPE: PRT
<213> ORGANISM: Homo Sapiens

<400> SEQUENCE: 372

Glu Ser Val Leu Thr Gln Pro Pro Ser Ala Ser Gly Thr Pro Gly Gln
1               5                   10                  15

Arg Val Thr Ile Ser Cys Ser Gly Ser Ser Asn Val Gly Ser Asn
            20                  25                  30

Pro Val Asn Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Val Phe Gly Gly Gly Thr Lys Leu Thr Val Leu Gly Gln
                100                 105                 110
```

```
Pro Lys Ala Ala Pro Ser Val Thr Leu Phe Pro Pro Ser Ser Glu Glu
    115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 373
<211> LENGTH: 451
<212> TYPE: PRT
<213> ORGANISM: Homo Sapiens

<400> SEQUENCE: 373

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Val Ser Trp Asn Gly Ala Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
```

```
                        260                 265                 270
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 374
<211> LENGTH: 216
<212> TYPE: PRT
<213> ORGANISM: Homo Sapiens

<400> SEQUENCE: 374

Glu Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 375
<211> LENGTH: 451
<212> TYPE: PRT
<213> ORGANISM: Homo Sapiens

<400> SEQUENCE: 375

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 376
<211> LENGTH: 216
<212> TYPE: PRT
<213> ORGANISM: Homo Sapiens

<400> SEQUENCE: 376

Glu Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 377
<211> LENGTH: 451
<212> TYPE: PRT
```

<213> ORGANISM: Homo Sapiens

<400> SEQUENCE: 377

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 378
<211> LENGTH: 216
<212> TYPE: PRT
<213> ORGANISM: Homo Sapiens

<400> SEQUENCE: 378

Glu Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Pro Val Asn Trp Tyr Gln Gln Leu Pro Gly Thr Ala Pro Lys Leu Leu
        35                  40                  45
Ile Tyr Arg Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Arg Leu
                85                  90                  95
Asn Gly Trp Gly Phe Gly Gly Thr Lys Leu Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 379
<211> LENGTH: 451
<212> TYPE: PRT
<213> ORGANISM: Homo Sapiens

<400> SEQUENCE: 379

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Gln Met Thr Trp Ile Arg Gln Thr Pro Gly Lys Gly Leu Glu Trp Val
        35                  40                  45
```

```
Ser Gly Ile Ser Trp Asn Gly Gly Ser Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Asp Tyr Leu Val Tyr Ser Ala Tyr Tyr Phe Asp Ser Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
450
```

```
<210> SEQ ID NO 380
<211> LENGTH: 216
<212> TYPE: PRT
<213> ORGANISM: Homo Sapiens

<400> SEQUENCE: 380

Glu Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Gly Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 381
<211> LENGTH: 451
<212> TYPE: PRT
<213> ORGANISM: Homo Sapiens

<400> SEQUENCE: 381

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Thr Trp Ile Arg Gln Thr Pro Gly Lys Gly Leu Glu Trp Val
            35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ala Tyr Tyr Phe Asp Ser Trp
            100                 105                 110

Gly Gln Gly Thr Leu Val Thr Val Ser Ser Ala Ser Thr Lys Gly Pro
```

```
            115                 120                 125
Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 382
<211> LENGTH: 216
<212> TYPE: PRT
<213> ORGANISM: Homo Sapiens

<400> SEQUENCE: 382

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Pro Val Asn Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Arg Leu
                 85                  90                  95

Ser Gly Trp Ala Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 383
<211> LENGTH: 451
<212> TYPE: PRT
<213> ORGANISM: Homo Sapiens

<400> SEQUENCE: 383

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Gln Met Thr Trp Ile Arg Gln Thr Pro Gly Lys Gly Leu Glu Trp Val
         35                  40                  45

Ser Gly Ile Ser Trp Asn Gly Ser Thr His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Asp Tyr Leu Val Tyr Ser Ser Tyr Tyr Phe Lys Ser Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 384
<211> LENGTH: 216
<212> TYPE: PRT
<213> ORGANISM: Homo Sapiens

<400> SEQUENCE: 384

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Ala Phe Gly Gly Gly Thr Lys Leu Thr Val Leu Gly Gln

```
                100                 105                 110
Pro Lys Ala Ala Pro Ser Val Thr Leu Phe Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 385
<211> LENGTH: 451
<212> TYPE: PRT
<213> ORGANISM: Homo Sapiens

<400> SEQUENCE: 385

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Tyr Phe Lys Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 386
<211> LENGTH: 216
<212> TYPE: PRT
<213> ORGANISM: Homo Sapiens

<400> SEQUENCE: 386

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Asn Gly Trp Ala Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 387
<211> LENGTH: 451
<212> TYPE: PRT
<213> ORGANISM: Homo Sapiens

<400> SEQUENCE: 387

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Phe Lys Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
```

-continued

```
                325                 330                 335
Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 388
<211> LENGTH: 216
<212> TYPE: PRT
<213> ORGANISM: Homo Sapiens

<400> SEQUENCE: 388

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Gly Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 389
<211> LENGTH: 451
```

<212> TYPE: PRT
<213> ORGANISM: Homo Sapiens

<400> SEQUENCE: 389

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly
        450

<210> SEQ ID NO 390
<211> LENGTH: 216
<212> TYPE: PRT
<213> ORGANISM: Homo Sapiens

<400> SEQUENCE: 390

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Gly Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 391
<211> LENGTH: 451
<212> TYPE: PRT
<213> ORGANISM: Homo Sapiens

<400> SEQUENCE: 391

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45
```

```
Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Phe Lys Ser Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450
```

<210> SEQ ID NO 392
<211> LENGTH: 216
<212> TYPE: PRT
<213> ORGANISM: Homo Sapiens

<400> SEQUENCE: 392

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Gly Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 393
<211> LENGTH: 451
<212> TYPE: PRT
<213> ORGANISM: Homo Sapiens

<400> SEQUENCE: 393

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
        35                  40                  45

Ser Gly Ile Ser Trp Asn Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Ser Ser Tyr Tyr Phe Lys Ser Trp
            100                 105                 110

```
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 394
<211> LENGTH: 216
<212> TYPE: PRT
<213> ORGANISM: Homo Sapiens

<400> SEQUENCE: 394

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
```

```
Pro Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Gly Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 395
<211> LENGTH: 451
<212> TYPE: PRT
<213> ORGANISM: Homo Sapiens

<400> SEQUENCE: 395

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gln Met Thr Trp Ile Arg Gln Thr Pro Gly Lys Gly Leu Glu Trp Val
            35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Tyr Phe Lys Ser Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
```

```
                180                 185                 190
Val Pro Ser Ser Leu Gly Thr Gln Thr Tyr Ile Cys Asn Val Asn
            195                 200                 205
His Lys Pro Ser Asn Thr Lys Val Asp Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
        260                 265                 270
His Glu Asp Pro Glu Val Lys Phe Asn Trp Tyr Val Asp Gly Val Glu
    275                 280                 285
Val His Asn Ala Lys Thr Lys Pro Arg Glu Glu Gln Tyr Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
            325                 330                 335
Ile Glu Lys Thr Ile Ser Lys Ala Lys Gly Gln Pro Arg Glu Pro Gln
        340                 345                 350
Val Tyr Thr Leu Pro Pro Ser Arg Asp Glu Leu Thr Lys Asn Gln Val
    355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
        420                 425                 430
Met His Glu Ala Leu His Asn His Tyr Thr Gln Lys Ser Leu Ser Leu
            435                 440                 445
Ser Pro Gly
    450

<210> SEQ ID NO 396
<211> LENGTH: 216
<212> TYPE: PRT
<213> ORGANISM: Homo Sapiens

<400> SEQUENCE: 396

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Pro Val Asn Trp Tyr Gln Gln Leu Pro Gly Thr Ala Pro Lys Leu Leu
        35                  40                  45
Ile Tyr Arg Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ser Leu
                85                  90                  95
```

```
Ser Gly Trp Ala Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 397
<211> LENGTH: 451
<212> TYPE: PRT
<213> ORGANISM: Homo Sapiens

<400> SEQUENCE: 397

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Thr Trp Ile Arg Gln Ala Pro Gly Lys Gly Leu Glu Trp Val
        35                  40                  45

Ser Gly Ile Ser Trp Asn Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Leu Val Tyr Lys Ser Tyr Tyr Phe Lys Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 398
<211> LENGTH: 10
<212> TYPE: PRT
<213> ORGANISM: Homo sapiens

<400> SEQUENCE: 398

Gly Tyr Ser Phe Thr Ser Tyr Trp Ile Gly
1               5                   10

<210> SEQ ID NO 399
<211> LENGTH: 20
<212> TYPE: PRT
<213> ORGANISM: Homo sapiens

<400> SEQUENCE: 399

Trp Met Gly Ile Ile Asp Pro Gly Asp Ser Arg Thr Arg Tyr Ser Pro
1               5                   10                  15

Ser Phe Gln Gly
            20

<210> SEQ ID NO 400
<211> LENGTH: 11
<212> TYPE: PRT
<213> ORGANISM: Homo sapiens

<400> SEQUENCE: 400

Gly Gln Leu Tyr Gly Gly Thr Tyr Met Asp Gly
1               5                   10

<210> SEQ ID NO 401
<211> LENGTH: 14
```

```
<212> TYPE: PRT
<213> ORGANISM: Homo sapiens

<400> SEQUENCE: 401

Thr Gly Thr Ser Ser Asp Ile Gly Gly Tyr Asn Ser Val Ser
1               5                   10

<210> SEQ ID NO 402
<211> LENGTH: 11
<212> TYPE: PRT
<213> ORGANISM: Homo sapiens

<400> SEQUENCE: 402

Leu Met Ile Tyr Gly Val Asn Asn Arg Pro Ser
1               5                   10

<210> SEQ ID NO 403
<211> LENGTH: 10
<212> TYPE: PRT
<213> ORGANISM: Homo sapiens

<400> SEQUENCE: 403

Ser Ser Tyr Asp Ile Glu Ser Ala Thr Pro
1               5                   10

<210> SEQ ID NO 404
<211> LENGTH: 120
<212> TYPE: PRT
<213> ORGANISM: Homo sapiens

<400> SEQUENCE: 404

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Ala Pro Gly Lys Gly Leu Glu Trp Met
        35                  40                  45

Gly Ile Ile Asp Pro Gly Asp Ser Arg Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gln Leu Tyr Gly Gly Thr Tyr Met Asp Gly Trp Gly Gln
            100                 105                 110

Gly Thr Leu Val Thr Val Ser Ser
        115                 120

<210> SEQ ID NO 405
<211> LENGTH: 113
<212> TYPE: PRT
<213> ORGANISM: Homo sapiens

<400> SEQUENCE: 405

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Ser Val Ser Trp Tyr Gln Gln His Pro Gly Lys Ala Pro Lys Leu
        35                  40                  45
```

Met Ile Tyr Gly Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Ile Glu
                 85                  90                  95

Ser Ala Thr Pro Val Phe Gly Gly Gly Thr Lys Leu Thr Val Leu Gly
                100                 105                 110

Gln

<210> SEQ ID NO 406
<211> LENGTH: 360
<212> TYPE: DNA
<213> ORGANISM: Homo sapiens

<400> SEQUENCE: 406
caggtggaat tggttcagag cggcgcggaa gtgaaaaaac cgggcgaaag cctgaaaatt      60
agctgcaaag gttccggata ttcctttact tcttattgga ttggttgggt gcgccaggcc     120
cctgggaagg gtctcgagtg gatgggcatt atcgatccgg gtgatagccg tacccgttat     180
tctccgagct ttcagggcca ggtgaccatt agcgcggata aaagcattag caccgcgtat     240
cttcaatgga gcagcctgaa agcgagcgat acggccatgt attattgcgc gcgtggtcag     300
ctttatggtg gtacttatat ggatggttgg ggccaaggca ccctggtgac ggttagctca     360

<210> SEQ ID NO 407
<211> LENGTH: 339
<212> TYPE: DNA
<213> ORGANISM: Homo sapiens

<400> SEQUENCE: 407
gatatcgcac tgacccagcc agcttcagtg agcggctcac caggtcagag cattaccatc      60
tcgtgtacgg gtactagcag cgatattggt ggttataatt ctgtgtcttg gtaccagcag     120
catcccggga aggcgccgaa acttatgatt tatggtgtta ataatcgtcc ctcaggcgtg     180
agcaaccgtt ttagcggatc caaaagcggc aacaccgcga gcctgaccat tagcggcctg     240
caagcggaag acgaagcgga ttattattgc tcttcttatg atattgagtc tgctactcct     300
gtgtttggcg gcggcacgaa gttaaccgtc ctaggtcag                            339

<210> SEQ ID NO 408
<211> LENGTH: 450
<212> TYPE: PRT
<213> ORGANISM: Homo sapiens

<400> SEQUENCE: 408

Gln Val Glu Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Ala Pro Gly Lys Gly Leu Glu Trp Met
             35                  40                  45

Gly Ile Ile Asp Pro Gly Asp Ser Arg Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gln Leu Tyr Gly Thr Tyr Met Asp Gly Trp Gly Gln
                100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 409
<211> LENGTH: 217
<212> TYPE: PRT
<213> ORGANISM: Homo sapiens

<400> SEQUENCE: 409

Asp Ile Ala Leu Thr Gln Pro Ala Ser Val Ser Gly Ser Pro Gly Gln

```
1               5                   10                  15
Ser Ile Thr Ile Ser Cys Thr Gly Thr Ser Ser Asp Ile Gly Gly Tyr
                20                  25                  30
Asn Ser Val Ser Trp Tyr Gln Gln His Pro Gly Lys Ala Pro Lys Leu
            35                  40                  45
Met Ile Tyr Gly Val Asn Asn Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Asp Ile Glu
                85                  90                  95
Ser Ala Thr Pro Val Phe Gly Gly Gly Thr Lys Leu Thr Val Leu Gly
                100                 105                 110
Gln Pro Lys Ala Ala Pro Ser Val Thr Leu Phe Pro Pro Ser Ser Glu
            115                 120                 125
Glu Leu Gln Ala Asn Lys Ala Thr Leu Val Cys Leu Ile Ser Asp Phe
        130                 135                 140
Tyr Pro Gly Ala Val Thr Val Ala Trp Lys Gly Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 410
<211> LENGTH: 1353
<212> TYPE: DNA
<213> ORGANISM: Homo sapiens

<400> SEQUENCE: 410

```
caggtggaat tggttcagag cggcgcggaa gtgaaaaaac cgggcgaaag cctgaaaatt      60
agctgcaaag gttccggata ttcctttact tcttattgga ttggttgggt gcgccaggcc     120
cctgggaagg gtctcgagtg gatgggcatt atcgatccgg gtgatagccg tacccgttat     180
tctccgagct ttcagggcca ggtgaccatt agcgcggata aaagcattag caccgcgtat     240
cttcaatgga gcagcctgaa agcgagcgat acggccatgt attattgcgc gcgtggtcag     300
ctttatggtg gtacttatat ggatggttgg ggccaaggca ccctggtgac ggttagctca     360
gcctccacca agggtccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
```

```
agcacgtacc gggtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

```
<210> SEQ ID NO 411
<211> LENGTH: 654
<212> TYPE: DNA
<213> ORGANISM: Homo sapiens

<400> SEQUENCE: 411
gatatcgcac tgacccagcc agcttcagtg agcggctcac caggtcagag cattaccatc     60
tcgtgtacgg gtactagcag cgatattggt ggttataatt ctgtgtcttg gtaccagcag    120
catccccgga aggcgccgaa acttatgatt tatggtgtta ataatcgtcc ctcaggcgtg    180
agcaaccgtt ttagcggatc caaaagcggc aacaccgcga gcctgaccat tagcggcctg    240
caagcggaag acgaagcgga ttattattgc tcttcttatg atattgagtc tgctactcct    300
gtgtttggcg gcggcacgaa gttaaccgtc ctaggtcagc ccaaggctgc ccctcggtc     360 actctgttcc cgcccctcct ctgaggagct tcaagccaac aggccacact ggtgtgtctc    420
ataagtgact tctacccggg agccgtgaca gtggcctgga agggagatag cagccccgtc    480
aaggcgggag tggagaccac cacaccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggccccta cagaatgttc atag          654
```

```
<210> SEQ ID NO 412
<211> LENGTH: 1210
<212> TYPE: PRT
<213> ORGANISM: Homo sapiens

<400> SEQUENCE: 412

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
    65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
```

```
              130                 135                 140
His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560
```

```
Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975
```

```
Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 413
<211> LENGTH: 622
<212> TYPE: PRT
<213> ORGANISM: Homo sapiens

<400> SEQUENCE: 413

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125
```

```
Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540
```

```
Pro His Val Glu Gly Leu Lys Ala Glu Glu Arg His Arg Pro Val Arg
545                 550                 555                 560

Asp Trp Ile Leu Arg Gln Arg Gln Asp Leu Asp Thr Leu Gly Leu
            565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
            595                 600                 605

Val Leu Thr Val Leu Ala Leu Leu Ala Ser Thr Leu Ala
            610                 615                 620

<210> SEQ ID NO 414
<211> LENGTH: 459
<212> TYPE: PRT
<213> ORGANISM: Homo sapiens

<400> SEQUENCE: 414

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
            35                  40                  45

Leu Gly Gly Gly Ser Ser Gly Glu Asp Asp Pro Leu Gly Glu Glu Asp
50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
            115                 120                 125

Ala His Arg Asp Lys Glu Gly Asp Asp Gln Ser His Trp Arg Tyr Gly
130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
            195                 200                 205

Gly Leu Glu Met Ala Leu Gly Pro Gly Arg Glu Tyr Arg Ala Leu Gln
            210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
            275                 280                 285

Tyr Glu Gln Leu Leu Ser Arg Leu Glu Glu Ile Ala Glu Glu Gly Ser
            290                 295                 300
```

```
Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
            325                 330                 335

Ala Gln Gly Val Ile Trp Thr Val Phe Asn Gln Thr Val Met Leu Ser
        340                 345                 350

Ala Lys Gln Leu His Thr Leu Ser Asp Thr Leu Trp Gly Pro Gly Asp
    355                 360                 365

Ser Arg Leu Gln Leu Asn Phe Arg Ala Thr Gln Pro Leu Asn Gly Arg
370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
            420                 425                 430

Val Gln Met Arg Arg Gln His Arg Arg Gly Thr Lys Gly Gly Val Ser
        435                 440                 445

Tyr Arg Pro Ala Glu Val Ala Glu Thr Gly Ala
    450                 455

<210> SEQ ID NO 415
<211> LENGTH: 61
<212> TYPE: PRT
<213> ORGANISM: Homo sapiens

<400> SEQUENCE: 415

Met Lys Arg Phe Leu Phe Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60

<210> SEQ ID NO 416
<211> LENGTH: 1255
<212> TYPE: PRT
<213> ORGANISM: Homo sapiens

<400> SEQUENCE: 416

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110
```

```
Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525
```

-continued

Val Asn Cys Ser Gln Phe Leu Arg Gly Gln Glu Cys Val Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met

```
                945                 950                 955                 960
            Ile Asp Ser Glu Cys Arg Pro Arg Phe Arg Glu Leu Val Ser Glu Phe
                            965                 970                 975
            Ser Arg Met Ala Arg Asp Pro Gln Arg Phe Val Val Ile Gln Asn Glu
                            980                 985                 990
            Asp Leu Gly Pro Ala Ser Pro Leu Asp Ser Thr Phe Tyr Arg Ser Leu
                            995                 1000                1005
            Leu Glu Asp Asp Met Gly Asp Leu Val Asp Ala Glu Glu Tyr
                            1010                1015                1020
            Leu Val Pro Gln Gln Gly Phe Phe Cys Pro Asp Pro Ala Pro Gly
                            1025                1030                1035
            Ala Gly Gly Met Val His His Arg His Arg Ser Ser Ser Thr Arg
                            1040                1045                1050
            Ser Gly Gly Gly Asp Leu Thr Leu Gly Leu Glu Pro Ser Glu Glu
                            1055                1060                1065
            Glu Ala Pro Arg Ser Pro Leu Ala Pro Ser Glu Gly Ala Gly Ser
                            1070                1075                1080
            Asp Val Phe Asp Gly Asp Leu Gly Met Gly Ala Ala Lys Gly Leu
                            1085                1090                1095
            Gln Ser Leu Pro Thr His Asp Pro Ser Pro Leu Gln Arg Tyr Ser
                            1100                1105                1110
            Glu Asp Pro Thr Val Pro Leu Pro Ser Glu Thr Asp Gly Tyr Val
                            1115                1120                1125
            Ala Pro Leu Thr Cys Ser Pro Gln Pro Glu Tyr Val Asn Gln Pro
                            1130                1135                1140
            Asp Val Arg Pro Gln Pro Pro Ser Pro Arg Glu Gly Pro Leu Pro
                            1145                1150                1155
            Ala Ala Arg Pro Ala Gly Ala Thr Leu Glu Arg Pro Lys Thr Leu
                            1160                1165                1170
            Ser Pro Gly Lys Asn Gly Val Val Lys Asp Val Phe Ala Phe Gly
                            1175                1180                1185
            Gly Ala Val Glu Asn Pro Glu Tyr Leu Thr Pro Gln Gly Gly Ala
                            1190                1195                1200
            Ala Pro Gln Pro His Pro Pro Ala Phe Ser Pro Ala Phe Asp
                            1205                1210                1215
            Asn Leu Tyr Tyr Trp Asp Gln Asp Pro Pro Glu Arg Gly Ala Pro
                            1220                1225                1230
            Pro Ser Thr Phe Lys Gly Thr Pro Thr Ala Glu Asn Pro Glu Tyr
                            1235                1240                1245
            Leu Gly Leu Asp Val Pro Val
                            1250                1255

<210> SEQ ID NO 417
<211> LENGTH: 297
<212> TYPE: PRT
<213> ORGANISM: Homo sapiens

<400> SEQUENCE: 417

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
                20                  25                  30

Arg Met Ser Ser Leu Val Gly Pro Thr Gln Ser Phe Phe Met Arg Glu
            35                  40                  45
```

```
Ser Lys Thr Leu Gly Ala Val Gln Ile Met Asn Gly Leu Phe His Ile
    50              55                  60

Ala Leu Gly Gly Leu Leu Met Ile Pro Ala Gly Ile Tyr Ala Pro Ile
 65              70                  75                  80

Cys Val Thr Val Trp Tyr Pro Leu Trp Gly Gly Ile Met Tyr Ile Ile
                 85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 418
<211> LENGTH: 595
<212> TYPE: PRT
<213> ORGANISM: Homo sapiens

<400> SEQUENCE: 418

Met Arg Val Leu Leu Ala Ala Leu Gly Leu Leu Phe Leu Gly Ala Leu
 1               5                  10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
 65              70                  75                  80

Cys Thr Ala Cys Val Thr Cys Ser Arg Asp Asp Leu Val Glu Lys Thr
                 85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125
```

```
Ser Val Cys Pro Ala Gly Met Ile Val Lys Phe Pro Gly Thr Ala Gln
130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Arg Ala Arg Cys Val Pro Tyr Pro
290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
530                 535                 540
```

```
Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
            565                 570                 575

Leu Ser Val Glu Glu Glu Gly Lys Glu Asp Pro Leu Pro Thr Ala Ala
        580                 585                 590

Ser Gly Lys
        595

<210> SEQ ID NO 419
<211> LENGTH: 847
<212> TYPE: PRT
<213> ORGANISM: Homo sapiens

<400> SEQUENCE: 419

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320
```

```
Glu Glu Val Phe Leu Gln Val Gln Tyr Ala Pro Pro Ser Thr Val
            325                 330                 335
Gln Ile Leu His Ser Pro Ala Val Glu Gly Ser Gln Val Glu Phe Leu
            340                 345                 350
Cys Met Ser Leu Ala Asn Pro Leu Pro Thr Asn Tyr Thr Trp Tyr His
            355                 360                 365
Asn Gly Lys Glu Met Gln Gly Arg Thr Glu Glu Lys Val His Ile Pro
        370                 375                 380
Lys Ile Leu Pro Trp His Ala Gly Thr Tyr Ser Cys Val Ala Glu Asn
385                 390                 395                 400
Ile Leu Gly Thr Gly Gln Arg Gly Pro Gly Ala Glu Leu Asp Val Gln
            405                 410                 415
Tyr Pro Pro Lys Lys Val Thr Thr Val Ile Gln Asn Pro Met Pro Ile
            420                 425                 430
Arg Glu Gly Asp Thr Val Thr Leu Ser Cys Asn Tyr Asn Ser Ser Asn
            435                 440                 445
Pro Ser Val Thr Arg Tyr Glu Trp Lys Pro His Gly Ala Trp Glu Glu
        450                 455                 460
Pro Ser Leu Gly Val Leu Lys Ile Gln Asn Val Gly Trp Asp Asn Thr
465                 470                 475                 480
Thr Ile Ala Cys Ala Ala Cys Asn Ser Trp Cys Ser Trp Ala Ser Pro
            485                 490                 495
Val Ala Leu Asn Val Gln Tyr Ala Pro Arg Asp Val Arg Val Arg Lys
            500                 505                 510
Ile Lys Pro Leu Ser Glu Ile His Ser Gly Asn Ser Val Ser Leu Gln
            515                 520                 525
Cys Asp Phe Ser Ser Ser His Pro Lys Glu Val Gln Phe Phe Trp Glu
            530                 535                 540
Lys Asn Gly Arg Leu Leu Gly Lys Glu Ser Gln Leu Asn Phe Asp Ser
545                 550                 555                 560
Ile Ser Pro Glu Asp Ala Gly Ser Tyr Ser Cys Trp Val Asn Asn Ser
            565                 570                 575
Ile Gly Gln Thr Ala Ser Lys Ala Trp Thr Leu Glu Val Leu Tyr Ala
            580                 585                 590
Pro Arg Arg Leu Arg Val Ser Met Ser Pro Gly Asp Gln Val Met Glu
            595                 600                 605
Gly Lys Ser Ala Thr Leu Thr Cys Glu Ser Asp Ala Asn Pro Pro Val
        610                 615                 620
Ser His Tyr Thr Trp Phe Asp Trp Asn Asn Gln Ser Leu Pro Tyr His
625                 630                 635                 640
Ser Gln Lys Leu Arg Leu Glu Pro Val Lys Val Gln His Ser Gly Ala
            645                 650                 655
Tyr Trp Cys Gln Gly Thr Asn Ser Val Gly Lys Gly Arg Ser Pro Leu
            660                 665                 670
Ser Thr Leu Thr Val Tyr Tyr Ser Pro Glu Thr Ile Gly Arg Arg Val
            675                 680                 685
Ala Val Gly Leu Gly Ser Cys Leu Ala Ile Leu Ile Leu Ala Ile Cys
            690                 695                 700
Gly Leu Lys Leu Gln Arg Arg Trp Lys Arg Thr Gln Ser Gln Gln Gly
705                 710                 715                 720
Leu Gln Glu Asn Ser Ser Gly Gln Ser Phe Phe Val Arg Asn Lys Lys
            725                 730                 735
```

Val Arg Arg Ala Pro Leu Ser Glu Gly Pro His Ser Leu Gly Cys Tyr
                740                 745                 750

Asn Pro Met Met Glu Asp Gly Ile Ser Tyr Thr Thr Leu Arg Phe Pro
            755                 760                 765

Glu Met Asn Ile Pro Arg Thr Gly Asp Ala Glu Ser Ser Glu Met Gln
        770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845

<210> SEQ ID NO 420
<211> LENGTH: 364
<212> TYPE: PRT
<213> ORGANISM: Homo sapiens

<400> SEQUENCE: 420

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

```
Leu Cys Leu Cys Leu Ile Phe Phe Ile Val Lys Thr His Arg Arg Lys
            275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
            355                 360

<210> SEQ ID NO 421
<211> LENGTH: 572
<212> TYPE: PRT
<213> ORGANISM: Homo sapiens

<400> SEQUENCE: 421

Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
    50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
    210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

Phe Leu Asn Tyr Ser Thr Ile Asn Tyr Lys Trp Ser Phe Gly Asp Asn
```

```
                    275                 280                 285
Thr Gly Leu Phe Val Ser Thr Asn His Thr Val Asn His Thr Tyr Val
    290                 295                 300
Leu Asn Gly Thr Phe Ser Leu Asn Leu Thr Val Lys Ala Ala Ala Pro
305                 310                 315                 320
Gly Pro Cys Pro Pro Pro Pro Pro Arg Pro Ser Lys Pro Thr
            325                 330                 335
Pro Ser Leu Ala Thr Thr Leu Lys Ser Tyr Asp Ser Asn Thr Pro Gly
                340                 345                 350
Pro Ala Gly Asp Asn Pro Leu Glu Leu Ser Arg Ile Pro Asp Glu Asn
            355                 360                 365
Cys Gln Ile Asn Arg Tyr Gly His Phe Gln Ala Thr Ile Thr Ile Val
        370                 375                 380
Glu Gly Ile Leu Glu Val Asn Ile Ile Gln Met Thr Asp Val Leu Met
385                 390                 395                 400
Pro Val Pro Trp Pro Glu Ser Ser Leu Ile Asp Phe Val Val Thr Cys
                405                 410                 415
Gln Gly Ser Ile Pro Thr Glu Val Cys Thr Ile Ser Asp Pro Thr
            420                 425                 430
Cys Glu Ile Thr Gln Asn Thr Val Cys Ser Pro Val Asp Val Asp Glu
                435                 440                 445
Met Cys Leu Leu Thr Val Arg Arg Thr Phe Asn Gly Ser Gly Thr Tyr
        450                 455                 460
Cys Val Asn Leu Thr Leu Gly Asp Asp Thr Ser Leu Ala Leu Thr Ser
465                 470                 475                 480
Thr Leu Ile Ser Val Pro Asp Arg Asp Pro Ala Ser Pro Leu Arg Met
                485                 490                 495
Ala Asn Ser Ala Leu Ile Ser Val Gly Cys Leu Ala Ile Phe Val Thr
            500                 505                 510
Val Ile Ser Leu Leu Val Tyr Lys Lys His Lys Glu Tyr Asn Pro Ile
        515                 520                 525
Glu Asn Ser Pro Gly Asn Val Val Arg Ser Lys Gly Leu Ser Val Phe
    530                 535                 540
Leu Asn Arg Ala Lys Ala Val Phe Phe Pro Gly Asn Gln Glu Lys Asp
545                 550                 555                 560
Pro Leu Leu Lys Asn Gln Glu Phe Lys Gly Val Ser
                565                 570

<210> SEQ ID NO 422
<211> LENGTH: 848
<212> TYPE: PRT
<213> ORGANISM: Homo sapiens

<400> SEQUENCE: 422

Met Leu Gln Thr Lys Asp Leu Ile Trp Thr Leu Phe Phe Leu Gly Thr
1               5                   10                  15
Ala Val Ser Leu Gln Val Asp Ile Val Pro Ser Gln Gly Glu Ile Ser
            20                  25                  30
Val Gly Glu Ser Lys Phe Phe Leu Cys Gln Val Ala Gly Asp Ala Lys
        35                  40                  45
Asp Lys Asp Ile Ser Trp Phe Ser Pro Asn Gly Glu Lys Leu Thr Pro
    50                  55                  60
Asn Gln Gln Arg Ile Ser Val Val Trp Asn Asp Asp Ser Ser Ser Thr
65                  70                  75                  80
```

-continued

```
Leu Thr Ile Tyr Asn Ala Asn Ile Asp Asp Ala Gly Ile Tyr Lys Cys
                 85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
```

```
                500             505             510
Ser Thr Ala Gln Val Gln Phe Asp Glu Pro Glu Ala Thr Gly Gly Val
            515                 520                 525

Pro Ile Leu Lys Tyr Lys Ala Glu Trp Arg Ala Val Gly Glu Glu Val
        530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
                610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
                660                 665                 670

Tyr Val Val Ala Glu Asn Gln Gln Gly Lys Ser Lys Ala Ala His Phe
                675                 680                 685

Val Phe Arg Thr Ser Ala Gln Pro Thr Ala Ile Pro Ala Asn Gly Ser
            690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
                740                 745                 750

Ala Gly Pro Gly Ala Lys Gly Lys Asp Met Glu Glu Gly Lys Ala Ala
            755                 760                 765

Phe Ser Lys Asp Glu Ser Lys Glu Pro Ile Val Glu Val Arg Thr Glu
        770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
                820                 825                 830

Thr Val Pro Asn Asp Ala Thr Gln Thr Lys Glu Asn Glu Ser Lys Ala
                835                 840                 845

<210> SEQ ID NO 423
<211> LENGTH: 193
<212> TYPE: PRT
<213> ORGANISM: Homo sapiens

<400> SEQUENCE: 423

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30
```

```
Cys Leu Val Val Cys Ile Gln Arg Phe Ala Gln Ala Gln Gln Gln Leu
             35                  40                  45

Pro Leu Glu Ser Leu Gly Trp Asp Val Ala Glu Leu Gln Leu Asn His
 50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                 85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

<210> SEQ ID NO 424
<211> LENGTH: 232
<212> TYPE: PRT
<213> ORGANISM: Homo sapiens

<400> SEQUENCE: 424

```
Met His Arg Arg Arg Ser Arg Ser Cys Arg Glu Asp Gln Lys Pro Val
  1               5                  10                  15

Met Asp Asp Gln Arg Asp Leu Ile Ser Asn Asn Glu Gln Leu Pro Met
             20                  25                  30

Leu Gly Arg Arg Pro Gly Ala Pro Glu Ser Lys Cys Ser Arg Gly Ala
             35                  40                  45

Leu Tyr Thr Gly Phe Ser Ile Leu Val Thr Leu Leu Ala Gly Gln
 50                  55                  60

Ala Thr Thr Ala Tyr Phe Leu Tyr Gln Gln Gln Gly Arg Leu Asp Lys
 65                  70                  75                  80

Leu Thr Val Thr Ser Gln Asn Leu Gln Leu Glu Asn Leu Arg Met Lys
                 85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
            115                 120                 125

Gln Asn Ala Thr Lys Tyr Gly Asn Met Thr Glu Asp His Val Met His
            130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
            195                 200                 205
```

Glu Ser Leu Glu Leu Glu Asp Pro Ser Ser Gly Leu Gly Val Thr Lys
210                 215                 220

Gln Asp Leu Gly Pro Val Pro Met
225                 230

<210> SEQ ID NO 425
<211> LENGTH: 557
<212> TYPE: PRT
<213> ORGANISM: Homo sapiens

<400> SEQUENCE: 425

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

```
Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Gly Glu Gly Tyr Glu Glu Pro Asp Ser Glu Glu
            405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
                485                 490                 495

Gly Ser Gln Ser Tyr Glu Asp Met Arg Gly Ile Leu Tyr Ala Ala Pro
            500                 505                 510

Gln Leu Arg Ser Ile Arg Gly Gln Pro Gly Pro Asn His Glu Glu Asp
        515                 520                 525

Ala Asp Ser Tyr Glu Asn Met Asp Asn Pro Asp Gly Pro Asp Pro Ala
    530                 535                 540

Trp Gly Gly Gly Gly Arg Met Gly Thr Trp Ser Thr Arg
545                 550                 555

<210> SEQ ID NO 426
<211> LENGTH: 273
<212> TYPE: PRT
<213> ORGANISM: Homo sapiens

<400> SEQUENCE: 426

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
```

```
                165                 170                 175
Trp Gly Ile Ala Leu Leu Val Leu Val Cys Val Leu Ala Leu Ala
            180                 185                 190
Ile Val Tyr Leu Ile Ala Leu Ala Val Cys Gln Cys Arg Arg Lys Asn
            195                 200                 205
Tyr Gly Gln Leu Asp Ile Phe Pro Ala Arg Asp Thr Tyr His Pro Met
            210                 215                 220
Ser Glu Tyr Pro Thr Tyr His Thr His Gly Arg Tyr Val Pro Pro Ser
225                 230                 235                 240
Ser Thr Asp Arg Ser Pro Tyr Glu Lys Val Ser Ala Gly Asn Gly Gly
                245                 250                 255
Ser Ser Leu Ser Tyr Thr Asn Pro Ala Val Ala Ala Thr Ser Ala Asn
                260                 265                 270
Leu

<210> SEQ ID NO 427
<211> LENGTH: 310
<212> TYPE: PRT
<213> ORGANISM: Homo sapiens

<400> SEQUENCE: 427

Met Arg Arg Ala Ala Leu Trp Leu Trp Leu Cys Ala Leu Ala Leu Ser
1               5                   10                  15
Leu Gln Pro Ala Leu Pro Gln Ile Val Ala Thr Asn Leu Pro Pro Glu
                20                  25                  30
Asp Gln Asp Gly Ser Gly Asp Asp Ser Asp Asn Phe Ser Gly Ser Gly
            35                  40                  45
Ala Gly Ala Leu Gln Asp Ile Thr Leu Ser Gln Gln Thr Pro Ser Thr
        50                  55                  60
Trp Lys Asp Thr Gln Leu Leu Thr Ala Ile Pro Thr Ser Pro Glu Pro
65                  70                  75                  80
Thr Gly Leu Glu Ala Thr Ala Ala Ser Thr Ser Thr Leu Pro Ala Gly
                85                  90                  95
Glu Gly Pro Lys Glu Gly Glu Ala Val Val Leu Pro Glu Val Glu Pro
                100                 105                 110
Gly Leu Thr Ala Arg Glu Gln Glu Ala Thr Pro Arg Pro Arg Glu Thr
            115                 120                 125
Thr Gln Leu Pro Thr Thr His Gln Ala Ser Thr Thr Thr Ala Thr Thr
        130                 135                 140
Ala Gln Glu Pro Ala Thr Ser His Pro His Arg Asp Met Gln Pro Gly
145                 150                 155                 160
His His Glu Thr Ser Thr Pro Ala Gly Pro Ser Gln Ala Asp Leu His
                165                 170                 175
Thr Pro His Thr Glu Asp Gly Gly Pro Ser Ala Thr Glu Arg Ala Ala
            180                 185                 190
Glu Asp Gly Ala Ser Ser Gln Leu Pro Ala Ala Glu Gly Ser Gly Glu
        195                 200                 205
Gln Asp Phe Thr Phe Glu Thr Ser Gly Glu Asn Thr Ala Val Val Ala
        210                 215                 220
Val Glu Pro Asp Arg Arg Asn Gln Ser Pro Val Asp Gln Gly Ala Thr
225                 230                 235                 240
Gly Ala Ser Gln Gly Leu Leu Asp Arg Lys Glu Val Leu Gly Gly Val
                245                 250                 255
Ile Ala Gly Gly Leu Val Gly Leu Ile Phe Ala Val Cys Leu Val Gly
```

```
                    260                 265                 270
Phe Met Leu Tyr Arg Met Lys Lys Lys Asp Glu Gly Ser Tyr Ser Leu
            275                 280                 285
Glu Glu Pro Lys Gln Ala Asn Gly Gly Ala Tyr Gln Lys Pro Thr Lys
        290                 295                 300
Gln Glu Glu Phe Tyr Ala
305                 310

<210> SEQ ID NO 428
<211> LENGTH: 1048
<212> TYPE: PRT
<213> ORGANISM: Homo sapiens

<400> SEQUENCE: 428

Met Ala Phe Pro Pro Arg Arg Arg Leu Arg Leu Gly Pro Arg Gly Leu
1               5                   10                  15
Pro Leu Leu Leu Ser Gly Leu Leu Pro Leu Cys Arg Ala Phe Asn
            20                  25                  30
Leu Asp Val Asp Ser Pro Ala Glu Tyr Ser Gly Pro Glu Gly Ser Tyr
        35                  40                  45
Phe Gly Phe Ala Val Asp Phe Phe Val Pro Ser Ala Ser Ser Arg Met
    50                  55                  60
Phe Leu Leu Val Gly Ala Pro Lys Ala Asn Thr Thr Gln Pro Gly Ile
65                  70                  75                  80
Val Glu Gly Gly Gln Val Leu Lys Cys Asp Trp Ser Ser Thr Arg Arg
                85                  90                  95
Cys Gln Pro Ile Glu Phe Asp Ala Thr Gly Asn Arg Asp Tyr Ala Lys
            100                 105                 110
Asp Asp Pro Leu Glu Phe Lys Ser His Gln Trp Phe Gly Ala Ser Val
        115                 120                 125
Arg Ser Lys Gln Asp Lys Ile Leu Ala Cys Ala Pro Leu Tyr His Trp
    130                 135                 140
Arg Thr Glu Met Lys Gln Glu Arg Glu Pro Val Gly Thr Cys Phe Leu
145                 150                 155                 160
Gln Asp Gly Thr Lys Thr Val Glu Tyr Ala Pro Cys Arg Ser Gln Asp
                165                 170                 175
Ile Asp Ala Asp Gly Gln Gly Phe Cys Gln Gly Gly Phe Ser Ile Asp
            180                 185                 190
Phe Thr Lys Ala Asp Arg Val Leu Leu Gly Gly Pro Gly Ser Phe Tyr
        195                 200                 205
Trp Gln Gly Gln Leu Ile Ser Asp Gln Val Ala Glu Ile Val Ser Lys
    210                 215                 220
Tyr Asp Pro Asn Val Tyr Ser Ile Lys Tyr Asn Asn Gln Leu Ala Thr
225                 230                 235                 240
Arg Thr Ala Gln Ala Ile Phe Asp Asp Ser Tyr Leu Gly Tyr Ser Val
                245                 250                 255
Ala Val Gly Asp Phe Asn Gly Asp Gly Ile Asp Asp Phe Val Ser Gly
            260                 265                 270
Val Pro Arg Ala Ala Arg Thr Leu Gly Met Val Tyr Ile Tyr Asp Gly
        275                 280                 285
Lys Asn Met Ser Ser Leu Tyr Asn Phe Thr Gly Glu Gln Met Ala Ala
    290                 295                 300
Tyr Phe Gly Phe Ser Val Ala Ala Thr Asp Ile Asn Gly Asp Asp Tyr
305                 310                 315                 320
```

-continued

```
Ala Asp Val Phe Ile Gly Ala Pro Leu Phe Met Asp Arg Gly Ser Asp
                325                 330                 335

Gly Lys Leu Gln Glu Val Gly Gln Val Ser Val Ser Leu Gln Arg Ala
            340                 345                 350

Ser Gly Asp Phe Gln Thr Thr Lys Leu Asn Gly Phe Glu Val Phe Ala
        355                 360                 365

Arg Phe Gly Ser Ala Ile Ala Pro Leu Gly Asp Leu Asp Gln Asp Gly
    370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
            405                 410                 415

Pro Ser Gln Ile Leu Glu Gly Gln Trp Ala Ala Arg Ser Met Pro Pro
        420                 425                 430

Ser Phe Gly Tyr Ser Met Lys Gly Ala Thr Asp Ile Asp Lys Asn Gly
    435                 440                 445

Tyr Pro Asp Leu Ile Val Gly Ala Phe Gly Val Asp Arg Ala Ile Leu
    450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
            485                 490                 495

Ala Leu Lys Val Ser Cys Phe Asn Val Arg Phe Cys Leu Lys Ala Asp
        500                 505                 510

Gly Lys Gly Val Leu Pro Arg Lys Leu Asn Phe Gln Val Glu Leu Leu
    515                 520                 525

Leu Asp Lys Leu Lys Gln Lys Gly Ala Ile Arg Arg Ala Leu Phe Leu
530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
            565                 570                 575

Glu Phe Arg Asp Lys Leu Thr Pro Ile Thr Ile Phe Met Glu Tyr Arg
        580                 585                 590

Leu Asp Tyr Arg Thr Ala Ala Asp Thr Thr Gly Leu Gln Pro Ile Leu
    595                 600                 605

Asn Gln Phe Thr Pro Ala Asn Ile Ser Arg Gln Ala His Ile Leu Leu
610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
            645                 650                 655

Leu Ile Val Lys Ala Gln Asn Gln Gly Glu Gly Ala Tyr Glu Ala Glu
        660                 665                 670

Leu Ile Val Ser Ile Pro Leu Gln Ala Asp Phe Ile Gly Val Val Arg
    675                 680                 685

Asn Asn Glu Ala Leu Ala Arg Leu Ser Cys Ala Phe Lys Thr Glu Asn
690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
            725                 730                 735

Met Asp Thr Ser Val Lys Phe Asp Leu Gln Ile Gln Ser Ser Asn Leu
```

-continued

```
                740                 745                 750
Phe Asp Lys Val Ser Pro Val Ser His Lys Val Asp Leu Ala Val
            755                 760                 765
Leu Ala Ala Val Glu Ile Arg Gly Val Ser Ser Pro Asp His Ile Phe
            770                 775                 780
Leu Pro Ile Pro Asn Trp Glu His Lys Glu Asn Pro Glu Thr Glu Glu
785                 790                 795                 800
Asp Val Gly Pro Val Gln His Ile Tyr Glu Leu Arg Asn Asn Gly
            805                 810                 815
Pro Ser Ser Phe Ser Lys Ala Met Leu His Leu Gln Trp Pro Tyr Lys
            820                 825                 830
Tyr Asn Asn Asn Thr Leu Leu Tyr Ile Leu His Tyr Asp Ile Asp Gly
            835                 840                 845
Pro Met Asn Cys Thr Ser Asp Met Glu Ile Asn Pro Leu Arg Ile Lys
            850                 855                 860
Ile Ser Ser Leu Gln Thr Thr Glu Lys Asn Asp Thr Val Ala Gly Gln
865                 870                 875                 880
Gly Glu Arg Asp His Leu Ile Thr Lys Arg Asp Leu Ala Leu Ser Glu
            885                 890                 895
Gly Asp Ile His Thr Leu Gly Cys Gly Val Ala Gln Cys Leu Lys Ile
            900                 905                 910
Val Cys Gln Val Gly Arg Leu Asp Arg Gly Lys Ser Ala Ile Leu Tyr
            915                 920                 925
Val Lys Ser Leu Leu Trp Thr Glu Thr Phe Met Asn Lys Glu Asn Gln
            930                 935                 940
Asn His Ser Tyr Ser Leu Lys Ser Ser Ala Ser Phe Asn Val Ile Glu
945                 950                 955                 960
Phe Pro Tyr Lys Asn Leu Pro Ile Glu Asp Ile Thr Asn Ser Thr Leu
            965                 970                 975
Val Thr Thr Asn Val Thr Trp Gly Ile Gln Pro Ala Pro Met Pro Val
            980                 985                 990
Pro Val Trp Val Ile Ile Leu Ala Val Leu Ala Gly Leu Leu Leu Leu
            995                 1000                1005
Ala Val Leu Val Phe Val Met Tyr Arg Met Gly Phe Phe Lys Arg
            1010                1015                1020
Val Arg Pro Pro Gln Glu Glu Gln Glu Arg Glu Gln Leu Gln Pro
            1025                1030                1035
His Glu Asn Gly Glu Gly Asn Ser Glu Thr
            1040                1045

<210> SEQ ID NO 429
<211> LENGTH: 188
<212> TYPE: PRT
<213> ORGANISM: Homo sapiens

<400> SEQUENCE: 429

Met Asp Cys Arg Lys Met Ala Arg Phe Ser Tyr Ser Val Ile Trp Ile
1               5                   10                  15
Met Ala Ile Ser Lys Val Phe Glu Leu Gly Leu Val Ala Gly Leu Gly
            20                  25                  30
His Gln Glu Phe Ala Arg Pro Ser Arg Gly Tyr Leu Ala Phe Arg Asp
            35                  40                  45
Asp Ser Ile Trp Pro Gln Glu Glu Pro Ala Ile Arg Pro Arg Ser Ser
            50                  55                  60
```

```
Gln Arg Val Pro Pro Met Gly Ile Gln His Ser Lys Glu Leu Asn Arg
 65                  70                  75                  80

Thr Cys Cys Leu Asn Gly Gly Thr Cys Met Leu Gly Ser Phe Cys Ala
                 85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Phe Met
                165                 170                 175

Leu Val Gly Ile Cys Leu Ser Ile Gln Ser Tyr Tyr
                180                 185

<210> SEQ ID NO 430
<211> LENGTH: 750
<212> TYPE: PRT
<213> ORGANISM: Homo sapiens

<400> SEQUENCE: 430

Met Trp Asn Leu Leu His Glu Thr Asp Ser Ala Val Ala Thr Ala Arg
 1               5                  10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255
```

```
Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
            290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670
```

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
                740                 745                 750

<210> SEQ ID NO 431
<211> LENGTH: 976
<212> TYPE: PRT
<213> ORGANISM: Homo sapiens

<400> SEQUENCE: 431

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu Leu
                20                  25                  30

Asp Phe Ala Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
290                 295                 300

```
Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
            325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
            370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720
```

Arg Gly Ile Ala Ala Gly Met Lys Tyr Leu Ala Asn Met Asn Tyr Val
            725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
            755                 760                 765

Glu Ala Thr Tyr Thr Thr Ser Gly Gly Lys Ile Pro Ile Arg Trp Thr
            770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
            835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
            885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
            915                 920                 925

Gly Tyr Thr Ala Ile Glu Lys Val Val Gln Met Thr Asn Asp Asp Ile
            930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 432
<211> LENGTH: 668
<212> TYPE: PRT
<213> ORGANISM: Homo sapiens

<400> SEQUENCE: 432

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
            50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
            85                  90                  95

Ser Ser Asn Ile Ile Ser Val Ala Glu Asn Gly Leu Gln Cys Pro Thr
            100                 105                 110

Pro Gln Thr Val Ile Thr Ser Leu Gln Gln Glu Leu Cys Pro Ser Phe
            115                 120                 125

```
Leu Leu Pro Ser Ala Pro Ala Leu Gly Arg Cys Phe Pro Trp Thr Asn
        130                 135                 140
Val Thr Pro Pro Ala Leu Pro Gly Ile Thr Asn Asp Thr Thr Ile Gln
145                 150                 155                 160
Gln Gly Ile Ser Gly Leu Ile Asp Ser Leu Asn Ala Arg Asp Ile Ser
                165                 170                 175
Val Lys Ile Phe Glu Asp Phe Ala Gln Ser Trp Tyr Trp Ile Leu Val
            180                 185                 190
Ala Leu Gly Val Ala Leu Val Leu Ser Leu Leu Phe Ile Leu Leu Leu
        195                 200                 205
Arg Leu Val Ala Gly Pro Leu Val Leu Val Leu Ile Leu Gly Val Leu
210                 215                 220
Gly Val Leu Ala Tyr Gly Ile Tyr Tyr Cys Trp Glu Glu Tyr Arg Val
225                 230                 235                 240
Leu Arg Asp Lys Gly Ala Ser Ile Ser Gln Leu Gly Phe Thr Thr Asn
                245                 250                 255
Leu Ser Ala Tyr Gln Ser Val Gln Glu Thr Trp Leu Ala Ala Leu Ile
            260                 265                 270
Val Leu Ala Val Leu Glu Ala Ile Leu Leu Met Leu Ile Phe Leu
        275                 280                 285
Arg Gln Arg Ile Arg Ile Ala Ile Ala Leu Leu Lys Glu Ala Ser Lys
290                 295                 300
Ala Val Gly Gln Met Met Ser Thr Met Phe Tyr Pro Leu Val Thr Phe
305                 310                 315                 320
Val Leu Leu Leu Ile Cys Ile Ala Tyr Trp Ala Met Thr Ala Leu Tyr
                325                 330                 335
Leu Ala Thr Ser Gly Gln Pro Gln Tyr Val Leu Trp Ala Ser Asn Ile
            340                 345                 350
Ser Ser Pro Gly Cys Glu Lys Val Pro Ile Asn Thr Ser Cys Asn Pro
        355                 360                 365
Thr Ala His Leu Val Asn Ser Ser Cys Pro Gly Leu Met Cys Val Phe
370                 375                 380
Gln Gly Tyr Ser Ser Lys Gly Leu Ile Gln Arg Ser Val Phe Asn Leu
385                 390                 395                 400
Gln Ile Tyr Gly Val Leu Gly Leu Phe Trp Thr Leu Asn Trp Val Leu
                405                 410                 415
Ala Leu Gly Gln Cys Val Leu Ala Gly Ala Phe Ala Ser Phe Tyr Trp
            420                 425                 430
Ala Phe His Lys Pro Gln Asp Ile Pro Thr Phe Pro Leu Ile Ser Ala
        435                 440                 445
Phe Ile Arg Thr Leu Arg Tyr His Thr Gly Ser Leu Ala Phe Gly Ala
450                 455                 460
Leu Ile Leu Thr Leu Val Gln Ile Ala Arg Val Ile Leu Glu Tyr Ile
465                 470                 475                 480
Asp His Lys Leu Arg Gly Val Gln Asn Pro Val Ala Arg Cys Ile Met
                485                 490                 495
Cys Cys Phe Lys Cys Cys Leu Trp Cys Leu Glu Lys Phe Ile Lys Phe
            500                 505                 510
Leu Asn Arg Asn Ala Tyr Ile Met Ile Ala Ile Tyr Gly Lys Asn Phe
        515                 520                 525
Cys Val Ser Ala Lys Asn Ala Phe Met Leu Leu Met Arg Asn Ile Val
530                 535                 540
```

```
Arg Val Val Val Leu Asp Lys Val Thr Asp Leu Leu Phe Phe Gly
545                 550                 555                 560

Lys Leu Leu Val Val Gly Gly Val Leu Ser Phe Phe Phe
                565             570             575

Ser Gly Arg Ile Pro Gly Leu Gly Lys Asp Phe Lys Ser Pro His Leu
            580                 585                 590

Asn Tyr Tyr Trp Leu Pro Ile Met Thr Ser Ile Leu Gly Ala Tyr Val
        595                 600                 605

Ile Ala Ser Gly Phe Phe Ser Val Phe Gly Met Cys Val Asp Thr Leu
            610                 615                 620

Phe Leu Cys Phe Leu Glu Asp Leu Glu Arg Asn Asn Gly Ser Leu Asp
625                 630                 635                 640

Arg Pro Tyr Tyr Met Ser Lys Ser Leu Leu Lys Ile Leu Gly Lys Lys
                645                 650                 655

Asn Glu Ala Pro Pro Asp Asn Lys Lys Arg Lys Lys
            660                 665
```

<210> SEQ ID NO 433
<211> LENGTH: 214
<212> TYPE: PRT
<213> ORGANISM: Artificial Sequence
<220> FEATURE:
<223> OTHER INFORMATION: Recombinant antibody

<400> SEQUENCE: 433

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 434
<211> LENGTH: 449

<212> TYPE: PRT
<213> ORGANISM: Artificial Sequence
<220> FEATURE:
<223> OTHER INFORMATION: Recombinant antibody

<400> SEQUENCE: 434

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

-continued

Ser Asn Gly Gln Pro Glu Asn Asn Tyr Lys Thr Thr Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 435
<211> LENGTH: 214
<212> TYPE: PRT
<213> ORGANISM: Artificial Sequence
<220> FEATURE:
<223> OTHER INFORMATION: Recombinant antibody

<400> SEQUENCE: 435

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 436
<211> LENGTH: 444
<212> TYPE: PRT
<213> ORGANISM: Artificial Sequence
<220> FEATURE:
<223> OTHER INFORMATION: Recombinant antibody

<400> SEQUENCE: 436

Gln Val Gln Leu Gln Glu Ser Gly Pro Gly Leu Val Lys Pro Ser Glu
1               5                   10                  15

-continued

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly

<210> SEQ ID NO 437
<211> LENGTH: 10
<212> TYPE: PRT
<213> ORGANISM: Artificial Sequence
<220> FEATURE:
<223> OTHER INFORMATION: Antibody fragment

<400> SEQUENCE: 437

Gly Phe Thr Phe Ser Ser Tyr Gly Met Ser
1               5                   10

<210> SEQ ID NO 438
<211> LENGTH: 17
<212> TYPE: PRT
<213> ORGANISM: Artificial Sequence
<220> FEATURE:
<223> OTHER INFORMATION: Antibody fragment

<400> SEQUENCE: 438

Gly Ile Ser Ser Leu Gly Ser Thr Thr Tyr Tyr Ala Asp Ser Val Lys
1               5                   10                  15

Gly

<210> SEQ ID NO 439
<211> LENGTH: 12
<212> TYPE: PRT
<213> ORGANISM: Artificial Sequence
<220> FEATURE:
<223> OTHER INFORMATION: Antibody fragment

<400> SEQUENCE: 439

Thr Gly Ser Pro Gly Thr Phe Met His Gly Asp His
1               5                   10

<210> SEQ ID NO 440
<211> LENGTH: 11
<212> TYPE: PRT
<213> ORGANISM: Artificial Sequence
<220> FEATURE:
<223> OTHER INFORMATION: Antibody fragment

<400> SEQUENCE: 440

Arg Ala Ser Gln Asp Ile Asn Asn Tyr Leu Ser
1               5                   10

<210> SEQ ID NO 441
<211> LENGTH: 8
<212> TYPE: PRT
<213> ORGANISM: Artificial Sequence
<220> FEATURE:
<223> OTHER INFORMATION: Antibody fragment

<400> SEQUENCE: 441

Tyr Gly Ala Ser Asn Leu Gln Ser
1               5

<210> SEQ ID NO 442
<211> LENGTH: 8
<212> TYPE: PRT
<213> ORGANISM: Artificial Sequence
<220> FEATURE:
<223> OTHER INFORMATION: Antibody fragment

<400> SEQUENCE: 442

Gln Gln Tyr Tyr Gly Arg Pro Thr
1               5

<210> SEQ ID NO 443
<211> LENGTH: 119
<212> TYPE: PRT
<213> ORGANISM: Artificial Sequence
<220> FEATURE:
<223> OTHER INFORMATION: Antibody fragment

<400> SEQUENCE: 443

Glu Leu Val Glu Ser Gly Gly Leu Val Gln Pro Gly Gly Ser Leu
1               5                   10                  15

Arg Leu Ser Cys Ala Ala Ser Gly Phe Thr Phe Ser Tyr Gly Met
                20                  25                  30

Ser Trp Val Arg Gln Ala Pro Gly Lys Gly Leu Glu Trp Val Ser Gly
            35                  40                      45

Ile Ser Ser Leu Gly Ser Thr Thr Tyr Tyr Ala Asp Ser Val Lys Gly
        50                  55                  60

Arg Phe Thr Ile Ser Arg Asp Asn Ser Lys Asn Thr Leu Tyr Leu Gln
65              70                  75                  80

Met Asn Ser Leu Arg Ala Glu Asp Thr Ala Val Tyr Tyr Cys Ala Arg
                85                  90                  95

Thr Gly Ser Pro Gly Thr Phe Met His Gly Asp His Trp Gly Gln Gly
            100                 105                 110

Thr Leu Val Thr Val Ser Ser
        115

<210> SEQ ID NO 444
<211> LENGTH: 109
<212> TYPE: PRT
<213> ORGANISM: Artificial Sequence
<220> FEATURE:
<223> OTHER INFORMATION: Antibody fragment

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Ser Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Phe Ala Val Tyr Tyr Cys Gln Gln Tyr Tyr Gly Arg Pro Thr
                85                  90                  95

Thr Phe Gly Gln Gly Thr Lys Val Glu Ile Lys Arg Thr
            100                 105

<210> SEQ ID NO 445
<211> LENGTH: 451
<212> TYPE: PRT
<213> ORGANISM: Artificial Sequence
<220> FEATURE:
<223> OTHER INFORMATION: anti-carboanhydrase IX antibody heavy chain

<400> SEQUENCE: 445

Gln Val Glu Leu Val Glu Ser Gly Gly Gly Leu Val Gln Pro Gly Gly

```
1               5                   10                  15
Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
            35                  40                  45

Ser Gly Ile Ser Ser Leu Gly Ser Thr Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Ser Pro Gly Thr Phe Met His Gly Asp His Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
            435                 440                 445
Pro Gly Lys
    450

<210> SEQ ID NO 446
<211> LENGTH: 214
<212> TYPE: PRT
<213> ORGANISM: Artificial Sequence
<220> FEATURE:
<223> OTHER INFORMATION: anti-carboanhydrase IX antibody light chain

<400> SEQUENCE: 446

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ser Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Gly Arg Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```